US007700655B2

(12) United States Patent
Muto et al.

(10) Patent No.: US 7,700,655 B2
(45) Date of Patent: Apr. 20, 2010

(54) ANTIALLERGIC AGENTS

(75) Inventors: Susumu Muto, Tokyo (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 0 days.

(21) Appl. No.: 11/783,324

(22) Filed: Apr. 9, 2007

(65) Prior Publication Data
US 2007/0185110 A1 Aug. 9, 2007

Related U.S. Application Data

(62) Division of application No. 10/515,623, filed as application No. PCT/JP03/07120 on Jun. 5, 2003, now abandoned.

(30) Foreign Application Priority Data

Jun. 6, 2002 (JP) .............................. 2002-165148

(51) Int. Cl.
*A61K 31/165* (2006.01)
(52) U.S. Cl. .................... 514/620; 564/162; 564/165
(58) Field of Classification Search ................ 514/299, 514/317, 387, 365, 372, 427, 438, 617, 620; 564/162, 165
See application file for complete search history.

(56) References Cited

U.S. PATENT DOCUMENTS

| | | | |
|---|---|---|---|
| 3,331,874 A | 7/1967 | Stecker | |
| 3,332,996 A | 7/1967 | Zerweck et al. | |
| 3,906,023 A | 9/1975 | Buchel et al. | |
| 4,358,443 A | 11/1982 | Coburn et al. | |
| 4,560,549 A | 12/1985 | Ritchey | |
| 4,659,710 A | 4/1987 | Sato et al. | |
| 4,661,630 A | 4/1987 | Harigaya et al. | |
| 4,690,924 A | 9/1987 | Sato et al. | |
| 4,725,590 A | 2/1988 | Ritchey | |
| 4,742,083 A | 5/1988 | Ritchey | |
| 4,786,644 A | 11/1988 | Glamkowski et al. | |
| 4,939,133 A | 7/1990 | Connor et al. | |
| 4,952,588 A | 8/1990 | Glamkowski et al. | |
| 4,966,906 A | 10/1990 | Glamkowski et al. | |
| 5,126,341 A | 6/1992 | Suzuki et al. | |
| 5,589,514 A | 12/1996 | Naik et al. | |
| 5,661,153 A | 8/1997 | Isobe et al. | |
| 5,679,696 A * | 10/1997 | Fenton et al. ................ 514/354 |
| 5,776,977 A | 7/1998 | Naik et al. | |
| 5,811,428 A | 9/1998 | Suto et al. | |
| 5,852,028 A | 12/1998 | Suto et al. | |
| 5,935,966 A | 8/1999 | Suto et al. | |
| 6,002,884 A | 12/1999 | Okumura et al. | |
| 6,117,859 A | 9/2000 | Evans et al. | |
| 6,159,988 A | 12/2000 | Naik et al. | |
| 6,166,028 A | 12/2000 | Bloom et al. | |
| 6,225,329 B1 | 5/2001 | Richter et al. | |
| 6,262,044 B1 | 7/2001 | MØller et al. | |
| 6,410,586 B1 | 6/2002 | Moller et al. | |
| 6,414,013 B1 | 7/2002 | Fancelli et al. | |
| 6,566,394 B1 | 5/2003 | Takeuchi et al. | |
| 6,653,309 B1 | 11/2003 | Saunders et al. | |
| 6,734,180 B1 | 5/2004 | Nunokawa et al. | |
| 6,787,652 B1 | 9/2004 | Dow et al. | |
| 2002/0002199 A1 | 1/2002 | Jeppesen et al. | |
| 2002/0019412 A1 | 2/2002 | Andresen et al. | |

(Continued)

FOREIGN PATENT DOCUMENTS

DE 1 017 606 10/1957

(Continued)

OTHER PUBLICATIONS

Sant, et al., "The Mast Cell in Interstitial Cystitis: Role of Pathophysilogy and Pathogensis", Urology 69 (Suppl 4A): 34-40, 2007.*
Cited ref_Google search_Mast cell and hysteromyoma, (2009).*
Kim, et al., "The Journal of Clinical Investigation," 2001, vol. 108, No. 3, p. 437-446.
Yuan, et al., "Science," 2001, vol. 293, p. 1673-1677.
Macielag, et al., "The Journal of Medicinal Chemistry," 1998, vol. 41, No. 16 p. 2939-2945.

(Continued)

*Primary Examiner*—Yong Chu
(74) *Attorney, Agent, or Firm*—Greenblum & Bernstein, P.L.C.

(57) ABSTRACT

A medicament for the preventive and/or therapeutic treatment of allergic diseases and/or endometriosis and/or hysteromyoma which comprises as an active ingredient a substance selected from the group consisting of a compound represented by the following general formula (I) and a pharmacologically acceptable salt thereof, and a hydrate thereof and a solvate thereof:

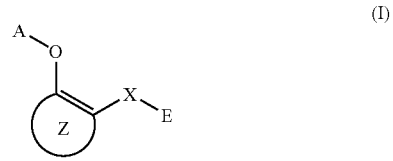

(I)

wherein X represents a connecting group whose number of atoms in the main chain is 2 to 5 (said connecting group may be substituted), A represents hydrogen atom or acetyl group, E represents an aryl group which may be substituted or a hetero aryl group which may be substituted, ring Z represents an arene which may have one or more substitutents in addition to the group represented by formula —O-A wherein A has the same meaning as that defined above and the group represented by formula —X-E wherein each of X and E has the same meaning as that defined above, or a heteroarene which may have one or more substitutents in addition to the group represented by formula —O-A wherein A has the same meaning as that defined above and the group represented by formula —X-E wherein each of X and E has the same meaning as that defined above.

16 Claims, 2 Drawing Sheets

U.S. PATENT DOCUMENTS

| | | |
|---|---|---|
| 2002/0165398 A1 | 11/2002 | Jeppesen et al. |
| 2003/0069267 A1 | 4/2003 | Moller et al. |
| 2003/0083386 A1 | 5/2003 | Yuan et al. |
| 2004/0048891 A1 | 3/2004 | Kato et al. |
| 2004/0087650 A1 | 5/2004 | Saunders et al. |
| 2004/0122244 A1 | 6/2004 | Suzuki et al. |
| 2004/0157844 A1 | 8/2004 | Dow et al. |
| 2004/0259877 A1 | 12/2004 | Muto et al. |
| 2006/0014811 A1 | 1/2006 | Muto et al. |
| 2006/0019958 A1 | 1/2006 | Muto et al. |
| 2007/0042997 A1 | 2/2007 | Itai et al. |
| 2008/0090779 A1 | 4/2008 | Muto et al. |
| 2008/0249071 A1 | 10/2008 | Muto et al. |
| 2008/0311074 A1 | 12/2008 | Muto et al. |
| 2008/0318956 A1 | 12/2008 | Muto et al. |

FOREIGN PATENT DOCUMENTS

| | | |
|---|---|---|
| DE | 996074 | 6/1965 |
| EP | 0081782 | 6/1983 |
| EP | 0198456 | 10/1986 |
| EP | 0221211 | 5/1987 |
| EP | 0221346 | 5/1987 |
| EP | 0317991 | 5/1989 |
| EP | 0452873 | 10/1991 |
| EP | 0483881 | 5/1992 |
| EP | 0551849 | 7/1993 |
| EP | 0931544 | 7/1999 |
| EP | 1008346 | 6/2000 |
| EP | 1018514 | 12/2000 |
| EP | 1088819 | 4/2001 |
| EP | 1113000 | 4/2001 |
| EP | 1205478 | 5/2002 |
| EP | 1219596 | 7/2002 |
| EP | 1344525 | 9/2003 |
| EP | 1352650 | 10/2003 |
| EP | 1510210 | 3/2005 |
| EP | 1512396 | 3/2005 |
| EP | 1514544 | 3/2005 |
| EP | 1535609 | 6/2005 |
| EP | 1535610 | 6/2005 |
| EP | 15335610 | 6/2005 |
| EP | 1555018 | 7/2005 |
| FR | 1481713 | 6/1966 |
| GB | 996074 | 6/1965 |
| GB | 1 079 177 | 8/1967 |
| GB | 1099865 | 7/1969 |
| GB | 2031410 | 4/1980 |
| JP | 37 000225 | 1/1962 |
| JP | 52-110835 | 9/1977 |
| JP | 62-30780 | 2/1987 |
| JP | 62-081359 | 4/1987 |
| JP | 63-104912 | 5/1988 |
| JP | 10-87491 | 9/1989 |
| JP | 2-138260 | 5/1990 |
| JP | 4-217916 | 8/1992 |
| JP | 4-217981 | 8/1992 |
| JP | 6-009476 | 1/1994 |
| JP | 62-99329 | 10/1994 |
| JP | 8-175990 | 7/1996 |
| JP | 9-227561 | 2/1997 |
| JP | 97/09315 | 3/1997 |
| JP | 9-169747 | 6/1997 |
| JP | 10-45738 | 2/1998 |
| JP | 11-21225 | 1/1999 |
| JP | 11-021243 | 1/1999 |
| JP | 11-217361 | 8/1999 |
| JP | 110512399 | 10/1999 |
| JP | 2000-80041 | 3/2000 |
| JP | 2000-169479 | 6/2000 |
| JP | 2001-114768 | 1/2001 |
| JP | 2001-522834 | 11/2001 |
| JP | 2002-506072 | 2/2002 |
| JP | 2004-501146 | 1/2004 |
| WO | 93/24115 | 12/1993 |
| WO | 96/17832 | 6/1996 |
| WO | 98/20864 | 5/1998 |
| WO | 98/32017 | 7/1998 |
| WO | 99/24404 | 5/1999 |
| WO | 99/40907 | 8/1999 |
| WO | 99/46236 | 9/1999 |
| WO | 99/46244 | 9/1999 |
| WO | 99/46267 | 9/1999 |
| WO | 99/55663 | 11/1999 |
| WO | 99/65449 | 12/1999 |
| WO | 00/03991 | 1/2000 |
| WO | 00/05234 | 5/2000 |
| WO | 00/35442 | 6/2000 |
| WO | 01/00213 | 1/2001 |
| WO | 01/10865 | 2/2001 |
| WO | 01/12588 | 2/2001 |
| WO | 01/44217 | 6/2001 |
| WO | 01/68648 | 9/2001 |
| WO | 01/98290 | 12/2001 |
| WO | 02/16633 | 2/2002 |
| WO | 02/076918 | 3/2002 |
| WO | 02/28819 | 4/2002 |
| WO | 02/49632 | 6/2002 |
| WO | 02/067919 | 9/2002 |
| WO | 02/076926 | 10/2002 |
| WO | 1314712 | 5/2003 |
| WO | 02/051397 | 7/2003 |
| WO | 03/103647 | 12/2003 |
| WO | 03/103648 | 12/2003 |
| WO | 03/103654 | 12/2003 |
| WO | 03/103655 | 12/2003 |
| WO | 03/103656 | 12/2003 |
| WO | 03/103657 | 12/2003 |
| WO | 03/103658 | 12/2003 |
| WO | 03/103665 | 12/2003 |
| WO | 2004/006906 | 1/2004 |
| WO | 2005/007151 | 1/2005 |
| WO | 1535609 | 6/2005 |

OTHER PUBLICATIONS

Waisser, et al., "Archiv der Pharmazie," 1998, vol. 331, No. 1, p. 3-6.
Inaba, et al., "Chemical and Pharmaceutical Bulletin," 2000, vol. 48, p. 131-139.
Yamamoto, et al., "Chemical and Pharmaceutical Bulletin," 1996, vol. 44, p. 734-745.
Hunt, et al., "The Journal of the Chemical Society," 1956, p. 3099-3107.
Zwaagstra, et al., "European The Journal of Medicinal Chemistry," 1996, vol. 31, p. 861-874.
Sharanin, et al., "Zhournal Organicheskoi Khimii: Russian The Journal of Organic Chemistry," 1980, vol. 16, p. 2185-2188.
South, et al., "The Journal of Heterocyclic Chemistry," 1991, vol. 28, p. 1017-1024.
Tajika, "Yakugaku Zasshi: The Journal of the Pharmaceutical Society of Japan," 1961, vol. 81, p. 1456-1459, together with partial English language translation of the same.
Okamiya, "Nihon Kagaku Zasshi," 1962, vol. 83, p. 209-211, together with partial English language translation of the same.
Yura, et al., "Chemical and Pharmaceutical Bulletin," 1962, vol. 10, p. 376-382.
Diez-Barra, et al., "Tetrahedron," 1997, vol. 53, No. 33, p. 11437-11448.
Djuric, et al., "The Journal of Medicinal Chemistry," 2000, vol. 43, No. 16, p. 2975-2981.
English language Abstract of JP 2000-80041.
English language Abstract of JP 9-169747.
English language Abstract of JP 63-104912.
English language Abstract of JP 11-21243.

Aisen, "Journal of Pain and Symptom Management," 2002, vol. 23, No. 4, p. S35-40.
Baud, et al., "Trends in Cell Biology," 2001, vol. 11, No. 9, p. 372-377.
Clark, et al., "Nucleic Acids Research," 1986, vol. 14, No. 20, p. 7897-7914.
Daidone, et al., "Farmaco," 1989, vol. 44, No. 5, p. 465-473.
DiDonato, et al., "Nature," 1997, vol. 388, p. 548-554.
Dou, et al., "Proceedings of The National Academy of Sciences of the United States of America," 2003, vol. 100, No. 2, p. 721-726.
Dumas, et al., "Bioorganic and Medicinal Chemistry Letters," 1999, vol. 9, No. 17, p. 2531-2536.
Eldar-Finkelman, "Trends of Molecular Medicine," 2002, vol. 8, No. 3, p. 126-132.
Frame, et al., "The Biochemical Journal," 2001, vol. 359, No. PTI, p. 1-16.
Hill, et al., "Cell," 1993, vol. 73, No. 2, p. 395-406.
Hoshi, et al., "Proceedings of the National Academy of Sciences of the United States of America," 1996, vol. 93, No. 7, p. 2719-2723.
Hsi, et al., "The Journal of Organic Chemistry," 1972, vol. 37, No. 22, p. 3427-3431.
Ishige, et al., "Yakugaku Zasshi," 1999, vol. 119, No. 7, p. 510-518.
Kang, et al., "Neuroreport," 2001, vol. 12, No. 7, p. 1449-1452.
Karin, et al., "Proceedings of The National Academy of Science of the United States of America," 1998, vol. 95, No. 16, p. 9067-9069.
Karttunen, et al., "Proceedings of the National Academy of Sciences of United States of America," 1991, vol. 88, No. 9, p. 3972-3976.
Kaytor, et al., "Current Opinion of Neurobiology," 2002, vol. 12, No. 3, p. 275-278.
Klosa, "Journal fuer Praktische Chemie," 1964, vol. 25, No. 1-2, p. 48-55, together with English language Abstract(Chemical Abstract) of the same, col. 4022, paragraph 6-col. 4023.
Konta, et al., "The Journal of Biological Chemistry," 2001, vol. 276, No. 16, p. 12697-12701.
Kopp, et al., "Science," 1994, vol. 265, p. 956-959.
Ladva, et al., "Indian Journal of Chemistry, Section B," 1996, vol. 35B, No. 10, p. 1062-1066.
Lee, et al., "Proceedings of the National Academy of Science of the United States of America," 1998, vol. 95, No. 16, p. 9319-9324.
Madan et al., "Molecular Pharmacology", 2000, vol. 58, No. 3., pp. 526-534.
Mailliot, et al., "Annals of The New York Academy of Science," 2000, vol. 920, p. 107-114.
Manna, et al., "The Journal of Immunology," 1999, vol. 162, No. 4, p. 2095-2102.
Matsumoto, et al., "Bioorganic and Medicinal Chemistry Letters," 2000, vol. 10, No. 9, p. 865-869.
Mattson, et al., "The Journal of Clinical Investigation," 2001, vol. 107, No. 3, p. 247-254.
Mattson, et al., "Cell and Tissue Research," 2000, vol. 301, No. 1, p. 173-187.
Millet, et al., "The Journal of Biological Chemistry," 2000, vol. 275, No. 20, p. 15114-15121.
Mori, et al., "Yakugaku Zasshi," 1975, vol. 95, No. 12, p. 1477-1482, together with an English language abstract of the same.
Nedospasov et al., "Cold Spring Harbor Symposia on Quantitative Biology,"1986, vol. 51, No. 1, p. 611-624.
Noble, et al., "Neuron," 2003, vol. 38, No. 4, p. 555-565.
Ohsugi, et al., "Yakugaku Zasshi," 1976, vol. 96, No. 2, p. 165-169, together with an English language abstract of the same.
Okamoto, 18th Meeting of the Japanese Inflammatory Society, Symposium "Mechanism of Antirheumatic Pharmaceutical Composition and New Development," Tokyo, 2000 Presentation Abstract p. 57, with English translation.
Palanki, et al., "Current Medicinal Chemistry," 2002, vol. 9, No. 2, p. 219-227.
Phlel, et al., "Nature," 2003, vol. 423, No. 6938, p. 435-439.
Piu, et al., "Molecular and Cellular Biology," 2001, vol. 21, No. 9, p. 3012-3024.
Régnier, et al., "Cell," 1997, vol. 90, No. 2, p. 373-383.
Robert-Piessard, et al., "Pharmaceutical Science," 1997, vol. 3, No. 5/6, p. 295-299.
Sato, et al., "The Journal of Biological Chemistry," 2002, vol. 277, No. 44, p. 42060-42065.
Scheinman, et al., "Science," 1995, vol. 270, p. 283-286.
Sullivan, et al., "The Journal of Medicinal Chemistry," 1998, vol. 41, No. 4, p. 413-419.
Umezawa, "Surgery Frontier," 2002, vol. 9, No. 2, p. 88-91, together with English language translation of the same.
Upadhyay, et al., "Indian Journal of Heterocyclic Chemistry," 1991, vol. 1, No. 2, p. 71-74.
Verma, et al., "Genes and Development" 1995, vol. 9 No. 22, p. 2723-2735.
Wajant, "Cellular Signaling," 2001, vol. 13, No. 6, p. 389-400.
West, et al., "Analytical Biochemistry," 1990, vol. 190, No. 2, p. 254-258.
Won, et al., "Neuroscience," 1999, vol. 94, No. 1, p. 83-91.
Woronicz, et al., "Science," 1997, vol. 278, p. 866-869.
Xu, et al., "The Journal of Neuroscience," 2001, vol. 21, No. 1, RC118, 5 pages.
Yamamoto, et al., "The Journal of Clinical Investigation," 2001, vol. 107, No. 2, p. 135-142.
Yin, et al., "Cell," 1998, vol. 93, No. 5, p. 875-884.
Yin, et al., "Nature," 1998, vol. 396, p. 77-80.
Zandi, et al., "Cell," 1997, vol. 91, No. 2, p. 243-252.
English language Abstract of JP 10-45738.
English language Abstract of JP9-227561.
English language Abstract of JP 10-87491.
English language Abstract of JP 11-217361.
English language Abstract of JP 8-175990.
English language Abstract of JP 4-217916.
English language Abstract of JP 62-30780.
English language Abstract of JP 2000-169479.
English language Abstract of JP 52-110835.
English Language abstract of JP 2002-506072.
English Language abstract of JP 62-81359.
English Language abstract of JP 2-138260.
U.S. Appl. No. 10/433,619, to Muto et al.
U.S. Appl. No. 10/515,341, to Muto et al.
U.S. Appl. No. 10/515,343, to Muto et al.
U.S. Appl. No. 10/515,342, to Muto et al.
U.S. Appl. No. 10/515,294, to Muto et al.
U.S. Appl. No. 10/516,622, to Muto et al.
U.S. Appl. No. 10/516,292, to Muto et al.
U.S. Appl. No. 10/516,293, to Muto et al.
English Language Translation of JP 37-225, Jan. 23, 1962.
English language Abstract of JP 11-21225.
Berking, et al., "American Journal of Pathology," 2001, vol. 158, No. 3, pp. 943-953.
Singh, et al., "Histology and Histopathology," 2000, vol. 15, pp. 843-849.
Recio, et al., "Cancer Research," 2002, vol. 62, No. 22, pp. 6724-6730.
Caplus Abstract of JP 37000225, Jan. 23, 1962.
Matsuzaki, et al., "Amer. J. Reproductive Immunol.," 1986, vol. 40, p. 291-294.
Uchiide, et al., "Nikkei Medical," 2002, No. 415, p. 28, with English translation.
Uchiide, et al., "Fertility and Sterility," 2002, vol. 78, No. 4, p. 782-786.
Chegini, "Frontiers in Bioscience," 2002, vol. 7, p. e91-115.
English language abstract of JP 37 000 225, 1962.
Extended European Search Report for EP 07 01 5427, Jul. 29, 2009.
Database Crossfire Beilstein XP002536489 (Abstract), Database Accession Nos. 2818733 and 2819714, 1964.
Database Crossfire Beilstein XP002536490 (Abstract), Database Accession No. 2698830, 1965.
Database Crossfire Beilstein XP002536491 (Abstract), Database Accession No. 3372658, 1959.

* cited by examiner

ANTIALLERGIC AGENTS

CROSS-REFERENCE TO RELATED APPLICATIONS

The present application is a divisional application of U.S. application Ser. No. 10/515,623 filed Jun. 20, 2005 now abandoned, which is incorporated by reference herein in its entirety, and which is a National Stage Application of International Application No. PCT/JP03/07120, filed Jun. 5, 2003, which claims priority under the Paris Convention from Japanese Patent Application No. 2002-165148, filed Jun. 6, 2002.

FIELD OF INVENTION

The present invention relates to pharmaceutical compositions effective for preventive and/or therapeutic treatment of allergic diseases such as pollinosis, bronchial asthma, atopic dermatitis, urticaria; endometriosis, and hysteromyoma.

BACKGROUND ART

Allergic diseases are understood to be caused by production of IgE by an antigen stimulation invaded in a body, and successive release of various chemical mediators such as inflammatory cytokine, histamine, leukotriene and the like by a degranulation from an activated mast cell stimulated by a complex of the antigen and IgE, thereby constriction of airway, accentuation of vascular permeability, inflammation of skin, bronchi and the like are induced. Accordingly, antiallergic agents are understood mainly as drugs inhibiting allergic reaction type I and successively induced allergic inflammation, particularly as drugs inhibiting the production and release of the mediators from mast cells, or those as being antagonists against the aforementioned actions. At present, steroids, antihistaminic drugs, suppressants or inhibitors of the release of mediators and the like have been used as antiallergic agents. Although steroids are very effective drugs, they have a problem of side effects. Antihistaminic drugs are only for symptomatic therapies and fail to achieve radical therapy. Suppressants or inhibitors of the release of mediators are considered to have a high effectiveness. However, some of them lack immediate effectiveness or have central side effects. Accordingly, the antiallergic drugs currently available are not fully satisfactory as they are.

Patients with endometriosis are increasing in recent years, and currently, 10 to 14% of females are considered to be suffered from the disease. Endometriosis has been focused as a cause of sterility, as well as the disease lowers the quality of life of patients with severe pains during menstruation and coitus. For a treatment of the disease, a therapy by using a hormone drug has been currently applied as a pseudo menopausal therapy. However, the aforementioned therapy induces strong side effects, and it also has a risk of causing osteoporosis during a long-term administration. Therefore, at present, a drug or a method for treatment with safety and high efficacy is not available.

In recent years, it was found that mast cells exist apparently with high density in the lesion of endometriosis (American Journal of Reproductive Immunology (New York: 1998), (Denmark), Vol. 40, No. 4, p. 291-294), and that mast cells are activated to lead degranulation (Nikkei Medical, 2002, No. 415, p. 28; Fertility and Sterility, (USA), 2002, Vol. 78, No. 4, p. 782-786). Furthermore, a relation between endometriosis and allergy is strongly suggested, because interstitial hyperplasia, which is a major step of infiltration and lesion of mast cells, is significantly inhibited by the administration of a leukotriene antagonist having antiallergic action to an endometriosis model rat (Nikkei Medical, 2002, No. 415, p. 28; Fertility and Sterility, (USA), 2002, Vol. 78, No. 4, p. 782-786).

Therefore, an antiallergic drug, which strongly inhibits activation of mast cells and can be used as a therapeutic agent for radical treatment of allergic diseases, is usable as an effective therapeutic agent for endometriosis.

45% of patients with endometriosis are suffered from hysteromyoma, which suggests a relation of hysteromyoma and allergy in the same manner as endometriosis. Accordingly, it is highly probable that an antiallergic agent, which can be used as a therapeutic agent for radical treatment of allergic diseases, is useful as a therapeutic agent for hysteromyoma.

N-phenylsalicylamide derivatives are disclosed as a plant growth inhibitor in the specification of U.S. Pat. No. 4,358,443. As medicaments, said derivatives are disclosed as anti-inflammatory agents in the specification of European Patent No. 0,221,211, Japanese Patent Unexamined Publication (KOKAI) No. (Sho) 62-99329, and the specification of U.S. Pat. No. 6,117,859. Furthermore, they are disclosed as NF-κB inhibitors in the pamphlets of International Publication WO99/65499, International Publication WO02/49632, and International Publication WO02/076918, and as inhibitors against the production of cytokines in the pamphlet of International Publication WO02/051397.

DISCLOSURE OF THE INVENTION

An object of the present invention is to provide medicaments that enable radical preventive and/or therapeutic treatment of allergy by an inhibition of allergic reactions. To achieve the aforementioned object, the inventors of the present invention conducted various researches on the antiallergic actions of salicylamide derivatives which are generally believed to have low toxicity. As a result, they found that N-substituted salicylamide derivatives, particularly N-arylsalicylamide derivatives, specifically N-phenylsalicylamide derivatives wherein aniline moiety is substituted in both of 2- and 5-positions or in both of 3- and 5-positions, and N-thiazol-2-yl-salicylamide derivatives wherein thiazole ring is substituted in both of 4- and 5-positions have extremely superior activity in inhibitory action against the proliferation of mast cells, inhibitory action against the degranulation from mast cells by antigen and IgE stimulation, and inhibitory action against the production of IgE from activated B cells, and that radical preventive and/or therapeutic treatment of allergic diseases can be achieved. The inventors also conducted researches on hydroxyaryl derivatives which are analogous compounds thereof. The present invention was achieved on the basis of these findings.

The present invention thus provides:

(1) A medicament for preventive and/or therapeutic treatment of allergic diseases and/or endometriosis and/or hysteromyoma which comprises as an active ingredient a substance selected from the group consisting of a compound represented by the following general formula (I) and a pharmacologically acceptable salt thereof, and a hydrate thereof and a solvate thereof:

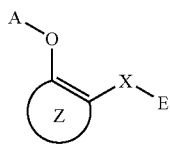

(I)

wherein X represents a connecting group whose number of atoms in a main chain is 2 to 5 (said connecting group may be substituted), A represents hydrogen atom or acetyl group, E represents an aryl group which may be substituted or a heteroaryl group which may be substituted, ring Z represents an arene which may have one or more substitutents in addition to the group represented by formula —O-A wherein A has the same meaning as that defined above and the group represented by formula —X-E wherein each of X and E has the same meaning as that defined above, or a heteroarene which may have one or more substitutents in addition to the group represented by formula —O-A wherein A has the same meaning as that defined above and the group represented by formula —X-E wherein each of X and E has the same meaning as that defined above.

Examples of preferred medicaments provided by the present invention include:

(2) the aforementioned medicament which comprises as an active ingredient a substance selected from the group consisting of the compound and a pharmacologically acceptable salt thereof, and a hydrate thereof and a solvate thereof, wherein X is a group selected from the following connecting group α (said group may be substituted):

[Connecting group α] The groups of the following formulas:

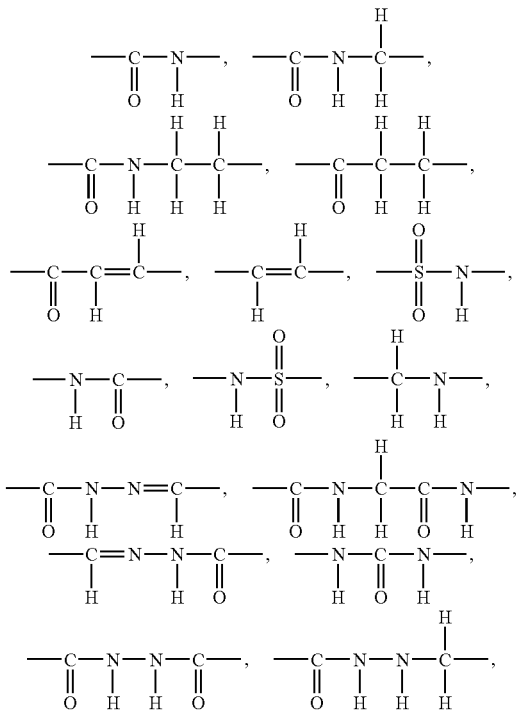

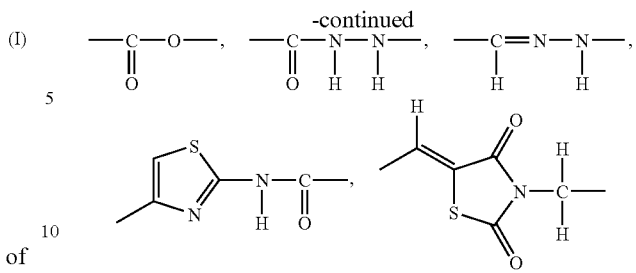

wherein a bond at the left end binds to ring Z and a bond at the right end binds to E;

(3) the aforementioned medicament which comprises as an active ingredient a substance selected from the group consisting of the compound and a pharmacologically acceptable salt thereof, and a hydrate thereof and a solvate thereof, wherein X is a group represented by the following formula (said group may be substituted):

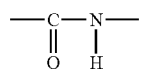

wherein a bond at the left end binds to ring Z and a bond at the right end binds to E;

(4) the aforementioned medicament which comprises as an active ingredient a substance selected from the group consisting of the compound and a pharmacologically acceptable salt thereof, and a hydrate thereof and a solvate thereof, wherein A is a hydrogen atom;

(5) the aforementioned medicament which comprises as an active ingredient a substance selected from the group consisting of the compound and a pharmacologically acceptable salt thereof, and a hydrate thereof and a solvate thereof, wherein ring Z is a $C_6$ to $C_{10}$ arene which may have one or more substitutents in addition to the group represented by formula —O-A wherein A has the same meaning as that defined in the general formula (I) and the group represented by formula —X-E wherein each of X and E has the same meaning as that defined in the general formula (I), or a 5 to 13-membered heteroarene which may have one or more substitutents in addition to the group represented by formula —O-A wherein A has the same meaning as that defined in the general formula (I) and the group represented by formula —X-E wherein each of X and E has the same meaning as that defined in the general formula (I);

(6) the aforementioned medicament which comprises as an active ingredient a substance selected from the group consisting of the compound and a pharmacologically acceptable salt thereof, and a hydrate thereof and a solvate thereof, wherein ring Z is a ring selected from the following ring group β:

[Ring Group β] benzene ring, naphthalene ring, thiophene ring, pyridine ring, indole ring, quinoxaline ring, and carbazole ring wherein said ring may have one or more substitutents in addition to the group represented by formula —O-A wherein A has the same meaning as that defined in the general formula (I) and the group represented by formula —X-E wherein each of X and E has the same meaning as that defined in the general formula (I);

(7) the aforementioned medicament which comprises as an active ingredient a substance selected from the group consisting of the compound and a pharmacologically acceptable salt thereof, and a hydrate thereof and a solvate thereof, wherein ring Z is a benzene ring which may have one or more substitutents in addition to the group represented by formula —O-A wherein A has the same meaning as that defined in the general formula (I) and the group represented by formula —X-E wherein each of X and E has the same meaning as that defined in the general formula (I);

(8) the aforementioned medicament which comprises as an active ingredient a substance selected from the group consisting of the compound and a pharmacologically acceptable salt thereof, and a hydrate thereof and a solvate thereof, wherein ring Z is a benzene ring which is substituted with halogen atom(s) in addition to the group represented by formula —O-A wherein A has the same meaning as that defined in the general formula (I) and the group represented by formula —X-E wherein each of X and E has the same meaning as that defined in the general formula (I);

(9) the aforementioned medicament which comprises as an active ingredient a substance selected from the group consisting of the compound and a pharmacologically acceptable salt thereof, and a hydrate thereof and a solvate thereof, wherein ring Z is a naphthalene ring which may have one or more substitutents in addition to the group represented by formula —O-A wherein A has the same meaning as that defined in the general formula (I) and the group represented by formula —X-E wherein each of X and E has the same meaning as that defined in the general formula (I);

(10) the aforementioned medicament which comprises as an active ingredient a substance selected from the group consisting of the compound and a pharmacologically acceptable salt thereof, and a hydrate thereof and a solvate thereof, wherein E is a $C_6$ to $C_{10}$ aryl group which may be substituted or a 5 to 13-membered heteroaryl group which may be substituted;

(11) the aforementioned medicament which comprises as an active ingredient a substance selected from the group consisting of the compound and a pharmacologically acceptable salt thereof, and a hydrate thereof and a solvate thereof, wherein E is a phenyl group which may be substituted;

(12) the aforementioned medicament which comprises as an active ingredient a substance selected from the group consisting of the compound and a pharmacologically acceptable salt thereof, and a hydrate thereof and a solvate thereof, wherein E is 3,5-bis(trifluoromethyl)phenyl group;

(13) the aforementioned medicament which comprises as an active ingredient a substance selected from the group consisting of the compound and a pharmacologically acceptable salt thereof, and a hydrate thereof and a solvate thereof, wherein E is a 5-membered heteroaryl group which may be substituted.

From another aspect, the present invention provides use of each of the aforementioned substances for manufacture of the medicament according to the aforementioned (1) to (13).

The present invention further provides a method for preventive and/or therapeutic treatment of allergic diseases and/or endometriosis and/or hysteromyoma in a mammal including a human, which comprises the step of administering preventively and/or therapeutically effective amount of the aforementioned substances to a mammal including a human.

The present invention further provides:
(1) a compound represented by the general formula (I-1) or a salt thereof, or a hydrate thereof or a solvate thereof:

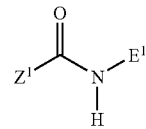

(I-1)

wherein $Z^1$ represents 2-hydroxyphenyl group which may be substituted in the 5-position or 2-acetoxyphenyl group which may be substituted in the 5-position, and $E^1$ represents a phenyl group which may be substituted.

Preferably, provided is:
(2) the compound or a salt thereof, or a hydrate thereof or a solvate thereof, wherein $E^1$ is 2,5-bis(trifluoromethyl)phenyl group or 3,5-bis(trifluoromethyl)phenyl group, except that the following compounds are excluded:
N-[3,5-bis(trifluoromethyl)phenyl]-2-hydroxybenzamide,
N-[3,5-bis(trifluoromethyl)phenyl]-5-chloro-2-hydroxybenzamide,
N-[3,5-bis(trifluoromethyl)phenyl]-5-bromo-2-hydroxybenzamide,
N-[3,5-bis(trifluoromethyl)phenyl]-2-hydroxy-5-iodobenzamide, and
N-[3,5-bis(trifluoromethyl)phenyl]-2-hydroxy-5-nitrobenzamide.

More preferably, provided is:
(3) the compound or a salt thereof, or a hydrate thereof or a solvate thereof, wherein $Z^1$ is 2-hydroxyphenyl group which is substituted with a halogen atom in the 5-position or 2-acetoxyphenyl group which is substituted with a halogen atom in the 5-position.

Moreover, the present invention provides:
(1) a compound represented by the general formula (I-2) or a salt thereof, or a hydrate thereof or a solvate thereof:

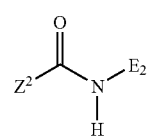

(I-2)

wherein $Z^2$ represents 2-hydroxyphenyl group which may be substituted in the 5-position or 2-acetoxyphenyl group which may be substituted in the 5-position,
$E^2$ represents a 2,5-di-substituted phenyl group wherein one of said substitutents is trifluoromethyl group or a 3,5-di-substituted phenyl group wherein one of said substitutents is trifluoromethyl group, provided that the following compounds are excluded:
5-chloro-N-[5-chloro-3-(trifluoromethyl)phenyl]-2-hydroxybenzamide,
5-fluoro-2-hydroxy-N-[2-(2,2,2-trifluoroethoxy)-5-(trifluoromethyl)phenyl]benzamide,
5-fluoro-2-hydroxy-N-[2-(6,6,6-trifluorohexyloxy)-5-(trifluoromethyl)phenyl]-benzamide,
5-chloro-N-[2-(4-chlorophenoxy)-5-(trifluoromethyl)phenyl]-2-hydroxybenzamide,
5-chloro-2-hydroxy-N-[2-(4-methylphenoxy)-5-(trifluoromethyl)phenyl]benzamide, 5-chloro-N-[2-(4-chlorophenyl)sulfanyl-5-(trifluoromethyl) phenyl]-2-hydroxybenzamide,
5-chloro-2-hydroxy-N-[2-(1-naphthyloxy)-5-(trifluoromethyl)phenyl]benzamide, and
5-chloro-2-hydroxy-N-[2-(2-naphthyloxy)-5-(trifluoromethyl)phenyl]benzamide.

Preferably, provided is:
(2) the compound or a salt thereof, or a hydrate thereof or a solvate thereof, wherein $Z^2$ is 2-hydroxyphenyl group which is substituted with a halogen atom in the 5-position or 2-acetoxyphenyl group which is substituted with a halogen atom in the 5-position.

Moreover, the present invention provides:
(1) a compound represented by the general formula (I-3) or a salt thereof, or a hydrate thereof or a solvate thereof:

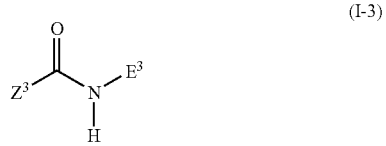

(I-3)

wherein $Z^3$ represents 2-hydroxyphenyl group which may be substituted in the 5-position or 2-acetoxyphenyl group which may be substituted in the 5-position,
$E^3$ represents a group represented by the following formula:

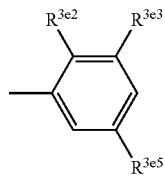

wherein one of $R^{3e2}$ and $R^{3e3}$ represents hydrogen atom and the other represents a hydrocarbon group which may be substituted or hydroxyl group which may be substituted, and
$R^{3e5}$ represents a $C_2$ to $C_6$ hydrocarbon group which may be substituted.

Preferably, provided is:
(2) the compound or a salt thereof, or a hydrate thereof or a solvate thereof, wherein $Z^3$ is 2-hydroxyphenyl group which is substituted with a halogen atom in the 5-position or 2-acetoxyphenyl group which is substituted with a halogen atom in the 5-position.

The present invention also provides:
(1) a compound represented by the general formula (I-4) or a salt thereof, or a hydrate thereof or a solvate thereof:

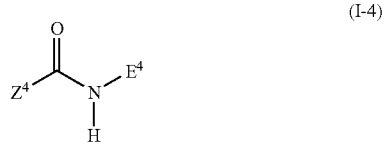

(I-4)

wherein $Z^4$ represents 2-hydroxyphenyl group which may be substituted in the 5-position or 2-acetoxyphenyl group which may be substituted in the 5-position,
$E^4$ represents a group represented by the following formula:

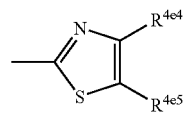

wherein $R^{4e4}$ represents a hydrocarbon group which may be substituted,
$R^{4e5}$ represents a halogen atom, cyano group, an acyl group which may be substituted, or a heterocyclic group which may be substituted.

Preferably, provided is:
(2) the compound or a salt thereof, or a hydrate thereof or a solvate thereof, wherein $Z^4$ is 2-hydroxyphenyl group which is substituted with a halogen atom in the 5-position or 2-acetoxyphenyl group which is substituted with a halogen atom in the 5-position.

BEST MODE FOR CARRYING OUT THE INVENTION

Figure 1:
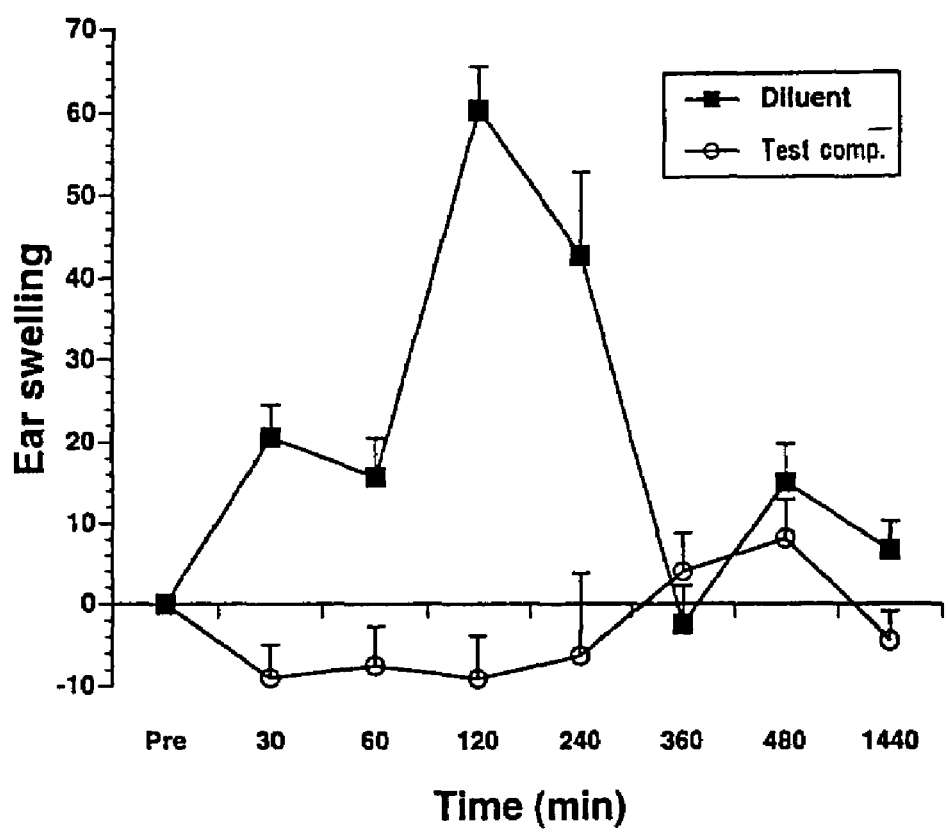
FIG. 1 shows inhibitory effect of the medicament of the present invention (compound No. 50) against immediate type allergy.

Reference to the disclosure of the pamphlet of International Publication WO02/49632 is useful for better understanding of the present invention. The entire disclosure of the aforementioned pamphlet of International Publication WO02/49632 is incorporated by reference in the disclosures of the present specification.

The terms used in the present specification have the following meanings.

As the halogen atom, any of fluorine atom, chlorine atom, bromine atom, or iodine atom may be used unless otherwise specifically referred to.

Examples of the hydrocarbon group include, for example, an aliphatic hydrocarbon group, an aryl group, an arylene group, an aralkyl group, a bridged cyclic hydrocarbon group, a spiro cyclic hydrocarbon group, and a terpene hydrocarbon.

Examples of the aliphatic hydrocarbon group include, for example, alkyl group, alkenyl group, alkynyl group, alkylene group, alkenylene group, alkylidene group and the like which are straight chain or branched chain monovalent or bivalent acyclic hydrocarbon groups; cycloalkyl group, cycloalkenyl group, cycloalkanedienyl group, cycloalkyl-alkyl group, cycloalkylene group, and cycloalkenylene group, which are saturated or unsaturated monovalent or bivalent alicyclic hydrocarbon groups.

Examples of the alkyl group include, for example, methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-ethylbutyl, 1-ethyl-1-methylpropyl, n-heptyl, n-octyl, n-nonyl, n-decyl, n-undecyl, n-dodecyl, n-tridecyl, n-tetradecyl, and n-pentadecyl, which are $C_1$ to $C_{15}$ straight chain or branched chain alkyl groups.

Examples of the alkenyl group include, for example, vinyl, prop-1-en-1-yl, allyl, isopropenyl, but-1-en-1-yl, but-2-en-1-yl, but-3-en-1-yl, 2-methylprop-2-en-1-yl, 1-methylprop-2-en-1-yl, pent-1-en-1-yl, pent-2-en-1-yl, pent-3-en-1-yl, pent-4-en-1-yl, 3-methylbut-2-en-1-yl, 3-methylbut-3-en-1-yl, hex-1-en-1-yl, hex-2-en-1-yl, hex-3-en-1-yl, hex-4-en-1-yl, hex-5-en-1-yl, 4-methylpent-3-en-1-yl, 4-methylpent-3-en-1-yl, hept-1-en-1-yl, hept-6-en-1-yl, oct-1-en-1-yl, oct-7-en-1-yl, non-1-en-1-yl, non-8-en-1-yl, dec-1-en-1-yl, dec-9-en-1-yl, undec-1-en-1-yl, undec-10-en-1-yl, dodec-1-en-1-yl, dodec-11-en-1-yl, tridec-1-en-1-yl, tridec-12-en-1-yl, tetradec-1-en-1-yl, tetradec-13-en-1-yl, pentadec-1-en-1-yl, and pentadec-14-en-1-yl, which are $C_2$ to $C_{15}$ straight chain or branched chain alkenyl groups.

Examples of the alkynyl group include, for example, ethynyl, prop-1-yn-1-yl, prop-2-yn-1-yl, but-1-yn-1-yl, but-3-yn-1-yl, 1-methylprop-2-yn-1-yl, pent-1-yn-1-yl, pent-4-yn-1-yl, hex-1-yn-1-yl, hex-5-yn-1-yl, hept-1-yn-1-yl, hept-6-yn-1-yl, oct-1-yn-1-yl, oct-7-yn-1-yl, non-1-yn-1-yl, non-8-yn-1-yl, dec-1-yn-1-yl, dec-9-yn-1-yl, undec-1-yn-1-yl, undec-10-yn-1-yl, dodec-1-yn-1-yl, dodec-11-yn-1-yl, tridec-1-yn-1-yl, tridec-12-yn-1-yl, tetradec-1-yn-1-yl, tetradec-13-yn-1-yl, pentadec-1-yn-1-yl, and pentadec-14-yn-1-yl, which are $C_2$ to $C_{15}$ straight chain or branched chain alkynyl groups.

Examples of the alkylene group include, for example, methylene, ethylene, ethane-1,1-diyl, propane-1,3-diyl, propane-1,2-diyl, propane-2,2-diyl, butane-1,4-diyl, pentane-1,5-diyl, hexane-1,6-diyl, and 1,1,4,4-tetramethylbutane-1,4-diyl group, which are $C_1$ to $C_8$ straight chain or branched chain alkylene groups.

Examples of the alkenylene group include, for example, ethene-1,2-diyl, propene-1,3-diyl, but-1-ene-1,4-diyl, but-2-ene-1,4-diyl, 2-methylpropene-1,3-diyl, pent-2-ene-1,5-diyl, and hex-3-ene-1,6-diyl, which are $C_1$ to $C_6$ straight chain or branched chain alkylene groups.

Examples of the alkylidene group include, for example, methylidene, ethylidene, propylidene, isopropylidene, butylidene, pentylidene, and hexylidene, which are $C_1$ to $C_6$ straight chain or branched chain alkylidene groups.

Examples of the cycloalkyl group include, for example, cyclopropyl, cyclobutyl, cyclopentyl, cyclohexyl, cycloheptyl, and cyclooctyl, which are $C_3$ to $C_8$ cycloalkyl groups.

The aforementioned cycloalkyl group may be fused with benzene ring, naphthalene ring and the like, and examples include, for example, 1-indanyl, 2-indanyl, 1,2,3,4-tetrahydronaphthalen-1-yl, and 1,2,3,4-tetrahydronaphthalen-2-yl.

Examples of the cycloalkenyl group include, for example, 2-cyclopropen-1-yl, 2-cyclobuten-1-yl, 2-cyclopenten-1-yl, 3-cyclopenten-1-yl, 2-cyclohexen-1-yl, 3-cyclohexen-1-yl, 1-cyclobuten-1-yl, and 1-cyclopenten-1-yl, which are $C_3$ to $C_6$ cycloalkenyl groups.

The aforementioned cycloalkenyl group may be fused with benzene ring, naphthalene ring and the like, and examples include, for example, 1-indanyl, 2-indanyl, 1,2,3,4-tetrahydronaphthalen-1-yl, 1,2,3,4-tetrahydronaphthalen-2-yl, 1-indenyl, and 2-indenyl.

Examples of the cycloalkanedienyl group include, for example, 2,4-cyclopentadien-1-yl, 2,4-cyclohexanedien-1-yl, and 2,5-cyclohexanedien-1-yl, which are $C_5$ to $C_6$ cycloalkanedienyl groups.

The aforementioned cycloalkanedienyl group may be fused with benzene ring, naphthalene ring and the like, and examples include, for example, 1-indenyl and 2-indenyl.

Examples of the cycloalkyl-alkyl group include the groups in which one hydrogen atom of the alkyl group is substituted with a cycloalkyl group, and include, for example, cyclopropylmethyl, 1-cyclopropylethyl, 2-cyclopropylethyl, 3-cyclopropylpropyl, 4-cyclopropylbutyl, 5-cyclopropylpentyl, 6-cyclopropylhexyl, cyclobutylmethyl, cyclopentylmethyl, cyclobutylmethyl, cyclopentylmethyl, cyclohexylmethyl, cyclohexylpropyl, cyclohexylbutyl, cycloheptylmethyl, cyclooctylmethyl, and 6-cyclooctylhexyl, which are $C_4$ to $C_{14}$ cycloalkyl-alkyl groups.

Examples of the cycloalkylene group include, for example, cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,1-diyl, cycloheptane-1,2-diyl, cyclooctane-1,1-diyl, and cyclooctane-1,2-diyl, which are $C_3$ to $C_8$ cycloalkylene groups.

Examples of the cycloalkenylene group include, for example, 2-cyclopropene-1,1-diyl, 2-cyclobutene-1,1-diyl, 2-cyclopentene-1,1-diyl, 3-cyclopentene-1,1-diyl, 2-cyclohexene-1,1-diyl, 2-cyclohexene-1,2-diyl, 2-cyclohexene-1,4-diyl, 3-cyclohexene-1,1-diyl, 1-cyclobutene-1,2-diyl, 1-cyclopentene-1,2-diyl, and 1-cyclohexene-1,2-diyl, which are $C_3$ to $C_6$ cycloalkenylene groups.

Examples of the aryl group include a monocyclic or a fused polycyclic aromatic hydrocarbon group, and include, for example, phenyl, 1-naphthyl, 2-naphthyl, anthryl, phenanthryl, and acenaphthylenyl, which are $C_6$ to $C_{14}$ aryl groups.

The aforementioned aryl group may be fused with the aforementioned $C_3$ to $C_8$ cycloalkyl group, $C_3$ to $C_6$ cycloalkenyl group, $C_5$ to $C_6$ cycloalkanedienyl group or the like, and examples include, for example, 4-indanyl, 5-indanyl, 1,2,3,4-tetrahydronaphthalen-5-yl, 1,2,3,4-tetrahydronaphthalen-6-yl, 3-acenaphthenyl, 4-acenaphthenyl, inden-4-yl, inden-5-yl, inden-6-yl, inden-7-yl, 4-phenalenyl, 5-phenalenyl, 6-phenalenyl, 7-phenalenyl, 8-phenalenyl, and 9-phenalenyl.

Examples of the arylene group include, for example, 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,4-diyl, naphthalene-2,5-diyl, naphthalene-2,6-diyl, naphthalene-2,7-diyl, naphthalene-2,8-diyl, and anthracene-1,4-diyl, which are $C_6$ to $C_{14}$ arylene groups.

Examples of the aralkyl group include the groups in which one hydrogen atom of the alkyl group is substituted with an aryl group, and include, for example, benzyl, 1-naphthylmethyl, 2-naphthylmethyl, anthracenylmethyl, phenanthrenylmethyl, acenaphthylenylmethyl, diphenylmethyl, 1-phenethyl, 2-phenethyl, 1-(1-naphthyl)ethyl, 1-(2-naphthyl)ethyl, 2-(1-naphthyl)ethyl, 2-(2-naphthyl)ethyl, 3-phenylpropyl, 3-(1-naphthyl)propyl, 3-(2-naphthyl)propyl, 4-phenylbutyl, 4-(1-naphthyl)butyl, 4-(2-naphthyl)butyl, 5-phenylpentyl, 5-(1-naphthyl)pentyl, 5-(2-naphthyl)pentyl, 6-phenylhexyl, 6-(1-naphthyl)hexyl, and 6-(2-naphthyl)hexyl, which are $C_7$ to $C_{16}$ aralkyl groups.

Examples of the bridged cyclic hydrocarbon group include, for example, bicyclo[2.1.0]pentyl, bicyclo[2.2.1]heptyl, bicyclo[2.2.1]octyl, and adamantyl.

Examples of the spiro cyclic hydrocarbon group include, for example, spiro[3.4]octyl, and spiro[4.5]deca-1,6-dienyl.

Examples of the terpene hydrocarbon include, for example, geranyl, neryl, linalyl, phytyl, menthyl, and bornyl.

Examples of the halogenated alkyl group include the groups in which one hydrogen atom of the alkyl group is substituted with a halogen atom, and include, for example, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, 2,2,2-trifluoroethyl, pentafluoroethyl, 3,3,3-trifluoropropyl, heptafluoropropyl, heptafluoroisopropyl, nonafluorobutyl, and perfluorohexyl, which are $C_1$ to $C_6$ straight chain or branched chain halogenated alkyl groups substituted with 1 to 13 halogen atoms.

Examples of the heterocyclic group include, for example, a monocyclic or a fused polycyclic hetero aryl group which comprises at least one atom of 1 to 3 kinds of hetero atoms selected from oxygen atom, sulfur atom, nitrogen atom and the like as ring-constituting atoms (ring forming atoms), and a monocyclic or a fused polycyclic non-aromatic heterocyclic group which comprises at least one atom of 1 to 3 kinds of hetero atoms selected from oxygen atom, sulfur atom, nitrogen atom and the like as ring-constituting atoms (ring forming atoms).

Examples of the monocyclic heteroaryl group include, for example, 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1-imidazolyl, 2-imidazolyl, 4-imidazolyl, 5-imidazolyl, 1-pyrazolyl, 3-pyrazolyl, 4-pyrazolyl, 5-pyrazolyl, (1,2,3-oxadiazol)-4-yl, (1,2,3-oxadiazol)-5-yl, (1,2,4-oxadiazol)-3-yl, (1,2,4-oxadiazol)-5-yl, (1,2,5-oxadiazol)-3-yl, (1,2,5-oxadiazol)-4-yl, (1,3,4-oxadiazol)-2-yl, (1,3,4-oxadiazol)-5-yl, furazanyl, (1,2,3-thiadiazol)-4-yl, (1,2,3-thiadiazol)-5-yl, (1,2,4-thiadiazol)-3-yl, (1,2,4-thiadiazol)-5-yl, (1,2,5-thiadiazol)-3-yl, (1,2,5-thiadiazol)-4-yl, (1,3,4-thiadiazolyl)-2-yl, (1,3,4-thiadiazolyl)-5-yl, (1H-1,2,3-triazol)-1-yl, (1H-1,2,3-triazol)-4-yl, (1H-1,2,3-triazol)-5-yl, (2H-1,2,3-triazol)-2-yl, (2H-1,2,3-triazol)-4-yl, (1H-1,2,4-triazol)-1-yl, (1H-1,2,4-triazol)-3-yl, (1H-1,2,4-triazol)-5-yl, (4H-1,2,4-triazol)-3-yl, (4H-1,2,4-triazol)-4-yl, (1H-tetrazol)-1-yl, (1H-tetrazol)-5-yl, (2H-tetrazol)-2-yl, (2H-tetrazol)-5-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, (1,2,3-triazin)-4-yl, (1,2,3-triazin)-5-yl, (1,2,4-triazin)-3-yl, (1,2,4-triazin)-5-yl, (1,2,4-triazin)-6-yl, (1,3,5-triazin)-2-yl, 1-azepinyl, 2-azepinyl, 3-azepinyl, 4-azepinyl, (1,4-oxazepin)-2-yl, (1,4-oxazepin)-3-yl, (1,4-oxazepin)-5-yl, (1,4-oxazepin)-6-yl, (1,4-oxazepin)-7-yl, (1,4-thiazepin)-2-yl, (1,4-thiazepin)-3-yl, (1,4-thiazepin)-5-yl, (1,4-thiazepin)-6-yl, and (1,4-thiazepin)-7-yl, which are 5 to 7-membered monocyclic heteroaryl groups.

Examples of the fused polycyclic heteroaryl group include, for example, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzo[b]thienyl, 3-benzo[b]thienyl, 4-benzo[b]thienyl, 5-benzo[b]thienyl, 6-benzo[b]thienyl, 7-benzo[b]thienyl, 1-benzo[c]thienyl, 4-benzo[c]thienyl, 5-benzo[c]thienyl, 1-indolyl, 1-indolyl, 2-indolyl, 3-indolyl, 4-indolyl, 5-indolyl, 6-indolyl, 7-indolyl, (2H-isoindol)-1-yl, (2H-isoindol)-2-yl, (2H-isoindol)-4-yl, (2H-isoindol)-5-yl, (1H-indazol)-1-yl, (1H-indazol)-3-yl, (1H-indazol)-4-yl, (1H-indazol)-5-yl, (1H-indazol)-6-yl, (1H-indazol)-7-yl, (2H-indazol)-1-yl, (2H-indazol)-2-yl, (2H-indazol)-4-yl, (2H-indazol)-5-yl, 2-benzoxazolyl, 2-benzoxazolyl, 4-benzoxazolyl, 5-benzoxazolyl, 6-benzoxazolyl, 7-benzoxazolyl, (1,2-benzisoxazol)-3-yl, (1,2-benzisoxazol)-4-yl, (1,2-benzisoxazol)-5-yl, (1,2-benzisoxazol)-6-yl, (1,2-benzisoxazol)-7-yl, (2,1-benzisoxazol)-3-yl, (2,1-benzisoxazol)-4-yl, (2,1-benzisoxazol)-5-yl, (2,1-benzisoxazol)-6-yl, (2,1-benzisoxazol)-7-yl, 2-benzothiazolyl, 4-benzothiazolyl, 5-benzothiazolyl, 6-benzothiazolyl, 7-benzothiazolyl, (1,2-benzisothiazol)-3-yl, (1,2-benzisothiazol)-4-yl, (1,2-benzisothiazol)-5-yl, (1,2-benzisothiazol)-6-yl, (1,2-benzisothiazol)-7-yl, (2,1-benzisothiazol)-3-yl, (2,1-benzisothiazol)-4-yl, (2,1-benzisothiazol)-5-yl, (2,1-benzisothiazol)-6-yl, (2,1-benzisothiazol)-7-yl, (1,2,3-benzoxadiazol)-4-yl, (1,2,3-benzoxadiazol)-5-yl, (1,2,3-benzoxadiazol)-6-yl, (1,2,3-benzoxadiazol)-7-yl, (2,1,3-benzoxadiazol)-4-yl, (2,1,3-benzoxadiazol)-5-yl, (1,2,3-benzothiadiazol)-4-yl, (1,2,3-benzothiadiazol)-5-yl, (1,2,3-benzothiadiazol)-6-yl, (1,2,3-benzothiadiazol)-7-yl, (2,1,3-benzothiadiazol)-4-yl, (2,1,3-benzothiadiazol)-5-yl, (1H-benzotriazol)-1-yl, (1H-benzotriazol)-4-yl, (1H-benzotriazol)-5-yl, (1H-benzotriazol)-6-yl, (1H-benzotriazol)-7-yl, (2H-benzotriazol)-2-yl, (2H-benzotriazol)-4-yl, (2H-benzotriazol)-5-yl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolinyl, 4-cinnolinyl, 5-cinnolinyl, 6-cinnolinyl, 7-cinnolinyl, 8-cinnolinyl, 2-quinazolinyl, 4-quinazolinyl, 5-quinazolinyl, 6-quinazolinyl, 7-quinazolinyl, 8-quinazolinyl, 2-quinoxalinyl, 5-quinoxalinyl, 6-quinoxalinyl, 1-phthalazinyl, 5-phthalazinyl, 6-phthalazinyl, 2-naphthyridinyl, 3-naphthyridinyl, 4-naphthyridinyl, 2-purinyl, 6-purinyl, 7-purinyl, 8-purinyl, 2-pteridinyl, 4-pteridinyl, 6-pteridinyl, 7-pteridinyl, 1-carbazolyl, 2-carbazolyl, 3-carbazolyl, 4-carbazolyl, 9-carbazolyl, 2-(α-carbolinyl), 3-(α-carbolinyl), 4-(α-carbolinyl), 5-(α-carbolinyl), 6-(α-carbolinyl), 7-(α-carbolinyl), 8-(α-carbolinyl), 9-(α-carbolinyl), 1-(β-carbolinyl), 3-(β-carbolinyl), 4-(β-carbolinyl), 5-(β-carbolinyl), 6-(β-carbolinyl), 7-(β-carbolinyl), 8-(β-carbolinyl), 9-(β-carbolinyl), 1-(γ-carbolinyl), 2-(γ-carbolinyl), 4-(γ-carbolinyl), 5-(γ-carbolinyl), 6-(γ-carbolinyl), 7-(γ-carbolinyl), 8-(γ-carbolinyl), 9-(γ-carbolinyl), 1-acridinyl, 2-acridinyl, 3-acridinyl, 4-acridinyl, 9-acridinyl, 1-phenoxazinyl, 2-phenoxazinyl, 3-phenoxazinyl, 4-phenoxazinyl, 10-phenoxazinyl, 1-phenothiazinyl, 2-phenothiazinyl, 3-phenothiazinyl, 4-phenothiazinyl, 10-phenothiazinyl, 1-phenazinyl, 2-phenazinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 2-phenanthrolinyl, 3-phenanthrolinyl, 4-phenanthrolinyl, 5-phenanthrolinyl, 6-phenanthrolinyl, 7-phenanthrolinyl, 8-phenanthrolinyl, 9-phenanthrolinyl, 10-phenanthrolinyl, 1-thianthrenyl, 2-thianthrenyl, 1-indolizinyl, 2-indolizinyl, 3-indolizinyl, 5-indolizinyl, 6-indolizinyl, 7-indolizinyl, 8-indolizinyl, 1-phenoxathiinyl, 2-phenoxathiinyl, 3-phenoxathiinyl, 4-phenoxathiinyl, thieno[2,3-b]furyl, pyrrolo[1,2-b]pyridazinyl, pyrazolo[1,5-a]pyridyl, imidazo[11,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-a]pyridazinyl, which are 8 to 14-membered fused polycyclic heteroaryl groups.

Examples of the monocyclic non-aromatic heterocyclic group include, for example, 1-aziridinyl, 1-azetidinyl, 1-pyrrolidinyl, 2-pyrrolidinyl, 3-pyrrolidinyl, 2-tetrahydrofuryl, 3-tetrahydrofuryl, thiolanyl, 1-imidazolidinyl, 2-imidazolidinyl, 4-imidazolidinyl, 1-pyrazolidinyl, 3-pyrazolidinyl, 4-pyrazolidinyl, 1-(2-pyrrolinyl), 1-(2-imidazolinyl), 2-(2-imidazolinyl), 1-(2-pyrazolinyl), 3-(2-pyrazolinyl), piperidino, 2-piperidinyl, 3-piperidinyl, 4-piperidinyl, 1-homopiperidinyl, 2-tetrahydropyranyl, morpholino, (thiomorpholin)-4-yl, 1-piperazinyl, and 1-homopiperazinyl, which are 3 to 7-membered saturated or unsaturated monocyclic non-aromatic heterocyclic groups.

Examples of the fused polycyclic non-aromatic heterocyclic group include, for example, 2-quinuclidinyl, 2-chromanyl, 3-chromanyl, 4-chromanyl, 5-chromanyl, 6-chromanyl, 7-chromanyl, 8-chromanyl, 1-isochromanyl, 3-isochromanyl, 4-isochromanyl, 5-isochromanyl, 6-isochromanyl, 7-isochromanyl, 8-isochromanyl, 2-thiochromanyl, 3-thiochromanyl, 4-thiochromanyl, 5-thiochromanyl, 6-thiochromanyl, 7-thiochromanyl, 8-thiochromanyl, 1-isothiochromanyl, 3-isothiochromanyl, 4-isothiochromanyl, 5-isothiochromanyl, 6-isothiochromanyl, 7-isothiochromanyl, 8-isothiochromanyl, 1-indolinyl, 2-indolinyl, 3-indolinyl, 4-indolinyl, 5-indolinyl, 6-indolinyl, 7-indolinyl, 1-isoindolinyl, 2-isoindolinyl, 4-isoindolinyl, 5-isoindolinyl, 2-(4H-chromenyl), 3-(4H-chromenyl), 4-(4H-chromenyl), 5-(4H-chromenyl), 6-(4H-chromenyl), 7-(4H-chromenyl), 8-(4H-chromenyl), 1-isochromenyl, 3-isochromenyl, 4-isochromenyl, 5-isochromenyl, 6-isochromenyl, 7-isochromenyl, 8-isochromenyl, 1-(1H-pyrrolidinyl), 2-(1H-pyrrolidinyl), 3-(1H-pyrrolidinyl), 5-(1H-pyrrolidinyl), 6-(1H-pyrrolidinyl), and 7-(1H-pyrrolidinyl), which are 8 to 10-membered saturated or unsaturated fused polycyclic non-aromatic heterocyclic groups.

Among the aforementioned heterocyclic groups, a monocyclic or a fused polycyclic hetero aryl groups which may have 1 to 3 kinds of hetero atoms selected from oxygen atom, sulfur atom, nitrogen atom and the like, in addition to the nitrogen atom that has the bond, as ring-constituting atoms (ring forming atoms), and a monocyclic or a fused polycyclic non-aromatic heterocyclic groups which may have 1 to 3 kinds of hetero atoms selected from oxygen atom, sulfur atom, nitrogen atom and the like, in addition to the nitrogen atom that has the bond, as ring-constituting atoms (ring forming atoms) are referred to as "cyclic amino group." Examples include, for example, 1-pyrrolidinyl, 1-imidazolidinyl, 1-pyrazolidinyl, 1-oxazolidinyl, 1-thiazolidinyl, piperidino, morpholino, 1-piperazinyl, thiomorpholin-4-yl, 1-homopiperidinyl, 1-homopiperazinyl, 2-pyrrolin-1-yl, 2-imidazolin-1-yl, 2-pyrazolin-1-yl, 1-indolinyl, 2-isoindolinyl, 1,2,3,4-tetrahydroquinolin-1-yl, 1,2,3,4-tetrahydroisoquinolin-2-yl, 1-pyrrolyl, 1-imidazolyl, 1-pyrazolyl, 1-indolyl, 1-indazolyl, and 2-isoindolyl.

The aforementioned cycloalkyl group, cycloalkenyl group, cycloalkanedienyl group, aryl group, cycloalkylene group, cycloalkenylene group, arylene group, bridged cyclic hydrocarbon group, spiro cyclic hydrocarbon group, and heterocyclic group are generically referred to as "cyclic group." Furthermore, among said cyclic groups, particularly, aryl group, arylene group, monocyclic heteroaryl group, and fused polycyclic heteroaryl group are generically referred to as "aromatic ring group."

Examples of the hydrocarbon-oxy group include the groups in which a hydrogen atom of the hydroxy group is substituted with a hydrocarbon group, and examples of the hydrocarbon include similar groups to the aforementioned hydrocarbon groups. Examples of the hydrocarbon-oxy group include, for example, alkoxy group (alkyl-oxy group), alkenyl-oxy group, alkynyl-oxy group, cycloalkyl-oxy group, cycloalkyl-alkyl-oxy group and the like, which are aliphatic hydrocarbon-oxy groups; aryl-oxy group; aralkyl-oxy group; and alkylene-dioxy group.

Examples of the alkoxy (alkyl-oxy group) include, for example, methoxy, ethoxy, n-propoxy, isopropoxy, n-butoxy, isobutoxy, sec-butoxy, tert-butoxy, n-pentyloxy, isopentyloxy, 2-methylbutoxy, 1-methylbutoxy, neopentyloxy, 1,2-dimethylpropoxy, 1-ethylpropoxy, n-hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, 1-ethylbutoxy, 1-ethyl-1-methylpropoxy, n-heptyloxy, n-octyloxy, n-nonyloxy, n-decyloxy, n-undecyloxy, n-dodecyloxy, n-tridecyloxy, n-tetradecyloxy, and n-pentadecyloxy, which are $C_1$ to $C_{15}$ straight chain or branched chain alkoxy groups.

Examples of the alkenyl-oxy group include, for example, vinyloxy, (prop-1-en-1-yl)oxy, allyloxy, isopropenyloxy, (but-1-en-1-yl)oxy, (but-2-en-1-yl)oxy, (but-3-en-1-yl)oxy, (2-methylprop-2-en-1-yl)oxy, (1-methylprop-2-en-1-yl)oxy, (pent-1-en-1-yl)oxy, (pent-2-en-1-yl)oxy, (pent-3-en-1-yl)oxy, (pent-4-en-1-yl)oxy, (3-methylbut-2-en-1-yl)oxy, (3-methylbut-3-en-1-yl)oxy, (hex-1-en-1-yl)oxy, (hex-2-en-1-yl)oxy, (hex-3-en-1-yl)oxy, (hex-4-en-1-yl)oxy, (hex-5-en-1-yl)oxy, (4-methylpent-3-en-1-yl)oxy, (4-methylpent-3-en-1-yl)oxy, (hept-1-en-1-yl)oxy, (hept-6-en-1-yl)oxy, (oct-1-en-1-yl)oxy, (oct-7-en-1-yl)oxy, (non-1-en-1-yl)oxy, (non-8-en-1-yl)oxy, (dec-1-en-1-yl)oxy, (dec-9-en-1-yl)oxy, (undec-1-en-1-yl)oxy, (undec-10-en-1-yl)oxy, (dodec-1-en-1-yl)oxy, (dodec-11-en-1-yl)oxy, (tridec-1-en-1-yl)oxy, (tridec-12-en-1-yl)oxy, (tetradec-1-en-1-yl)oxy, (tetradec-13-en-1-yl)oxy, (pentadec-1-en-1-yl)oxy, and (pentadec-14-en-1-yl)oxy, which are $C_2$ to $C_{15}$ straight chain or branched chain alkenyl-oxy groups.

Examples of the alkynyl-oxy group include, for example, ethynyloxy, (prop-1-yn-1-yl)oxy, (prop-2-yn-1-yl)oxy, (but-1-yn-1-yl)oxy, (but-3-yn-1-yl)oxy, (1-methylprop-2-yn-1-yl)oxy, (pent-1-yn-1-yl)oxy, (pent-4-yn-1-yl)oxy, (hex-1-yn-1-yl)oxy, (hex-5-yn-1-yl)oxy, (hept-1-yn-1-yl)oxy, (hept-6-yn-1-yl)oxy, (oct-1-yn-1-yl)oxy, (oct-7-yn-1-yl)oxy, (non-1-yn-1-yl)oxy, (non-8-yn-1-yl)oxy, (dec-1-yn-1-yl)oxy, (dec-9-yn-1-yl)oxy, (undec-1-yn-1-yl)oxy, (undec-10-yn-1-yl)oxy, (dodec-1-yn-1-yl)oxy, (dodec-11-yn-1-yl)oxy, (tridec-1-yn-1-yl)oxy, (tridec-12-yn-1-yl)oxy, (tetradec-1-yn-1-yl)oxy, (tetradec-13-yn-1-yl)oxy, (pentadec-1-yn-1-yl)oxy, and (pentadec-14-yn-1-yl)oxy, which are $C_2$ to $C_{15}$ straight chain or branched chain alkynyl-oxy groups.

Examples of the cycloalkyl-oxy group include, for example, cyclopropoxy, cyclobutoxy, cyclopentyloxy, cyclohexyloxy, cycloheptyloxy, and cyclooctyloxy, which are $C_3$ to $C_8$ cycloalkyl-oxy groups.

Examples of the cycloalkyl-alkyl-oxy group include, for example, cyclopropylmethoxy, 1-cyclopropylethoxy, 2-cyclopropylethoxy, 3-cyclopropylpropoxy, 4-cyclopropylbutoxy, 5-cyclopropylpentyloxy, 6-cyclopropylhexyloxy, cyclobutylmethoxy, cyclopentylmethoxy, cyclobutylmethoxy, cyclopentylmethoxy, cyclohexylmethoxy, 2-cyclohexylethoxy, 3-cyclohexylpropoxy, 4-cyclohexylbutoxy, cycloheptylmethoxy, cyclooctylmethoxy, and 6-cyclooctylhexyloxy, which are $C_4$ to $C_{14}$ cycloalkyl-alkyl-oxy groups.

Examples of the aryl-oxy group include, for example, phenoxy, 1-naphthyloxy, 2-naphthyloxy, anthryloxy, phenanthryloxy, and acenaphthylenyloxy, which are $C_6$ to $C_{14}$ aryl-oxy groups.

Examples of the aralkyl-oxy group include, for example, benzyloxy, 1-naphthylmethoxy, 2-naphthylmethoxy, anthracenylmethoxy, phenanthrenylmethoxy, acenaphthylenylmethoxy, diphenylmethoxy, 1-phenethyloxy, 2-phenethyloxy, 1-(1-naphthyl)ethoxy, 1-(2-naphthyl)ethoxy, 2-(1-naphthyl)ethoxy, 2-(2-naphthyl)ethoxy, 3-phenylpropoxy, 3-(1-naphthyl)propoxy, 3-(2-naphthyl)propoxy, 4-phenylbutoxy, 4-(1-naphthyl)butoxy, 4-(2-naphthyl)butoxy, 5-phenylpentyloxy, 5-(1-naphthyl)pentyloxy, 5-(2-naphthyl)pentyloxy, 6-phenylhexyloxy, 6-(1-naphthyl)hexyloxy, and 6-(2-naphthyl)hexyloxy, which are $C_7$ to $C_{16}$ aralkyl-oxy groups.

Examples of the alkylenedioxy group include, for example, methylenedioxy, ethylenedioxy, 1-methylmethylenedioxy, and 1,1-dimethylmethylenedioxy.

Examples of the halogenated alkoxy group (halogenated alkyl-oxy group) include the groups in which a hydrogen atom of the hydroxy group is substituted with a halogenated alkyl group, and include, for example, fluoromethoxy, difluoromethoxy, chloromethoxy, bromomethoxy, iodomethoxy, trifluoromethoxy, trichloromethoxy, 2,2,2-trifluoroethoxy, pentafluoroethoxy, 3,3,3-trifluoropropoxy, heptafluoropropoxy, heptafluoroisopropoxy, nonafluorobutoxy, and perfluorohexyloxy, which are $C_1$ to $C_6$ straight chain or branched chain halogenated alkoxy groups substituted with 1 to 13 halogen atoms.

Examples of the heterocyclic-oxy group include the groups in which a hydrogen atom of the hydroxy group is substituted with a heterocyclic group, and examples of the heterocyclic ring include similar groups to the aforementioned heterocyclic groups. Examples of the heterocyclic-oxy group include, for example, a monocyclic heteroaryl-oxy group, a fused polycyclic heteroaryl-oxy group, a monocyclic non-aromatic heterocyclic-oxy group, and a fused polycyclic non-aromatic heterocyclic-oxy group.

Examples of the monocyclic heteroaryl-oxy group include, for example, 3-thienyloxy, (isoxazol-3-yl)oxy, (thiazol-4-yl)oxy, 2-pyridyloxy, 3-pyridyloxy, 4-pyridyloxy, and (pyrimidin-4-yl)oxy.

Examples of the fused polycyclic heteroaryl-oxy group include, for example, 5-indolyloxy, (benzimidazol-2-yl)oxy, 2-quinolyloxy, 3-quinolyloxy, and 4-quinolyloxy.

Examples of the monocyclic non-aromatic heterocyclic-oxy group include, for example, 3-pyrrolidinyloxy, and 4-piperidinyloxy.

Examples of the fused polycyclic non-aromatic heterocyclic-oxy group include, for example, 3-indolynyloxy, and 4-chromanyloxy.

Examples of the hydrocarbon-sulfanyl group include the groups in which a hydrogen atom of the sulfanyl group is substituted with a hydrocarbon group, and examples of the hydrocarbon include similar groups to the aforementioned hydrocarbon groups. Examples of the hydrocarbon-sulfanyl groups include, for example, alkyl-sulfanyl group, alkenyl-sulfanyl group, alkynyl-sulfanyl group, cycloalkyl-sulfanyl group, cycloalkyl-alkyl-sulfanyl group and the like, which are aliphatic hydrocarbon-sulfanyl groups; aryl-sulfanyl group, and aralkyl-sulfanyl group.

Examples of the alkyl-sulfanyl group include, for example, methylsulfanyl, ethylsulfanyl, n-propylsulfanyl, isopropylsulfanyl, n-butylsulfanyl, isobutylsulfanyl, sec-butylsulfanyl, tert-butylsulfanyl, n-pentylsulfanyl, isopentylsulfanyl, (2-methylbutyl)sulfanyl, (1-methylbutyl)sulfanyl, neopentylsulfanyl, (1,2-dimethylpropyl)sulfanyl, (1-ethylpropyl)sulfanyl, n-hexylsulfanyl, (4-methylpentyl)sulfanyl, (3-methylpentyl)sulfanyl, (2-methylpentyl)sulfanyl, (1-methylpentyl)sulfanyl, (3,3-dimethylbutyl)sulfanyl, (2,2-dimethylbutyl)sulfanyl, (1,1-dimethylbutyl)sulfanyl, (1,2-dimethylbutyl)sulfanyl, (1,3-dimethylbutyl)sulfanyl, (2,3-dimethylbutyl)sulfanyl, (2-ethylbutyl)sulfanyl, (1-ethylbutyl)sulfanyl, (1-ethyl-1-methylpropyl)sulfanyl, n-heptylsulfanyl, n-octylsulfanyl, n-nonylsulfanyl, n-decylsulfanyl, n-undecylsulfanyl, n-dodecylsulfanyl, n-tridecylsulfanyl, n-tetradecylsulfanyl, and n-pentadecylsulfanyl, which are $C_1$ to $C_{15}$ straight chain or branched chain alkyl-sulfanyl groups.

Examples of the alkenyl-sulfanyl group include, for example, vinylsulfanyl, (prop-1-en-1-yl)sulfanyl, allylsulfanyl, isopropenylsulfanyl, (but-1-en-1-yl)sulfanyl, (but-2-en-1-yl)sulfanyl, (but-3-en-1-yl)sulfanyl, (2-methylprop-2-en-1-yl)sulfanyl, (1-methylprop-2-en-1-yl)sulfanyl, (pent-1-en-1-yl)sulfanyl, (pent-2-en-1-yl)sulfanyl, (pent-3-en-1-yl)sulfanyl, (pent-4-en-1-yl)sulfanyl, (3-methylbut-2-en-1-yl)sulfanyl, (3-methylbut-3-en-1-yl)sulfanyl, (hex-1-en-1-yl)sulfanyl, (hex-2-en-1-yl)sulfanyl, (hex-3-en-1-yl)sulfanyl, (hex-4-en-1-yl)sulfanyl, (hex-5-en-1-yl)sulfanyl, (4-methylpent-3-en-1-yl)sulfanyl, (4-methylpent-3-en-1-yl)sulfanyl, (hept-1-en-1-yl)sulfanyl, (hept-6-en-1-yl)sulfanyl, (oct-1-en-1-yl)sulfanyl, (oct-7-en-1-yl)sulfanyl, (non-1-en-1-yl)sulfanyl, (non-8-en-1-yl)sulfanyl, (dec-1-en-1-yl)sulfanyl, (dec-9-en-1-yl)sulfanyl, (undec-1-en-1-yl)sulfanyl, (undec-10-en-1-yl)sulfanyl, (dodec-1-en-1-yl)sulfanyl, (dodec-11-en-1-yl)sulfanyl, (tridec-1-en-1-yl)sulfanyl, (tridec-12-en-1-yl)sulfanyl, (tetradec-1-en-1-yl)sulfanyl, (tetradec-13-en-1-yl)sulfanyl, (pentadec-1-en-1-yl)sulfanyl, and (pentadec-14-en-1-yl)sulfanyl, which are $C_2$ to $C_{15}$ straight chain or branched chain alkenyl-sulfanyl groups.

Examples of the alkynyl-sulfanyl group include, for example, ethynylsulfanyl, (prop-1-yn-1-yl)sulfanyl, (prop-2-yn-1-yl)sulfanyl, (but-1-yn-1-yl)sulfanyl, (but-3-yn-1-yl)sulfanyl, (1-methylprop-2-yn-1-yl)sulfanyl, (pent-1-yn-1-yl)sulfanyl, (pent-4-yn-1-yl)sulfanyl, (hex-1-yn-1-yl)sulfanyl, (hex-5-yn-1-yl)sulfanyl, (hept-1-yn-1-yl)sulfanyl, (hept-6-yn-1-yl)sulfanyl, (oct-1-yn-1-yl)sulfanyl, (oct-7-yn-1-yl)sulfanyl, (non-1-yn-1-yl)sulfanyl, (non-8-yn-1-yl)sulfanyl, (dec-1-yn-1-yl)sulfanyl, (dec-9-yn-1-yl)sulfanyl, (undec-1-yn-1-yl)sulfanyl, (undec-10-yn-1-yl)sulfanyl, (dodec-1-yn-1-yl)sulfanyl, (dodec-11-yn-1-yl)sulfanyl, (tridec-1-yn-1-yl)sulfanyl, (tridec-12-yn-1-yl)sulfanyl, (tetradec-1-yn-1-yl)sulfanyl, (tetradec-13-yn-1-yl)sulfanyl, (pentadec-1-yn-1-yl)sulfanyl, and (pentadec-14-yn-1-yl)sulfanyl, which are $C_2$ to $C_{15}$ straight chain or branched chain alkynyl-sulfanyl groups.

Examples of the cycloalkyl-sulfanyl group include, for example, cyclopropylsulfanyl, cyclobutylsulfanyl, cyclopentylsulfanyl, cyclohexylsulfanyl, cycloheptylsulfanyl, and cyclooctylsulfanyl, which are $C_3$ to $C_8$ cycloalkyl-sulfanyl groups.

Examples of the cycloalkyl-alkyl-sulfanyl group include, for example, (cyclopropylmethyl)sulfanyl, (1-cyclopropylethyl)sulfanyl, (2-cyclopropylethyl)sulfanyl, (3-cyclopropylpropyl)sulfanyl, (4-cyclopropylbutyl)sulfanyl, (5-cyclopropylpentyl)sulfanyl, (6-cyclopropylhexyl)sulfanyl, (cyclobutylmethyl)sulfanyl, (cyclopentylmethyl)sulfanyl, (cyclobutylmethyl)sulfanyl, (cyclopentylmethyl)sulfanyl, (cyclohexylmethyl)sulfanyl, (2-cyclohexylethyl)sulfanyl, (3-cyclohexylpropyl)sulfanyl, (4-cyclohexylbutyl)sulfanyl, (cycloheptylmethyl)sulfanyl, (cyclooctylmethyl)sulfanyl, and (6-cyclooctylhexyl)sulfanyl, which are $C_4$ to $C_{14}$ cycloalkyl-alkyl-sulfanyl groups.

Examples of the aryl-sulfanyl group include, for example, phenylsulfanyl, 1-naphthylsulfanyl, 2-naphthylsulfanyl, anthrylsulfanyl, fenanthrylsulfanyl, and acenaphthylenylsulfanyl, which are $C_6$ to $C_{14}$ aryl-sulfanyl groups.

Examples of the aralkyl-sulfanyl group include, for example, benzylsulfanyl, (1-naphthylmethyl)sulfanyl, (2-naphthylmethyl)sulfanyl, (anthracenylmethyl)sulfanyl, (phenanthrenylmethyl)sulfanyl, (acenaphthylenylmethyl)sulfanyl, (diphenylmethyl)sulfanyl, (1-phenethyl)sulfanyl, (2-phenethyl)sulfanyl, (1-(1-naphthyl)ethyl)sulfanyl, (1-(2-naphthyl)ethyl)sulfanyl, (2-(1-naphthyl)ethyl)sulfanyl, (2-(2-naphthyl)ethyl)sulfanyl, (3-phenylpropyl)sulfanyl, (3-(1-naphthyl)propyl)sulfanyl, (3-(2-naphthyl)propyl)sulfanyl, (4-phenylbutyl)sulfanyl, (4-(1-naphthyl)butyl)sulfanyl, (4-(2-naphthyl)butyl)sulfanyl, (5-phenylpentyl)sulfanyl, (5-(1-naphthyl)pentyl)sulfanyl, (5-(2-naphthyl)pentyl)sulfanyl, (6-phenylhexyl)sulfanyl, (6-(1-naphthyl)hexyl)sulfanyl, and (6-(2-naphthyl)hexyl)sulfanyl, which are $C_7$ to $C_{16}$ aralkyl-sulfanyl groups.

Examples of the halogenated alkyl-sulfanyl group include the groups in which a hydrogen atom of the sulfanyl group is substituted with a halogenated alkyl group, and include, for example, (fluoromethyl)sulfanyl, (chloromethyl)sulfanyl, (bromomethyl)sulfanyl, (iodomethyl)sulfanyl, (difluoromethyl)sulfanyl, (trifluoromethyl)sulfanyl, (trichloromethyl)sulfanyl, (2,2,2-trifluoroethyl)sulfanyl, (pentafluoroethyl)sulfanyl, (3,3,3-trifluoropropyl)sulfanyl, (heptafluoropropyl)sulfanyl, (heptafluoroisopropyl)sulfanyl, (nonafluorobutyl)sulfanyl, and (perfluorohexyl)sulfanyl, which are $C_1$ to $C_6$ straight chain or branched chain halogenated alkyl-sulfanyl groups substituted with 1 to 13 halogen atoms.

Examples of the heterocyclic-sulfanyl group include the groups in which a hydrogen atom of the sulfanyl group is substituted with a heterocyclic group, and examples of the heterocyclic ring include similar groups to the aforementioned heterocyclic groups. Examples of the heterocyclic-sulfanyl group include, for example, a monocyclic heteroaryl-sulfanyl group, a fused polycyclic heteroaryl-sulfanyl group, a monocyclic non-aromatic heterocyclic-sulfanyl group, and a fused polycyclic non-aromatic heterocyclic-sulfanyl group.

Examples of the monocyclic heteroaryl-sulfanyl group include, for example, (imidazol-2-yl)sulfanyl, (1,2,4-triazol-2-yl)sulfanyl, (pyridin-2-yl)sulfanyl, (pyridin-4-yl)sulfanyl, and (pyrimidin-2-yl)sulfanyl.

Examples of the fused polycyclic heteroaryl-sulfanyl group include, for example, (benzimidazol-2-yl)sulfanyl, (quinolin-2-yl)sulfanyl, and (quinolin-4-yl)sulfanyl.

Examples of the monocyclic non-aromatic heterocyclic-sulfanyl groups include, for example, (3-pyrrolidinyl)sulfanyl, and (4-piperidinyl)sulfanyl.

Examples of the fused polycyclic non-aromatic heterocyclic-sulfanyl group include, for example, (3-indolinyl)sulfanyl, and (4-chromanyl)sulfanyl.

Examples of the acyl group include, for example, formyl group, glyoxyloyl group, thioformyl group, carbamoyl group, thiocarbamoyl group, sulfamoyl group, sulfinamoyl group, carboxy group, sulfo group, phosphono group, and groups represented by the following formulas:

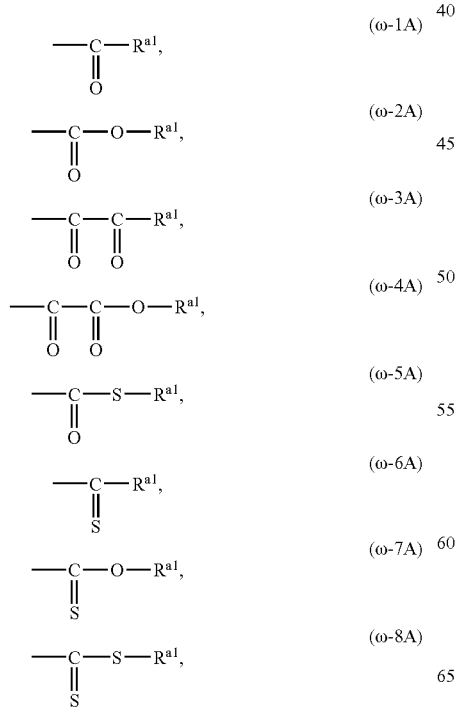

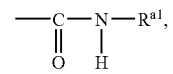
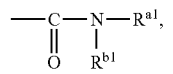
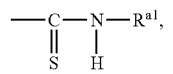
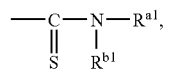
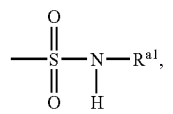
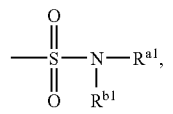
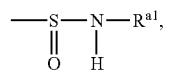
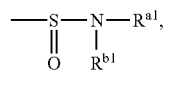
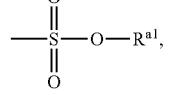
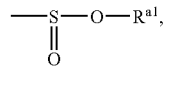
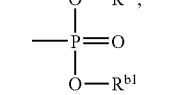
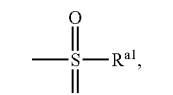

wherein $R^{a1}$ and $R^{b1}$ may be the same or different and represent a hydrocarbon group or a heterocyclic group, or $R^{a1}$ and $R^{b1}$ combine to each other, together with the nitrogen atom to which they bind, to form a cyclic amino group.

In the definition of the aforementioned acyl group, among the groups represented by the formula (ω-1A), those groups in which $R^{a1}$ is a hydrocarbon group are referred to as "hydrocarbon-carbonyl group" whose examples include, for example, acetyl, propionyl, butyryl, isobutyryl, valeryl, isovaleryl, pivaloyl, lauroyl, myristoryl, palmitoyl, acryloyl, propioloyl, methacryloyl, crotonoyl, isocrotonoyl, cyclohexylcarbonyl, cyclohexylmethylcarbonyl, benzoyl, 1-naphthoyl, 2-naphthoyl, and phenylacetyl, and those groups in which $R^{a1}$ is a heterocyclic group are referred to as "heterocyclic ring-carbonyl group" whose examples include, for example, 2-thenoyl, 3-furoyl, nicotinoyl, and isonicotinoyl.

Among the groups represented by the formula (ω-2A), those groups in which $R^{a1}$ is a hydrocarbon group are referred to as "hydrocarbon-oxy-carbonyl group" whose examples include, for example, methoxycarbonyl, ethoxycarbonyl, phenoxycarbonyl, and benzyloxycarbonyl, and those groups in which $R^{a1}$ is a heterocyclic group are referred to as "heterocyclic ring-oxy-carbonyl group" whose examples include, for example, 3-pyridyloxycarbonyl.

Among the groups represented by the formula (ω-3A), those groups in which $R^{a1}$ is a hydrocarbon group are referred to as "hydrocarbon-carbonyl-carbonyl group" whose examples include, for example, pyruvoyl, and those groups in which $R^{a1}$ is a heterocyclic group are referred to as "heterocyclic ring-carbonyl-carbonyl group."

Among the groups represented by the formula (ω-4A), those groups in which $R^{a1}$ is a hydrocarbon group are referred to as "hydrocarbon-oxy-carbonyl-carbonyl group" whose examples include, for example, methoxalyl and ethoxalyl groups, and those groups in which $R^{a1}$ is a heterocyclic group are referred to as "heterocyclic ring-oxy-carbonyl-carbonyl group."

Among the groups represented by the formula (ω-5A), those groups in which $R^{a1}$ is a hydrocarbon group are referred to as "hydrocarbon-sulfanyl-carbonyl group," and those groups in which $R^{a1}$ is a heterocyclic group are referred to as "heterocyclic ring-sulfanyl-carbonyl group."

Among the groups represented by the formula (ω-6A), those groups in which $R^{a1}$ is a hydrocarbon group are referred to as "hydrocarbon-thiocarbonyl group," and those groups in which $R^{a1}$ is a heterocyclic group are referred to as "heterocyclic ring-thiocarbonyl group."

Among the groups represented by the formula (ω-7A), those groups in which $R^{a1}$ is a hydrocarbon group are referred to as "hydrocarbon-oxy-thiocarbonyl group," and those groups in which $R^{a1}$ is a heterocyclic group are referred to as "heterocyclic ring-oxy-thiocarbonyl group."

Among the groups represented by the formula (ω-8A), those groups in which $R^{a1}$ is a hydrocarbon group are referred to as "hydrocarbon-sulfanyl-thiocarbonyl group," and those groups in which $R^{a1}$ is a heterocyclic group are referred to as "heterocyclic ring-sulfanyl-thiocarbonyl group."

Among the groups represented by the formula (ω-9A), those groups in which $R^{a1}$ is a hydrocarbon group are referred to as referred to as "N-hydrocarbon-carbamoyl group" whose examples include, for example, N-methylcarbamoyl group, and those groups in which $R^{a1}$ is a heterocyclic group are referred to as "N-heterocyclic ring-carbamoyl group."

Among the groups represented by the formula (ω-10A), those groups in which both $R^{a1}$ and $R^{b1}$ are hydrocarbon groups are referred to as "N,N-di(hydrocarbon)-carbamoyl group" whose examples include, for example, N,N-dimethylcarbamoyl group, those groups in which both $R^{a1}$ and $R^{b1}$ are heterocyclic groups are referred to as "N,N-di(heterocyclic ring)-carbamoyl group," those groups in which $R^{a1}$ is a hydrocarbon group and $R^{b1}$ is a heterocyclic group are referred to as "N-hydrocarbon-N-heterocyclic ring-substituted carbamoyl group," and those groups in which $R^{a1}$ and $R^{b1}$ combine to each other, together with the nitrogen atom to which they bind, to form a cyclic amino group are referred to as "cyclic amino-carbonyl group" whose examples include, for example, morpholino-carbonyl.

Among the groups represented by the formula (ω-11A), those groups in which $R^{a1}$ is a hydrocarbon group are referred to as "N-hydrocarbon-thiocarbamoyl group," and those groups in which $R^{a1}$ is a heterocyclic group are referred to as "N-heterocyclic ring-thiocarbamoyl group."

Among the groups represented by the formula (ω-12A), those groups in which both $R^{a1}$ and $R^{b1}$ are hydrocarbon groups are referred to as "N,N-di(hydrocarbon)-thiocarbamoyl group," those groups in which both $R^{a1}$ and $R^{b1}$ are heterocyclic groups are referred to as "N,N-di(heterocyclic ring)-thiocarbamoyl group," those groups in which $R^{a1}$ is a hydrocarbon group and $R^{b1}$ is a heterocyclic group are referred to as "N-hydrocarbon-N-heterocyclic ring-thiocarbamoyl group," and those groups in which $R^{a1}$ and $R^{b1}$ combine to each other, together with the nitrogen atom to which they bind, to form a cyclic amino group are referred to as "cyclic amino-thiocarbonyl group."

Among the groups represented by the formula (ω-13A), those groups in which $R^{a1}$ is a hydrocarbon group are referred to as "N-hydrocarbon-sulfamoyl group," and those groups in which $R^{a1}$ is a heterocyclic group are referred to as "N-heterocyclic ring-sulfamoyl group."

Among the groups represented by the formula (ω-14A), those groups in which both $R^{a1}$ and $R^{b1}$ are hydrocarbon groups are referred to as "N,N-di(hydrocarbon)-sulfamoyl group" whose examples include, for example, N,N-dimethylsulfamoyl group, those groups in which both $R^{a1}$ and $R^{b1}$ are heterocyclic groups are referred to as "N,N-di(heterocyclic ring)-sulfamoyl group," those groups in which $R^{a1}$ is a hydrocarbon group and $R^{b1}$ is a heterocyclic group are referred to as "N-hydrocarbon-N-heterocyclic ring-sulfamoyl group," and those groups in which $R^{a1}$ and $R^{b1}$ combine to each other, together with the nitrogen atom to which they bind, to form a cyclic amino group are referred to as "cyclic amino-sulfonyl group" whose examples include, for example 1-pyrrolylsulfonyl.

Among the groups represented by the formula (ω-15A), those groups in which $R^{a1}$ is a hydrocarbon group are referred to as "N-hydrocarbon-sulfinamoyl group," and those groups in which $R^{a1}$ is a heterocyclic group are referred to as "N-heterocyclic ring-sulfinamoyl group."

Among the groups represented by the formula (ω-16A), those groups in which both $R^{a1}$ and $R^{b1}$ are hydrocarbon groups are referred to as "N,N-di(hydrocarbon)-sulfinamoyl group," those groups in which both $R^{a1}$ and $R^{b1}$ are heterocyclic groups are referred to as "N,N-di(heterocyclic ring)-sulfinamoyl group," those groups in which $R^{a1}$ is a hydrocarbon group and $R^{b1}$ is a heterocyclic group are referred to as "N-hydrocarbon-N-heterocyclic ring-sulfinamoyl group," and those groups in which $R^{a1}$ and $R^{b1}$ combine to each other, together with the nitrogen atom to which they bind, to form a cyclic amino group are referred to as "cyclic amino-sulfinyl group."

Among the groups represented by the formula (ω-17A), those groups in which $R^{a1}$ is a hydrocarbon group are referred to as "hydrocarbon-oxy-sulfonyl group," and those groups in which $R^{a1}$ is a heterocyclic group are referred to as "heterocyclic ring-oxy-sulfonyl group."

Among the groups represented by the formula (ω-18A), those groups in which $R^{a1}$ is a hydrocarbon group are referred to as "hydrocarbon-oxy-sulfinyl group," and those groups in which $R^{a1}$ is a heterocyclic group are referred to as "heterocyclic ring-oxy-sulfinyl group."

Among the groups represented by the formula (ω-19A), those groups in which both $R^{a1}$ and $R^{b1}$ are hydrocarbon groups are referred to as "O,O'-di(hydrocarbon)-phosphono group," those groups in which both $R^{a1}$ and $R^{b1}$ are heterocyclic groups are referred to as "O,O'-di(heterocyclic ring)-phosphono group," and those groups in which $R^{a1}$ is a hydrocarbon group and $R^{b1}$ is a heterocyclic group are referred to as "O-hydrocarbon-O'-heterocyclic ring-phosphono group."

Among the groups represented by the formula (ω-20A), those groups in which $R^{a1}$ is a hydrocarbon group are referred to as "hydrocarbon-sulfonyl group" whose examples include, for example, methanesulfonyl and benzenesulfonyl, and those groups in which $R^{a1}$ is a heterocyclic group are referred to as "heterocyclic ring-sulfonyl group."

Among the groups represented by the formula (ω-21A), those groups in which $R^{a1}$ is a hydrocarbon group are referred to as "hydrocarbon-sulfinyl group" whose examples include, for example, methylsulfinyl and benzenesulfinyl, and those groups in which $R^{a1}$ is a heterocyclic group are referred to as "heterocyclic ring-sulfinyl group."

Examples of the hydrocarbon in the groups represented by the aforementioned formulas (ω-1A) through (ω-21A) include the similar groups to the aforementioned hydrocarbon group. Examples of the hydrocarbon-carbonyl group represented by the formula (ω-1A) include, for example, an alkyl-carbonyl group, an alkenyl-carbonyl group, an alkynyl-carbonyl group, a cycloalkyl-carbonyl group, a cycloalkenyl-carbonyl group, a cycloalkanedienyl-carbonyl group, a cycloalkyl-alkyl-carbonyl group, which are aliphatic hydrocarbon-carbonyl groups; an aryl-carbonyl group; an aralkyl-carbonyl group; a bridged cyclic hydrocarbon-carbonyl group; a spirocyclic hydrocarbon-carbonyl group; and a terpene family hydrocarbon-carbonyl group. In the following, groups represented by the formulas (ω-2A) through (ω-21A) are similar to those explained above.

Examples of the heterocyclic ring in the groups represented by the aforementioned formulas (ω-1A) through (ω-21A) include similar groups to the aforementioned heterocyclic group. Examples of the heterocyclic ring-carbonyl group represented by the formula (ω-1A) include, for example, a monocyclic heteroaryl-carbonyl group, a fused polycyclic heteroaryl-carbonyl group, a monocyclic non-aromatic heterocyclic ring-carbonyl group, and a fused polycyclic non-aromatic heterocyclic ring-carbonyl group. In the following, groups represented by the formulas (ω-2A) through (ω-21A) are similar to those explained above.

Examples of the cyclic amino in the groups represented by the aforementioned formulas (ω-10A) through (ω-16A) include similar groups to the aforementioned cyclic amino group.

In the present specification, when a certain functional group is defined as "which may be substituted," the definition means that the functional group may sometimes have one or more substitutents at chemically substitutable positions, unless otherwise specifically mentioned. Kind of substitutents, number of substitutents, and the position of substitutents existing in the functional groups are not particularly limited, and when two or more substitutents exist, they may be the same or different. Examples of the substitutent existing in the functional group include, for example, halogen atoms, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, methooxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, hydrocarbon group, heterocyclic group, hydrocarbon-oxy group, heterocyclic ring-oxy group, hydrocarbon-sulfanyl group, heterocyclic ring-sulfanyl group, acyl group, amino group, hydrazino group, hydrazono group, diazenyl group, ureido group, thioureido group, guanidino group, carbamoimidoyl group (amidino group), azido group, imino group, hydroxyamino group, hydroxyimino group, aminooxy group, diazo group, semicarbazino group, semicarbazono group, allophanyl group, hydantoyl group, phosphano group, phosphoroso group, phospho group, boryl group, silyl group, stannyl group, selanyl group, oxido group and the like.

When two or more substitutents exist according to the aforementioned definition of "which may be substituted," said two or more substitutents may combine to each other, together with atom(s) to which they bind, to form a ring. For these cyclic groups, as ring-constituting atoms (ring forming atoms), one to three kinds of one or more hetero atoms selected from oxygen atom, sulfur atom, nitrogen atom and the like may be included, and one or more substitutents may exist on the ring. The ring may be monocyclic or fused polycyclic, and aromatic or non-aromatic.

The above substitutents according to the aforementioned definition of "which may be substituted" may further be substituted with the aforementioned substitutents at the chemically substitutable positions on the substitutent. Kind of substitutents, number of substitutents, and positions of substitutents are not particularly limited, and when the substitutents are substituted with two or more substitutents, they may be the same or different. Examples of the substitutent include, for example, a halogenated alkyl-carbonyl group whose examples include, for example, trifluoroacetyl, a halogenated alkyl-sulfonyl group whose examples include, for example, trifluoromethanesulfonyl, an acyl-oxy group, an acyl-sulfanyl group, an N-hydrocarbon-amino group, an N,N-di(hydrocarbon)-amino group, an N-heterocyclic ring-amino group, an N-hydrocarbon-N-heterocyclic ring-amino group, an acyl-amino group, and a di(acyl)-amino group. Moreover, substitution on the aforementioned substitutents may be repeated multiple orders.

Examples of the acyl-oxy group include the groups in which hydrogen atom of hydroxy group is substituted with acyl group, and include, for example, formyloxy group, glyoxyloyloxy group, thioformyloxy group, carbamoloxy group, thiocarbamoyloxy group, sulfamoyloxy group, sulfinamoloxy group, carboxyoxy group, sulphooxy group, phosphonooxy group, and groups represented by the following formulas:

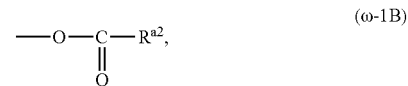 (ω-1B)

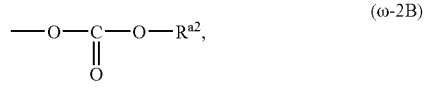 (ω-2B)

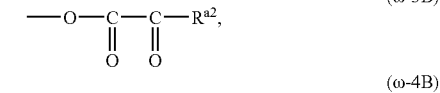 (ω-3B)

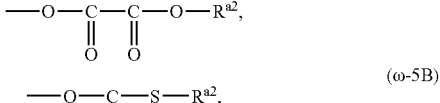 (ω-4B)

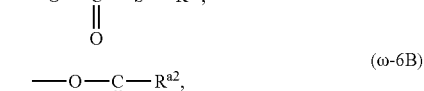 (ω-5B)

 (ω-6B)

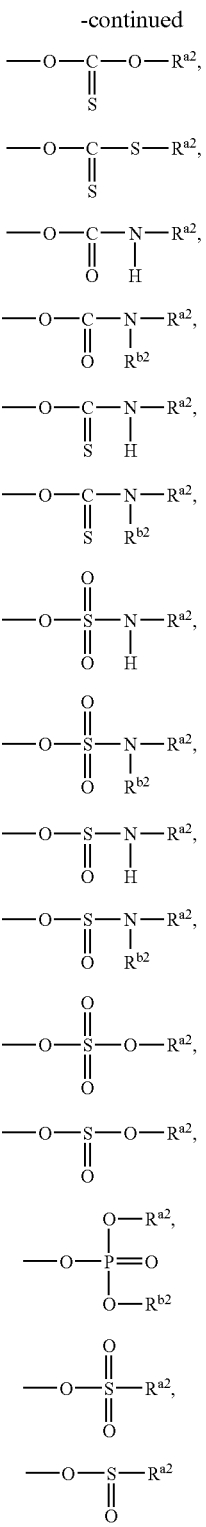

wherein $R^{a2}$ and $R^{b2}$ may be the same or different and represent a hydrocarbon group or a heterocyclic group, or $R^{a2}$ and $R^{b2}$ combine to each other, together with the nitrogen atom to which they bind, to form a cyclic amino group.

In the definition of the aforementioned acyl-oxy group, among the groups represented by the formula (ω-1B), those groups in which $R^{a2}$ is a hydrocarbon group are referred to as "hydrocarbon-carbonyl-oxy group" whose examples include, for example, acetoxy and benzoyloxy, and those groups in which $R^{a2}$ is a heterocyclic group are referred to as "heterocyclic ring-carbonyl-oxy group."

Among the groups represented by the formula (ω-2B), those groups in which $R^{a2}$ is a hydrocarbon group are referred to as "hydrocarbon-oxy-carbonyl-oxy group," and those groups in which $R^{a2}$ is a heterocyclic group are referred to as "heterocyclic ring-oxy-carbonyl-oxy group."

Among the groups represented by the formula (ω-3B), those groups in which $R^{a2}$ is a hydrocarbon group are referred to as "hydrocarbon-carbonyl-carbonyl-oxy group," and those groups in which $R^{a2}$ is a heterocyclic group are referred to as "heterocyclic ring-carbonyl-carbonyl-oxy group."

Among the groups represented by the formula (ω-4B), those groups in which $R^{a2}$ is a hydrocarbon group are referred to as "hydrocarbon-oxy-carbonyl-carbonyl-oxy group," and those groups in which $R^{a2}$ is a heterocyclic group are referred to as "heterocyclic ring-oxy-carbonyl-carbonyl-oxy group."

Among the groups represented by the formula (ω-5B), those groups in which $R^{a2}$ is a hydrocarbon group are referred to as "hydrocarbon-sulfanyl-carbonyl-oxy group," and those groups where $R^{a2}$ is a heterocyclic group are referred to as "heterocyclic ring-sulfanyl-carbonyl-oxy group."

Among the groups represented by the formula (ω-6B), those groups in which $R^{a2}$ is a hydrocarbon group are referred to as "hydrocarbon-thiocarbonyl-oxy group," and those groups where $R^{a2}$ is a heterocyclic group are referred to as "heterocyclic ring-thiocarbonyl-oxy group."

Among the groups represented by the formula (ω-7B), those groups in which $R^{a2}$ is a hydrocarbon group are referred to as "hydrocarbon-oxy-thiocarbonyl-oxy group," and those groups in which $R^{a2}$ is a heterocyclic group are referred to as "heterocyclic ring-oxy-thiocarbonyl-oxy group."

Among the groups represented by the formula (ω-8B), those groups in which $R^{a2}$ is a hydrocarbon group are referred to as "hydrocarbon-sulfanyl-thiocarbonyl-oxy group," and those groups wherein $R^{a2}$ is a heterocyclic group are referred to as "heterocyclic ring-sulfanyl-thiocarbonyl-oxy group."

Among the groups represented by the formula (ω-9B), those groups in which $R^{a2}$ is a hydrocarbon group are referred to as "N-hydrocarbon-carbamoyl-oxy group," and those groups in which $R^{a2}$ is a heterocyclic group are referred to as "N-heterocyclic ring-carbamoyl-oxy group."

Among the groups represented by the formula (ω-10B), those groups in which both $R^{a2}$ and $R^{b2}$ are hydrocarbon groups are referred to as "N,N-di(hydrocarbon)-carbamoyl-oxy group," those groups in which both $R^{a2}$ and $R^{b2}$ are heterocyclic groups are referred to as "N,N-di(heterocyclic ring)-carbamoyl-oxy group," those groups in which $R^{a2}$ is a hydrocarbon group and $R^{b2}$ is a heterocyclic group are referred to as "N-hydrocarbon-N-heterocyclic ring-carbamoyl-oxy group," and those groups in which $R^{a2}$ and $R^{b2}$ combine to each other, together with the nitrogen atom to which they bind, to form a cyclicic amino group are referred to as "cyclicamino-carbonyl-oxy group."

Among the groups represented by the formula (ω-11B), those groups in which $R^{a2}$ is a hydrocarbon group are referred to as "N-hydrocarbon-thiocarbamoyl-oxy group," and those groups in which $R^{a2}$ is a heterocyclic group are referred to as "N-heterocyclic ring-thiocarbamoyl-oxy group."

Among the groups represented by the formula (ω-12B), those groups in which both $R^{a2}$ and $R^{b2}$ are hydrocarbon groups are referred to as "N,N-di(hydrocarbon)-thiocarbamoyl-oxy group," those groups in which both $R^{a2}$ and $R^{b2}$ are heterocyclic groups are referred to as "N,N-di(heterocyclic ring)-thiocarbamoyl-oxy group," those groups in which $R^{a2}$ is a hydrocarbon group and $R^{b2}$ is a heterocyclic group are referred to as "N-hydrocarbon-N-heterocyclic ring-thiocarbamoyl-oxy group," and those groups in which $R^{a2}$ and $R^{b2}$ combine to each other, together with the nitrogen atom to which they bind, to form a cyclic amino group are referred to as "cyclicamino-thiocarbonyl-oxy group."

Among the groups represented by the formula (ω-13B), those groups in which $R^{a2}$ is a hydrocarbon group are referred to as "N-hydrocarbon-sulfamoyl-oxy group," and those groups in which $R^{a2}$ is a heterocyclic group are referred to as "N-heterocyclic ring-sulfamoyl-oxy group."

Among the groups represented by the formula (ω-14B), those groups in which both $R^{a2}$ and $R^{b2}$ are hydrocarbon groups are referred to as "N,N-di(hydrocarbon)-sulfamoyl-oxy group," those groups in which both $R^{a2}$ and $R^{b2}$ are heterocyclic groups are referred to as "N,N-di(heterocyclic ring)-sulfamoyl-oxy group," those groups in which $R^{a2}$ is a hydrocarbon group and $R^{b2}$ is a heterocyclic group are referred to as "N-hydrocarbon-N-heterocyclic ring-sulfamoyl-oxy group," and those groups in which $R^{a2}$ and $R^{b2}$ combine to each other, together with the nitrogen atom to which they bind, to form a cyclic amino group are referred to as "cyclic amino-sulfonyl-oxy group."

Among the groups represented by the formula (ω-15B), those groups in which $R^{a2}$ is a hydrocarbon group are referred to as "N-hydrocarbon-sulfinamoyl-oxy group," and those groups where $R^{a2}$ is a heterocyclic group are referred to as "N-heterocyclic ring-sulfinamoyl-oxy group."

Among the groups represented by the formula (ω-16B), those groups in which both $R^{a2}$ and $R^{b2}$ are hydrocarbon groups are referred to as "N,N-di(hydrocarbon)-sulfinamoyl-oxy group," those groups in which both $R^{a2}$ and $R^{b2}$ are heterocyclic groups are referred to as "N,N-di(heterocyclic ring)-sulfinamoyl-oxy group," those groups in which $R^{a2}$ is a hydrocarbon group and $R^{b2}$ is a heterocyclic group are referred to as "N-hydrocarbon-N-heterocyclic ring-sulfinamoyl-oxy group," and those groups in which $R^{a2}$ and $R^{b2}$ combine to each other, together with the nitrogen atom to which they bind, to form a cyclic amino group are referred to as "cyclic amino-sulfinyl-oxy group."

Among the groups represented by the formula (ω-17B), those groups in which $R^{a2}$ is a hydrocarbon group are referred to as "hydrocarbon-oxy-sulfonyl-oxy group," and those groups in which $R^{a2}$ is a heterocyclic group are referred to as "heterocyclic ring-oxy-sulfonyl-oxy group."

Among the groups represented by the formula (ω-18B), those groups in which $R^{a2}$ is a hydrocarbon group are referred to as "hydrocarbon-oxy-sulfinyl-oxy group," those groups in which $R^{a2}$ is a heterocyclic group are referred to as "heterocyclic ring-oxy-sulfinyl-oxy group."

Among the groups represented by the formula (ω-19B), those groups in which both $R^{a2}$ and $R^{b2}$ are hydrocarbon groups are referred to as "O,O'-di(hydrocarbon)-phosphono-oxy group," those groups in which both $R^{a2}$ and $R^{b2}$ are heterocyclic groups are referred to as "O,O'-di(heterocyclic ring)-phosphono-oxy group," and those groups in which $R^{a2}$ is a hydrocarbon group and $R^{b2}$ is a heterocyclic group are referred to as "O-hydrocarbon substituted-O'-heterocyclic ring substituted phophono-oxy group."

Among the groups represented by the formula (ω-20B), those groups in which $R^{a2}$ is a hydrocarbon group are referred to as "hydrocarbon-sulfonyl-oxy group," and those groups in which $R^{a2}$ is a heterocyclic group referred to as "heterocyclic ring-sulfonyl-oxy group."

Among the groups represented by the formula (ω-21B), those groups in which $R^{a2}$ is a hydrocarbon group are referred to as "hydrocarbon-sulfinyl-oxy group," and those groups in which $R^{a2}$ is a heterocyclic group are referred to as "heterocyclic ring-sulfinyl-oxy group."

Examples of the hydrocarbon in the groups represented by the aforementioned formulas (ω-1B) through (ω-21B) include the similar groups to the aforementioned hydrocarbon group. Examples of the hydrocarbon-carbonyl-oxy group represented by the formula (ω-1B) include, for example, an alkyl-carbonyl-oxy group, an alkenyl-carbonyl-oxy group, an alkynyl-carbonyl-oxy group, a cycloalkyl-carbonyl-oxy group, a cycloalkenyl-carbonyl-oxy group, a cycloalkanedienyl-carbonyl-oxy group, and a cycloalkyl-alkyl-carbonyl-oxy group, which are aliphatic hydrocarbon-carbonyl-oxy groups; an aryl-carbonyl-oxy group; an aralkyl-carbonyl-oxy group; a bridged cyclic hydrocarbon-carbonyl-oxy group; a spirocyclic hydrocarbon-carbonyl-oxy group; and a terpene family hydrocarbon-carbonyl-oxy group. In the following, groups represented by the formulas (ω-2B) through (ω-21B) are similar to those explained above.

Examples of the heterocyclic ring in the groups represented by the aforementioned formulas (ω-1B) through (ω-21B) include similar groups to the aforementioned heterocyclic group. Examples of the heterocyclic ring-carbonyl group represented by the formula (ω-1B) include, for example, a monocyclic heteroaryl-carbonyl group, a fused polycyclic heteroaryl-carbonyl group, a monocyclic non-aromatic heterocyclic ring-carbonyl group, and a fused polycyclic non-aromatic heterocyclic ring-carbonyl group. In the following, groups represented by the formulas (ω-2B) through (ω-21B) are similar to those groups explained above.

Examples of the cyclic amino in the groups represented by the aforementioned formulas (ω-10B) through (ω-16B) include similar groups to the aforementioned cyclic amino group.

The aforementioned acyl-oxy group, hydrocarbon-oxy group, and heterocyclic-oxy group are generically referred to as "substituted oxy group." Moreover, these substituted oxy group and hydroxy group are generically referred to as "hydroxy group which may be substituted."

Examples of the acyl-sulfanyl group include the groups in which hydrogen atom of sulfanyl group is substituted with acyl group, and include, for example, formylsulfanyl group, glyoxyloylsulfanyl group, thioformylsulfanyl group, carbamoyloxy group, thicarbamoyloxy group, sulfamoyloxy group, sulfinamoyloxy group, carboxyoxy group, sulphooxy group, phosphonooxy group, and groups represented by the following formulas:

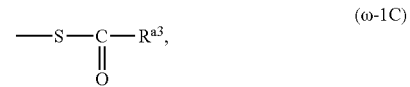
(ω-1C)

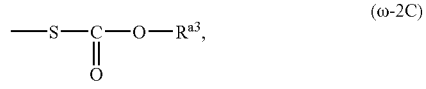
(ω-2C)

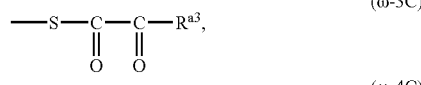
(ω-3C)

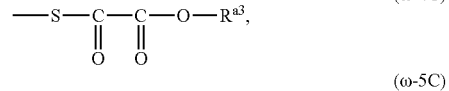
(ω-4C)

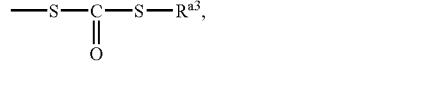
(ω-5C)

-continued

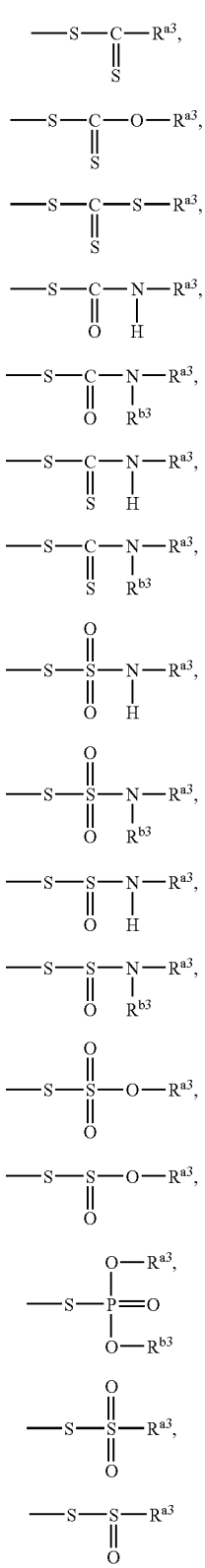

(ω-6C)
(ω-7C)
(ω-8C)
(ω-9C)
(ω-10C)
(ω-11C)
(ω-12C)
(ω-13C)
(ω-14C)
(ω-15C)
(ω-16C)
(ω-17C)
(ω-18C)
(ω-19C)
(ω-20C)
(ω-21C)

wherein $R^{a3}$ and $R^{b3}$ may be the same or different and represent a hydrocarbon group which may be substituted or a heterocyclic group which may be substituted, or $R^{a3}$ and $R^{b3}$ combine to each other, together with the nitrogen atom to which they bind, to form a cyclic amino group which may be substituted.

In the definition of the aforementioned acyl-sulfanyl group, among the groups represented by the formula (ω-1C), those groups in which $R^{a3}$ is a hydrocarbon group are referred to as "hydrocarbon-carbonyl-sulfanyl group," and those groups in which $R^{a3}$ is a heterocyclic group are referred to as "heterocyclic ring-carbonyl-sulfanyl group."

Among the groups represented by the formula (ω-2C), those groups in which $R^{a3}$ is a hydrocarbon group are referred to as "hydrocarbon-oxy-carbonyl-sulfanyl group," and those groups in which $R^{a3}$ is a heterocyclic group are referred to as "heterocyclic ring-oxy-carbonyl-sulfanyl group."

Among the groups represented by the formula (ω-3C), those groups in which $R^{a3}$ is a hydrocarbon group are referred to as "hydrocarbon-carbonyl-carbonyl-sulfanyl group," and those groups in which $R^{a3}$ is a heterocyclic group are referred to as "heterocyclic ring-carbonyl-carbonyl-sulfanyl group."

Among the groups represented by the formula (ω-4C), those groups in which $R^{a3}$ is a hydrocarbon group are referred to as "hydrocarbon-oxy-carbonyl-carbonyl-sulfanyl group," and those groups in which $R^{a3}$ is a heterocyclic group are referred to as "heterocyclic ring-oxy-carbonyl-carbonyl-sulfanyl group."

Among the groups represented by the formula (ω-5C), those groups in which $R^{a3}$ is a hydrocarbon group are referred to as "hydrocarbon-sulfanyl-carbonyl-sulfanyl group," and those groups in which $R^{a3}$ is a heterocyclic group are referred to as "heterocyclic ring-sulfanyl-carbonyl-sulfanyl group."

Among the groups represented by the formula (ω-6C), those groups in which $R^{a3}$ is a hydrocarbon group are referred to as "hydrocarbon-thiocarbonyl-sulfanyl group," and those groups in which $R^{a3}$ is a heterocyclic group are referred to as "heterocyclic ring-thiocarbonyl-sulfanyl group."

Among the groups represented by the formula (ω-7C), those groups in which $R^{a3}$ is a hydrocarbon group are referred to as "hydrocarbon-oxy-thiocarbonyl-sulfanyl group," and those groups in which $R^{a3}$ is a heterocyclic group are referred to as "heterocyclic ring-oxy-thiocarbonyl-sulfanyl group."

Among the groups represented by the formula (ω-8C), those groups in which $R^{a3}$ is a hydrocarbon group are referred to as "hydrocarbon-sulfanyl-thiocarbonyl-sulfanyl group," and those groups in which $R^{a3}$ is a heterocyclic group are referred to as "heterocyclic ring-sulfanyl-thiocarbonyl-sulfanyl group."

Among the groups represented by the formula (ω-9C), those groups in which $R^{a3}$ is a hydrocarbon group are referred to as "N-hydrocarbon-carbamoyl-sulfanyl group," and those groups in which $R^{a3}$ is a heterocyclic group are referred to as "N-heterocyclic ring-carbamoyl-sulfanyl group."

Among the groups represented by the formula (ω-10C), those groups in which both $R^{a3}$ and $R^{b3}$ are a hydrocarbon groups are referred to as "N,N-di(hydrocarbon)-carbamoyl-sulfanyl group," those groups in which both $R^{a3}$ and $R^{b3}$ are heterocyclic groups are referred to as "N,N-di(heterocyclic ring)-carbamoyl-sulfanyl group," those groups in which $R^{a3}$ is a hydrocarbon group and $R^{b3}$ is a heterocyclic group are referred to as "N-hydrocarbon-N-heterocyclic ring-carbamoyl-sulfanyl group," and those groups in which $R^{a3}$ and $R^{b3}$ combine to each other, together with the nitrogen atom to which they bind, to form a cyclic amino group are referred to as "cyclicamino-carbonyl-sulfamoyl group."

Among the groups represented by the formula (ω-11C), those groups in which $R^{a3}$ is a hydrocarbon group are referred to as "N-hydrocarbon-thiocarbamoyl-sulfanyl group," and those groups in which $R^{a3}$ is a heterocyclic group are referred to as "N-heterocyclic ring-thiocarbamoyl-sulfanyl group."

Among the groups represented by the formula (ω-12C), those groups in which both $R^{a3}$ and $R^{b3}$ are hydrocarbon groups are referred to as "N,N-di(hydrocarbon)-thiocarbamoyl-sulfanyl group," those groups in which and $R^{a3}$ and $R^{b3}$ are heterocyclic groups are referred to as "N,N-di(heterocyclic ring)-thiocarbamoyl-sulfanyl group," those groups in which $R^{a3}$ is a hydrocarbon group and $R^{b3}$ is a heterocyclic group are referred to as "N-hydrocarbon-N-heterocyclic ring-thiocarbamoyl-sulfanyl group," and those groups in which $R^{a3}$ and $R^{b3}$ combine to each other, together with the nitrogen atom to which they bind, to form a cyclic amino group are referred to as "cyclicamino-thiocarbonyl-sulfamoyl group."

Among the groups represented by the formula (ω-13C), those groups in which $R^{a3}$ is a hydrocarbon group are referred to as "N-hydrocarbon-sulfamoyl-sulfanyl group," and those groups in which $R^{a3}$ is a heterocyclic group are referred to as "N-heterocyclic ring-sulfamoyl-sulfanyl group."

Among the groups represented by the formula (ω-14C), those groups in which both $R^{a3}$ and $R^{b3}$ are hydrocarbon groups are referred to as "N,N-di(hydrocarbon)-sulfamoyl-sulfanyl group," those groups in which both $R^{a3}$ and $R^{b3}$ are heterocyclic groups are referred to as "N,N-di(heterocyclic ring)-sulfamoyl-sulfinyl group," those groups in which $R^{a3}$ is a hydrocarbon group and $R^{b3}$ is a heterocyclic group are referred to as "N-hydrocarbon-N-heterocyclic ring-sulfamoyl-sulfanyl group," and those groups in which $R^{a3}$ and $R^{b3}$ combine to each other, together with the nitrogen atom to which they bind, to form a cyclic amino group are referred to as "cyclicamino-sulfonyl-sulfanyl group."

Among the groups represented by the formula (ω-15C), those groups in which $R^{a3}$ is a hydrocarbon group are referred to as "N-hydrocarbon-sulfinamoyl-sulfanyl group," and those groups in which $R^{a3}$ is a heterocyclic group are referred to as "N-heterocyclic ring-sulfinamoyl-sulfanyl group."

Among the groups represented by the formula (ω-16C), those groups in which both $R^{a3}$ and $R^{b3}$ are hydrocarbon groups are referred to as "N,N-di(hydrocarbon)-sulfinamoyl-sulfanyl group," those groups in which both $R^{a3}$ and $R^{b3}$ are heterocyclic groups are referred to as "N,N-di(heterocyclic ring)-sulfinamoyl-sulfanyl group," those groups in which $R^{a3}$ is a hydrocarbon group and $R^{b3}$ is a heterocyclic group are referred to as "N-hydrocarbon-N-heterocyclic ring-sulfinamoyl-sulfanyl group," and those groups in which $R^{a3}$ and $R^{b3}$ combine to each other, together with the nitrogen atom to which they bind, to form a cyclic amino group are referred to as "cyclicamino-sulfanyl-sulfanyl group."

Among the groups represented by the formula (ω-17C), those groups in which $R^{a3}$ is a hydrocarbon group are referred to as "hydrocarbon-oxy-sulfonyl-sulfanyl group," and those groups in which $R^{a3}$ is a heterocyclic group are referred to as "heterocyclic ring-oxy-sulfonyl-sulfanyl group."

Among the groups represented by the formula (ω-18C), those groups in which $R^{a3}$ is a hydrocarbon group are referred to as "hydrocarbon-oxy-sulfinyl-sulfanyl group," and those groups in which $R^{a3}$ is a heterocyclic group are referred to as "heterocyclic ring-oxy-sulfinyl-sulfanyl group."

Among the groups represented by the formula (ω-19C), those groups in which both $R^{a3}$ and $R^{b3}$ are hydrocarbon groups are referred to as "O,O'-di(hydrocarbon)-phosphono-sulfanyl group," those groups in which both $R^{a3}$ and $R^{b3}$ are heterocyclic groups are referred to as "O,O'-di(heterocyclic ring)-phosphono-sulfanyl group," and those groups in which $R^{a3}$ is a hydrocarbon group and $R^{b3}$ is a heterocyclic group are referred to as "O-hydrocarbon-O'-heterocyclic ring-phosphono-sulfanyl group."

Among the groups represented by the formula (ω-20C), those groups in which $R^{a3}$ is a hydrocarbon group are referred to as "hydrocarbon-sulfonyl-sulfanyl group," and those groups in which $R^{a3}$ is a heterocyclic group are referred to as "heterocyclic ring-sulfonyl-sulfanyl group."

Among the groups represented by the formula (ω-21C), those groups in which $R^{a3}$ is a hydrocarbon group are referred to as "hydrocarbon-sulfinyl-sulfanyl group," and those groups in which $R^{a3}$ is a heterocyclic group are referred to as "heterocyclic ring-sulfinyl-sulfanyl group."

Examples of the hydrocarbon in the groups represented by the aforementioned formulas (ω-1C) through (ω-21C) include similar groups to the aforementioned hydrocarbon group. Examples of the hydrocarbon-carbonyl-sulfanyl group represented by the formula (ω-1C) include, for example, an alkyl-carbonyl-sulfanyl group, an alkenyl-carbonyl-sulfanyl group, an alkynyl-carbonyl-sulfanyl group, a cycloalkyl-carbonyl-sulfanyl group, a cycloalkenyl-carbonyl-sulfanyl group, a cycloalkanedienyl-carbonyl-sulfanyl group, a cycloalkyl-alkyl-carbonyl-sulfanyl group which are aliphatic hydrocarbon-carbonyl-sulfanyl groups; an aryl-carbonyl-sulfanyl group; an aralkyl-carbonyl-sulfanyl group; a bridged cyclic hydrocarbon-carbonyl-sulfanyl group; a spiro cyclic hydrocarbon-carbonyl-sulfanyl group; and a terpene family hydrocarbon-carbonyl-sulfanyl group. In the following, groups represented by the formulas (ω-2C) through (ω-21C) are similar to those explained above.

Examples of the heterocyclic ring in the groups represented by the aforementioned formulas (ω-1C) through (ω-21C) include similar groups to the aforementioned heterocyclic group. Examples of the heterocyclic ring-carbonyl-sulfanyl group represented by the formula (ω-1C) include, for example, a monocyclic heteroaryl-carbonyl-sulfanyl group, a fused polycyclic heteroaryl-carbonyl-sulfanyl group, a monocyclic non-aromatic heterocyclic ring-carbonyl-sulfanyl group, and a fused polycyclic non-aromatic heterocyclic ring-carbonyl-sulfanyl group. In the following, groups represented by the formula (ω-2C) through (ω-21C) are similar to those groups explained above.

Examples of the cyclic amino in the groups represented by the aforementioned formulas (ω-10C) through (ω-16C) include similar groups to the aforementioned cyclic amino group.

The aforementioned acyl-sulfanyl group, hydrocarbon-sulfanyl group, and heterocyclic-sulfanyl group are generically referred to as "substituted sulfanyl group." Moreover, these substituted sulfanyl group and sulfanyl group are generically referred to as "sulfanyl group which may be substituted."

Examples of the N-hydrocarbon-amino group include the groups in which one hydrogen atom of amino group is substituted with a hydrocarbon group, and include, for example, an N-alkyl-amino group, an N-alkenyl-amino group, an N-alkynyl-amino group, an N-cycloalkyl-amino group, an N-cycloalkyl-alkyl-amino group, an N-aryl-amino group, and an N-aralkyl-amino group.

Examples of the N-alkyl-amino group include, for example, methylamino, ethylamino, n-propylamino, isopropylamino, n-butylamino, isobutylamino, sec-butylamino, tert-butylamino, n-pentylamino, isopentylamino, (2-methylbutyl)amino, (1-methylbutyl)amino, neopentylamino, (1,2-dimethylpropyl)amino, (1-ethylpropyl)amino, n-hexylamino, (4-methylpentyl)amino, (3-methylpentyl)amino, (2-methylpentyl)amino, (1-methylpentyl)amino, (3,3-dimethylbutyl)amino, (2,2-dimethylbutyl)amino, (1,1-dimethylbutyl)amino, (1,2-dimethylbutyl)amino, (1,3-dimethylbutyl) amino, (2,3-dimethylbutyl)amino, (2-ethylbutyl)amino, (1-ethylbutyl)amino, (1-ethyl-1-methylpropyl)amino, n-heptylamino, n-octylamino, n-nonylamino, n-decylamino, n-undecylamino, n-dodecylamino, n-tridecylamino, n-tetradecylamino, and n-pentadecylamino, which are $C_1$ to $C_{15}$ straight chain or branched chain N-alkyl amino groups.

Examples of the N-alkenyl-amino group include, for example, vinyl amino, (prop-1-en-1-yl)amino, allylamino, isopropenylamino, (but-1-en-1-yl)amino, (but-2-en-1-yl)amino, (but-3-en-1-yl)amino, (2-methylprop-2-en-1-yl)amino, (1-methylprop-2-en-1-yl)amino, (pent-1-en-1-yl)amino, (pent-2-en-1-yl)amino, (pent-3-en-1-yl)amino, (pent-4-en-1-yl)amino, (3-methylbut-2-en-1-yl)amino, (3-methylbut-3-en-1-yl)amino, (hex-1-en-1-yl)amino, (hex-2-en-1-yl)amino, (hex-3-en-1-yl)amino, (hex-4-en-1-yl)amino, (hex-5-en-1-yl)amino, (4-methylpent-3-en-1-yl)amino, (4-methylpent-3-en-1-yl)amino, (hept-1-en-1-yl)amino, (hept-6-en-1-yl)amino, (oct-1-en-1-yl)amino, (oct-7-en-1-yl)amino, (non-1-en-1-yl)amino, (non-8-en-1-yl)amino, (dec-1-en-1-yl)amino, (dec-9-en-1-yl)amino, (undec-1-en-1-yl)amino, (undec-10-en-1-yl)amino, (dodec-1-en-1-yl)amino, (dodec-11-en-1-yl)amino, (tridec-1-en-1-yl)amino, (tridec-12-en-1-yl)amino, (tetradec-1-en-1-yl)amino, (tetradec-13-en-1-yl)amino, (pentadec-1-en-1-yl)amino, and (pentadec-14-en-1-yl)amino, which are $C_2$ to $C_{15}$ straight chain or branched chain N-alkenyl amino groups.

Examples of the N-alkynyl-amino group include, for example, ethynylamino, (prop-1-yn-1-yl)amino, (prop-2-yn-1-yl)amino, (but-1-yn-1-yl)amino, (but-3-yn-1-yl)amino, (1-methylprop-2-yn-1-yl)amino, (pent-1-yn-1-yl)amino, (pent-4-yn-1-yl)amino, (hex-1-yn-1-yl)amino, (hex-5-yn-1-yl)amino, (hept-1-yn-1-yl)amino, (hept-6-yn-1-yl)amino, (oct-1-yn-1-yl)amino, (oct-7-yn-1-yl)amino, (non-1-yn-1-yl)amino, (non-8-yn-1-yl)amino, (dec-1-yn-1-yl)amino, (dec-9-yn-1-yl)amino, (undec-1-yn-1-yl)amino, (undec-10-yn-1-yl)amino, (dodec-1-yn-1-yl)amino, (dodec-11-yn-1-yl)amino, (tridec-1-yn-1-yl)amino, (tridec-12-yn-1-yl)amino, (tetradec-1-yn-1-yl)amino, (tetradec-13-yn-1-yl)amino, (pentadec-1-yn-1-yl)amino, and (pentadec-14-yn-1-yl)amino, which are $C_2$ to $C_{15}$ straight chain or branched chain N-alkynyl-amino groups.

Examples of the N-cycloalkyl-amino group include, for example, cyclopropylamino, cyclobutylamino, cyclopentylamino, cyclohexylamino, cycloheptylamino, and cyclooctylamino, which are $C_3$ to $C_8$ N-cycloalkyl-amino groups.

Examples of the N-cycloalkyl-alkyl-amino group include, for example, (cyclopropylmethyl)amino, (1-cyclopropylethyl)amino, (2-cyclopropylethyl)amino, (3-cyclopropylpropyl)amino, (4-cyclopropylbutyl)amino, (5-cyclopropylpentyl)amino, (6-cyclopropylhexyl)amino, (cyclobutylmethyl)amino, (cyclopentylmethyl)amino, (cyclobutylmethyl)amino, (cyclopentylmethyl)amino, (cyclohexylmethyl)amino, (2-cyclohexylethyl)amino, (3-cyclohexylpropyl)amino, (4-cyclohexylbutyl)amino, (cycloheptylmethyl)amino, (cyclooctylmethyl)amino, and (6-cyclooctylhexyl)amino, which are $C_4$ to $C_{14}$ N-cycloalkyl-alkyl-amino groups.

Examples of the N-aryl-amino group include, for example, phenylamino, 1-naphthylamino, 2-naphtylamino, anthrylamino, phenanthrylamino, and acenaphthylenylamino, which are $C_6$ to $C_{14}$ N-mono-arylamino groups.

Examples of the N-aralkyl-amino group include, for example, benzylamino, (1-naphthylmethyl)amino, (2-naphthylmethyl)amino, (anthracenylmethyl)amino, (phenanthrenylmethyl)amino, (acenaphthylenylmethyl)amino, (diphenylmethyl)amino, (1-phenethyl)amino, (2-phenethyl)amino, (1-(1-naphthyl)ethyl)amino, (1-(2-naphthyl)ethyl)amino, (2-(1-naphthyl)ethyl)amino, (2-(2-naphthyl)ethyl)amino, (3-phenylpropyl)amino, (3-(1-naphthyl)propyl)amino, (3-(2-naphthyl)propyl)amino, (4-phenylbutyl)amino, (4-(1-naphthyl)butyl)amino, (4-(2-naphthyl)butyl)amino, (5-phenylpentyl)amino, (5-(1-naphthyl)pentyl)amino, (5-(2-naphthyl)pentyl)amino, (6-phenylhexyl)amino, (6-(1-naphthyl)hexyl)amino, and (6-(2-naphthyl)hexyl)amino, which are $C_7$ to $C_{16}$ N-aralkyl-amino groups.

Examples of the N,N-di(hydrocarbon)-amino group include the groups in which two hydrogen atoms of amino group are substituted with hydrocarbon groups, and include, for example, N,N-dimethylamino, N,N-diethylamino, N-ethyl-N-methylamino, N,N-di-n-propylamino, N,N-diisopropylamino, N-allyl-N-methylamino, N-(prop-2-yn-1-yl)-N-methylamino, N,N-dicyclohexylamino, N-cyclohexyl-N-methylamino, N-cyclohexylmethylamino-N-methylamino, N,N-diphenylamino, N-methyl-N-phenylamino, N,N-dibenzylamino, and N-benzyl-N-methylamino.

Examples of the N-heterocyclic ring-amino group include the groups in which one hydrogen atom of amino group is substituted with a heterocyclic group, and include, for example, (3-pyrrolizinyl)amino, (4-piperidinyl)amino, (2-tetrahydropyranyl)amino, (3-indolinyl)amino, (4-chromanyl)amino, (3-thienyl)amino, (3-pyridyl)amino, (3-quinolyl)amino, and (5-indolyl)amino.

Examples of the N-hydrocarbon-N-heterocyclic ring-amino group include the groups in which two hydrogen atoms of amino group are substituted with hydrocarbon group and heterocyclic group respectively, and include, for example, N-methyl-N-(4-piperidinyl)amino, N-(4-chromanyl)-N-methylamino, N-methyl-N-(3-thienyl)amino, N-methyl-N-(3-pyridyl)amino, N-methyl-N-(3-quinolyl)amino.

Examples of the acyl-amino group include the groups in which one hydrogen atom of the amino group is substituted with an acyl group, and include, for example, formylamino group, glyoxyloylamino group, thioformylamino group, carbamoylamino group, thiocarbamoylamino group, sulfamoylamino group, sulfinamoylamino group, carboxyamino group, sulphoamino group, phosphonoamino group, and groups represented by the following formulas:

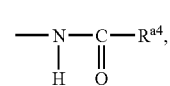
(ω-1D)

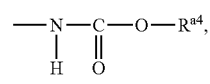
(ω-2D)

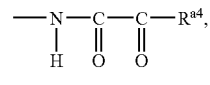
(ω-3D)

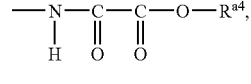
(ω-4D)

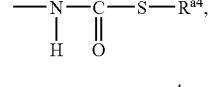
(ω-5D)

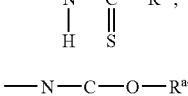
(ω-6D)

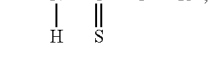
(ω-7D)

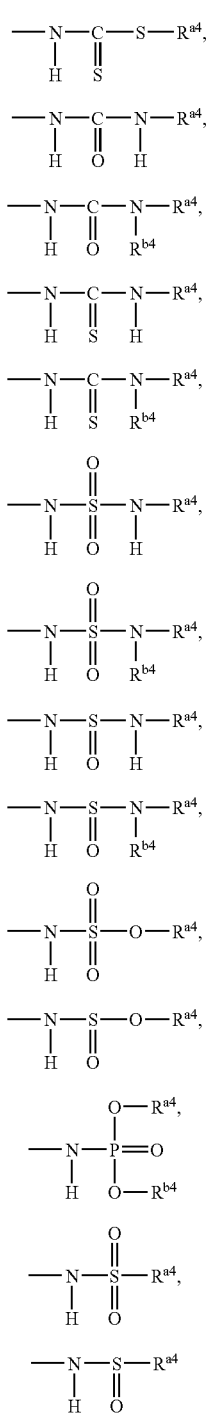

wherein $R^{a4}$ and $R^{b4}$ may be the same or different and represent a hydrocarbon group which may be substituted or a heterocyclic group which may be substituted, or $R^{a4}$ and $R^{b4}$ combine to each other, together with the nitrogen atom to which they bind, to form a cyclic amino group which may be substituted.

In the definition of the aforementioned acyl-amino group, among the groups represented by the formula (ω-1D), those groups in which $R^{a4}$ is a hydrocarbon group are referred to as "hydrocarbon-carbonyl-amino group," and those groups in which $R^{a4}$ is a heterocyclic group are referred to as "heterocyclic ring-carbonyl-amino group."

Among the groups represented by the formula (ω-2D), those groups in which $R^{a4}$ is a hydrocarbon group are referred to as "hydrocarbon-oxy-carbonyl-amino group," and those groups in which $R^{a4}$ is a heterocyclic group are referred to as "heterocyclic ring-oxy-carbonyl-amino group."

Among the groups represented by the formula (ω-3D), those groups in which $R^{a4}$ is a hydrocarbon group are referred to as "hydrocarbon-carbonyl-carbonyl-amino group," and those groups in which $R^{a4}$ is a heterocyclic group are referred to as "heterocyclic ring-carbonyl-carbonyl-amino group."

Among the groups represented by the formula (ω-4D), those groups in which $R^{a4}$ is a hydrocarbon group are referred to as "hydrocarbon-oxy-carbonyl-carbonyl-amino group," and those groups in which $R^{a4}$ is a heterocyclic group are referred to as "heterocyclic ring-oxy-carbonyl-carbonyl-amino group."

Among the groups represented by the formula (ω-5D), those groups in which $R^{a4}$ is a hydrocarbon group are referred to as "hydrocarbon-sulfanyl-carbonyl-amino group," and those groups in which $R^{a4}$ is a heterocyclic group are referred to as "heterocyclic ring-sulfanyl-carbonyl-amino group."

Among the groups represented by the formula (ω-6D), those groups in which $R^{a4}$ is a hydrocarbon group are referred to as "hydrocarbon-thiocarbonyl-amino group," and those groups in which $R^{a4}$ is a heterocyclic group are referred to as "heterocyclic ring-thiocarbonyl-amino group."

Among the groups represented by the formula (ω-7D), those groups in which $R^{a4}$ is a hydrocarbon group are referred to as "hydrocarbon-oxy-thiocarbonyl-amino group," and those groups in which $R^{a4}$ is a heterocyclic group are referred to as "heterocyclic ring-oxy-thiocarbonyl-amino group."

Among the groups represented by the formula (ω-8D), those groups in which $R^{a4}$ is a hydrocarbon group are referred to as "hydrocarbon-sulfanyl-thiocarbonyl-amino group," and those groups in which $R^{a4}$ is a heterocyclic group are referred to as "heterocyclic ring-sulfanyl-thiocarbonyl-amino group."

Among the groups represented by the formula (ω-9D), those groups in which $R^{a4}$ is a hydrocarbon group are referred to as "N-hydrocarbon-carbamoyl group," and those groups in which $R^{a4}$ is a heterocyclic group are referred to as "N-heterocyclic ring-carbamoyl-amino group."

Among the groups represented by the formula (ω-10D), those groups in which both $R^{a4}$ and $R^{b4}$ are hydrocarbon groups are referred to as "N,N-di(hydrocarbon)-carbamoyl-amino group," those groups in which both $R^{a4}$ and $R^{b4}$ are heterocyclic groups are referred to as "N,N-di(heterocyclic ring)-carbamoyl-amino group," those groups in which $R^{a4}$ is a hydrocarbon group and $R^{b4}$ is a heterocyclic group are referred to as "N-hydrocarbon-N-heterocyclic ring-carbamoyl-amino group," and those groups in which $R^{a4}$ and $R^{b4}$ combine to each other, together with the nitrogen atom to which they bind, to form a cyclic amino group are referred to as "cyclic amino-carbonyl-amino group."

Among the groups represented by the formula (ω-11D), those groups in which $R^{a4}$ is a hydrocarbon group are referred to as "N-hydrocarbon-thiocarbamoyl-amino group," and those groups in which $R^{a4}$ is a heterocyclic ring group are referred to as "N-heterocyclic-thiocarbamoyl-amino group."

Among the groups represented by the formula (ω-12D), those groups in which both $R^{a4}$ and $R^{b4}$ are hydrocarbon groups are referred to as "N,N-di(hydrocarbon)-thiocarbamoyl-amino group," those groups in which both $R^{a4}$ and $R^{b4}$ are heterocyclic groups are referred to as "N,N-di(heterocyclic ring)-thiocarbamoyl-amino group," those groups in which $R^{a4}$ is a hydrocarbon group and $R^{b4}$ is a heterocyclic group are referred to as "N-hydrocarbon-N-heterocyclic ring-thiocarbamoyl-amino group," and those groups in which $R^{a4}$ and $R^{b4}$ combine to each other, together with the nitrogen atom to which they bind, to form a cyclic amino group are referred to as "cyclic amino-thiocarbonyl-amino group."

Among the groups represented by the formula (ω-13D), those groups in which $R^{a4}$ is a hydrocarbon group are referred to as "N-hydrocarbon-sulfamoyl-amino group," and those groups in which $R^{a4}$ is a heterocyclic group are referred to as "N-heterocyclic ring-sulfamoyl-amino group."

Among the groups represented by the formula (ω-14D), those groups in which both $R^{a4}$ and $R^{b4}$ are hydrocarbon groups are referred to as "di(hydrocarbon)-sulfamoyl-amino group," those groups in which both $R^{a4}$ and $R^{b4}$ are heterocyclic groups are referred to as "N,N-di(heterocyclic ring)-sulfamoyl-amino group," those groups in which $R^{a4}$ is a hydrocarbon group and $R^{b4}$ is a heterocyclic group are referred to as "N-hydrocarbon-N-heterocyclic ring-sulfamoyl-amino group," and those groups in which $R^{a4}$ and $R^{b4}$ combine to each other, together with the nitrogen atom to which they bind, to form a cyclic amino group are referred to as "cyclic amino-sulfonyl-amino group."

Among the groups represented by the formula (ω-15D), those groups in which $R^{a4}$ is a hydrocarbon group are referred to as "N-hydrocarbon-sulfinamoyl-amino group," and those groups in which $R^{a4}$ is a heterocyclic group are referred to as "N-heterocyclic ring-sulfinamoyl-amino group."

Among the groups represented by the formula (ω-16D), those groups in which both $R^{a4}$ and $R^{b4}$ are hydrocarbon groups are referred to as "N,N-di(hydrocarbon)-sulfinamoyl-amino group," those groups in which both $R^{a4}$ and $R^{b4}$ are heterocyclic groups are referred to as "N,N-di(heterocyclic ring)-sulfinamoyl-amino group," groups in which $R^{a4}$ is a hydrocarbon group and $R^{b4}$ is a heterocyclic group are referred to as "N-hydrocarbon-N-heterocyclic ring-sulfinamoyl-amino group," and those groups in which $R^{a4}$ and $R^{b4}$ combine to each other, together with the nitrogen atom to which they bind, to form a cyclic amino group are referred to as "cyclic amino-sulfinyl-amino group."

Among the groups represented by the formula (ω-17D), those groups in which $R^{a4}$ is a hydrocarbon group are referred to as "hydrocarbon-oxy-sulfonyl-amino group," and those groups in which $R^{a4}$ is a heterocyclic group are referred to as "heterocyclic ring-oxy-sulfoyl-amino group."

Among the groups represented by the formula (ω-18D), those groups in which $R^{a4}$ is a hydrocarbon group are referred to as "hydrocarbon-oxy-sulfinyl-amino group," and those groups in which $R^{a4}$ is a heterocyclic group are referred to as "heterocyclic ring-oxy-sulfinyl-amino group."

Among the groups represented by the formula (ω-19D), those groups in which both $R^{a4}$ and $R^{b4}$ are hydrocarbon groups are referred to as "O,O'-di(hydrocarbon)-phosphono-amino group," those groups in which both $R^{a4}$ and $R^{b4}$ are heterocyclic groups are referred to as "O,O'-di(heterocyclic ring)-phosphono-amino group," and those groups in which $R^{a4}$ is a hydrocarbon group and $R^{b4}$ is a heterocyclic group are referred to as "O-hydrocarbon-O'-heterocyclic ring-phosphono-amino group."

Among the groups represented by the formula (ω-20D), those groups in which $R^{a4}$ is a hydrocarbon group are referred to as "hydrocarbon-sulfonyl-amino group," and those groups in which $R^{a4}$ is a heterocyclic group are referred to as "heterocyclic ring-sulfonyl-amino group."

Among the groups represented by the formula (ω-21D), those groups in which $R^{a4}$ is a hydrocarbon group are referred to as "hydrocarbon-sulfinyl-amino group," and those groups in which $R^{a4}$ is a heterocyclic group are referred to as "heterocyclic ring-sulfinyl-amino group."

Examples of the hydrocarbon in the groups represented by the aforementioned formulas (ω-1D) through (ω-21D) include the similar groups to the aforementioned hydrocarbon group. Examples of the hydrocarbon-carbonyl-amino groups represented by the formula (ω-1D) include, for example, an alkyl-carbonyl-amino group, an alkenyl-carbonyl-amino group, an alkynyl-carbonyl-amino group, a cycloalkyl-carbonyl-amino group, a cycloalkenyl-carbonyl-amino group, a cycloalkanedienyl-carbonyl-amino group, a cycloalkyl-alkyl-carbonyl-amino group which are aliphatic hydrocarbon-carbonyl-amino groups; an aryl-carbonyl-amino group; an aralkyl-carbonyl-amino group; a bridged cyclic hydrocarbon-carbonyl-amino group; a spiro cyclic hydrocarbon-carbonyl-amino group; and a terpene family hydrocarbon-carbonyl-amino group. In the following, groups represented by the formulas (ω-2D) through (ω-21D) are similar to those explained above.

Examples of the heterocyclic ring in the groups represented by the aforementioned formulas (ω-1D) through (ω-21D) include similar groups to the aforementioned heterocyclic group. Examples of the heterocyclic ring-carbonyl-amino group represented by the formula (ω-1D) include, for example, a monocyclic heteroaryl-carbonyl-amino group, a fused polycyclic heteroaryl-carbonyl-amino group, a monocyclic non-aromatic heterocyclic-carbonyl-amino group, and a fused polycyclic non-aromatic heterocyclic-carbonyl-amino group. In the following, groups represented by the formulas (ω-2D) through (ω-21D) are similar to those groups explained above.

Examples of the cyclic amino in the groups represented by the aforementioned formulas (ω-10D) through (ω-16D) include similar groups to the aforementioned cyclic amino group.

Examples of the di(acyl)-amino group include the groups in which two hydrogen atoms of amino group are substituted with acyl groups in the definitions of the aforementioned substitutents according to "which may be substituted." Examples include, for example, di(formyl)-amino group, di(glyoxyloyl)-amino group, di(thioformyl)-amino group, di(carbamoyl)-amino group, di(thiocarbamoyl)-amino group, di(sulfamoyl)-amino group, di(sulfinamoyl)-amino group, di(carboxy)-amino group, di(sulfo)-amino group, di(phosphono)-amino group, and groups represented by the following formulas:

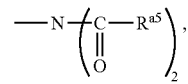
(ω-1E)

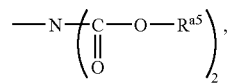
(ω-2E)

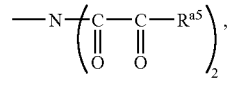
(ω-3E)

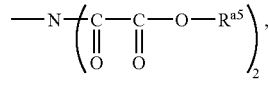
(ω-4E)

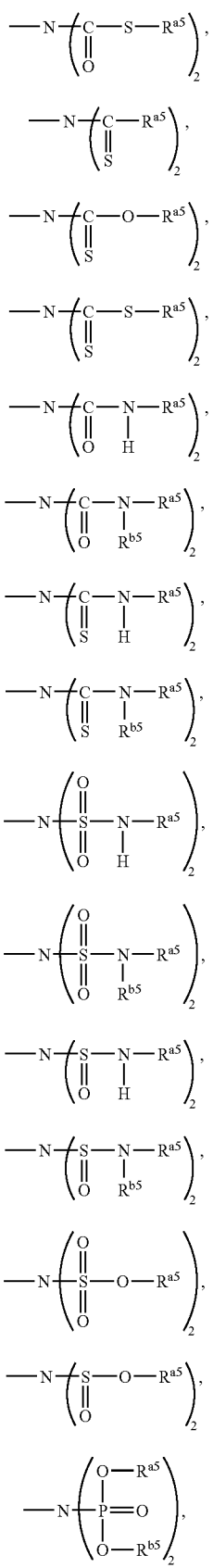

wherein $R^{a5}$ and $R^{b5}$ may be the same or different and represent hydrogen atom, a hydrocarbon group which may be substituted or a heterocyclic group which may be substituted, or $R^{a5}$ and $R^{b5}$ combine to each other, together with the nitrogen atom to which they bind, to form a cyclic amino group which may be substituted.

In the definition of aforementioned di(acyl)-amino group, among the groups represented by the formula (ω-1E), those groups in which $R^{a5}$ is a hydrocarbon group are referred to as "bis(hydrocarbon-carbonyl)-amino group," and those groups in which $R^{a5}$ is a heterocyclic group are referred to as "bis(heterocyclic ring-carbonyl)-amino group."

Among the groups represented by the formula (ω-2E), those groups in which $R^{a5}$ is a hydrocarbon group are referred to as "bis(hydrocarbon-oxy-carbonyl)-amino group," and those groups in which $R^{a5}$ is a heterocyclic group are referred to as "bis(heterocyclic ring-oxy-carbonyl)-amino group."

Among the groups represented by the formula (ω-3E), those groups in which $R^{a5}$ is a hydrocarbon group are referred to as "bis(hydrocarbon-carbonyl-carbonyl)-amino group," and those groups in which $R^{a5}$ is a heterocyclic group are referred to as "bis(heterocyclic ring-carbonyl-carbonyl)-amino group."

Among the groups represented by the formula (ω-4E), those groups in which $R^{a5}$ is a hydrocarbon group are referred to as "bis(hydrocarbon-oxy-carbonyl-carbonyl)-amino group," and those groups in which $R^{a5}$ is a heterocyclic group are referred to as "bis(heterocyclic ring-oxy-carbonyl-carbonyl)-amino group."

Among the groups represented by the formula (ω-5E), those groups in which $R^{a5}$ is a hydrocarbon group are referred to as "bis(hydrocarbon-sulfanyl-carbonyl)-amino group," and those groups in which $R^{a5}$ is a heterocyclic group are referred to as "bis(heterocyclic ring-sulfanyl-carbonyl)-amino group."

Among the groups represented by the formula (ω-6E), those groups in which $R^{a5}$ is a hydrocarbon group are referred to as "bis(hydrocarbon-thiocarbonyl)-amino group," and those groups in which $R^{a5}$ is a heterocyclic group are referred to as "bis(heterocyclic ring-thiocarbonyl)-amino group."

Among the groups represented by the formula (ω-7E), those groups in which $R^{a5}$ is a hydrocarbon group are referred to as "bis(hydrocarbon-oxy-thiocarbonyl)-amino group," and those groups in which $R^{a5}$ is a heterocyclic group are referred to as "bis(heterocyclic ring-oxy-thiocarbonyl)-amino group."

Among the groups represented by the formula (ω-8E), those groups in which $R^{a5}$ is a hydrocarbon group are referred to as "bis(hydrocarbon-sulfanyl-thiocarbonyl)-amino group," and those groups in which $R^{a5}$ is a heterocyclic group are referred to as "bis(heterocyclic ring-sulfanyl-thiocarbonyl)-amino group."

Among the groups represented by the formula (ω-9E), those groups in which $R^{a5}$ is a hydrocarbon group are referred to as "bis(N-hydrocarbon-carbamoyl)-amino group," and those groups in which $R^{a5}$ is a heterocyclic group are referred to as "bis(N-heterocyclic ring-carbamoyl)-amino group."

Among the groups represented by the formula (ω-10E), those groups in which both $R^{a5}$ and $R^{b5}$ are hydrocarbon groups are referred to as "bis[N,N-di(hydrocarbon)-carbamoyl]-amino group," those groups in which both $R^{a5}$ and $R^{b5}$ are heterocyclic groups are referred to as "bis[N,N-di(heterocyclic ring)-carbamoyl]-amino group," groups in which $R^{a5}$ is a hydrocarbon group and $R^{b5}$ is a heterocyclic group are referred to as "bis(N-hydrocarbon-N-heterocyclic ring-carbamoyl)-amino group," and those groups in which $R^{a5}$ and $R^{b5}$ combine to each other, together with the nitrogen atom to which they bind, to form a cyclic amino groups are referred to as "bis(cyclic amino-carbonyl)amino group."

Among the groups represented by the formula (ω-11E), those groups in which $R^{a5}$ is a hydrocarbon group are referred to as "bis(N-hydrocarbon-thiocarbamoyl)-amino group," and those groups in which $R^{a5}$ is a heterocyclic group are referred to as "bis(N-heterocyclic ring-thiocarbamoyl)-amino group."

Among the groups represented by the formula (ω-12E), those groups in which both $R^{a5}$ and $R^{b5}$ are hydrocarbon groups are referred to as "bis[N,N-di(hydrocarbon)-thiocarbamoyl]-amino group," those groups in which both $R^{a5}$ and $R^{b5}$ are heterocyclic groups are referred to as "bis[N,N-di(heterocyclic ring)-thiocarbamoyl]-amino group," those groups in which $R^{a5}$ is a hydrocarbon group and $R^{b5}$ is a heterocyclic group are referred to as "bis(N-hydrocarbon-N-heterocyclic ring-thiocarbamoyl)-amino group," and those groups in which $R^{a5}$ and $R^{b5}$ combine to each other, together with the nitrogen atom to which they bind, to form a cyclic amino group are referred to as "bis(cyclic amino-thiocarbonyl)-amino group."

Among the groups represented by the formula (ω-13E), those groups in which $R^{a5}$ is a hydrocarbon group are referred to as "bis(N-hydrocarbon-sulfamoyl)-amino group," and those groups in which $R^{a5}$ is a heterocyclic group are referred to as "bis(N-heterocyclic ring-sulfamoyl)-amino group."

Among the groups represented by the formula (ω-14E), those groups in which both $R^{a5}$ and $R^{b5}$ are hydrocarbon groups are referred to as "bis[N,N-di(hydrocarbon)-sulfamoyl]-amino group," those groups in which both $R^{a5}$ and $R^{b5}$ are heterocyclic groups are referred to as "bis[N,N-di(heterocyclic ring)-sulfamoyl]-amino group," those groups in which $R^{a5}$ is a hydrocarbon group and $R^{b5}$ is a heterocyclic group are referred to as "bis(N-hydrocarbon-N-heterocyclic ring-sulfamoyl)-amino group," and those groups in which $R^{a5}$ and $R^{b5}$ combine to each other, together with the nitrogen atom to which they bind, to form a cyclic amino group are referred to as "bis(cyclic amino-sulfonyl)amino group."

Among the groups represented by the formula (ω-15E), those groups in which $R^{a5}$ is a hydrocarbon group are referred to as "bis(N-hydrocarbon-sulfinamoyl)-amino group," and those groups in which $R^{a5}$ is a heterocyclic group are referred to as "bis(N-heterocyclic ring-sulfinamoyl)-amino group."

Among the groups represented by the formula (ω-16E), those groups in which $R^{a5}$ and $R^{b5}$ are hydrocarbon groups are referred to as "bis[N,N-di(hydrocarbon)-sulfinamoyl]-amino group," those groups in which $R^{a5}$ and $R^{b5}$ are heterocyclic groups are referred to as "bis[N,N-di(heterocyclic ring)-sulfinamoyl]-amino group," those groups in which $R^{a5}$ is a hydrocarbon group and $R^{b5}$ is a heterocyclic group are referred to as "bis(N-hydrocarbon-N-heterocyclic ring-sulfinamoyl)-amino group," and those groups in which $R^{a5}$ and $R^{b5}$ combine to each other, together with the nitrogen atom to which they bind, to form a cyclic amino group are referred to as "bis(cyclic amino-sulfinyl)amino group."

Among the groups represented by the formula (ω-17E), those groups in which $R^{a5}$ is a hydrocarbon group are referred to as "bis(hydrocarbon-oxy-sulfonyl)-amino group," and those groups in which $R^{a5}$ is a heterocyclic group are referred to as "bis(heterocyclic ring-oxy-sulfonyl)-amino group."

Among the groups represented by the formula (ω-18E), those groups in which $R^{a5}$ is a hydrocarbon group are referred to as "bis(hydrocarbon-oxy-sulfinyl)-amino group," and those groups in which $R^{a5}$ is a heterocyclic group are referred to as "bis(heterocyclic ring-oxy-sulfinyl)-amino group."

Among the groups represented by the formula (ω-19E), those groups in which both $R^{a5}$ and $R^{b5}$ are hydrocarbon groups are referred to as "bis[O,O'-di(hydrocarbon)-phosphono]-amino group," those groups in which both $R^{a5}$ and $R^{b5}$ are heterocyclic groups are referred to as "bis[O,O'-di(heterocyclic ring)-phosphono]-amino group," and those groups in which $R^{a5}$ is a hydrocarbon group and $R^{b5}$ is a heterocyclic group are referred to as "bis(O-hydrocarbon-O'-heterocyclic ring-phosphono)-amino group."

Among the groups represented by the formula (ω-20E), those groups in which $R^{a5}$ is a hydrocarbon group are referred to as "bis(hydrocarbon-sulfonyl)-amino group," and those groups in which $R^{a5}$ is a heterocyclic group are referred to as "bis(heterocyclic ring-sulfonyl)-amino group."

Among the groups represented by the formula (ω-21E), those groups in which $R^{a5}$ is a hydrocarbon group are referred to as "bis(hydrocarbon-sulfinyl)-amino group," and those groups in which $R^{a5}$ is a heterocyclic group are referred to as "bis(heterocyclic ring-sulfinyl)-amino group."

Examples of the hydrocarbon in the groups represented by the aforementioned formulas (ω-1E) through (ω-21E) include the similar groups to the aforementioned hydrocarbon group. Examples of the bis(hydrocarbon-carbonyl)-amino groups represented by the formula (ω-1E) include, for example, a bis(alkyl-carbonyl)-amino group, a bis(alkenyl-carbonyl)-amino group, a bis(alkynyl-carbonyl)-amino group, a bis(cycloalkyl-carbonyl)-amino group, a bis(cycloalkenyl-carbonyl)-amino group, a bis(cycloalkanedienyl-carbonyl)-amino group, a bis(cycloalkyl-alkyl-carbonyl)-amino group which are bis(aliphatic hydrocarbon-carbonyl)-amino groups; a bis(aryl-carbonyl)-amino group; a bis(aralkyl-carbonyl)-amino group; a bis(bridged cyclic hydrocarbon-carbonyl)-amino group; a bis(spiro cyclic hydrocarbon-carbonyl)-amino group; and a bis(terpene family hydrocarbon-carbonyl)-amino group. In the following, groups represented by the formulas (ω-2E) through (ω-21E) are similar to those explained above.

Examples of the heterocyclic ring in the groups represented by the aforementioned formulas (ω-1E) through (ω-21E) include similar groups to the aforementioned heterocyclic group. Examples of the bis(heterocyclic ring-carbonyl)-amino group represented by the formula (ω-1E) include, for example, a bis(monocyclic heteroaryl-carbonyl)-amino group, a bis(fused polycyclic heteroaryl-carbonyl)-amino group, a bis(monocyclic non-aromatic heterocyclic-carbonyl)-amino group, and a bis(fused polycyclic non-aromatic heterocyclic-carbonyl)-amino group. In the following, groups represented by the formulas (ω-2E) through (ω-21E) are similar to those groups explained above.

Examples of the cyclic amino in the groups represented by the aforementioned formulas (ω-10E) through (ω-16E) include similar groups to the aforementioned cyclic amino group.

The aforementioned acyl-amino group and di(acyl)-amino group are generically referred to as "acyl substituted amino group." Furthermore, the aforementioned N-hydrocarbon-amino group, N,N-di(hydrocarbon)-amino group, N-heterocyclic-amino group, N-hydrocarbon-N-heterocyclic-amino group, cyclic amino group, acyl-amino group, and di(acyl)-amino group are generically referred to as "substituted amino group."

In the following, compounds represented by the aforementioned general formula (I) are explained in details.

"Connecting group whose number of atoms of main chain is 2 to 5" in the definition of X means connecting groups wherein 2 to 5 atoms in a main chain link together between rings Z and E. The aforementioned "number of atoms of the main chain" is counted so as to minimize the number of connecting atoms existing between the rings Z and E, regardless of the presence or absence of hetero atom(s). For example, the number of atoms of 1,2-cyclopentylene is counted as 2, the number of atoms of 1,3-cyclopentylene is counted as 3, the number of atoms of 1,4-phenylene is counted as 4, and the number of atoms of 2,6-pyridine-diyl is counted as 3.

The aforementioned "connecting group whose number of atoms of main chain is 2 to 5" is formed by one functional group selected from the following group of divalent group ζ-1, or formed by combining 2 to 4 functional groups of 1 to 4 kinds selected from the following divalent group ζ-2.

[Divalent group ζ-1] the following formulas:

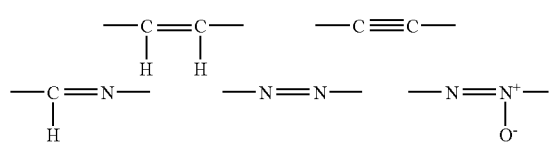

[Divalent group ζ-2] the following formulas:

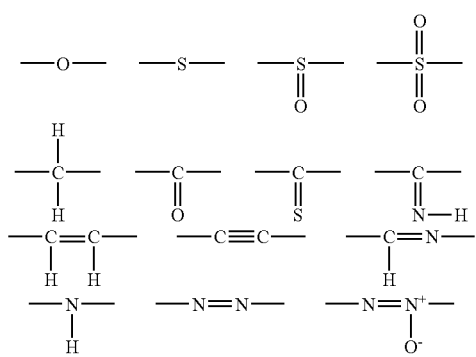

When 2 or more divalent groups combine, each group may be the same or different.

The aforementioned "connecting group wherein the number of atoms of the main chain is 2 to 5," is preferably a group selected from the following "connecting group α."

[Connecting group α] the following formulas:

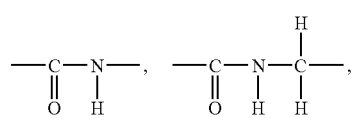

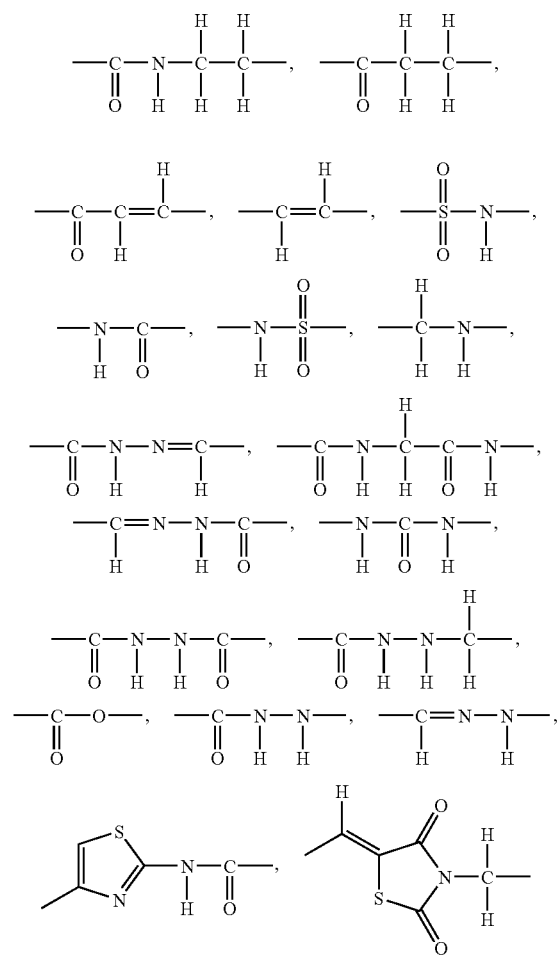

wherein a bond at the left end binds to ring Z and a bond at the right end binds to E.

The group represented by the following formula is most preferred:

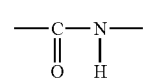

wherein the bond at the left end binds to ring Z and the bond at the right end binds to E.

Examples of the substitutent, according to "connecting group which may be substituted" in the definition of "a connecting group whose number of atoms of the main chain is 2 to 5," include similar groups to the substitutents in the definition of the aforementioned "which may be substituted." A $C_1$ to $C_6$ alkyl group is preferred, and a methyl group is more preferred. The substitutent may combine with a substitutent of the ring E or Z, together with atoms to which they bind, to form a cyclic group which may be substituted. Examples include the compounds represented by the general formula (I) being those represented by the following formulas:

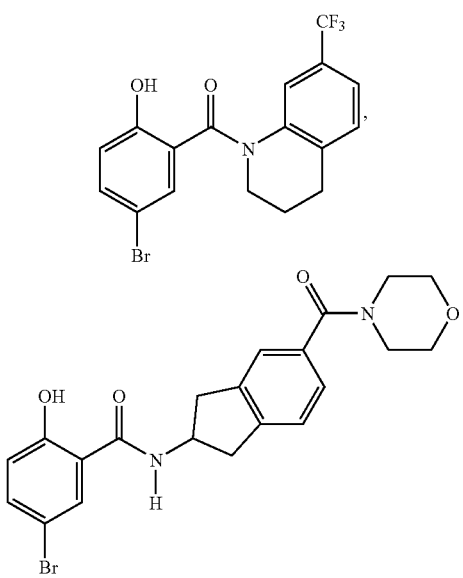

In the aforementioned general formula (I), examples of A include hydrogen atom or acetyl group, and hydrogen atom is preferred.

Examples of the "arene" in "an arene which may have one or more substitutents in addition to the group represented by formula —O-A wherein A has the same meaning as that defined above and the group represented by formula —X-E wherein each of X and E has the same meaning as that defined above" in the definition of ring Z include a monocyclic or fused heterocyclic aromatic hydrocarbon, and include, for example, benzene ring, naphthalene ring, anthracene ring, phenanthrene ring, and acenaphylene ring. $C_6$ to $C_{10}$ arenes such as benzene ring, naphthalene ring and the like are preferred, benzene ring and naphthalene ring are more preferred, and benzene ring is most preferred.

Examples of the substitutent in the definition of "an arene which may have one or more substitutents in addition to the group represented by formula —O-A wherein A has the same meaning as that defined above and the group represented by formula —X-E wherein each of X and E has the same meaning as that defined above" in the aforementioned definition of ring Z include similar groups to the substitutent explained for the definition "which may be substituted." The position of substitutents existing on the arene is not particularly limited, and when two or more substitutents exist, they may be the same or different.

When "an arene which may have one or more substitutents in addition to the group represented by formula —O-A wherein A has the same meaning as that defined above and the group represented by formula —X-E wherein each of X and E has the same meaning as that defined above" in the aforementioned definition of ring Z is "a benzene ring which may have one or more substitutents in addition to the group represented by formula —O-A wherein A has the same meaning as that defined above and the group represented by formula —X-E wherein each of X and E has the same meaning as that defined above," "a benzene ring which has one to three substitutents in addition to the group represented by formula —O-A wherein A has the same meaning as that defined above and the group represented by formula —X-E wherein each of X and E has the same meaning as that defined above" is preferred, and "a benzene ring which has one substitutent in addition to the group represented by formula —O-A wherein A has the same meaning as that defined above and the group represented by formula —X-E wherein each of X and E has the same meaning as that defined above" is more preferred. Preferred examples of said substitutents include groups selected from the following Substituent Group γ-1z. Halogen atom and tert-butyl group [(1,1-dimethyl)ethyl group] are more preferred, and halogen atom is most preferred.

[Substituent Group γ-1z] halogen atom, nitro group, cyano group, hydroxy group, methoxy group, methyl group, isopropyl group, tert-butyl group, 1,1,3,3-tetramethylbutyl group, 2-phenylethen-1-yl group, 2,2-dicyanoethen-1-yl group, 2-cyano-2-(methoxycarbonyl)ethen-1-yl group, 2-carboxy-2-cyanoethen-1-yl group, ethynyl group, phenylethynyl group, (trimethylsilyl)ethynyl group, trifluoromethyl group, pentafluoroethyl group, phenyl group, 4-(trifluoromethyl)phenyl group, 4-fluorophenyl group, 2,4-difluorophenyl group, 2-phenethyl group, 1-hydroxyethyl group, 1-(methoxyimino)ethyl group, 1-[(benzyloxy)imino]ethyl group, 2-thienyl group [thiophen-2-yl group], 3-thienyl group [thiophen-3-yl group], 1-pyrrolyl group [pyrrol-1-yl group], 2-methylthiazol-4-yl group, imidazo[1,2-a]pyridin-2-yl group, 2-pyridyl group [pyridin-2-yl group], acetyl group, isobutyryl group, piperidinocarbonyl group, 4-benzylpiperidinocarbonyl group, (pyrrol-1-yl)sulfonyl group, carboxy group, methoxycarbonyl group, N-[3,5-bis(trifluoromethyl)phenyl]carbamoyl group, N,N-dimethylcarbamoyl group, sulfamoyl group, N-[3,5-bis(trifluoromethyl)phenyl]sulfamoyl group, N,N-dimethylsulfamoyl group, amino group, N,N-dimethylamino group, acetylamino group, benzoylamino group, methanesulfonylamino group, benzenesulfonylamino group, 3-phenylureido group, (3-phenyl)thioureido group, (4-nitrophenyl)diazenyl group, and {[4-(pyridin-2-yl)sulfamoyl]phenyl}diazenyl group When "an arene which may have one or more substitutents in addition to the group represented by formula —O-A wherein A has the same meaning as that defined above and the group represented by formula —X-E wherein each of X and E has the same meaning as that defined above" in the aforementioned definition of ring Z is "a benzene ring which may have one or more substitutents in addition to the group represented by formula —O-A wherein A has the same meaning as that defined above and the group represented by formula —X-E wherein each of X and E has the same meaning as that defined above," it is most preferable that one substitutent exists and locates on the position of $R^z$ when the following partial formula (Iz-1) in the general formula containing ring Z

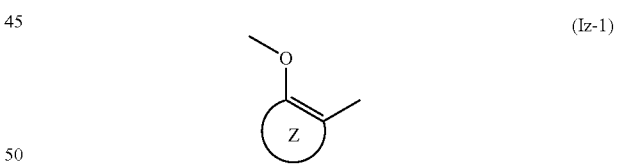

is represented by the following formula (Iz-2).

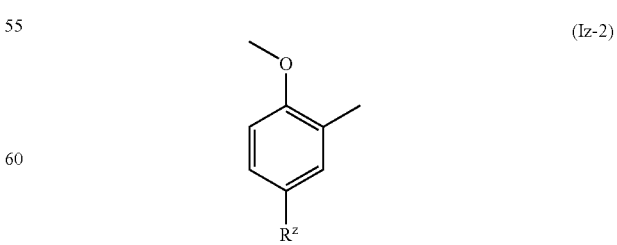

At this time, said substitutents can be defined as $R^z$. Preferred examples of $R^z$ include a group selected from the following Substituent Group γ-2z. Halogen atom and tert-butyl group are more preferred, and halogen atom is most preferred.

[Substituent Group γ-2z] halogen atom, nitro group, cyano group, methoxy group, methyl group, isopropyl group, tert-butyl group, 1,1,3,3-tetramethylbutyl group, 2-phenylethen-1-yl group, 2,2-dicyanoethen-1-yl group, 2-cyano-2-(methoxycarbonyl)ethen-1-yl group, 2-carboxy-2-cyanoethen-1-yl group, ethynyl group, phenylethynyl group, (trimethylsilyl)ethynyl group, trifluoromethyl group, pentafluoroethyl group, phenyl group, 4-(trifluoromethyl)phenyl group, 4-fluorophenyl group, 2,4-difluorophenyl group, 2-phenethyl group, 1-hydroxyethyl group, 1-(methoxyimino)ethyl group, 1-[(benzyloxy)imino]ethyl group, 2-thienyl group, 3-thienyl group, 1-pyrrolyl group, 2-methylthiazol-4-yl group, imidazo[1,2-a]pyridin-2-yl group, 2-pyridyl group, acetyl group, isobutyryl group, piperidinocarbonyl group, 4-benzylpiperidinocarbonyl group, (pyrrol-1-yl)sulfonyl group, carboxy group, methoxycarbonyl group, N-[3,5-bis(trifluoromethyl)phenyl]carbamoyl group, N,N-dimethylcarbamoyl group, sulfamoyl group, N-[3,5-bis(trifluoromethyl)phenyl]sulfamoyl group, N,N-dimethylsulfamoyl group, amino group, N,N-dimethylamino group, acetylamino group, benzoylamino group, methanesulfonylamino group, benzenesulfonylamino group, 3-phenylureido group, (3-phenyl)thioureido group, (4-nitrophenyl)diazenyl group, and {[4-(pyridin-2-yl)sulfamoyl]phenyl}diazenyl group When "an arene which may have one or more substitutents in addition to the group represented by formula —O-A wherein A has the same meaning as that defined above and the group represented by formula —X-E wherein each of X and E has the same meaning as that defined above" in the aforementioned definition of ring Z is "a naphthalene ring which may have one or more substitutents in addition to the group represented by formula —O-A wherein A has the same meaning as that defined above and the group represented by formula —X-E wherein each of X and E has the same meaning as that defined above," naphthalene ring is preferred.

Examples of the "hetero arene" in "a hetero arene which may have one or more substitutents in addition to the group represented by formula —O-A wherein A has the same meaning as that defined above and the group represented by formula —X-E wherein each of X and E has the same meaning as that defined above" in the aforementioned definition of ring Z include a monocyclic or a fused polycyclic aromatic heterocyclic rings containing at least one of 1 to 3 kinds of heteroatoms selected from oxygen atom, sulfur atom and nitrogen atom and the like as ring-constituting atoms (ring forming atoms), and include, for example, furan ring, thiophene ring, pyrrole ring, oxazole ring, isoxazole ring, thiazole ring, isothiazole ring, imidazole ring, pyrazole ring, 1,2,3-oxadiazole ring, 1,2,3-thiadiazole ring, 1,2,3-triazole ring, pyridine ring, pyridazine ring, pyrimidine ring, pyrazine ring, 1,2,3-triazine ring, 1,2,4-triazine ring, 1H-azepine ring, 1,4-oxepine ring, 1,4-thiazepine ring, benzofuran ring, isobenzofuran ring, benzo[b]thiophene ring, benzo[c]thiophene ring, indole ring, 2H-isoindole ring, 1H-indazole ring, 2H-indazole ring, benzoxazole ring, 1,2-benzisoxazole ring, 2,1-benzisoxazole ring, benzothiazole ring, 1,2-benzisothiazole ring, 2,1-benzisothiazole ring, 1,2,3-benzoxadiazol ring, 2,1,3-benzoxadiazol ring, 1,2,3-benzothiadiazole ring, 2,1,3-benzothiadiazole ring, 1H-benzotriazole ring, 2H-benzotriazole ring, quinoline ring, isoquinoline ring, cinnoline ring, quinazoline ring, quinoxaline ring, phthalazine ring, naphthyridine ring, 1H-1,5-benzodiazepine ring, carbazole ring, α-carboline ring, β-carboline ring, γ-carboline ring, acridine ring, phenoxazine ring, phenothiazine ring, phenazine ring, phenanthridine ring, phenanthroline ring, thianthrene ring, indolizine ring, and phenoxathiine ring, which are 5 to 14-membered monocyclic or fused polycyclic aromatic heterocyclic rings. 5 to 13-membered monocyclic or fused polycyclic aromatic heterocyclic rings are preferred, and thiophene ring, pyridine ring, indole ring, quinoxaline ring, and carbazole ring are more preferred.

Examples of the substituent in the definition of "a hetero arene which may have one or more substitutents in addition to the group represented by formula —O-A wherein A has the same meaning as that defined above and the group represented by formula —X-E wherein each of X and E has the same meaning as that defined above" in the aforementioned definition of ring Z include similar groups to the substitutent explained for the aforementioned definition "which may be substituted." The position of substitutents existing on the hetero arene is not particularly limited, and when two or more substitutents exist, they may be the same or different.

Halogen atoms are preferred as the substitutent in the definition of "a hetero arene which may have one or more substitutents in addition to the group represented by formula —O-A wherein A has the same meaning as that defined above and the group represented by formula —X-E wherein each of X and E has the same meaning as that defined above" in the aforementioned definition of ring Z.

Examples of the aryl group of "an aryl group which may be substituted" in the definition of E include similar groups to the aryl group in the definition of the aforementioned "hydrocarbon group," and $C_6$ to $C_{10}$ aryl groups such as phenyl group, 1-naphthyl group, 2-naphthyl group and the like are preferred, and phenyl group is most preferred.

Examples of the substitutent in the definition of "an aryl group which may be substituted" in the definition of E include similar groups to the substitutent explained for the definition "which may be substituted." The position of substitutents existing on the aryl group is not particularly limited, and when two or more substitutents exist, they may be the same or different.

When "an aryl group which may be substituted" in the aforementioned definition of E is "a phenyl group which may be substituted," "a mono-substituted phenyl group," "a di-substituted phenyl group," and "a phenyl group which has three or more substitutents" are preferred, and "a di-substituted phenyl group" is more preferred.

When "an aryl group which may be substituted" in the aforementioned definition of E is "a di-substituted phenyl group," preferred examples of the group include groups represented by the following Substituent Group δ-1e.

[Substituent Group δ-1e] 3,5-bis(trifluoromethyl)phenyl group, 3,4-propylenedioxyphenyl group, 3,5-dichlorophenyl group, 2,4-dihydroxyphenyl group, 2,5-dimethoxyphenyl group, 2-chloro-5-(trifluoromethyl)phenyl group, 3,5-bis[(1,1-dimethyl)ethyl]phenyl group, 2,5-bis(trifluoromethyl)phenyl group, 4-chloro-2-(trifluoromethyl)phenyl group, 2-fluoro-3-(trifluoromethyl)phenyl group, 4-fluoro-3-(trifluoromethyl)phenyl group, 4-chloro-3-(trifluoromethyl)phenyl group, 3-fluoro-5-(trifluoromethyl)phenyl group, 3-bromo-5-(trifluoromethyl)phenyl group, 2-fluoro-5-(trifluoromethyl)phenyl group, 4-nitro-3-(trifluoromethyl)phenyl group, 2-nitro-5-(trifluoromethyl)phenyl group, 4-cyano-3-(trifluoromethyl)phenyl group, 2-methyl-3-(trifluoromethyl)phenyl group, 4-methyl-3-(trifluoromethyl)phenyl group, 2-methyl-5-(trifluoromethyl)phenyl group, 4-methoxy-3-(trifluoromethyl)phenyl group, 3-methoxy-5-(trifluoromethyl)phenyl group, 2-methoxy-5-(trifluoromethyl)phenyl group, 2-methylsulfanyl-5-(trifluoromethyl)phenyl group, 2-(1-pyrrolidinyl)-5-(trifluoromethyl)phenyl group, 2-morpholino-5-(trifluoromethyl)phenyl group, 2-chloro-4-(trifluoromethyl)phenyl group, 2,5-dichlorophenyl group, 3,4-dichlorophenyl group, 3,5-difluorophenyl group, 3,5-dinitrophenyl group, 2,5-bis[(1,1-dimethyl)ethyl]phenyl group, 5-[(1,1-dimethyl)ethyl]-2-methoxyphenyl group, 3,5-dimethylphenyl group, 4-methoxybiphenyl-3-yl group, 3,5-dimethoxyphenyl group, 3,5-bis(methoxycarbonyl)phenyl group, 2-bromo-5-(trifluoromethyl)phenyl group, 3-methoxycarbonyl-5-(trifluoromethyl)phenyl group, 3-carboxy-5-(trifluoromethyl)phenyl group, 2-(2-naphthyloxy)-5-(trifluoromethyl)phenyl group, 2-(2,4-dichlorophenoxy)-5-(trifluoromethyl)phenyl group, 2-[4-(trifluoromethyl)piperidin-1-yl]-5-(trifluoromethyl)phenyl group, 2-(2,2,2-trifluoroethoxy)-5-(trifluoromethyl)phenyl group, 2-(2-methoxyphenoxy)-5-(trifluoromethyl)phenyl group, 2-(4-chloro-3,5-dimethylphenoxy)-5-(trifluoromethyl)phenyl group, 2-piperidino-5-(trifluoromethyl)phenyl group, 2-(4-methylphenoxy)-5-(trifluoromethyl)phenyl group, 2-(4-chlorophenoxy)-5-(trifluoromethyl)phenyl group, 3,5-dicarboxyphenyl group, 5-isopropyl-2-methylphenyl group, 2,5-diethoxyphenyl group, 2,5-dimethylphenyl group, 5-chloro-2-cyano group, 5-diethylsulfamoyl-2-methoxyphenyl group, 2-chloro-5-nitrophenyl group, 2-methoxy-5-(phenylcarbamoyl)phenyl group, 5-acetylamino-2-methoxyphenyl group, 5-methoxy-2-methylphenyl group, 2,5-dibutoxyphenyl group, 2,5-diisopentyloxy group, 5-carbamoyl-2-methoxyphenyl group, 5-[(1,1-dimethyl)propyl]-2-phenoxyphenyl group, 2-hexyloxy-5-methanesulfonyl group, 5-(2,2-dimethylpropionyl)-2-methylphenyl group, 5-methoxy-2-(1-pyrrolyl)phenyl group, 5-chloro-2-(p-toluenesulfonyl)phenyl group, 2-chloro-5-(p-toluenesulfonyl)phenyl group, 2-fluoro-5-methanesulfonyl group, 2-methoxy-5-phenoxy group, 4-methylbiphenyl-3-yl group, 2-methoxy-5-(1-methyl-1-phenylethyl)phenyl group, 5-morpholino-2-nitrophenyl group, 5-fluoro-2-(1-imidazolyl)phenyl group, 2-butyl-5-nitrophenyl group, 5-[(1,1-dimethyl)]propyl-2-hydroxyphenyl group, 2-methoxy-5-methylphenyl group, 2,5-difluorophenyl group, 4-isopropyl-2-(trifluoromethyl)phenyl group, 2-nitro-4-(trifluoromethyl)phenyl group, 4-bromo-3-(trifluoromethyl)phenyl group, 4-bromo-2-(trifluoromethyl)phenyl group, 2-bromo-4-(trifluoromethyl)phenyl group, 4-fluoro-2-(trifluoromethyl)phenyl group, 4-isopropoxy-2-(trifluoromethyl)phenyl group, 4-cyano-2-(trifluoromethyl)phenyl group, 2,6-diisopropylphenyl group, 2,6-dimethylphenyl group, 3,4-dimethylphenyl group, 2,4-dichlorophenyl group, 2,3-dimethylphenyl group, indan-5-yl group, 2,4-dimethylphenyl group, 2,6-dichlorophenyl group, 4-bromo-2-(trifluoromethoxy)phenyl group, 3,4-ethylenedioxyphenyl group, 3-chloro-4-cyanophenyl group, 3-chloro-4-(trifluoromethoxy)phenyl group, 2-chloro-4-cyanophenyl group, 2,3-dichlorophenyl group, 4-isopropyl-3-methylphenyl group, 4-[(1,1-dimethyl)propyl]-2-hydroxyphenyl group, 3-chloro-2-cyanophenyl group, 2-cyano-4-methylphenyl group, 2,2-difluoro-1,3-benzodioxol-4-yl group, 2,2,3,3-tetrafluoro-1,4-benzodioxen-5-yl group, 3-chloro-4-(trifluoromethylsulfanyl)phenyl group, 2-nitro-4-(trifluoromethoxy)phenyl group, 2,2-difluoro-1,3-benzodioxol-5-yl group, 2-methyl-4-(trifluoromethoxy)phenyl group, 4-bromo-2-fluorophenyl group, 2,4-bis(methanesulfonyl)phenyl group, 2,2,3,3-tetrafluoro-1,4-benzodioxen-6-yl group, 2-benzoyl-4-chlorophenyl group, 2-bromo-4-fluorophenyl group, 3,4-dimethoxyphenyl group, 3,4-difluorophenyl group, 3-chloro-4-methoxyphenyl group, 2-chloro-4-nitrophenyl group, 2,4-difluorophenyl group, 2-benzoyl-5-methylphenyl group, 2-bromo-4-(trifluoromethoxy)phenyl group, 3,4-dihexyloxyphenyl group, 2,4-bis(trifluoromethyl)phenyl group, 4-cyano-2-(trifluoromethoxy)phenyl group, 2-(4-cyanophenoxy)-5-(trifluoromethyl)phenyl group, and 2-(4-methoxyphenoxy)-5-(trifluoromethyl)phenyl group When "an aryl group which may be substituted" in the aforementioned definition of E is "a di-substituted phenyl group," "a 2,5-di-substituted phenyl group," and "a 3,5-di-substituted phenyl group" are preferred.

When "an aryl group which may be substituted" in the aforementioned definition of E is "a 2,5-di-substituted phenyl group," preferred examples of the group include groups represented by the following Substituent Group δ-2e.

[Substituent Group δ-2e] 2,5-dimethoxyphenyl group, 2-chloro-5-(trifluoromethyl)phenyl group, 2,5-bis(trifluoromethyl)phenyl group, 2-fluoro-5-(trifluoromethyl)phenyl group, 2-nitro-5-(trifluoromethyl)phenyl group, 2-methyl-5-(trifluoromethyl)phenyl group, 2-methoxy-5-(trifluoromethyl)phenyl group, 2-methylsulfanyl-5-(trifluoromethyl)phenyl group, 2-(1-pyrrolidinyl)-5-(trifluoromethyl)phenyl group, 2-morpholino-5-(trifluoromethyl)phenyl group, 2,5-dichlorophenyl group, 2,5-bis[(1,1-dimethyl)ethyl]phenyl group, 5-[(1,1-dimethyl)ethyl]-2-methoxyphenyl group, 4-methoxybiphenyl-3-yl group, 2-bromo-5-(trifluoromethyl)phenyl group, 2-(2-naphthyloxy)-5-(trifluoromethyl)phenyl group, 2-(2,4-dichlorophenoxy)-5-(trifluoromethyl)phenyl group, 2-[4-(trifluoromethyl)piperidin-1-yl]-5-(trifluoromethyl)phenyl group, 2-(2,2,2-trifluoroethoxy)-5-(trifluoromethyl)phenyl group, 2-(2-methoxyphenoxy)-5-(trifluoromethyl)phenyl group, 2-(4-chloro-3,5-dimethylphenoxy)-5-(trifluoromethyl)phenyl group, 2-piperidino-5-(trifluoromethyl)phenyl group, 2-(4-methylphenoxy)-5-(trifluoromethyl)phenyl group, 2-(4-chlorophenoxy)-5-(trifluoromethyl)phenyl group, 5-isopropyl-2-methylphenyl group, 2,5-diethoxyphenyl group, 2,5-dimethylphenyl group, 5-chloro-2-cyano group, 5-diethylsulfamoyl-2-methoxyphenyl group, 2-chloro-5-nitrophenyl group, 2-methoxy-5-(phenylcarbamoyl)phenyl group, 5-acetylamino-2-methoxyphenyl group, 5-methoxy-2-methylphenyl group, 2,5-dibutoxyphenyl group, 2,5-diisopentyloxy group, 5-carbamoyl-2-methoxyphenyl group, 5-[(1,1-dimethyl)propyl]-2-phenoxyphenyl group, 2-hexyloxy-5-methanesulfonyl group, 5-(2,2-dimethylpropionyl)-2-methylphenyl group, 5-methoxy-2-(1-pyrrolyl)phenyl group, 5-chloro-2-(p-toluenesulfonyl)phenyl group, 2-chloro-5-(p-toluenesulfonyl)phenyl group, 2-fluoro-5-methanesulfonyl group, 2-methoxy-5-phenoxy group, 2-methoxy-5-(1-methyl-1-phenylethyl)phenyl group, 5-morpholino-2-nitrophenyl group, 5-fluoro-2-(1-imidazolyl)phenyl group, 2-butyl-5-nitrophenyl group, 5-[(1,1-dimethyl)propyl]-2-hydroxyphenyl group, 2-methoxy-5-methylphenyl group, 2,5-difluorophenyl group, 2-benzoyl-5-methylphenyl group, 2-(4-cyanophenoxy)-5-(trifluoromethyl)phenyl group, and 2-(4-methoxyphenoxy)-5-(trifluoromethyl)phenyl group When "an aryl group which may be substituted" in the aforementioned definition of E is "a 2,5-di-substituted phenyl group," "a 2,5-di-substituted phenyl group wherein at least one of said substitutents is trifluoromethyl group" is more preferred, a group selected from the following Substituent Group δ-3e is further preferred, and 2,5-bis(trifluoromethyl)phenyl group is most preferred.

[Substituent Group δ-3e] 2-chloro-5-(trifluoromethyl)phenyl group, 2,5-bis(trifluoromethyl)phenyl group, 2-fluoro-5-(trifluoromethyl)phenyl group, 2-nitro-5-(trifluoromethyl)phenyl group, 2-methyl-5-(trifluoromethyl)phenyl group, 2-methoxy-5-(trifluoromethyl)phenyl group, 2-methylsulfanyl-5-(trifluoromethyl)phenyl group, 2-(1-pyrrolidinyl)-5-(trifluoromethyl)phenyl group, 2-morpholino-5-(trifluoromethyl)phenyl group, 2-bromo-5-(trifluoromethyl)phenyl group, 2-(2-naphthyloxy)-5-(trifluoromethyl)phenyl group, 2-(2,4-dichlorophenoxy)-5-(trifluoromethyl)phenyl group, 2-[4-(trifluoromethyl)piperidin-1-yl]-5-(trifluoromethyl) phenyl group, 2-(2,2,2-trifluoroethoxy)-5-(trifluoromethyl) phenyl group, 2-(2-methoxyphenoxy)-5-(trifluoromethyl) phenyl group, 2-(4-chloro-3,5-dimethylphenoxy)-5-(trifluoromethyl)phenyl group, 2-piperidino-5-(trifluoromethyl)phenyl group, 2-(4-methylphenoxy)-5-(trifluoromethyl)phenyl group, 2-(4-chlorophenoxy)-5-(trifluoromethyl)phenyl group, 2-(4-cyanophenoxy)-5-(trifluoromethyl)phenyl group, and 2-(4-methoxyphenoxy)-5-(trifluoromethyl)phenyl group When "an aryl group which may be substituted" in the aforementioned definition of E is "a 3,5-di-substituted phenyl group," preferred examples of the group include groups represented by the following Substituent Group δ-4e.

[Substituent Group δ-4e] 3,5-bis(trifluoromethyl)phenyl group, 3,5-dichlorophenyl group, 3,5-bis[(1,1-dimethyl)ethyl]phenyl group, 3-fluoro-5-(trifluoromethyl)phenyl group, 3-bromo-5-(trifluoromethyl)phenyl group, 3-methoxy-5-(trifluoromethyl)phenyl group, 3,5-difluorophenyl group, 3,5-dinitrophenyl group, 3,5-dimethylphenyl group, 3,5-dimethoxyphenyl group, 3,5-bis(methoxycarbonyl)phenyl group, 3-methoxycarbonyl-5-(trifluoromethyl)phenyl group, 3-carboxy-5-(trifluoromethyl)phenyl group, and 3,5-dicarboxyphenyl group When "an aryl group which may be substituted" in the aforementioned definition of E is "a 3,5-di-substituted phenyl group," "a 3,5-di-substituted phenyl group wherein at least one of said substitutents is trifluoromethyl group" is more preferred, a group selected from the following Substituent Group δ-5e is further preferred, and 3,5-bis(trifluoromethyl) phenyl group is most preferred.

[Substituent Group δ-5e] 3,5-bis(trifluoromethyl)phenyl group, 3-fluoro-5-(trifluoromethyl)phenyl group, 3-bromo-5-(trifluoromethyl)phenyl group, 3-methoxy-5-(trifluoromethyl)phenyl group, 3-methoxycarbonyl-5-(trifluoromethyl) phenyl group, and 3-carboxy-5-(trifluoromethyl)phenyl group When "an aryl group which may be substituted" in the aforementioned definition of E is "a mono-substituted phenyl group," preferred examples of the group include groups represented by the following Substituent Group δ-6e.

[Substituent Group δ-6e] 4-methoxyphenyl group, 4-chlorophenyl group, 2-methoxyphenyl group, 2-(trifluoromethyl) phenyl group, 3-(trifluoromethyl)phenyl group, 4-(trifluoromethyl)phenyl group, 3-chlorophenyl group, biphenyl-3-yl group, 3-acetylphenyl group, 3-(acetylamino)phenyl group, 3-carbamoylphenyl group, 3-methylcarbomoylphenyl group, 4-methylphenyl group, 3-(trifluoromethoxy)phenyl group, 2-benzylphenyl group, 4-(trifluoromethoxy)phenyl group, 4-[(1,1-dimethyl)ethyl]phenyl group, 3-isopropoxyphenyl group, 4-isopropoxyphenyl group, 4-hexylphenyl group, 3-methylphenyl group, 4-cyclohexylphenyl group, 4-benzylphenyl group, 2-chlorophenyl group, 2-methylphenyl group, 4-butylphenyl group, 4-benzyloxyphenyl group, 3-benzylphenyl group, 4-hexyloxyphenyl group, 3-isopropylphenyl group, 4-cyanophenyl group, 3-cyanophenyl group, 4-(ethoxycarbonylmethyl)phenyl group, 3-(trifluoromethyl-sulfanyl)phenyl group, 4-(trifluoromethylsulfanyl)phenyl group, 4-(trifluoromethanesulfonyl)phenyl group, 3-ethynylphenyl group, 4-(1-methylpropyl)phenyl group, 3-benzoylphenyl group, 3-methoxyphenyl group, 4-(acetylamino) phenyl group, 4-sulfamoylphenyl group, 4-difluoromethoxy) phenyl group, 3-methylsulfanylphenyl group, 4-methanesulfonylphenyl group, 3-(butylsulfamoyl)phenyl group, 3-benzyloxyphenyl group, 4-(p-toluenesulfonylamino)phenyl group, 4-morpholinophenyl group, 3-[(1,1-dimethyl)ethyl]phenyl group, 3-(5-methylfuran-2-yl)phenyl group, 3-sulfamoylphenyl group, 3-(trifluoromethanesulfonyl)phenyl group, 3-hexyloxyphenyl group, 4-acetylphenyl group, biphenyl-2-yl group, biphenyl-4-yl group, 3-[5-phenyl-3-(trifluoromethyl)pyrazol-1-yl]phenyl group, 3-{5-[(1,1-dimethyl)ethyl]-3-(trifluoromethyl)pyrazol-1-yl}phenyl group, 4-[3,5-bis(trifluoromethyl)pyrazol-1-yl]phenyl group, 3-[3,5-bis(trifluoromethyl)pyrazol-1-yl]phenyl group, and 4-[5-phenyl-3-(trifluoromethyl)pyrazol-1-yl] phenyl group When "an aryl group which may be substituted" in the aforementioned definition of E is "a phenyl group which has three or more substitutents," preferred examples of the group include groups represented by the following Substituent Group δ-7e.

[Substituent Group δ-7e] 3,5-bis(trifluoromethyl)-2-bromophenyl group, 3,4,5-trichlorophenyl group, 3,5-dichloro-4-hydroxyphenyl group, pentafluorophenyl group, 3,5,5,8,8-pentamethyl-5,6,7,8-tetrahydronaphthalen-2-yl group, 3,5-bis(trifluoromethyl)-2-methylphenyl group, 2,6-dichloro-4-(trifluoromethyl)phenyl group, 2,4-dimethoxy-5-(trifluoromethyl)phenyl group, 2,4-difluoro-5-(trifluoromethyl)phenyl group, 4-chloro-2-(4-chlorobenzenesulfonyl)-5-(trifluoromethyl)phenyl group, 5-chloro-2-nitro-4-(trifluoromethyl)phenyl group, 2,3-difluoro-4-(trifluoromethyl)phenyl group, 2,3,5,6-tetrafluoro-4-(trifluoromethyl)phenyl group, 2,4,6-trimethylphenyl group, 2-cyano-4,5-dimethoxyphenyl group, 2,4-dichloro-5-isopropoxyphenyl group, 2,3,5-trifluorophenyl group, 2,4,5-trichlorophenyl group, and 5-ethoxy-4-fluoro-2-nitrophenyl group When "an aryl group which may be substituted" in the aforementioned definition of E is "a naphthyl group which may be substituted," preferred examples of the group include 1-naphthyl group, 4-methoxynaphthalen-2-yl group, and 4-hydroxy-3-methylnaphthalen-1-yl group.

Examples of the "heteroaryl group" in "a heteroaryl group which may be substituted" in the definition of E include similar groups to the "monocyclic heteroaryl group" and "fused polycyclic heteroaryl group" in the definition of the aforementioned "heterocyclic group." A 5 to 13-membered heteroaryl group is preferred, and preferred examples of the group include thienyl group, pyrazolyl group, oxazolyl group, 1,3,4-thiadiazolyl group, pyridyl group, pyrimidinyl group, indolyl group, quinolyl group, carbazolyl group, thiazolyl group, and pyrazinyl group.

A 5-membered heteroaryl group is more preferred as the "heteroaryl group" in "a heteroaryl group which may be substituted" in the definition of E. Thienyl group, pyrazolyl group, oxazolyl group, 1,3,4-thiadiazolyl group, and thiazolyl group are further preferred, and thiazolyl group is most preferred.

Examples of the substituent in the definition of "a heteroaryl group which may be substituted" in the aforementioned definition of E include similar groups to the substitutent explained for the definition "which may be substituted." The position of substitutents existing on the heteroaryl group is not particularly limited, and when two or more substitutents exist, they may be the same or different.

When "a heteroaryl group which may be substituted" in the aforementioned definition of E is "a thiazolyl group which may be substituted," "a thiazol-2-yl group which may be substituted." "A mono-substituted thiazol-2-yl group" and "a di-substituted thiazol-2-yl group" are more preferred, and "a di-substituted thiazol-2-yl group" is further preferred.

When "a heteroaryl group which may be substituted" in the aforementioned definition of E is "a di-substituted thiazol-2-yl group," a group selected from the following Substituent Group δ-8e is preferred, and 4-[(1,1-dimethyl)ethyl]-5-[(2,2-dimethyl)propionyl]thiazol-2-yl group is most preferred.

[Substituent Group δ-8e] 5-bromo-4-[(1,1-dimethyl)ethyl]thiazol-2-yl group, 5-bromo-4-(trifluoromethyl)thiazol-2-yl group, 5-cyano-4-[(1,1-dimethyl)ethyl]thiazol-2-yl group, 5-methylthiazol-2-yl group, 4,5-dimethylthiazol-2-yl group, 5-methyl-4-phenylthiazol-2-yl group, 5-(4-fluorophenyl)-4-methylthiazol-2-yl group, 4-methyl-5-[3-(trifluoromethyl)phenyl]thiazol-2-yl group, 4-[(1,1-dimethyl)ethyl]-5-ethylthiazol-2-yl group, 4-ethyl-5-phenylthiazol-2-yl group, 4-isopropyl-5-phenylthiazol-2-yl group, 4-butyl-5-phenylthiazol-2-yl group, 4-[(1,1-dimethyl)ethyl]-5-[(2,2-dimethyl)propionyl]thiazol-2-yl group, 4-[(1,1-dimethyl)ethyl]-5-(ethoxycarbonyl)thiazol-2-yl group, 4-[(1,1-dimethyl)ethyl]-5-piperidinothiazol-2-yl group, 4-[(1,1-dimethyl)ethyl]-5-morpholinothiazol-2-yl group, 4-[(1,1-dimethyl)ethyl]-5-(4-methylpiperazin-1-yl)thiazol-2-yl group, 4-[(1,1-dimethyl)ethyl]-5-(4-phenylpiperazin-1-yl)thiazol-2-yl group, 5-carboxymethyl-4-phenylthiazol-2-yl group, 4,5-diphenylthiazol-2-yl group, 4-benzyl-5-phenylthiazol-2-yl group, 5-phenyl-4-(trifluoromethyl)thiazol-2-yl group, 5-acetyl-4-phenylthiazol-2-yl group, 5-benzoyl-4-phenylthiazol-2-yl group, 5-ethoxycarbonyl-4-phenylthiazol-2-yl group, 5-ethoxycarbonyl-4-(pentafluorophenyl)thiazol-2-yl group, 5-methylcarbamoyl-4-phenylthiazol-2-yl group, 5-ethylcarbamoyl-4-phenylthiazol-2-yl group, 5-isopropylcarbamoyl-4-phenylthiazol-2-yl group, 5-(2-phenylethyl)carbamoyl-4-phenylthiazol-2-yl group, 5-ethoxycarbonyl-4-(trifluoromethyl)thiazol-2-yl group, 5-carboxy-4-[(1,1-dimethyl)ethyl]thiazol-2-yl group, 5-(ethoxycarbonyl)methyl-4-phenylthiazol-2-yl group, 5-carboxy-4-phenylthiazol-2-yl group, and 5-propylcarbamoyl-4-phenylthiazol-2-yl group.

When "a heteroaryl group which may be substituted" in the aforementioned definition of E is "a mono-substituted thiazol-2-yl group," preferred examples of the group include groups represented by the following Substituent Group δ-9e.

[Substituent Group δ-9e] 4-[(1,1-dimethyl)ethyl]thiazol-2-yl group, 4-phenylthiazol-2-yl group, 4-[3,5-bis(trifluoromethyl)phenyl]thiazol-2-yl group, 4-(2,4-dichlorophenyl)thiazol-2-yl group, 4-(3,4-dichlorophenyl)thiazol-2-yl group, 4-[4-(trifluoromethyl)phenyl]thiazol-2-yl group, 4-(2,5-difluorophenyl)thiazol-2-yl group, 4-(4-methoxyphenyl)thiazol-2-yl group, 4-[3-(trifluoromethyl)phenyl]thiazol-2-yl group, and 4-(pentafluorophenyl)thiazol-2-yl group The compounds represented by the aforementioned general formula (I-1) are explained in details.

Examples of the substituent in the definition of "2-hydroxyphenyl group which may be substituted in the 5-position" and "2-acetoxyphenyl group which may be substituted in the 5-position" in the definition of $Z^1$ include similar groups to the substituent explained for the definition "which may be substituted."

"2-Hydroxyphenyl group which is substituted in the 5-position" is preferred as the "2-hydroxyphenyl group which may be substituted in the 5-position" in the definition of $Z^1$.

Preferred examples of the substituent in the definition of "2-hydroxyphenyl group which may be substituted in the 5-position" and "2-hydroxyphenyl group which is substituted in the 5-position" in the definition of $Z^1$ include a group selected from the following Substituent Group $\gamma^1$-1z. A halogen atom and tert-butyl group are more preferred, and a halogen atom is most preferred.

[Substituent Group $\gamma^1$-1z] a halogen atom, nitro group, cyano group, methoxy group, methyl group, isopropyl group, tert-butyl group, 1,1,3,3-tetramethylbutyl group, 2-phenylethen-1-yl group, 2,2-dicyanoethen-1-yl group, 2-cyano-2-(methoxycarbonyl)ethen-1-yl group, 2-carboxy-2-cyanoethen-1-yl group, ethynyl group, phenylethynyl group, (trimethylsilyl)ethynyl group, trifluoromethyl group, pentafluoroethyl group, phenyl group, 4-(trifluoromethyl)phenyl group, 4-fluorophenyl group, 2,4-difluorophenyl group, 2-phenethyl group, 1-hydroxyethyl group, 1-(methoxyimino)ethyl group, 1-[(benzyloxy)imino]ethyl group, 2-thienyl group, 3-thienyl group, 1-pyrrolyl group, 2-methylthiazol-4-yl group, imidazo[1,2-a]pyridin-2-yl group, 2-pyridyl group, acetyl group, isobutyryl group, piperidinocarbonyl group, 4-benzylpiperidinocarbonyl group, (pyrrol-1-yl)sulfonyl group, carboxy group, methoxycarbonyl group, N-[3,5-bis(trifluoromethyl)phenyl]carbamoyl group, N,N-dimethylcarbamoyl group, sulfamoyl group, N-[3,5-bis(trifluoromethyl)phenyl]sulfamoyl group, N,N-dimethylsulfamoyl group, amino group, N,N-dimethylamino group, acetylamino group, benzoylamino group, methanesulfonylamino group, benzenesulfonylamino group, 3-phenylureido group, (3-phenyl)thioureido group, (4-nitrophenyl)diazenyl group, and ([4-(pyridin-2-yl)sulfamoyl]phenyl)diazenyl group "2-Acetoxyphenyl group which is substituted in the 5-position" is preferred as the "2-acetoxyphenyl group which may be substituted in the 5-position" in the definition of $Z^1$.

A halogen atom is preferred as the substituent in the definition of "2-acetoxyphenyl group which may be substituted in the 5-position" and "2-acetoxyphenyl group which is substituted in the 5-position" in the definition of $Z^1$.

The definition "which may be substituted" in the definition of "a phenyl group which may be substituted" in the definition of $E^1$ has the same meaning as "which may be substituted."

Examples of the substituent in the definition of "a phenyl group which may be substituted" in the definition of $E^1$ include similar groups to the substituents explained for the definition "which may be substituted." A position of a substituent existing on the phenyl group is not particularly limited, and when two or more substituents exist, they may be the same or different.

Preferred examples of "a phenyl group which may be substituted" in the definition of $E^1$ include 3,5-bis(trifluoromethyl)phenyl group, 2,5-bis(trifluoromethyl)phenyl group, a phenyl group which has three or more substituents wherein at least one of said substituents is trifluoromethyl group, and a di-substituted phenyl group wherein at least one of said substituents is trifluoromethyl group, (provided that a 2,5-di-substituted phenyl group and a 3,5-di-substituted phenyl group are excluded as said di-substituted phenyl group.) 3,5-Bis(trifluoromethyl)phenyl group and 2,5-bis(trifluoromethyl)phenyl group are more preferred.

When "a phenyl group which may be substituted" in the definition of $E^1$ is "a phenyl group which has three or more substituents wherein at least one of said substituents is trifluoromethyl group," preferred examples of the group include groups represented by the following Substituent Group $\delta^1$-1e.

[Substituent Group $\delta^1$-1e] 3,5-bis(trifluoromethyl)-2-bromophenyl group, 3,5-bis(trifluoromethyl)-2-methylphenyl group, 2,6-dichloro-4-(trifluoromethyl)phenyl group, 2,4-dimethoxy-5-(trifluoromethyl)phenyl group, 2,4-difluoro-5-(trifluoromethyl)phenyl group, 4-chloro-2-(4-chlorobenzenesulfonyl)-5-(trifluoromethyl)phenyl group, 5-chloro-2-nitro-4-(trifluoromethyl)phenyl group, 2,3-difluoro-4-

(trifluoromethyl)phenyl group, and 2,3,5,6-tetrafluoro-4-(trifluoromethyl)phenyl group When "a phenyl group which may be substituted" in the definition of $E^1$ is "a di-substituted phenyl group wherein at least one of said substitutents is trifluoromethyl group, (provided that a 2,5-di-substituted phenyl group and a 3,5-di-substituted phenyl group are excluded from said di-substituted phenyl group)" preferred examples of the group include groups represented by the following Substituent Group $\delta^1$-2e.

[Substituent Group $\delta^1$-2e] 4-chloro-2-(trifluoromethyl)phenyl group, 2-fluoro-3-(trifluoromethyl)phenyl group, 4-fluoro-3-(trifluoromethyl)phenyl group, 4-chloro-3-(trifluoromethyl)phenyl group, 4-nitro-3-(trifluoromethyl)phenyl group, 4-cyano-3-(trifluoromethyl)phenyl group, 2-methyl-3-(trifluoromethyl)phenyl group, 4-methyl-3-(trifluoromethyl)phenyl group, 4-methoxy-3-(trifluoromethyl)phenyl group, 2-chloro-4-(trifluoromethyl)phenyl group, 4-isopropyl-2-(trifluoromethyl)phenyl group, 2-nitro-4-(trifluoromethyl)phenyl group, 4-bromo-3-(trifluoromethyl)phenyl group, 4-bromo-2-(trifluoromethyl)phenyl group, 2-bromo-4-(trifluoromethyl)phenyl group, 4-fluoro-2-(trifluoromethyl)phenyl group, 4-isopropoxy-2-(trifluoromethyl)phenyl group, 4-cyano-2-(trifluoromethyl)phenyl group, and 2,4-bis(trifluoromethyl)phenyl group Compounds represented by the aforementioned general formula (I-2) are explained in details.

Examples of the substitutent in the definition of "2-hydroxyphenyl group which may be substituted in the 5-position" and "2-acetoxyphenyl group which may be substituted in the 5-position" in the definition of $Z^2$ include similar groups to the substitutent explained for the definition "which may be substituted."

"2-Hydroxyphenyl group which is substituted in the 5-position" is preferred as the "2-hydroxyphenyl group which may be substituted in the 5-position" in the definition of $Z^2$.

A halogen atom, nitro group, methyl group, and methoxy group are preferred as the substitutent in the definition of "2-hydroxyphenyl group which may be substituted in the 5-position" and "2-hydroxyphenyl group which is substituted in the 5-position" in the definition of $Z^2$, and a halogen atom is most preferred.

"2-Acetoxyphenyl group which is substituted in the 5-position" is preferred as the "2-acetoxyphenyl group which may be substituted in the 5-position" in the definition of $Z^2$.

A halogen atom is preferred as the substitutent in the definition of "2-acetoxyphenyl group which may be substituted in the 5-position" and "2-acetoxyphenyl group which is substituted in the 5-position" in the definition of $Z^2$.

Examples of the substitutent in the definition of "a 2,5-di-substituted phenyl group wherein one of said substitutents is trifluoromethyl group" and "a 3,5-di-substituted phenyl group wherein one of said substitutents is trifluoromethyl group" in the definition of $E^2$ include similar groups to the substitutent explained for the definition "which may be substituted."

A group selected from the following Substituent Group $\delta^2$-1e is preferred as "a 2,5-di-substituted phenyl group wherein one of said substitutents is trifluoromethyl group" in the definition of $E^2$.

[Substituent Group $\delta^2$-1e] 2-chloro-5-(trifluoromethyl)phenyl group, 2,5-bis(trifluoromethyl)phenyl group, 2-fluoro-5-(trifluoromethyl)phenyl group, 2-nitro-5-(trifluoromethyl)phenyl group, 2-methyl-5-(trifluoromethyl)phenyl group, 2-methoxy-5-(trifluoromethyl)phenyl group, 2-methylsulfanyl-5-(trifluoromethyl)phenyl group, 2-(1-pyrrolidinyl)-5-(trifluoromethyl)phenyl group, 2-morpholino-5-(trifluoromethyl)phenyl group, 2-bromo-5-(trifluoromethyl)phenyl group, 2-(2-naphthyloxy)-5-(trifluoromethyl)phenyl group, 2-(2,4-dichlorophenoxy)-5-(trifluoromethyl)phenyl group, 2-[4-(trifluoromethyl)piperidin-1-yl]-5-(trifluoromethyl)phenyl group, 2-(2,2,2-trifluoroethoxy)-5-(trifluoromethyl)phenyl group, 2-(2-methoxyphenoxy)-5-(trifluoromethyl)phenyl group, 2-(4-chloro-3,5-dimethylphenoxy)-5-(trifluoromethyl)phenyl group, 2-piperidino-5-(trifluoromethyl)phenyl group, 2-(4-methylphenoxy)-5-(trifluoromethyl)phenyl group, 2-(4-chlorophenoxy)-5-(trifluoromethyl)phenyl group, 2-(4-cyanophenoxy)-5-(trifluoromethyl)phenyl group, and 2-(4-methoxyphenoxy)-5-(trifluoromethyl)phenyl group A group selected from the following Substituent Group $\delta^2$-2e is preferred as "a 3,5-di-substituted phenyl group wherein one of said substitutents is trifluoromethyl group" in the definition of $E^2$.

[Substituent Group $\delta^2$-2e] 3,5-bis(trifluoromethyl)phenyl group, 3-fluoro-5-(trifluoromethyl)phenyl group, 3-bromo-5-(trifluoromethyl)phenyl group, 3-methoxy-5-(trifluoromethyl)phenyl group, 3-methoxycarbonyl-5-(trifluoromethyl)phenyl group, and 3-carboxy-5-(trifluoromethyl)phenyl group Compounds represented by the aforementioned general formula (I-3) are explained in details.

Examples of the substitutent in the definition of "2-hydroxyphenyl group which may be substituted in the 5-position" and "2-acetoxyphenyl group which may be substituted in the 5-position" in the definition of $Z^3$ include similar groups to the substitutent explained for the definition "which may be substituted."

"2-Hydroxyphenyl group which is substituted in the 5-position" is preferred as the "2-hydroxyphenyl group which may be substituted in the 5-position" in the definition of $Z^3$.

A halogen atom, nitro group, methyl group and methoxy group are preferred as the substitutent in the definition of "2-hydroxyphenyl group which may be substituted in the 5-position" and "2-hydroxyphenyl group which is substituted in the 5-position" in the definition of $Z^3$, and a halogen atom is most preferred.

"2-Acetoxyphenyl group which is substituted in the 5-position" is preferred as the "2-acetoxyphenyl group which may be substituted in the 5-position" in the definition of $Z^3$.

A halogen atom is preferred as the substitutent in the definition of "2-acetoxyphenyl group which may be substituted in the 5-position" and "2-acetoxyphenyl group which is substituted in the 5-position" in the definition of $Z^3$.

Examples of the substitutent in the definition of "a hydrocarbon group which may be substituted" in the definition of $R^{3e2}$ and $R^{3e3}$ and "a $C_2$ to $C_6$ hydrocarbon group which may be substituted" in the definition of $R^{3e5}$ include similar groups to the substitutent explained for the definition "which may be substituted."

Examples of the "hydrocarbon group" in the definition of "a hydrocarbon group which may be substituted" in the definition of $R^{3e2}$ and $R^{3e3}$ and "a $C_2$ to $C_6$ hydrocarbon group which may be substituted" in the definition of $R^{3e5}$ include similar groups to the "hydrocarbon group" in the aforementioned definition.

Examples of the "hydroxy group which may be substituted" in the definition of $R^{3e2}$ and $R^{3e3}$ include similar groups to the "hydroxy group which may be substituted" explained for the definition "which may be substituted."

As $E^3$, 3,5-bis[(1,1-dimethyl)ethyl]phenyl group, 2,5-bis[(1,1-dimethyl)ethyl]phenyl group, 5-[(1,1-dimethyl)ethyl]-2-methoxyphenyl group, 4-methoxybiphenyl-3-yl group, 5-[(1,1-dimethyl)propyl]-2-phenoxyphenyl group, 4-methylbiphenyl-3-yl group and 5-[(1,1-dimethyl)propyl]-2-hydroxyphenyl group are preferred, and 3,5-bis[(1,1-dimethyl)ethyl]phenyl group is more preferred.

Compounds represented by the aforementioned general formula (I-4) are explained in details.

Examples of the substituent in the definition of "2-hydroxyphenyl group which may be substituted in the 5-position" and "2-acetoxyphenyl group which may be substituted in the 5-position" in the definition of $Z^4$ include similar groups to the substituent explained for the definition "which may be substituted."

"2-Hydroxyphenyl group which is substituted in the 5-position" is preferred as the "2-hydroxyphenyl group which may be substituted in the 5-position" in the definition of $Z^4$.

A halogen atom, phenyl group, 4-fluorophenyl group, 2,4-difluorophenyl group, 4-(trifluoromethyl)phenyl group, 1-pyrrolyl group and 2-thienyl group are preferred as the substitutent in the definition of "2-hydroxyphenyl group which may be substituted in the 5-position" and "2-hydroxyphenyl group which is substituted in the 5-position" in the definition of $Z^4$, and a halogen atom is most preferred.

"2-Acetoxyphenyl group which is substituted in the 5-position" is preferred as the "2-acetoxyphenyl group which may be substituted in the 5-position" in the definition of $Z^4$.

A halogen atom is preferred as the substitutent in the definition of "2-acetoxyphenyl group which may be substituted in the 5-position" and "2-acetoxyphenyl group which is substituted in the 5-position" in the definition of $Z^4$.

Examples of the substitutent in the definition of "a hydrocarbon group which may be substituted" in the definition of $R^{4e4}$, and "an acyl group which may be substituted" and "a heterocyclic group which may be substituted" in the definition of $R^{4e5}$ include similar groups to the substitutent explained for the definition "which may be substituted."

Examples of the "hydrocarbon group" in the definition of "a hydrocarbon group which may be substituted" in the definition of $R^{4e4}$ include similar groups to the "hydrocarbon group" in the aforementioned definition.

Examples of the "acyl group" in the definition of "an acyl group which may be substituted" in the definition of $R^{4e5}$ include similar groups to the "acyl group" in the aforementioned definition.

Examples of the "heterocyclic group" in the definition of "a heterocyclic group which may be substituted" in the definition of $R^{4e5}$ include similar groups to the "heterocyclic group" in the aforementioned definition.

A group selected from the following Substituent Group $\delta^4$-1e is preferred as $E^4$, and 4-[(1,1-dimethyl)ethyl]-5-[(2,2-dimethyl)propionyl]thiazol-2-yl group is most preferred.

[Substituent Group $\delta^4$-1e] 5-bromo-4-[(1,1-dimethyl)ethyl]thiazol-2-yl group, 5-bromo-4-(trifluoromethyl)thiazol-2-yl group, 5-cyano-4-[(1,1-dimethyl)ethyl]thiazol-2-yl group, 5-methylthiazol-2-yl group, 4-[(1,1-dimethyl)ethyl]-5-[(2,2-dimethyl)propionyl]thiazol-2-yl group, 4-[(1,1-dimethyl)ethyl]-5-(ethoxycarbonyl)thiazol-2-yl group, 4-[(1,1-dimethyl)ethyl]-5-piperidinothiazol-2-yl group, 4-[(1,1-dimethyl)ethyl]-5-morpholinothiazol-2-yl group, 4-[(1,1-dimethyl)ethyl]-5-(4-methylpiperazin-1-yl)thiazol-2-yl group, 4-[(1,1-dimethyl)ethyl]-5-(4-phenylpiperazin-1-yl)thiazol-2-yl group, 5-carboxymethyl-4-phenylthiazol-2-yl group, 5-acetyl-4-phenylthiazol-2-yl group, 5-benzoyl-4-phenylthiazol-2-yl group, 5-ethoxycarbonyl-4-phenylthiazol-2-yl group, 5-ethoxycarbonyl-4-(pentafluorophenyl)thiazol-2-yl group, 5-methylcarbamoyl-4-phenylthiazol-2-yl group, 5-ethylcarbamoyl-4-phenylthiazol-2-yl group, 5-isopropylcarbamoyl-4-phenylthiazol-2-yl group, 5-(2-phenylethyl)carbamoyl-4-phenylthiazol-2 yl group, 5-ethoxycarbonyl-4-(trifluoromethyl)thiazol-2-yl group, 5-carboxy-4-[(1,1-dimethyl)ethyl]thiazol-2-yl group, 5-carboxy-4-phenylthiazol-2-yl group, and 5-propylcarbamoyl-4-phenylthiazol-2-yl group.

Among the compound represented by the general formulas (I), (I-1), (I-2), (I-3) and (I-4), preferred compounds are those other than "substituted benzoic acid derivatives represented by the following general formula (X-1) and/or compounds represented by the following Compound Group φ-1."

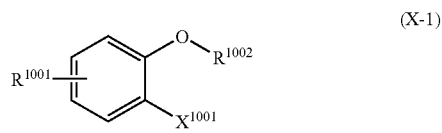
(X-1)

wherein $R^{1001}$ represents the following general formula (X-2):

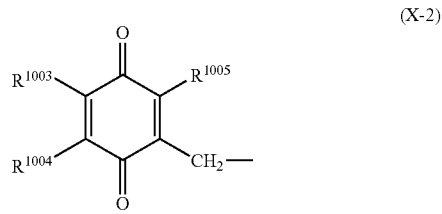
(X-2)

or the following general formula (X-3):

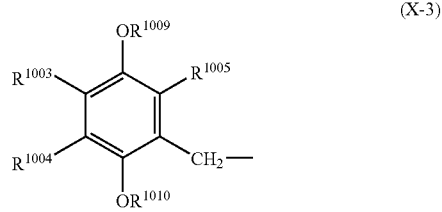
(X-3)

wherein each of $R^{1003}$, $R^{1004}$ and $R^{1005}$ independently represents hydrogen atom, an alkyl group having from 1 to 6 carbons or an alkoxy group having from 1 to 6 carbons, each of $R^{1009}$ and $R^{1010}$ independently represents hydrogen atom, an alkyl group having from 1 to 6 carbons, or an acyl group having from 2 to 11 carbons;

$R^{1002}$ represents hydrogen atom, a lower alkyl group having from 1 to 6 carbons, which may be substituted, an aryl group having from 6 to 12 carbons, which may be substituted, a heteroaryl group having from 4 to 11 carbons, which may be substituted, an aralkyl group having from 7 to 14 carbons, which may be substituted, a heteroarylalkyl group having from 5 to 13 carbons, which may be substituted, or an acyl group having from 2 to 11 carbons;

$X^{1001}$ represents carboxy group which may be esterified or amidated.

[Compound Group φ-1]

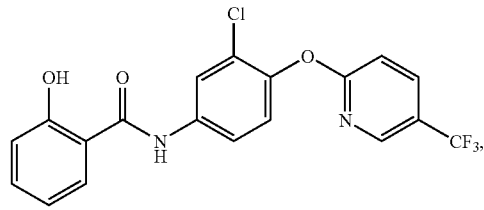

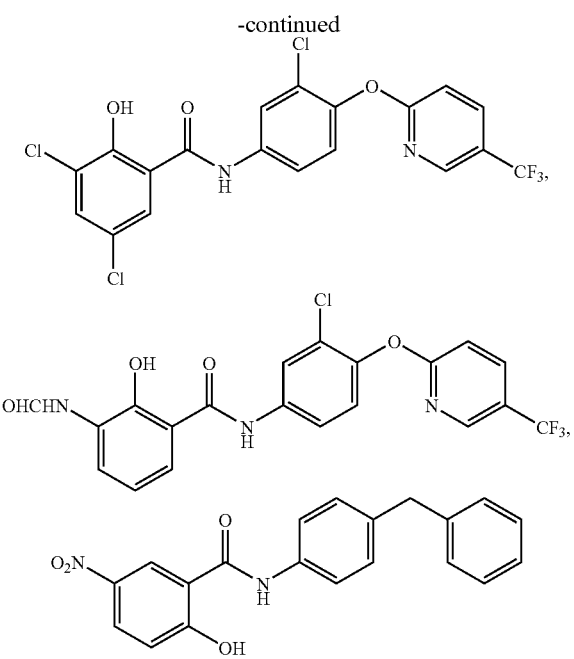

Each compound defined by the aforementioned general formulas (I-1), (I-2), (I-3), and (I-4), or a pharmacologically acceptable salt thereof, or a hydrate thereof or a solvate thereof is novel. Uses of the compound according to the aforementioned chemical substance invention are not particularly limited.

The compounds represented by the aforementioned general formulas (I), (I-1), (I-2), (I-3) and (I-4) may form salts. Examples of pharmacologically acceptable salts include, when acidic groups exist, metal salts such as lithium salt, sodium salt, potassium salt, magnesium salt, calcium salts, or ammonium salts such as ammonium salt, methylammonium salt, dimethylammonium salt, trimethylammonium salt, dicyclohexylammonium salt, and when basic groups exist, mineral acid salts such as hydrochloride, oxalate, hydrosulfate, nitrate, phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, lactate. Salts may sometimes be formed with amino acids such as glycine. As active ingredients of the medicament of the present invention, pharmacologically acceptable salts may also be suitably used.

The compounds or salts thereof represented by the aforementioned general formulas (I), (I-1), (I-2), (I-3) and (I-4) may exist as hydrates or solvates. As active ingredients of the medicament of the present invention, any of the aforementioned substances may be used. Furthermore, the compounds represented by the aforementioned general formulas (I), (I-1), (I-2), (I-3) and (I-4) may sometimes have one or more asymmetric carbons, and may exist as steric isomers such as optically active substance and diastereomer. As active ingredients of the medicament of the present invention, pure forms of stereoisomers, arbitrary mixture of enantiomers or diastereomers, and racemates may be used.

Furthermore, when the compounds represented by the general formulas (I), (I-1), (I-2), (I-3) and (I-4) has, for example, 2-hydroxypyridine form, the compounds may exist as 2-pyridone form which is a tautomer. As active ingredients of the medicament of the present invention, pure forms of tautomers or a mixture thereof may be used. When the compounds represented by the general formulas (I), (I-1), (I-2), (I-3) and (I-4) have olefinic double bonds, the configuration may be in either E or Z, and as active ingredients of the medicament of the present invention, geometrical isomer in either of the configurations or a mixture thereof may be used.

Examples of the compounds included in the general formulas (I), (I-1), (I-2), (I-3) and (I-4) as active ingredients of the medicaments of the present invention are shown below. However, the active ingredients of the medicaments of the present invention are not limited to the compound set out below.

The abbreviations used in the following tables have the following meanings.

Me: methyl group, Et: ethyl group.

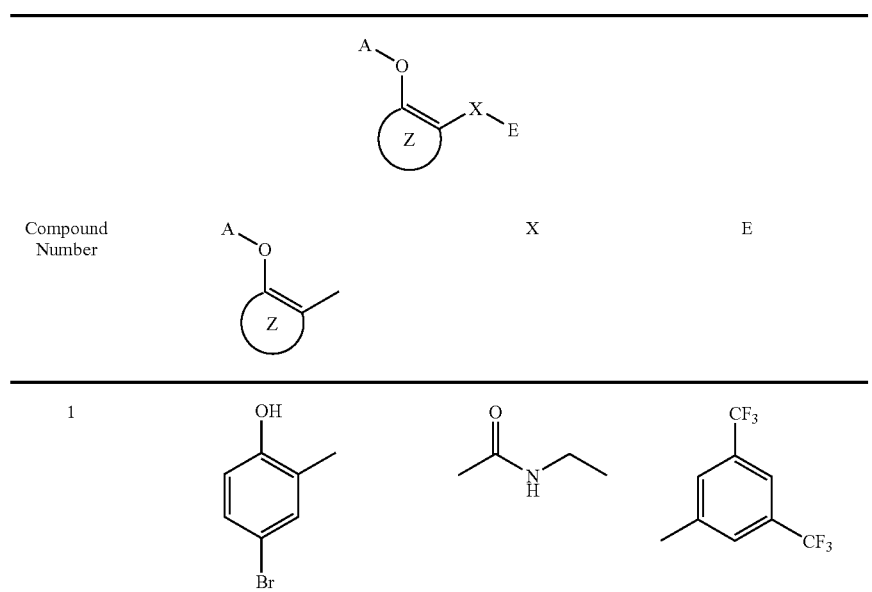

-continued
2 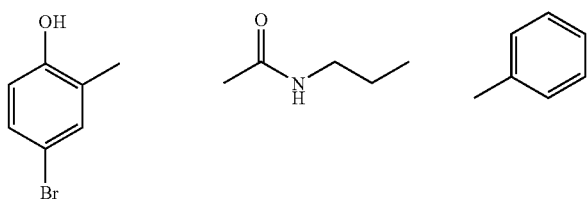
3 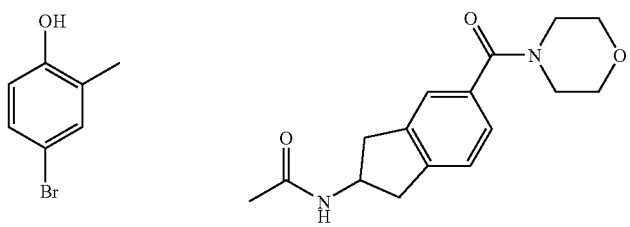
4 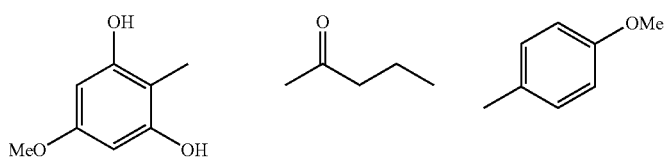
5 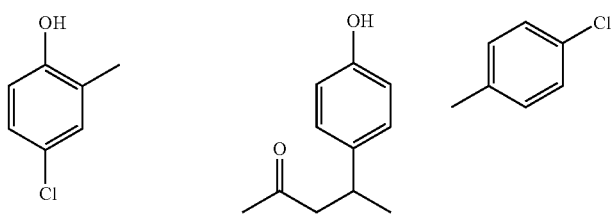
6 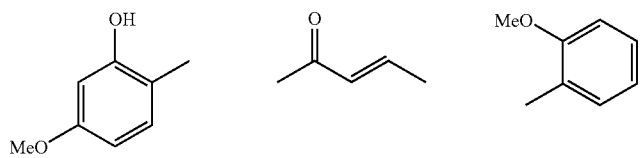
7 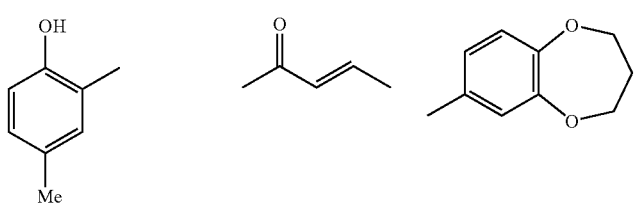
8 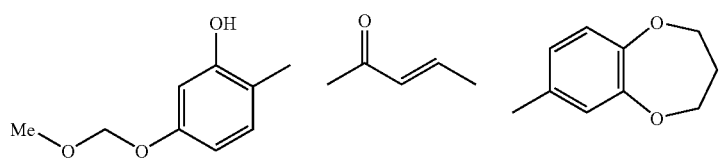
9 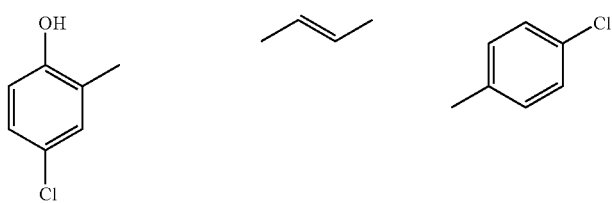

-continued
| | | | |
|---|---|---|---|
| 10 | 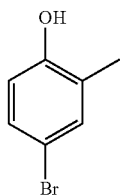 | 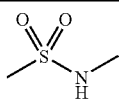 | 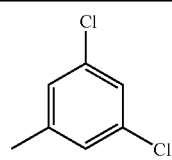 |
| 11 | 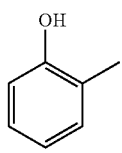 | 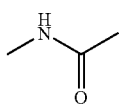 | 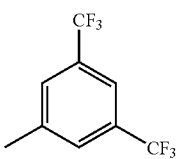 |
| 12 | 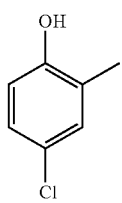 | 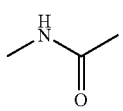 | 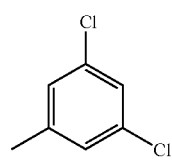 |
| 13 | 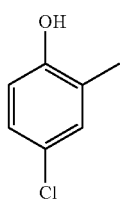 | 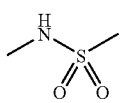 | 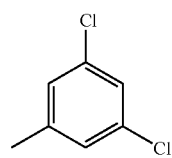 |
| 14 | 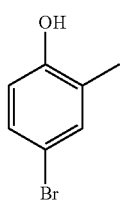 | 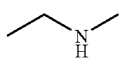 | 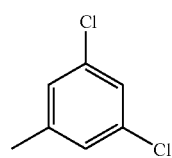 |
| 15 | 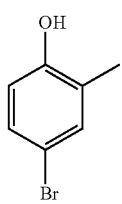 | 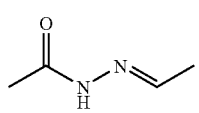 | 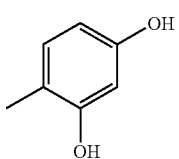 |
| 16 | 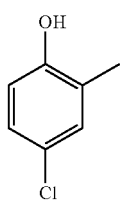 | 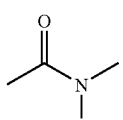 | 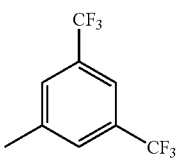 |
| 17 | 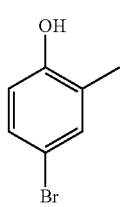 | | 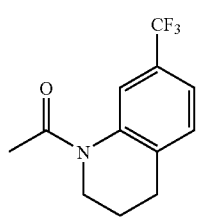 |

-continued

| Compound Number | A-O-[Z]- (with methyl) | E |
|---|---|---|
| 18 | 2-hydroxy-1-methylnaphthalene | 3,5-dichlorophenyl |
| 19 | 3-hydroxy-2-methylnaphthalene (2-naphthol, 3-methyl) | 3,5-dichlorophenyl |
| 20 | 3-hydroxy-2-methylnaphthalene | 2,5-dimethoxyphenyl (with methyl) |
| 21 | 1-hydroxy-2-methylnaphthalene | 3,5-bis(trifluoromethyl)phenyl |
| 22 | 1-hydroxy-2-methylnaphthalene | 4-(fluorosulfonyl)phenyl |
| 23 | 1-hydroxy-2-methyl-4-[(2,5-dichlorophenyl)azo]naphthalene | 4-(fluorosulfonyl)phenyl |

| | | |
|---|---|---|
| 24 | 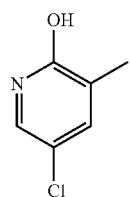 | 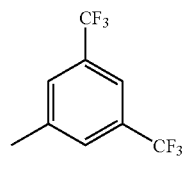 |
| 25 | 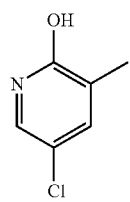 | 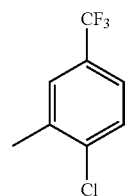 |
| 26 | 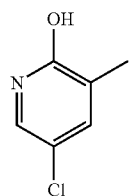 | 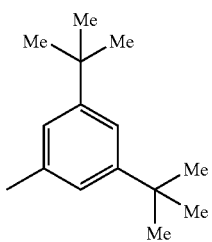 |
| 27 | 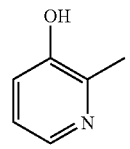 | 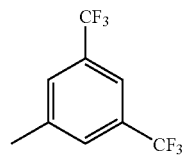 |
| 28 | 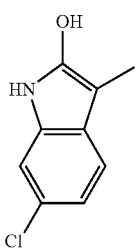 | 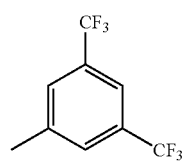 |
| 29 | 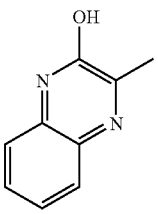 | 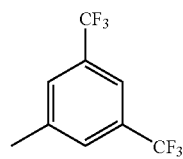 |
| 30 | 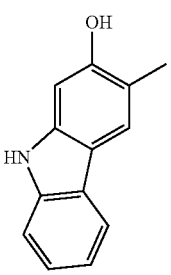 | 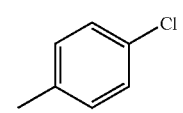 |

-continued
| | | |
|---|---|---|
| 31 | 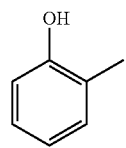 | 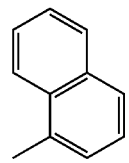 |
| 32 | 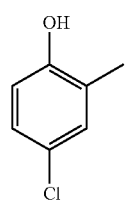 | 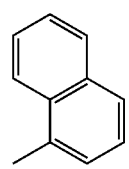 |
| 33 | 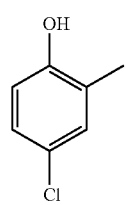 | 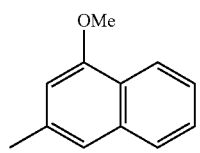 |
| 34 | 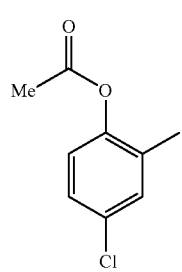 | 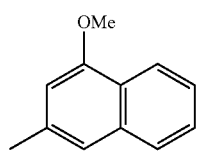 |
| 35 | 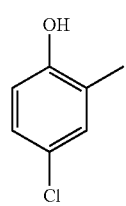 | 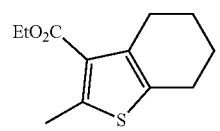 |
| 36 | 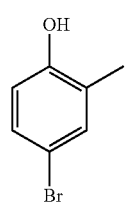 | 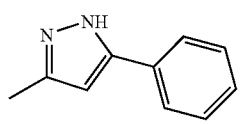 |
| 37 | 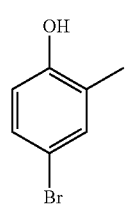 | 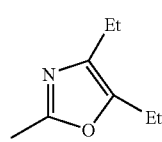 |

-continued
| 38 | 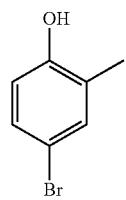 | 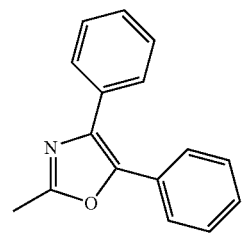 |
| --- | --- | --- |
| 39 | 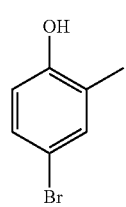 | 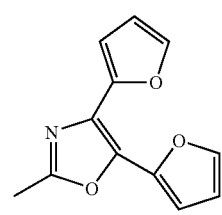 |
| 40 | 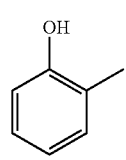 | 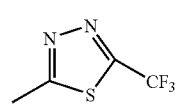 |
| 41 | 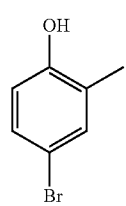 | 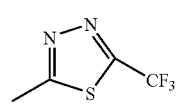 |
| 42 | 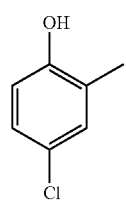 | 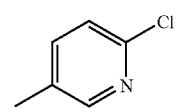 |
| 43 | 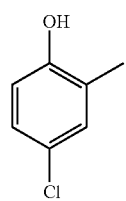 | 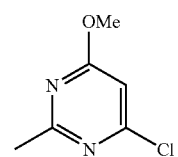 |
| 44 | 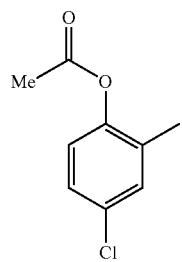 | 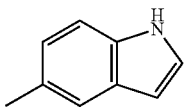 |

-continued
| | | |
|---|---|---|
| 45 | 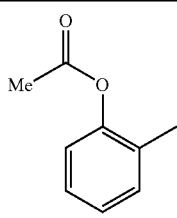 | 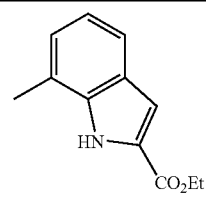 |
| 46 | 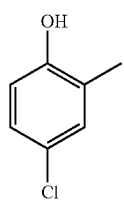 | 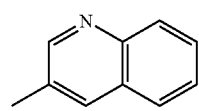 |
| 47 | 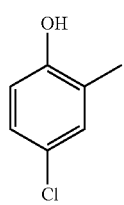 | 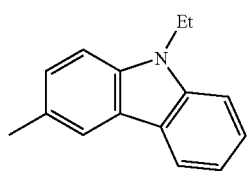 |
| 48 | 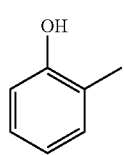 | 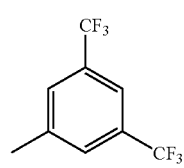 |
| 49 | 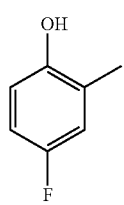 | 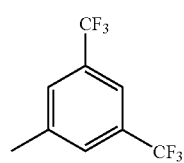 |
| 50 | 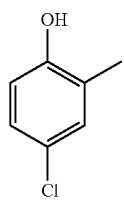 | 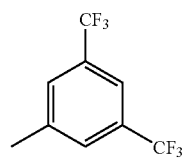 |
| 51 | 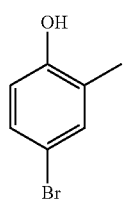 | 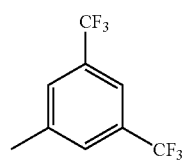 |
| 52 | 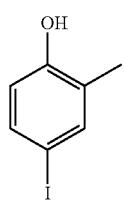 | 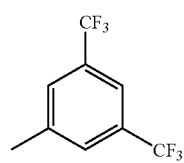 |

-continued
| | | |
|---|---|---|
| 53 | 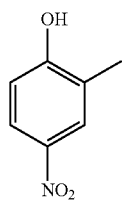 | 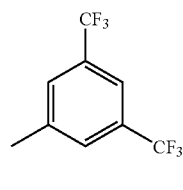 |
| 54 | 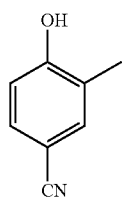 | 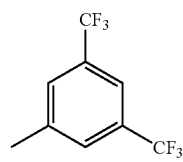 |
| 55 | 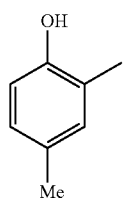 | 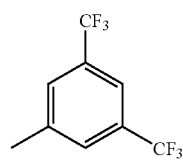 |
| 56 | 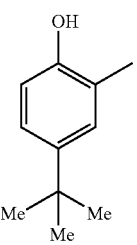 | 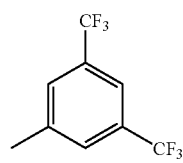 |
| 57 | 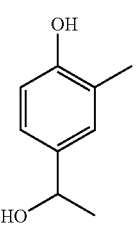 | 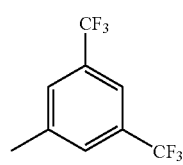 |
| 58 | 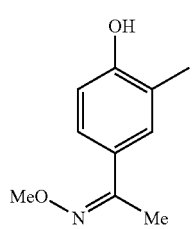 | 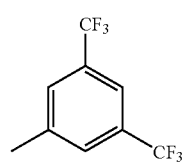 |
| 59 | 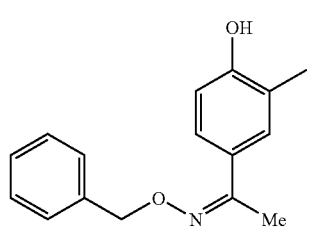 | 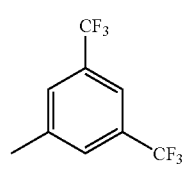 |

-continued
| | | |
|---|---|---|
| 60 | 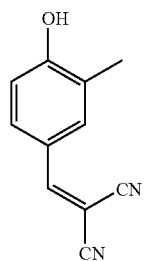 | 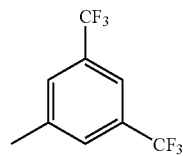 |
| 61 | 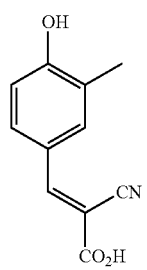 | 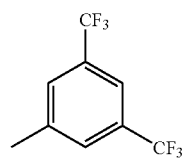 |
| 62 | 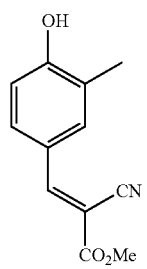 | 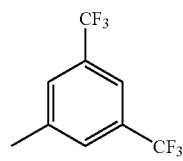 |
| 63 | 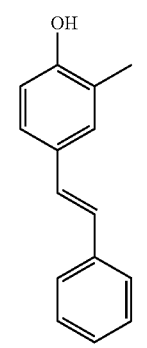 | 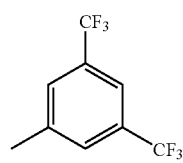 |
| 64 | 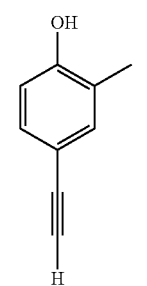 | 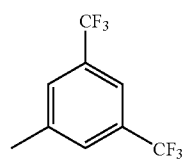 |

-continued
| | | |
|---|---|---|
| 65 | 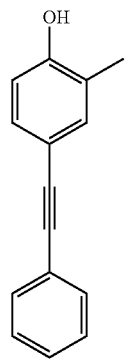 | 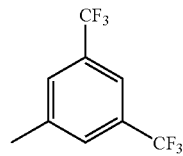 |
| 66 | 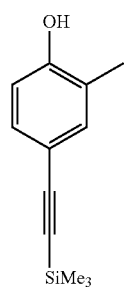 | 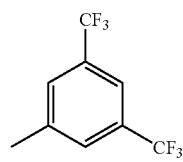 |
| 67 | 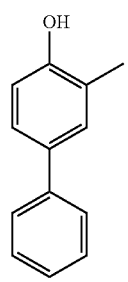 | 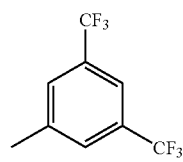 |
| 68 | 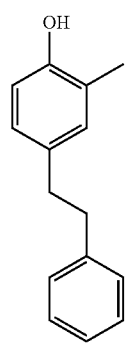 | 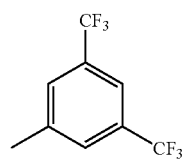 |
| 69 | 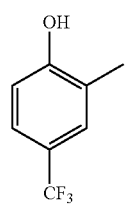 | 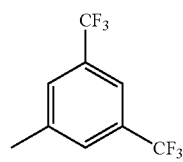 |

| | | |
|---|---|---|
| 70 | 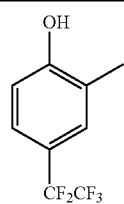 | 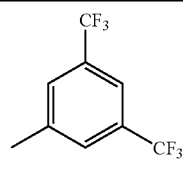 |
| 71 | 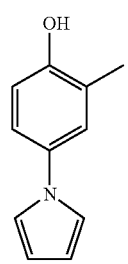 | 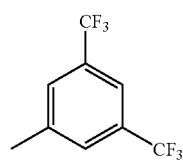 |
| 72 | 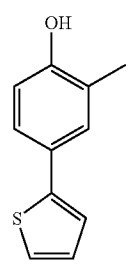 | 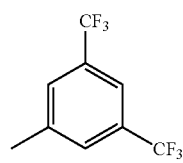 |
| 73 | 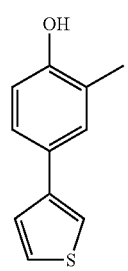 | 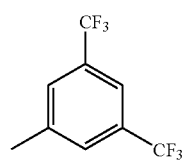 |
| 74 | 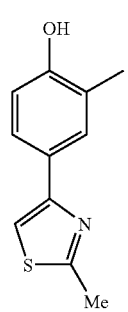 | 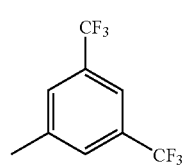 |
| 75 | 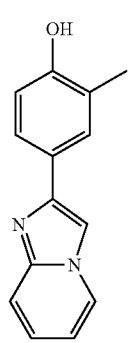 | 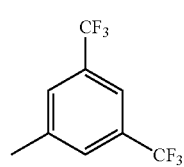 |

-continued
| | | |
|---|---|---|
| 76 | 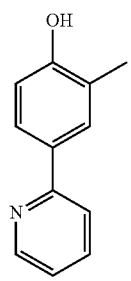 | 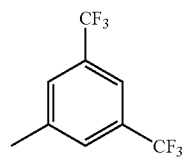 |
| 77 | 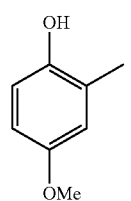 | 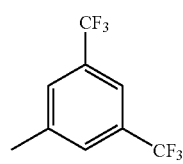 |
| 78 | 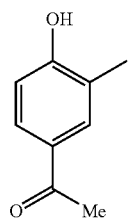 | 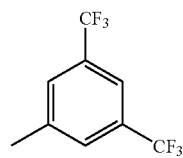 |
| 79 | 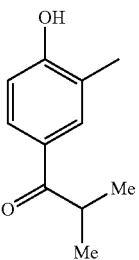 | 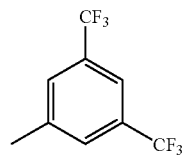 |
| 80 | 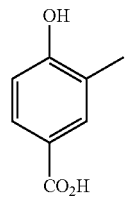 | 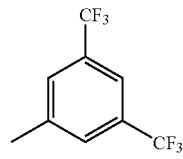 |
| 81 | 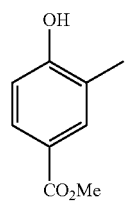 | 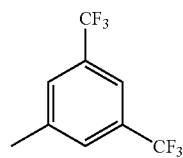 |

-continued
| | | |
|---|---|---|
| 82 | 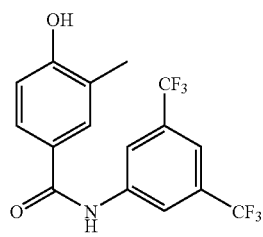 | 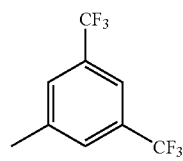 |
| 83 | 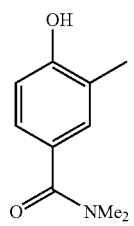 | 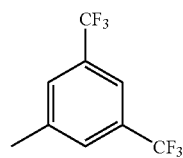 |
| 84 | 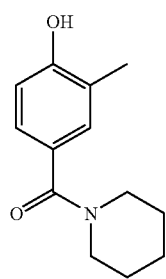 | 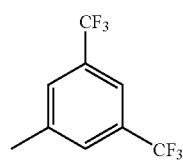 |
| 85 | 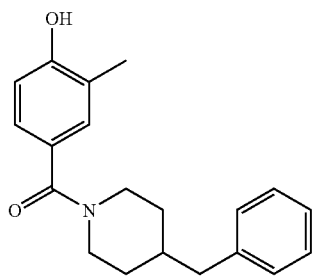 | 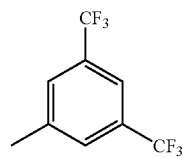 |
| 86 | 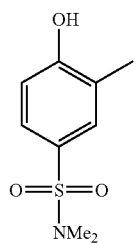 | 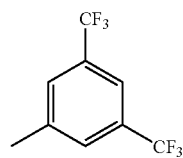 |
| 87 | 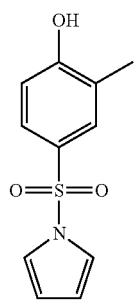 | 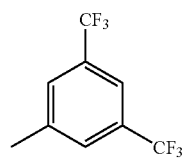 |

| | | |
|---|---|---|
| 88 | 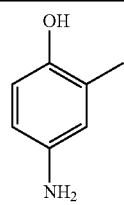 | 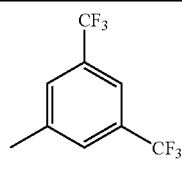 |
| 89 | 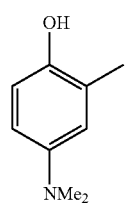 | 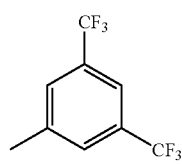 |
| 90 | 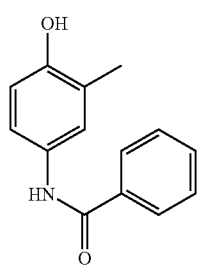 | 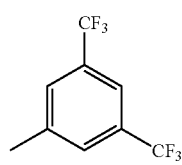 |
| 91 | 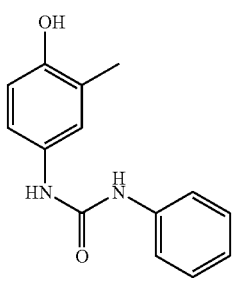 | 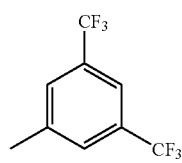 |
| 92 | 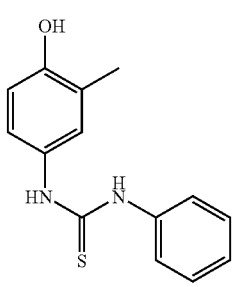 | 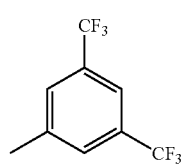 |
| 93 | 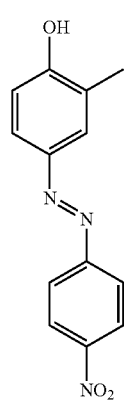 | 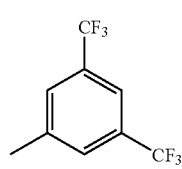 |

94 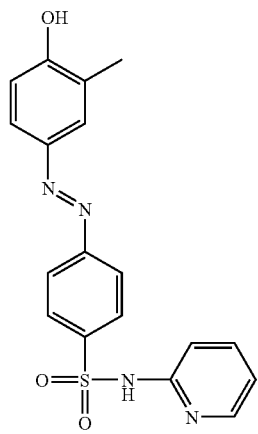 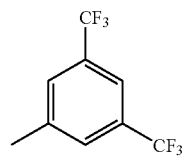
95 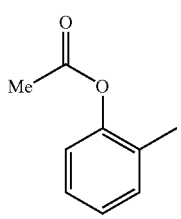 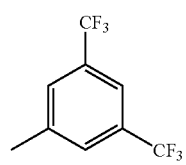
96 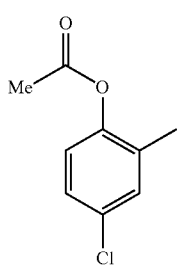 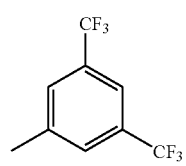
97 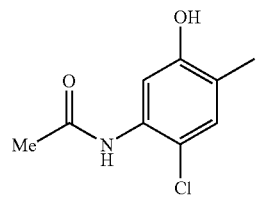 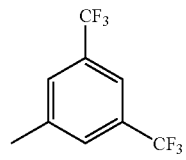
98 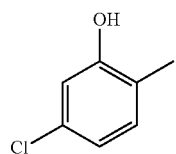 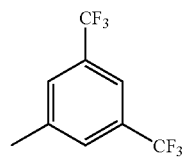
99 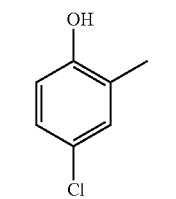 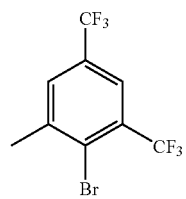

| | | |
|---|---|---|
| 100 | 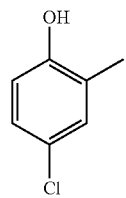 | 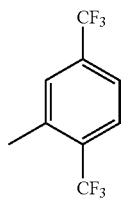 |
| 101 | 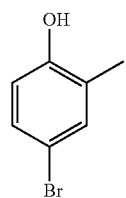 | 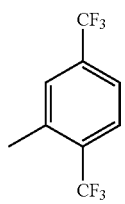 |
| 102 | 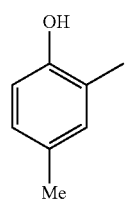 | 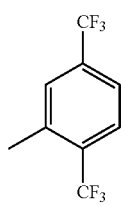 |
| 103 | 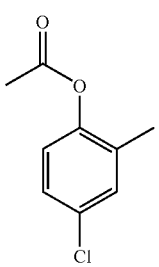 | 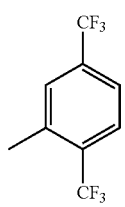 |
| 104 | 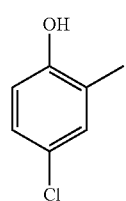 | 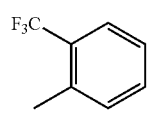 |
| 105 | 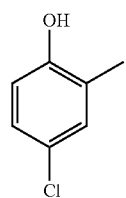 | 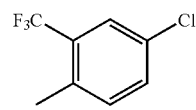 |
| 106 | 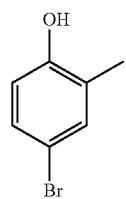 | 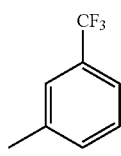 |

-continued
| | | |
|---|---|---|
| 107 | 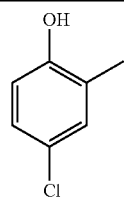 | 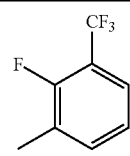 |
| 108 | 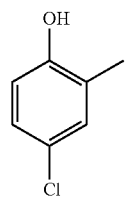 | 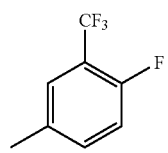 |
| 109 | 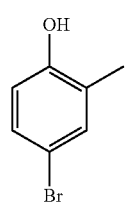 | 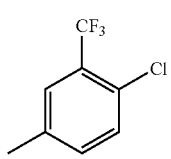 |
| 110 | 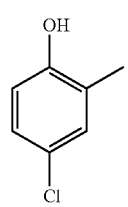 | 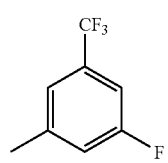 |
| 111 | 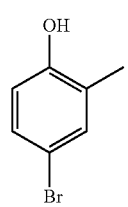 | 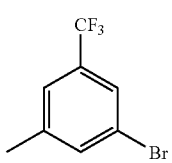 |
| 112 | 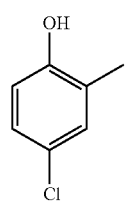 | 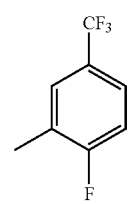 |
| 113 | 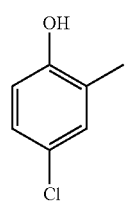 | 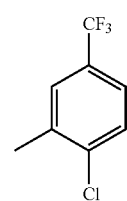 |
| 114 | 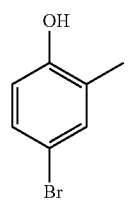 | 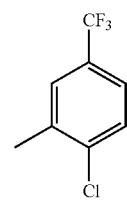 |

-continued
| | | |
|---|---|---|
| 115 | 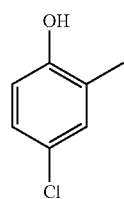 | 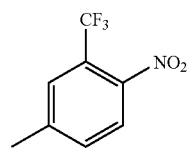 |
| 116 | 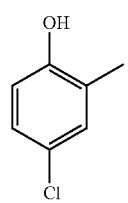 | 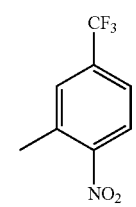 |
| 117 | 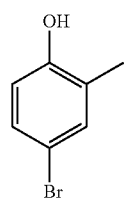 | 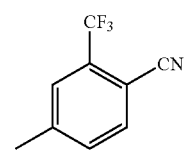 |
| 118 | 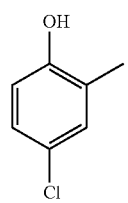 | 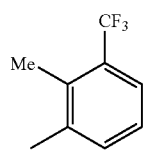 |
| 119 | 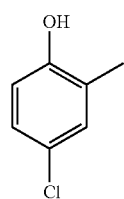 | 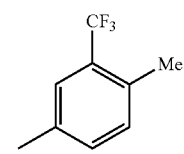 |
| 120 | 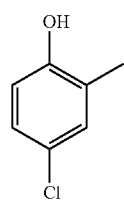 | 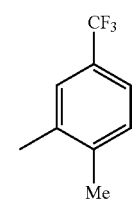 |
| 121 | 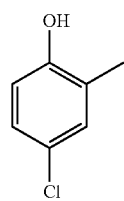 | 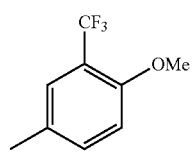 |

| | | |
|---|---|---|
| 122 | 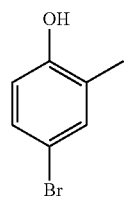 | 3-methoxy-5-(trifluoromethyl)toluene |
| 123 | 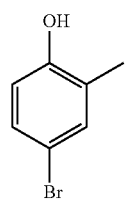 | 4-methoxy-3-methyl-(trifluoromethyl)benzene |
| 124 | 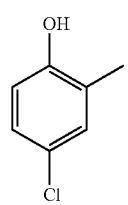 | 4-methoxy-2-methyl-(trifluoromethyl)benzene |
| 125 | 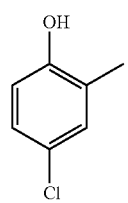 | 4-(methylthio)-3-methyl-(trifluoromethyl)benzene |
| 126 | 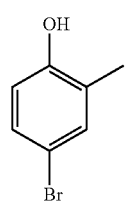 | 1-(2-methyl-4-(trifluoromethyl)phenyl)pyrrolidine |
| 127 | 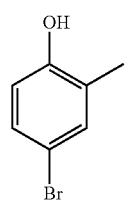 | 4-(2-methyl-4-(trifluoromethyl)phenyl)morpholine |
| 128 | 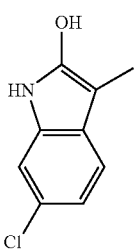 | 4-methyl-(trifluoromethyl)benzene |

-continued
| | | |
|---|---|---|
| 129 | 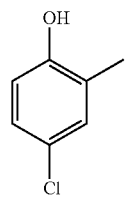 | 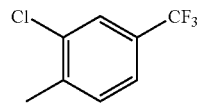 |
| 130 | 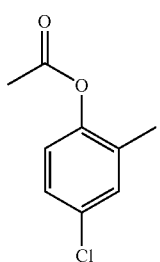 | 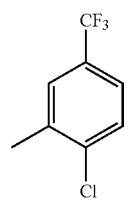 |
| 131 | 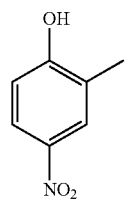 | 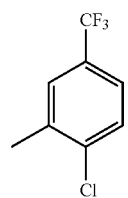 |
| 132 | 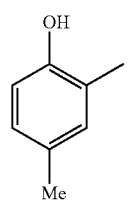 | 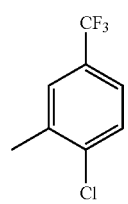 |
| 133 | 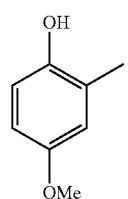 | 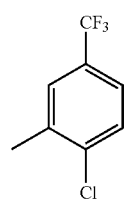 |
| 134 | 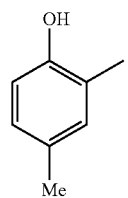 | 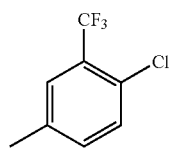 |
| 135 | 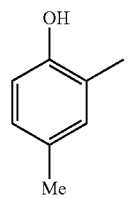 | 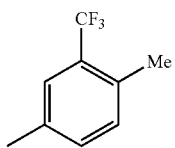 |

-continued
| | | |
|---|---|---|
| 136 | 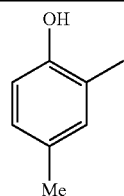 | 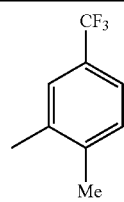 |
| 137 | 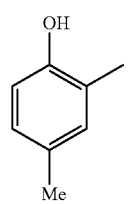 | 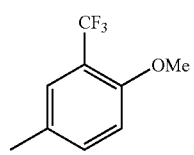 |
| 138 | 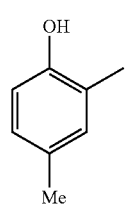 | 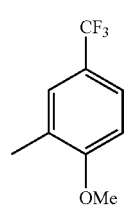 |
| 139 | 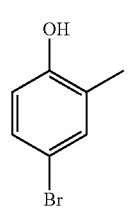 | 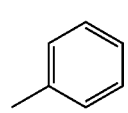 |
| 140 | 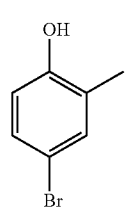 | 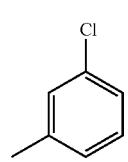 |
| 141 | 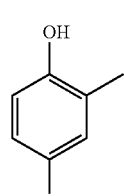 | 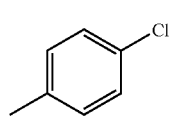 |
| 142 | 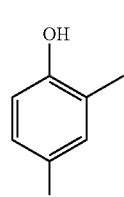 | 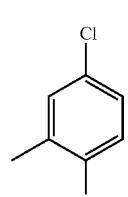 |
| 143 | 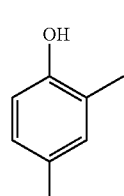 | 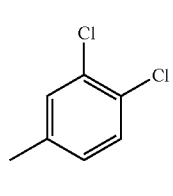 |

-continued
| | | |
|---|---|---|
| 144 | 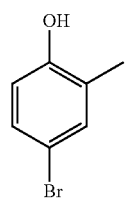 | 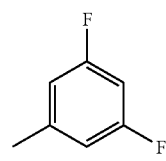 |
| 145 | 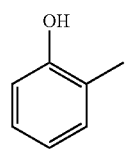 | 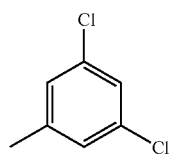 |
| 146 | 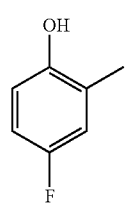 | 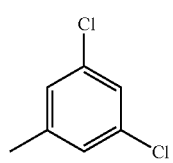 |
| 147 | 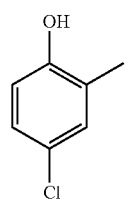 | 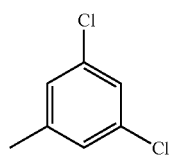 |
| 148 | 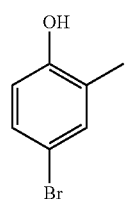 | 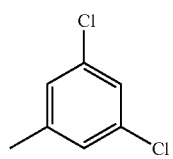 |
| 149 | 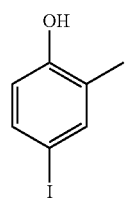 | 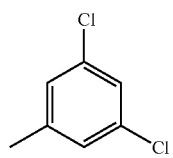 |
| 150 | 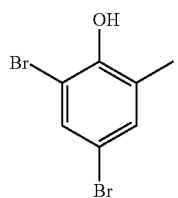 | 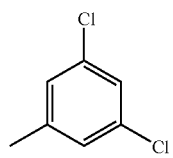 |
| 151 | 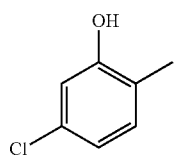 | 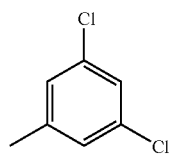 |

-continued
| | | |
|---|---|---|
| 152 | 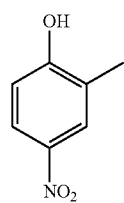 | 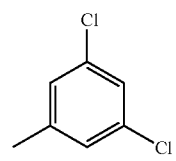 |
| 153 | 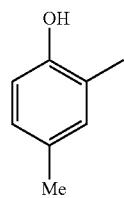 | 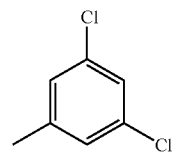 |
| 154 | 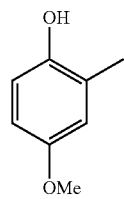 | 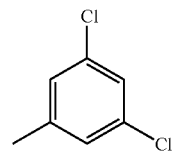 |
| 155 | 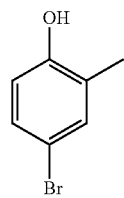 | 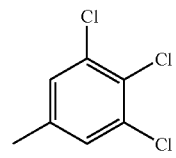 |
| 156 | 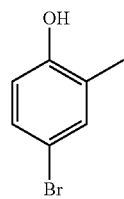 | 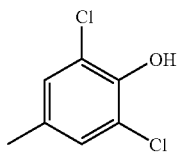 |
| 157 | 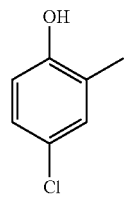 | 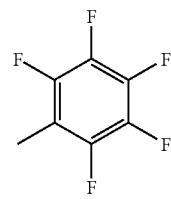 |
| 158 | 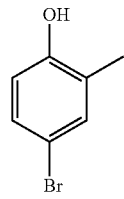 | 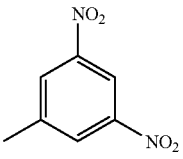 |

-continued
| | | |
|---|---|---|
| 159 | 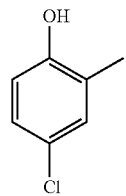 | 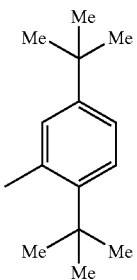 |
| 160 | 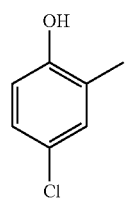 | 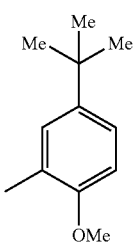 |
| 161 | 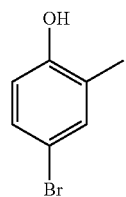 | 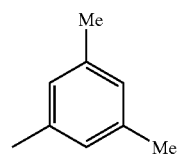 |
| 162 | 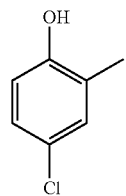 | 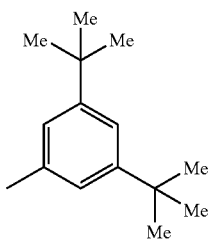 |
| 163 | 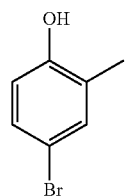 | 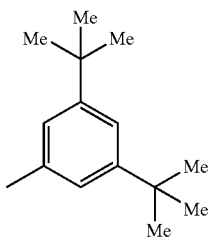 |
| 164 | 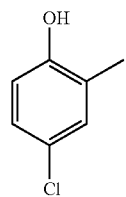 | 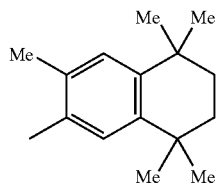 |

| | | |
|---|---|---|
| 165 | 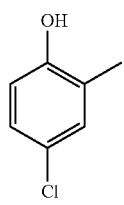 | 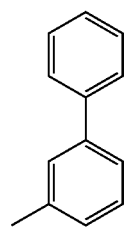 |
| 166 | 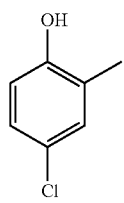 | 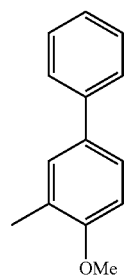 |
| 167 | 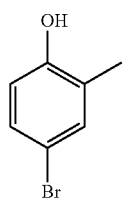 | 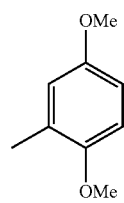 |
| 168 | 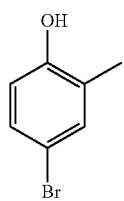 | 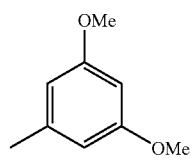 |
| 169 | 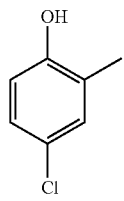 | 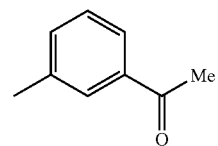 |
| 170 | 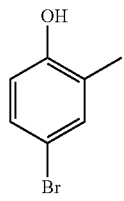 | 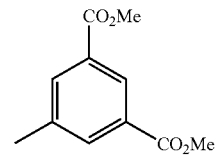 |
| 171 | 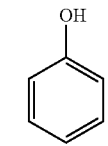 | 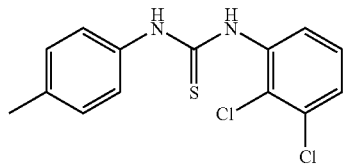 |

-continued
| | | |
|---|---|---|
| 172 | 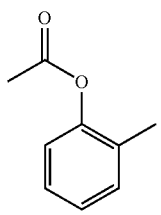 | 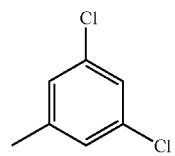 |
| 173 | 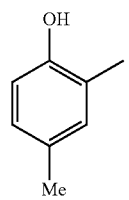 | 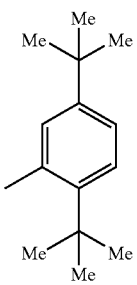 |
| 174 | 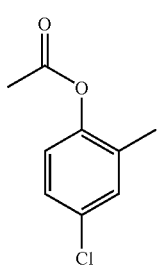 | 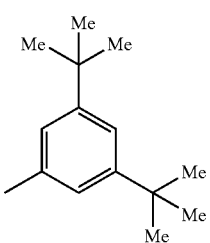 |
| 175 | 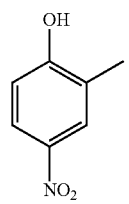 | 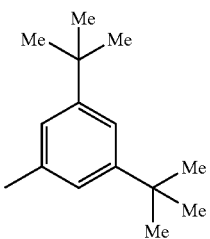 |
| 176 | 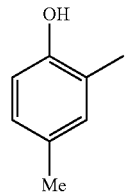 | 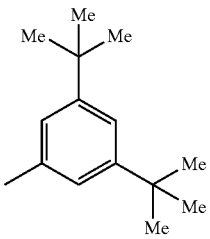 |
| 177 | 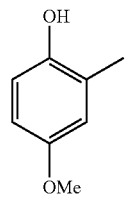 | 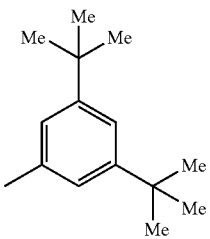 |

-continued
| | | |
|---|---|---|
| 178 | 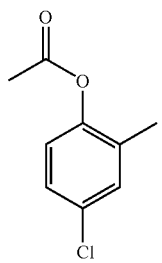 | 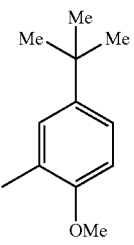 |
| 179 | 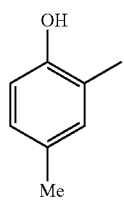 | 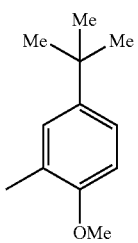 |
| 180 | 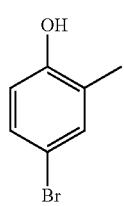 | 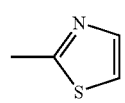 |
| 181 | 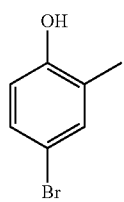 | 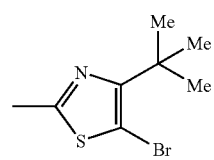 |
| 182 | 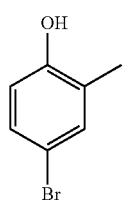 | 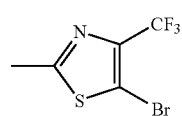 |
| 183 | 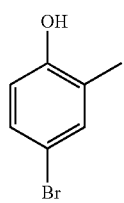 | 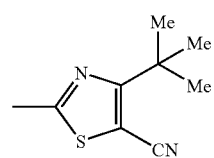 |
| 184 | 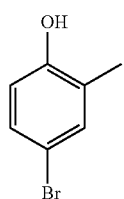 | 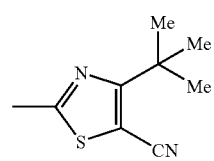 |

-continued
| | | |
|---|---|---|
| 185 | 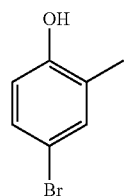 | 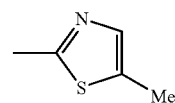 |
| 186 | 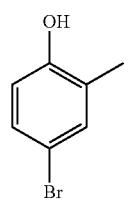 | 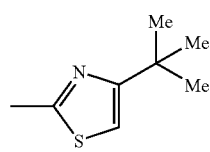 |
| 187 | 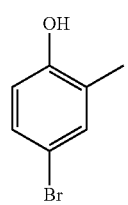 | 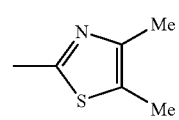 |
| 188 | 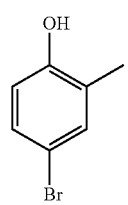 | 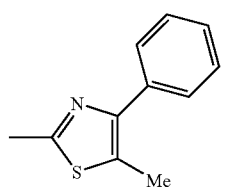 |
| 189 | 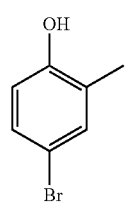 | 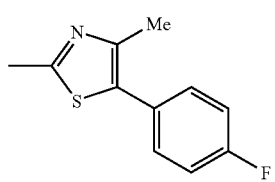 |
| 190 | 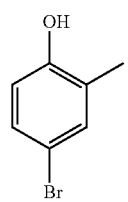 | 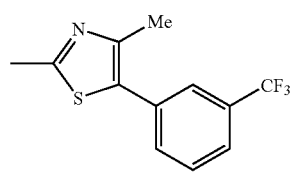 |
| 191 | 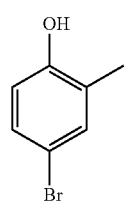 | 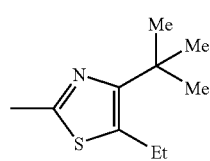 |
| 192 | 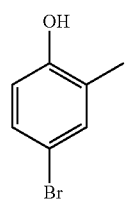 | 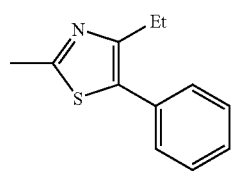 |

-continued
| 193 | 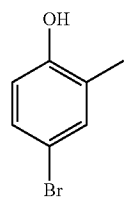 | 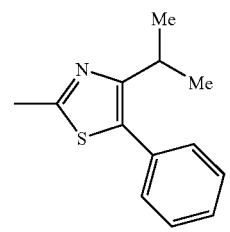 |
| 194 | 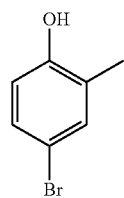 | 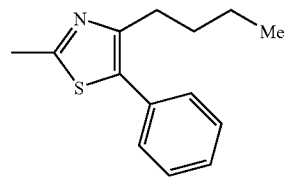 |
| 195 | 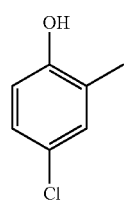 | 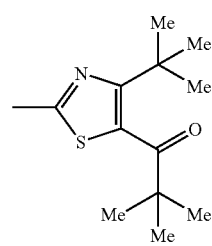 |
| 196 | 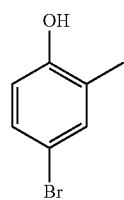 | 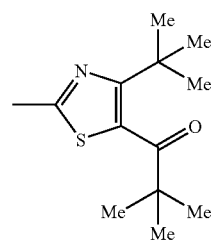 |
| 197 | 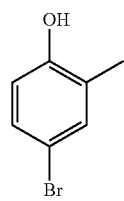 | 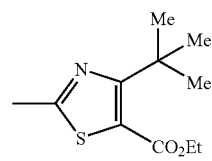 |
| 198 | 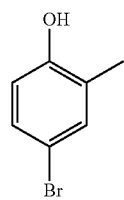 | 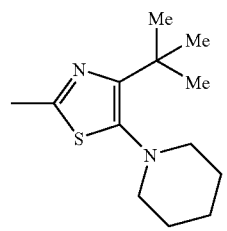 |
| 199 | 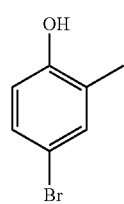 | 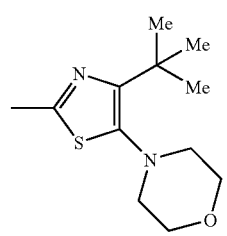 |

-continued
| | | |
|---|---|---|
| 200 | 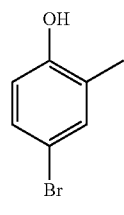 | 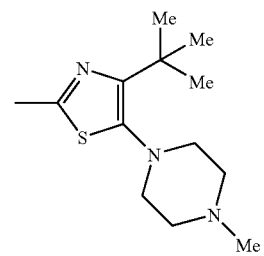 |
| 201 | 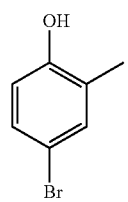 | 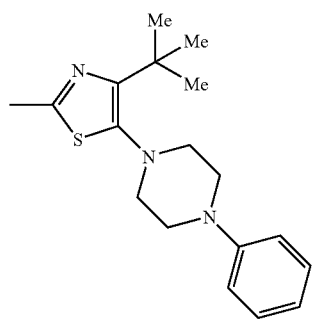 |
| 202 | 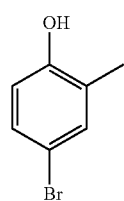 | 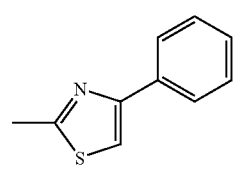 |
| 203 | 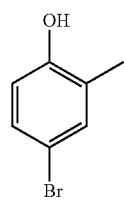 | 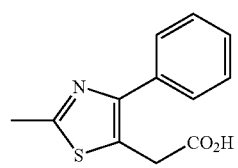 |
| 204 | 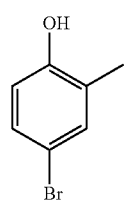 | 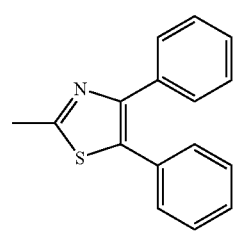 |
| 205 | 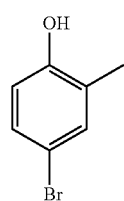 | 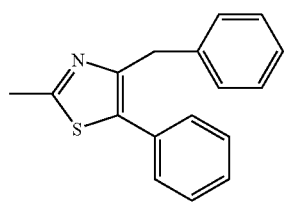 |
| 206 | 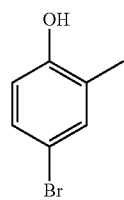 | 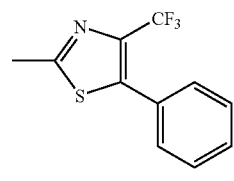 |

-continued
| | | |
|---|---|---|
| 207 | 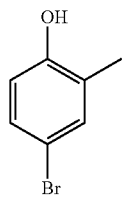 | 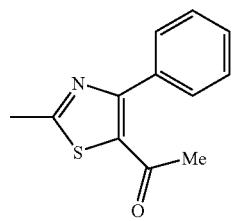 |
| 208 | 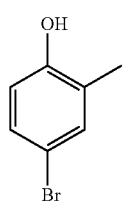 | 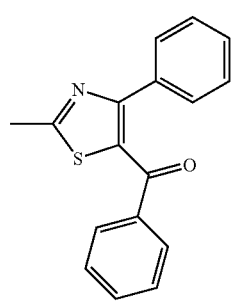 |
| 209 | 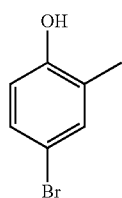 | 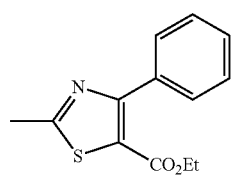 |
| 210 | 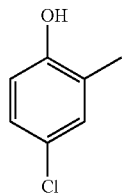 | 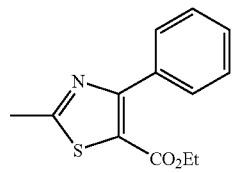 |
| 211 | 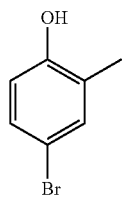 | 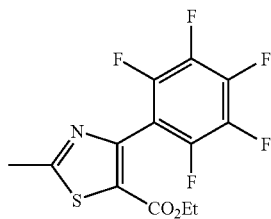 |
| 212 | 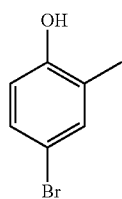 | 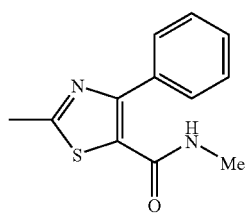 |
| 213 | 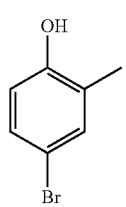 | 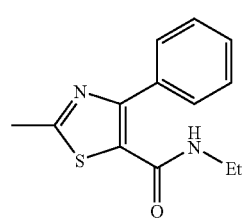 |

-continued
| | | |
|---|---|---|
| 214 | 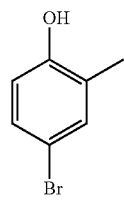 | 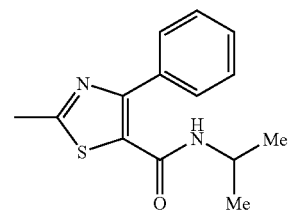 |
| 215 | 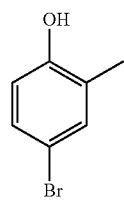 | 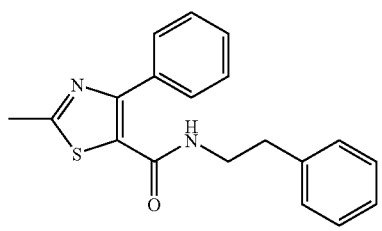 |
| 216 | 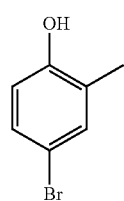 | 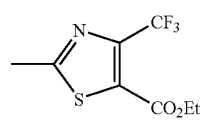 |
| 217 | 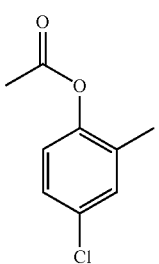 | 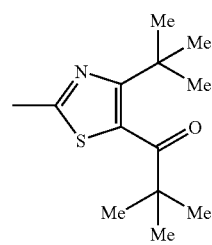 |
| 218 | 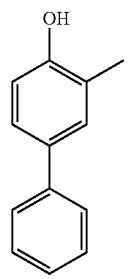 | 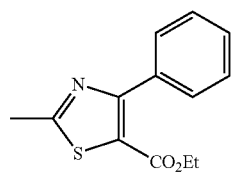 |
| 219 | 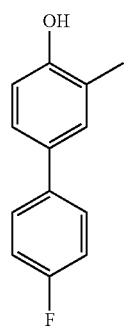 | 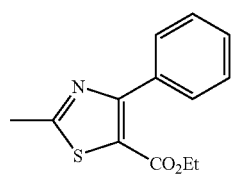 |

-continued
| | | |
|---|---|---|
| 220 | 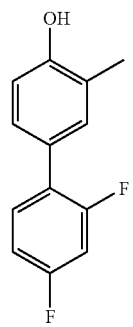 | 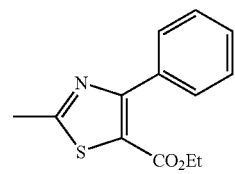 |
| 221 | 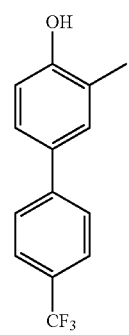 | 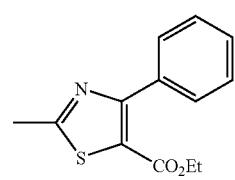 |
| 222 | 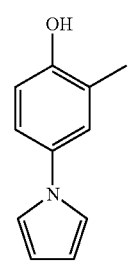 | 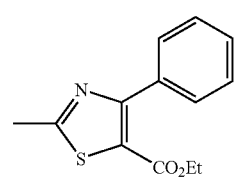 |
| 223 | 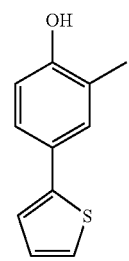 | 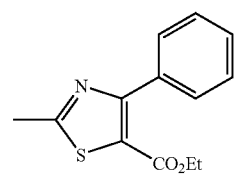 |

-continued
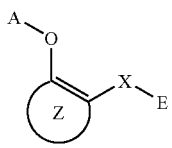
| Compound Number | 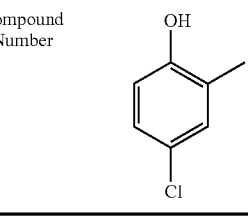 | X | E |
|---|---|---|---|
| 301 | 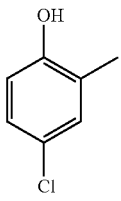 | 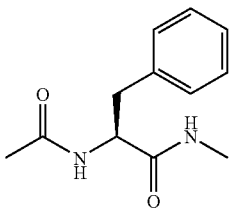 | 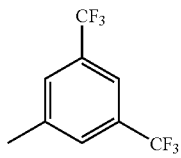 |
| 302 | 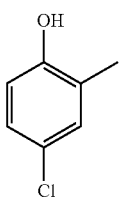 | 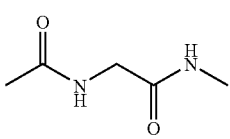 | 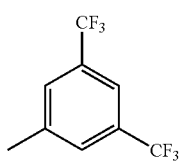 |
| 303 | 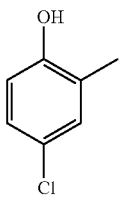 | 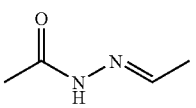 | 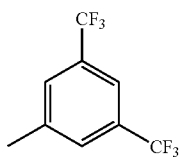 |
| 304 | 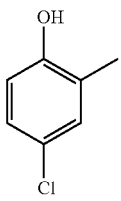 | 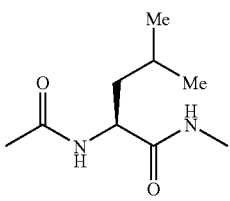 | 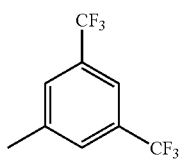 |
| 305 | 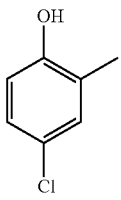 | 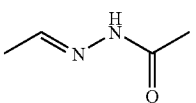 | 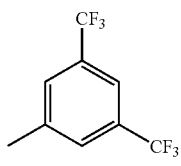 |
| 306 | | | |

-continued
| 307 | 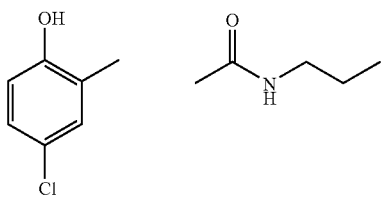 | 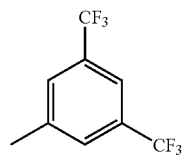 |
| --- | --- | --- |
| 308 | 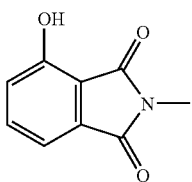 | 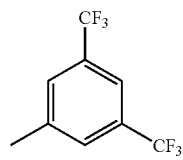 |
| 309 | 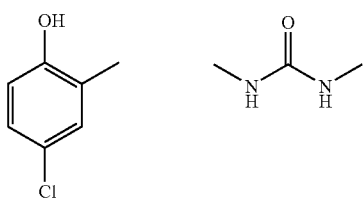 | 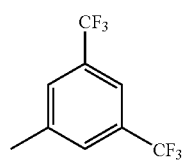 |
| 310 | 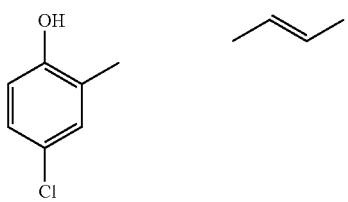 | 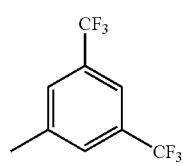 |
| 311 | 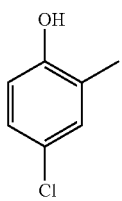 | 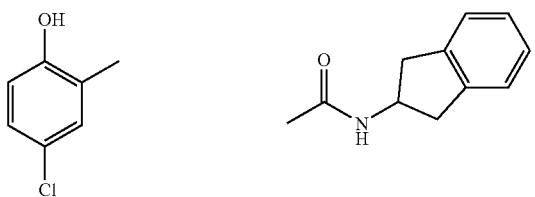 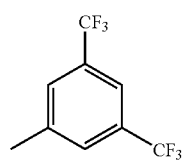 |
| 312 | 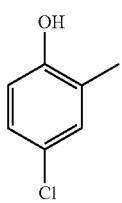 | 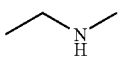 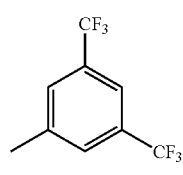 |
| 313 | | 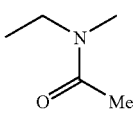 |

-continued
| 314 |  |  |  |
| 315 |  |  |  |
| 316 | 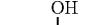 |  |  |
| 317 | 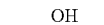 |  | 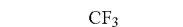 |
| 318 |  |  | 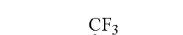 |
| 319 |  |  |  |
| 320 | |  |  |
| 321 |  |  |  |

-continued
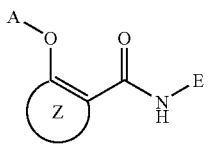
| Compound Number | 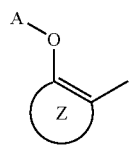 | E |
|---|---|---|
| 322 | 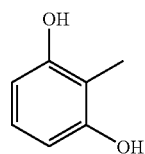 | 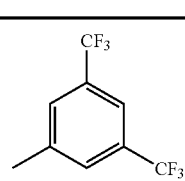 |
| 323 | 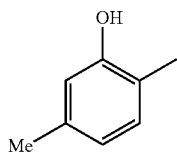 | 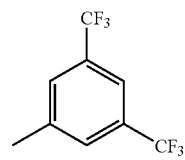 |
| 324 | 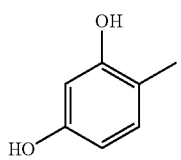 | 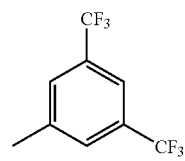 |
| 325 | 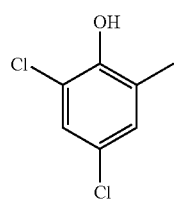 | 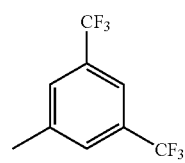 |
| 326 | 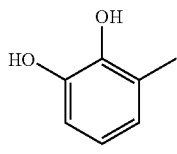 | 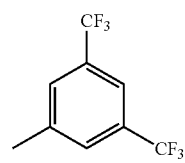 |
| 327 | 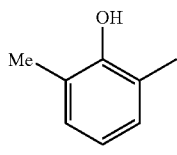 | 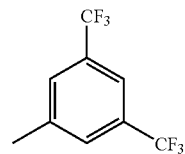 |
| 328 | | 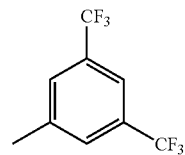 |

-continued
| | | |
|---|---|---|
| 329 | 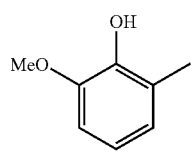 | 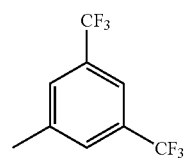 |
| 330 | 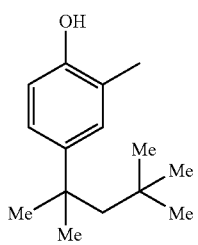 | 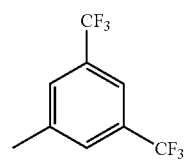 |
| 331 | 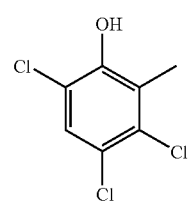 | 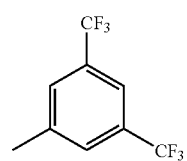 |
| 332 | 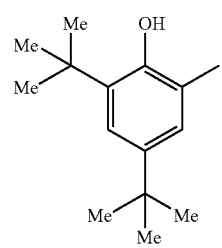 | 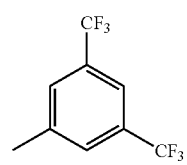 |
| 333 | 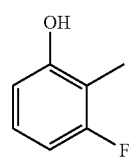 | 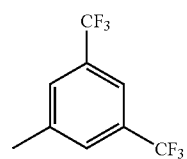 |
| 334 | 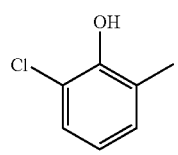 | 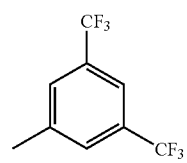 |
| 335 | 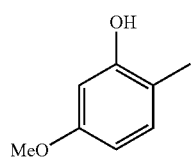 | 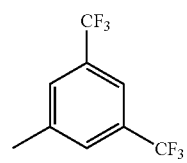 |
| 336 | 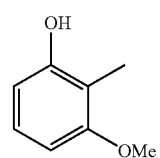 | 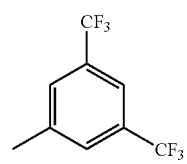 |

-continued
| | | |
|---|---|---|
| 337 | 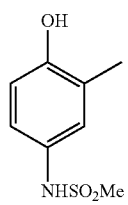 | 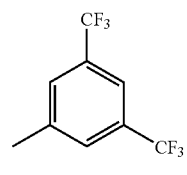 |
| 338 | 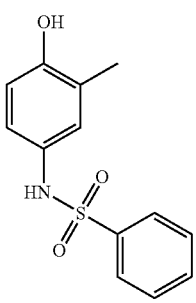 | 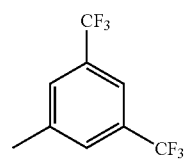 |
| 339 | 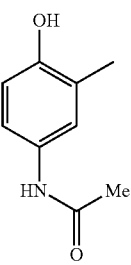 | 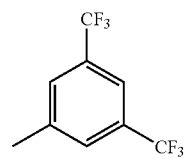 |
| 340 | 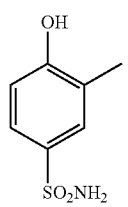 | 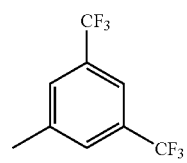 |
| 341 | 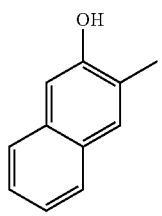 | 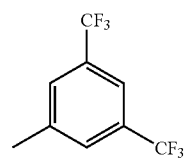 |
| 342 | 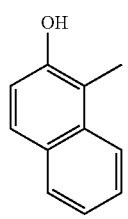 | 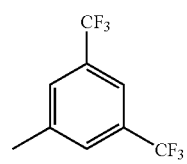 |
| 343 | 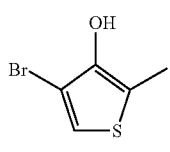 | 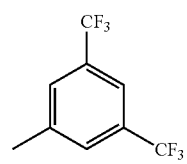 |

-continued
| | | |
|---|---|---|
| 344 | 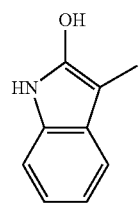 | 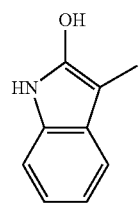 |
| 345 | 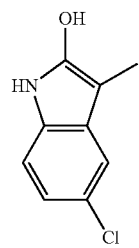 | |
| 346 | 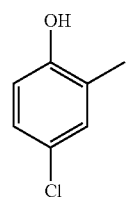 | |
| 347 | 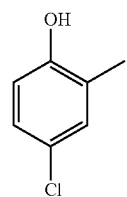 | |
| 348 | 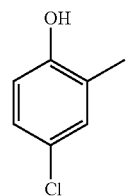 | |
| 349 | 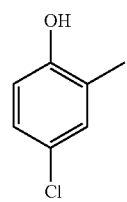 | |
| 350 | 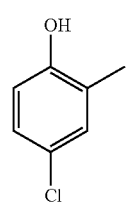 | |

-continued
| | | |
|---|---|---|
| 351 | 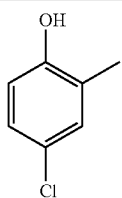 | 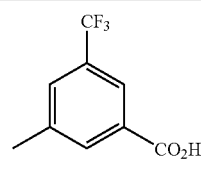 |
| 352 | 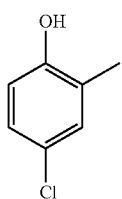 | 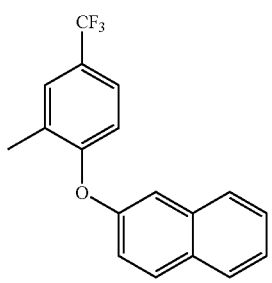 |
| 353 | 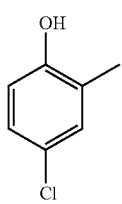 | 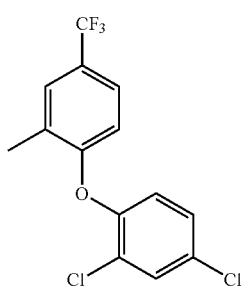 |
| 354 | 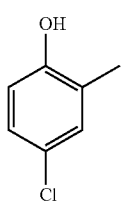 | 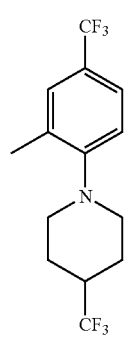 |
| 355 | 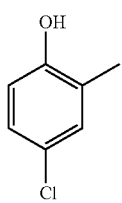 | 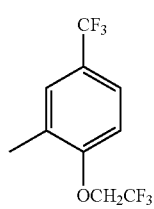 |
| 356 | 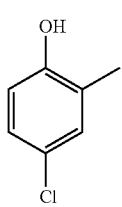 | 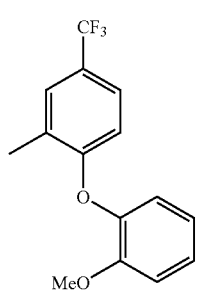 |

-continued
| | | |
|---|---|---|
| 357 | 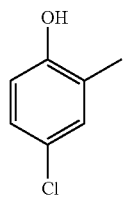 | 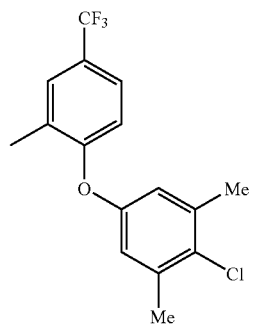 |
| 358 | 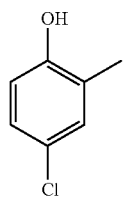 | 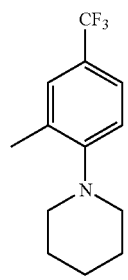 |
| 359 | 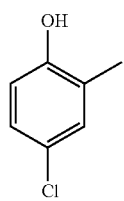 | 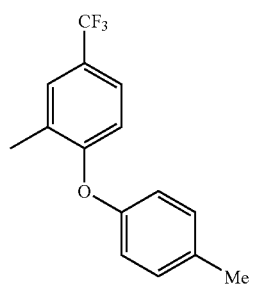 |
| 360 | 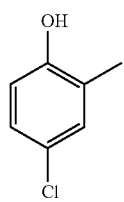 | 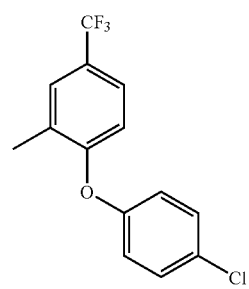 |
| 361 | 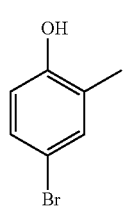 | 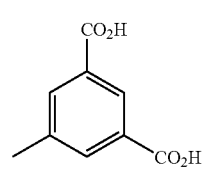 |
| 362 | 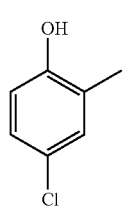 | 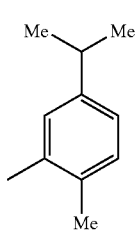 |

-continued
| | | |
|---|---|---|
| 363 | 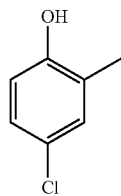 | 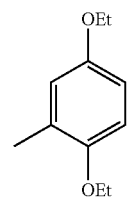 |
| 364 | 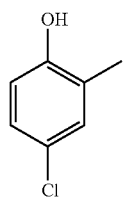 | 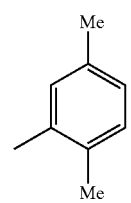 |
| 365 | 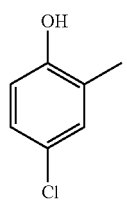 | 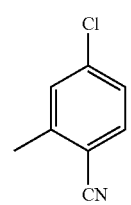 |
| 366 | 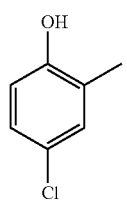 | 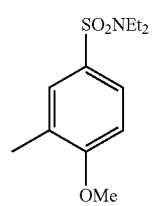 |
| 367 | 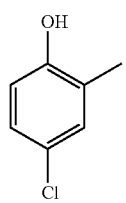 | 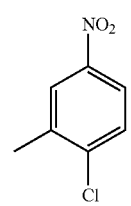 |
| 368 | 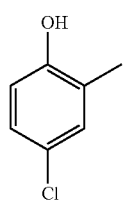 | 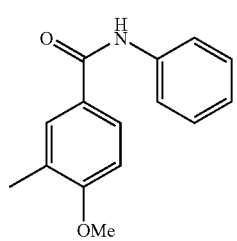 |
| 369 | 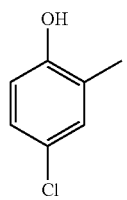 | 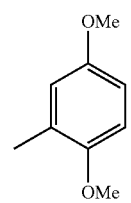 |

-continued
| | | |
|---|---|---|
| 370 | 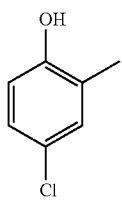 | 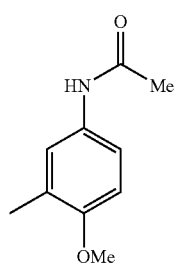 |
| 371 | 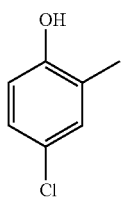 | 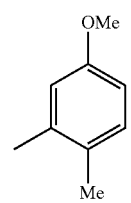 |
| 372 | 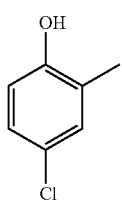 | 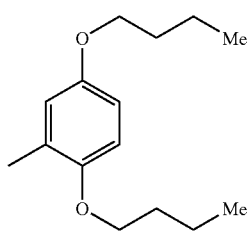 |
| 373 | 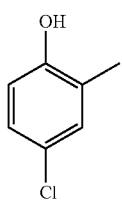 | 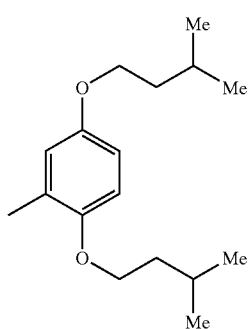 |
| 374 | 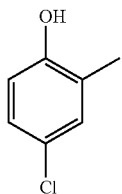 | 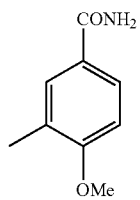 |
| 375 | 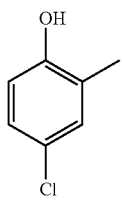 | 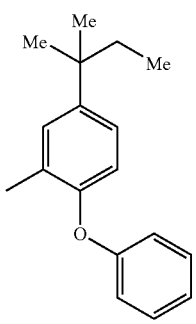 |

-continued
| | | |
|---|---|---|
| 376 | 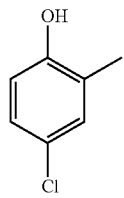 | 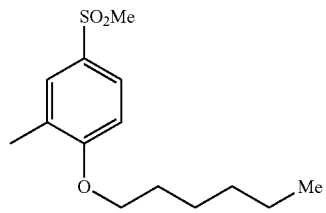 |
| 377 | 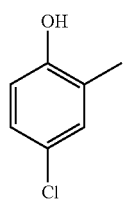 | 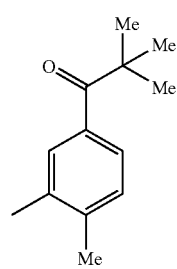 |
| 378 | 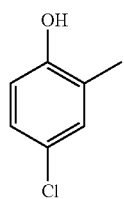 | 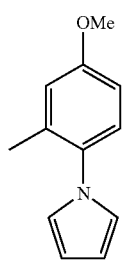 |
| 379 | 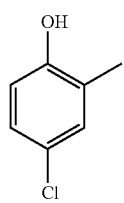 | 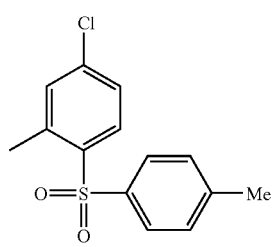 |
| 380 | 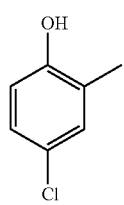 | 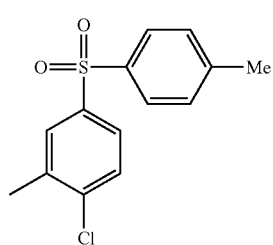 |
| 381 | 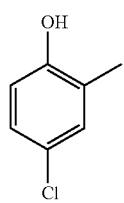 | 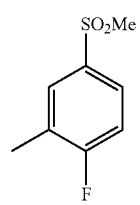 |

-continued
| | | |
|---|---|---|
| 382 | 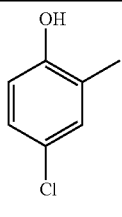 | 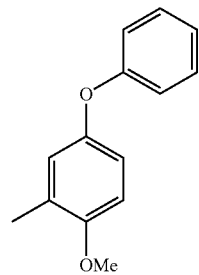 |
| 383 | 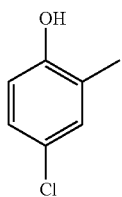 | 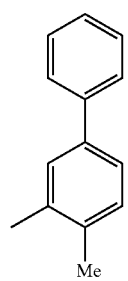 |
| 384 | 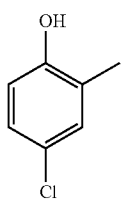 | 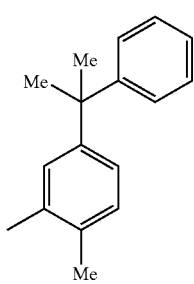 |
| 385 | 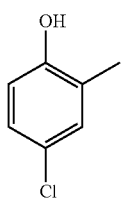 | 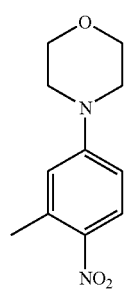 |
| 386 | 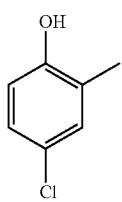 | 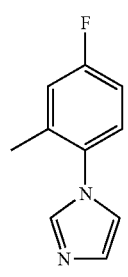 |
| 387 | 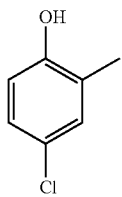 | 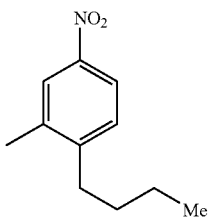 |

-continued
| | | |
|---|---|---|
| 388 | 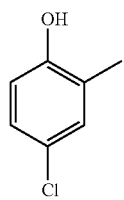 | 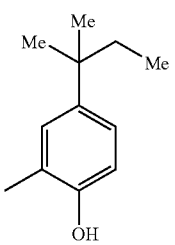 |
| 389 | 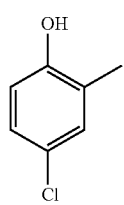 | 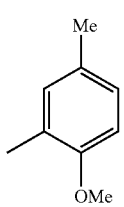 |
| 390 | 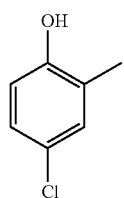 | 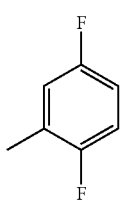 |
| 391 | 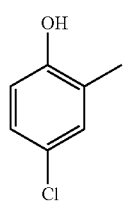 | 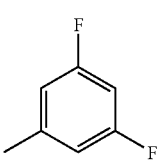 |
| 392 | 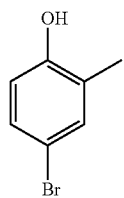 | 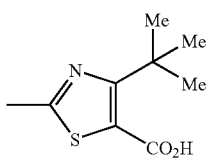 |
| 393 | 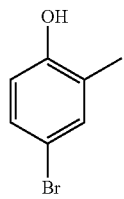 | 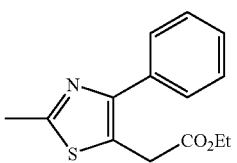 |
| 394 | 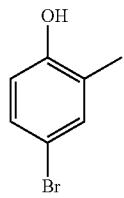 | 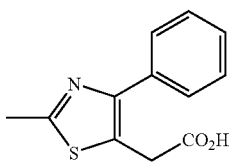 |

| | | |
|---|---|---|
| 395 | 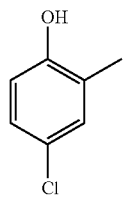 | 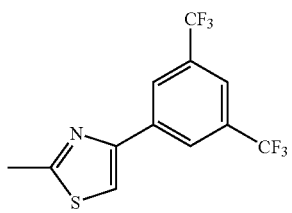 |
| 396 | 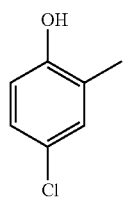 | 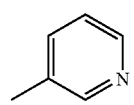 |
| 397 | 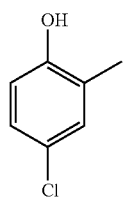 | 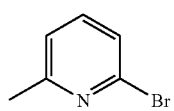 |
| 398 | 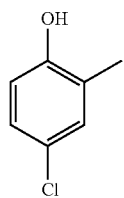 | 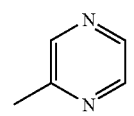 |
| 399 | 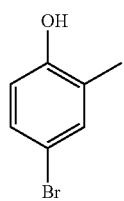 | 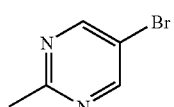 |
| 400 | 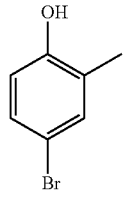 | 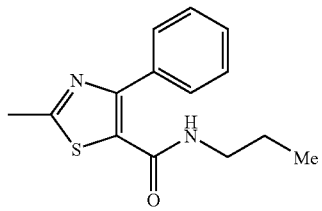 |
| 401 | 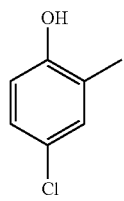 | 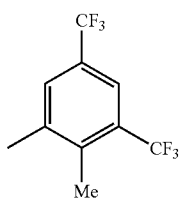 |

| | | |
|---|---|---|
| 402 | 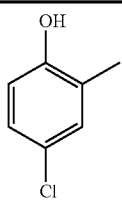 | 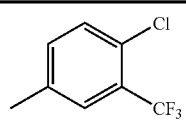 |
| 403 | 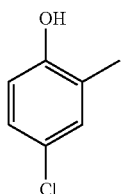 | 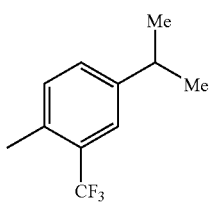 |
| 404 | 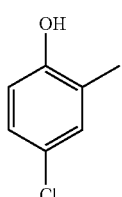 | 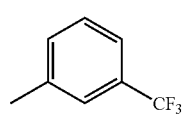 |
| 405 | 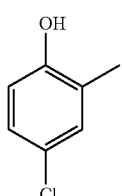 | 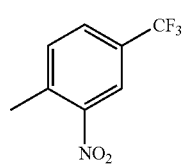 |
| 406 | 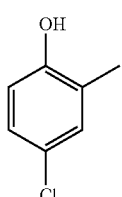 | 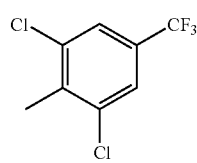 |
| 407 | 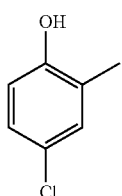 | 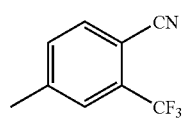 |
| 408 | 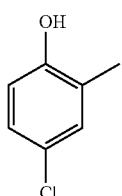 | 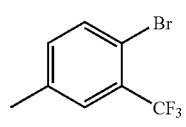 |
| 409 | 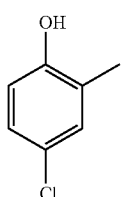 | 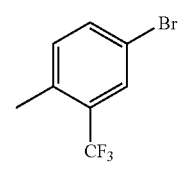 |

-continued
| | | |
|---|---|---|
| 410 | 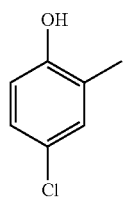 | 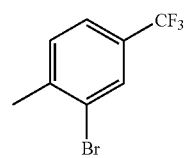 |
| 411 | 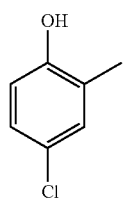 | 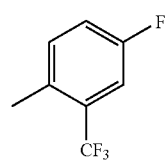 |
| 412 | 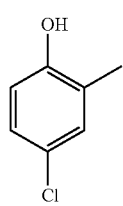 | 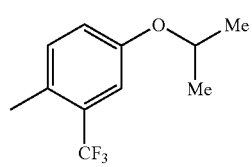 |
| 413 | 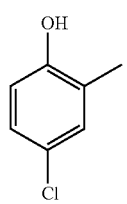 | 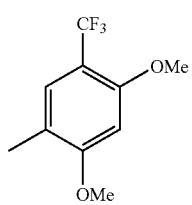 |
| 414 | 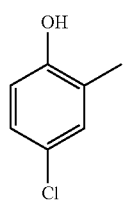 | 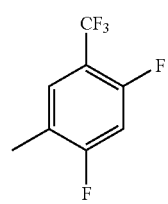 |
| 415 | 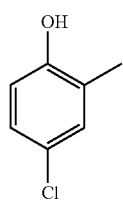 | 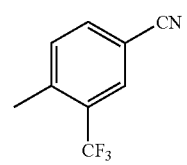 |
| 416 | 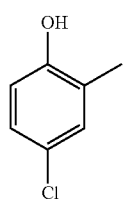 | 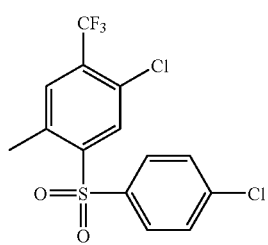 |

-continued
| | | |
|---|---|---|
| 417 | 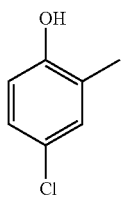 | 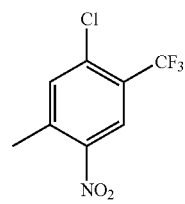 |
| 418 | 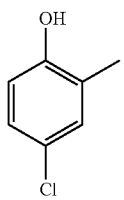 | 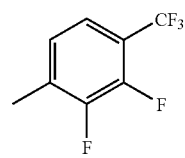 |
| 419 | 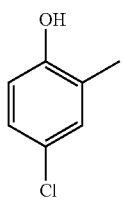 | 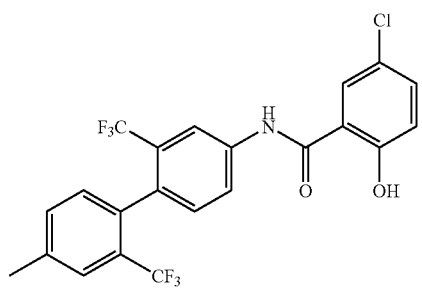 |
| 420 | 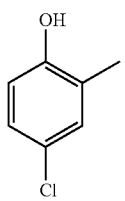 | 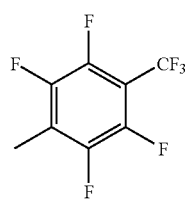 |
| 421 | 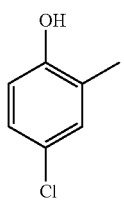 | 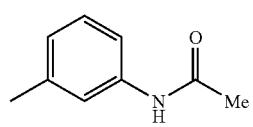 |
| 422 | 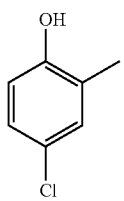 | 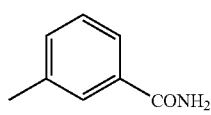 |
| 423 | 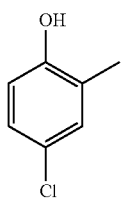 | 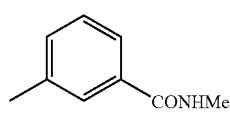 |

-continued
| | | |
|---|---|---|
| 424 | 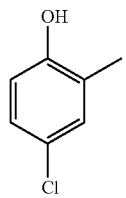 | 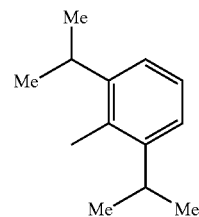 |
| 425 | 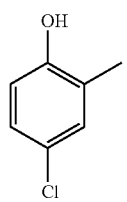 | 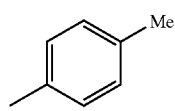 |
| 426 | 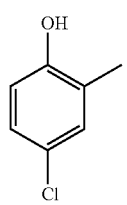 | 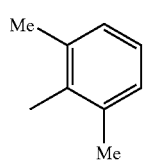 |
| 427 | 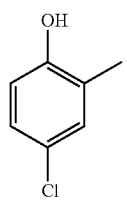 | 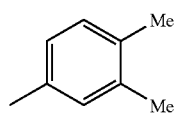 |
| 428 | 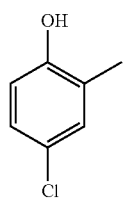 | 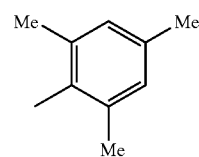 |
| 429 | 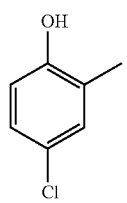 | 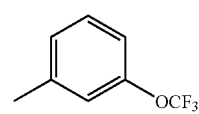 |
| 430 | 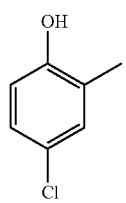 | 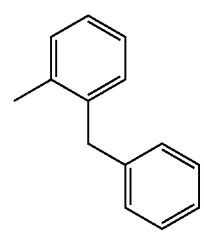 |

-continued
| | | |
|---|---|---|
| 431 | 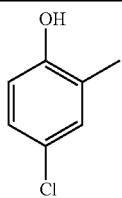 | 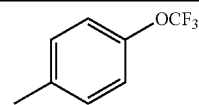 |
| 432 | 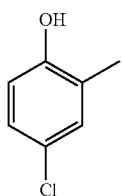 | 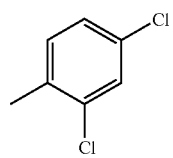 |
| 433 | 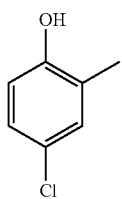 | 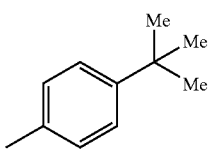 |
| 434 | 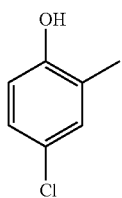 | 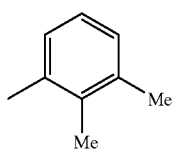 |
| 435 | 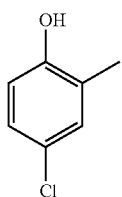 | 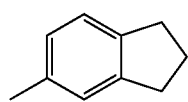 |
| 436 | 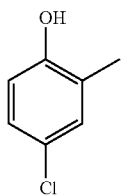 | 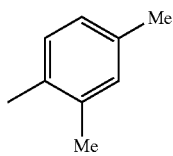 |
| 437 | 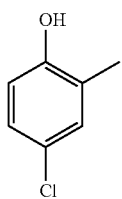 | 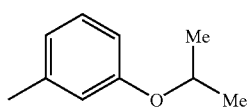 |
| 438 | 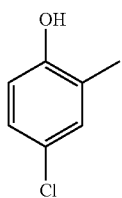 | 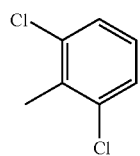 |

| | | |
|---|---|---|
| 439 | 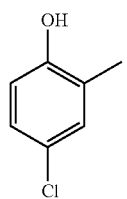 | 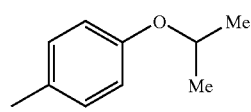 |
| 440 | 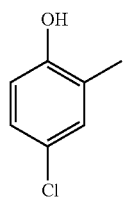 | 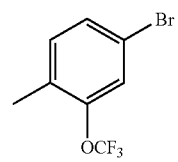 |
| 441 | 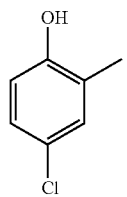 | 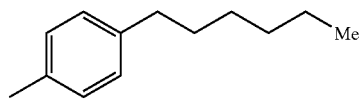 |
| 442 | 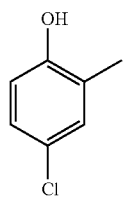 | 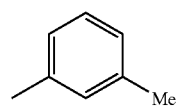 |
| 443 | 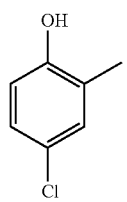 | 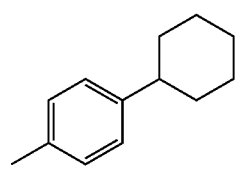 |
| 444 | 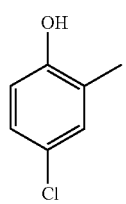 | 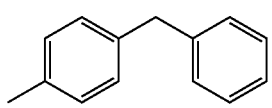 |
| 445 | 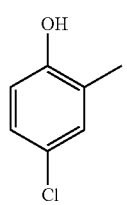 | 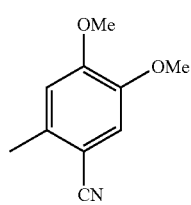 |

-continued
| | | |
|---|---|---|
| 446 | 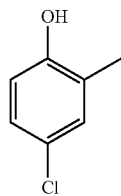 | 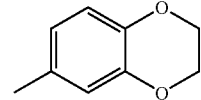 |
| 447 | 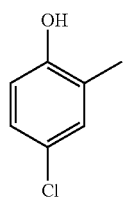 | 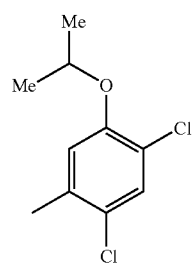 |
| 448 | 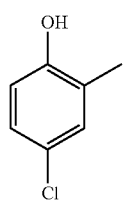 | 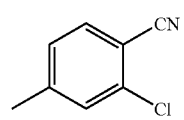 |
| 449 | 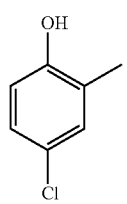 | 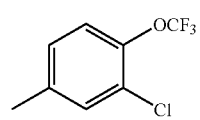 |
| 450 | 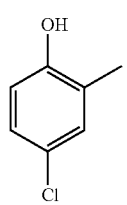 | 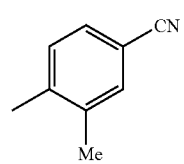 |
| 451 | 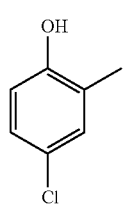 | 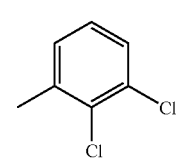 |
| 452 | 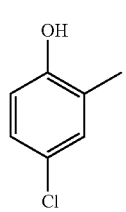 | 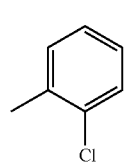 |

-continued
| | | |
|---|---|---|
| 453 | 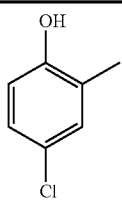 | 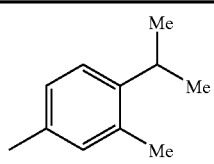 |
| 454 | 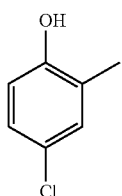 | 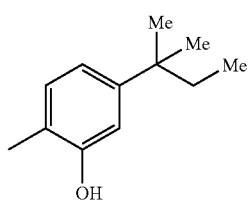 |
| 455 | 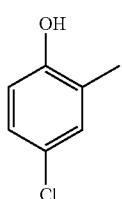 | 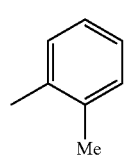 |
| 456 | 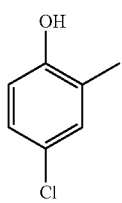 | 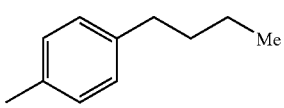 |
| 457 | 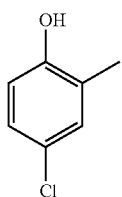 | 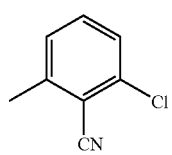 |
| 458 | 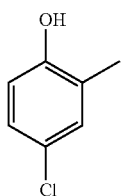 | 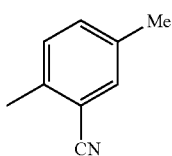 |
| 459 | 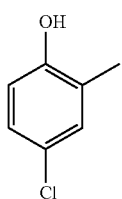 | 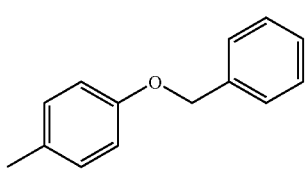 |
| 460 | 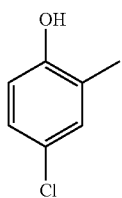 | 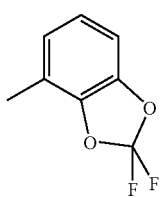 |

-continued
| | | |
|---|---|---|
| 461 | 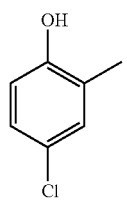 | 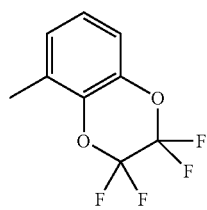 |
| 462 | 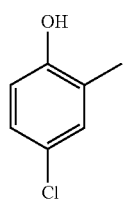 | 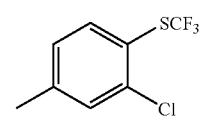 |
| 463 | 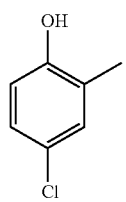 | 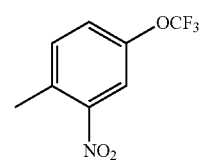 |
| 464 | 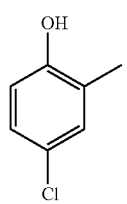 | 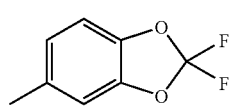 |
| 465 | 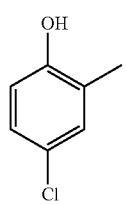 | 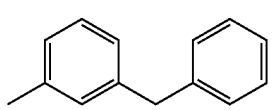 |
| 466 | 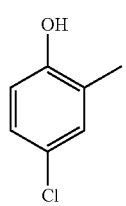 | 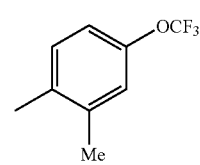 |
| 467 | 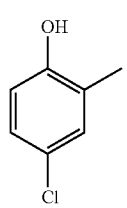 | 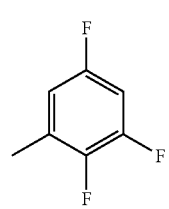 |

| | | |
|---|---|---|
| 468 | 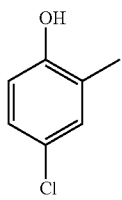 | 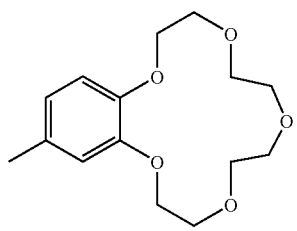 |
| 469 | 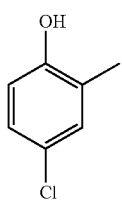 | 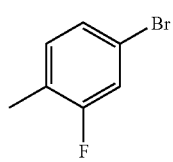 |
| 470 | 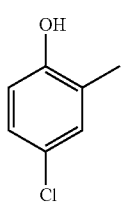 | 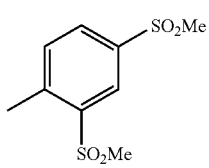 |
| 471 | 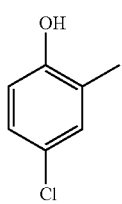 | 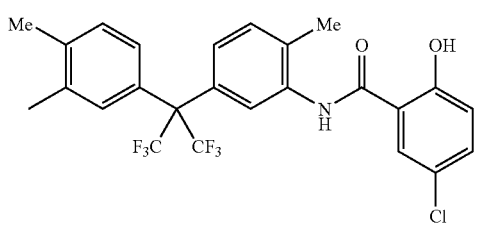 |
| 472 | 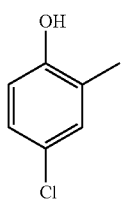 | 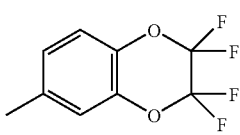 |
| 473 | 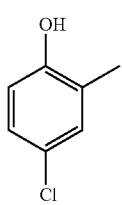 | 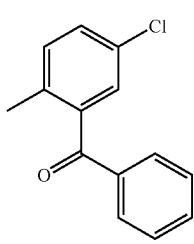 |
| 474 | 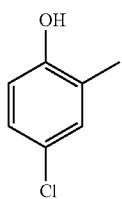 | 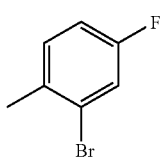 |

-continued
| | | |
|---|---|---|
| 475 | 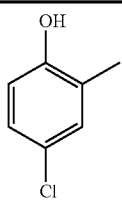 | 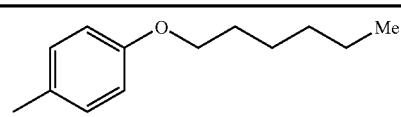 |
| 476 | 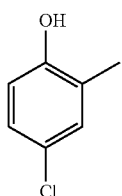 | 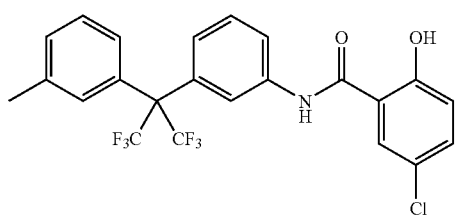 |
| 477 | 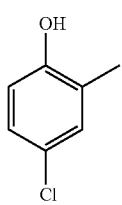 | 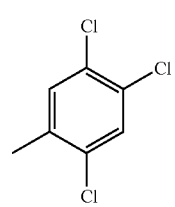 |
| 478 | 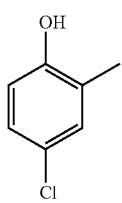 | 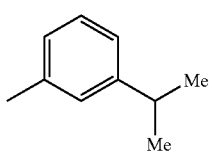 |
| 479 | 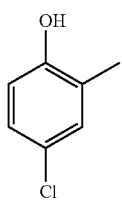 | 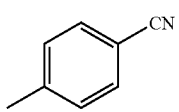 |
| 480 | 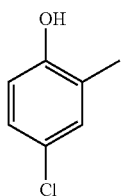 | 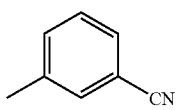 |
| 481 | 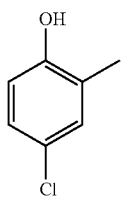 | 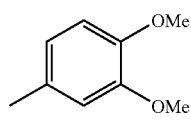 |
| 482 | 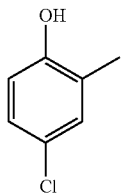 | 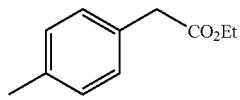 |

-continued
| | | |
|---|---|---|
| 483 | 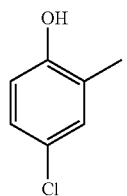 | 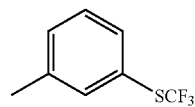 |
| 484 | 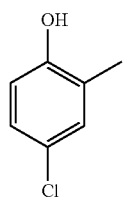 | 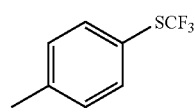 |
| 485 | 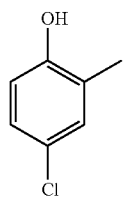 | 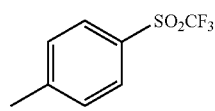 |
| 486 | 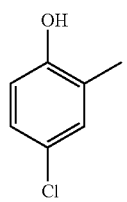 | 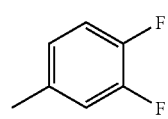 |
| 487 | 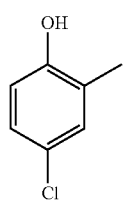 | 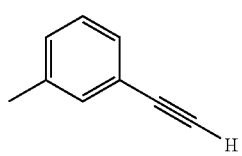 |
| 488 | 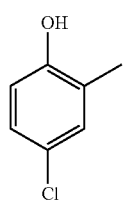 | 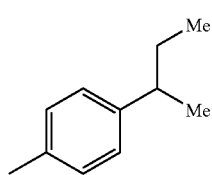 |
| 489 | 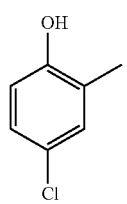 | 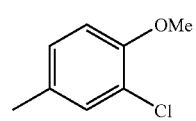 |

-continued
| | | |
|---|---|---|
| 490 | 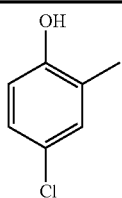 | 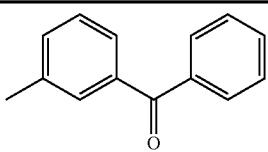 |
| 491 | 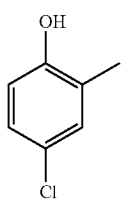 | 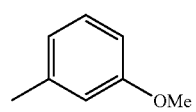 |
| 492 | 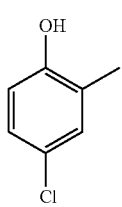 | 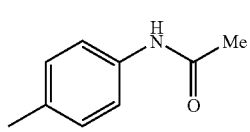 |
| 493 | 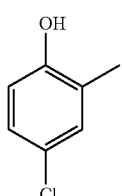 | 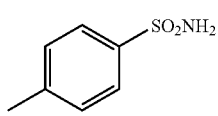 |
| 494 | 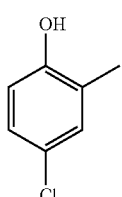 | 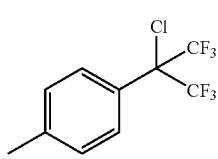 |
| 495 | 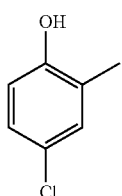 | 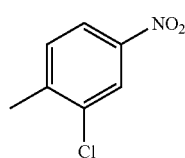 |
| 496 | 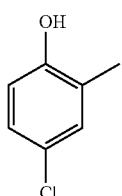 | 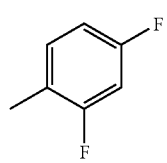 |
| 497 | 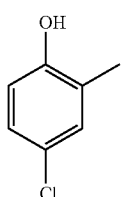 | 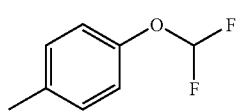 |

-continued
| | | |
|---|---|---|
| 498 | 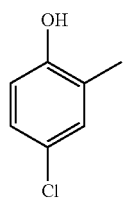 | 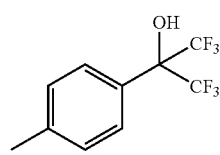 |
| 499 | 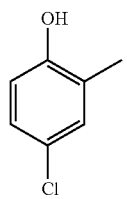 | 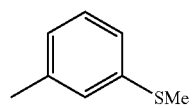 |
| 500 | 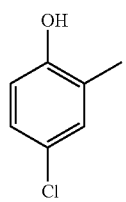 | 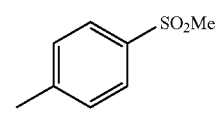 |
| 501 | 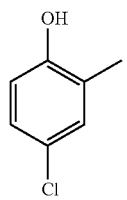 | 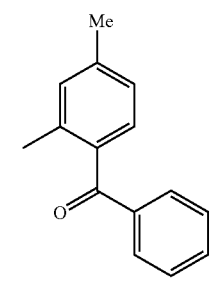 |
| 502 | 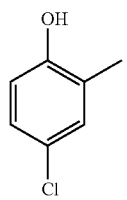 | 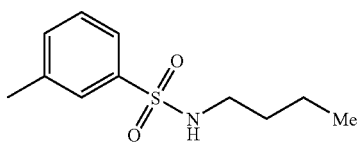 |
| 503 | 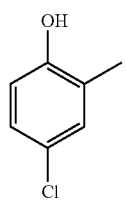 | 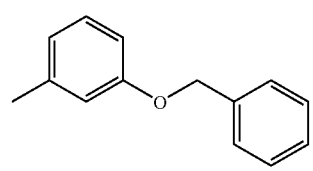 |
| 504 | 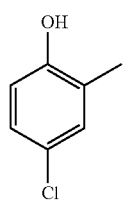 | 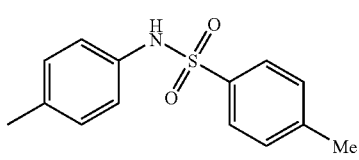 |

-continued
| | | |
|---|---|---|
| 505 | 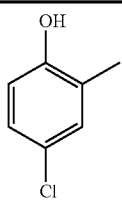 | 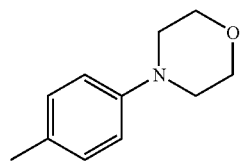 |
| 506 | 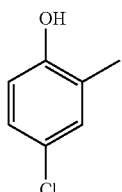 | 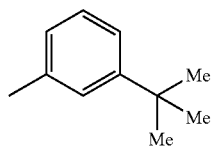 |
| 507 | 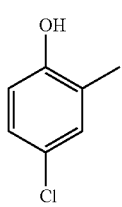 | 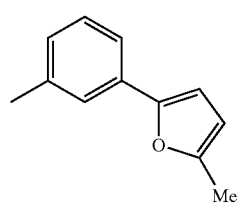 |
| 508 | 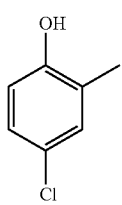 | 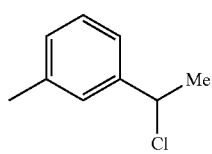 |
| 509 | 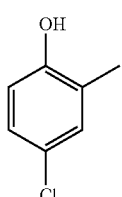 | 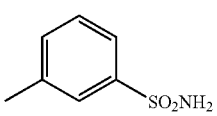 |
| 510 | 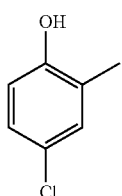 | 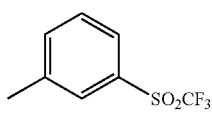 |
| 511 | 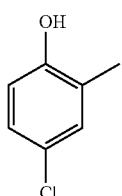 | 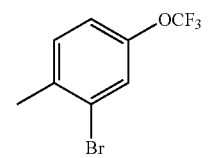 |
| 512 | 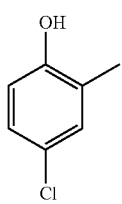 | 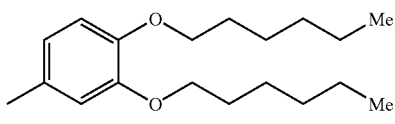 |

-continued
| | | |
|---|---|---|
| 513 | 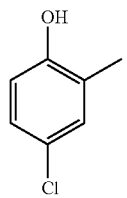 | 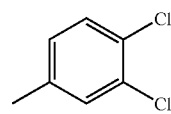 |
| 514 | 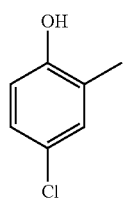 | 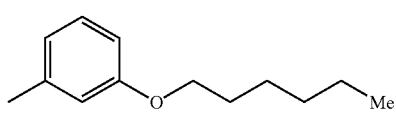 |
| 515 | 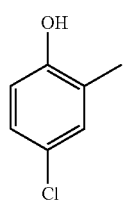 | 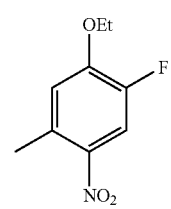 |
| 516 | 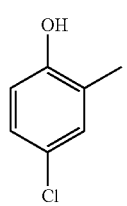 | 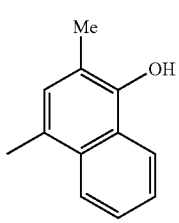 |
| 517 | 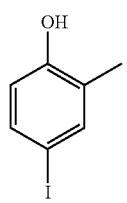 | 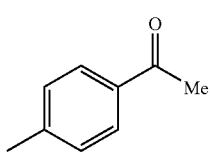 |
| 518 | 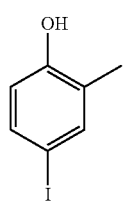 | 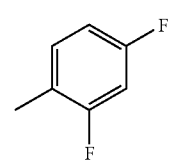 |
| 519 | 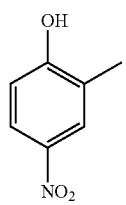 | 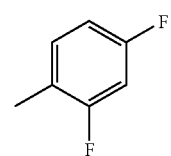 |
| 520 | 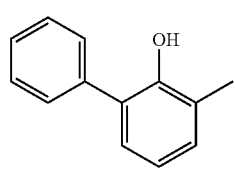 | 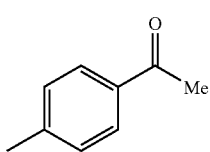 |

-continued
521 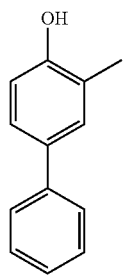 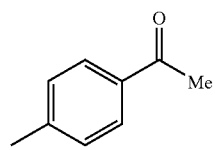
522 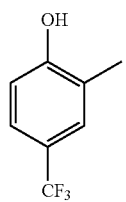 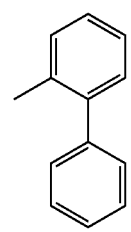
523 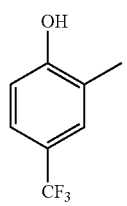 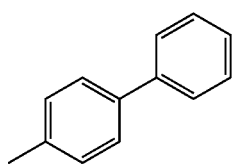
524 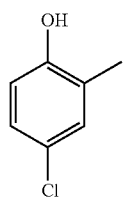 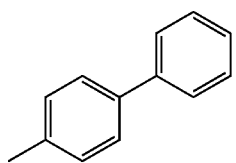
525 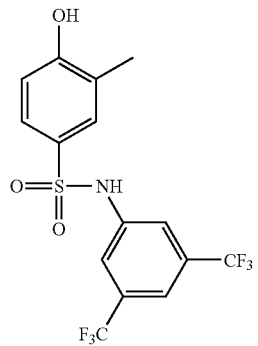 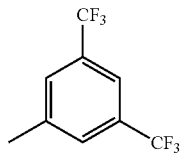
526 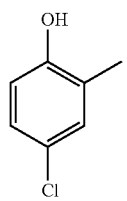 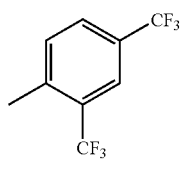

-continued
| | | |
|---|---|---|
| 527 | 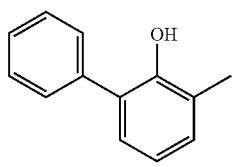 | 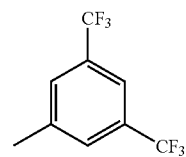 |
| 528 | 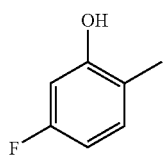 | 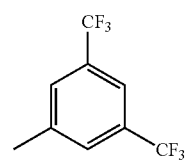 |
| 529 | 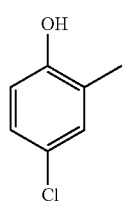 | 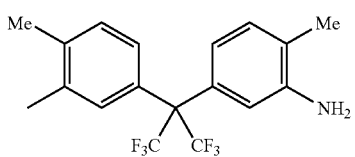 |
| 530 | 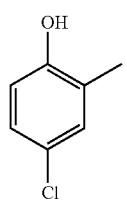 | 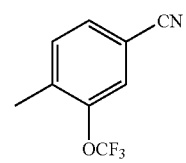 |
| 531 | 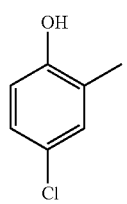 | 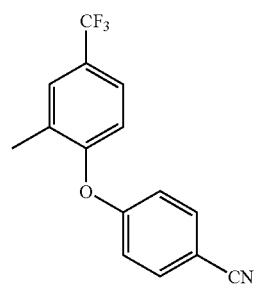 |
| 532 | 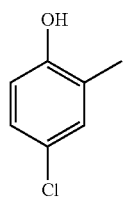 | 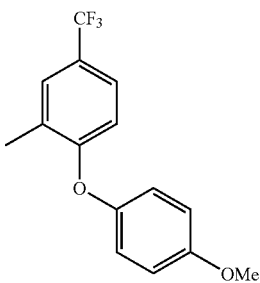 |
| 533 | 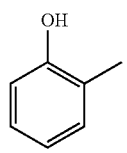 | 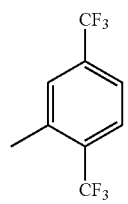 |

| | | |
|---|---|---|
| 534 | 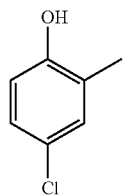 | 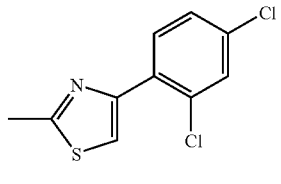 |
| 535 | 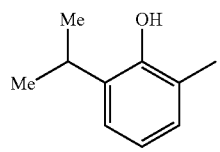 | 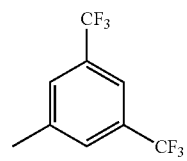 |
| 536 | 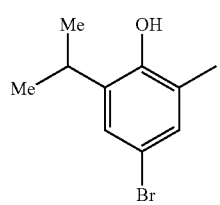 | 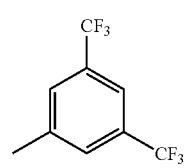 |
| 537 | 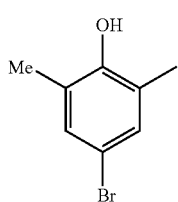 | 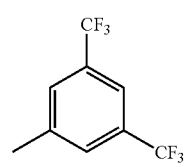 |
| 538 | 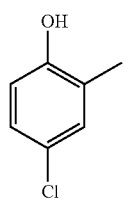 | 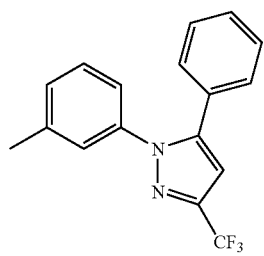 |
| 539 | 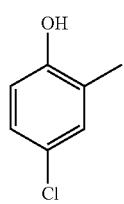 | 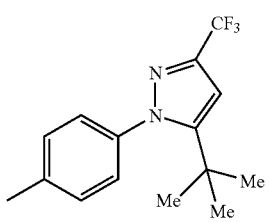 |
| 540 | 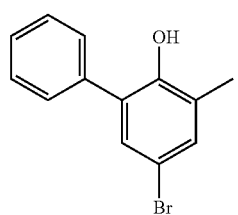 | 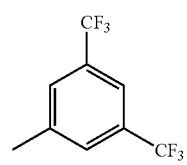 |

| | | |
|---|---|---|
| 541 | 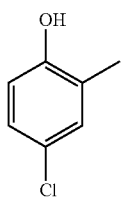 | 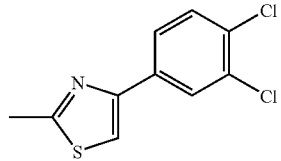 |
| 542 | 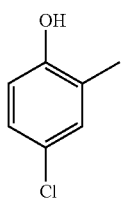 | 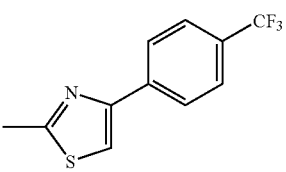 |
| 543 | 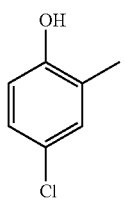 | 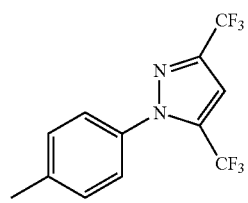 |
| 544 | 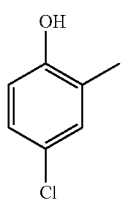 | 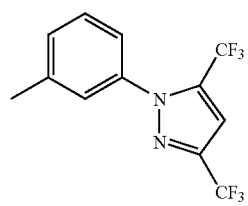 |
| 545 | 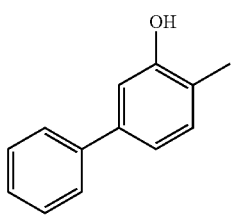 | 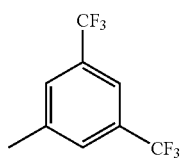 |
| 546 | 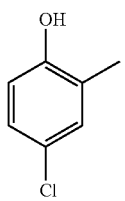 | 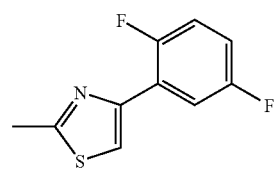 |
| 547 | 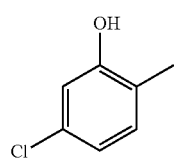 | 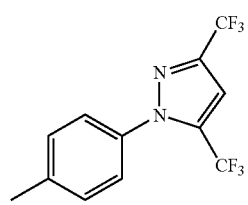 |

-continued
| | | |
|---|---|---|
| 548 | 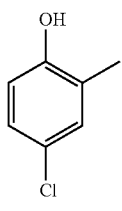 | 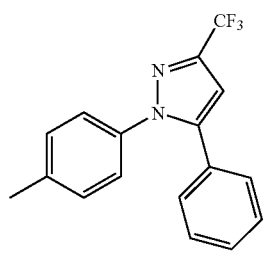 |
| 549 | 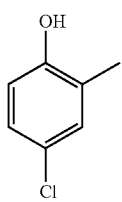 | 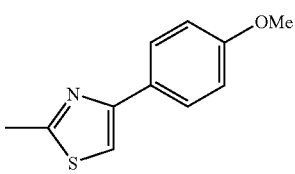 |
| 550 | 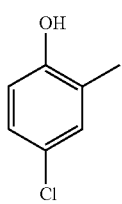 | 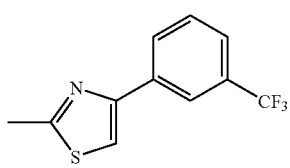 |
| 551 | 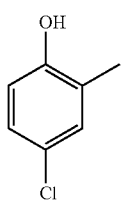 | 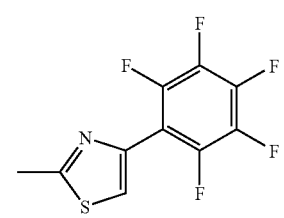 |
| 552 | 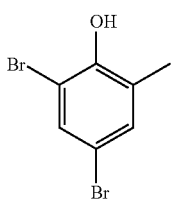 | 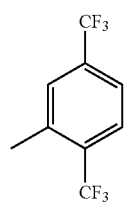 |
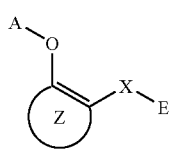
| Compound | | X | E |
|---|---|---|---|
| 553 | 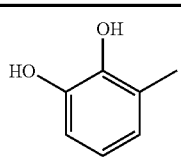 | 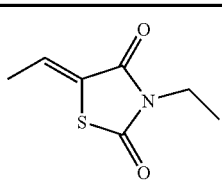 | 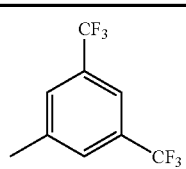 |
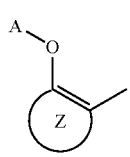

| | | | |
|---|---|---|---|
| 554 | 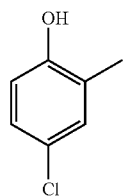 | 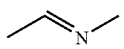 | 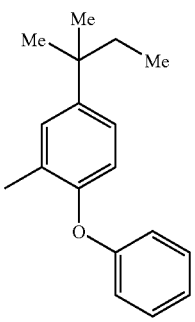 |
| 555 | 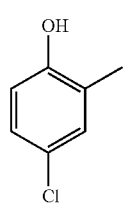 | 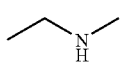 | 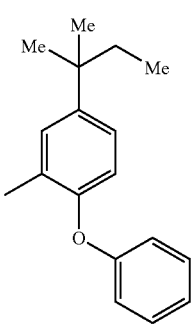 |

Methods for preparation of the compounds represented by the general formulas (I), (I-1), (I-2), (I-3) and (I-4) are not particularly limited. Reference to methods described in the pamphlet of International Publication WO02/49632 is useful.

The compounds represented by the general formulas (I), (I-1), (I-2), (I-3) and (I-4) can be prepared, for example, by methods shown bellow.

<Method 1>

The compounds represented by the general formula (I), wherein X is —CONH— (the hydrogen atom on the nitrogen may be substituted) and the compounds represented by the general formulas (I-1), (I-2), (I-3) and (I-4) can be prepared, for example, by a method described in the reaction scheme 1.

Reaction Scheme 1

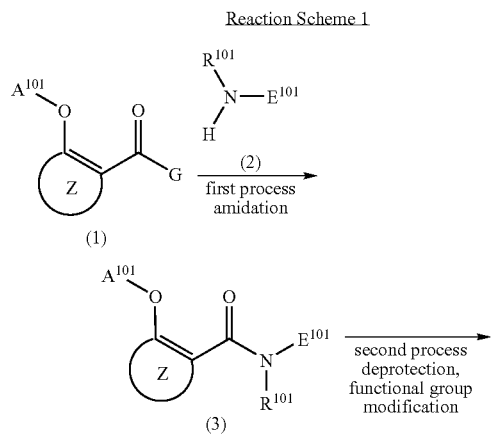

-continued

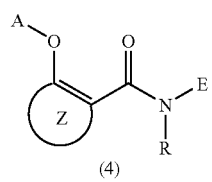

wherein each of A, ring Z, and E has the same meaning as that defined in the general formula (I), $A^{101}$ represents a hydrogen atom or protecting groups of hydroxy group (preferably, an alkyl group such as methyl group and the like; an aralkyl group such as benzyl group and the like; an acetyl group, an alkoxyalkyl group such as methoxymethyl group and the like; a substituted silyl group such as trimethylsilyl group or the like), each of R and $R^{101}$ represents a hydrogen atom, a $C_1$ to $C_6$ alkyl group or the like, $E^{101}$ represents E or precursor of E in the definition of the general formula (I), G represents a hydroxy group, halogen atoms (preferably, a chlorine atom), a hydrocarbon-oxy group (preferably, an aryl-oxy group which may be substituted by halogen atom), an acyl-oxy group, an imido-oxy group or the like.

(First Step)

The amide (3) can be prepared by dehydrocondensation of the carboxylic acid derivative (1) and the amine (2). This reaction is carried out at a reaction temperature of from 0° C. to 180° C., without solvent or in an aprotic solvent, in the presence of an acid halogenating agent or a dehydrocondensing agent, and in the presence or absence of a base.

As the halogenating agent, examples include, for example, thionyl chloride, thionyl bromide, sulfuryl chloride, phosphorus oxychloride, phosphorus trichloride, phosphorus pentachloride or the like. When $A^{101}$ is hydrogen atom, phosphorus trichloride is preferable, and when $A^{101}$ is acetyl group or the like, phosphorus oxychloride is preferable. As the dehydrocondensing agent, examples include, for example, N,N'-dicyclohexylcarbodiimide, 1-ethyl-3-(3-dimethylaminopropyl)carbodiimide hydrochloride, diphenylphosphorylazide or the like. As the base, examples include inorganic bases such as sodium carbonate, potassium carbonate, sodium hydrogencarbonate or the like, or organic bases such as pyridine, triethylamine, N,N'-diethylaniline or the like. As the aprotic solvent, examples include dichloromethane, dichloroethane, chloroform, tetrahydrofuran, 1,4-dioxane, benzene, toluene, monochlorobenzene, o-dichlorobenzene, N,N'-dimethylformamide, N-methylpyrrolidone or the like, when the reaction is carried out in the presence of the acid halogenating agent, particularly, toluene, monochlorobenzene, o-dichlorobenzene are preferable.

A target compound can also be prepared, for example, by a method or similar method described in Journal of Medicinal Chemistry, (USA), 1998, Vol. 41, No. 16, p. 2939-2945, in which the acid chloride is prepared and isolated beforehand from carboxylic acid, then the result is made to react with an amine having $E^{101}$.

When G is hydroxy group, the reaction condition described in Archiv der Pharmazie, (Germany), 1998, Vol. 331, No. 1, p. 3-6 can be used as a preferred reaction condition.

Kinds of carboxylic acid derivative (1) and amine (2) are not particularly limited, and new compounds synthesized by referring to well-known preparation method described in the literature or commercially available reagents can be used for the aforementioned reaction.

(Second Step)

When the amide (3) has a protecting group and/or has a favorable substitutent for functional group modification, for example, an amino group and a protected amino group or its precursor; a carboxy group and a protected carboxy group or its precursor; a hydroxy group and a protected hydroxy group or its precursor, the final target compound (4) can be prepared by a reaction for deprotection and/or functional group modification in this step. Various well-known methods can be used for the reaction. For the reaction of deprotection and functional group modification, for example, methods described in "Protective Groups in Organic Syntheses", (USA), Theodra W. Green, Peter G. M. Wuts, Eds., Third edition, April in 1999, John Wiley & Sons, and "Handbook of Reagents for Organic Synthesis", (USA), 4 Volumes, June in 1999, John Wiley & Sons can be used, and for the reaction of functional group modification, for example, methods described in "Palladium Reagents in Organic Syntheses", (USA), Richard F. Heck, 1985, Academic Press, and "Palladium Reagents and Catalysts: Innovations in Organic Synthesis", (USA), J. Tsuji, 1999, John Wiley & Sons, or the like can be used.

The aforementioned methods are applicable by appropriately combining raw materials even for the compounds wherein X is other connecting group, for example, —SO$_2$NH—, —NHCO—, —NHSO$_2$—, —CONHCH$_2$—, —CONHCH$_2$CH$_2$—, —CONHCH$_2$CONH—, —CONHNHCO—, —CONHNHCH$_2$—, —COO—, —CONHNH—; wherein the hydrogen atom on said connecting group may be substituted.

In the general formula (I), when X is the formula: —CONHCH$_2$— wherein the hydrogen atom on said connecting group may be substituted, the target compound can be prepared by using an amine represented by the formula: H$_2$N—CH$_2$-E$^{101}$, wherein E$^{101}$ has the same meaning as that defined above, instead of the amine (2).

In the general formula (I), when X is the formula: —CONHCH$_2$CH$_2$— wherein the hydrogen atom on said connecting group may be substituted, the target compound can be prepared by using an amine represented by the formula: H$_2$N—CH$_2$CH$_2$-E$^{101}$, wherein E$^{101}$ has the same meaning as that defined above, instead of the amine (2).

In the general formula (I), when X is the formula: —SO$_2$NH—, the target compound can be prepared by using a sulfonyl chloride represented by the formula: A$^{101}$-O-(ring Z)-SO$_2$Cl, wherein each of A$^{101}$ and ring Z has the same meaning as that defined above, instead of the carboxylic acid derivative (1).

In the general formula (I), when X is the formula: —NHCO—, the target compound can be prepared by using an amine represented by the formula: A$^{101}$-O-(ring Z)-NH$_2$, wherein each of A$^{101}$ and ring Z has the same meaning as that defined above, and a carboxylic acid represented by the formula: E$^{101}$-O—COOH, wherein -E$^{101}$ has the same meaning as that defined above, or a carboxylic acid chloride represented by the formula: E$^{101}$-COCl, wherein -E$^{101}$ has the same meaning as that defined above.

In the general formula (I), when X is the formula: —NHSO$_2$—, wherein said connecting group may be substituted, the target compound can be prepared by using an amine represented by the formula: HO-(ring Z)-NH$_2$, wherein ring Z has the same meaning as that defined above, and a sulfonyl chloride represented by the formula: E$^{101}$SO$_2$Cl, wherein E$^{101}$ has the same meaning as that defined above.

In the general formula (I), when X is the formula: —CONHNHCO—, the target compound can be prepared by using a hydrazide represented by the formula: HO-(ring Z)-CONHNH$_2$, wherein ring Z has the same meaning as that defined above, and a carboxylic acid chloride represented by the formula: E$^{101}$-COCl, wherein -E$^{101}$ has the same meaning as that defined above.

In the general formula (I), when X is the formula: —COO—, the target compound can be prepared by using a phenol derivative represented by the formula: HO-E$^{101}$, wherein -E$^{101}$ has the same meaning as that defined above, instead of the amine (2).

In the general formula (I), when X is the formula: —CONHNH—, the target compound can be prepared by using a hydrazine represented by the formula: H$_2$N—NH-E$^{101}$, wherein E$^{101}$ has the same meaning as that defined above, instead of the amine (2).

In the general formula (I), when X is the formula: —CONHCH$_2$CONH—, the target compound can be prepared by using an amine represented by the formula: H$_2$N—CH$_2$CONH-E$^{101}$, wherein E$^{101}$ has the same meaning as that defined above, instead of the amine (2).

The amine represented by the formula: H$_2$N—CH$_2$CONH-E$^{101}$, can be prepared, for example, by condensation of the amine (2) and a N-protected amino acid (for example, N-(tert-butoxycarbonyl)glycine), according to the aforementioned method 1, followed by a deprotection reaction.

In the general formula (I), when X is the following formula:

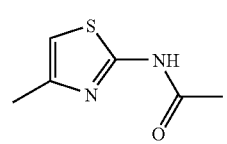

wherein said connecting group may be substituted, the target compound can be prepared by using an amine represented by the following formula:

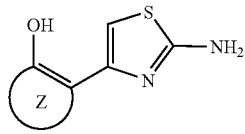

wherein ring Z has the same meaning as that defined above, and a carboxylic acid represented by the formula: $E^{101}$-COOH, wherein $E^{101}$ has the same meaning as that defined above, or a carboxylic acid chloride represented by the formula: $E^{101}$-COCl, wherein $E^{101}$ has the same meaning as that defined above.

The amine represented by the following formula:

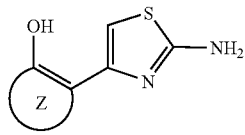

can be prepared, for example, by a method described in the reaction scheme 1-2.

Reaction Scheme 1-2

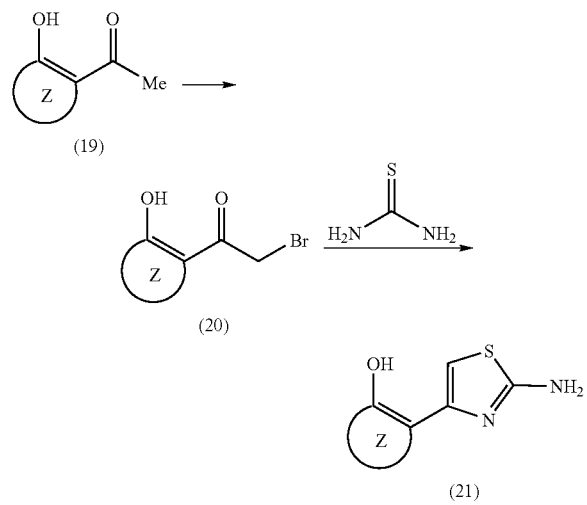

wherein ring Z has the same meaning as that defined above.

The bromoacetophenone (20) can be prepared by bromination of the acetophenone (19).

This reaction is carried out at a reaction temperature of from 0° C. to 100° C. in a solvent, in the presence of a brominating agent.

As the brominating agent, for example, phenyltrimethylammonium tribromide can preferably be used.

As the reaction solvent, any solvent can be used as long as it does not inhibit the reaction, for example, ethers such as tetrahydrofuran can be used.

The amine (21) can be prepared by reacting the bromoacetophenone (20) with thiourea.

This reaction is carried out at a reaction temperature of from 0° C. to 120° C. in a solvent.

As the reaction solvent, any solvent can be used as long as it does not inhibit the reaction, for example, alcohols such as ethanol can be used.

<Method 2>

The compounds represented by the general formula (I), wherein X is —$CH_2NH$— can be prepared, for example, by a method described in the reaction scheme 2.

Reaction Scheme 2

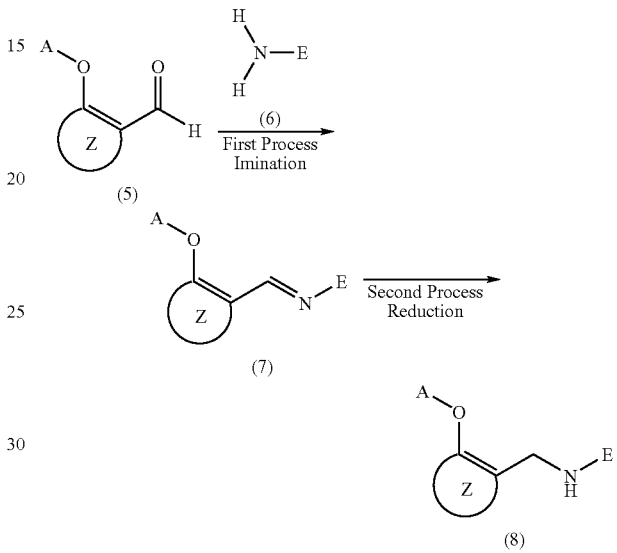

wherein each of A, ring Z, and E has the same meaning as that defined in the general formula (I).

The imine derivative of the formula (7) can be prepared by dehydrocondensation of the aldehyde (5) and the amine (6). This reaction is carried out at a reaction temperature of from 0° C. to 100° C. in a solvent, in the presence or absence of a dehydrating agent. As the dehydrating agent, examples include anhydrous magnesium sulfate, molecular sieves or the like. As the solvent, examples include inert solvent, and tetrahydrofuran, 1,4-dioxane, methanol, ethanol or the like are preferable.

The aforementioned methods are applicable by appropriately combining raw materials even for the compounds wherein X is other connecting group, for example, —CONHN=CH—, —CH=NNHCO—, —CHNNH—; wherein the hydrogen atom on said connecting group may be substituted.

In the general formula (I), when X is the formula: —CONHN=CH—, the target compound can be prepared by using a hydrazide represented by the formula: HO-(ring Z)-CONHNH$_2$, wherein ring Z has the same meaning as that defined above, and an aldehyde represented by the formula: E-CHO, wherein E has the same meaning as that defined above.

In the general formula (I), when X is the formula: —CH=NNHCO—, the target compound can be prepared by using an aldehyde represented by the formula: HO-(ring Z)-CHO, wherein ring Z has the same meaning as that defined above, and a hydrazide represented by the formula: E-CONHNH$_2$, wherein E has the same meaning as that defined above.

In the general formula (I), when X is the formula: —CH=NNH—, the target compound can be prepared by using an aldehyde represented by the formula: HO-(ring Z)-CHO, wherein ring Z has the same meaning as that defined above, and a hydrazine represented by the formula: E-NHNH$_2$, wherein E has the same meaning as that defined above.

The target compound (8) can be prepared by reduction of the imine derivative (7). This reaction is carried out at a reaction temperature of from 0° C. to 100° C. in a solvent, in the presence of a reducing agent. As the reducing agent, examples include sodium borohydride, lithium borohydride or the like. As the solvent, examples include inert solvent, and tetrahydrofuran, 1,4-dioxane, methanol, ethanol or the like are preferable. This reaction can also be carried out by a method of catalytic hydrogenation. As the catalyst, examples include palladium carbon, platinum carbon, palladium hydroxide, palladium black or the like. As solvent, examples include inert solvent, and tetrahydrofuran, 1,4-dioxane, methanol, ethanol or the like are preferable. The reaction is carried out at a reaction temperature of from 0° C. to 200° C., and the hydrogen pressure may be an ordinary pressure or a positive pressure.

<Method 3>

The compounds represented by the general formula (I), wherein X is —CH=CH— (the hydrogen atom on said connecting group may be substituted), can be prepared, for example, by methods described in the reaction scheme 3-1 or the reaction scheme 3-2.

Reaction Scheme 3-1

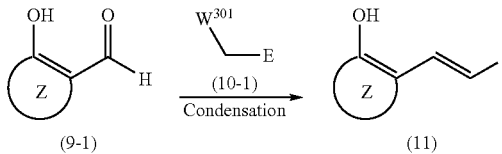

wherein each of ring Z and E has the same meaning as that defined in the general formula (I), W$^{301}$ represents O,O'-dihydrocarbon-phosphono group or triarylphosphonium group The target compound (11) can be prepared by dehydrocondensation of the aldehyde (9-1) and the phosphorus compound (10-1). This reaction is carried out in a solvent at a reaction temperature of from 0° C. to the boiling point of the solvent, in the presence of a base. As the base, examples include inorganic base such as sodium carbonate, potassium carbonate, sodium hydrogencarbonate or the like, or organic base such as pyridine, triethylamine, N,N-diethylaniline or the like. As the solvent, examples include inert solvent, and tetrahydrofuran, 1,4-dioxane, methanol, ethanol, water or the like are preferable.

Reaction Scheme 3-2

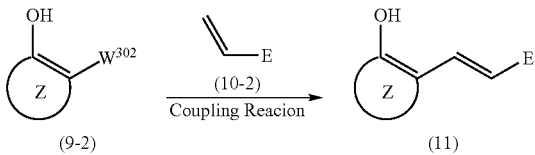

wherein each of ring Z and E has the same meaning as that defined in the general formula (I), W$^{302}$ represents halogen atoms (preferably, iodine atom and bromine atom), (trifluoromethanesulfonyl)oxy group and the like.

The target compound (11) can be prepared by reacting the halogenated compound (9-2) with the styrene compound (10-2) in the presence of a transition-metal complex catalyst. This reaction is carried out in a solvent at a reaction temperature of from 0° C. to the boiling point of the solvent, in the presence or absence of a ligand and/or a base. As the transition-metal complex catalyst, examples include palladium catalyst such as palladium acetate and dichlorobis(triphenylphosphine) palladium. As the ligand, examples include phosphine ligand such as triphenylphosphine. As the base, examples include inorganic base such as sodium carbonate, potassium carbonate, and sodium hydrogen carbonate, or organic base such as pyridine, triethylamine, and N,N-diethylaniline. As the solvent, examples include inert solvents, and N,N-dimethylformamide, tetrahydrofuran, 1,4-dioxane or the like are preferable.

<Method 4>

The compounds represented by the general formula (I), wherein X is —COCH=CH— and —COCH$_2$CH$_2$— (the hydrogen atom on said connecting group may be substituted), can be prepared, for example, by a method described in the reaction scheme 4.

Reaction Scheme 4

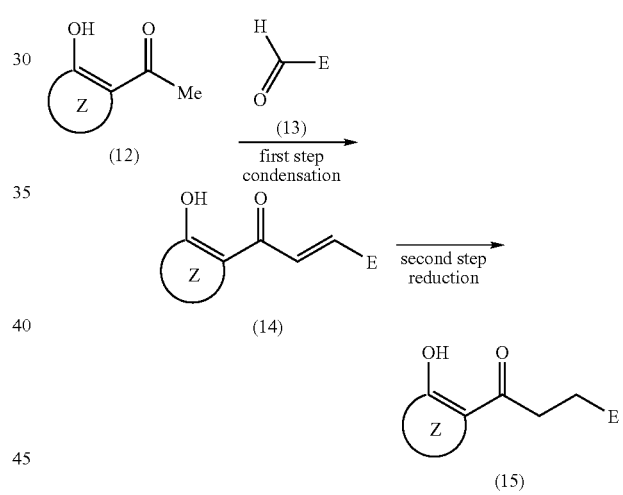

wherein each of rings Z and E has the same meaning as that defined in the general formula (I).

The target compound enone (14) can be prepared by dehydrocondensation of the ketone (12) and the aldehyde (13). This reaction is carried out in a solvent at a reaction temperature of from 0° C. to the boiling point of the solvent, in the presence of a base. As the base, examples include inorganic base such as sodium hydroxide, potassium hydroxide, sodium carbonate, potassium carbonate, sodium hydrogencarbonate or the like, or organic base such as pyridine, triethylamine, N,N-diethylaniline or the like. Examples include inert solvent, and tetrahydrofuran, 1,4-dioxane, methanol, ethanol, water or the like are preferable.

Next, the target compound (15) can be prepared by reduction of the enone (14). This reaction is carried out at a reaction temperature of from 0° C. to 100° C. in solvent, in the presence of a reducing agent. As the reducing agent, examples include sodium borohydride, lithium borohydride or the like. As the solvent, examples include inert solvent, and tetrahydrofuran, 1,4-dioxane, methanol, ethanol or the like are preferable. Moreover, this reaction is carried out by a method of catalytic hydrogenation also. As the catalyst, examples include palladium carbon, platinum carbon, palladium hydroxide, palladium black or the like. As solvent, examples include inert solvent, and tetrahydrofuran, 1,4-dioxane, methanol, ethanol or the like are preferable. The reaction is carried out at a reaction temperature of from 0° C. to 200° C., and the hydrogen pressure is at normal pressure or applied pressure.

<Method 5>

The compounds represented by the general formula (I), wherein X is —NHCONH— (the hydrogen atom on said connecting group may be substituted), can be prepared, for example, by a method described in the reaction scheme 5.

Reaction Scheme 5

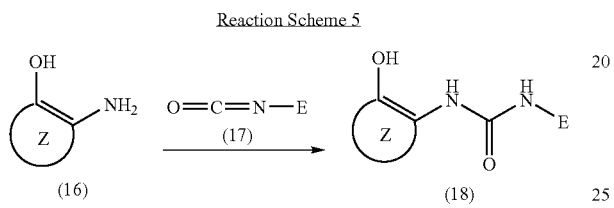

wherein each of ring Z and E has the same meaning as that defined in the general formula (I).

First, the target compound urea (18) can be prepared by reacting the amine (16) with the isocyanate (17). This reaction is carried out in a solvent at a reaction temperature of from 0° C. to the boiling point of the solvent, in the presence or absence of a base. As the base, examples include inorganic base such as sodium hydroxide, potassium hydroxide, sodium carbonate, potassium carbonate, sodium hydrogencarbonate or the like, or organic base such as pyridine, triethylamine, N,N-diethylaniline or the like. Examples include inert solvent, and tetrahydrofuran, 1,4-dioxane, methanol, ethanol, water or the like are preferable.

<Method 6>

The compounds represented by the general formula (I), wherein X is the formula: —CONHNHCH$_2$— (the hydrogen atom on said connecting group may be substituted), can be prepared, for example, by a method described in the reaction scheme 6.

Reaction Scheme 6

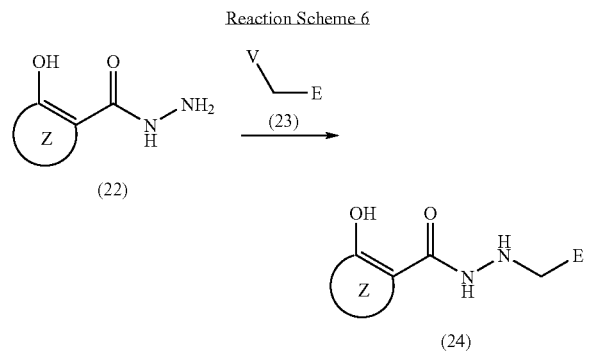

wherein each of ring Z and E has the same meaning as that defined above, and V represents a leaving group such as halogen atom.

The target compound hydrazide (24) can be prepared by reacting the hydrazide (22) with the benzyl derivative (23).

This reaction is carried out at a reaction temperature of from 0° C. to 180° C. in a solvent, in the presence or absence of a base.

As the base, for example, organic base such as pyridine, triethylamine or the like can preferably be used.

As the reaction solvent, any solvent can be used as long as it does not inhibit the reaction, for example, halogenated solvent such as dichloromethane; ethers such as tetrahydrofuran; and hydrocarbon solvent such as toluene can be used.

<Method 7>

The compounds represented by the general formula (I), wherein X is the formula:

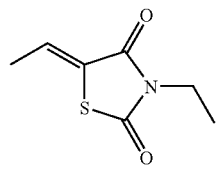

can be prepared, for example, by a method described in the reaction scheme 7.

Reaction Scheme 7

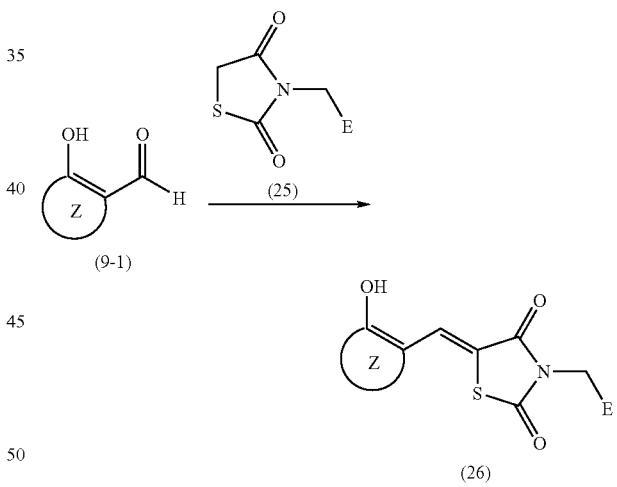

wherein each of ring Z and E has the same meaning as that defined above.

The target compound 5-(benzylidene)-3-benzylthiazolidin-2,4-dione derivative (26) can be prepared by reacting the aldehyde (9-1) with the 3-benzylthiazolidin-2,4-dione derivative (25).

This reaction is carried out at a reaction temperature of from 0° C. to 180° C. in a solvent, in the presence of a catalyst. As the catalyst, for example, a mixture of piperidine/acetic acid can preferably be used. As the reaction solvent, any solvent can be used as long as it does not inhibit the reaction, for example, hydrocarbon solvent such as toluene can be used.

The 3-benzylthiazolidine-2,4-dione derivative represented by the following formula:

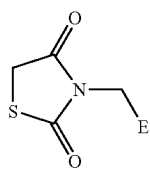

wherein E has the same meaning as that defined above, can be prepared, for example, by a method described in the reaction scheme 7-1.

Reaction Scheme 7-1

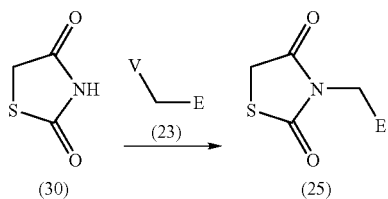

wherein each of E and V has the same meaning as that defined above.

The target compound 3-benzylthiazolidine-2,4-dione derivative (28) can be prepared by reacting thiazolidine-2,4-dione (30) with the benzyl derivative (23).

This reaction is carried out at a reaction temperature of from 0° C. to 180° C. in a solvent, in the presence of a base. As the base, for example, inorganic base such as sodium hydroxide, potassium carbonate or the like, or organic base such as pyridine, triethylamine or the like can preferably be used.

As the reaction solvent, any solvent can be used as long as it does not inhibit the reaction, for example, water; alcohols such as ethanol or the like; halogenated solvent such as dichloromethane or the like; ethers such as tetrahydrofuran or the like; or amides such as N,N-dimethylformamide or the like can be used.

The compounds represented by the general formulas (I), (I-1), (I-2), (I-3) and (I-4) prepared by the aforementioned methods can be isolated and purified by methods widely known by those skilled in the art, for example, extraction, precipitation, fractional chromatography, fractional crystallization, suspension and washing, and recrystallization. Furthermore, each of the pharmaceutically acceptable salt of the compound of the present invention, the hydrate thereof and the solvate thereof can be prepared by methods widely known by those skilled in the art.

In the examples of the specification, preparation methods of typical compounds included in the general formulas (I), (I-1), (I-2), (I-3) and (I-4) are explained in details. Therefore, those skilled in the art can prepare any compound fall within the general formulas (I), (I-1), (I-2), (I-3) and (I-4) by referring to the explanations of the aforementioned general preparation methods and those of specific preparation methods of the examples, by choosing appropriate reaction raw materials, reaction reagents, and reaction conditions, and by adding appropriate modification and alteration of these methods, if necessary.

The compounds represented by the general formulas (I), (I-1), (I-2), (I-3), and (I-4) have antiallergic action, and accordingly, they are useful as active ingredients of the medicaments for the preventive and/or therapeutic treatment of allergic diseases. The aforementioned medicaments have inhibitory activity against the proliferation of mast cells, inhibitory activity against the production of IgE from activated B cells, and inhibitory activity against the degranulation from activated mast cells. Therefore, they can be suitably used as a suppressant against allergic reaction expression. More specifically, the medicaments of the present invention are useful for the preventive and/or therapeutic treatment of the following diseases wherein allergic reaction is believed to be involved, for example, allergic diseases such as contact dermatitis, atopic dermatitis, eczema, pruritus, pollinosis, asthma, bronchitis, urticaria, vasculitis, rhinitis, gastrointestinal symptoms, diarrhea, interstitial pneumonia, arthritis, ophthalmia, conjunctivitis, neuritis, otitis media, granulomatosis, encephalomyelitis, cystitis, laryngitis, peliosis, food allergy, insect allergy, drug allergy, metal allergy, anaphylactic shock and the like, and/or endometriosis and/or hysteromyoma.

Furthermore, in endometriosis, it is known that an adhesion of the uterus with its peripheral tissue frequently occurs due to an abnormal proliferation of endometrial tissue outside the uterus. It is known that this is caused by an inflammatory reaction by allergy and the like, and a phenomenon called as "remodeling" including fibrosis and hyperplasia of tissue as typical examples occurs (Frontiers in Bioscience, (USA), 2002, Vol. 7, the April 1 issue, p. e91-115). As for the fibrosis of tissue, it is widely known that one of the causes is a production of a large amount of collagen, which is triggered by infiltration of effecter cells and activation of proliferation of fibroblast by inflammation. This remodeling phenomenon is considered to be occurred on the basis of a mechanism common in the remodeling of cardiac muscle after myocardial infarction, the remodeling of a vessel by arteriosclerosis, the remodeling of bronchus by bronchial asthma or the like, as well as in the adhesion of a tissue in endometriosis. Accordingly, an inhibitor against the proliferation or activation of a fibroblast is considered to be useful as a therapeutic drug not only for endometriosis but for diseases in which fibrosis or remodeling of a tissue is believed to be involved, for example, myocardial infarction, arteriosclerosis, asthma, nephritis, interstitial pneumonia, pulmonary fibrosis, hepatic cirrhosis and the like.

The compounds of the present invention was found to inhibit cell proliferation of HT-1080, which is a fibrosarcoma cell having properties similar to those of fibroblast and collagen productivity, under proliferative stimulation by PDGF (platelet-derived growth factor). Therefore, they are considered to be useful as a therapeutic drug and/or a preventive drug for diseases in which fibrosis or remodeling of tissue is involved.

As the active ingredient of the medicament on the present invention, one or more kinds of substances selected from the group consisting of the compound represented by the general formulas (I), (I-1), (I-2), (I-3) and (I-4) and a pharmacologically acceptable salt thereof, and a hydrate thereof and a solvate thereof may be used. The aforementioned substance, per se, may be administered as the medicament of the present invention, however, preferably, the medicament of the present invention is provided in the form of a pharmaceutical composition comprising the aforementioned substance which is an active ingredient together with one or more pharmacologically acceptable pharmaceutical additives. In the aforementioned pharmaceutical compositions, a ratio of the active ingredient to the pharmaceutical additives is 1 weight % to 90 weight %.

The pharmaceutical compositions of the present invention may be administered as pharmaceutical compositions for oral administration, for example, granules, subtilized granules, powders, hard capsules, soft capsules, syrup, emulsion, suspension, or solution, or may be administered as pharmaceutical compositions for parenteral administration, for example, injections for intravenous administration, intramuscular administration, or subcutaneous administration, drip infusions, suppositories, percutaneous absorbent, transmucosal absorption preparations, nasal drops, ear drops, instillation, and inhalants. Preparations made as pharmaceutical compositions in a form of powder may be dissolved when necessary and used as injections or drip infusions.

For preparation of pharmaceutical compositions, solid or liquid pharmaceutical additives may be used. Pharmaceutical additives may either be organic or inorganic. When an oral solid preparation is prepared, an excipient is added to the active ingredient, and further binders, disintegrator, lubricant, colorant, corrigent are added, if necessary, to manufacture preparations in the forms of tablets, coating tablets, granules, powders, capsules and the like by ordinary procedures. Examples of the excipient include lactose, sucrose, saccharose, glucose, corn starch, starch, talc, sorbit, crystal cellulose, dextrin, kaolin, calcium carbonate, and silicon dioxide. Examples of the binder include, for example, polyvinyl alcohol, polyvinyl ether, ethyl cellulose, methyl cellulose, gum Arabic, tragacanth, gelatine, shellac, hydroxypropyl cellulose, hydroxypropyl methyl cellulose, calcium citrate, dextrin, and pectin. Examples of the lubricant include, for example, magnesium stearate, talc, polyethylene glycol, silica, and hydrogenated vegetable oil. As the coloring agent, any material can be used which are approved to be added to ordinary pharmaceuticals. As the corrigent, cocoa powder, menthol, aromatic acid, peppermint oil, d-borneol, cinnamon powder and the like can be used. These tables and granules may be applied with sugarcoating, gelatin coating, or an appropriate coating, if necessary. Preservatives, antioxidant and the like may be added, if required.

For liquid preparations for oral administration such as emulsions, syrups, suspensions, and solutions, ordinary used inactive diluents, for example, water or vegetable oil may be used. For these preparations, besides inactive diluents, adjuvants such as wetting agents, suspending aids, sweating agents, flavoring agents, coloring agents or preservatives may be blended. After a liquid preparation is manufactured, the preparation may be filled in capsules made of a absorbable substance such as gelatin. Examples of solvents or suspending agents used for the preparations of parenteral administration such as injections or suppositories include, for example, water, propylene glycol, polyethylene glycol, benzyl alcohol, ethyl oleate, and lecithin. Examples of base materials used for preparation of suppositories include, for example, cacao butter, emulsified cacao butter, lauric fat, and witepsol. Methods for preparation of the aforementioned preparations are not limited, and any method ordinarily used in the art may be used.

When the composition are prepared in the form of injections, carriers such as, for example, diluents including water, ethanol, macrogol, propylene glycol, citric acid, acetic acid, phosphoric acid, lactic acid, sodium lactate, sulfuric acid and sodium hydroxide, pH modifiers and buffer solutions including sodium citrate, sodium acetate and sodium phosphate, stabilizers such as sodium pyrosulfite, ethylenediaminetetraacetic acid, thioglycolic acid and thiolactate may be used. For the preparation, a sufficient amount of a salt, glucose, mannitol or glycerin may be blended in the preparation to manufacture an isotonic solution, and an ordinary solubilizer, a soothing agent, or a topical anesthetic may be used.

When the preparation in the form of an ointment such as a paste, a cream, and a gel is manufactured, an ordinarily used base material, a stabilizer, a wetting agent, and a preservative may be blended, if necessary, and may be prepared by mixing the components by a common method. As the base material, for example, white petrolatum, polyethylene, paraffin, glycerin, cellulose derivatives, polyethylene glycol, silicon, and bentonite may be used. As the preservative, paraoxy methyl benzoate, paraoxy ethyl benzoate, paraoxy propyl benzoate and the like may be used. When the preparation in the form of a patch is manufactured, the aforementioned ointment, cream gel, or paste and the like may be applied by a common method to an ordinary support. As the support, fabric made of cotton, span rayon, and synthetic fibersor or nonwoven fabric, and a film or a foam sheet such as made of soft vinyl chloride, polyethylene, and polyurethane and the like may be preferably used.

A dose of the medicament of the present invention is not particularly limited. For oral administration, a dose may generally be 0.01 to 5,000 mg per day for an adult as the weight of the compound of the present invention. It is preferred to increase or decrease the above dose appropriately depending on the age, pathological conditions, and symptoms of a patient. The above dose may be administered once a day or 2 to 3 times a day as divided portions with appropriate intervals, or intermittent administration for every several days may be applied. When the medicament is used as an injection, the dose may be 0.001 to 100 mg per day for an adult as the weight of the compound of the present invention.

EXAMPLES

The present invention will be explained more specifically with reference to the following examples. However the scope of the present invention is not limited to the following examples. The compound number in the following examples correspond to those in the table shown above. And the commercially available compounds, which were purchased and used for the examinations, are contained in these examples. As for such compounds, the suppliers of the reagents and the catalog code numbers are shown.

Example 1

Preparation of the Compound of Compound No. 1

Under argon atmosphere, 1-(3-dimethylaminopropyl)-3-ethylcarbodiimide hydrochloride (it is abbreviated as WSC.HCl hereafter; 192 mg, 1 mmol) was added to a mixture of 5-bromosalicylic acid (217 mg, 1 mmol), 3,5-bis(trifluoromethyl)benzylamine (243 mg, 1 mmol), 4-dimethylaminopyridine (12 mg, 0.1 mmol) and tetrahydrofuran (10 mL), and the mixture was stirred at room temperature for 1 hour. The reaction mixture was poured into diluted hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=4:1) to give the title compound (244.8 mg, 55.4%) as a white solid.

$^1$H-NMR(DMSO-d$_6$): δ 4.69(2H, d, J=5.7 Hz), 6.93(1H, d, J=8.7 Hz), 7.56(1H, dd, J=8.7, 2.4 Hz), 8.02(1H, d, J=2.4 Hz), 8.06(3H, s), 9.41(1H, t, J=5.7 Hz), 12.13(1H, s).

Example 2

Preparation of the Compound of Compound No. 2

(1) 2-Acetoxy-N-(2-phenethyl)benzamide

O-Acetylsalicyloyl chloride (0.20 g, 1.00 mmol) was dissolved in benzene (8 mL). Phenethylamine (0.12 g, 1.00 mmol) and pyridine (0.3 mL) were added, and the mixture was stirred at room temperature for 2 hours. The reaction mixture was poured into diluted hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1→1:1) to give the title compound (155.5 mg, 54.9%) as a white crystal.

$^1$H-NMR(CDCl$_3$): δ 2.09(3H, s), 2.92(2H, t, J=6.8 Hz), 3.71(2H, q, J=6.8 Hz), 6.32(1H, brs), 7.07(1H, dd, J=8.4, 1.2 Hz), 7.23-7.35(6H, m), 7.44(1H, ddd, J=8.0, 7.6, 1.6 Hz), 7.73(1H, dd, J=7.6, 1.6 Hz).

When the preparation method described in Example 2(1) is referred in the following examples, organic bases such as pyridine, triethylamine or the like were used as the base. As the reaction solvent, solvents such as dichloromethane, tetrahydrofuran, benzene or the like were used alone or as a mixture.

(2) 2-Hydroxy-N-(2-phenethyl)benzamide

Methanol (5 mL) and 2N sodium hydroxide (0.1 mL) were added to 2-acetoxy-N-(2-phenethyl)benzamide (155.5 mg), and the mixture was stirred at room temperature for 30 minutes. The reaction mixture was poured into diluted hydrochloric acid and extracted with ethyl acetate. After the organic layer was washed with water and brine, dried over anhydrous sodium sulfate, the residue obtained by evaporation under reduced pressure was crystallized (dichloromethane/hexane) to give the title compound (106.9 mg, 80.7%) as a white solid.

$^1$H-NMR(DMSO-d$_6$): δ 2.86(2H, t, J=7.6 Hz), 3.52(1H, q, J=7.6 Hz), 6.84-6.88(2H, m), 7.18-7.31(5H, m), 7.37(1H, ddd, J=8.4, 7.2, 1.6 Hz), 7.80(1H, dd, J=8.4, 1.6 Hz), 8.84 (1H, s), 12.51(1H, s).

When the method described in Example 2(2) is referred in the following examples, inorganic bases such as sodium hydroxide, potassium carbonate or the like were used as the base. As the reaction solvent, solvents such as water, methanol, ethanol, tetrahydrofuran or the like were used alone or as a mixture.

(3) 5-Bromo-2-hydroxy-N-(2-phenethyl)benzamide (Compound No. 2)

Carbon tetrachloride (5 mL), iron powder (0.03 g) and bromine (25 μl, 0.48 mmol) were added to 2-hydroxy-N-(2-phenethyl)benzamide (79.6 mg, 0.33 mmol), and the mixture was stirred at room temperature for 1 hour. The reaction mixture was poured into aqueous sodium hydrogen sulfite and extracted with ethyl acetate. After the organic layer was washed with brine, dried over anhydrous sodium sulfate, the residue obtained by evaporation under reduced pressure was purified by chromatography on silica gel (n-hexane:ethyl acetate=5:1) to give the title compound (62 mg, 58.7%) as a white powder.

$^1$H-NMR(DMSO-d$_6$): δ 2.85(2H, t, J=7.6 Hz), 3.52(1H, q, J=7.6 Hz), 6.87(1H, d, J=8.8 Hz), 7.18-7.31(5H, m), 7.52(1H, dd, J=8.8, 2.4 Hz), 8.01(1H, d, J=2.4 Hz), 8.90(1H, s), 12.51 (1H, s).

Example 3

Preparation of the Compound of Compound No. 3

WSC.HCl (96 mg, 0.5 mmol) was added to a solution of 5-bromosalicylic acid (109 mg, 0.5 mmol), 2-amino-5-(morpholino)carbonylindane (141 mg, 0.5 mmol) and triethylamine (70 μL, 0.5 mmol) in dichloromethane (5 mL), and the mixture was stirred at 40° C. for 1.5 hours. After cooling the reaction mixture was diluted with ethyl acetate, washed successively with 2N hydrochloric acid, water, and brine, dried over anhydrous magnesium sulfate, concentrated, and the residue was purified by column chromatography on silica gel (dichloromethane:methanol=19:1) to give the title compound (26 mg, 11.9%) as a white crystal.

$^1$H-NMR(CDCl$_3$): δ 2.66(1H, dd, J=16.2, 7.2 Hz), 2.82 (1H, dd, J=16.2, 7.2 Hz), 3.16-3.25(2H, m), 3.43-3.86(8H, m), 4.79-4.92(1H, m), 6.88(1H, d, J=8.7 Hz), 7.14-7.15(3H, m), 7.46(1H, dd, J=8.7, 2.4 Hz), 7.74(1H, d, J=7.8 Hz), 7.84 (1H, d, J=2.4 Hz).

[2-Amino-5-(morpholino)carbonylindane: Refer to "Chemical and Pharmaceutical Bulletin", 2000, Vol. 48, p. 131.]

Example 4

The compound of Compound No. 4

This compound is a commercially available compound.

Supplier: Apin Chemicals.

Catalog code number: N 0100D.

Example 5

The Compound of Compound No. 5

This compound is a commercially available compound.

Supplier: Specs.

Catalog code number: AI-233/31581024.

Example 6

The Compound of Compound No. 6

This compound is a commercially available compound.

Supplier: Maybridge.

Catalog code number: RJC 00106.

Example 7

The Compound of Compound No. 7

This compound is a commercially available compound.

Supplier: Maybridge.

Catalog code number: BTB 13230.

Example 8

The Compound of Compound No. 8

This compound is a commercially available compound.

Supplier: Maybridge.

Catalog code number: BTB 114482.

Example 9

Preparation of the Compound of Compound No. 9

5-Chlorosalicylaldehyde (313 mg, 2 mmol) and 4-chlorobenzyltriphenylphosphonium chloride (847 mg, 2 mmol) were dissolved in N,N-dimethylfomamide (20 mL). Potassium carbonate (1.382 g, 10 mmol) dissolved in water (10 mL) was added, and the mixture was refluxed for 5 hours. After cooling, the reaction mixture was poured into 2N hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=3:1) to give the title compound (44.6 mg, 8.4%) as a light gray solid.

$^1$H-NMR(CDCl$_3$): δ 5.04(1H, s), 6.74(1H, d, J=9.0 Hz), 7.05(1H, d, J=16.5 Hz), 7.10(1H, dd, J=8.4, 2.4 Hz), 7.26(1H, d, J=16.5 Hz), 7.33(2H, d, J=8.4 Hz), 7.45(2H, d, J=8.4 Hz), 7.49(1H, d, J=2.4 Hz).

Example 10

Preparation of the Compound of Compound No. 10

(1) 5-Bromo-N-(3,5-dichlorophenyl)-2-methoxybenzenesulfonamide

5-Bromo-2-methoxybenzenesulfonyl chloride (857 mg, 3 mmol) was dissolved in dichloromethane (6 mL). A solution of 3,5-dichloroaniline (510 mg, 3.15 mmol) and pyridine (261 mg, 3.3 mmol) in dichloromethane (2 mL) was added dropwise under ice cooling and argon atmosphere, and the mixture was stirred at room temperature for 6 hours. After the reaction mixture was diluted with dichloromethane, washed successively with 2N hydrochloric acid, water, and brine, dried over anhydrous magnesium sulfate, the solvent was evaporated under reduced pressure. The obtained residue was crystallized from n-hexane-ethyl acetate to give 5-bromo-2-methoxy-N-(3,5-dichloro)benzenesulfonamide (900 mg, 73.0%) as a white crystal.

$^1$H-NMR(DMSO-d$_6$): δ 4.03(3H, s), 6.92(1H, d, J=9.0 Hz), 7.01(2H, d, J=1.8 Hz), 7.07-7.08(1H, m), 7.24(1H, brs), 7.63(1H, dd, J=8.7, 2.4 Hz), 7.99(1H, d, J=2.4 Hz).

(2) 5-Bromo-N-(3,5-dichlorophenyl)-2-hydroxybenzenesulfonamide (Compound No. 10)

A mixture of the white crystal of 5-Bromo-N-(3,5-dichlorophenyl)-2-methoxybenzenesulfonamide (206 mg, 0.5 mmol), lithium iodide (134 mg, 1 mmol) and 2,4,6-collidine (5 mL) was refluxed for 30 minutes under argon atmosphere. After cooling to room temperature, the reaction mixture was poured into 2N hydrochloric acid and extracted with ethyl acetate. After the ethyl acetate layer was washed successively with water and brine, dried over anhydrous magnesium sulfate, the solvent was evaporated under reduced pressure. The obtained residue was crystallized from n-hexane-ethyl acetate to give the title compound (90 mg, 45.3%) as a white crystal.

mp 158-159° C.

$^1$H-NMR(DMSO-d$_6$): δ 6.92(1H, d, J=8.7 Hz), 7.11(2H, d, J=2.1 Hz), 7.21-7.22(1H, m), 7.62(1H, dd, J=8.7, 2.7 Hz), 7.80(1H, d, J=2.4 Hz), 10.70(1H, br), 11.37(1H, br).

Example 11

Preparation of the Compound of Compound No. 11

2-Aminophenol (120 mg, 1.1 mmol) was dissolved in dichloromethane (5 mL). A solution of 3,5-bis(trifluoromethyl)benzoyl chloride (300 mg, 1.1 mmol) in dichloromethane (3 mL) and pyridine (0.5 mL) was added dropwise under ice cooling and argon atmosphere, and the mixture was stirred at room temperature for 1 hour. The reaction mixture was poured into 2N hydrochloric acid and extracted with ethyl acetate. After the ethyl acetate layer was washed successively with water and brine, dried over anhydrous magnesium sulfate, the solvent was evaporated under reduced pressure. The obtained residue was dissolved in ethanol (5 mL). 2N Sodium hydroxide (0.1 mL, 0.2 mmol) was added dropwise, and the mixture was stirred at room temperature for 30 minutes. The reaction mixture was poured into 2N hydrochloric acid and extracted with ethyl acetate. After the ethyl acetate layer was washed successively with water and brine, dried over anhydrous sodium sulfate, the solvent was evaporated under reduced pressure. The obtained residue was purified by column chromatography on silica gel (n-hexane:ethyl acetate=4:1) to give the title compound (288 mg, 73.6%) as a light pink crystal.

mp 183° C. (dec.).

$^1$H-NMR(DMSO-d$_6$): δ 6.83(1H, td, J=8.0, 1.2 Hz), 6.93 (1H, dd, J=8.0, 1.2 Hz), 7.08(1H, td, J=8.0, 1.6 Hz), 7.50(1H, d, J=8.0 Hz), 8.35(2H, s), 9.61(1H, s), 10.15(1H, s).

Example 12

Preparation of the Compound of Compound No. 12

2-Amino-4-chlorophenol (316 mg, 2.2 mmol) and triethylamine (243 mg, 2.4 mmol) were dissolved in dichloromethane (8 mL). A solution of 3,5-dichlorobenzoyl chloride (419 mg, 2 mmol) in dichloromethane (2 mL) was added dropwise under ice cooling and argon atmosphere, and the mixture was stirred at room temperature for 15 hours. After the reaction mixture was diluted with ethyl acetate, washed successively with water and brine, dried over anhydrous magnesium sulfate, the solvent was evaporated under reduced pressure. The obtained residue was purified by column chromatography on silica gel (n-hexane:ethyl acetate=3:1) to give a light brown solid. The solid was suspended and washed with n-hexane-ethyl acetate under heating at reflux to give the title compound (205 mg, 32.4%) as a white crystal.

mp 251-252° C.

$^1$H-NMR(DMSO-d$_6$): δ 6.93(1H, d, J=9.0 Hz), 7.11(1H, dd, J=8.7, 2.7 Hz), 7.67(2H, d, J=2.7 Hz), 7.86-7.87(1H, m), 7.97(1H, d, J=1.8 Hz), 9.85(1H, s), 10.03(1H, s).

Example 13

Preparation of the Compound of Compound No. 13

2-Amino-4-chlorophenol (287 mg, 2 mmol) and 3,5-dichlorobenzenesulfonyl chloride (540 mg, 2.2 mmol) were dissolved in dichloromethane (4 mL). Pyridine (1 mL) was added dropwise under ice cooling and argon atmosphere, and the mixture was stirred at room temperature for 1 hour. The reaction mixture was poured into 2N hydrochloric acid and extracted with ethyl acetate. After the ethyl acetate layer was washed successively with water and brine, dried over anhydrous magnesium sulfate, the solvent was evaporated under reduced pressure. The obtained residue was purified by column chromatography on silica gel (n-hexane:ethyl acetate=3:1→1:1) to give a reddish brown solid. The solid was crystallized from n-hexane-ethyl acetate to give the title compound (445 mg, 63.1%) as a slight dark brown crystal.

mp 190-191° C.

$^1$H-NMR(DMSO-$d_6$): δ 6.68(1H, d, J=9.0 Hz), 7.08(1H, dd, J=8.7, 2.7 Hz), 7.17(1H, d, J=2.4 Hz), 7.70(2H, d, J=1.8 Hz), 7.95-7.96(1H, m), 10.00(1H, s), 10.06(1H, s).

Example 14

Preparation of the Compound of Compound No. 14

(1) 4-Bromo-2-[(3,5-diphenylimino)methyl]phenol

A mixture of 5-bromosalicylaldehyde (1.01 g, 5 mmol), 3,5-dichloroaniline (810 mg, 5 mmol) and ethanol (25 mL) was refluxed for 1 hour under argon atmosphere. After the reaction mixture was cooled to room temperature, the separated crystal was filtered to give the title compound (1.52 g, 88.2%) as an orange crystal.

mp 161-163° C.

$^1$H-NMR(CDCl$_3$): δ 6.94(1H, d, J=9.0 Hz), 7.16(2H, d, J=1.8 Hz), 7.30-7.31(1H, m), 7.47-7.53(2H, m), 8.51(1H, s).

(2) N-[(5-Bromo-2-hydroxyphenyl)methyl]-3,5-dichloroaniline (Compound No. 14)

4-Bromo-2-[(3,5-diphenylimino)methyl]phenol (1.04 g, 3 mmol) was dissolved in tetrahydrofuran (12 mL) and ethanol (6 mL). Sodium borohydride (113 mg, 3 mmol) was added under ice cooling and argon atmosphere, and the mixture was stirred at room temperature for 12 hours. Acetone (10 mL) was added to the reaction mixture. Water was added to the residue obtained by concentration under reduced pressure, and it was extracted with dichloromethane. After the dichloromethane layer was washed successively with water and brine, dried over anhydrous magnesium sulfate, the solvent was evaporated under reduced pressure. The obtained residue was purified by column chromatography on silica gel (n-hexane:ethyl acetate=4:1) to give a light yellow viscous material. This was crystallized by n-hexane to give the title compound (971 mg, 93.3%) as a white crystal.

mp 125-126° C.

$^1$H-NMR(CDCl$_3$): δ 4.31(2H, s), 6.64(2H, d, J=1.8 Hz), 6.74-6.77(1H, m), 6.84-6.85(1H, m), 7.30-7.34(2H, m).

Example 15

The Compound of Compound No. 15

This compound is a commercially available compound.

Supplier: Sigma-Aldrich.

Catalog code number: S3203-5.

Example 16

Preparation of the Compound of Compound No. 16

A mixture of 5-chlorosalicylic acid (173 mg, 1 mmol), 3,5-bis(trifluoromethyl)-N-methylaniline (243 mg, 1 mmol), phosphorus trichloride (44 µl, 0.5 mmol) and monochlorobenzene (5 mL) was refluxed for 3 hours under argon atmosphere. After the reaction mixture was cooled to room temperature, n-hexane (50 mL) was added, and the separated crude crystal was filtered and dissolved in ethyl acetate (50 mL). After the ethyl acetate solution was washed successively with water and brine, dried over anhydrous sodium sulfate, the solvent was evaporated under reduced pressure. The obtained residue was purified by column chromatography on silica gel (n-hexane:ethyl acetate=2:1) to give the title compound (75 mg, 18.9%) as a white crystal.

$^1$H-NMR(CDCl$_3$): δ 3.57(3H, s), 6.59(1H, d, J=2.4 Hz), 6.94(1H, d, J=9.0 Hz), 7.21(1H, dd, J=9.0, 2.7 Hz), 7.58(2H, s), 7.80(1H, s), 10.00(1H, brs).

When the method described in Example 16 is referred in the following examples, phosphorus trichloride was used as the acid halogenating agent. As the reaction solvent, solvents such as monochlorobenzene, toluene or the like were used.

Example 17

Preparation of the Compound of Compound No. 17

Using 5-bromosalicylic acid and 7-trifluoromethyl-1,2,3,4-tetrahydroquinoline as the raw materials, the same operation as the Example 16 gave the title compound.

Yield: 42.0%. $^1$H-NMR(CDCl$_3$): δ 2.08(2H, m), 2.92(2H, t, J=6.6 Hz), 3.95(2H, t, J=6.6 Hz), 6.91-6.94(2H, m), 7.14 (1H, s), 7.32-7.35(2H, m), 7.40(1H, dd, J=8.7, 2.4 Hz), 10.06 (1H, s).

Example 18

Preparation of the Compound of Compound No. 18

Using 2-hydroxynaphthalene-1-carboxylic acid and 3,5-dichloroaniline as the raw materials, the same operation as the Example 16 gave the title compound.

Yield: 51.2%. mp 246-248° C. $^1$H-NMR(DMSO-$d_6$): δ 7.26(1H, d, J=9.3 Hz), 7.31-7.37(2H, m), 7.44-7.50(1H, m), 7.65-7.68(1H, m), 7.85-7.90(4H, m), 10.23(1H, s), 10.74(1H, s).

Example 19

Preparation of the Compound of Compound No. 19

Using 3-hydroxynaphthalene-2-carboxylic acid and 3,5-dichloroaniline as the raw materials, the same operation as the Example 16 gave the title compound.

Yield: 44.3%. mp 254-255° C. $^1$H-NMR(DMSO-$d_6$): δ 7.34-7.39(3H, m), 7.49-7.54(1H, m), 7.76-7.79(1H, m), 7.89 (2H, d, J=1.8 Hz), 7.92(1H, m), 8.39(1H, s), 10.75(1H, s), 11.01(1H, s).

Example 20

The Compound of Compound No. 20

This compound is a commercially available compound.

Supplier: Sigma-Aldrich.

Catalog code number: S01361-8.

Example 21

Preparation of the Compound of Compound No. 21

Using 1-hydroxynaphthalene-2-carboxylic acid and 3,5-bis(trifluoromethyl)aniline as the raw materials, the same operation as the Example 16 gave the title compound.

Yield: 65.5%. $^1$H-NMR(DMSO-d$_6$): δ 7.51(1H, d, J=9.0 Hz), 7.60(1H, td, J=7.8, 0.9 Hz), 7.70(1H, td, J=7.8, 0.9 Hz), 7.89(1H, s), 7.93(1H, d, J=8.4 Hz), 8.09(1H, d, J=9.0 Hz), 8.33(1H, d, J=8.7 Hz), 8.51(2H, s), 10.92(1H, s), 13.36(1H, s).

Example 22

The Compound of Compound No. 22

This compound is a commercially available compound.

Supplier: Sigma-Aldrich.

Catalog code number: S58026-0.

Example 23

The Compound of Compound No. 23

This compound is a commercially available compound.

Supplier: Sigma-Aldrich.

Catalog code number: S63263-5.

Example 24

Preparation of the Compound of Compound No. 24

5-Chloro-2-hydroxynicotinic acid (174 mg, 1 mmol), 3,5-bis(trifluoromethyl)aniline (275 mg, 1.2 mmol) and pyridine (316 mg, 4 mmol) were dissolved in tetrahydrofuran (20 mL) and dichloromethane (10 mL). Phosphorus oxychloride (0.112 ml, 1.2 mmol) was added, and the mixture was stirred at room temperature for 2 hours. The reaction mixture was poured into ethyl acetate (100 mL) and 0.2N hydrochloric acid (100 mL), filtered through celite after stirring for 30 minutes, and the water layer of the filtrate was extracted with ethyl acetate. After the combined ethyl acetate layer was washed successively with water and brine, dried over anhydrous magnesium sulfate, the solvent was evaporated under reduced pressure. The residue was purified by column chromatography on silica gel (n-hexane:ethyl acetate=2:1→1:1) to give a light yellow solid. This was suspended and washed with ethanol under heating at reflux to give the title compound (183 mg, 47.6%) as a white crystal.

mp>270° C.

$^1$H-NMR(DMSO-d$_6$): δ 7.83(1H, s), 8.15(1H, d, J=3.3 Hz), 8.36(1H, d, J=3.0 Hz), 8.40(2H, s), 12.43(1H, s).

When the preparation method described in Example 24 is referred in the following examples, phosphorus oxychloride was used as the acid halogenating agent. Pyridine was used as the base. As the reaction solvent, solvents such as dichloromethane, tetrahydrofuran or the like were used alone or as a mixture.

Example 25

Preparation of the Compound of Compound No. 25

Using 5-chloro-2-hydroxynicotinic acid and 2-chloro-5-(trifluoromethyl)aniline as the raw materials, the same operation as the Example 24 gave the title compound.

Yield: 42.9%. $^1$H-NMR(DMSO-d$_6$): δ 7.52(1H, dd, J=8.4, 2.1 Hz), 7.81(1H, d, J=8.4 Hz), 8.16(1H, s), 8.39(1H, d, J=2.7 Hz), 8.96(1H, d, J=2.1 Hz), 12.76(1H, s), 13.23(1H, s).

Example 26

Preparation of the Compound of Compound No. 26

Using 5-chloro-2-hydroxynicotinic acid and 3,5-bis[(1,1-dimethyl)ethyl]aniline as the raw materials, the same operation as the Example 24 gave the title compound.

Yield: 59.1%. $^1$H-NMR(DMSO-d$_6$): δ 1.29(18H, s), 7.18 (1H, t, J=1.8 Hz), 7.52(2H, d, J=1.8 Hz), 8.07(1H, d, J=2.4 Hz), 8.35(1H, d, J=3.3 Hz), 11.92(1H, s), 13.10(1H, s).

Example 27

Preparation of the Compound of Compound No. 27

Using 3-hydroxypyridine-2-carboxylic acid and 3,5-bis(trifluoromethyl)aniline as the raw materials, the same operation as the Example 24 gave the title compound.

Yield: 45.0%. $^1$H-NMR(CDCl$_3$): δ 7.40(1H, dd, J=8.4, 1.8 Hz), 7.46(1H, dd, J=8.4, 4.2 Hz), 7.68(1H, s), 8.16(1H, dd, J=4.2, 1.2 Hz), 8.25(2H, s), 10.24(1H, s), 11.42(1H, s).

Example 28

Preparation of the Compound of Compound No. 28

Under argon atmosphere, 3,5-bis(trifluoromethyl)phenylisocyanate (255 mg, 11.0 mmol) was dissolved in tetrahydrofuran (5 mL). A solution of 6-chloro-oxindole (184 mg, 1.1 mmol) in tetrahydrofuran (5 ml) and triethylamine (0.3 mL) were added, and the mixture was stirred at room temperature for 4 hours. The reaction mixture was poured into diluted hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=4:1) to give the title compound (172.2 mg, 40.7%) as a pink solid.

$^1$H-NMR(DMSO-d$_6$): δ 3.97(2H, s), 7.29(1H, dd, J=8.1, 2.1 Hz), 7.41(1H, d, J=8.1 Hz), 7.88(1H, s), 8.04(1H, d, J=2.1 Hz), 8.38(2H, s), 10.93(1H, s).

Example 29

Preparation of the Compound of Compound No. 29

Using 3-hydroxyquinoxaline-2-carboxylic acid and 3,5-bis(trifluoromethyl)aniline as the raw materials, the same operation as the Example 16 gave the title compound.

Yield: 2.7%. $^1$H-NMR(DMSO-d$_6$): δ 7.40-7.45(2H, m), 7.69(1H, td, J=8.4, 1.5 Hz), 7.90-7.93(2H, m), 8.41(2H, s), 11.64(1H, s), 13.02(1H, s).

Example 30

The Compound of Compound No. 30

This compound is a commercially available compound.

Supplier: Sigma-Aldrich.

Catalog code number: S83846-2.

Example 31

The Compound of Compound No. 31

This compound is a commercially available compound.

Supplier: Maybridge.

Catalog code number: RDR 01818.

Example 32

Preparation of the Compound of Compound No. 32

Using 5-chlorosalicylic acid and 1-naphthylamine as the raw materials, the same operation as the Example 16 gave the title compound.
Yield: 65.0%. $^1$H-NMR(DMSO-d$_6$): δ 7.09(1H, d, J=8.7 Hz), 7.51-7.61(4H, m), 7.85(1H, d, J=8.4 Hz), 7.96(1H, d, J=7.5 Hz), 7.99-8.05(2H, m), 8.13(1H, d, J=2.7 Hz), 10.88(1H, s), 12.31(1H, s).

Example 33

Preparation of the Compound of Compound No. 33

Using 5-chlorosalicylic acid and 4-methoxy-2-naphthylamine as the raw materials, the same operation as the Example 16 gave the title compound.
Yield: 84.3%. $^1$H-NMR(DMSO-d$_6$): δ 3.99(3H, s), 7.05(1H, d, J=9.0 Hz), 7.30(1H, d, J=1.5 Hz), 7.39-7.45(1H, m), 7.48-7.54(2H, m), 7.83(1H, d, J=7.8 Hz), 8.00(1H, s), 8.02(1H, d, J=2.4 Hz), 8.09(1H, d, J=7.8 Hz), 10.54(1H, s), 11.88(1H, s).

Example 34

Preparation of the Compound of Compound No. 34

(1) 2-Acetoxy-5-chlorobenzoic acid

Concentrated sulfuric acid (0.08 mL) was added slowly to a mixture of 5-chlorosalicylic acid (13.35 g, 77 mmol) and acetic anhydride (20 mL). After the reaction mixture was solidified, it was poured into ice water and extracted with ethyl acetate. The organic layer was washed with water and brine, and dried over anhydrous sodium sulfate. The residue obtained by evaporation of the solvent under reduced pressure was washed with n-hexane under suspension to give the title compound (15.44 g, 93.0%) as a white crystal.
$^1$H-NMR(DMSO-d$_6$): δ 2.25(3H, s), 7.27(1H, d, J=8.7 Hz), 7.72(1H, dd, J=8.7, 2.7 Hz), 7.89(1H, d, J=2.7 Hz), 13.47(1H, s).

(2) 2-Acetoxy-5-chloro-N-(1-methoxynaphthalen-3-yl)benzamide (Compound No. 34)

Using 2-acetoxy-5-chlorobenzoic acid and 4-methoxy-2-naphthylamine as the raw materials, the same operation as the Example 24 gave the title compound.
Yield: 39.9%, red solid. $^1$H-NMR(DMSO-d$_6$): δ 2.23(3H, s), 3.96(3H, s), 7.23(1H, d, J=1.2 Hz), 7.34(1H, d, J=8.7 Hz), 7.40(1H, dt, J=8.1, 1.2 Hz), 7.50(1H, dt, J=8.1, 1.5 Hz), 7.67(1H, dd, J=8.7, 2.7 Hz), 7.81(1H, d, J=8.7 Hz), 7.82(1H, d, J=3.0 Hz), 8.02(1H, s), 8.08(1H, d, J=8.7 Hz), 10.58(1H, s).

Example 35

Preparation of the Compound of Compound No. 35

Using 5-chlorosalicylic acid and 2-amino-4,5,6,7-tetrahydrobenzo[b]thiophene-3-carboxylic acid ethyl ester as the raw materials, the same operation as the Example 16 gave the title compound.
Yield: 49.6%. $^1$H-NMR(DMSO-d$_6$): δ 1.32(3H, t, J=7.2 Hz), 1.74(4H, br), 2.63(2H, br), 2.75(2H, br), 4.30(2H, q, J=7.2 Hz), 7.05(1H, d, J=9.0 Hz), 7.50(1H, dd, J=8.7, 3.0 Hz), 7.92(1H, d, J=3.0 Hz), 12.23(1H, s), 13.07(1H, s).

Example 36

Preparation of the Compound of Compound No. 36

Using 5-bromosalicylic acid and 3-amino-5-phenylpyrazole as the raw materials, the same operation as the Example 16 gave the title compound.
Yield: 9.2%. $^1$H-NMR(DMSO-d$_6$): δ 6.98(1H, d, J=8.8 Hz), 7.01(1H, s), 7.35(1H, t, J=7.6 Hz), 7.46(2H, t, J=7.6 Hz), 7.58(1H, dd, J=8.8, 2.8 Hz), 7.74-7.76(2H, m), 8.19(1H, s), 10.86(1H, s), 12.09(1H, s), 13.00(1H, brs).

Example 37

Preparation of the Compound of Compound No. 37

(1) 2-Amino-4,5-diethyloxazole

Propioin (1.03 g, 8.87 mmol) was dissolved in ethanol (15 mL). Cyanamide (0.75 g, 17.7 mmol) and sodium ethoxide (1.21 g, 17.7 mmol) were added, and the mixture was stirred at room temperature for 3.5 hours. The reaction mixture was poured into water and extracted with ethyl acetate. After the organic layer was washed with water and brine, dried over anhydrous sodium sulfate, the residue obtained by evaporation under reduced pressure was purified by chromatography on silica gel (dichloromethane:methanol=9:1) to give the title compound (369.2 mg, 29.7%) as an yellow amorphous.
$^1$H-NMR(DMSO-d$_6$): δ 1.04(3H, t, J=7.5 Hz), 1.06(3H, t, J=7.5 Hz), 2.20(2H, q, J=7.5 Hz), 2.43(2H, q, J=7.5 Hz), 6.15(2H, s).

(2) 2-Acetoxy-5-bromo-N-(4,5-diethyloxazol-2-yl)benzamide

Using 2-acetoxy-5-bromobenzoic acid and 2-amino-4,5-diethyloxazole as the raw materials, the same operation as the Example 24 gave the title compound.
Yield: 22.0%. $^1$H-NMR(CDCl$_3$): δ 1.22(3H, t, J=7.5 Hz), 1.23(3H, t, J=7.5 Hz), 2.38(3H, s), 2.48(2H, q, J=7.5 Hz), 2.57(2H, q, J=7.5 Hz), 6.96(1H, d, J=8.7 Hz), 7.58(1H, dd, J=8.7, 2.7 Hz), 8.32(1H, s), 11.40(1H, br).

[2-Acetoxy-5-bromosalicylic acid: It was obtained, using 5-bromosalicylic acid and acetic anhydride as the raw materials, by the same operation as the Example 34(1) with reference to "Europian Journal of Medicinal Chemistry", 1996, Vol. 31, p. 861-874.]

(3) 5-Bromo-N-(4,5-diethyloxazol-2-yl)-2-hydroxybenzamide (Compound No. 37)

Using 2-acetoxy-5-bromo-N-(4,5-diethyloxazol-2-yl) benzamide as the raw material, the same operation as the Example 2(2) gave the title compound.

Yield: 70.2%. $^1$H-NMR(CDCl$_3$) δ: 1.25(3H, t, J=7.5 Hz), 1.26(3H, t, J=7.5 Hz), 2.52(22H, q, J=7.5 Hz), 2.60(2H, q, J=7.5 Hz), 6.84(1H, d, J=8.7 Hz), 7.43(1H, dd, J=8.7, 3.0 Hz), 8.17(1H, d, J=3.0 Hz), 11.35(1H, br), 12.83(1H, br).

Example 38

Preparation of the Compound of Compound No. 38

Using 5-bromosalicylic acid and 2-amino-4,5-diphenyloxazole as the raw materials, the same operation as the Example 16 gave the title compound.

Yield: 32.6%. mp 188-189° C. $^1$H-NMR(DMSO-d$_6$): δ 6.98(1H, d, J=8.7 Hz), 7.40-7.49(6H, m), 7.53-7.56(2H, m), 7.59-7.63(3H, m), 8.01(1H, d, J=2.4 Hz), 11.80(2H, brs).

[2-Amino-4,5-diphenyloxazole: Refer to "Zhournal Organicheskoi Khimii: Russian Journal of Organic Chemistry", (Russia), 1980, Vol. 16, p. 2185.]

Example 39

Preparation of the Compound of Compound No. 39

(1) 2-Amino-4,5-bis(furan-2-yl)oxazole

Furoin (0.50 g, 2.60 mmol) was dissolved in ethanol (15 mL). Cyanamide (218.8 mg, 5.20 mmol) and sodium ethoxide (530.8 mg, 7.80 mmol) were added, and the mixture was stirred at room temperature for 2 hours. The reaction mixture was poured into water and extracted with ethyl acetate. After the organic layer was washed with water and brine, dried over anhydrous sodium sulfate, the residue obtained by evaporation under reduced pressure was purified by chromatography on silica gel (hexane:ethyl acetate=1:1→1:2) to give the title compound (175.0 mg, 31.1%) as a dark brown crystal.

$^1$H-NMR(DMSO-d$_6$): δ 6.59(1H, dd, J=3.3, 2.1 Hz), 6.62 (1H, dd, J=3.3, 2.1 Hz), 6.73(1H, dd, J=3.3, 0.6 Hz), 6.80(1H, dd, J=3.3, 0.9 Hz), 7.05(2H, s), 7.75-7.76(2H, m).

(2) 5-Bromo-N-[4,5-bis(furan-2-yl)oxazol-2-yl]-2-hydroxybenzamide (Compound No. 39)

Using 5-bromosalicylic acid and 2-amino-4,5-bis(furan-2-yl)oxazole as the raw materials, the same operation as the Example 16 gave the title compound.

Yield: 12.9%. $^1$H-NMR(DMSO-d$_6$): δ 6.65(1H, dd, J=3.6, 1.8 Hz), 6.68(1H, dd, J=3.6, 1.8 Hz), 6.75(1H, d, J=8, 7 Hz), 6.92(1H, dd, J=3.6, 0.9 Hz), 6.93(1H, d, J=3.3 Hz), 7.37(1H, dd, J=8.7, 2.7 Hz), 7.80(1H, dd, J=1.8, 0.9 Hz), 7.84(1H, dd, J=1.8, 0.9 Hz), 7.92(1H, d, J=3.0 Hz), 14.88(2H, br).

Example 40

Preparation of the Compound of Compound No. 40

(1) 2-Acetoxy-N-(5-trifluoromethyl-1,3,4-thiadiazol-2-yl)benzamide

Using O-acetylsalicyloyl chloride and 2-amino-5-(trifluoromethyl)-1,3,4-thiadiazole as the raw materials, the same operation as the Example 2(1) gave the title compound.

Yield: 51.1%. $^1$H-NMR(DMSO-d$_6$): δ 2.23(3H, s), 7.32 (1H, dd, J=8.0, 1.2 Hz), 7.45(1H, td, J=7.6, 1.2 Hz), 7.69(1H, td, J=8.0, 2.0 Hz), 7.87(1H, dd, J=8.0, 2.0 Hz), 13.75(1H, brs).

(2) 2-Hydroxy-N-(5-trifluoromethyl-1,3,4-thiadiazol-2-yl)benzamide (Compound No. 40)

Using 2-acetoxy-N-(5-trifluoromethyl-1,3,4-thiadiazol-2-yl)benzamide as the raw material, the same operation as the Example 2(2) gave the title compound.

Yield: 92.9%. $^1$H-NMR(DMSO-d$_6$): δ 7.00(1H, td, J=8.0, 0.8 Hz), 7.06(1H, d, J=8.4 Hz), 7.51(1H, ddd, J=8.4, 7.6, 2.0 Hz), 7.92(1H, dd, J=8.0, 1.6 Hz), 12.16(1H, br).

Example 41

Preparation of the Compound of Compound No. 41

Using 5-bromosalicylic acid and 2-amino-5-trifluoromethyl-1,3,4-thiadiazole as the raw materials, the same operation as the Example 16 gave the title compound.

Yield: 80.2%. $^1$H-NMR(DMSO-d$_6$): δ 7.01(1H, d, J=9.0 Hz), 7.63(1H, dd, J=8.7, 2.7 Hz), 7.97(1H, d, J=2.4 Hz).

Example 42

Preparation of the Compound of Compound No. 42

Using 5-chlorosalicylic acid and 5-amino-2-chloropyridine as the raw materials, the same operation as the Example 16 gave the title compound.

Yield: 12.2%. $^1$H-NMR(DMSO-d$_6$): δ 7.04(1H, d, J=9.0 Hz), 7.49(1H, dd, J=9.0, 3.0 Hz), 7.54(1H, d, J=8.4 Hz), 7.88(1H, d, J=2.7 Hz), 8.21(1H, dd, J=8.7, 2.7 Hz), 8.74(1H, d, J=2.7 Hz), 10.62(1H, s), 11.57(1H, s).

Example 43

Preparation of the Compound of Compound No. 43

Using 5-chlorosalicylic acid and 2-amino-6-chloro-4-methoxypyrimidine as the raw materials, the same operation as the Example 16 gave the title compound.

Yield: 2.2%, white solid. $^1$H-NMR(DMSO-d$_6$): δ 3.86(3H, s), 6.85(1H, s), 7.01(1H, d, J=9.0 Hz), 7.47(1H, dd, J=9.0, 3.0 Hz), 7.81(1H, d, J=3.0 Hz), 11.08(1H, s), 11.65(1H, s).

Example 44

Preparation of the Compound of Compound No. 44

Using 2-acetoxy-5-chlorobenzoic acid and 5-aminoindole as the raw materials, the same operation as the Example 24 gave the title compound.

Yield: 13.3%. $^1$H-NMR(DMSO-d$_6$): δ 2.20(3H, s), 6.41 (1H, t, J=2.1 Hz), 7.27-7.36(4H, m), 7.63(1H, dd, J=8.7, 2.7 Hz), 7.74(1H, d, J=2.7 Hz), 7.93(1H, s), 10.21(1H, s), 11.04 (1H, s).

Example 45

The Compound of Compound No. 45

This compound is a commercially available compound.

Supplier: Peakdale.

Catalog code number: PFC-0448.

Example 46

Preparation of the Compound of Compound No. 46

Using 5-chlorosalicylic acid and 3-aminoquinoline as the raw materials, the same operation as the Example 16 gave the title compound.
Yield: 4.3%. $^1$H-NMR(DMSO-d$_6$): δ 7.07(1H, d, J=8.7 Hz), 7.51(1H, dd, J=9.0, 3.0 Hz), 7.61(1H, dt, J=7.8, 1.2 Hz), 7.70(1H, dt, J=7.8, 1.5 Hz), 7.98(2H, d, J=3.0 Hz), 8.01(1H, s), 8.82(1H, d, J=2.4 Hz), 10.80(1H, s), 11.74(1H, s).

Example 47

Preparation of the Compound of Compound No. 47

Using 5-chlorosalicylic acid and 3-amino-9-ethylcarbazole as the raw materials, the same operation as the Example 16 gave the title compound.
Yield: 64.6%. $^1$H-NMR(DMSO-d$_6$): δ 1.33(3H, t, J=7.0 Hz), 4.46(2H, q, J=7.0 Hz), 7.04(1H, d, J=9.0 Hz), 7.21(1H, t, J=7.3 Hz), 7.45-7.52(2H, m), 7.64-7.65(2H, m), 7.70(1H, d, J=8.4, 1.9 Hz), 8.11-8.15(2H, m), 8.49(1H, d, J=1.9 Hz), 10.55(1H, s), 12.22(1H, s).

Example 48

Preparation of the Compound of Compound No. 95

Using O-acetylsalicyloyl chloride and 3,5-bis(trifluoromethyl)aniline as the raw materials, the same operation as the Example 2(1) gave the title compound.
Yield: 84.2%. $^1$H-NMR(DMSO-d$_6$): δ 2.36(3H, s), 7.19 (1H, dd, J=8.0, 1.2 Hz), 7.39(1H, td, J=7.6, 1.2 Hz), 7.57(1H, ddd, J=8.0, 7.6, 1.6 Hz), 7.65(1H, s), 7.83(1H, dd, J=8.0, 1.6 Hz), 8.11(2H, s), 8.31(1H, s).

Example 49

Preparation of the Compound of Compound No. 48

Using 2-acetoxy-N-[3,5-bis(trifluoromethyl)phenyl]benzamide (Compound No. 95) as the raw material, the same operation as the Example 2(2) gave the title compound.
Yield: 45.1%. $^1$H-NMR(DMSO-d$_6$): δ 6.96-7.02(2H, m), 7.45(1H, ddd, J=8.0, 7.2, 1.6 Hz), 7.81(1H, s), 7.87(1H, dd, J=8.0, 1.6 Hz), 8.46(2H, s), 10.80(1H, s), 11.26(1H, s).

Example 50

Preparation of the Compound of Compound No. 49

Using 5-fluorosalicylic acid and 3,5-bis(trifluoromethyl) aniline as the raw materials, the same operation as the Example 16 gave the title compound.

Yield: 58.7%. $^1$H-NMR(DMSO-d$_6$): δ 7.04(1H, ddd, J=9.0, 4.5, 1.2 Hz), 7.30-7.37(1H, m), 7.66(1H, ddd, J=9.0, 3.3, 1.2 Hz), 7.84(1H, s), 8.46(2H, s), 10.85(1H, s), 11.21(1H, brs).

Example 51

Preparation of the Compound of Compound No. 50

Using 5-chlorosalicylic acid and 3,5-bis(trifluoromethyl) aniline as the raw materials, the same operation as the Example 16 gave the title compound.
Yield: 85.5%. $^1$H-NMR(DMSO-d$_6$): δ 7.05(1H, d, J=8.7 Hz), 7.49(1H, dd, J=8.7, 2.7 Hz), 7.85(1H, s), 7.87(1H, d, J=2.7 Hz), 8.45(2H, s), 10.85(1H, s), 11.39(1H, s).

Example 52

Preparation of the Compound of Compound No. 51

Using 5-bromosalicylic acid and 3,5-bis(trifluoromethyl) aniline as the raw materials, the same operation as the Example 16 gave the title compound.
Yield: 88.5%. $^1$H-NMR(DMSO-d$_6$): δ 6.98(1H, d, J=8.8 Hz), 7.59(1H, dd, J=8.8, 2.8 Hz), 7.83(1H, s), 7.98(1H, d, J=2.8 Hz), 8.43(2H, s), 10.82(1H, s), 11.37(1H, s).

This compound was obtained also by the following preparation method.

Iron powder (30 mg, 0.54 mmol) and bromine (0.02 mL, 0.39 mmol) were added to a solution of 2-acetoxy-N-[3,5-bis (trifluoromethyl)]benzamide (Compound No. 95; 100 mg, 0.25 mmol) in carbon tetrachloride (8 mL), and the mixture was stirred at 50° C. for 4 hours. After the reaction mixture was cooled to room temperature, it was poured into aqueous NaHSO$_4$ and extracted with ethyl acetate. The ethyl acetate layer was washed with water and brine, and dried over anhydrous sodium sulfate. The residue obtained by evaporation of the solvent under reduced pressure was purified by column chromatography on silica gel (n-hexane:ethyl acetate=4:1) to give the title compound (600 mg, 54.9%) as a white solid.

Example 53

Preparation of the Compound of Compound No. 52

Using 5-iodosalicylic acid and 3,5-bis(trifluoromethyl) aniline as the raw materials, the same operation as the Example 16 gave the title compound.
Yield: 62.2%. $^1$H-NMR(DMSO-d$_6$): δ 6.86(1H, d, J=8.4 Hz), 7.74(1H, dd, J=8.7, 2.4 Hz), 7.84(1H, s), 8.13(1H, d, J=2.1 Hz), 8.84(2H, s), 10.82(1H, s), 11.41(1H, s).

Example 54

Preparation of the Compound of Compound No. 53

Using 5-nitrosalicylic acid and 3,5-bis(trifluoromethyl) aniline as the raw materials, the same operation as the Example 16 gave the title compound.
Yield: 57.2%. $^1$H-NMR(DMSO-d$_6$): δ 7.18(1H, d, J=9.0 Hz), 7.86(1H, s), 8.31(1H, dd, J=9.0, 3.0 Hz), 8.45(2H, s), 8.70(1H, d, J=3.0 Hz), 11.12(1H, s).

Example 55

Preparation of the Compound of Compound No. 54

(1) 2-Benzyloxy-5-formylbenzoic acid benzyl ester

A mixture of 5-formylsalicylic acid (4.98 g, 30 mmol), benzyl bromide (15.39 g, 90 mmol), potassium carbonate (16.59 g, 120 mmol), and methyl ethyl ketone (350 mL) was refluxed for 8 hours. After cooling, the solvent was evaporated under reduced pressure. 2N Hydrochloric acid was added to the residue, and the mixture was extracted with ethyl acetate. The layer was washed with water and brine, and dried over anhydrous magnesium sulfate. The residue obtained by evaporation of the solvent under reduced pressure was purified by column chromatography on silica gel (n-hexane:ethyl acetate=3:1), suspended and washed with isopropyl ether under heating at reflux to give the title compound (5.98 g, 57.5%) as a white solid.

$^1$H-NMR(CDCl$_3$): δ 5.27(2H, s), 5.37(2H, s), 7.15(1H, d, J=9.0 Hz), 7.26-7.46(10H, m), 7.99(1H, dd, J=9.0, 2.4 Hz), 8.36(1H, d, J=2.4 Hz), 9.91(1H, s).

(2) 2-Benzyloxy-5-cyanobenzoic acid benzyl ester

A mixture of 2-benzyloxy-5-formylbenzoic acid benzyl ester (693 mg, 2 mmol), hydroxylamine hydrochloride (167 mg, 2.4 mmol), and N-methylpyrrolidone (3 mL) was stirred at 115□ for 4 hours. After the reaction mixture was cooled, 2N hydrochloric acid (5 mL) and water (30 mL) were added and the mixture was extracted with ethyl acetate. The organic layer was washed with 2N aqueous sodium hydroxide, water, and brine, and dried over anhydrous magnesium sulfate. The residue obtained by evaporation of the solvent under reduced pressure was suspended and washed with isopropyl ether under heating at reflux to give the title compound (527 mg, 76.7%) as a white solid.

$^1$H-NMR(CDCl$_3$): δ 5.23(2H, s), 5.35(2H, s), 7.08(1H, d, J=8.7 Hz), 7.33-7.43(10H, m), 7.70(1H, dd, J=8.7, 2.4 Hz), 8.13(1H, d, J=2.4 Hz).

(3) 5-Cyanosalicylic acid

Ethanol (10 mL) and tetrahydrofuran (10 mL) were added to 2-benzyloxy-5-cyanobenzoic acid benzyl ester (446 mg, 1.3 mmol) and 5% palladium on carbon (45 mg), and the mixture was hydrogenated at room temperature for 2 hours. After the insoluble matter was filtered off, the solvent was evaporated under reduced pressure to give the title compound (212 mg, 100.0%) as a white solid.

$^1$H-NMR(DMSO-d$_6$): δ 7.02(1H, d, J=8.7 Hz), 7.82(1H, dd, J=8.7, 2.4 Hz), 8.12(1H, d, J=2.1 Hz).

(4) N-[3,5-Bis(trifluoromethyl)phenyl]-5-cyano-2-hydroxybenzamide (Compound No. 54)

Using 5-cyanosalicylic acid and 3,5-bis(trifluoromethyl)aniline as the raw materials, the same operation as the Example 16 gave the title compound.

Yield: 16.6%. $^1$H-NMR(DMSO-d$_6$): δ 7.15(1H, d, J=8.7 Hz), 7.85(1H, s), 7.86(1H, dd, J=8.7, 2.1 Hz), 8.22(1H, d, J=2.4 Hz), 8.43(2H, s), 10.93(1H, s), 12.00(1H, brs).

Example 56

Preparation of the Compound of Compound No. 55

Using 5-methylsalicylic acid and 3,5-bis(trifluoromethyl)aniline as the raw materials, the same operation as the Example 16 gave the title compound.

Yield: 54.9%. $^1$H-NMR(DMSO-d$_6$): δ 6.92(1H, d, J=8.7 Hz), 7.28(1H, dd, J=8.7, 1.8 Hz), 7.71(1H, d, J=1.8 Hz), 7.82(1H, s), 8.47(2H, s), 10.80(1H, s), 11.14(1H, s).

Example 57

Preparation of the Compound of Compound No. 56

(1) 5-[(1,1-Dimethyl)ethyl]salicylic acid

Sulfamic acid (1.76 g, 18.1 mmol) and sodium dihydrogenphosphate (7.33 g, 47 mmol) were added to a solution of 5-[(1,1-dimethyl)ethyl]-2-hydroxybenzaldehyde (2.15 g, 12.1 mmol) in 1,4-dioxane (100 mL) and water (40 mL). A solution of sodium chlorite (1.76 g, 15.5 mmol) in water (10 mL) was added to the mixture under ice cooling, and it was stirred for 1 hour. Then, sodium sulfite (1.80 g, 14.3 mmol) was added to the mixture, and it was stirred for 30 minutes. Concentrated hydrochloric acid was added to the reaction mixture, and pH was adjusted to 1. The residue obtained by evaporation of 1,4-dioxane under reduced pressure was extracted with ethyl acetate. The organic layer was washed with water and brine, and dried over anhydrous magnesium sulfate. The residue obtained by evaporation of the solvent under reduced pressure was washed with n-hexane under suspension to give the title compound (1.81 g, 77.4%) as a white powder.

$^1$H-NMR(DMSO-d$_6$): δ 1.26(9H, s), 6.90(1H, d, J=9.0 Hz), 7.58(1H, dd, J=8.7, 2.4 Hz), 7.75(1H, d, J=2.4 Hz), 11.07(1H, brs).

(2) N-[3,5-Bis(trifluoromethyl)phenyl]-5-[(1,1-dimethyl)ethyl]-2-hydroxybenzamide (Compound No. 56)

Using 5-[(1,1-dimethyl)ethyl]salicylic acid and 3,5-bis(trifluoromethyl)aniline as the raw materials, the same operation as the Example 16 gave the title compound.

Yield: 53.8%. $^1$H-NMR(DMSO-d$_6$): δ 1.30(9H, s), 6.96 (1H, d, J=8.7 Hz), 7.50(1H, dd, J=8.7, 2.4 Hz), 7.82(1H, d, J=2.4 Hz), 7.83(1H, s), 8.46(2H, s), 10.80(1H, s) 11.12(1H, s).

Example 58

Preparation of the Compound of Compound No. 78

(1) 5-Acetyl-2-benzyloxybenzoic acid methyl ester

A mixture of 5-acetylsalicylic acid methyl ester (13.59 g, 70 mmol), benzyl bromide (17.96 g, 105 mmol), potassium carbonate (19.35 g, 140 mmol) and methyl ethyl ketone (350 mL) was refluxed for 8 hours. After cooling, the solvent was evaporated under reduced pressure. 2N Hydrochloric acid was added to the residue, and it was extracted with ethyl acetate. After the ethyl acetate layer was washed with water and brine, dried over anhydrous magnesium sulfate and concentrated, the residue was recrystallized from isopropyl ether to give the title compound (14.20 g, 71.4%) as a white solid.

$^1$H-NMR(CDCl$_3$): δ 2.58(3H, s), 3.93(3H, s), 5.27(2H, s), 7.07(1H, d, J=8.7 Hz), 7.26-7.43(3H, m), 7.47-7.50(2H, m), 8.07(1H, dd, J=8.7, 2.4 Hz), 8.44(1H, d, J=2.4 Hz).

(2) 5-Acetyl-2-benzyloxybenzoic acid

5-Acetyl-2-benzyloxybenzoic acid methyl ester (5.69 g, 20 mmol) was dissolved in a mixed solvent of methanol (20 mL) and tetrahydrofuran (20 mL). 2N Sodium hydroxide (11 mL) was added dropwise, and the mixture was stirred for 8 hours. The solvent was evaporated under reduced pressure. 2N Hydrochloric acid was added to the residue, and it was extracted with dichloromethane. After the dichloromethane layer was washed with water and brine, dried over anhydrous magnesium sulfate and concentrated, the residue was washed with isopropyl ether to give the title compound (4.92 g, 91.0%) as a white solid.

$^1$H-NMR(DMSO-d$_6$): δ 2.55(3H, s), 5.32(2H, s), 7.30-7.43(4H, m), 7.49-7.52(2H, m), 8.09(1H, dd, J=9.0, 2.7 Hz), 8.22(1H, d, J=2.4 Hz).

(3) 5-Acetyl-2-benzyloxy-N-[3,5-bis(trifluoromethyl)phenyl]benzamide

Using 5-acetyl-2-benzyloxybenzoic acid and 3,5-bis(trifluoromethyl)aniline as the raw materials, the same operation as the Example 24 gave the title compound.

Yield: 63.1%. $^1$H-NMR(DMSO-d$_6$): δ 2.57(3H, s), 7.11 (1H, d, J=8.7 Hz), 7.86(1H, s), 8.05(1H, dd, J=8.4, 2.1 Hz), 8.44(1H, d, J=2.1 Hz), 8.47(2H, s), 10.96(1H, s), 11.97(1H, brs).

(4) 5-Acetyl-N-[3,5-bis(trifluoromethyl)phenyl]-2-hydroxybenzamide (Compound No. 78)

Ethanol (6 mL) and tetrahydrofuran (72 mL) were added to 5-acetyl-2-benzyloxy-N-[3,5-bis(trifluoromethyl)phenyl]benzamide (602 mg, 1.25 mmol) and 5% palladium on carbon (60 mg), and the mixture was hydrogenated at room temperature for 30 minutes. After the insoluble matter was filtered off, the solvent was evaporated under reduced pressure and the residue was recrystallized from n-hexane-ethyl acetate to give the title compound (230 mg, 47.0%) as a white solid.

$^1$H-NMR(DMSO-d$_6$): δ 2.59(3H, s), 5.35(2H, s), 7.32-7.36(3H, m), 7.43(1H, d, J=8.7 Hz), 7.52-7.55(2H, m), 7.82 (1H, s), 8.16(1H, dd, J=8.7, 2.4 Hz), 8.25(1H, d, J=2.4 Hz), 8.31(2H, s), 10.89(1H, s).

Example 59

Preparation of the Compound of Compound No. 57

5-Acetyl-N-[3,5-bis(trifluoromethyl)phenyl]-2-hydroxybenzamide (Compound No. 78; 50.5 mg, 0.13 mmol) was suspended in ethanol (2 mL). Sodium borohydride (23.6 mg, 0.62 mmol) was added, and the mixture was stirred at room temperature for 12 hours. The reaction mixture was poured into diluted hydrochloric acid and extracted with ethyl acetate. After the organic layer was washed with water and brine, dried over anhydrous sodium sulfate, the residue obtained by evaporation under reduced pressure was washed with isopropyl ether/n-hexane under suspension to give the title compound (39.7 mg, 78.3%) as a white powder.

$^1$H-NMR(DMSO-d$_6$): δ 1.34(3H, d, J=6.3 Hz), 4.71(1H, q, J=6.3 Hz), 5.18(1H, brs), 6.97(1H, d, J=8.4 Hz), 7.44(1H, dd, J=8.4, 2.1 Hz), 7.84(1H, s), 7.86(1H, d, J=2.1 Hz), 8.48(2H, s), 10.85(1H, s), 11.32(1H, s).

Example 60

Preparation of the Compound of Compound No. 58

5-Acetyl-N-[3,5-bis(trifluoromethyl)phenyl]-2-hydroxybenzamide (Compound No. 78; 100.0 mg, 0.26 mmol) was dissolved in ethanol (3 mL). Pyridine (45 μl, 0.56 mmol) and O-methylhydroxylamine hydrochloride (25.8 mg, 0.31 mmol) were added, and the mixture was refluxed for 1 hour. After cooling, the reaction mixture was poured into diluted hydrochloric acid and extracted with ethyl acetate. After the organic layer was washed with water and brine, dried over anhydrous sodium sulfate, the residue obtained by evaporation under reduced pressure was purified by chromatography on silica gel (hexane:ethyl acetate=4:1) to give the title compound (102.1 mg, 95.3%) as a white crystal.

$^1$H-NMR(DMSO-d$_6$): δ 2.19(3H, s), 3.91(3H, s), 7.05(1H, d, J=8.7 Hz), 7.77(1H, dd, J=8.7, 2.4 Hz), 7.85(1H, s), 8.09 (1H, d, J=2.4 Hz), 8.47(2H, s), 10.87(1H, s), 11.48(1H, s).

Example 61

Preparation of the Compound of Compound No. 59

Using 5-acetyl-N-[3,5-bis(trifluoromethyl)phenyl]-2-hydroxybenzamide (Compound No. 78) and O-benzylhydroxylamine hydrochloride as the raw materials, the same operation as the Example 60 gave the title compound.

Yield: 79.9%. $^1$H-NMR(DMSO-d$_6$): δ 2.24(3H, s), 5.20 (2H, s), 7.04(1H, d, J=8.7 Hz), 7.29-7.47(5H, m), 7.76(1H, dd, J=8.7, 2.4 Hz), 7.85(1H, s), 8.07(1H, d, J=2.1 Hz), 8.46 (2H, s), 10.87(1H, s), 11.47(1H, s).

Example 62

Preparation of the Compound of Compound No. 60

(1) 5-(2,2-Dicyanoethen-1-yl)-2-hydroxybenzoic acid

Malononitrile (132 mg, 2 mmol) was dissolved in ethanol (6 mL), and 5-formylsalicylic acid (332 mg, 2 mmol) was added. After cooling with ice bath, benzylamine (0.1 mL) was added and the mixture was stirred at room temperature for 2 hours. The separated yellow crystal was filtered and recrystallized (ethanol) to give the title compound (139.9 mg, 32.7%) as a light yellow solid.

$^1$H-NMR(DMSO-d$_6$): δ 7.12(1H, d, J=8.7 Hz), 8.09(1H, dd, J=8.7, 2.4 Hz), 8.41(1H, s), 8.50(1H, d, J=2.4 Hz).

(2) N-[3,5-Bis(trifluoromethyl)phenyl]-5-(2,2-dicyanoethen-1-yl)-2-hydroxybenzamide (Compound No. 60)

Using 5-(2,2-dicyanoethen-1-yl)-2-hydroxybenzoic acid and 3,5-bis(trifluoromethyl)aniline as the raw materials, the same operation as the Example 16 gave the title compound.

Yield: 9.1%. $^1$H-NMR(DMSO-d$_6$): δ 7.13(1H, d, J=9.0 Hz), 7.83(H, s), 8.04(1H, dd, J=9.0, 2.4 Hz), 8.36(1H, s), 8.38(1H, d, J=2.4 Hz), 8.43(2H, s), 11.43(1H, s).

Example 63

Preparation of the Compound of Compound No. 62

(1) 5-[(2-Cyano-2-methoxycarbonyl)ethen-1-yl]-2-hydroxybenzoic acid

Triethylamine (0.2 ml) was added to a mixture of 5-formyl-salicylic acid (332 mg, 2 mmol). Cyanoacetic acid methyl ester (198 mg, 2 mmol) and acetic acid (6 mL), and the mixture was refluxed for 5 hours. After cooling, the reaction mixture was poured into water, and the separated crystal was filtered and recrystallized (n-hexane) to give the title compound (327.7 mg, 66.3%) as a light yellow solid.
$^1$H-NMR(DMSO-d$_6$): δ 3.85(3H, s), 7.15(1H, d, J=8.7 Hz), 8.20(1H, dd, J=8.7, 2.4 Hz), 8.37(1H, s), 8.66(1H, d, J=2.4 Hz).

(2) 3-({N-[3,5-Bis(trifluoromethyl)phenyl]carbamoyl}-4-hydroxyphenyl)-2-cyanoacrylic acid methyl ester (Compound No. 62)

Using 5-[(2-cyano-2-methoxycarbonyl)ethen-1-yl]-2-hydroxybenzoic acid and 3,5-bis(trifluoromethyl)aniline as the raw materials, the same operation as the Example 16 gave the title compound.
Yield: 66.3%. $^1$H-NMR(DMSO-d$_6$): δ 3.85(3H, s), 7.19 (1H, d, J=9.0 Hz), 7.85(1H, s), 8.20(1H, dd, J=8.7, 2.1 Hz), 8.33(1H, s), 8.45(2H, s), 8.50(1H, d, J=2.1 Hz), 11.00(1H, s), 11.03(1H, s).

Example 64

Preparation of the Compound of Compound No. 61

3-({N-[3,5-Bis(trifluoromethyl)phenyl]carbamoyl}-4-hydroxyphenyl)-2-cyanoacrylic acid methyl ester (Compound No. 62; 50 mg, 0.11 mmol) was dissolved in ethanol (5 mL). 2N Sodium hydroxide (0.11 ml, 0.22 mmol) was added, and the mixture was stirred at room temperature for 3 hours. The reaction mixture was poured into diluted hydrochloric acid and extracted with ethyl acetate. After the organic layer was washed with brine, dried over anhydrous magnesium sulfate, the residue obtained by evaporation under reduced pressure was recrystallized (ethyl acetate) to give the title compound (13.5 mg, 30.4%) as a light yellow solid.
$^1$H-NMR(DMSO-d$_6$): δ 7.12(1H, d, J=8.4 Hz), 7.84(1H, s), 7.94(1H, dd, J=8.4, 2.1 Hz), 8.38(1H, d, J=2.1 Hz), 8.45 (2H, s), 9.87(1H, s), 11.41(1H, s).

Example 65

Preparation of the Compound of Compound No. 63

A mixture of N-[3,5-bis(trifluoromethyl)phenyl]-2-hydroxy-5-iodobenzamide (Compound No. 52; 475 mg, 1 mmol), styrene (130 mg, 1.25 mmol), palladium acetate (4.5 mg, 0.02 mmol), tris(ortho-tolyl)phosphine (12.2 mg, 0.04 mmol), diisopropylamine (388 mg, 3 mmol) and N,N-dimethylformamide (2 mL) was refluxed for 8 hours. After cooling, water was added to the reaction mixture, and it was extracted with ethyl acetate. After the ethyl acetate layer was washed with water and brine, dried over anhydrous magnesium sulfate and concentrated, the residue was purified by column chromatography on silica gel (n-hexane:isopropyl ether=2:1→1:1) to give the title compound (173 mg, 38.3%) as a pale yellow solid.
$^1$H-NMR(DMSO-d$_6$): δ 7.04(1H, d, J=8.4 Hz), 7.20-7.29 (3H, m), 7.38(2H, t, J=7.5 Hz), 7.59(2H, d, J=7.5 Hz), 7.72 (1H, dd, J=8.4, 2.1 Hz), 7.86(1H, s), 8.07(1H, d, J=2.1 Hz), 8.49(2H, s), 10.89(1H, s), 11.33(1H, brs).

Example 66

Preparation of the Compound of Compound No. 66

N-[3,5-Bis(trifluoromethyl)phenyl]-2-hydroxy-5-iodo-benzamide (Compound No. 52; 950 mg, 2 mmol) and trimethylsilylacetylene (246 mg, 2.5 mmol) were dissolved in triethylamine (2 mL) and N,N-dimethylformamide (4 mL). Tetrakis(triphenylphosphine)palladium (23 mg, 0.02 mmol) and cuprous iodide (4 mg, 0.02 mmol) were added under argon atmosphere, and the mixture was stirred at 40° C. for 2 hours. After cooling to room temperature, the reaction mixture was poured into ethyl acetate (100 mL) and 1N citric acid (100 mL), stirred, and filtered through celite. After the ethyl acetate layer was washed successively with water and brine, dried over anhydrous magnesium sulfate, the solvent was evaporated under reduced pressure. The obtained residue was purified by column chromatography on silica gel (n-hexane: ethyl acetate=19:1) to give a light orange solid. This was crystallized by n-hexane to give the title compound (286 mg, 32.1%) as a white crystal.
$^1$H-NMR(DMSO-d$_6$): δ 0.23(9H, s), 7.00(1H, d, J=8.7 Hz), 7.54(1H, dd, J=8.7, 2.4 Hz), 7.85(1H, s), 7.98(1H, d, J=2.1 Hz), 8.46(2H, s), 10.86(1H, s), 11.69(1H, s).

Example 67

Preparation of the Compound of Compound No. 64

N-[3,5-Bis(trifluoromethyl)phenyl]-2-hydroxy-5-[(trimethylsilyl)ethynyl]-benzamide (Compound No. 66; 233 mg, 0.5 mmol) was dissolved in methanol (1 mL). 2N Sodium hydroxide (1 mL) was added, and the mixture was stirred at room temperature for 1 hour. The reaction mixture was poured into 2N hydrochloric acid and extracted with ethyl acetate. After the ethyl acetate layer was washed successively with water and brine, dried over anhydrous magnesium sulfate, the solvent was evaporated under reduced pressure. The obtained residue was crystallized from ethanol-water to give the title compound (67 mg, 35.9%) as a light gray crystal.
$^1$H-NMR(DMSO-d$_6$): δ 4.11(1H, s), 7.02(1H, d, J=8.4 Hz), 7.55(1H, dd, J=8.4, 2.1 Hz), 7.85(1H, s), 7.98(1H, d, J=2.1 Hz), 8.46(2H, s), 8.46(2H, s), 10.86(1H, s), 11.62(1H, s).

Example 68

Preparation of the Compound of Compound No. 65

Using N-[3,5-bis(trifluoromethyl)phenyl]-2-hydroxy-5-iodobenzamide (Compound No. 52) and phenylacetylene as the raw materials, the same operation as the Example 66 gave the title compound.
Yield: 40.8%. $^1$H-NMR(DMSO-d$_6$): δ 7.06(1H, d, J=8.4 Hz), 7.42-7.46(3H, m), 7.53-7.57(2H, m), 7.64(1H, dd, J=8.7, 2.1 Hz), 7.86(1H, s), 8.06(1H, d, J=2.1 Hz), 8.48(2H, s), 10.94(1H, s), 11.64(1H, brs).

Example 69

Preparation of the Compound of Compound No. 67

N-[3,5-Bis(trifluoromethyl)phenyl]-2-hydroxy-5-iodobenzamide (Compound No. 52; 200 mg, 0.42 mmol) was dissolved in 1,2-dimethoxyethane (3 mL). Tetrakis(triphenylphosphine)palladium (16 mg, 0.0014 mmol) was added under argon atmosphere, and the mixture was stirred at room temperature for 5 minutes. Then dihydroxyphenylborane (57 mg, 0.47 mmol) and 1M sodium carbonate (1.3 mL) were added and the mixture was refluxed for 2 hours. After cooling to room temperature, the reaction mixture was poured into diluted hydrochloric acid and extracted with ethyl acetate. After the ethyl acetate layer was washed successively with water and brine, dried over anhydrous sodium sulfate, the solvent was evaporated under reduced pressure. The obtained residue was purified by column chromatography on silica gel (n-hexane:ethyl acetate=6:1→3:1) to give the title compound (109 mg, 61.1%) as a white crystal.

$^1$H-NMR(DMSO-d$_6$): δ 7.12(1H, d, J=8.7 Hz), 7.33-7.38 (1H, m), 7.48(2H, t, J=7.5 Hz), 7.67-7.70(2H, m), 7.79(1H, dd, J=8.4, 2.4 Hz), 7.87(1H, s), 8.17(1H, d, J=2.4 Hz), 8.49 (2H, s), 10.92(1H, s), 11.41(1H, s).

Example 70

Preparation of the Compound of Compound No. 68

Using N-[3,5-bis(trifluoromethyl)phenyl]-2-hydroxy-5-(phenylethynyl)benzamide (Compound No. 65) as the raw material, the same operation as the Example 58(4) gave the title compound.

Yield: 86.2%. $^1$H-NMR(DMSO-d$_6$): δ 2.88(4H, s), 6.93 (1H, d, J=8.1 Hz), 7.15-7.34(6H, m), 7.76(1H, d, J=2.4 Hz), 7.84(1H, s), 8.47(2H, s), 10.79(1H, s), 11.15(1H, s).

Example 71

Preparation of the Compound of Compound No. 69

Using 2-hydroxy-5-(trifluoromethyl)benzoic acid and 3,5-bis(trifluoromethyl)aniline as the raw materials, the same operation as the Example 16 gave the title compound.

Yield: 44.7%. $^1$H-NMR(CDCl$_3$): δ 7.17(1H, d, J=9.0 Hz) 7.72-7.75(2H, m), 7.86(1H, s), 8.17(2H, s), 8.35(1H, s) 11.88 (1H, s).

[2-Hydroxy-5-(trifluoromethyl)benzoic acid: Refer to "Chemical and Pharmaceutical Bulletin", 1996, Vol. 44, p. 734.]

Example 72

Preparation of the Compound of Compound No. 70

Using 2-hydroxy-5-(pentafluoroethyl)benzoic acid and 3,5-bis(trifluoromethyl)aniline as the raw materials, the same operation as the Example 16 gave the title compound.

$^1$H-NMR(CDCl$_3$): δ 7.19(1H, d, J=9.0 Hz) 7.70(1H, dd, J=8.7, 2.1 Hz), 7.81(1H, d, J=2.1 Hz), 8.17(2H, s), 8.37(1H, s), 11.92(1H, s).

s[2-Hydroxy-5-(pentafluoromethyl)benzoic acid: Refer to "Chemical and Pharmaceutical Bulletin", 1996, Vol. 44, p. 734.]

Example 73

Preparation of the Compound of Compound No. 71

Using 2-hydroxy-5-(pyrrol-1-yl)benzoic acid and 3,5-bis (trifluoromethyl)aniline as the raw materials, the same operation as the Example 16 gave the title compound.

Yield: 57.8%. $^1$H-NMR(DMSO-d$_6$): δ 6.27(2H, dd, J=2.4, 1.8 Hz), 7.10(1H, d, J=9.0 Hz), 7.29(2H, dd, J=2.4, 1.8 Hz), 7.66(1H, dd, J=9.0, 2.7 Hz), 7.86(1H, s), 7.98(1H, d, J=2.4 Hz), 8.47(2H, s), 10.89(1H, s), 11.24(1H, s).

Example 74

Preparation of the Compound of Compound No. 72

Using N-[3,5-bis(trifluoromethyl)phenyl]-2-hydroxy-5-iodobenzamide (Compound No. 52) and 2-thiopheneboronic acid as the raw materials, the same operation as the Example 69 gave the title compound.

Yield: 44.4%. $^1$H-NMR(DMSO-d$_6$): δ 7.08(1H, d, J=8.4 Hz), 7.14(1H, dd, J=5.4, 3.6 Hz), 7.45(1H, dd, J=3.6, 1.2 Hz), 7.51(1H, dd, J=5.1, 0.9 Hz), 7.75(1H, dd, J=8.4, 2.4 Hz), 7.59(1H, s), 8.08(1H, d, J=2.4 Hz), 8.48(2H, s), 10.91(1H, s), 11.38(1H, s).

Example 75

Preparation of the Compound of Compound No. 73

Using N-[3,5-bis(trifluoromethyl)phenyl]-2-hydroxy-5-iodobenzamide (Compound No. 52) and 3-thiopheneboronic acid as the raw materials, the same operation as the Example 69 gave the title compound.

Yield: 38.7%. $^1$H-NMR(DMSO-d$_6$): δ 7.06(1H, d, J=8.7 Hz), 7.57(1H, dd, J=4.8, 1.5 Hz), 7.66(1H, dd, J=4.8, 3.0 Hz), 7.81-7.84(2H, m), 7.86(1H, s), 8.18(1H, d, J=2.1 Hz), 8.49 (2H, s), 10.90(1H, s), 11.33(1H, s).

Example 76

Preparation of the Compound of Compound No. 74

(1) 2-Benzyloxy-5-(2-bromoacetyl)-N-[3,5-bis(trifluoromethyl)phenyl]benzamide

5-Acetyl-2-benzyloxy-N-[3,5-bis(trifluoromethyl)phenyl]benzamide (compound of Example 58(3); 4.81 g, 10 mmol) was dissolved in tetrahydrofuran (30 ml). Phenyltrimethylammonium tribromide (3.75 g, 10 mmol) was added, and the mixture was stirred at room temperature for 12 hours. The reaction mixture was poured into water and extracted with ethyl acetate. After the organic layer was washed with aqueous sodium hydrogen sulfite, water and brine, dried over anhydrous magnesium sulfate, the residue obtained by evaporation under reduced pressure was purified by chromatography on silica gel (n-hexane:ethyl acetate=4:1), and recrystallized (ethyl acetate/n-hexane) to give the title compound (2.39 g, 42.7%) as a white solid.

$^1$H-NMR(DMSO-d$_6$): δ 4.91(2H, s), 5.36(2H, s), 7.32-7.35(3H, m), 7.47(1H, d, J=9.0 Hz), 7.52-7.56(2H, m), 7.82 (1H, s), 8.21(1H, dd, J=8.7, 2.4 Hz), 8.29(1H, d, J=2.4 Hz), 8.31(2H, s), 10.91(1H, s).

(2) 2-Benzyloxy-N-[3,5-bis(trifluoromethyl)phenyl]-5-(2-methylthiazol-4-yl)benzamide A mixture of 2-benzyloxy-5-(2-bromoacetyl)-N-[3,5-bis(trifluoromethyl)phenyl]benzamide (280 mg, 0.5 mmol), thioacetamide (41 mg, 0.55 mmol), sodium hydrogen carbonate (50 mg, 0.6 mmol) and ethanol (15 mL) was refluxed for 1 hour. The reaction mixture was poured into water, neutralized by sodium hydrogen carbonate, and extracted with ethyl acetate. After the organic layer was washed with water and brine, dried over anhydrous magnesium sulfate, the residue obtained by evaporation under reduced pressure was purified by chromatography on silica gel (hexane:ethyl acetate=4:1) to give the title compound (181 mg, 67.5%) as a white solid.

$^1$H-NMR(DMSO-$d_6$): δ 2.72(3H, s), 5.29(2H, s), 7.33-7.36(3H, m), 7.40(1H, d, J=9.0 Hz), 7.54-7.57(2H, m), 7.81 (1H, s), 7.94(1H, s), 8.12(1H, dd, J=8.7, 2.1 Hz), 8.27(1H, d, J=2.1 Hz), 8.31(2H, s), 10.86(1H, s).

(3) N-[3,5-Bis(trifluoromethyl)phenyl]-2-hydroxy-5-(2-methylthiazol-4-yl)benzamide (Compound No. 74)

2-Benzyloxy-N-[3,5-bis(trifluoromethyl)phenyl]-5-(2-methylthiazol-4-yl)benzamide (160 mg, 0.3 mmol) and 10% Pd—C (240 mg) were dissolved in ethanol (10 ml) and stirred for 3.5 hours under hydrogen atmosphere. The reaction mixture was filtered and the filtrate was evaporated under reduced pressure to give the title compound (103.4 mg, 79.2%) as a white solid.

$^1$H-NMR(DMSO-$d_6$): δ 2.72(3H, s), 7.08(1H, d, J=8.7 Hz), 7.83(1H, s), 7.85(1H, s), 8.01(1H, dd, J=8.7, 2.4 Hz), 8.42(1H, d, J=2.1 Hz), 8.50(2H, s), 10.96(1H, s), 11.40(1H, s).

Example 77

Preparation of the Compound of Compound No. 75

A mixture of 2-benzyloxy-5-(2-bromoacetyl)-N-[3,5-bis(trifluoromethyl)-phenyl]benzamide (compound of Example 58(3); 280 mg, 0.5 mmol), 2-aminopyridine (51.8 mg, 0.55 mmol), sodium hydrogen carbonate (50 mg, 0.6 mmol) and ethanol (10 mL) was refluxed for 2 hours. After cooling, the reaction mixture was poured into aqueous sodium hydrogen carbonate and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=1:2) to give a white solid (130.3 mg, 45.9%). Then, a mixture of this solid (108 mg, 0.19 mmol), 10% Pd—C (11 mg), ethanol (8 mL) and ethyl acetate (8 mL) was stirred for 7 hours under hydrogen atmosphere. The reaction mixture was filtered and the residue obtained by evaporation of the filtrate under reduced pressure was purified by chromatography on silica gel (n-hexane:ethyl acetate=1:3) to give the title compound (18.3 mg, 20.2%) as a white solid.

$^1$H-NMR(DMSO-$d_6$): δ 6.90(1H, dt, J=6.6, 0.9 Hz), 7.10 (1H, d, J=8.7 Hz), 7.25(1H, m), 7.57(1H, d, J=9.0 Hz), 7.86 (1H, s), 8.04(1H, dd, J=8.7, 2.1 Hz), 8.35(1H, s), 8.48-8.56 (4H, m), 11.00(1H, s), 11.41(1H, s).

Example 78

Preparation of the Compound of Compound No. 76

(1) N-[3,5-Bis(trifluoromethyl)phenyl]-5-iodo-2-methoxymethoxybenzamide

A mixture of N-[3,5-bis(trifluoromethyl)phenyl]-2-hydroxy-5-iodobenzamide (Compound No. 52; 4.75 g, 10 mmol), chloromethyl methyl ether (1.14 ml, 15 mmol), potassium carbonate (2.76 g, 20 mmol) and acetone (50 mL) was refluxed for 8 hours. The reaction mixture was poured into diluted hydrochloric acid and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=3:1), and recrystallized (n-hexane/ethyl acetate) to give the title compound (3.96 g, 76.3%) as a white solid.

$^1$H-NMR(DMSO-$d_6$): δ 3.38(3H, s), 5.28(2H, s), 7.12(1H, d, J=9.0 Hz), 7.81(1H, s), 7.82(1H, dd, J=8.7, 2.4 Hz), 7.88 (1H, d, J=2.4 Hz), 8.40(2H, s), 10.87(1H, s).

(2) N-[3,5-Bis(trifluoromethyl)phenyl]-2-methoxymethoxy-5-(pyridin-2-yl)benzamide N-[3,5-Bis(trifluoromethyl)phenyl]-5-iodo-2-methoxymethoxybenzamide (0.20 g, 0.39 mmol) was dissolved in N,N-dimethylformamide (8 ml). Tri-n-butyl(2-pyridyl)tin (0.13 ml, 0.41 mmol) and dichlorobis(triphenylphosphine) palladium (32.1 mg, 0.05 mmol) were added, and the mixture was stirred at 100° C. for 1.5 hours. After cooling, the reaction mixture was poured into water and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1→1:1) to give the title compound (37.9 mg, 20.8%) as a white powder.

$^1$H-NMR(CDCl$_3$): δ 3.64(3H, s), 5.53(2H, s), 7.23-7.28 (1H, m), 7.36(1H, d, J=8.7 Hz), 7.65(1H, s), 7.77-7.84(2H, m), 8.20(2H, s), 8.31(1H, dd, J=8.7, 2.4 Hz), 8.68-8.70(1H, m), 8.83(1H, d, J=2.4 Hz), 10.12(1H, s).

(3) N-[3,5-Bis(trifluoromethyl)phenyl]-2-hydroxy-5-(pyridin-2-yl)benzamide (Compound No. 76)

Methanol (3 ml) and concentrated hydrochloric acid (0.5 ml) were added to N-[3,5-bis(trifluoromethyl)phenyl]-2-methoxymethoxy-5-(pyridin-2-yl)benzamide (37.9 mg, 0.08 mmol), and the mixture was refluxed for 2 hours. After cooling, the reaction mixture was poured into saturated aqueous sodium hydrogen carbonate and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1) to give the title compound (16.2 mg, 47.2%) as a white powder.

$^1$H-NMR(DMSO-$d_6$): δ 7.13(1H, d, J=8.4 Hz), 7.33(1H, ddd, J=7.5, 6.3, 1.2 Hz), 7.86-7.91(2H, m), 7.97(1H, d, J=7.8

Hz), 8.20(1H, dd, J=8.7, 2.1 Hz), 8.50(2H, s), 8.59(1H, d, J=2.4 Hz), 8.64-8.66(1H, m), 10.97(1H, s), 11.53(1H, s).

Example 79

Preparation of the Compound of Compound No. 77

Using 5-methoxysalicylic acid and 3,5-bis(trifluoromethyl)aniline as the raw materials, the same operation as the Example 16 gave the title compound.

Yield: 56.8%. $^1$H-NMR(DMSO-d$_6$): δ 3.77(3H, s), 6.97 (1H, d, J=9.0 Hz), 7.10(1H, dd, J=9.0, 3.0 Hz), 7.43(1H, d, J=3.0 Hz), 7.84(1H, s), 8.47(2H, s), 10.84(1H, s), 10.91(1H, s).

Example 80

Preparation of the Compound of Compound No. 79

(1) 5-Acetyl-2-methoxybenzoic acid methyl ester

A mixture of 5-acetylsalicylic acid methyl ester (5.00 g, 25.7 mmol), sodium carbonate (7.10 g, 51.4 mmol) and N,N-dimethylformamide (25 mL) was cooled with ice bath. Methyl iodide (2.5 mL, 40.1 mmol) was added, and the mixture was stirred at room temperature for 3 hours. The reaction mixture was poured into water, neutralized by hydrochloric acid, and extracted with ethyl acetate. After the organic layer was washed with water and brine, dried over anhydrous sodium sulfate, the residue obtained by evaporation under reduced pressure was washed under suspension (isopropyl ether/n-hexane) to give the title compound (5.17 g, 96.5%) as a white crystal.

$^1$H-NMR(CDCl$_3$): δ 2.59(3H, s), 3.92(3H, s), 3.99(3H, s), 7.04(1H, d, J=8.7 Hz), 8.12(1H, dd, J=8.7, 2.4 Hz), 8.41(1H, d, J=2.4 Hz).

(2) 5-Isobutyryl-2-methoxybenzoic acid methyl ester

A mixture of 5-acetyl-2-methoxybenzoic acid methyl ester (0.50 g, 2.40 mmol), potassium tert-butoxide (0.81 g, 7.22 mmol) and tetrahydrofuran (10 mL) was cooled with ice bath. Methyl iodide (0.5 mL, 8.03 mmol) was added, and the mixture was stirred at room temperature for 1 hour. The reaction mixture was poured into water, neutralized by hydrochloric acid, and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=3:1→2:1) to give the title compound (143.1 mg, 25.2%) as a light yellow oil.

$^1$H-NMR(CDCl$_3$): δ 1.22(6H, d, J=6.9 Hz), 3.52(1H, m), 3.92(3H, s), 3.98(3H, s), 7.05(1H, d, J=8.7 Hz), 8.13(1H, dd, J=8.7, 2.4 Hz), 8.42(1H, d, J=2.4 Hz).

(3) 5-Isobutyryl-2-methoxybenzoic acid

5-Isobutyryl-2-methoxybenzoic acid methyl ester (143.1 mg, 0.60 mmol) was dissolved in methanol (5 mL). 2N Aqueous sodium hydroxide (1 ml) was added, and the mixture was refluxed for 1 hour. After cooling, the reaction mixture was poured into 2N hydrochloric acid and extracted with ethyl acetate. The organic layer was washed with water and brine, dried over anhydrous sodium sulfate, and evaporated under reduced pressure to give the title compound (134 mg, yield: quantitative) as a white crystal.

$^1$H-NMR(CDCl$_3$): δ 1.22(6H, d, J=6.9 Hz), 3.59(1H, m), 4.15(3H, s), 7.16(1H, d, J=8.7 Hz), 8.24(1H, dd, J=8.7, 2.4 Hz), 8.73(1H, d, J=2.1 Hz).

(4) 5-Isobutyryl-N-[3,5-bis(trifluoromethyl)phenyl]-2-methoxybenzamide

Using 5-isobutyryl-2-methoxybenzoic acid and 3,5-bis(trifluoromethyl)aniline as the raw materials, the same operation as the Example 16 gave the title compound.

Yield: 61.4%. $^1$H-NMR(CDCl$_3$): δ 1.23(6H, d, J=6.9 Hz), 3.64(1H, m), 4.20(3H, s), 7.18(1H, d, J=8.7 Hz), 7.65(1H, s), 8.19(2H, s), 8.22(1H, dd, J=8.7, 2.1 Hz), 8.88(1H, d, J=2.1 Hz), 9.98(1H, s).

(5) N-[3,5-Bis(trifluoromethyl)phenyl]-2-hydroxy-5-isobutyrylbenzamide (Compound No. 79)

A mixture of 5-isobutyryl-N-[3,5-bis(trifluoromethyl)phenyl]-2-methoxybenzamide (143.4 mg, 0.33 mmol), 2,4,6-collidine (3 ml) and lithium iodide (53.1 mg, 0.40 mmol) was refluxed for 1 hour. After cooling, the reaction mixture was poured into 2N hydrochloric acid and extracted with ethyl acetate. After the organic layer was washed with brine, dried over anhydrous sodium sulfate, the residue obtained by evaporation under reduced pressure was purified by chromatography on silica gel (n-hexane:ethyl acetate=3:1) and crystallized (ethyl acetate/isopropyl ether) to give the title compound (90.3 mg, 65.3%) as a white crystal.

$^1$H-NMR(DMSO-d$_6$): δ 1.12(6H, d, J=6.9 Hz), 3.66(1H, m), 7.12(1H, d, J=8.4 Hz), 7.85(1H, s), 8.07(1H, dd, J=8.4, 2.4 Hz), 8.45(1H, d, J=2.4 Hz), 8.47(2H, s), 10.93(1H, s), 11.95(1H, brs).

Example 81

Preparation of the Compound of Compound No. 81

Using 4-hydroxyisophthalic acid 1-methyl ester and 3,5-bis(trifluoromethyl)aniline as the raw materials, the same operation as the Example 16 gave the title compound.

Yield: 91.5%. $^1$H-NMR(DMSO-d$_6$): δ 3.85(3H, s), 7.12 (1H, d, J=8.4 Hz), 7.86(1H, s), 8.02(1H, dd, J=8.7, 2.4 Hz), 8.46-8.47(3H, m), 10.96(1H, s), 12.03(1H, brs).

[4-Hydroxyisophthalic acid 1-methyl ester: Refer to "Journal of the Chemical Society", (England), 1956, p. 3099-3107.]

Example 82

Preparation of the Compound of Compound No. 80

N-[3,5-Bis(trifluoromethyl)phenyl]-4-hydroxyisophthalamic acid methyl ester (Compound No. 81; 2.85 g, 7 mmol) was suspended in a mixed solvent of methanol (14 mL) and tetrahydrofuran (14 mL). 2N Aqueous sodium hydroxide (14 mL) was added, and the mixture was refluxed for 2 hours. After cooling, 2N hydrochloric acid (20 ml) was added to the reaction mixture and the separated solid was filtered, washed with water, dried to give the title compound (2.68 g, 97.4%) as a white crystal.

$^1$H-NMR(DMSO-d$_6$): δ 7.10(1H, d, J=8.7 Hz), 7.82(1H, s), 7.86(1H, s), 8.01(1H, dd, J=8.7, 2.4 Hz), 8.47(2H, s), 8.48(1H, d, J=2.4 Hz), 10.97(1H, s), 11.98(1H, brs).

When the method described in Example 82 is referred in the following examples, inorganic bases such as sodium hydroxide, potassium carbonate or the like were used as the base. As the reaction solvent, solvents such as water, methanol, ethanol, tetrahydrofuran or the like were used alone or as a mixture.

Example 83

Preparation of the Compound of Compound No. 82

Using 4-hydroxyisophthalic acid (182 mg, 1 mmol), 3,5-bis(trifluoromethyl)-aniline (687 mg, 3 mmol), phosphorus trichloride (87 μl; 1 mmol) and toluene (10 mL), the same operation as the Example 16 gave the title compound (151 mg, 25.0%) as a white crystal.

$^1$H-NMR(DMSO-d$_6$): δ 7.18(1H, d, J=8.7 Hz), 7.82(1H, s), 7.86(1H, s), 8.11(1H, dd, J=8.7, 2.4 Hz), 8.50(2H, s), 8.54(2H, s), 8.56(1H, d, J=2.4 Hz), 10.79(1H, s), 10.99(1H, s), 11.84(1H, brs).

Example 84

Preparation of the Compound of Compound No. 83

(1) 4-Benzyloxy-N-[3,5-bis(trifluoromethyl)phenyl] isophthalamic acid methyl ester Sodium hydride (60%; 1.04 g, 26 mmol) was washed with n-hexane, and suspended in N,N-dimethylformamide (100 mL). A solution of N-[3,5-bis(trifluoromethyl)phenyl]-4-hydroxyisophthalamic acid methyl ester (Compound No. 81; 8.15 g, 20 mmol) in N,N-dimethylformamide (100 mL) was added dropwise under cooling with ice bath. After the addition was finished, the mixture was stirred at room temperature for 1 hour. A solution of benzyl bromide (4.45 g, 26 mmol) in N,N-dimethylformamide (10 mL) was added, and the mixture was stirred at 60° C. for 3 hours. After cooling, the reaction mixture was poured into ice and water, and extracted with ethyl acetate. After the organic layer was washed with water and brine, dried over anhydrous magnesium sulfate, the residue obtained by evaporation under reduced pressure was recrystallized (ethyl acetate/n-hexane) to give the title compound (5.38 g, 54.1%) as a white solid.

$^1$H-NMR(DMSO-d$_6$): δ 3.87(3H, s), 5.33(2H, s), 7.33-7.36(3H, m), 7.46(1H, d, J=8.7 Hz), 7.53-7.56(2H, m), 7.82 (1H, s), 8.15(1H, dd, J=8.7, 2.1 Hz), 8.25(1H, d, J=2.1 Hz) 8.28(2H, s), 10.87(1H, s).

(2) 4-Benzyloxy-N-[3,5-bis(trifluoromethyl)phenyl] isophthalamic acid

Using 4-benzyloxy-N-[3,5-bis(trifluoromethyl)phenyl] isophthalamic acid methyl ester as the raw material, the same operation as the Example 82 gave the title compound.

Yield: 79.7%. $^1$H-NMR(DMSO-d$_6$): δ 5.32(2H, s), 7.32-7.34(3H, m), 7.43(1H, d, J=8.7 Hz), 7.52-7.56(2H, m), 7.81 (1H, s), 8.12(1H, dd, J=8.7, 2.1 Hz), 8.22(1H, d, J=2.1 Hz), 8.28(2H, s), 10.85(1H, s), 13.81(1H, brs).

(3) 4-Benzyloxy-N$^3$-[3,5-bis(trifluoromethyl)phenyl]-N$^1$,N$^1$-dimethylisophthalamide WSC.HCl (95 mg, 0.50 mmol) was added to a solution of 4-benzyloxy-N-[3,5-bis(trifluoromethyl)phenyl]isophthalamic acid (242 mg, 0.50 mmol), dimethylamine hydrochloride (41 mg, 0.50 mmol) and triethylamine (51 mg, 0.50 mmol) in tetrahydrofuran (5 mL) under ice cooling, and the mixture was stirred at room temperature for 3 hours. The reaction mixture was poured into water and extracted with ethyl acetate. After the organic layer was washed with diluted hydrochloric acid, water and brine, dried over anhydrous magnesium sulfate, the residue obtained by evaporation of the solvent under reduced pressure was purified by chromatography on silica gel (hexane:ethyl acetate=1:4) to give the title compound (165 mg, 64.9%) as a white solid.

$^1$H-NMR(DMSO-d$_6$): δ 2.99(6H, s) 5.29(2H, s), 7.32-7.38 (4H, m), 7.52-7.56(2H, m), 7.64(1H, dd, J=8.7, 2.1 Hz), 7.73(1H, d, J=2.1 Hz), 7.80(1H, s), 8.28(2H, s), 10.83(1H, s).

When the method described in Example 84(3) is referred in the following examples, organic bases such as pyridine, triethylamine or the like were used as the base. As the reaction solvent, solvents such as dichloromethane, tetrahydrofuran or the like were used alone or as a mixture.

(4) N$^3$-[3,5-bis(trifluoromethyl)phenyl]-4-hydroxy-N$^1$,N$^1$-dimethylisophthalamide (Compound No. 83)

A solution of 4-benzyloxy-N$^3$-[3,5-bis(trifluoromethyl) phenyl]-N$^1$,N$^1$-dimethyl-isophthalamide (141 mg, 0.28 mmol) and 5% Pd—C (14 mg) in a mixed solvent of ethanol (5 ml) and ethyl acetate (5 ml) was stirred at room temperature for 1 hour under hydrogen atmosphere. The reaction mixture was filtered and the filtrate was evaporated under reduced pressure to give the title compound (106 mg, 91.2%) as a white solid.

$^1$H-NMR(DMSO-d$_6$): δ 2.98(6H, s), 7.02(1H, d, J=8.7 Hz), 7.52(1H, dd, J=8.7, 2.1 Hz), 7.84(1H, s), 7.95(1H, d, J=2.1 Hz), 8.46(2H, s), 11.10(1H, brs), 11.63(1H, brs).

Example 85

Preparation of the Compound of Compound No. 84

(1) 2-Benzyloxy-N-[3,5-bis(trifluoromethyl)phenyl]-5-(piperidine-1-carbonyl)-benzamide Using 4-benzyloxy-N-[3,5-bis(trifluoromethyl)phenyl] isophthalamic acid (compound of Example 84(2)) and piperidine as the raw materials, the same operation as the Example 84(3) gave the title compound.

Yield: 56.4%. $^1$H-NMR(CDCl$_3$): δ 1.53-1.70(6H, m), 3.44 (2H, brs), 3.70(2H, brs), 5.26(2H, s), 7.24(1H, d, J=8.7 Hz), 7.26(1H, s), 7.52-7.58(5H, m), 7.66(2H, s), 7.74(1H, dd, J=8.7, 2.4 Hz), 8.37(1H, d, J=2.1 Hz), 10.27(1H, s).

(2) N-[3,5-Bis(trifluoromethyl)phenyl]-2-hydroxy-5-(piperidine-1-carbonyl)benzamide (Compound No. 84)

Using 2-benzyloxy-N-[3,5-bis(trifluoromethyl)phenyl]-5-(piperidine-1-carbonyl)benzamide as the raw material, the same operation as the Example 84(4) gave the title compound.

Yield: 96.3%, white solid. $^1$H-NMR(DMSO-d$_6$): δ 1.51 (4H, brs), 1.60-1.65(2H, m), 3.47(4H, brs), 7.04(1H, d, J=8.4 Hz), 7.48(1H, dd, J=8.4, 2.1 Hz), 7.85(1H, s), 7.92(1H, d, J=2.1 Hz), 8.46(2H, s), 10.99(1H, s), 11.64(1H, brs).

Example 86

Preparation of the Compound of Compound No. 85

(1) 2-Benzyloxy-5-(4-benzylpiperidine-1-carbonyl)-N-[3,5-bis(trifluoromethyl)phenyl]-benzamide Using 4-benzyloxy-N-[3,5-bis(trifluoromethyl)phenyl] isophthalamic acid (compound of Example 84(2)) and 4-benzylpiperidine as the raw materials, the same operation as the Example 84(3) gave the title compound.

Yield: 76.7%. $^1$H-NMR(CD$_3$OD): δ 1.18-1.38(2H, m), 1.67(1H, brs), 1.74(1H, brs), 1.84-1.93(1H, m), 2.60(2H, d, J=7.2 Hz), 2.83(1H, brs), 3.10(1H, brs), 3.78(1H, brs), 4.59 (1H, brs), 5.34(2H, s), 7.15-7.18(3H, m), 7.24-7.28(2H, m), 7.40-7.46(4H, m), 7.57-7.63(3H, m), 7.65(1H, dd, J=8.7, 2.4 Hz), 7.96(2H, s), 8.05(1H, d, J=2.1 Hz).

(2) N-[3,5-Bis(trifluoromethyl)phenyl]-2-hydroxy-5-(4-benzylpiperidine-1-carbonyl)-benzamide (Compound No. 85)

Using 2-benzyloxy-5-(4-benzylpiperidine-1-carbonyl)-N-[3,5-bis(trifluoromethyl)phenyl]-benzamide as the raw material, the same operation as the Example 84(4) gave the title compound.

Yield: 54.3%, white solid. $^1$H-NMR(DMSO-d$_6$): δ 1.08-1.22(2H, m), 1.59-1.62(2H, m), 1.77-1.80(1H, m), 2.50-2.55 (2H, m), 2.87(2H, brs), 3.75(1H, br), 4.39(1H, br), 7.06(1H, d, J=8.4 Hz), 7.17-7.20(3H, m), 7.28(2H, t, J=7.2 Hz), 7.49 (1H, dd, J=8.4, 2.1 Hz), 7.84(1H, s), 7.93(1H, d, J=2.1 Hz), 8.47(2H, s), 10.89(1H, s), 11.65(1H, s).

Example 87

Preparation of the Compound of Compound No. 86

(1) 2-Methoxy-5-sulfamoylbenzoic acid

Methyl 2-methoxy-5-sulfamoylbenzoate (4.91 g, 20 mmol) was dissolved in methanol (30 mL). 2N Aqueous sodium hydroxide (30 mL, 60 mmol) was added, and the mixture was stirred at room temperature for 1 hour. The reaction mixture was poured into 2N hydrochloric acid, and the separated solid was filtered to give the title compound (4.55 g, 98.3%) as a white solid.

$^1$H-NMR(DMSO-d$_6$): δ 3.89(3H, s), 7.30(1H, d, J=8.7 Hz), 7.32(2H, s), 7.92(1H, dd, J=8.7, 2.7 Hz), 8.09(1H, d, J=2.7 Hz), 13.03(1H, br).

(2) N-[3,5-Bis(trifluoromethyl)phenyl]-2-methoxy-5-sulfamoylbenzamide

Using 2-methoxy-5-sulfamoylbenzoic acid and 3,5-bis(trifluoromethyl)aniline as the raw materials, the same operation as the Example 24 gave the title compound.

Yield: 24.2%. $^1$H-NMR(DMSO-d$_6$): δ 3.97(3H, s), 7.38 (2H, s), 7.39(1H, d, J=8.7 Hz), 7.85(1H, s), 7.96(1H, dd, J=8.7, 2.4 Hz), 8.06(1H, d, J=2.4 Hz), 8.43(2H, s), 10.87(1H, s).

(3) N-[3,5-Bis(trifluoromethyl)phenyl]-5-dimethylsulfamoyl-2-methoxybenzamide

A suspension of N-[3,5-bis(trifluoromethyl)phenyl]-2-methoxy-5-sulfamoylbenzamide (442 mg, 1.0 mmol), methyl iodide (710 mg, 5.0 mmol) and sodium carbonate (415 mg, 3.0 mmol) in acetonitrile (10 mL) was refluxed for 3 hours. After cooling to room temperature, the reaction mixture was poured into water and extracted with ethyl acetate. After the organic layer was washed with water and brine, dried over anhydrous magnesium sulfate, the residue obtained by evaporation of the solvent under reduced pressure was recrystallized from a mixed solvent of n-hexane and ethyl acetate (2:1) to give the title compound (207 mg, 44.1%) as a white solid.

$^1$H-NMR(DMSO-d$_6$): δ 2.62(6H, s), 3.99(3H, s), 7.45(1H, d, J=9.0 Hz), 7.85(1H, s), 7.91(1H, dd, J=8.7, 2.4 Hz), 7.95 (1H, d, J=2.4 Hz) 8.43(2H, s), 10.90(1H, s).

(4) N-[3,5-Bis(trifluoromethyl)phenyl]-5-dimethylsulfamoyl-2-hydroxybenzamide (Compound No. 86)

Using N-[3,5-bis(trifluoromethyl)phenyl]-5-dimethylsulfamoyl-2-methoxybenzamide as the raw material, the same operation as the Example 80(5) gave the title compound.

Yield: 45.5%. $^1$H-NMR(DMSO-d$_6$): δ 2.61(6H, s), 7.20 (1H, d, J=8.7 Hz), 7.77(1H, dd, J=8.7, 2.1 Hz), 7.86(1H, s), 8.14(1H, d, J=2.1 Hz) 8.45(2H, s), 11.16(1H, s), 12.15(1H, br).

Example 88

Preparation of the Compound of Compound No. 87

(1) N-[3,5-Bis(trifluoromethyl)phenyl]-2-methoxy-5-(pyrrole-1-sulfonyl)benzamide A mixture of N-[3,5-bis(trifluoromethyl)phenyl]-2-methoxy-5-sulfamoyl-benzamide (compound of Example 87(2); 442 mg, 1 mmol), 2,5-dimethoxytetrahydrofuran (159 mg, 1.2 mmol) and acetic acid (5 mL) was refluxed for 2 hours. After cooling, the reaction mixture was poured into water and extracted with ethyl acetate. After the organic layer was washed with water, saturated aqueous sodium hydrogen carbonate and brine, dried over anhydrous magnesium sulfate, the residue obtained by evaporation of the solvent under reduced pressure was purified by chromatography on silica gel (n-hexane:ethyl acetate=3:2) to give the title compound (436.5 mg, 88.6%) as a white solid.

$^1$H-NMR(DMSO-d$_6$): δ 3.96(3H, s), 6.36(2H, dd, J=2.4, 2.1 Hz), 7.37(2H, dd, J=2.4, 2.1 Hz), 7.42(1H, d, J=9.0 Hz), 7.85(1H, s), 8.80(1H, dd, J=9.0, 2.4 Hz) 8.18(1H, d, J=2.7 Hz), 8.38(2H, s), 10.92(1H, s).

(2) N-[3,5-Bis(trifluoromethyl)phenyl]-2-hydroxy-5-(pyrrole-1-sulfonyl)benzamide (Compound No. 87)

Using N-[3,5-bis(trifluoromethyl)phenyl]-2-methoxy-5-(pyrrole-1-sulfonyl)benzamide as the raw material, the same operation as the Example 80(5) gave the title compound.

Yield: 79.4%. $^1$H-NMR(DMSO-d$_6$): δ 6.36(2H, dd, J=2.4, 2.1 Hz), 7.18(1H, d, J=9.0 Hz), 7.34(2H, dd, J=2.4, 2.1 Hz), 7.86(1H, s), 7.99(1H, dd, J=9.0, 2.7 Hz) 8.31(1H, d, J=2.7 Hz), 8.42(2H, s), 10.98(1H, s).

Example 89

Preparation of the Compound of Compound No. 88

Using N-[3,5-bis(trifluoromethyl)phenyl]-2-hydroxy-5-nitrobenzamide (Compound No. 53) as the raw material, the same operation as the Example 84(4) gave the title compound.

Yield: 98.0%. $^1$H-NMR(DMSO-d$_6$): δ 4.79(2H, brs), 6.76 (1H, d, J=2.1 Hz), 6.76(1H, s), 7.09(1H, dd, J=2.1, 1.2 Hz), 7.80(1H, s), 8.45(2H, s), 10.30(1H, br), 10.84(1H, s).

Example 90

Preparation of the Compound of Compound No. 89

Using 5-dimethylaminosalicylic acid and 3,5-bis(trifluoromethyl)aniline as the raw materials, the same operation as the Example 16 gave the title compound.

Yield: 28.8%. $^1$H-NMR(DMSO-d$_6$): δ 2.85(6H, s), 6.92 (1H, d, J=9.0 Hz), 7.01(1H, dd, J=8.7, 3.0 Hz), 7.22(1H, d, J=3.0 Hz), 7.84(1H, s), 8.47(2H, s), 10.62(1H, s), 10.83(1H, s).

Example 91

Preparation of the Compound of Compound No. 90

Under argon atmosphere, a mixture of 5-amino-N-[3,5-bis (trifluoromethyl)-phenyl]-2-hydroxybenzamide (Compound No. 88; 364 mg, 1 mmol), pyridine (95 mg, 1.2 mmol) and tetrahydrofuran (10 mL) was cooled on ice. Benzoyl chloride (155 mg, 1.1 mmol) was added, and the mixture was stirred for 1 hour. The reaction mixture was poured into water and extracted with ethyl acetate. After the organic layer was washed with water and brine, dried over anhydrous magnesium sulfate, the residue obtained by evaporation under reduced pressure was purified by chromatography on silica gel (n-hexane:ethyl acetate=4:1) to give the title compound (121 mg, 25.7%) as a white solid.

$^1$H-NMR(DMSO-d$_6$): δ 7.04(1H, d, J=8.7 Hz), 7.51-7.62 (3H, m), 7.81(1H, dd, J=8.7, 2.4 Hz), 7.83(1H, s), 7.98(2H, d, J=7.2 Hz), 8.22(1H, d, J=2.4 Hz), 8.49(2H, s), 10.27(1H, s), 10.89(1H, s), 11.07(1H, s).

Example 92

Preparation of the Compound of Compound No. 91

5-Amino-N-[3,5-bis(trifluoromethyl)phenyl]-2-hydroxybenzamide (Compound No. 88; 100.2 mg, 0.28 mmol) was dissolved in acetonitrile (4 ml). 4-Dimethylaminopyridine (3 mg) and phenylisocyanate (30 μg, 0.28 mmol) were added, and the mixture was stirred at 60° C. for 5 minutes. The reaction mixture was concentrated and the residue was purified by chromatography on silica gel (n-hexane:ethyl acetate=1:1) to give the title compound (54.8 mg, 41.2%) as a light brown solid.

$^1$H-NMR(DMSO-d$_6$): δ 6.93-6.98(1H, m), 6.97(1H, d, J=9.3 Hz), 7.27(2H, t, J=7.8 Hz), 7.34-7.46(2H, m), 7.50(1H, dd, J=9.0, 2.4 Hz), 7.83(1H, s), 7.88(1H, s), 8.47(2H, s), 8.56(1H, s), 8.63(1H, s), 10.87(1H, s), 10.89(1H, s).

Example 93

Preparation of the Compound of Compound No. 92

Using 5-amino-N-[3,5-bis(trifluoromethyl)phenyl]-2-hydroxybenzamide (Compound No. 88) and phenylisothiocyanate as the raw materials, the same operation as the Example 92 gave the title compound.

Yield: 66.3%. $^1$H-NMR(DMSO-d$_6$): δ 7.00(1H, d, J=8.4 Hz), 7.13(1H, tt, J=7.5, 1.2 Hz), 7.34(2H, t, J=7.8 Hz), 7.45-7.51(3H, m), 7.84(1H, s), 7.87(1H, d, J=2.7 Hz), 8.47(2H, s), 9.65(1H, s), 9.74(1H, s), 10.84(1H, s), 11.32(1H, s).

Example 94

Preparation of the Compound of Compound No. 93

Using 5-[(4-nitrophenyl)diazenyl]salicylic acid and 3,5-bis(trifluoromethyl)aniline as the raw materials, the same operation as the Example 16 gave the title compound.

Yield: 11.3%. $^1$H-NMR(DMSO-d$_6$): δ 7.23(1H, d, J=9.0 Hz), 7.87(1H, s), 8.06(2H, d, J=9.0 Hz), 8.10(1H, dd, J=9.0, 2.4 Hz), 8.44(2H, d, J=9.0 Hz), 8.50(2H, s), 8.53(1H, d, J=2.4 Hz), 11.13(1H, s), 12.14(1H, br).

Example 95

Preparation of the Compound of Compound No. 94

Using 5-({[(4-pyridin-2-yl)sulfamoyl]phenyl}diazenyl) salicylic acid and 3,5-bis(trifluoromethyl)aniline as the raw materials, the same operation as the Example 16 gave the title compound.

Yield: 7.9%. $^1$H-NMR(DMSO-d$_6$): δ 6.87(1H, t, J=6.0 Hz), 7.22(1H, d, J=8.7 Hz), 7.21-7.23(1H, m), 7.77(1H, t, J=8.4 Hz), 7.87(1H, s), 7.95-7.98(3H, m), 8.03-8.07(4H, m), 8.47(1H, d, J=2.4 Hz), 8.49(2H, s), 11.14(1H, s), 12.03(1H, br).

Example 96

Preparation of the Compound of Compound No. 96

N-[3,5-Bis(trifluoromethyl)phenyl]-5-chloro-2-hydroxybenzamide (Compound No. 50; 1.51 g, 3 mmol) and pyridine (285 mg, 3.6 mmol) were dissolved in tetrahydrofuran (6 mL). Acetyl chloride (234 mg, 3.3 mmol) was added dropwise under ice cooling, and the mixture was stirred at room temperature for 1 hour. The solvent was evaporated under reduced pressure. 2 N hydrochloric acid was added to the residue, and it was extracted with ethyl acetate. After the ethyl acetate layer was washed with water and brine, dried over anhydrous magnesium sulfate and concentrated, the residue was recrystallized from n-hexane/ethyl acetate to give the title compound (1.06 g, 83.0%) as a white solid.

$^1$H-NMR(DMSO-d$_6$): δ 2.22(3H, s), 7.35(1H, d, J=9.0 Hz), 7.71(1H, dd, J=8.7, 2.7 Hz), 7.85(1H, s), 7.88(1H, d, J=2.7 Hz), 8.37(2H, s), 11.05(1H, brs).

When the method described in Example 96 is referred in the following examples, organic bases such as pyridine, triethylamine or the like were used as the base. As the reaction solvent, solvents such as dichloromethane, tetrahydrofuran, benzene or the like were used alone or as a mixture.

Example 97

Preparation of the Compound of Compound No. 97

(1) 4-Acetylamino-5-chloro-2-methoxybenzoic acid

Using 4-acetylamino-5-chloro-2-methoxybenzoic acid methyl ester as the raw material, the same operation as the Example 82 gave the title compound.

Yield: 88.0%. $^1$H-NMR(DMSO-d$_6$): δ 2.16(3H, s), 3.78 (3H, s), 7.72(1H, s), 7.77(1H, s), 9.57(1H, s), 12.74(1H, s).

(2) 4-Acetylamino-N-[3,5-bis(trifluoromethyl)phenyl]-5-chloro-2-methoxybenzamide Using 4-acetylamino-5-chloro-2-methoxybenzoic acid and 3,5-bis(trifluoromethyl)aniline as the raw materials, the same operation as the Example 24 gave the title compound.

Yield: 23.8%. $^1$H-NMR(DMSO-d$_6$): δ 2.17(3H, s), 3.89 (3H, s), 7.77-7.82(3H, m), 8.45-8.49(2H, m), 9.66(1H, s), 10.68(1H, s).

(3) 4-Acetylamino-N-[3,5-bis(trifluoromethyl)phenyl]-5-chloro-2-hydroxybenzamide (Compound No. 97)

Using 4-acetylamino-N-[3,5-bis(trifluoromethyl)phenyl]-5-chloro-2-methoxybenzamide as the raw material, the same operation as the Example 80(5) gave the title compound.

Yield: 72.8%. $^1$H-NMR(DMSO-d$_6$): δ 2.17(3H, s), 7.75 (1H, s), 7.82(1H, s), 7.95(1H, s), 8.44(2H, s), 9.45(1H, s), 11.16(1H, brs), 11.63(1H, brs).

Example 98

Preparation of the Compound of Compound No. 98

Using 4-chlorosalicylic acid and 3,5-bis(trifluoromethyl) aniline as the raw materials, the same operation as the Example 16 gave the title compound.

Yield: 55.8%. $^1$H-NMR(DMSO-d$_6$): δ 7.05-7.08(2H, m), 7.84-7.87(2H, m), 8.45(2H, s), 10.84(1H, s) 11.64(1H, brs).

Example 99

Preparation of the Compound of Compound No. 99

Using 5-chlorosalicylic acid and 3,5-bis(trifluoromethyl)-2-bromoaniline as the raw materials, the same operation as the Example 16 gave the title compound.

Yield: 14.5%. $^1$H-NMR(DMSO-d$_6$): δ 7.11(1H, d, J=9.0 Hz), 7.53(1H, dd, J=9.0, 2.7 Hz), 7.91(1H, d, J=1.8 Hz), 7.98(1H, d, J=2.7 Hz), 9.03(1H, d, J=1.8 Hz), 11.26(1H, brs).

Example 100

Preparation of the Compound of Compound No. 100

Using 5-chlorosalicylic acid and 2,5-bis(trifluoromethyl) aniline as the raw materials, the same operation as the Example 16 gave the title compound.

Yield: 3.6%. $^1$H-NMR(CDCl$_3$): δ 7.03(1H, d, J=8.7 Hz), 7.43-7.48(2H, m), 6.61(1H, d, J=8.1 Hz), 7.85(1H, d, J=8.4 Hz), 8.36(1H, br s), 8.60(1H, s), 11.31(1H, s).

Example 101

Preparation of the Compound of Compound No. 101

Using 5-bromosalicylic acid and 2,5-bis(trifluoromethyl) aniline as the raw materials, the same operation as the Example 16 gave the title compound.

Yield: 24.0%. $^1$H-NMR(DMSO-d$_6$): δ 7.03(1H, d, J=8.7 Hz), 7.65(1H, dd, J=8.7, 2.7 Hz), 7.76(1H, d, J=8.4 Hz), 8.03(1H, d, J=8.1 Hz) 8.11(1H, d, J=2.7 Hz), 8.74(1H, s), 11.02(1H, s), 12.34(1H, s).

Example 102

Preparation of the Compound of Compound No. 102

Using 5-methylsalicylic acid and 2,5-bis(trifluoromethyl) aniline as the raw materials, the same operation as the Example 16 gave the title compound.

Yield: 1.5%. $^1$H-NMR(CDCl$_3$): δ 2.36(3H, s), 6.97(1H, d, J=8.4 Hz), 7.23(1H, s), 7.32(1H, dd, J=8.4, 1.5 Hz), 7.57(1H, d, J=8.4 Hz), 7.83(1H, d, J=8.4 Hz), 8.46(1H, s), 8.69(1H, s), 11.19(1H, s).

Example 103

Preparation of the Compound of Compound No. 103

Using N-[2,5-bis(trifluoromethyl)phenyl]-5-chloro-2-hydroxybenzamide (Compound No. 100) and acetyl chloride as the raw materials, the same operation as the Example 96 gave the title compound.

Yield: 6.6%. $^1$H-NMR(CDCl$_3$): δ 2.35(3H, s), 7.17(1H, d, J=8.7 Hz), 7.54(1H, dd, J=8.7, 2.4 Hz), 7.55(1H, d, J=8.1 Hz), 7.80(1H, d, J=8.1 Hz), 7.95(1H, d, J=2.4 Hz), 8.60(1H, s), 8.73(1H, s).

Example 104

Preparation of the Compound of Compound No. 104

Using 5-chlorosalicylic acid and 2-(trifluoromethyl) aniline as the raw materials, the same operation as the Example 16 gave the title compound.

Yield: 58.0%. $^1$H-NMR(DMSO-d$_6$): δ 7.07(1H, d, J=8.7 Hz), 7.42(1H, t, J=7.5 Hz), 7.52(1H, dd, J=8.7, 2.7 Hz), 7.74(1H, t, J=8.1 Hz), 7.77(1H, t, J=8.1 Hz), 7.99(1H, d, J=2.7 Hz), 8.18(1H, d, J=8.1 Hz), 10.76(1H, s), 12.22(1H, s).

Example 105

Preparation of the Compound of Compound No. 105

Using 5-chlorosalicylic acid and 4-chloro-2-(trifluoromethyl)aniline as the raw materials, the same operation as the Example 16 gave the title compound.

Yield: 21.5%. $^1$H-NMR(DMSO-d$_6$): δ 7.07(1H, d, J=8.7 Hz), 7.52(1H, dd, J=8.7, 2.7 Hz), 7.80-7.85(2H, m), 7.97(1H, d, J=2.7 Hz), 8.26(1H, d, J=8.4 Hz), 10.80(1H, s), 12.26(1H, s).

Example 106

Preparation of the Compound of Compound No. 106

Using 5-bromosalicylic acid and 3-(trifluoromethyl) aniline as the raw materials, the same operation as the Example 16 gave the title compound.

Yield: 50.3%. $^1$H-NMR(DMSO-d$_6$): δ 6.98(1H, d, J=8.7 Hz), 7.48-7.52(1H, m), 7.59(1H, dd, J=8.7, 2.7 Hz), 7.62(1H, t, J=8.1 Hz), 7.92-7.96(1H, m), 8.02(1H, d, J=2.4 Hz), 8.20 (1H, s), 10.64(1H, s), 11.60(1H, s).

Example 107

Preparation of the Compound of Compound No. 107

Using 5-chlorosalicylic acid and 2-fluoro-3-(trifluoromethyl)aniline as the raw materials, the same operation as the Example 16 gave the title compound.

Yield: 71.7%, white solid. $^1$H-NMR(DMSO-d$_6$): δ 7.07 (1H, d, J=9.0 Hz), 7.46(1H, t, J=7.8 Hz), 7.52(1H, dd, J=9.0, 2.7 Hz), 7.58(1H, t, J=7.2 Hz), 7.96(1H, d, J=2.7 Hz), 8.49 (1H, t, J=7.2 Hz), 10.82(1H, s), 12.13(1H, brs).

Example 108

Preparation of the Compound of Compound No. 108

Using 5-chlorosalicylic acid and 4-fluoro-3-(trifluoromethyl)aniline as the raw materials, the same operation as the Example 16 gave the title compound.

Yield: 72.1%, white solid. $^1$H-NMR(DMSO-d$_6$):7.03(1H, d, J=9.0 Hz), 7.48(1H, dd, J=8.7, 2.7 Hz), 7.56(1H, d, J=9.9 Hz), 7.90(1H, d, J=2.7 Hz), 7.99-8.03(1H, m), 8.21(1H, dd, J=6.6, 2.4 Hz), 10.63(1H, s), 11.58(1H, s).

Example 109

Preparation of the Compound of Compound No. 109

Using 5-bromosalicylic acid and 4-chloro-3-(trifluoromethyl)aniline as the raw materials, the same operation as the Example 16 gave the title compound.

Yield: 37.4%. $^1$H-NMR(DMSO-d$_6$): δ 6.98(1H, d, J=8.7 Hz), 7.59(1H, dd, J=8.7, 2.4 Hz), 7.73(1H, d, J=8.7 Hz), 7.98(1H, d, J=2.4 Hz), 8.00(1H, dd, J=8.7, 2.4 Hz), 8.31(1H, d, J=2.4 Hz), 10.68(1H, s), 11.52(1H, brs).

Example 110

Preparation of the Compound of Compound No. 110

Using 5-chlorosalicylic acid and 3-fluoro-5-(trifluoromethyl)aniline as the raw materials, the same operation as the Example 16 gave the title compound.

Yield: 62.0%. $^1$H-NMR(DMSO-d$_6$): δ 7.04(1H, d, J=8.7 Hz), 7.42(1H, d, J=8.4 Hz), 7.48(1H, dd, J=9.0, 3.0 Hz), 7.85(1H, d, J=2.4 Hz), 7.94(1H, dd, J=11.4, 2.1 Hz), 7.99(1H, s), 10.73(1H, s), 11.46(1H, s).

Example 111

Preparation of the Compound of Compound No. 111

Using 5-bromosalicylic acid and 3-bromo-5-(trifluoromethyl)aniline as the raw materials, the same operation as the Example 16 gave the title compound.

Yield: 73.3%. $^1$H-NMR(DMSO-d$_6$): δ 6.99(1H, d, J=9.0 Hz), 7.60(1H, dd, J=9.0, 2.4 Hz), 7.72(1H, s), 7.97(1H, d, J=2.7 Hz), 8.16(1H, s), 8.28(1H, s), 10.69(1H, s), 11.45(1H, s).

Example 112

Preparation of the Compound of Compound No. 112

Using 5-chlorosalicylic acid and 2-fluoro-5-(trifluoromethyl)aniline as the raw materials, the same operation as the Example 16 gave the title compound.

Yield: 77.9%. $^1$H-NMR(DMSO-d$_6$): δ 7.07(1H, d, J=9.0 Hz), 7.52(1H, dd, J=9.0, 2.7 Hz), 7.58-7.61(2H, m), 7.95(1H, d, J=2.7 Hz), 8.71(1H, d, J=7.5 Hz), 10.90(1H, s), 12.23(1H, s).

Example 113

Preparation of the Compound of Compound No. 113

Using 5-chlorosalicylic acid and 2-chloro-5-(trifluoromethyl)aniline as the raw materials, the same operation as the Example 16 gave the title compound.

Yield: 49.1%. $^1$H-NMR(DMSO-d$_6$): δ 7.09(1H, d, J=9.0 Hz), 7.53(1H, dd, J=9.0, 3.0 Hz), 7.55(1H, dd, J=8.4, 2.7 Hz), 7.83(1H, d, J=8.4 Hz), 7.98(1H, d, J=3.0 Hz), 8.88(1H, d, J=2.7 Hz), 11.14(1H, s), 12.39(1H, s).

Example 114

Preparation of the Compound of Compound No. 114

Using 5-bromosalicylic acid and 2-chloro-5-(trifluoromethyl)aniline as the raw materials, the same operation as the Example 16 gave the title compound.

Yield: 34.2%. $^1$H-NMR(DMSO-d$_6$): δ 7.04(1H, d, J=8.7 Hz), 7.56(1H, ddd, J=8.1, 2.4, 1.2 Hz), 7.64(1H, dd, J=8.7, 2.7 Hz), 7.83(1H, dd, J=8.1, 1.2 Hz), 8.11(1H, d, J=2.7 Hz), 8.87(1H, d, J=2.4 Hz), 11.12(1H, s), 12.42(1H, s).

Example 115

Preparation of the Compound of Compound No. 115

Using 5-chlorosalicylic acid and 4-nitro-3-(trifluoromethyl)aniline as the raw materials, the same operation as the Example 16 gave the title compound.

Yield: 44.8%. $^1$H-NMR(DMSO-d$_6$): δ 7.04(1H, d, J=9.0 Hz), 7.49(1H, dd, J=9.0, 2.7 Hz), 7.81(1H, d, J=2.7 Hz), 8.23-8.24(2H, m), 8.43(1H, d, J=1.2 Hz), 11.02(1H, s), 11.30 (1H, br).

Example 116

Preparation of the Compound of Compound No. 116

Using 5-chlorosalicylic acid and 2-nitro-5-(trifluoromethyl)aniline as the raw materials, the same operation as the Example 16 gave the title compound.

Yield: 8.1%. $^1$H-NMR(DMSO-d$_6$): δ 7.08(1H, d, J=9.0 Hz), 7.53(1H, dd, J=8.7, 2.7 Hz), 7.73(1H, dd, J=8.4, 1.8 Hz), 7.95(1H, d, J=3.0 Hz), 8.36(1H, d, J=8.7 Hz), 9.01(1H, d, J=1.8 Hz), 12.04(1H, s), 12.20(1H, s).

Example 117

Preparation of the Compound of Compound No. 117

Using 5-bromosalicylic acid and 4-cyano-3-(trifluoromethyl)aniline as the raw materials, the same operation as the Example 16 gave the title compound.

Yield: 49.7%. ¹H-NMR(DMSO-d$_6$): δ 6.99(1H, d, J=8.7 Hz), 7.60(1H, dd, J=8.7, 2.4 Hz), 7.92(1H, d, J=2.7 Hz), 8.16(2H, s), 8.42(1H, s), 10.93(1H, s), 11.36(1H, s).

Example 118

Preparation of the Compound of Compound No. 118

Using 5-chlorosalicylic acid and 2-methyl-3-(trifluoromethyl)aniline as the raw materials, the same operation as the Example 16 gave the title compound.

Yield: 14.5%. ¹H-NMR(DMSO-d$_6$): δ 2.36(3H, d, J=1.2 Hz), 7.05(1H, d, J=8.7 Hz), 7.46(1H, t, J=8.1 Hz), 7.50(1H, dd, J=8.7, 2.7 Hz), 7.60(1H, d, J=7.2 Hz), 7.99(1H, d, J=7.2 Hz), 8.00(1H, d, J=2.4 Hz), 10.43(1H, s), 12.08(1H, s).

Example 119

Preparation of the Compound of Compound No. 119

Using 5-chlorosalicylic acid and 4-methyl-3-(trifluoromethyl)aniline as the raw materials, the same operation as the Example 16 gave the title compound.

Yield: 80.2%. ¹H-NMR(DMSO-d$_6$): δ 7.01(1H, d, J=8.7 Hz), 7.44(1H, d, J=8.4 Hz), 7.47(1H, dd, J=9.0, 2.7 Hz), 7.84(1H, dd, J=8.4, 2.1 Hz), 7.92(1H, d, J=2.7 Hz), 8.13(1H, d, J=2.1 Hz), 10.65(1H, s), 11.68(1H, br).

Example 120

Preparation of the Compound of Compound No. 120

Using 5-chlorosalicylic acid and 2-methyl-5-(trifluoromethyl)aniline as the raw materials, the same operation as the Example 16 gave the title compound.

Yield: 73.3%. ¹H-NMR(DMSO-d$_6$): δ 2.39(3H, s), 7.07 (1H, d, J=8.7 Hz), 7.44-7.54(3H, m), 7.99(1H, d, J=3.0 Hz), 8.43(1H, s), 10.52(1H, s), 12.17(1H, brs).

Example 121

Preparation of the Compound of Compound No. 121

Using 5-chlorosalicylic acid and 4-methoxy-3-(trifluoromethyl)aniline as the raw materials, the same operation as the Example 16 gave the title compound.

Yield: 79.1%. ¹H-NMR(DMSO-d$_6$): δ 3.89(3H, s), 7.02 (1H, d, J=9.0 Hz), 7.30(1H, d, J=9.0 Hz), 7.48(1H, dd, J=9.0, 3.0 Hz), 7.92(1H, dd, J=9.0, 2.4 Hz), 7.96(1H, d, J=2.7 Hz), 8.04(1H, d, J=2.4 Hz), 10.47(1H, s), 11.78(1H, s).

Example 122

Preparation of the Compound of Compound No. 122

Using 5-bromosalicylic acid and 3-methoxy-5-(trifluoromethyl)aniline as the raw materials, the same operation as the Example 16 gave the title compound.

Yield: 58.8%. ¹H-NMR(DMSO-d$_6$): δ 3.85(3H, s), 6.98 (1H, d, J=8.7 Hz), 7.03(1H, s), 7.57-7.61(2H, m), 7.77(1H, s), 8.00(1H, d, J=2.4 Hz), 10.57(1H, s), 11.56(1H, s).

Example 123

Preparation of the Compound of Compound No. 123

Using 5-bromosalicylic acid and 2-methoxy-5-(trifluoromethyl)aniline as the raw materials, the same operation as the Example 16 gave the title compound.

Yield: 71.3%. ¹H-NMR(DMSO-d$_6$): δ 3.99(3H, s), 7.03 (1H, d, J=9.0 Hz), 7.30(1H, d, J=8.7 Hz), 7.47-7.51(1H, m), 7.61(1H, dd, J=9.0, 2.4 Hz), 8.10(1H, d, J=2.4 Hz), 8.82(1H, d, J=2.1 Hz) 11.03(1H, s), 12.19(1H, s).

Example 124

Preparation of the Compound of Compound No. 124

Using 5-chlorosalicylic acid and 2-methoxy-5-(trifluoromethyl)aniline as the raw materials, the same operation as the Example 16 gave the title compound.

Yield: 83.4%. ¹H-NMR(DMSO-d$_6$): δ 4.00(3H, s), 7.08 (1H, d, J=9.0 Hz), 7.30(1H, d, J=8.7 Hz), 7.47-7.52(2H, m), 7.97(1H, d, J=2.7 Hz), 8.83(1H, d, J=2.4 Hz), 11.05(1H, s), 12.17(1H, s).

Example 125

Preparation of the Compound of Compound No. 125

Using 5-chlorosalicylic acid and 2-methylsulfanyl-5-(trifluoromethyl)aniline as the raw materials, the same operation as the Example 16 gave the title compound.

Yield: 79.2%. ¹H-NMR(DMSO-d$_6$): δ 2.57(3H, s), 7.07 (1H, d, J=8.7 Hz), 7.52(1H, dd, J=8.7, 2.4 Hz), 7.55(1H, dd, J=8.4, 1.5 Hz), 7.63(1H, d, J=8.1 Hz), 8.00(1H, d, J=2.4 Hz), 8.48(1H, d, J=1.5 Hz), 10.79(1H, s), 12.26(1H, s).

Example 126

Preparation of the Compound of Compound No. 126

Using 5-bromosalicylic acid and 2-(1-pyrrolidinyl)-5-(trifluoromethyl)aniline as the raw materials, the same operation as the Example 16 gave the title compound.

Yield: 44.5%. ¹H-NMR(DMSO-d$_6$): δ 1.86-1.91(4H, m), 3.20-3.26(4H, m), 6.99(1H, d, J=8.7 Hz), 7.07(1H, d, J=8.7 Hz), 7.43(1H, dd, J=8.7, 2.1 Hz), 7.62(1H, dd, J=8.7, 2.4 Hz), 7.94(1H, d, J=2.1 Hz), 8.17(1H, d, J=2.4 Hz), 10.54(1H, s), 12.21(1H, s).

Example 127

Preparation of the Compound of Compound No. 127

Using 5-bromosalicylic acid and 2-morpholino-5-(trifluoromethyl)aniline as the raw materials, the same operation as the Example 16 gave the title compound.

Yield: 65.9%. ¹H-NMR(DMSO-d$_6$): δ 2.90(4H, dd, J=4.5, 4.2 Hz), 3.84(4H, dd, J=4.8, 4.2 Hz), 7.09(1H, d, J=8.4 Hz), 7.48(2H, s), 7.61(1H, dd, J=8.4, 2.7 Hz), 8.13(1H, d, J=2.7 Hz), 8.90(1H, s), 11.21(1H, s), 12.04(1H, s).

Example 128

Preparation of the Compound of Compound No. 128

Using 5-chlorosalicylic acid and 4-(trifluoromethyl) aniline as the raw materials, the same operation as the Example 16 gave the title compound.

Yield: 75.0%, white solid ¹H-NMR(DMSO-d$_6$): δ 7.04 (1H, d, J=9.0 Hz), 7.48(1H, dd, J=8.7, 2.7 Hz), 7.74(2H, d, J=8.7 Hz), 7.90(1H, d, J=2.7 Hz), 7.95(2H, d, J=9.0 Hz), 10.65(1H, s), 11.59(1H, s).

Example 129

Preparation of the Compound of Compound No. 129

Using 5-bromosalicylic acid and 2-chloro-4-(trifluoromethyl)aniline as the raw materials, the same operation as the Example 16 gave the title compound.

Yield: 34.9%. $^1$H-NMR(DMSO-d$_6$): δ 7.04(1H, d, J=8.7 Hz), 7.64(1H, dd, J=8.7, 2.7 Hz), 7.79(1H, dd, J=9.0, 2.1 Hz), 7.99(1H, d, J=2.1 Hz), 8.11(1H, d, J=2.4 Hz), 8.73(1H, d, J=9.0 Hz), 11.15(1H, s), 12.42(1H, s).

Example 130

Preparation of the Compound of Compound No. 130

Using 5-chloro-N-[2-chloro-5-(trifluoromethyl)phenyl]-2-hydroxybenzamide (Compound No. 113) and acetyl chloride as the raw materials, the same operation as the Example 96 gave the title compound.

Yield: 34.0%. $^1$H-NMR(CDCl$_3$): δ 2.39(3H, s), 7.16(1H, d, J=8.7 Hz), 7.37(1H, ddd, J=8.7, 2.4, 0.6 Hz), 7.51-7.56(2H, m), 7.97(1H, d, J=3.0 Hz), 8.85(1H, s), 8.94(1H, d, J=1.8 Hz).

Example 131

Preparation of the Compound of Compound No. 131

Using 5-nitrosalicylic acid and 2-chloro-5-(trifluoromethyl)aniline as the raw materials, the same operation as the Example 16 gave the title compound.

Yield: 31.1%. $^1$H-NMR(DMSO-d$_6$): δ 6.98(1H, d, J=9.3 Hz), 7.52(1H, dd, J=8.4, 2.1 Hz), 7.81(1H, d, J=8.4 Hz), 8.21(1H, dd, J=9.0, 3.3 Hz), 8.82(1H, d, J=3.0 Hz), 8.93(1H, d, J=2.4 Hz), 12.18(1H, s).

Example 132

Preparation of the Compound of Compound No. 132

Using 5-methylsalicylic acid and 2-chloro-5-(trifluoromethyl)aniline as the raw materials, the same operation as the Example 16 gave the title compound.

Yield: 15.8%. $^1$H-NMR(CDCl$_3$): δ 2.36(3H, s), 6.95(1H, d, J=8.1 Hz), 7.26-7.31(2H, m), 7.37(1H, dd, J=8.4, 1.8 Hz), 7.56(1H, d, J=8.4 Hz), 8.65(1H, br s), 8.80(1H, d, J=1.8 Hz), 11.33(1H, br s).

Example 133

Preparation of the Compound of Compound No. 133

Using 5-methoxysalicylic acid and 2-chloro-5-(trifluoromethyl)aniline as the raw materials, the same operation as the Example 16 gave the title compound.

Yield: 56.4%. $^1$H-NMR(DMSO-d$_6$): δ 3.77(3H, s), 6.91 (1H, d, J=9.0 Hz), 7.07(1H, dd, J=8.7, 3.0 Hz), 7.20(1H, t, J=1.8 Hz), 7.52-7.54(3H, m), 10.33(1H, s), 11.44(1H, s).

Example 134

Preparation of the Compound of Compound No. 134

Using 5-methylsalicylic acid and 4-chloro-3-(trifluoromethyl)aniline as the raw materials, the same operation as the Example 16 gave the title compound.

Yield: 70.4%. $^1$H-NMR(DMSO-d$_6$): δ 2.29(3H, s), 6.91(1H, d, J=8.3 Hz), 7.27(1H, ddd, J=8.3, 2.2, 0.6 Hz), 7.71(1H, d, J=2.2 Hz), 7.72(1H, d, J=8.5 Hz), 8.02(1H, dd, J=8.5, 2.5 Hz), 8.33(1H, d, J=2.5 Hz), 10.64(1H, s), 11.25(1H, s).

Example 135

Preparation of the Compound of Compound No. 135

Using 5-methylsalicylic acid and 4-methyl-3-(trifluoromethyl)aniline as the raw materials, the same operation as the Example 16 gave the title compound.

Yield: 63.7%. $^1$H-NMR(DMSO-d$_6$): δ 2.29(3H, s), 2.42 (3H, s), 6.89(1H, d, J=8.4 Hz), 7.26(1H, ddd, J=8.4, 2.1, 0.6 Hz), 7.44(1H, d, J=8.1 Hz), 7.75(1H, d, J=2.1 Hz), 7.86(1H, dd, J=8.4, 1.8 Hz), 8.13(1H.d, J=2.1 Hz), 10.50(1H, s), 11.42 (1H, s).

Example 136

Preparation of the Compound of Compound No. 136

Using 5-methylsalicylic acid and 2-methyl-5-(trifluoromethyl)aniline as the raw materials, the same operation as the Example 16 gave the title compound.

Yield: 14.2%, white solid. $^1$H-NMR(DMSO-d$_6$): δ 2.29 (3H, s), 2.38(3H, s), 6.94(1H, d, J=8.4 Hz), 7.27(1H, ddd, J=8.4, 2.4, 0.6 Hz), 7.44(1H, dd, J=8.1, 1.5 Hz), 7.52(1H, d, J=7.8 Hz), 7.84(1H, d, J=2.4 Hz), 8.46(1H, d, J=1.5 Hz), 10.55(1H, s), 11.72(1H, s).

Example 137

Preparation of the Compound of Compound No. 137

Using 5-methylsalicylic acid and 4-methoxy-3-(trifluoromethyl)aniline as the raw materials, the same operation as the Example 16 gave the title compound.

Yield: 65.1%, slightly yellow solid. $^1$H-NMR(DMSO-d$_6$): δ 2.35(3H, s), 3.89(3H, s), 6.88(1H, d, J=8.4 Hz), 7.26(1H, dd, J=8.1, 1.8 Hz), 7.30(1H, d, J=8.4 Hz), 7.77(1H, d, J=2.1 Hz), 7.92(1H, dd, J=9.0, 2.7 Hz), 8.04(1H, d, J=2.7 Hz), 10.42(1H, s), 11.54(1H, s).

Example 138

Preparation of the Compound of Compound No. 138

Using 5-methylsalicylic acid and 2-methoxy-5-(trifluoromethyl)aniline as the raw materials, the same operation as the Example 16 gave the title compound.

Yield: 77.9%. $^1$H-NMR(CDCl$_3$): δ 2.35(3H, s), 4.02(3H, s), 6.93(1H, d, J=9.0 Hz), 6.98(1H, d, J=8.4 Hz), 7.25-7.28 (2H, m), 7.36(1H, ddd, J=8.4, 2.1, 0.9 Hz), 8.65(1H, br s), 8.73(1H, d, J=2.1 Hz), 11.69(1H, s).

Example 139

Preparation of the Compound of Compound No. 139

Using 5-bromosalicylic acid and aniline as the raw materials, the same operation as the Example 16 gave the title compound.

Yield: 68.8%. mp 229-230° C. $^1$H-NMR(DMSO-d$_6$): δ 6.96(1H, d, J=9.0 Hz), 7.12-7.18(1H, m), 7.35-1.41(2H, m), 7.58(1H, dd, J=8,7, 2.7 Hz), 7.67-7.71(2H, m), 8.08(1H, d, J=2.7 Hz), 10.43(1H, s), 11.87(1H, s).

Example 140

Preparation of the Compound of Compound No. 140

Using 5-bromosalicylic acid and 3-chloroaniline as the raw materials, the same operation as the Example 16 gave the title compound.

Yield: 63.1%. mp 231-232° C. $^1$H-NMR(DMSO-d$_6$): δ 6.97(1H, d, J=8.7 Hz), 7.19-7.22(1H, m), 7.38-7.43(1H, m), 7.57-7.63(2H, m), 7.91-7.92(1H, m), 8.01(1H, d, J=2.7 Hz), 10.49(1H, s), 11.64(1H, s).

Example 141

The Compound of Compound No. 141

This compound is a commercially available compound.
Supplier: Tokyo Kasei.
Catalog code number: B0897.

Example 142

Preparation of the Compound of Compound No. 142

Using 5-chlorosalicylic acid and 2,5-dichloroaniline as the raw materials, the same operation as the Example 16 gave the title compound.

Yield: 10.8%. $^1$H-NMR(DMSO-d$_6$): δ 7.08(1H, d, J=9.0 Hz), 7.24-7.28(1H, m), 7.50-7.54(1H, m), 7.61(1H, dd, J=9.0, 3.0 Hz), 7.97(1H, d, J=2.7 Hz), 8.58(1H, d, J=2.4 Hz), 11.02(1H, s), 12.35(1H, brs).

Example 143

Preparation of the Compound of Compound No. 143

Using 5-bromosalicylic acid and 3,4-dichloroaniline as the raw materials, the same operation as the Example 16 gave the title compound.

Yield: 58.2%. mp 249-251° C. $^1$H-NMR(DMSO-d$_6$): δ 6.97(1H, d, J=8.7 Hz), 7.57-7.70(3H, m), 7.98(1H, d, J=2.7 Hz), 8.10(1H, d, J=2.4 Hz), 10.54(1H, s), 11.55(1H, s).

Example 144

Preparation of the Compound of Compound No. 144

Using 5-bromosalicylic acid and 3,5-difluoroaniline as the raw materials, the same operation as the Example 16 gave the title compound.

Yield: 36.3%. mp 259-261° C. $^1$H-NMR(DMSO-d$_6$): δ 6.96-7.04(2H, m), 7.45-7.54(2H, m), 7.58(1H, dd, J=8.7, 2.7 Hz), 7.94(1H, d, J=2.7 Hz), 10.60(1H, s) 11.48(1H, s).

Example 145

Preparation of the Compound of Compound No. 172

Using O-acetylsalicyloyl chloride and 3,5-dichloroaniline as the raw materials, the same operation as the Example 2(1) gave the title compound.

Yield: 73.5%. mp 167-168° C. $^1$H-NMR(CDCl$_3$): δ 2.35 (3H, s), 7.14-7.18(2H, m), 7.35-7.40(1H, m), 7.52-7.57(3H, m), 7.81(1H, dd, J=7.8, 1.8 Hz), 8.05(1H, brs).

Example 146

Preparation of the Compound of Compound No. 145

Using 2-acetoxy-N-(3,5-dichlorophenyl)benzamide (Compound No. 172) as the raw material, the same operation as the Example 2(2) gave the title compound.

Yield: 60.3%. mp 218-219° C. $^1$H-NMR(DMSO-d$_6$): δ 6.95-7.02(2H, m), 7.35-7.36(1H, m), 7.42-7.47(1H, m), 7.83-7.87(3H, m), 10.54(1H, s), 11.35(1H, s).

Example 147

Preparation of the Compound of Compound No. 146

Using 5-fluorosalicylic acid and 3,5-dichloroaniline as the raw materials, the same operation as the Example 16 gave the title compound.

Yield: 33.3%. mp 258-260° C. $^1$H-NMR(DMSO-d$_6$): δ 7.00-7.05(1H, m), 7.28-7.37(2H, m), 7.63(1H, dd, J=9.3, 3.3 Hz), 7.84(2H, d, J=2.1 Hz), 10.56(1H, s), 11.23(1H, s).

Example 148

Preparation of the Compound of Compound No. 147

Using 5-chlorosalicylic acid and 3,5-dichloroaniline as the raw materials, the same operation as the Example 16 gave the title compound.

Yield: 41.2%. $^1$H-NMR(DMSO-d$_6$): δ 7.03(1H, d, J=9.0 Hz), 7.36-7.37(1H, m), 7.48(1H, dd, J=8.7, 2.7 Hz), 7.83-7.84(3H, m), 10.56(1H, s), 11.44(1H, s).

Example 149

Preparation of the Compound of Compound No. 148

Using 5-bromosalicylic acid and 3,5-dichloroaniline as the raw materials, the same operation as the Example 16 gave the title compound.

Yield: 61.6%. mp 243-244° C. $^1$H-NMR(DMSO-d$_6$): δ 6.98(1H, d, J=8.7 Hz), 7.36-7.37(1H, m), 7.59(1H, dd, J=9.0, 2.4 Hz), 7.83(2H, d, J=1.8 Hz), 7.95(1H, d, J=2.4 Hz), 10.56 (1H, s), 11.46(1H, s).

Example 150

Preparation of the Compound of Compound No. 149

Using 5-iodosalicylic acid and 3,5-dichloroaniline as the raw materials, the same operation as the Example 16 gave the title compound.

Yield: 65.4%. mp 244-245° C. $^1$H-NMR(DMSO-d$_6$): δ 6.84(1H, d, J=9.0 Hz), 7.35-7.37(1H, m), 7.72(1H, dd, J=9.0, 2.1 Hz), 7.83(2H, d, J=1.8 Hz), 8.09(1H, d, J=2.1 Hz), 10.55 (1H, s), 11.45(1H, s).

Example 151

Preparation of the Compound of Compound No. 150

Using 3,5-dibromosalicylic acid and 3,5-dichloroaniline as the raw materials, the same operation as the Example 16 gave the title compound.

Yield: 44.2%. mp 181-182° C. $^1$H-NMR(DMSO-d$_6$): δ 7.42-7.43(1H, m), 7.80(2H, d, J=1.8 Hz), 8.03(1H, d, J=2.1 Hz), 8.17(1H, d, J=2.1 Hz), 10.82(1H, s).

Example 152

Preparation of the Compound of Compound No. 151

Using 4-chlorosalicylic acid and 3,5-dichloroaniline as the raw materials, the same operation as the Example 16 gave the title compound.
Yield: 57.2%. mp 255-256° C. $^1$H-NMR(DMSO-d$_6$): δ 7.03-7.06(2H, m), 7.34-7.36(1H, m), 7.82-7.85(3H,m), 10.51 (1H, s), 11.70(1H, brs).

Example 153

Preparation of the Compound of Compound No. 152

Using 5-nitrosalicylic acid and 3,5-dichloroaniline as the raw materials, the same operation as the Example 16 gave the title compound.
Yield: 83.1%. mp 232-233° C. $^1$H-NMR(DMSO-d$_6$): δ 7.16(1H, d, J=9.6 Hz), 7.37-7.39(1H, m), 7.84(1H, d, J=2.1 Hz), 8.29(1H, dd, J=9.0, 3.0 Hz), 8.65(1H, d, J=3.0 Hz), 10.83(1H, s).

Example 154

Preparation of the Compound of Compound No. 153

Using 5-methylsalicylic acid and 3,5-dichloroaniline as the raw materials, the same operation as the Example 16 gave the title compound.
Yield: 71.0%. mp 216-217° C. $^1$H-NMR(DMSO-d$_6$): δ 2.28(3H, s), 6.90(1H, d, J=8.4 Hz), 7.26(1H, dd, J=8.7, 1.8 Hz), 7.34-7.36(1H, m), 7.67(1H, d, J=1.5 Hz), 7.85(2H, d, J=1.8 Hz), 10.52(1H, s), 11.15(1H, s).

Example 155

Preparation of the Compound of Compound No. 154

Using 5-methoxysalicylic acid and 3,5-dichloroaniline as the raw materials, the same operation as the Example 16 gave the title compound.
Yield: 29.8%. mp 230-232° C. $^1$H-NMR(DMSO-d$_6$): δ 3.76(3H, s), 6.95(1H, d, J=8.7 Hz), 7.08(1H, dd, J=9.0, 3.0 Hz), 7.35-7.36(1H, m), 7.40(1H, d, J=3.0 Hz), 7.85(2H, d, J=1.5 Hz), 10.55(1H, s), 10.95(1H, s).

Example 156

Preparation of the Compound of Compound No. 155

Using 5-bromosalicylic acid and 3,4,5-trichloroaniline as the raw materials, the same operation as the Example 16 gave the title compound.
Yield: 78.6%. mp 297-299° C. $^1$H-NMR(DMSO-d$_6$): δ 6.98(1H, d, J=9.0 Hz), 7.58(1H, dd, J=8.4, 2.4 Hz), 7.95(1H, d, J=2.4 Hz), 8.63(1H, s), 10.58(1H, s), 11.49(1H, s).

Example 157

Preparation of the Compound of Compound No. 156

Using 5-bromosalicylic acid and 3,5-dichloro-4-hydroxyaniline as the raw materials, the same operation as the Example 16 gave the title compound.
Yield: 22.5%. $^1$H-NMR(DMSO-d$_6$): δ 6.96(1H, d, J=8.7 Hz), 7.58(1H, dd, J=8.7, 2.4 Hz), 7.76(2H, s), 8.01(1H, d, J=2.4 Hz), 10.03(1H, s), 10.36(1H, s), 11.67(1H, brs).

Example 158

Preparation of the Compound of Compound No. 157

Using 5-chlorosalicylic acid and 2,3,4,5,6-pentafluoroaniline as the raw materials, the same operation as the Example 16 gave the title compound.
Yield: 58.6%. $^1$H-NMR(DMSO-d$_6$): δ 7.07(1H d, J=8.7 Hz), 7.53(1H, dd, J=8.7, 2.7 Hz), 7.91(1H, d, J=2.7 Hz), 10.38(1H, brs), 11.74(1H, brs).

Example 159

Preparation of the Compound of Compound No. 158

Using 5-bromosalicylic acid and 3,5-dinitroaniline as the raw materials, the same operation as the Example 16 gave the title compound.
Yield: 32.2%. mp 258-260° C. $^1$H-NMR(DMSO-d$_6$): δ 6.98-7.02(1H, m), 7.59-7.63(1H, m), 7.96-7.97(1H, m), 8.56-8.58(1H, m), 9.03-9.05(2H, m), 11.04(1H, s), 11.39(1H, brs).

Example 160

Preparation of the Compound of Compound No. 159

Using 5-chlorosalicylic acid and 2,5-bis[(1,1-dimethyl) ethyl]aniline as the raw materials, the same operation as the Example 16 gave the title compound.
Yield: 75.7%. $^1$H-NMR(DMSO-d$_6$): δ 1.27(9H, s), 1.33 (9H, s), 7.04(1H, d, J=9.0 Hz), 7.26(1H, dd, J=8.4, 2.1 Hz), 7.35-7.38(2H, m), 7.49(1H, dd, J=8.7, 2.7 Hz), 8.07(1H, d, J=2.4 Hz), 10.22(1H, s), 12.38(1H, br s).

Example 161

Preparation of the Compound of Compound No. 160

Using 5-chlorosalicylic acid and 5-[(1,1-dimethyl)ethyl]-2-methoxyaniline as the raw materials, the same operation as the Example 16 gave the title compound.
Yield: 89.5%. $^1$H-NMR(DMSO-d$_6$): δ 1.28(9H, s), 3.33 (3H, s), 7.01(1H, d, J=8.7 Hz), 7.05(1H, d, J=9.0 Hz), 7.11 (1H, dd, J=8.7, 2.4 Hz), 7.47(1H, dd, J=9.0, 3.0 Hz), 7.99(1H, d, J=3.0 Hz), 8.49(1H, d, J=2.4 Hz), 10.78(1H, s), 12.03(1H, s).

Example 162

Preparation of the Compound of Compound No. 161

Using 5-bromosalicylic acid and 3,5-dimethylaniline as the raw materials, the same operation as the Example 16 gave the title compound.
Yield: 58.1%. mp 188-190° C. $^1$H-NMR(DMSO-d$_6$): δ 2.28(6H, s), 6.80(1H, s), 6.96(1H, d, J=8.7 Hz), 7.33(2H, s), 7.58(1H, dd, J=9.0, 2.4 Hz), 8.10(1H, d, J=2.4 Hz), 10.29(1H, s), 11.93(1H, brs).

Example 163

Preparation of the Compound of Compound No. 162

Using 5-chlorosalicylic acid and 3,5-bis[(1,1-dimethyl) ethyl]aniline as the raw materials, the same operation as the Example 16 gave the title compound.

Yield: 34.1%. $^1$H-NMR(CDCl$_3$): δ 1.26(18H, s), 6.99(1H, d, J=8.7 Hz), 7.29(1H, t, J=1.8 Hz), 7.39(1, dd, J=9.0, 2.4 Hz), 7.41(2H, d, J=1.5 Hz), 7.51(1H, d, J=2.1 Hz), 7.81(1H, br s), 12.01(1H, s).

Example 164

Preparation of the Compound of Compound No. 163

Using 5-bromosalicylic acid and 3,5-bis[(1,1-dimethyl) ethyl]aniline as the raw materials, the same operation as the Example 16 gave the title compound.

Yield: 45.2%. $^1$H-NMR(DMSO-d$_6$): δ 1.30(18H, s), 6.95 (1H, d, J=8.7 Hz), 7.20(1H, t, J=1.5 Hz), 7.56(2H, d, J=1.5 Hz), 7.58(1H, dd, J=8.7, 2.4 Hz), 8.12(1H, d, J=2.7 Hz), 10.39(1H, s), 11.98(1H, s).

Example 165

Preparation of the Compound of Compound No. 164

Using 5-chlorosalicylic acid and 2-amino-3,5,5,8,8-pentamethyl-5,6,7,8-tetrahydronaphthalene as the raw materials, the same operation as the Example 16 gave the title compound.

Yield: 77.5%. $^1$H-NMR(DMSO-d$_6$): δ 1.23(6H, s), 1.24 (6H, s), 1.64(4H, s), 2.19(3H, s), 7.13(1H, d, J=9.0 Hz), 7.20(1H, s), 7.49(1H, dd, J=8.7, 2.7 Hz), 7.67(1H, s), 8.04 (1H, d, J=2.7 Hz), 10.23(1H, s), 12.26(1H, s).

Example 166

Preparation of the Compound of Compound No. 165

Using 5-chlorosalicylic acid and 3-aminobiphenyl as the raw materials, the same operation as the Example 16 gave the title compound.

Yield: 75.6%. $^1$H-NMR(DMSO-d$_6$): δ 7.04(1H, d, J=8.7 Hz), 7.35-7.44(1H, m), 7.45-7.54(5H, m), 7.65-7.68(2H, m), 7.72(1H, dt, J=7.2, 2.1 Hz), 7.99(1H, d, J=3.0 Hz), 8.03(1H, m), 10.50(1H, s), 11.83(1H, brs).

Example 167

Preparation of the Compound of Compound No. 166

Using 5-chlorosalicylic acid and 3-amino-4-methoxybiphenyl as the raw materials, the same operation as the Example 16 gave the title compound.

Yield: 37.0%. $^1$H-NMR(DMSO-d$_6$): δ 3.95(3H, s), 7.08 (1H, d, J=8.7 Hz), 7.20(1H, d, J=8.4 Hz), 7.34(1H, t, J=7.2 Hz), 7.40-7.50(4H, m), 7.62(1H, d, J=8.7 Hz), 8.00(1H, d, J=3.0 Hz), 8.77(1H, d, J=2.1 Hz), 10.92(1H, s), 12.09(1H, s).

Example 168

Preparation of the Compound of Compound No. 167

Using 5-bromosalicylic acid and 2,5-dimethoxyaniline as the raw materials, the same operation as the Example 16 gave the title compound.

Yield: 39.7%. $^1$H-NMR(DMSO-d$_6$): δ 3.72(3H, s), 3.84 (3H, s), 6.66(1H, ddd, J=9.0, 3.0, 0.6 Hz), 6.99-7.03(2H, m), 7.58(1H, ddd, J=9.0, 2.7, 0.6 Hz), 8.10(1H, dd, J=2.4, 0.6 Hz), 8.12(1H, d, J=3.0 Hz), 10.87(1H, s), 12.08(1H, s).

Example 169

Preparation of the Compound of Compound No. 168

Using 5-bromosalicylic acid and 3,5-dimethoxyaniline as the raw materials, the same operation as the Example 16 gave the title compound.

Yield: 40.3%. mp 207-209° C. $^1$H-NMR(DMSO-d$_6$): δ 3.75(6H, s), 6.30-6.32(1H, m), 6.94-6.97(3H, m), 7.57(1H, dd, J=8.7, 2.4 Hz), 8.04(1H, d, J=2.4 Hz), 10.32(1H, s), 11.78(1H, s).

Example 170

Preparation of the Compound of Compound No. 169

Using 5-chlorosalicylic acid and 3-acetylaniline as the raw materials, the same operation as the Example 16 gave the title compound.

Yield: 80.0%. $^1$H-NMR(DMSO-d$_6$): δ 2.60(3H, s), 7.03 (1H, d, J=9.0 Hz), 7.49(1H, dd, J=9.0, 3.0 Hz), 7.54(1H, t, J=8.1 Hz), 7.76(1H, dq, J=7.8, 0.9 Hz), 7.96-8.00(2H, m), 8.30(1H, t, J=1.8 Hz), 10.56(1H, s), 11.75(1H, s).

Example 171

Preparation of the Compound of Compound No. 170

Using 5-bromosalicylic acid and 5-aminoisophthalic acid dimethyl ester as the raw materials, the same operation as the Example 16 gave the title compound.

Yield: 74.1%. mp 254-256° C. $^1$H-NMR(DMSO-d$_6$): δ 3.92(6H, s), 6.97(1H, d, J=9.0 Hz), 7.60(1H, dd, J=9.0, 2.4 Hz), 8.06(1H, d, J=2.4 Hz), 8.24-8.25(1H, m), 8.62(2H, m), 10.71(1H, s), 11.57(1H, s).

Example 172

The Compound of Compound No. 171

This compound is a commercially available compound.
Supplier: Maybridge.
Catalog code number: RDR 01434

Example 173

Preparation of the Compound of Compound No. 173

Using 5-methylsalicylic acid and 2,5-bis[(1,1-dimethyl) ethyl]aniline as the raw materials, the same operation as the Example 16 gave the title compound.

Yield: 61.1%. $^1$H-NMR(DMSO-d$_6$): δ 1.27(9H, s), 1.33 (9H, s), 2.28(3H, s), 6.89(1H, d, J=8.1 Hz), 7.24(1H, d, J=2.1 Hz), 7.27(1H, d, J=2.1 Hz), 7.32(1H, d, J=2.4 Hz), 7.37(1H, d, J=8.4 Hz), 7.88(1H, d, J=1.5 Hz), 10.15(1H, s), 11.98(1H, br s).

Example 174

Preparation of the Compound of Compound No. 174

Using N-{3,5-bis[(1,1-dimethyl)ethyl]phenyl}-5-chloro-2-hydroxybenzamide (Compound No. 162) and acetyl chloride as the raw materials, the same operation as the Example 96 gave the title compound.

Yield: 66.1%. $^1$H-NMR(CDCl$_3$): δ 1.34(18H, s), 2.36(3H, s), 7.12(1H, d, J=8.4 Hz), 7.25(1H, d, J=1.5 Hz), 7.44(2H, d, J=1.2 Hz), 7.47(1H, dd, J=8.7, 2.7 Hz), 7.87(1H, d, J=2.4 Hz), 7.98(1H, s).

Example 175

Preparation of the Compound of Compound No. 175

Using 5-nitrosalicylic acid and 3,5-bis[(1,1-dimethyl)ethyl]aniline as the raw materials, the same operation as the Example 16 gave the title compound.

Yield: 46.7%. $^1$H-NMR(CDCl$_3$): δ 1.37(18H, s), 7.13(1H, d, J=9.3 Hz), 7.32(1H, t, J=1.8 Hz), 7.46(2H, d, J=1.8 Hz), 8.07(1H, s), 8.33(1H, dd, J=9.3, 2.1 Hz), 8.59(1H, d, J=2.4 Hz), 13.14(1H, s).

Example 176

Preparation of the Compound of Compound No. 176

Using 5-methylsalicylic acid and 3,5-bis[(1,1-dimethyl)ethyl]aniline as the raw materials, the same operation as the Example 16 gave the title compound.

Yield: 16.3%. $^1$H-NMR(CDCl$_3$): δ 1.35(18H, s), 2.35(3H, s), 6.94(1H, d, H=8.4 Hz), 7.23-7.28(2H, m), 7.31(1H, s), 7.42(1H, d, J=1.8 Hz), 7.88(1H, s), 11.86(1H, s).

Example 177

Preparation of the Compound of Compound No. 177

Using 5-methoxysalicylic acid and 3,5-bis[(1,1-dimethyl)ethyl]aniline as the raw materials, the same operation as the Example 16 gave the title compound.

Yield: 12.7%. $^1$H-NMR(DMSO-d$_6$): δ 1.30(18H, s), 3.77(3H, s), 6.91(1H, d, J=9.0 Hz), 7.07(1H, dd, J=8.7, 3.0 Hz), 7.19-7.20(1H, m), 7.52-7.54(3H, m), 10.33(1H, s), 11.44(1H, s).

Example 178

Preparation of the Compound of Compound No. 178

Using 5-chloro-N-{5-[(1,1-dimethyl)ethyl]-2-methoxyphenyl}-2-hydroxybenzamide (Compound No. 160) and acetyl chloride as the raw materials, the same operation as the Example 96 gave the title compound.

Yield: 87.5%. $^1$H-NMR(CDCl$_3$): δ 1.35(9H, s), 2.37(3H, s), 3.91(3H, s), 6.86(1H, d, J=8.7 Hz), 7.12(1H, dd, J=8.7, 2.4 Hz), 7.13(1H, d, J=9.0 Hz), 7.47(1H, dd, J=9.0, 2.4 Hz), 8.02(1H, d, J=2.7 Hz), 8.66(1H, d, J=2.4 Hz), 8.93(1H, s).

Example 179

Preparation of the Compound of Compound No. 179

Using 5-methylsalicylic acid and 5-[(1,1-dimethyl)ethyl]-2-methoxyaniline as the raw materials, the same operation as the Example 16 gave the title compound.

Yield: 84.7%. $^1$H-NMR(CDCl$_3$): δ 1.35(9H, s), 2.34(3H, s), 3.93(3H, s), 6.86(1H, d, J=8.7 Hz), 6.93(1H, d, J=8.4 Hz), 7.12(1H, dd, J=8.7, 2.4 Hz), 7.24(1H, dd, J=8.4, 1.8 Hz), 7.27(1H, br s), 8.48(1H, d, J=2.4 Hz), 8.61(1H, brs), 11.95(1H, s).

Example 180

Preparation of the Compound of Compound No. 179

Using 5-bromosalicylic acid and 2-aminothiazole as the raw materials, the same operation as the Example 16 gave the title compound.

Yield: 12.0%. mp 212° C. (dec.). $^1$H-NMR(DMSO-d$_6$): δ 6.94(1H, brd, J=8.0 Hz), 7.25(1H, brd, J=3.2 Hz), 7.56(2H, m), 8.05(1H, d, J=2.8 Hz).

Example 181

Preparation of the Compound of Compound No. 186

(1) 2-Amino-4-[(1,1-dimethyl)ethyl]thiazole

A mixture of 1-bromo-3,3-dimethyl-2-butanone (5.03 g, 28.1 mmol), thiourea (2.35 g, 30.9 mmol) and ethanol (30 mL) was refluxed for 1.5 hours. After cooling, the reaction mixture was poured into saturated aqueous sodium hydrogen carbonate and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1→1:1) to give the title compound (3.99 g, 90.9%) as an yellowish white powder.

$^1$H-NMR(CDCl$_3$): δ 1.26(9H, s), 4.96(2H, brs), 6.09(1H, s).

When the method described in Example 181(1) is referred in the following examples, solvents such as ethanol or the like were used as the reaction solvent.

(2) 2-Acetoxy-5-bromo-N-{4-[(1,1-dimethyl)ethyl]thiazol-2-yl}benzamide

Using 2-acetoxy-5-bromobenzoic acid and 2-amino-4-[(1,1-dimethyl)ethyl]thiazole as the raw materials, the same operation as the Example 24 gave the title compound.

Yield: 59.4%. $^1$H-NMR(CDCl$_3$): δ 1.31(9H, s), 2.44(3H, s), 6.60(1H, s), 7.13(1H, d, J=8.4 Hz), 7.68(1H, dd, J=8.7, 2.4 Hz), 8.17(1H, d, J=2.4 Hz), 9.72(1H, brs).

(3) 5-Bromo-N-{4-[(1,1-dimethyl)ethyl]thiazol-2-yl}-2-hydroxybenzamide (Compound No. 186)

2-Acetoxy-5-bromo-N-{4-[(1,1-dimethyl)ethyl]thiazol-2-yl}benzamide (100.1 mg, 0.25 mmol) was dissolved in tetrahydrofuran (3 mL). 2N Sodium hydroxide (0.2 ml) was added, and the mixture was stirred at room temperature for 20 minutes. The reaction mixture was poured into diluted hydrochloric acid and extracted with ethyl acetate. After the organic layer was washed with brine, dried over anhydrous sodium sulfate, the residue obtained by evaporation under reduced pressure was crystallized (isopropyl ether/n-hexane) to give the title compound (70.1 mg, 78.9%) as a white powder.

$^1$H-NMR(DMSO-d$_6$): δ 1.30(9H, s), 6.80(1H, brs), 6.95(1H, brs), 7.57(1H, brs), 8.06(1H, d, J=2.4 Hz), 11.82(1H, brs), 13.27(1H, brs).

Example 182

Preparation of the Compound of Compound No. 181

(1) 2-Acetoxy-5-bromo-N-(5-bromo-4-[(1,1-dimethyl)ethyl]thiazol-2-yl)benzamide

2-Acetoxy-5-bromo-N-{4-[(1,1-dimethyl)ethyl]thiazol-2-yl}benzamide (compound of Example 181(2); 0.20 g, 0.50 mmol) was dissolved in acetonitrile (10 mL). N-Bromosuccinimide (97.9 mg, 0.55 mmol) was added, and the mixture was stirred at room temperature for 1 hour. The reaction mixture was concentrated under reduced pressure, and the obtained residue was purified by chromatography on silica gel (n-hexane:ethyl acetate=3:1) to give the title compound as a crude product.

(2) 5-Bromo-N-{5-bromo-4-[(1,1-dimethyl)ethyl]thiazol-2-yl}-2-hydroxybenzamide (Compound No. 181)

Using 2-acetoxy-5-bromo-N-{5-bromo-4-[(1,1-dimethyl)ethyl]thiazol-2-yl}benzamide as the raw material, the same operation as the Example 2(2) gave the title compound.

Yield: 90.9% (2 steps). $^1$H-NMR(DMSO-$d_6$): δ 1.42(9H, s), 6.99(1H, d, J=8.7 Hz), 7.61(1H, dd, J=8.7, 2.7 Hz), 8.02 (1H, d, J=2.4 Hz), 11.79(1H, brs), 12.00(1H, brs).

Example 183

Preparation of the Compound of Compound No. 182

Using 5-bromosalicylic acid and 2-amino-5-bromo-4-(trifluoromethyl)thiazole as the raw materials, the same operation as the Example 16 gave the title compound.

Yield: 22.4%. mp 215° C. (dec.). $^1$H-NMR(DMSO-$d_6$): δ 7.00(1H, d, J=8.8 Hz), 7.61(1H, dd, J=8.8, 2.8 Hz), 7.97(1H, d, J=2.4 Hz). [2-Amino-5-bromo-4-(trifluoromethyl)thiazole: Refer to "Journal of Heterocyclic Chemistry", (USA), 1991, Vol. 28, p. 1017.]

Example 184

Preparation of the Compound of Compound No. 183

(1) α-Bromo-pivaloylacetonitrile

Pivaloylacetonitrile (1.00 g, 7.99 mmol) was dissolved in carbon tetrachloride (15 mL). N-Bromosuccinimide (1.42 g, 7.99 mmol) was added, and the mixture was refluxed for 15 minutes. After cooling, the insoluble matter was filtered off, and the residue obtained by evaporation of the filtrate under reduced pressure was purified by chromatography on silica gel (n-hexane:ethyl acetate=4:1) to give the title compound (1.43 g, 87.9%) as an yellowish brown oil.

$^1$H-NMR(CDCl$_3$): δ 1.33(9H, s), 5.10(1H, s).

When the method described in Example 184(1) is referred in the following examples, N-bromosuccinimide was used as the brominating agent. As the reaction solvent, solvents such as carbon tetrachloride or the like were used.

(2) 2-Amino-5-cyano-4-[(1,1-dimethyl)ethyl]thiazole

Using α-bromo-pivaloylacetonitrile and thiourea as the raw materials, the same operation as the Example 181(1) gave the title compound.

Yield: 66.3%. $^1$H-NMR(CDCl$_3$): δ 1.41(9H, s), 5.32(2H, s).

(3) 5-Chloro-N-{5-cyano-4-[(1,1-dimethyl)ethyl]thiazol-2-yl}-2-hydroxybenzamide (Compound No. 183)

Using 5-chlorosalicylic acid and 2-amino-5-cyano-4-[(1,1-dimethyl)-ethyl]thiazole as the raw materials, the same operation as the Example 16 gave the title compound.

Yield: 63.4%. $^1$H-NMR(DMSO-$d_6$): δ 1.43(9H, s), 7.06 (1H, d, J=8.7 Hz), 7.51(1H, dd, J=8.7, 3.0 Hz), 7.85(1H, d, J=2.7 Hz), 12.31(2H, br).

Example 185

Preparation of the Compound of Compound No. 184

Using 5-bromosalicylic acid and 2-amino-5-cyano-4-[(1,1-dimethyl)-ethyl]thiazole (compound of Example 184(2)) as the raw materials, the same operation as the Example 16 gave the title compound.

Yield: 61.3%. $^1$H-NMR(DMSO-$d_6$): δ 1.43(9H, s), 7.00 (1H, d, J=8.7 Hz), 7.62(1H, dd, J=8.7, 2.7 Hz), 7.97(1H, d, J=2.7 Hz), 11.75(1H, br), 12.43(1H, br).

Example 186

Preparation of the Compound of Compound No. 185

Using 5-bromosalicylic acid and 2-amino-5-methylthiazole as the raw materials, the same operation as the Example 16 gave the title compound.

Yield: 12.9%. $^1$H-NMR(DMSO-$d_6$): δ 2.33(3H, s), 6.91 (1H, d, J=7.6 Hz), 7.26(1H, s), 7.54(1H, d, J=9.6 Hz), 8.03 (1H, d, J=2.8 Hz).

Example 187

Preparation of the Compound of Compound No. 187

Using 5-bromosalicylic acid and 2-amino-4,5-dimethylthiazole as the raw materials, the same operation as the Example 16 gave the title compound.

Yield: 14.4%. $^1$H-NMR(DMSO-$d_6$): δ 2.18(3H, s), 2.22 (3H, s), 6.89(1H, d, J=8.8 Hz), 7.51(1H, d, J=6.8 Hz), 8.02 (1H, d, J=2.8 Hz), 13.23(1H, brs).

Example 188

Preparation of the Compound of Compound No. 188

Using 5-bromosalicylic acid and 2-amino-5-methyl-4-phenylthiazole as the raw materials, the same operation as the Example 16 gave the title compound.

Yield: 27.7%. mp 243-244° C. $^1$H-NMR(CD$_3$OD): δ 2.47 (3H, s), 6.92(1H, d, J=8.7 Hz), 7.36-7.41(1H, m), 7.44-7.50 (2H, m), 7.53(1H, dd, J=9.0, 2.7 Hz), 7.57-7.61(2H, m), 8.16(1H, d, J=2.7 Hz). [2-Amino-5-methyl-4-phenylthiazole: Refer to "Yakugaku Zasshi: Journal of The Pharmaceutical Society of Japan", 1961, Vol. 81, p. 1456.]

Example 189

Preparation of the Compound of Compound No. 189

Using (4-fluorophenyl)acetone as the raw material, the same operation as the Examples 184(1)-(3) gave the title compound.

Yield: 28.8% (3 steps).

(1) α-Bromo-(4-fluorophenyl)acetone

¹H-NMR(CDCl₃): δ 2.33(3H, s), 5.41(1H, s), 7.07(2H, t, J=8.7 Hz), 7.43(2H, dd, J=8.7, 5.1 Hz).

(2) 2-Amino-4-methyl-5-(4-fluorophenyl)thiazole

¹H-NMR(CDCl₃): δ 2.27(3H, s), 4.88(2H, s), 7.07(2H, t, J=8.7 Hz), 7.32(2H, dd, J=8.7, 5.4 Hz).

(3) 5-Bromo-N-[4-methyl-5-(4-fluorophenyl)thiazol-2-yl]-2-hydroxybenzamide (Compound No. 189)

¹H-NMR(DMSO-d₆): δ 2.36(3H, s), 6.95(1H, d, J=8.4 Hz), 7.33(2H, t, J=8.7 Hz), 7.52-7.59(3H, m), 8.06(1H, d, J=3.0 Hz), 12.01-13.65(2H, br).

Example 190

Preparation of the Compound of Compound No. 190

Using 3-(trifluoromethyl)phenylacetone as the raw material, the same operation as the Examples 184(1)-(3) gave the title compound.
Yield: 39.8% (3 steps).

(1) α-Bromo-3-(trifluoromethyl)phenylacetone

¹H-NMR(CDCl₃): δ 2.38(3H, s), 5.43(1H, s), 7.52(1H, t, J=7.8 Hz), 7.61-7.66(2H, m), 7.69-7.70(1H, m).

(2) 2-Amino-4-methyl-5-[3-(trifluoromethyl)phenyl]thiazole

¹H-NMR(CDCl₁): δ 2.32(3H, s), 4.95(2H, s), 7.46-7.56 (3H, m), 7.59-7.61(1H, m).

(3) 5-Bromo-N-{4-methyl-5-[3-(trifluoromethyl)phenyl}thiazol-2-yl]-2-hydroxy-benzamide (Compound No. 190)

¹H-NMR(DMSO-d₆): δ 2.40(3H, s), 6.97(1H, d, J=8.7 Hz), 7.59(1H, dd, J=8.7, 2.4 Hz), 7.71-7.84(4H, m), (2H, m), 8.06(1H, d, J=2.4 Hz), 12.09(1H, br), 12.91-13.63(1H, br).

Example 191

Preparation of the Compound of Compound No. 191

Using 2,2-dimethyl-3-hexanone as the raw material, the same operation as the Examples 184(1)-(3) gave the title compound.
Yield: 17.0% (3 steps).

(2) 2-Amino-4-[(1,1-dimethyl)ethyl]-5-ethylthiazole

¹H-NMR(CDCl₃): δ 1.21(3H, t, J=7.5 Hz), 1.32(9H, s), 2.79(2H, q, J=7.5 Hz), 4.63(2H, brs).

(3) 5-Bromo-N-{4-[(1,1-dimethyl)ethyl]-5-ethylthiazol-2-yl}-2-hydroxybenzamide (Compound No. 191)

¹H-NMR(CDCl₃): δ 1.32(3H, t, J=7.5 Hz), 1.41(9H, s), 2.88(2H, q, J=7.5 Hz), 6.84(1H, d, J=9.0 Hz), 7.44(1H, dd, J=8.7, 2.4 Hz), 8.05(1H, d, J=2.7 Hz), 11.46(1H, br).

Example 192

Preparation of the Compound of Compound No. 192

Using 5-bromosalicylic acid and 2-amino-4-ethyl-5-phenylthiazole as the raw materials, the same operation as the Example 16 gave the title compound.
Yield: 17.4%. mp 224-225° C. ¹H-NMR(DMSO-d₆): δ 1.24(3H, t, J=7.6 Hz), 2.70(2H, q, J=7.6 Hz), 6.95(1H, brd, J=7.6 Hz), 7.39-7.42(1H, m), 7.45-7.51(4H, m), 7.56(1H, brd, J=8.0 Hz), 8.06(1H, d, J=2.8 Hz), 11.98(1H, brs).

Example 193

Preparation of the Compound of Compound No. 193

Using benzyl isopropyl ketone as the raw material, the same operation as the Examples 184(1)-(3) gave the title compound.
Yield: 4.4% (3 steps).

(2) 2-Amino-4-isopropyl-5-phenylthiazole

¹H-NMR(CDCl₃): δ 1.23(6H, d, J=6.6 Hz), 3.05(1H, m), 4.94(2H, s), 7.28-7.41(5H, m).

(3) 5-Bromo-N-(4-isopropyl-5-phenylthiazol-2-yl)-2-hydroxybenzamide (Compound No. 193)

¹H-NMR(DMSO-d₆): δ 1.26(6H, d, J=6.0 Hz), 3.15(1H, m), 6.98(1H, brs), 7.43-7.53(5H, m), 7.59(1H, brs), 8.08(1H, d, J=2.7 Hz), 11.90(1H, brd), 13.33(1H, brd).

Example 194

Preparation of the Compound of Compound No. 194

Using 1-phenyl-2-hexanone as the raw material, the same operation as the Examples 184(1)-(3) gave the title compound.
Yield: 52.6% (3 steps).

(1) α-Bromo-1-phenyl-2-hexanone

¹H-NMR(CDCl₃): δ 0.85(3H, t, J=7.2 Hz), 1.19-1.32(2H, m), 1.50-1.60(2H, m), 2.59(2H, td, J=7.5, 3.9 Hz), 5.44(1H, s), 7.34-7.45(5H, m).

(2) 2-Amino-4-butyl-5-phenylthiazole

¹H-NMR(CDCl₃): δ 0.89(3H, t, J=7.5 Hz), 1.28-1.41(2H, m), 1.61-1.71(2H, m), 2.56-2.61(2H, m), 4.87(2H, s), 7.25-7.40(5H, m).

(3) 5-Bromo-N-(4-butyl-5-phenylthiazol-2-yl)-2-hydroxybenzamide (Compound No. 194)

¹H-NMR(DMSO-d₆): δ 0.85(3H, t, J=7.2 Hz), 1.23-1.35 (2H, m), 1.59-1.69(2H, m), 2.70(2H, t, J=7.2 Hz), 6.96(1H, d, J=6.9 Hz), 7.39-7.59(6H, m), 8.07(1H, d, J=2.4 Hz), 11.93 (1H, br), 13.18-13.59(1H, br).

Example 195

Preparation of the Compound of Compound No. 195

(1) 4-Bromo-2,2,6,6-tetramethyl-3,5-heptanedione [α-Bromo-dipivaloylmethane]

2,2,6,6-Tetramethyl-3,5-heptanedione (dipivaloylmethane; 1.00 g, 5.42 mmol) was dissolved in carbon tetrachloride (10 mL). N-Bromosuccinimide (965.8 mg, 5.42 mmol) was added, and the mixture was refluxed for 2 hours. After cooling, the insoluble matter was filtered off, and the filtrate was evaporated under reduced pressure to give the title compound (1.42 g, quant.) as a white crystal.

$^1$H-NMR(CDCl$_3$): δ 1.27(18H, s), 5.67(1H, s).

When the method described in Example 195(1) is referred in the following examples, N-bromosuccinimide was used as the brominating agent. As the reaction solvent, solvents such as carbon tetrachloride or the like were used.

(2) 2-Amino-4-[(1,1-dimethyl)ethyl]-5-[(2,2-dimethyl)propionyl]thiazole

A mixture of 4-bromo-2,2,6,6-tetramethyl-3,5-heptanedione(α-bromo-dipivaloylmethane; 1.42 g, 5.40 mmol), thiourea (451.8 mg, 5.94 mmol) and ethanol (15 mL) was refluxed for 2 hours. After cooling, the reaction mixture was poured into saturated aqueous sodium hydrogen carbonate and extracted with ethyl acetate. After the organic layer was washed with water and brine, dried over anhydrous sodium sulfate, the residue obtained by evaporation under reduced pressure was crystallized (dichloromethane/hexane) to give the title compound (1.23 g, 94.5%) as a white crystal.

$^1$H-NMR(CDCl$_3$): δ 1.26(9H, s), 1.29(9H, s), 5.03(2H, s).

(3) 5-Chloro-N-{4-[(1,1-dimethyl)ethyl]-5-[(2,2-dimethyl)propionyl]thiazol-2-yl}-2-hydroxybenzamide (Compound No. 195)

A mixture of 5-chlorosalicylic acid (143.6 mg, 0.83 mmol), 2-amino-4-[(1,1-dimethyl)ethyl]-5-[(2,2-dimethyl)propionyl]thiazole (200.0 mg, 0.83 mmol), phosphorus trichloride (40 μl, 0.46 mmol) and chlorobenzene (4 mL) was refluxed for 3 hours. The residue obtained by concentration of the reaction mixture under reduced pressure was purified by chromatography on silica gel (n-hexane:ethyl acetate=3:1) to give the title compound (159.1 mg, 48.4%) as a white powder.

$^1$H-NMR(CDCl$_3$): δ 1.33(9H, s), 1.35(9H, s), 6.99(1H, d, J=8.7 Hz), 7.43(1H, dd, J=9.0, 2.7 Hz), 7.70(1H, d, J=2.7 Hz), 10.52(2H, br).

When the method described in Example 195(3) is referred in the following examples, phosphorus trichloride was used as the acid halogenating agent. As the reaction solvent, solvents such as monochlorobenzene, toluene or the like were used.

Example 196

Preparation of the Compound of Compound No. 196

Using 5-bromosalicylic acid and 2-amino-4-[(1,1-dimethyl)ethyl]-5-[(2,2-dimethyl)propionyl]thiazole (compound of Example 195(2)) as the raw materials, the same operation as the Example 195(3) gave the title compound.

Yield: 23.8%. $^1$H-NMR(CDCl$_3$): δ 1.33(9H, s), 1.35(9H, s), 6.94(1H, d, J=8, 7 Hz), 7.55(1H, dd, J=8.7, 2.1 Hz), 7.85 (1H, d, J=2.1 Hz), 10.51(2H, br).

Example 197

Preparation of the Compound of Compound No. 197

Using pivaloylacetic acid ethyl ester as the raw material, the same operation as the Examples 195(1)-(3) gave the title compound.

Yield: 45.7% (3 steps).

(1) α-Bromo-pivaloylacetic acid ethyl ester $^1$H-NMR(CDCl$_3$): δ 1.28(9H, s), 1.29(3H, t, J=7.2 Hz), 4.26(2H, q, J=7.2 Hz), 5.24(1H, s).

(2) 2-Amino-4-[(1,1-dimethyl)ethyl]thiazole-5-carboxylic acid ethyl ester $^1$H-NMR(CDCl$_3$): δ 1.32(3H, t, J=7.2 Hz), 1.43(9H, s), 4.24(2H, q, J=7.2 Hz), 5.18(2H, s).

(3) 2-(5-Bromo-2-hydroxybenzoyl)amino-4-[(1,1-dimethyl)ethyl]thiazole-5-carboxylic acid ethyl ester (Compound No. 197)

$^1$H-NMR(DMSO-d$_6$): δ 1.30(3H, t, J=7.2 Hz), 1.44(9H, s), 4.27(2H, q, J=6.9 Hz), 7.00(1H, d, J=8.7 Hz), 7.63(1H, dd, J=8.7, 2.7 Hz), 8.02(1H, d, J=2.4 Hz), 11.80(1H, br), 12.12 (1H, br).

Example 198

Preparation of the Compound of Compound No. 198

(1) 2-Amino-5-bromo-4-[(1,1-dimethyl)ethyl]thiazole

2-Amino-4-[(1,1-dimethyl)ethyl]thiazole (compound of Example 181(1); 0.87 g, 5.6 mmol) was dissolved in carbon tetrachloride (9 mL). N-Bromosuccinimide (1.00 g, 5.6 mmol) was added, and the mixture was stirred at room temperature for 1 hour. Hexane was added to the reaction mixture. The insoluble matter was filtered off, and the residue obtained by evaporation of the filtrate under reduced pressure was purified by chromatography on silica gel (hexane:ethyl acetate=2:1) to give the title compound (1.23 g, 93.7%) as an yellowish gray powder.

$^1$H-NMR(CDCl$_3$): δ 1.39(9H, s), 4.81(2H, brs).

(2) 2-Amino-4-[(1,1-dimethyl)ethyl]-5-piperidinothiazole

A mixture of 2-amino-5-bromo-4-[(1,1-dimethyl)ethyl] thiazole (0.10 g, 0.42 mmol), piperidine (0.1 mL), potassium carbonate (0.20 g) and acetonitrile (4 mL) was refluxed for 3 hours. The reaction mixture was poured into water and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=2:1) to give the title compound (80.7 mg, 79.3%) as an yellow crystal.

$^1$H-NMR(CDCl$_3$): δ 1.32(9H, s), 1.64(4H, t, J=5.7 Hz), 1.71-1.77(2H, m), 2.35(2H, brs), 2.99(2H, brs), 4.68(2H, s).

When the preparation method described in Example 198 (2) is referred in the following examples, bases such as potassium carbonate or the like were used as the base. As the reaction solvent, solvents such as acetonitrile or the like were used.

(3) 2-Acetoxy-5-bromo-N-{4-[(1,1-dimethyl)ethyl]-5-piperidinothiazol-2-yl}benzamide Under argon atmosphere, phosphorus oxychloride (46 μl, 0.50 mmol) was added to a mixture of 2-acetoxy-5-bromobenzoic acid (90.3 mg, 0.35 mmol), 2-amino-4-[(1,1-dimethyl)ethyl]-5-piperidinothiazole (80.7 mg, 0.34 mmol), pyridine (0.1 mL) and tetrahydrofuran (3 mL), and the mixture was stirred at room temperature for 2 hours. The reaction mixture was poured into 2N hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=3:1) to give the title compound (84.3 mg) as a crude product.

When the preparation method described in Example 198 (3) is referred in the following examples, phosphorus oxychloride was used as the acid halogenating agent. As the reaction base, pyridine was used. As the reaction solvent, solvents such as dichloromethane, tetrahydrofuran or the like were used.

(4) 5-Bromo-N-{4-[(1,1-dimethyl)ethyl]-5-piperidinothiazol-2-yl}-2-hydroxybenzamide (Compound No. 198)

2-Acetoxy-5-bromo-N-{4-[(1,1-dimethyl)ethyl]-5-piperidinothiazol-2-yl}-benzamide (crude product, 84.3 mg) was dissolved in ethanol (3 mL). 2N Aqueous sodium hydroxide (0.1 mL) was added, and the mixture was stirred at room temperature for 1 hour. The reaction mixture was poured into 2N hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=4:1) to give the title compound (54.1 mg, 36.3%; 2 steps) as a white powder.

$^1$H-NMR(CDCl$_3$): δ 1.41(9H, s), 1.56(2H, brs), 1.67-1.74 (4H, m), 2.79(4H, brs), 6.85(1H, d, J=9.0 Hz), 7.45(1H, dd, J=9.0, 2.4 Hz), 8.06(1H, d, J=2.4 Hz), 11.70(2H, br).

When the preparation method described in Example 198 (4) is referred in the following examples, inorganic bases such as sodium hydroxide, potassium carbonate or the like were used as the base. As the reaction solvent, solvents such as water, methanol, ethanol, tetrahydrofuran or the like were used alone or as a mixture.

Example 199

Preparation of the Compound of Compound No. 199

Using 2-amino-5-bromo-4-[(1,1-dimethyl)ethyl]thiazole (compound of Example 198(1)) and morpholine as the raw materials, the same operation as the Examples 198(2)-(4) gave the title compound.
Yield: 17.1%.

(2) 2-Amino-4-[(1,1-dimethyl)ethyl]-5-morpholinothiazole $^1$H-NMR(CDCl$_3$): δ 1.33(9H, s), 2.76(4H, brs), 3.79(4H, brs), 4.66(2H, s).

(3) 2-Acetoxy-5-bromo-N-{4-[(1,1-dimethyl)ethyl]-5-morpholinothiazol-2-yl}benzamide The product was used for the next reaction as a crude product.

(4) 5-Bromo-N-{4-[(1,1-dimethyl)ethyl]-5-morpholinothiazol-2-yl}-2-hydroxybenzamide (Compound No. 199)

$^1$H-NMR(CDCl$_1$): δ 1.24(9H, s), 2.89(4H, dd, J=4.8, 4.2 Hz), 3.83(4H, dd, J=4.5, 4.2 Hz), 6.89(1H, d, J=9.0 Hz), 7.49(1H, dd, J=9.0, 2.4 Hz), 7.98(1H, d, J=2.1 Hz), 11.20(2H, br).

Example 200

Preparation of the Compound of Compound No. 200

Using 2-amino-5-bromo-4-[(1,1-dimethyl)ethyl]thiazole (compound of Example 198(1)) and 4-methylpiperazine as the raw materials, the same operation as the Examples 198 (2)-(4) gave the title compound.
Yield: 6.9%.

(2) 2-Amino-4-[(1,1-dimethyl)ethyl]-5-(4-methylpiperazin-1-yl)thiazole $^1$H-NMR(DMSO-d$_6$): δ 1.25(9H, s), 2.12(2H, brs), 2.19 (3H, s), 2.57(2H, brs), 2.72(4H, brs), 6.51(2H, s).

(3) 2-Acetoxy-N-{4-[(1,1-dimethyl)ethyl]-5-(4-methylpiperazin-1-yl)thiazol-2-yl}-benzamide The product was used for the next reaction as a crude product.

(4) 5-Bromo-N-{4-[(1,1-dimethyl)ethyl]-5-(4-methylpiperazin-1-yl)thiazol-2-yl}-2-hydroxybenzamide (Compound No. 200)

$^1$H-NMR(CD$_3$OD): δ 1.41(9H, s), 2.55(3H, s), 2.87(4H, brs), 3.03(4H, brs), 6.88(1H, d, J=8.7 Hz), 7.49(1H, dd, J=8.7, 2.7 Hz), 8.11(1H, d, J=2.7 Hz).

Example 201

Preparation of the Compound of Compound No. 201

Using 2-amino-5-bromo-4-[(1,1-dimethyl)ethyl]thiazole (compound of Example 198(1)) and 4-phenylpiperazine as the raw materials, the same operation as the Examples 198 (2)-(4) gave the title compound.
Yield: 6.9%.

(2) 2-Amino-4-[(1,1-dimethyl)ethyl]-5-(4-phenylpiperazin-1-yl)thiazole $^1$H-NMR(CDCl$_3$): δ 1.34(9H, s), 2.80(2H, brs), 3.03(4H, brs), 3.55(2H, brs), 4.69(2H, s), 6.88(1H, tt, J=7.2, 1.2 Hz), 6.95(2H, dd, J=9.0, 1.2 Hz), 7.28(2H, dd, J=8.7, 7.2 Hz).

(3) 2-Acetoxy-5-bromo-N-{4-[(1,1-dimethyl)ethyl]-5-(4-phenylpiperazin-1-yl)thiazol-2-yl}benzamide The product was used for the next reaction as a crude product.

(4) 5-Bromo-N-{4-[(1,1-dimethyl)ethyl]-5-(4-phenylpiperazin-1-yl)thiazol-2-yl}-2-hydroxybenzamide (Compound No. 201)

$^1$H-NMR(DMSO-d$_6$): δ 1.39(9H, s), 2.97(4H, s), 3.30(4H, s), 6.82(1H, t, J=7.5 Hz), 6.97(2H, brs), 6.99(2H, t, J=7.5 Hz), 7.58(1H, brs), 8.05(1H, d, J=2.4 Hz), 11.69(1H, brs), 11.82(1H, brs).

Example 202

Preparation of the Compound of Compound No. 202

Using 5-bromosalicylic acid and 2-amino-4-phenylthiazole as the raw materials, the same operation as the Example 195(3) gave the title compound.

Yield: 16.0%. mp 239° C. (dec.). $^1$H-NMR(DMSO-d$_6$): δ 7.02(1H, d, J=8.4 Hz), 7.34(1H, t, J=7.6 Hz), 7.44(2H, t, J=7.6 Hz), 7.62(1H, dd, J=8.4, 2.8 Hz), 7.67(1H, s), 7.92(2H, d, J=7.2 Hz), 8.08(111, d, J=2.8 Hz), 11.88(1H, brs), 12.05(1H, brs).

Example 203

Preparation of the Compound of Compound No. 203

(1) {2-[(5-Bromo-2-hydroxybenzoyl)amino]-4-phenylthiazol-5-yl}acetic acid methyl ester Using 5-bromosalicylic acid and 2-amino-4-phenylthiazole-5-acetic acid methyl ester as the raw materials, the same operation as the Example 195(3) gave the title compound.

Yield: 32.1%. mp 288.5-229.5° C. $^1$H-NMR(DMSO-d$_6$): δ 3.66(3H, s), 3.95(2H, s), 6.99(1H, d, J=8.0 Hz), 7.42(1H, d, J=6.0 Hz), 7.48(2H, brt, J=7.6 Hz), 7.56-7.61(3H, m), 8.07(1H, d, J=2.4 Hz), 11.85(1H, brs), 11.98(1H, brs).

(2) {2-[(5-Bromo-2-hydroxybenzoyl)amino]-4-phenylthiazol-5-yl}acetic acid (Compound No. 203)

{2-[(5-Bromo-2-hydroxybenzoyl)amino]-4-phenylthiazol-5-yl}acetic acid methyl ester (75 mg, 0.17 mmol) was dissolved in methanol (5 mL). 2N Sodium hydroxide (0.5 mL, 1 mmol) was added, and the mixture was stirred at room temperature for 12 hours. The reaction mixture was poured into 2N hydrochloric acid and extracted with ethyl acetate. After the ethyl acetate layer was washed successively with water and brine, dried over anhydrous sodium sulfate, the solvent was evaporated under reduced pressure. The obtained residue was suspended and washed with n-hexane-ethyl acetate under heating at reflux to give the title compound (56 mg, 77.3%) as a light yellow white crystal.

mp 284-286° C. $^1$H-NMR(DMSO-d$_6$): δ 3.84(2H, s), 6.98(1H, d, J=8.8 Hz), 7.42(1H, d, J=6.8 Hz), 7.49(2H, t, J=7.6 Hz), 7.58-7.61(3H, m), 8.07(1H, d, J=2.8 Hz), 12.25(H, brs).

Example 204

Preparation of the Compound of Compound No. 204

Using 5-bromosalicylic acid and 2-amino-4,5-diphenylthiazole as the raw materials, the same operation as the Example 195(3) gave the title compound.

Yield: 25.9%. mp 262-263° C. $^1$H-NMR(DMSO-d$_6$): δ 7.02(1H, d, J=8.1 Hz), 7.34-7.47(10H, m), 7.63(1H, d, J=6.9 Hz), 8.08(1H, d, J=2.4 Hz), 11.88(1H, brs), 12.08(1H, brs).

[2-Amino-4,5-diphenylthiazole: Refer to "Nihon Kagaku Zasshi", 1962, Vol. 83, p. 209.]

Example 205

Preparation of the Compound of Compound No. 205

Using 5-bromosalicylic acid and 2-amino-4-benzyl-5-phenylthiazole as the raw materials, the same operation as the Example 195(3) gave the title compound.

Yield: 28.1%. mp 198-200° C. $^1$H-NMR(DMSO-d$_6$): δ 4.08(2H, s), 6.95(1H, d, J=8.8 Hz), 7.15-7.22(3H, m), 7.30(2H, t, J=7.6 Hz), 7.38-7.43(1H, m), 7.47(4H, d, J=4.4 Hz), 7.57(1H, brd, J=8.8 Hz), 8.05(1H, d, J=2.4 Hz), 11.98(1H, brs).

[2-Amino-4-benzyl-5-phenylthiazole: Refer to "Chemical and Pharmaceutical Bulletin", 1962, Vol. 10, p. 376.]

Example 206

Preparation of the Compound of Compound No. 206

Using 5-bromosalicylic acid and 2-amino-5-phenyl-4-(trifluoromethyl)thiazole as the raw materials, the same operation as the Example 195(3) gave the title compound.

Yield: 33.2%. mp 250° C. (dec.). $^1$H-NMR(DMSO-d$_6$): δ 7.02(1H, d, J=8.8 Hz), 7.51(5H, s), 7.63(1H, dd, J=8.8, 2.4 Hz), 8.02(1H, d, J=2.8 Hz), 12.38(1H, brs).

Example 207

Preparation of the Compound of Compound No. 207

Using 1-phenyl-1,3-butanedione as the raw material, the same operation as the Examples 195(1)-(3) gave the title compound.

Yield: 8.9% (3 steps).

(1) α-Bromo-1-phenyl-1,3-butanedione $^1$H-NMR(CDCl$_3$): δ 2.46(3H, s), 5.62(1H, s), 7.48-7.54(2H, m), 7.64(1H, tt, J=7.5, 2.1 Hz), 7.97-8.01(2H, m).

(2) 2-Amino-5-acetyl-4-phenylthiazole $^1$H-NMR(DMSO-d$_6$): δ 2.18(3H, s), 7.50-7.55(2H, m), 7.59-7.68(3H, m), 8.69(2H, brs).

(3) 5-Bromo-N-(5-acetyl-4-phenylthiazol-2-yl)-2-hydroxybenzamide (Compound No. 207)

$^1$H-NMR(DMSO-d$_6$): δ 2.44(3H, s), 6.99(1H, d, J=9.0 Hz), 7.55-7.71(4H, m), 7.76-7.80(2H, m), 8.01(1H, d, J=2.4 Hz), 12.36(2H, br).

Example 208

Preparation of the Compound of Compound No. 208

Using 1,3-diphenyl-1,3-propanedione as the raw material, the same operation as the Examples 195(1)-(3) gave the title compound.

Yield: 49.7%.

(1) α-Bromo-1,3-diphenyl-1,3-propanedione $^1$H-NMR(CDCl$_3$): δ 6.55(1H, s), 7.45-7.50(4H, m), 7.61(2H, tt, J=7.2, 2.1 Hz), 7.98-8.01(4H, m).

(2) 2-Amino-5-benzoyl-4-phenylthiazole $^1$H-NMR(DMSO-d$_6$): δ 7.04-7.18(5H, m), 7.22-7.32(3H, m), 7.35-7.38(2H, m), 8.02(2H, s).

(3) 5-Bromo-N-(5-benzoyl-4-phenylthiazol-2-yl)-2-hydroxybenzamide (Compound No. 208)

$^1$H-NMR(DMSO-d$_6$): δ 7.03(1H, d, J=8.7 Hz), 7.17-7.30 (5H, m), 7.39-7.47(3H, m), 7.57-7.60(2H, m), 7.64(1H, dd, J=8.7, 2.7 Hz), 8.05(1H, d, J=2.4 Hz), 11.82(1H, brs), 12.35 (1H, brs).

Example 209

Preparation of the Compound of Compound No. 210

Using 5-chlorosalicylic acid and 2-amino-4-phenylthiazole-5-carboxylic acid ethyl ester as the raw materials, the same operation as the Example 195(3) gave the title compound.

Yield: 69.4%. $^1$H-NMR(DMSO-d$_6$): δ 1.22(3H, t, J=7.5 Hz), 4.21(2H, q, J=7.5 Hz), 7.07(1H, d, J=8.7 Hz), 7.43-7.47 (3H, m), 7.53(1H, dd, J=8.7, 2.4 Hz), 7.70-7.74(2H, m), 7.92(1H, d, J=3.0 Hz), 11.88(1H, br), 12.29(1H, brs).

Example 210

Preparation of the Compound of Compound No. 209

Using 5-bromosalicylic acid and 2-amino-4-phenylthiazole-5-carboxylic acid ethyl ester as the raw materials, the same operation as the Example 195(3) gave the title compound.

Yield: 28.6%. mp 197-199° C. $^1$H-NMR(DMSO-d$_6$): δ 1.21(3H, t, J=6.8 Hz), 4.20(2H, q, J=6.8 Hz), 7.01(1H, d, J=8.8 Hz), 7.43-7.48(3H, m), 7.63(1H, dd, J=8.8, 2.4 Hz), 7.70-7.72(2H, m), 8.04(1H, d, J=2.4 Hz), 12.33(1H, brs).

Example 211

Preparation of the Compound of Compound No. 211

Using pentafluorobenzoylacetic acid ethyl ester as the raw material, the same operation as the Examples 195-(1)-(3) gave the title compound.

Yield: 40.0% (3 steps).

(1) α-Bromo-pentafluorobenzoylacetic acid ethyl ester

It was used for the next reaction as a crude product.

(2) 2-Amino-4-(pentafluorophenyl)thiazole-5-carboxylic acid ethyl ester $^1$H-NMR(CDCl$_3$): δ 1.23(3H, t, J=7.2 Hz), 4.21(2H, q, J=7.2 Hz), 5.41(2H, s).

(3) Ethyl 2-(5-bromo-2-hydroxybenzoyl)amino-4-(pentafluorophenyl)thiazole-5-carboxylate (Compound No. 211)

$^1$H-NMR(DMSO-d$_6$): δ 1.20(3H, t, J=7.2 Hz), 2.51(2H, q, J=7.2 Hz), 7.02(1H, d, J=8.7 Hz), 7.64(1H, dd, J=8.7, 2.7 Hz), 7.90(1H, d, J=3.0 Hz), 11.92(1H, br), 12.58(1H, br).

Example 212

Preparation of the Compound of Compound No. 212

(1) 2-(5-Bromo-2-hydroxybenzoyl)amino-4-phenylthiazole-5-carboxylic acid

Using 2-(5-bromo-2-hydroxybenzoyl)amino-4-phenylthiazole-5-carboxylic acid ethyl ester (compound No. 209) as the raw material, the same operation as the Example 82 gave the title compound.

Yield: 67.0%. $^1$H-NMR(DMSO-d$_6$): δ 7.00(1H, d, J=8.8 Hz), 7.42-7.44(3H, m), 7.62(1H, dd, J=8.8, 2.4 Hz), 7.70-7.72(2H, m), 8.04(1H, d, J=2.4 Hz), 12.31(1H, brs), 12.99 (1H, brs).

(2) [2-(5-Bromo-2-hydroxybenzoyl)amino-4-phenylthiazol-5-yl]-N-methylcarboxamide (Compound No. 212)

A mixture of 2-(5-bromo-2-hydroxybenzoyl)amino-4-phenylthiazole-5-carboxylic acid (0.20 g, 0.48 mmol), methylamine 40% methanol solution (0.2 ml), 1-hydroxybenzotriazole hydrate (96.7 mg, 0.72 mmol), WSC.HCl (137.2 mg, 0.72 mmol) and tetrahydrofuran (15 mL) was stirred at room temperature for 18 hours. The reaction mixture was poured into 2N hydrochloric acid and extracted with ethyl acetate. After the organic layer was washed with water and brine, dried over anhydrous sodium sulfate, the residue obtained by evaporation under reduced pressure was purified by chromatography on silica gel (n-hexane:ethyl acetate=1: 2), and crystallized (dichloromethane/n-hexane) to give the title compound (87.9 mg, 42.6%) as a white powder.

$^1$H-NMR(DMSO-d$_6$): δ 2.70(3H, d, J=4.5 Hz), 7.02(1H, d, J=9.0 Hz), 7.40-7.48(3H, m), 7.63(1H, dd, J=9.0, 2.4 Hz), 7.68-7.71(2H, m), 8.06(1H, d, J=2.4 Hz), 8.16(1H, t, J=4.5 Hz), 11.88(1H, br), 12.15(1H, brs).

When the method described in Example 212(2) is referred in the following examples, WSC.HCl and 1-hydroxybenzotriazole hydrate were used as the dehydrocondensating agent. As the reaction solvent, solvents such as tetrahydrofuran or the like were used.

Example 213

Preparation of the Compound of Compound No. 213

Using 2-(5-bromo-2-hydroxybenzoyl)amino-4-phenylthiazole-5-carboxylic acid (compound of Example 212(1)) and 70% aqueous ethylamine solution as the raw materials, the same operation as the Example 212(2) gave the title compound.

Yield: 62.5%. $^1$H-NMR(DMSO-d$_6$): δ 1.05(3H, t, J=6.9 Hz), 3.15-3.24(2H, m), 7.02(1H, d, J=8.7 Hz), 7.40-7.47(3H, m), 7.63(1H, dd, J=8.7, 3.0 Hz), 7.69-7.72(2H, m), 8.06(1H, d, J=2.4 Hz), 8.20(1H, t, J=5.4 Hz), 11.84(1H, br), 12.14(1H, brs).

Example 214

Preparation of the Compound of Compound No. 214

Using 2-(5-bromo-2-hydroxybenzoyl)amino-4-phenylthiazole-5-carboxylic acid (compound of Example 212(1)) and isopropylamine as the raw materials, the same operation as the Example 212(2) gave the title compound.

Yield: 23.9%. $^1$H-NMR(DMSO-d$_6$): δ 1.07(6H, d, J=6.3 Hz), 4.02(1H, m), 7.02(1H, d, J=9.0 Hz), 7.40-7.52(3H, m), 7.64(1H, dd, J=8.7, 2.7 Hz), 7.69-7.73(2H, m), 8.06(1H, d, J=2.7 Hz), 11.89(1H, br), 12.14(1H, brs).

Example 215

Preparation of the Compound of Compound No. 215

Using 2-(5-bromo-2-hydroxybenzoyl)amino-4-phenylthiazole-5-carboxylic acid (compound of Example 212(1)) and 2-phenethylamine as the raw materials, the same operation as the Example 212(2) gave the title compound.
Yield: 62.2%. $^1$H-NMR(DMSO-d$_6$): δ 2.78(2H, t, J=7.5 Hz), 3.43(2H, q, J=7.5 Hz), 7.02(1H, d, J=9.0 Hz), 7.19-7.24 (3H, m), 7.27-7.33(2H, m), 7.39-7.41(3H, m), 7.61-7.65(3H, m), 8.06(1H, d, J=2.4 Hz), 8.25(1H, t, J=6.0 Hz), 11.85(1H, brs), 12.15(1H, brs).

Example 216

Preparation of the Compound of Compound No. 216

Using 5-bromosalicylic acid and 2-amino-4-(trifluoromethyl)thiazole-5-carboxylic acid ethyl ester as the raw materials, the same operation as the Example 195(3) gave the title compound.
Yield: 88.7%. $^1$H-NMR(DMSO-d$_6$): δ 1.32(3H, t, J=7.2 Hz), 4.33(2H, q, J=7.2 Hz), 7.01(1H, d, J=8.7 Hz), 7.63(1H, dd, J=8.7, 2.7 Hz), 7.98(1H, d, J=2.4 Hz), 12.64(1H, br).

Example 217

Preparation of the Compound of Compound No. 217

Using 5-chloro-N-{4-[(1,1-dimethyl)ethyl]-5-[(2,2-dimethyl)propionyl]thiazol-2-yl}-2-hydroxybenzamide (compound No. 195) and acetyl chloride as the raw materials, the same operation as the Example 96 gave the title compound.
Yield: 65.3%. $^1$H-NMR(CDCl$_1$): δ 1.32(9H, s), 1.33(9H, s), 2.46(3H, s), 7.22(1H, d, J=8.4 Hz), 7.56(1H, dd, J=8.7, 2.4 Hz), 8.05(1H, d, J=2.7 Hz), 9.82(1H, brs).

Example 218

Preparation of the Compound of Compound No. 218

Using 4-hydroxybiphenyl-3-carboxylic acid and 2-amino-4-phenylthiazole-5-carboxylic acid ethyl ester as the raw materials, the same operation as the Example 195(3) gave the title compound.
Yield: 61.7%. mp 207-208° C. $^1$H-NMR(DMSO-d$_6$): δ 1.23(3H, t, J=7.2 Hz), 4.22(2H, q, J=7.2 Hz), 7.16(1H, d, J=8.7 Hz), 7.36(1H, t, J=7.5 Hz), 7.45-7.50(5H, m), 7.69-7.76(4H, m), 7.85(1H, dd, J=8.7, 2.4 Hz), 8.31(1H, d, J=2.4 Hz), 11.73(1H, brs), 12.60(1H, brs).

[4-Hydroxybiphenyl-3-carboxylic acid: Refer to "Tetrahedron", 1997, Vol. 53, p. 11437.]

Example 219

Preparation of the Compound of Compound No. 219

Using (4'-fluoro-4-hydroxybiphenyl)-3-carboxylic acid and 2-amino-4-phenylthiazole-5-carboxylic acid ethyl ester as the raw materials, the same operation as the Example 195(3) gave the title compound.
Yield: 62.7%. mp 237-238° C. $^1$H-NMR(DMSO-d$_6$): δ 1.22(3H, t, J=7.2 Hz), 4.21(2H, q, J=7.2 Hz), 7.13(1H, d, J=8.4 Hz), 7.28(2H, t, J=8.8 Hz), 7.44-7.45(3H, m), 7.71-7.75(4H, m), 7.81(1H, dd, J=8.8, 2.4 Hz), 8.27(1H, d, J=2.4 Hz), 11.67(1H, brs), 12.58(1H, brs).

[(4'-Fluoro-4-hydroxybiphenyl)-3-carboxylic acid: Refer to "Tetrahedron", 1997, Vol. 53, p. 11437.]

Example 220

Preparation of the Compound of Compound No. 220

Using (2',4'-difluoro-4-hydroxybiphenyl)-3-carboxylic acid and 2-amino-4-phenylthiazole-5-carboxylic acid ethyl ester as the raw materials, the same operation as the Example 195(3) gave the title compound.
Yield: 45.6%. mp 206-207° C. $^1$H-NMR(DMSO-d$_6$): δ 1.22(3H, t, J=7.2 Hz), 4.22(2H, q, J=7, 2 Hz), 7.17(1H, d, J=9.0 Hz), 7.21(1H, td, J=8.7, 2.4 Hz), 7.38(1H, ddd, J=11.7, 9.3, 2.4 Hz), 7.44-7.46(3H, m), 7.60-7.75(4H, m), 8.13-8.14 (1H, m), 11.86(1H, brs), 12.46(1H, brs).

Example 221

Preparation of the Compound of Compound No. 221

(1) [4-Hydroxy-4'-(trifluoromethyl)biphenyl]-3-carboxylic acid

A mixture of 5-bromosalicylic acid (500 mg, 2.30 mmol), dihydroxy-4-(trifluoromethyl)phenylborane (488 mg, 2.57 mmol), palladium acetate (10 mg, 0.040 mmol) and 1M sodium carbonate (7 mL) was stirred at 80° C. for 1 hour. The reaction mixture was poured into 2N hydrochloric acid and extracted with ethyl acetate. After the ethyl acetate layer was washed successively with water and brine, dried over anhydrous sodium sulfate, the solvent was evaporated under reduced pressure. According to the fixed procedure, the obtained residue was methyl-esterified by trimethylsilyldiazomethane and methanol, and purified by column chromatography on silica gel (n-hexane:ethyl acetate=5:1) to give a colourless liquid (563 mg). This liquid was dissolved in methanol (10 mL). 2N Sodium hydroxide (3 mL) was added, and the mixture was stirred at 60° C. for 1 hour. After the reaction mixture was cooled to room temperature, it was poured into 2N hydrochloric acid and extracted with ethyl acetate. After the ethyl acetate layer was washed successively with water and saturated brine, dried over anhydrous magnesium sulfate, the solvent was evaporated under reduced pressure. The obtained residue was suspended and washed with n-hexane-dichloromethane under heating at reflux to give the title compound (458 mg, 70.4%) as a white crystal.
mp 185° C. (dec). $^1$H-NMR(DMSO-d$_6$): δ 7.09(1H, d, J=8.8 Hz), 7.77(2H, d, J=8.0 Hz), 7.85(2H, d, J=8.0 Hz), 7.90(1H, dd, J=8.8, 2.0 Hz), 8.10(1H, d, J=2.4 Hz), 11.80(1H, brs).

(2) 2-{[4-Hydroxy-4'-(trifluoromethyl)biphenyl]-3-carbonyl}amino-4-phenylthiazole-5-carboxylic acid ethyl ester (Compound No. 221)

Using [4-hydroxy-4'-(trifluoromethyl)biphenyl]-3-carboxylic acid and 2-amino-4-phenylthiazole-5-carboxylic acid ethyl ester as the raw materials, the same operation as the Example 195(3) gave the title compound.
Yield: 41.7%. mp 236-237° C. $^1$H-NMR(DMSO-d$_6$): δ 1.22(3H, t, J=7.2 Hz), 4.21(2H, q, J=7.2 Hz), 7.18(1H, d, J=8.8 Hz), 7.44-7.45(3H, m), 7.72-7.74(2H, m), 7.81(2H, d, J=8.4 Hz), 7.91(1H, dd, J=8.8, 2.4 Hz), 7.93(2H, d, J=8.4 Hz), 8.36(1H, d, J=2.4 Hz), 11.78(1H, brs), 12.62(1H, brs).

Example 222

Preparation of the Compound of Compound No. 222

Using 2-hydroxy-5-(1-pyrrolyl)benzoic acid and 2-amino-4-phenylthiazole-5-carboxylic acid ethyl ester as the raw materials, the same operation as the Example 195(3) gave the title compound.

Yield: 55.0%. $^1$H-NMR(DMSO-d$_6$): δ 1.22(3H, t, J=7.2 Hz), 4.22(2H, q, J=7.2 Hz), 6.26(2H, t, J=2.1 Hz), 7.13(1H, d, J=8.7 Hz), 7.32(2H, t, J=2.1 Hz), 7.43-7.47(3H, m), 7.70-7.75(3H, m), 8.09(1H, d, J=2.7 Hz), 11.58(1H, brs), 12.55 (1H, brs).

Example 223

Preparation of the Compound of Compound No. 223

(1) 2-Hydroxy-5-(2-thienyl)benzoic acid

5-Bromosalicylic acid (500 mg, 2.30 mmol) was dissolved in 1,2-dimethoxyethane (5 mL). Tetrakis(triphenylphosphine)palladium (80 mg, 0.07 mmol) was added under argon atmosphere, and the mixture was stirred at room temperature for 10 minutes. Then dihydroxy-2-thienylborane (324 mg, 2.53 mmol) and 1M sodium carbonate (7 mL) were added, and the mixture was refluxed for 2 hours. After the reaction mixture was cooled to room temperature, it was poured into 2N hydrochloric acid and extracted with ethyl acetate. After the ethyl acetate layer was washed successively with water and brine, dried over anhydrous sodium sulfate, the solvent was evaporated under reduced pressure. According to the fixed procedure, the obtained residue was methyl-esterified by trimethylsilyldiazomethane and methanol, and purified by column chromatography on silica gel (n-hexane:ethyl acetate=5:1) to give an yellow liquid (277 mg). This was dissolved in methanol (5 mL). 2N Sodium hydroxide (1.5 mL) was added, and the mixture was stirred at 60° C. for 1 hour. After the reaction mixture was cooled to room temperature, it was poured into 2N hydrochloric acid and extracted with ethyl acetate. After the ethyl acetate layer was washed successively with water and brine, dried over anhydrous magnesium sulfate, the residue obtained by evaporation of the solvent under reduced pressure was crystallized from n-hexane-dichloromethane to give the title compound (58 mg, 11.5%) as a white crystal.

$^1$H-NMR(DMSO-d$_6$): δ 6.95(1H, d, J=8.8 Hz), 7.09(1H, dd, J=4.8, 3.6 Hz), 7.37(1H, dd, J=4.0, 1.2 Hz), 7.45(1H, dd, J=5.2, 1.2 Hz), 7.74(1H, dd, J=8.8, 2.8 Hz), 7.96(1H, d, J=2.8 Hz).

(2) 2-[2-Hydroxy-5-(2-thienyl)benzoyl]amino-4-phenylthiazole-5-carboxylic acid ethyl ester (Compound No. 223)

Using 2-hydroxy-5-(2-thienyl)benzoic acid and 2-amino-4-phenylthiazole-5-carboxylic acid ethyl ester as the raw materials, the same operation as the Example 195(3) gave the title compound.

Yield: 58.2%. mp 213-214° C. $^1$H-NMR(DMSO-d$_6$): δ 1.22(3H, t, J=7.2 Hz), 4.21(2H, q, J=7.2 Hz), 7.10(1H, d, J=9.2 Hz), 7.12(1H, dd, J=4.8, 3.6 Hz), 7.44-7.46(4H, m), 7.50(1H, dd, J=4.8, 1.2 Hz), 7.71-7.74(2H, m), 7.79(1H, dd, J=8.8, 2.4 Hz), 8.21(1H, d, J=2.4 Hz), 11.78(1H, brs), 12.44 (1H, brs).

Example 301

Preparation of the Compound of Compound No. 301

(1) 5-Chloro-2-methoxy-β-phenylstyrene

Palladium acetate (21 mg, 7 mol %) was added to a solution of 2-bromo-4-chloroanisole (300 mg, 1.4 mmol), styrene (211 mg, 2 mmol), triethylamine (13 μL, 0.1 mmol) and triphenylphosphine (50 mg, 1.9 mmol) in acetonitrile (6 mL), and the mixture was refluxed for 8 hours under argon atmosphere. After the reaction mixture was cooled to room temperature, the solvent was concentrated under reduced pressure and the obtained residue was diluted with ethyl acetate (15 mL). After the solution was washed successively with 2N hydrochloric acid, water and brine, dried over anhydrous sodium sulfate, the residue obtained by evaporation of the solvent under reduced pressure was purified by column chromatography on silica gel (n-hexane:ethyl acetate=10:1) to give the title compound (118 mg, 35.6%) as a white powder.

$^1$H-NMR(CDCl$_3$): δ 3.85(3H, s), 6.80(1H, d, J=8.8 Hz), 7.08(1H, d, J=16.8 Hz), 7.17(1H, dd, J=8.8, 2.5 Hz), 7.20-7.42(4H, m), 7.51-7.55(3H, m).

(2) 4-Chloro-2-styrylphenol (Compound No. 301)

Under argon atmosphere, 1 mol/L boron tribromide/dichloromethane solution (0.5 mL, 0.5 mmol) was added to a solution of 5-chloro-2-methoxy-β-phenylstyrene (80 mg, 0.3 mmol) in dichloromethane (2 mL) at room temperature, and the mixture was stirred for 12 hours. The reaction mixture was diluted with ethyl acetate (15 mL), and after it was washed successively with water and brine, dried over anhydrous sodium sulfate, the residue obtained by evaporation of the solvent under reduced pressure was purified by column chromatography on silica gel (n-hexane:ethyl acetate=3:1) to give the title compound (34.2 mg, 45.4%) as a white powder.

$^1$H-NMR(CDCl$_3$): δ 4.95 (1H, brs), 6.74(1H, d, J=8.7 Hz), 7.09(1H, dd, =8.7, 2.4 Hz), 7.10(1H, d, J=16.2 Hz), 7.28-7.39 (4H, m), 7.49-7.54(3H, m).

Example 302

Preparation of the Compound of Compound No. 302

(1) (S)-2-Amino-3-phenyl-N-[3,5-bis(trifluoromethyl)phenyl]propionamide

A mixture of 3,5-bis(trifluoromethyl)aniline (0.20 g, 0.87 mmol), N-(tert-butoxycarbonyl)-L-phenylalanine (254.8 mg, 0.96 mmol), phosphorus trichloride (40 μL, 0.46 mmol) and toluene (4 mL) was stirred at 80° C. for 1.5 hours under argon atmosphere. After the reaction mixture was cooled to room temperature, it was poured into aqueous sodium hydrogen carbonate and extracted with ethyl acetate. After the ethyl acetate layer was washed with brine, dried over anhydrous sodium sulfate, the residue obtained by evaporation of the solvent under reduced pressure was crystallized by isopropyl ether/n-hexane to give the title compound (333.7 mg, 92.9%) as an yellow white powder.

$^1$H-NMR(DMSO-d$_6$): δ 3.13(1H, dd, J=13.8, 8.1 Hz), 3.29 (1H, dd, J=13.8, 6.0 Hz), 4.37(1H, s), 7.25-7.38(5H, m), 7.86(1H, s), 8.30(2H, s), 8.48(3H, s), 11.95(1H, s).

When the method described in Example 302(1) is referred in the following examples, phosphorus trichloride was used as the acid halogenating agent. As the reaction solvent, solvents such as toluene, monochlorobenzene or the like were used.

(2) (S)-2-Acetoxy-5-chloro-N-(2-phenyl-1-{[3,5-bis(trifluoromethyl)phenyl]carbamoyl}-ethyl)benzamide WSC.HCl (184 mg, 0.96 mmol) was added to a solution of 2-acetoxy-5-chlorobenzoic acid (104 mg, 0.48 mmol), (S)-2-amino-3-phenyl-N-[3,5-bis(trifluoromethyl)phenyl]propionamide (0.20 g, 0.48 mmol) and 1-hydroxybenzotriazole (71.4 mg, 0.53 mmol) in N,N-dimethylformamide (4 mL), and the mixture was stirred at room temperature for 3 hours. The reaction mixture was poured into diluted hydrochloric acid and extracted with ethyl acetate. After the ethyl acetate layer was washed successively with water and brine, dried over anhydrous sodium sulfate, the residue obtained by evaporation of the solvent under reduced pressure was purified by column chromatography on silica gel (n-hexane:ethyl acetate=3:1→2:1) to give the title compound (141.4 mg, 51.4%) as a white crystal.

$^1$H-NMR(DMSO-d$_6$): δ 2.05(3H, s), 3.04(1H, dd, J=13.8, 9.9 Hz), 3.19(1H, dd.J=13.8, 4.8 Hz), 4.73-4.81(1H, m), 7.22-7.35(6H, m), 7.54(1H, d, J=2.4 Hz), 7.60(1H, dd, J=8.7, 2.4 Hz), 7.81(1H, s), 8.27(2H, s), 8.91(1H, d, J=7.8 Hz), 10.81(1H, s).

When the method described in Example 302(2) is referred in the following examples, WSC.HCl and 1-hydroxybenzotriazole hydrate were used as the dehydrocondensating agent. As the reaction solvent, solvents such as N,N-dimethylformamide or the like were used.

(3) (S)-5-Chloro-2-hydroxy-N-(2-phenyl-1-{[3,5-bis(trifluoromethyl)phenyl]carbamoyl}-ethyl)benzamide (Compound No. 302)

5N Aqueous sodium hydroxide (0.2 mL) was added to a solution of (S)-2-acetoxy-5-chloro-N-(2-phenyl-1-{[3,5-bis(trifluoromethyl)phenyl]carbamoyl}-ethyl)benzamide (141.4 mg, 0.25 mmol) in a mixed solvent of methanol/tetrahydrofuran (2 mL+2 mL), and the mixture was stirred at room temperature for 20 minutes. The reaction mixture was poured into diluted hydrochloric acid and extracted with ethyl acetate. After the ethyl acetate layer was washed successively with water and brine, dried over anhydrous sodium sulfate, the residue obtained by evaporation of the solvent under reduced pressure was crystallized by ethyl acetate/isopropyl ether/n-hexane to give the title compound (74.4 mg, 56.8%) as a white powder.

$^1$H-NMR(DMSO-d$_6$): δ 3.13(1H, dd, J=13.8, 9.0 Hz), 3.26 (1H, dd, J=14.1, 4.8 Hz), 4.85-4.92(1H, m), 6.95(1H, d, J=8.7 Hz), 7.19-7.23(1H, m), 7.26-7.31(4H, m), 7.45(1H, dd, J=8.7, 2.4 Hz), 7.81(1H, s), 7.97(1H, d, J=2.4 Hz), 8.26(2H, s), 9.12(1H, d, J=7.2 Hz), 10.89(1H, s), 12.01(1H, s).

When the method described in Example 302(3) is referred in the following examples, inorganic bases such as sodium hydroxide, potassium carbonate or the like were used as the base. As the reaction solvent, solvents such as water, methanol, ethanol, tetrahydrofuran or the like were used alone or as a mixture.

Example 303

Preparation of the Compound of Compound No. 303

(1) [1-({[3,5-Bis(trifluoromethyl)phenyl]amino}carbonyl)methyl]carbamic acid 1,1-dimethyl ester Under argon atmosphere, N-(tert-butoxycarbonyl)glycine (183.5 mg, 1.05 mmol) and triethylamine (0.25 mL, 1.79 mmol) were added to a solution of 3,5-bis(trifluoromethyl)aniline (0.20 g, 0.87 mmol) in tetrahydrofuran (4 mL), and after cooling with ice bath, phosphorus oxychloride (96 μL, 1.05 mmol) was added and the mixture was stirred at room temperature for 5 hours. The reaction mixture was poured into water and extracted with ethyl acetate. After the ethyl acetate layer was washed successively with water and brine, dried over anhydrous sodium sulfate, the residue obtained by evaporation of the solvent under reduced pressure was purified by column chromatography on silica gel (n-hexane:ethyl acetate=2:1→3:2) to give the title compound (101.9 mg, 30.3%) as a white crystal.

$^1$H-NMR(CDCl$_3$): δ 1.49(9H, s), 3.99(2H, d, J=6.0 Hz), 5.37(1H, t, J=6.0 Hz), 7.57(1H, s), 8.00(2H, s), 9.06(1H, brs).

(2) 2-Amino-N-[3,5-bis(trifluoromethyl)phenyl]acetamide hydrochloride

4N Hydrochloric acid/ethyl acetate solution (1 mL) was added to [1-({[3,5-bis(trifluoromethyl)phenyl]amino}carbonyl)methyl]carbamic acid 1,1-dimethyl ester (101.9 mg, 0.26 mmol), and the mixture was stirred at room temperature for 1 hour. n-Hexane (15 mL) was added to the reaction mixture and the separated white solid was filtered to give the title compound (80.8 mg, 96.4%) as a white powder.

$^1$H-NMR(CD$_3$OD): δ 3.89(2H, s), 7.71(1H, s), 8.22(2H, s).

(3) 2-Acetoxy-5-chloro-N-({[3,5-bis(trifluoromethyl)phenyl]carbamoyl}-methyl)benzamide WSC.HCl (95.9 mg, 0.5 mmol) was added to a solution of 2-acetoxy-5-chlorobenzoic acid (59.1 mg, 0.28 mmol), 2-amino-N-[3,5-bis(trifluoromethyl)phenyl]acetamide hydrochloride (80.8 mg, 0.25 mmol) and 1-hydroxybenzotriazole (37.2 mg, 0.28 mmol) in N,N-dimethylformamide (3 mL), and the mixture was stirred at room temperature for 3 hours. The reaction mixture was poured into diluted hydrochloric acid and extracted with ethyl acetate. After the ethyl acetate layer was washed with brine, dried over anhydrous sodium sulfate, the residue obtained by evaporation of the solvent under reduced pressure was purified by column chromatography on silica gel (n-hexane:ethyl acetate=3:2→1:1) to give the title compound (83.7 mg, 69.3%) as a white crystal.

$^1$H-NMR(CDCl$_3$): δ 2.40(3H, s), 4.40(2H, d, J=5.4 Hz), 7.17(1H, d.J=8.4 Hz), 7.40(1H, t, J=5.4 Hz), 7.53(1H, dd, J=8.4, 2.4 Hz), 7.62(1H, s), 7.82(1H, d, J=2.4 Hz), 8.19(2H, s), 9.20(1H, s).

(4) 5-Chloro-2-hydroxy-N-({[3,5-bis(trifluoromethyl)phenyl]carbamoyl}-methyl)benzamide (Compound No. 303)

5N Aqueous sodium hydroxide (0.1 mL) was added to a solution of 2-acetoxy-5-chloro-N-({[3,5-bis(trifluoromethyl)phenyl]carbamoyl}methyl)benzamide (83.7 mg, 0.17 mmol) in methanol/tetrahydrofuran (2 mL+1 mL), and the mixture was stirred at room temperature for 20 minutes. The reaction mixture was poured into diluted hydrochloric acid and extracted with ethyl acetate. After the ethyl acetate layer was washed with water and brine, dried over anhydrous sodium sulfate, the residue obtained by evaporation of the solvent under reduced pressure was purified by column chromatography on silica gel (n-hexane:ethyl acetate=2:1) and washed with n-hexane under suspension to give the title compound (47.7 mg, 63.7%) as a white crystal.

$^1$H-NMR(DMSO-d$_6$): δ 4.18(2H, d, J=5.4 Hz), 7.00(1H, d, J=9.0 Hz), 7.47(1H, dd, J=9.0, 2.7 Hz), 7.80(1H, s), 7.96(1H, d, J=2.7 Hz), 8.27(2H, s), 9.25(1H, t, J=5.4 Hz), 10.78(1H, s), 12.14(1H, s).

Example 304

Preparation of the Compound of Compound No. 304

(1) 5-Chlorosalicylhydrazide

A mixture of 5-chloro-2-hydroxybenzoic acid methyl ester (0.50 g, 2.7 mmol), hydrazine monohydrate (0.3 mL, 6.2 mmol) and ethanol (5 mL) was refluxed for 6 hours. After the reaction mixture was cooled to room temperature, n-hexane was added and the separated crystal was filtered to give the title compound (395.9 mg, 79.2%) as a white crystal.

$^1$H-NMR(DMSO-d$_6$): δ 6.90(1H, d, J=8.7 Hz), 7.38(1H, dd, J=8.7, 2.7 Hz), 7.85(1H, d, J=8.7 Hz), 10.23(brs).

(2) 5-Chlorosalicylic acid [3,5-bis(trifluoromethyl)benzylidene]hydrazide (Compound No. 304)

A mixture of 5-chlorosalicylhydrazide (213.9 mg, 1.2 mmol), 3,5-bis(trifluoromethyl)benzaldehyde (190 μL, 1.2 mmol), concentrated sulfuric acid (3 drops) and ethanol (5 mL) was refluxed for 30 minutes. 3,5-Bis(trifluoromethyl)benzaldehyde (100 μL, 0.61 mmol) was added and the mixture was refluxed for further 1 hour. After the reaction mixture was cooled to room temperature, it was poured into water and extracted with ethyl acetate. After the ethyl acetate layer was washed with brine, dried over sodium sulfate, the residue obtained by evaporation of the solvent under reduced pressure was purified by column chromatography on silica gel (n-hexane:ethyl acetate=3:1→2:1) and washed with n-hexane under suspension to give the title compound (362.6 mg, 76.8%) as a white powder.

$^1$H-NMR(DMSO-d$_6$): δ 7.03(1H, d, J=9.0 Hz), 7.49(1H, dd, J=9.0, 2.7 Hz), 7.86(1H, d, J=3.0 Hz), 8.20(1H, s), 8.40(2H, s), 8.59(1H, s), 11.65(1H, s), 12.14(1H, s).

Example 305

Preparation of the Compound of Compound No. 305

(1) (S)-2-Amino-4-methyl-N-[3,5-bis(trifluoromethyl)phenyl]pentanamide

Using N-(tert-butoxycarbonyl)-L-leucine and 3,5-bis(trifluoromethyl)aniline as the raw materials, the same operation as the Example 302(1) gave the title compound.

Yield: 25.2%. $^1$H-NMR(CDCl$_3$): δ 0.98(3H, d, J=6.3 Hz), 1.01(3H, d, J=6.3 Hz), 1.39-1.48(1H, m), 1.74-1.89(2H, m), 3.55(1H, dd, J=9.9, 3.6 Hz), 7.58(1H, s), 8.12(2H, s), 10.01 (1H, s).

(2) (S)-5-Chloro-2-hydroxy-N-(3-methyl-1-{[3,5-bis(trifluoromethyl)phenyl]carbamoyl}-butyl)benzamide (Compound No. 305)

Using 2-acetoxy-5-chlorobenzoic acid and (S)-2-amino-4-methyl-N-[3,5-bis-(trifluoromethyl)phenyl]pentanamide as the raw materials, the same operation as the Example 302(2)-(3) gave the title compound.

Yield: 24.8% (2 steps). $^1$H-NMR(DMSO-d$_6$): δ 0.95(3H, d, J=5.7 Hz), 0.97(3H, d, J=6.0 Hz), 1.65-1.84(3H, m), 4.65-4.72(1H, m), 6.98(1H, d, J=9.0 Hz), 7.47(1H, dd, J=8.7, 2.4 Hz), 7.79(1H, s), 8.06(1H, d, J=2.7 Hz), 8.32(2H, s), 9.03(1H, d, J=8.1 Hz), 10.85(1H, s), 12.20(1H, s).

Example 306

Preparation of the Compound of Compound No. 306

Using 5-chlorosalicylaldehyde and 3,5-bis(trifluoromethyl)benzhydrazide as the raw materials, the same operation as the Example 304(2) gave the title compound.

Yield: 24.7%.

$^1$H-NMR(DMSO-d$_6$): δ 6.97(1H, d, J=8.7 Hz), 7.34(1H, dd, J=9.0, 2.7 Hz), 7.73(1H, d, J=2.4 Hz), 8.41(1H, s), 8.59 (2H, s), 8.67(1H, s), 11.07(1H, s), 12.45(1H, s).

Example 307

Preparation of the Compound of Compound No. 307

Using 5-chlorosalicylic acid and 3,5-bis(trifluoromethyl) phenethylamine as the raw materials, the same operation as the Example 16 gave the title compound.

Yield: 30.2%. $^1$H-NMR(CDCl$_3$): δ 3.10(2H, t, J=6.9 Hz), 3.71-3.77(2H, m), 6.34(1H, brs), 6.95(1H, d, J=8.7 Hz), 7.23 (1H, d, J=2.7 Hz), 7.36(1H, dd, J=8.7, 2.4 Hz), 7.70(2H, s), 7.80(1H, s), 12.06(1H, s).

Example 308

Preparation of the Compound of Compound No. 308

A mixture of 3-hydroxyphthalic anhydride (100 mg, 0.6 mmol), 3,5-bis(trifluoromethyl)aniline (168 mg, 0.7 mmol) and acetic acid (5 mL) was refluxed for 6 hours under argon atmosphere. After the reaction mixture was cooled to room temperature, acetic acid was evaporated under reduced pressure and the obtained residue was dissolved in ethyl acetate (15 mL). After the ethyl acetate solution was washed successively with water and brine, dried over anhydrous sodium sulfate, the residue obtained by evaporation of the solvent under reduced pressure was purified by column chromatography on silica gel (n-hexane:ethyl acetate=3:1) to give the title compound (100 mg, 43.7%) as a white powder.

$^1$H-NMR(DMSO-d$_6$): δ 7.31(1H, d, J=8.1 Hz), 7.42(1H, d, J=7.5 Hz), 7.72(1H, dd, J=8.1, 7.5 Hz), 8.21(1H, s), 8.24(2H, s), 11.28(1H, s).

Example 309

Preparation of the Compound of Compound No. 309

3,5-Bis(trifluoromethyl)phenylisocyanate (180 μL, 1.04 mmol) was added to a solution of 2-amino-4-chlorophenol (143.6 mg, 1 mmol) in a mixed solvent of tetrahydrofuran/toluene (0.5 mL+4.5 mL), and the mixture was stirred at 100° C. for 1 hour. After the reaction mixture was cooled to room temperature, the residue obtained by evaporation of the solvent under reduced pressure was purified by column chromatography on silica gel (n-hexane:ethyl acetate=1:1) and crystallized by isopropyl ether/n-hexane to give the title compound (288.5 mg, 72.4%) as a light yellowish brown powder.

$^1$H-NMR(DMSO-d$_6$): δ 6.84-6.91(2H, m), 7.67(1H, s), 8.06(2H, s), 8.14(1H, d, J=2.1 Hz), 8.45(1H, s), 10.10(1H, s), 10.44(1H, s).

Example 310

Preparation of the Compound of Compound No. 310

(1) 5-Chloro-2-methoxy-β-[3,5-bis(trifluoromethyl)phenyl]styrene

A solution of sodium nitrite (57 mg, 0.8 mmol) in water (1 mL) was added to a solution of 2-amino-4-chloroanisole (131 mg, 0.8 mmol) in 48% hydrogen tetrafluoroborate (0.3 mL) under ice cooling and argon atmosphere. After the mixture was stirred at 0° C. for 1 hour, a solution of 3,5-bis(trifluoromethyl)styrene (100 mg, 0.4 mmol) in methanol (3 mL) was added and the mixture was stirred at 50° C. for 1 hour. After the reaction mixture was cooled to room temperature, the residue obtained by evaporation of the solvent under reduced pressure was diluted with ethyl acetate. After the solution was washed successively with 2N hydrochloric acid, water and brine, dried over anhydrous sodium sulfate, the residue obtained by evaporation of the solvent under reduced pressure was purified by column chromatography on silica gel (n-hexane:ethyl acetate=5:1) to give the title compound (52.8 mg, 33.3%) as a white powder.

$^1$H-NMR(CDCl$_3$): δ 3.85(3H, s), 6.80(1H, d, J=8.8 Hz), 7.08(1H, d, J=16.8 Hz), 7.17(1H, dd, J=8.8, 2.5 Hz), 7.20-7.42(4H, m), 7.51-7.55(3H, m).

(2) 4-Chloro-2-[3,5-bis(trifluoromethyl)styryl]phenol (Compound No. 310)

Using 5-chloro-2-methoxy-β-[3,5-bis(trifluoromethyl)phenyl]styrene as the raw material, the same operation as the Example 301(2) gave the title compound.

Yield: 18.1%. $^1$H-NMR(CDCl$_3$): δ 5.16(1H, brs), 6.76(1H, d, J=8.4 Hz), 7.15(1H, dd, J=8.4, 2.7 Hz), 7.19(1H, d, J=16.5 Hz), 7.45(1H, d, J=15.5 Hz), 7.53(1H, d, J=2.4 Hz), 7.76(1H, s), 7.93(2H, s).

Example 311

Preparation of the Compound of Compound No. 311

Using 5-chlorosalicylic acid and 2-aminoindane as the raw materials, the same operation as the Example 16 gave the title compound.

Yield: 45.3%. $^1$H-NMR(DMSO-d$_6$): δ 2.98(2H, dd, J=16.2, 5.7 Hz), 3.29(2H, dd, J=16.2, 7.5 Hz), 4.69-4.79(1H, m), 6.93(1H, d, J=8.7 Hz), 7.16-7.20(2H, m), 7.23-7.28(2H, m), 7.43(1H, dd, J=8.7, 2.4 Hz), 8.02(1H, d, J=2.4 Hz), 9.03 (1H, d, J=6.9 Hz), 12.66(1H, s).

Example 312

Preparation of the Compound of Compound No. 312

(1) 4-Chloro-2-({[3,5-bis(trifluoromethyl)phenyl]imino}methyl)phenol

Using 5-chlorosalicylaldehyde and 3,5-bis(trifluoromethyl)aniline as the raw materials, the same operation as the Example 14(1) gave the title compound.

Yield: 76.6%. $^1$H-NMR(DMSO-d$_6$): δ 7.04(1H, d, J=9.0 Hz), 7.50(1H, dd, J=9.0, 2.7 Hz), 7.80(1H, d, J=2.7 Hz), 8.01(1H, s), 8.12(2H, s), 9.03(1H, s), 12.09(1H, brs).

(2) N-[(5-Chloro-2-hydroxyphenyl)methyl]-3,5-bis(trifluoromethyl)aniline (Compound No. 312)

Using 4-chloro-2-({[3,5-bis(trifluoromethyl)phenyl]imino}methyl)phenol as the raw material, the same operation as the Example 14(2) gave the title compound.

Yield: 78.1%. $^1$H-NMR(CDCl$_3$): δ 4.40(3H, s), 6.27(1H, s), 6.80(1H, d, J=8.4 Hz), 7.11(2H, s), 7.17-7.20(2H, m), 7.30(1H, s).

Example 313

Preparation of the Compound of Compound No. 313

WSC.HCl (138 mg, 0.7 mmol) was added to a solution of N-[(5-chloro-2-hydroxyphenyl)methyl]-3,5-bis(trifluoromethyl)aniline (Compound No. 312; 88.8 mg, 0.24 mmol) and acetic acid (43 mg, 0.7 mmol) in dichloromethane (2 mL) under argon atmosphere, and the mixture was stirred at room temperature for 12 hours. After the reaction mixture was diluted with ethyl acetate, washed successively with water and brine, dried over anhydrous sodium sulfate, the residue obtained by evaporation of the solvent under reduced pressure was purified by column chromatography on silica gel (n-hexane:ethyl acetate=3:1) to give the title compound (69 mg, 70.4%) as a white powder.

$^1$H-NMR(CDCl$_3$): δ 1.92(3H, s), 4.73(2H, s), 6.54(1H, d, J=2.4 Hz), 6.95(1H, d, J=8.4 Hz), 7.22(1H, dd, J=8.7, 2.4 Hz), 7.53(2H, s), 7.99(1H, s), 9.21(1H, s).

Example 314

Preparation of the Compound of Compound No. 314

3,5-Bis(trifluoromethyl)benzoyl chloride (100 μL, 0.55 mmol) was added to a solution of 5-chlorosalicylhydrazide (compound of Example 304(1); 0.1 g, 0.53 mmol) in pyridine (3 mL) and the mixture was stirred at room temperature for 6 hours. The reaction mixture was poured into 2N hydrochloric acid and extracted with ethyl acetate. After the ethyl acetate layer was washed with brine and dried over anhydrous sodium sulfate, the residue obtained by evaporation of the solvent under reduced pressure was washed with ethyl acetate/isopropyl ether/n-hexane under suspension to give the title compound (169 mg, 74.7%) as a white powder.

$^1$H-NMR(DMSO-$d_6$): δ 7.04(1H, d, J=9.0 Hz), 7.51(1H, dd, J=8.7, 2.4 Hz), 7.92(1H, d, J=2.4 Hz), 8.43(1H, s), 8.57 (2H, s), 10.79(1H, s), 11.37(1H, s), 11.81(1H, s).

Example 315

Preparation of the Compound of Compound No. 315

A mixture of 5-chlorosalicylhydrazide (compound of Example 304(1); 0.10 g, 0.53 mmol), 3,5-bis(trifluoromethyl)benzyl bromide (120 μL, 0.65 mmol), triethylamine (0.2 mL, 1.43 mmol) and toluene (4 mL) was stirred at 100° C. for 2 hours. After the reaction mixture was cooled to room temperature, it was poured into diluted hydrochloric acid and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=3:1) and crystallized by n-hexane to give the title compound (45.6 mg, 20.9%) as a white powder.

$^1$H-NMR(CDCl$_3$): δ 4.22(2H, d, J=4.8 Hz), 5.13(1H, q, J=4.8 Hz), 6.96(1H, d, J=8.7 Hz), 7.23(1H, d, J=2.4 Hz), 7.37(1H, dd, J=9.0, 2.4 Hz), 7.69(1H, d, J=4.8 Hz), 7.85(1H, s), 7.88(2H, s), 11.54(1H, s).

Example 316

Preparation of the Compound of Compound No. 316

A mixture of 5-chlorosalicylic acid (172.6 mg, 1 mmol), 3,5-bis(trifluoromethyl)phenol (152 μL, 1 mmol), phosphorus oxychloride (40 μL, 0.43 mmol) and xylene (3 mL) was stirred at 140° C. for 2 hours. After the reaction mixture was cooled to room temperature, it was poured into water and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=10:1→5:1) to give the title compound (53.6 mg, 13.9%) as a white crystal.

$^1$H-NMR(CDCl$_3$): δ 7.04(1H, d, J=9.0 Hz), 7.54(1H, dd, J=9.0, 2.7 Hz), 7.75(2H, s), 7.86(1H, s), 8.02(1H, d, J=2.7 Hz), 10.09(1H, s).

Example 317

Preparation of the Compound of Compound No. 317

WSC.HCl (30.9 mg, 0.2 mmol) was added to a solution of 5-chlorosalicylic acid (35 mg, 0.2 mmol) and 3,5-bis(trifluoromethyl)phenylhydrazine (50 mg, 0.2 mmol) in dichloromethane (2 mL) under argon atmosphere, and the mixture was stirred at room temperature for 1 hour. After the reaction mixture was diluted with ethyl acetate, washed successively with water and brine, dried over anhydrous sodium sulfate, the residue obtained by evaporation of the solvent under reduced pressure was purified by column chromatography on silica gel (n-hexane:ethyl acetate=3:1) to give the title compound (56.3 mg, 69.6%) as a white powder.

$^1$H-NMR(CDCl$_3$): δ 6.61(1H, d, J=2.7 Hz), 6.99(1H, d, J=8.7 Hz), 7.28(2H, s), 7.41-7.45(2H, m), 7.62(1H, d, J=2.4 Hz), 8.53(1H, brs), 11.11(1H, s).

Example 318

Preparation of the Compound of Compound No. 318

(1) 2-Bromo-1-(5-chloro-2-hydroxyphenyl)ethanone

Phenyltrimethylammonium tribromide (0.44 g, 1.17 mmol) was added to a solution of 5'-chloro-2'-hydroxyacetophenone (0.20 g, 1.17 mmol) in tetrahydrofuran (6 mL) and the mixture was stirred at room temperature for 8 hours. The reaction mixture was poured into water and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=5:1) to give the title compound (220.7 mg, 75.6%) as an yellow oil.

$^1$H-NMR(CDCl$_3$): δ 4.41(2H, s), 7.00(1H, d, J=9.3 Hz), 7.47(1H, dd, J=8.7, 2.4 Hz), 7.71(1H, d, J=2.7 Hz), 11.63(1H, s).

(2) 2-(2-Aminothiazol-4-yl)-4-chlorophenol

A mixture of 2-bromo-1-(5-chloro-2-hydroxyphenyl)ethanone (156.9 mg, 0.63 mmol), thiourea (47.9 mg, 0.63 mmol) and ethanol (3 mL) was refluxed for 2 hours. After the reaction mixture was cooled to room temperature, it was poured into saturated sodium hydrogen carbonate solution and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=2:1) to give the title compound (98.6 mg, 64.5%) as a light yellowish white powder.

$^1$H-NMR(DMSO-$d_6$): δ 6.85(1H, d, J=8.7 Hz), 7.14(1H, dd, J=8.7, 3.0 Hz), 7.25(1H, s), 7.48(2H, s), 7.79(1H, d, J=3.0 Hz), 11.95(1H, s).

(3) N-[4-(5-Chloro-2-hydroxymethyl)thiazol-2-yl]-[3,5-bis(trifluoromethyl)phenyl]-benzamide (Compound No. 318)

Phosphorus trichloride (36 μL, 0.41 mmol) was added to a mixture of 2-(2-aminothiazol-4-yl)-4-chlorophenol (98.6 mg, 0.41 mmol), 3,5-bis(trifluoromethyl)benzoid acid (104.9 mg, 0.41 mmol), chlorobenzene (3 mL) and N-methyl-2-pyrrolidinone (3 mL), and the mixture was refluxed for 3 hours. After the reaction mixture was cooled to room temperature, it was poured into water and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=4:1→2:1) and washed with isopropyl ether/n-hexane under suspension to give the title compound (19.6 mg, 10.3%) as a white powder.

$^1$H-NMR(DMSO-$d_6$): δ 6.98(1H, d, J=8.4 Hz), 7.21(1H, dd, J=8.7, 2.7 Hz), 7.95(1H, s), 8.08(1H, d, J=2.7 Hz), 8.45 (1H, s), 8.77(2H, s), 10.90(1H, s), 13.15(1H, s).

Example 319

Preparation of the Compound of Compound No. 319

(1) 3-[3,5-Bis(trifluoromethyl)benzyl]thiazolidine-2,4-dione

5N Aqueous sodium hydroxide (0.5 mL) was added to a mixture of 2,4-thiazolidinedione (198.7 mg, 1.69 mmol), 3,5-bis(trifluoromethyl)benzyl bromide (0.50 g, 1.63 mmol) and ethanol (5 mL), and the mixture was refluxed for 4 hours. After the reaction mixture was cooled to room temperature, it was poured into water and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=3:1→2:1) to give the title compound (405.6 mg, 72.5%) as a white crystal.

$^1$H-NMR(CDCl$_3$): δ 4.01(2H, s), 4.87(2H, s), 7.84(1H, s), 7.86(2H, s).

(2) 5-(5-Chloro-2-hydroxybenzylidene)-3-[3,5-bis(trifluoromethyl)benzyl]thiazolidine-2,4-dione (Compound No. 319)

A mixture of 3-[3,5-bis(trifluoromethyl)benzyl]thiazolidine-2,4-dione (0.20 g, 0.58 mmol), piperidine (3 drops), acetic acid (3 drops) and toluene (5 mL) was stirred at room temperature for 10 minutes, then 5-chlorosalicylaldehyde (92.3 mg, 0.59 mmol) was added and the mixture was refluxed for 1 hour. After the reaction mixture was cooled to room temperature, it was poured into water and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=2:1→3:2) to give the title compound (173.2 mg, 62.0%) as a light yellow powder.

$^1$H-NMR(DMSO-d$_6$): δ 5.03(2H, s), 7.00(1H, d, J=9.0 Hz), 7.33(1H, d, J=2.4 Hz), 7.38(1H, dd, J=8.7, 2.7 Hz), 8.03(1H, s), 8.05(2H, s), 8.07(1H, s), 10.95(1H, s).

Example 320

Preparation of the Compound of Compound No. 320

A mixture of 3-hydroxyphthalic anhydride (33.5 mg, 0.2 mmol), 3,5-bis(trifluoromethyl)benzyl amine (62 mg, 0.2 mmol) and chlorobenzene (5 mL) was refluxed for 3 hours under argon atmosphere. After the reaction mixture was cooled to room temperature, the solvent was evaporated under reduced pressure and the obtained residue was crystallized from n-hexane/ethyl acetate to give the title compound (68.5 mg, 85.2%) as a white crystal.

$^1$H-NMR(CDCl$_3$): δ 4.90(2H, s), 7.19(1H, dd, J=8.4, 0.6 Hz), 7.41(1H, dd, J=7.2, 0.6 Hz), 7.61(1H, dd, J=8.4, 7.2 Hz), 7.75(1H, brs), 7.82(1H, brs), 7.86(2H, s).

Example 321

Preparation of the Compound of Compound No. 321

A mixture of 5-chlorosalicylaldehyde (150 mg, 1 mmol), 3,5-bis(trifluoromethyl)phenylhydrazine (200 mg, 0.9 mmol) and methanol (5 mL) was refluxed for 1 hour under argon atmosphere. After the reaction mixture was cooled to room temperature, methanol was evaporated under reduced pressure and the obtained residue was crystallized from n-hexane/ethyl acetate to give the title compound (224 mg, 66.6%) as a white powder.

$^1$H-NMR(CDCl$_3$): δ 6.97(1H, d, J=8.71 Hz), 7.17(1H, d, J=2.4 Hz), 7.24(1H, dd, J=9.0, 2.7 Hz), 7.35(2H, s), 7.41(1H, s), 7.82(1H, s), 7.87(1H, s), 10.29(1H, s).

Example 322

Preparation of the Compound of Compound No. 322

Using 6-hydroxysalicylic acid and 3,5-bis(trifluoromethyl)aniline as the raw materials, the same operation as the Example 16 gave the title compound.

Yield: 86.9%. $^1$H-NMR(DMSO-d$_6$): δ 6.36(2H, d, J=8.4 Hz), 7.13(1H, t, J=8.4 Hz), 7.79(1H, s), 8.38(2H, s), 11.40(2H, brs), 11.96(1H, brs).

Example 323

Preparation of the Compound of Compound No. 323

Using 4-methylsalicylic acid and 3,5-bis(trifluoromethyl)aniline as the raw materials, the same operation as the Example 16 gave the title compound.

Yield: 42.9%. $^1$H-NMR(DMSO-d$_6$): δ 2.32(3H, s) 6.82 (1H, d, J=6.6 Hz) 6.84(1H, s) 7.83(1H, s) 7.84(1H, d, J=8.5 Hz) 8.47(2H, s) 10.76(1H, s) 11.44(1H, s).

Example 324

Preparation of the Compound of Compound No. 324

Using 5-bromo-4-hydroxysalicylic acid and 3,5-bis(trifluoromethyl)aniline as the raw material, the same operation as the Example 16 gave the title compound.

Yield: 82.4%. $^1$H-NMR(CDCl$_3$): δ 5.89(1H, s) 6.70(1H, s) 7.69(2H, s) 7.95(1H, s) 8.12(2H, s) 11.62(1H, s).

Example 325

Preparation of the Compound of Compound No. 325

Using 4-hydroxysalicylic acid and 3,5-bis(trifluoromethyl)aniline as the raw materials, the same operation as the Example 16 gave the title compound.

Yield: 29.9%. $^1$H-NMR(DMSO-d$_6$): δ 6.37(1H, d, J=2.5 Hz), 6.42(1H, dd, J=8.8, 2.5 Hz), 7.81(1H, s), 7.86(1H, d, J=8.5 Hz), 8.44(2H, s), 10.31(1H, s), 10.60(1H, s), 11.77(1H, s).

Example 326

Preparation of the Compound of Compound No. 326

Using 3,5-dichlorosalicylic acid and 3,5-bis(trifluoromethyl)aniline as the raw materials, the same operation as the Example 16 gave the title compound.

Yield: 44.8%. $^1$H-NMR(DMSO-d$_6$): δ 7.85(1H, d, J=2.5 Hz), 7.91(1H, s), 8.01(1H, d, J=2.5 Hz), 8.42(2H, s), 11.10 (1H, s).

Example 327

Preparation of the Compound of Compound No. 327

Using 3-hydroxysalicylic acid and 3,5-bis(trifluoromethyl)aniline as the raw materials, the same operation as the Example 16 gave the title compound.

Yield: 22.7%. $^1$H-NMR(DMSO-$d_6$): δ 6.81(1H, t, J=8.0 Hz), 7.01(1H, dd, J=8.0, 1.5 Hz), 7.35(1H, dd, J=8.0, 1.5 Hz), 7.84(1H, s), 8.46(2H, s), 9.56(1H, s), 10.79(1H, s), 10.90(1H, brs).

Example 328

Preparation of the Compound of Compound No. 328

Using 3-methylsalicylic acid and 3,5-bis(trifluoromethyl)aniline as the raw materials, the same operation as the Example 16 gave the title compound.
Yield: 54.9%. $^1$H-NMR(DMSO-$d_6$): δ 2.22(3H, s), 6.94 (1H, t, J=7.4 Hz), 7.42(1H, d, J=7.4 Hz), 7.84-7.85(2H, m), 8.47(2H, s), 10.87(1H, s), 11.87(1H, s).

Example 329

Preparation of the Compound of Compound No. 329

Using 3-methoxysalicylic acid and 3,5-bis(trifluoromethyl)aniline as the raw materials, the same operation as the Example 16 gave the title compound.
Yield: 34.6%. $^1$H-NMR(DMSO-$d_6$): δ 3.85(3H, s), 6.94 (1H, t, J=8.0 Hz), 7.20(1H, dd, J=8.0, 1.4 Hz), 7.44(1H, dd, J=8.0, 1.4 Hz), 7.84(1H, s), 8.45(2H, s), 10.82(1H, s), 10.94 (1H, brs).

Example 330

Preparation of the Compound of Compound No. 330

Using 5-[(1,1,3,3-tetramethyl)butyl]salicylic acid and 3,5-bis(trifluoromethyl)aniline as the raw materials, the same operation as the Example 16 gave the title compound.
Yield: 64.2%. $^1$H-NMR(DMSO-$d_6$): δ 0.70(9H, s), 1.35 (6H, s), 1.72(2H, s), 6.95(1H, d, J=8.4 Hz), 7.50(1H, dd, J=8.0, 2.1 Hz), 7.83(1H, s), 7.84(1H, d, J=2.1 Hz), 8.46(1H, s), 10.77(1H, s), 11.20(1H, s).

Example 331

Preparation of the Compound of Compound No. 331

Using 3,5,6-trichlorosalicylic acid and 3,5-bis(trifluoromethyl)aniline as the raw materials, the same operation as the Example 16 gave the title compound.
Yield: 26.2%. $^1$H-NMR(DMSO-$d_6$): δ 7.88(1H, s), 7.93 (1H, s), 8.33(2H, s), 10.88(1H, s), 11.36(1H, s).

Example 332

Preparation of the Compound of Compound No. 332

Using 3,5-bis[(1,1-dimethyl)ethyl]salicylic acid and 3,5-bis(trifluoromethyl)aniline as the raw materials, the same operation as the Example 16 gave the title compound.
Yield: 65.0%. $^1$H-NMR(DMSO-$d_6$): δ 1.34(9H, s), 1.40 (9H, s), 7.49(1H, d, J=2.2 Hz), 7.82(1H, d, J=2.2 Hz), 7.91 (1H, s), 8.40(2H, s), 10.82(1H, s), 12.44(1H, s).

Example 333

Preparation of the Compound of Compound No. 333

Using 6-fluorosalicylic acid and 3,5-bis(trifluoromethyl)aniline as the raw materials, the same operation as the Example 16 gave the title compound.
Yield: 35.9%. $^1$H-NMR(DMSO-$d_6$): δ 6.73-6.82(2H, m), 7.32(1H, ddd, J=1.4, 8.5, 15.3 Hz), 7.83(1H, s), 8.39(2H, s), 10.50(1H, d, J=1.4 Hz), 11.11(1H, s).

Example 334

Preparation of the Compound of Compound No. 334

Using 3-chlorosalicylic acid and 3,5-bis(trifluoromethyl)aniline as the raw materials, the same operation as the Example 16 gave the title compound.
Yield: 61.3%. $^1$H-NMR(DMSO-$d_6$): δ 7.05(1H, dd, J=7.6, 8.0 Hz), 7.69(1H, dd, J=1.4, 13.3 Hz), 7.90(1H, s), 7.93(1H, dd, J=1.4, 8.0 Hz), 8.44(2H, s), 11.01(1H, s), 11.92(1H, br.s).

Example 335

Preparation of the Compound of Compound No. 335

Using 4-methoxysalicylic acid and 3,5-bis(trifluoromethyl)aniline as the raw materials, the same operation as the Example 16 gave the title compound.
Yield: 14.2%. $^1$H-NMR(DMSO-$d_6$): δ 3.81(3H, s), 6.54 (1H, d, J=2.5 Hz), 6.61(1H, dd, J=2.5, 8.8 Hz), 7.83(1H, s), 7.95(1H, d, J=8.8 Hz), 8.45(2H, s), 10.69(1H, s), 11.89(1H, s).

Example 336

Preparation of the Compound of Compound No. 336

Using 6-methoxysalicylic acid and 3,5-bis(trifluoromethyl)aniline as the raw materials, the same operation as the Example 16 gave the title compound.
Yield: 63.1%. $^1$H-NMR(DMSO-$d_6$): δ 3.24(3H, s), 6.03 (1H, d, J=8.0 Hz), 6.05(1H, d, J=8.5 Hz), 6.71(1H, dd, J=8.2, 8.5 Hz), 7.25(1H, s), 7.88(2H, s), 9.67(1H, s), 10.31(1H, s)

Example 337

Preparation of the Compound of Compound No. 337

Using 5-amino-N-[3,5-bis(trifluoromethyl)phenyl]-2-hydroxybenzamide (Compound No. 88) and methanesulfonyl chloride as the raw materials, the same operation as the Example 91 gave the title compound.
Yield: 22.6%. $^1$H-NMR(DMSO-$d_6$): δ 2.93(3H, s), 7.02 (1H, d, J=8.4 Hz), 7.31(1H, dd, J=8.4, 2.7 Hz), 7.68(1H, d, J=2.7 Hz), 7.83(1H, s), 8.46(2H, s), 9.48(1H, s), 10.85(1H, s), 11.15(1H, s).

Example 338

Preparation of the Compound of Compound No. 338

Using 5-amino-N-[3,5-bis(trifluoromethyl)phenyl]-2-hydroxybenzamide (Compound No. 88) and benzenesulfonyl chloride as the raw materials, the same operation as the Example 91 gave the title compound.

Yield: 45.3%. $^1$H-NMR(DMSO-d$_6$): δ 6.89(1H, d, J=8.7 Hz), 7.10(1H, dd, J=8.7, 2.7 Hz), 7.51-7.64(4H, m), 7.68-7.71(2H, m), 7.81(1H, s), 8.42(2H, s), 10.03(1H, s), 10.87 (1H, s), 11.13(1H, brs).

Example 339

Preparation of the Compound of Compound No. 339

Using 5-amino-N-[3,5-bis(trifluoromethyl)phenyl]-2-hydroxybenzamide (Compound No. 88) and acetyl chloride as the raw materials, the same operation as the Example 91 gave the title compound.

Yield: 44.8%. $^1$H-NMR(DMSO-d$_6$): δ 2.02(3H, s), 6.97 (1H, d, J=8.7 Hz), 7.61(1H, dd, J=8.7, 2.7 Hz), 7.82(1H, s), 7.99(1H, d, J=2.7 Hz), 8.46(2H, s), 9.90(1H, s), 10.85(1H, s), 10.94(1H, s).

Example 340

Preparation of the Compound of Compound No. 340

Using N-[3,5-bis(trifluoromethyl)phenyl]-2-methoxy-5-sulfamoyl-benzamide (compound of Example 87(2)) as the raw material, the same operation as the Example 80(5) gave the title compound.

Yield: 59.9%. $^1$H-NMR(DMSO-d$_6$): δ 7.17(1H, d, J=8.7 Hz), 7.31(2H, s), 7.85(1H, s), 7.86(1H, dd, J=8.4, 2.4 Hz), 8.26(1H, d, J=2.7 Hz), 8.47(2H, s), 10.95(1H, s), 11.90(1H, s).

Example 341

Preparation of the Compound of Compound No. 341

Using 3-hydroxynaphthalene-2-carboxylic acid and 3,5-bis(trifluoromethyl)aniline as the raw materials, the same operation as the Example 16 gave the title compound.

Yield: 46.9%. $^1$H-NMR(DMSO-d$_6$): δ 7.36-7.41(2H, m), 7.50-7.55(1H, m), 7.79(1H, d, J=8.2 Hz), 7.85(1H, d, J=0.6 Hz), 7.96(1H, d, J=8.0 Hz), 8.51(2H, s), 10.98(1H, s), 11.05 (1H, s).

Example 342

Preparation of the Compound of Compound No. 342

Using 2-hydroxynaphthalene-1-carboxylic acid and 3,5-bis(trifluoromethyl)aniline as the raw materials, the same operation as the Example 16 gave the title compound.

Yield: 30.2%. $^1$H-NMR(DMSO-d$_6$): δ 7.27(1H, d, J=8.8 Hz), 7.32-7.38(1H, m), 7.45-7.50(1H, m), 7.72(1H, d, J=8.5 Hz), 7.82-7.93(3H, m), 8.50(1H, s), 10.28(1H, s), 11.07(1H, brs).

Example 343

Preparation of the Compound of Compound No. 343

(1) 4-Bromo-3-hydroxythiophene-2-carboxylic acid

A mixture of 4-bromothiophene-2-carboxylic acid methyl ester (500 mg, 2.1 mmol), sodium hydroxide (261 mg, 6.3 mmol) in a mixed solvent of methanol/water (2.5 mL+2.5 mL) was refluxed for 2 hours. After the reaction mixture was cooled to room temperature, 2N hydrochloric acid was added to adjust pH to 1, and it was diluted with ethyl acetate. After the ethyl acetate layer was washed successively with water and brine, dried over anhydrous sodium sulfate, the solvent was evaporated under reduced pressure to give the title compound (326 mg, 69.4%) as a red brown powder.

$^1$H-NMR(CDCl$_3$): δ 4.05(1H, brs), 7.40(1H, s).

(2) 4-Bromo-3-hydroxy-N-[3,5-bis(trifluoromethyl) phenyl]thiophene-2-carboxamide (Compound No. 343)

Using 4-bromo-3-hydroxythiophene-2-carboxylic acid and 3,5-bis(trifluoromethyl)aniline as the raw materials, the same operation as the Example 16 gave the title compound.

Yield: 82.4%. $^1$H-NMR(CDCl$_3$): δ 7.42(1H, s), 7.67(1H, brs), 7.78(1H, brs), 8.11(2H, s), 9.91(1H, brs).

Example 344

Preparation of the Compound of Compound No. 344

Using 3,5-bis(trifluoromethyl)phenylisocyanate and oxindole as the raw materials, the same operation as the Example 28 gave the title compound.

Yield: 44.8%. $^1$H-NMR(DMSO-d$_6$): δ 3.98(2H, s), 7.22 (1H, td, J=7.8, 1.2 Hz), 7.33-7.40(2H, m), 7.87(1H, s), 8.02 (1H, d, J=7.8 Hz), 8.38(2H, s), 11.00(1H, s).

Example 345

Preparation of the Compound of Compound No. 345

Using 3,5-bis(trifluoromethyl)phenylisocyanate and 5-chlorooxindole as the raw materials, the same operation as the Example 28 gave the title compound.

Yield: 31.1%. p $^1$H-NMR(DMSO-d$_6$): δ 3.99(2H, s), 7.41 (1H, dd, J=8.7, 2.4 Hz), 7.47(1H, d, J=2.1 Hz), 7.87(1H, s), 8.01(1H, d, J=8.4 Hz), 8.38(2H, s), 10.93(1H, s).

Example 346

Preparation of the Compound of Compound No. 346

Using 5-chlorosalicylic acid and 3-bromo-5-(trifluoromethyl)aniline as the raw materials, the same operation as the Example 16 gave the title compound.

Yield: 37.1%. $^1$H-NMR(DMSO-d$_6$): δ 7.03(1H, d, J=9.3 Hz), 7.48(1H, dd, J=8.7, 2.4 Hz), 7.72(1H, s), 7.84(1H, d, J=2.7 Hz), 8.16(1H, s), 8.28(1H, s), 10.69(1H, s), 11.42(1H, s).

Example 347

Preparation of the Compound of Compound No. 347

Using 5-chlorosalicylic acid and 3-methoxy-5-(trifluoromethyl)aniline as the raw materials, the same operation as the Example 16 gave the title compound.

Yield: 68.0%. $^1$H-NMR(DMSO-d$_6$): δ 3.85(3H, s), 7.02 (1H, s), 7.03(1H, d, J=8.7 Hz), 7.48(1H, dd, J=8.7, 2.7 Hz), 7.61(1H, s), 7.77(1H, s), 7.88(1H, d, J=2.7 Hz), 10.57(1H, s), 11.53(1H, s).

Example 348

Preparation of the Compound of Compound No. 348

Using 5-chlorosalicylic acid and 2-morpholino-5-(trifluoromethyl)aniline as the raw materials, the same operation as the Example 16 gave the title compound.

Yield: 64.80%. $^1$H-NMR(DMSO-d$_6$): δ 2.90(4H, m), 3.84 (4H, m), 7.15(1H, d, J=9.0 Hz), 7.48(2H, s), 7.50(1H, dd, J=9.0, 2.7 Hz), 8.00(1H, d, J=2.7 Hz), 8.91(1H, s), 11.24(1H, s), 12.05(1H, s).

Example 349

Preparation of the Compound of Compound No. 349

Using 5-chlorosalicylic acid and 2-bromo-5-(trifluoromethyl)aniline as the raw material, the same operation as the Example 16 gave the title compound.
Yield: 59.2%. $^1$H-NMR(DMSO-d$_6$): δ 7.10(1H, d, J=8.7 Hz), 7.48(1H, dd, J=8.4, 2.1 Hz), 7.53(1H, dd, J=8.7, 3.0 Hz), 7.97-7.99(2H, m), 8.81(1H, d, J=2.1 Hz), 11.03(1H, s), 12.38 (1H, s).

Example 350

Preparation of the Compound of Compound No. 350

Using 5-chlorosalicylic acid and 3-amino-5-(trifluoromethyl)benzoic acid methyl ester as the raw materials, the same operation as the Example 16 gave the title compound.
Yield: 67.0%. $^1$H-NMR(DMSO-d$_6$): δ 3.91(3H, s), 7.02 (1H, d, J=9.3 Hz), 7.43(1H, dd, J=9.0, 2.4 Hz), 7.57(1H, d, J=2.4 Hz), 8.13(1H, s), 8.23(1H, s), 8.29(1H, s), 8.36(1H, s), 11.52(1H, s).

Example 351

Preparation of the Compound of Compound No. 351

2N Aqueous sodium hydroxide (0.6 mL) was added to a mixture of 5-chloro-2-hydroxy-N-[3-methoxycarbonyl-5-(trifluoromethyl)phenyl]benzamide (Compound No. 350; 105 mg, 0.281 mmol) and methanol (2.5 mL), and the mixture was stirred at room temperature for 3 hours. Water was added to the reaction mixture and it was washed with ethyl acetate. After the water layer was acidified by addition of diluted hydrochloric acid, it was extracted with ethyl acetate. After the ethyl acetate layer was washed successively with water and brine, dried over anhydrous sodium sulfate, the residue obtained by evaporation of the solvent under reduced pressure was crystallized by isopropyl ether to give the title compound (100 mg, 99.0%) as a white solid.
$^1$H-NMR(DMSO-d$_6$): δ 7.04(1H, d, J=9.0 Hz), 7.49(1H, dd, J=8.7, 2.7 Hz), 7.91(1H, d, J=2.7 Hz), 7.93(1H, s), 8.43 (1H, s), 8.59(1H, s), 10.78(1H, s), 11.48(1H, s).

Example 352

Preparation of the Compound of Compound No. 352

Using 5-chlorosalicylic acid and 2-(2-naphthyloxy)-5-(trifluoromethyl)aniline as the raw materials, the same operation as the Example 16 gave the title compound.
Yield: 89.6%. $^1$H-NMR(CDCl$_3$): δ 6.94(1H, d, J=9.6 Hz), 6.98(1H, d, J=9.2 Hz), 7.25-7.41(4H, m), 7.48-7.57(3H, m), 7.81(1H, d, J=6.9 Hz), 7.88(1H, d, J=6.9 Hz), 7.95(1H, d, J=8.9 Hz), 8.72(1H, s), 8.83(1H, d, J=2.0 Hz), 11.70(1H, s).

Example 353

Preparation of the Compound of Compound No. 353

Using 5-chlorosalicylic acid and 2-(2,4-dichlorophenoxy)-5-(trifluoromethyl)aniline as the raw materials, the same operation as the Example 16 gave the title compound.

Yield: 4.7%. $^1$H-NMR(CDCl$_1$): δ 6.78(1H d, J=8.9 Hz), 7.02(1H, d, J=8.6 Hz), 7.16(1H, d, J=8.6 Hz), 7.33-7.38(3H, m), 7.42(1H, dd, J=8.6, 2.6 Hz), 7.49(1H, d, J=2.6 Hz) 7.58 (1H, d, J=2.3 Hz), 8.66(1H, brs,), 8.82(1H, d, J=2.0 Hz), 11.65(1H, s).

Example 354

Preparation of the Compound of Compound No. 354

Using 5-chlorosalicylic acid and 2-[(4-trifluoromethyl)piperidino]-5-(trifluoromethyl)aniline as the raw materials, the same operation as the Example 16 gave the title compound.
Yield: 60.5%. $^1$H-NMR(CDCl$_3$): δ 1.85-2.05(2H, m), 2.15 (2H, d, J=10.9 Hz), 2.28(1H, m), 2.82(2H, t, J=11.0 Hz), 3.16(2H, d, J=12.2 Hz), 7.02(1H, d, J=8.9 Hz), 7.31(1H, d, J=8.3 Hz), 7.42(2H, m), 7.50(1H, d, J=2.6 Hz), 8.75(1H, s), 9.60(1H, s), 11.94(1H, s)

Example 355

Preparation of the Compound of Compound No. 355

Using 5-chlorosalicylic acid and 2-(2,2,2-trifluoroethoxy)-5-(trifluoromethyl)-aniline as the raw materials, the same operation as the Example 16 gave the title compound.
Yield: 94.5%. $^1$H-NMR(CDCl$_3$): δ 4.58(2H, q, J=7.9 Hz), 6.99-7.05(2H, m), 7.41-7.50(3H, m), 8.63(1H, brs), 8.79(1H, d, J=2.0 Hz), 11.59(1H, s).

Example 356

Preparation of the Compound of Compound No. 356

Using 5-chlorosalicylic acid and 2-(2-methoxyphenoxy)-5-(trifluoromethyl)aniline as the raw materials, the same operation as the Example 16 gave the title compound.
Yield: 80.6%. $^1$H-NMR(DMSO-d$_6$): δ 3.74(3H, s), 6.70 (1H, d, J=8.4 Hz), 7.02(1H, d, J=8.7 Hz), 7.07(1H, dd, J=1.5, 7.8 Hz), 7.24-7.39(4H, m), 7.49(1H, dd, J=3.0, 8.7 Hz), 8.00 (1H, d, J=3.0 Hz), 8.92(1H, d, J=2.1 Hz), 11.36(1H, s), 12.18 (1H, s).

Example 357

Preparation of the Compound of Compound No. 357

Using 5-chlorosalicylic acid and 2-(4-chloro-3,5-dimethylphenoxy)-5-(trifluoromethyl)aniline as the raw materials, the same operation as the Example 16 gave the title compound.
Yield: 91.5%. $^1$H-NMR(DMSO-d$_6$): δ 2.34(6H, s), 7.03 (1H, d, J=8.8 Hz), 7.05(1H, d, J=8.1 Hz), 7.11(2H, s), 7.43-7.47(1H, m), 7.48(1H, dd, J=2.9, 8.8 Hz), 7.97(1H, d, J=2.6 Hz), 8.94(1H, d, J=2.2 Hz), 11.25(1H, s), 12.12(1H, s).

Example 358

Preparation of the Compound of Compound No. 358

Using 5-chlorosalicylic acid and 2-piperidino-5-(trifluoromethyl)aniline as the raw materials, the same operation as the Example 16 gave the title compound.
Yield: 73.7%. $^1$H-NMR(CDCl$_3$): δ 1.68-1.72(2H, m), 1.80-1.88(4H, m), 2.89(4H, t, J=5.2 Hz), 7.01(1H, d, J=8.7

Hz), 7.31(1H, d, J=8.4 Hz), 7.39-7.43(2H, m), 7.55(1H, d, J=2.4 Hz), 8.73(1H, d, J=1.8 Hz), 9.71(1H, s), 12.05(1H, s)

Example 359

Preparation of the Compound of Compound No. 359

Using 5-chlorosalicylic acid and 2-(4-methylphenoxy)-5-(trifluoromethyl)-aniline as the raw materials, the same operation as the Example 16 gave the title compound.

Yield: 67.3%. $^1$H-NMR(DMSO-d$_6$): δ 2.33(3H, s), 6.93 (1H, d, J=8.8 Hz), 7.03(1H, dd, J=0.5, 8.8 Hz), 7.12(2H, d, J=8.2 Hz), 7.29(2H, d, J=8.5 Hz), 7.43(1H, dd, J=2.0, 8.6 Hz), 7.48(1H, ddd, J=0.8, 2.7, 8.8 Hz), 7.98(1H, dd, J=0.8, 2.7 Hz), 8.94(1H, d, J=2.2 Hz), 11.29(1H, s), 12.15(1H, s).

Example 360

Preparation of the Compound of Compound No. 360

Using 5-chlorosalicylic acid and 2-(4-chlorophenoxy)-5-(trifluoromethyl)-aniline as the raw materials, the same operation as the Example 16 gave the title compound.

Yield: 74.5%. $^1$H-NMR(DMSO-d$_6$): δ 7.01(1H, d, J=8.8 Hz), 7.06(1H, d, J=8.5 Hz), 7.22(1H, d, J=8.5 Hz), 7.43-7.48 (2H, m), 7.50(2H, d, J=8.2 Hz), 7.94(1H, dd, J=0.5, 2.7 Hz), 8.92(1H, d, J=2.2 Hz), 11.20(1H, s), 12.10(1H, s).

Example 361

Preparation of the Compound of Compound No. 361

Using 5-bromo-2-hydroxy-N-[3,5-bis(methoxycarbonyl) phenyl]benzamide (Compound No. 170) as the raw material, the same operation as the Example 351 gave the title compound.

Yield: 89.0%. $^1$H-NMR(DMSO-d$_6$): δ 6.98(1H, d, J=8.7 Hz), 7.60(1H, dd, J=8.7, 2.4 Hz), 7.24(1H, dd, J=8.7, 2.7 Hz), 8.08(1H, d, J=2.7 Hz), 8.24(1H, t, J=1.5 Hz), 8.57(2H, d, J=1.2 Hz), 10.67(1H, s), 11.64(1H, s).

Example 362

Preparation of the Compound of Compound No. 362

Using 5-chlorosalicylic acid and 2-methyl-5-[(1-methyl) ethyl]aniline as the raw materials, the same operation as the Example 16 gave the title compound.

Yield: 19.1%. $^1$H-NMR(CDCl$_3$): δ 1.26(6H, d, J=6.9 Hz), 2.30(3H, s), 2.87-2.96(1H, m), 7.00(1H, d, J=8.7 Hz), 7.08 (1H, dd, J=7.8, 1.8 Hz), 7.20(1H, d, J=7.8 Hz), 7.40(1H, dd, J=8.7, 2.4 Hz), 7.49(1H, d, J=2.7 Hz), 7.50(1H, s), 7.71(1H, s), 11.99(1H, s).

Example 363

Preparation of the Compound of Compound No. 363

Using 5-chlorosalicylic acid and 2,5-diethoxyaniline as the raw materials, the same operation as the Example 16 gave the title compound.

Yield: 59.2%. $^1$H-NMR(DMSO-d$_6$): δ 1.32(3H, t, J=6.9 Hz), 1.41(3H, t, J=6.9 Hz), 3.97(2H, q, J=6.9 Hz), 4.06(2H, q, J=6.9 Hz), 6.61(1H, dd, J=9.0, 3.0 Hz), 6.98(1H, d, J=8.7 Hz), 7.10(1H, d, J=8.7 Hz), 7.48(1H, dd, J=8.7, 2.7 Hz), 7.97(1H, d, J=2.7 Hz), 8.16(1H, d, J=3.0 Hz), 10.96(1H, s), 11.91(1H, s).

Example 364

Preparation of the Compound of Compound No. 364

Using 5-chlorosalicylic acid and 2,5-dimethylaniline as the raw materials, the same operation as the Example 16 gave the title compound.

Yield: 90.5%. $^1$H-NMR(CDCl$_3$): δ 2.28(3H, s), 2.35(3H, s), 6.99(1H, d, J=8.8 Hz), 7.02(1H, brs), 7.15(1H, d, J=7.7 Hz), 7.40(1H, dd, J=8.8, 2.5 Hz), 7.45(1H, brs), 7.49(1H, d, J=2.5 Hz) 7.70(1H, br), 11.96(1H, brs).

Example 365

Preparation of the Compound of Compound No. 365

Using 5-chlorosalicylic acid and 5-chloro-2-cyanoaniline as the raw materials, the same operation as the Example 16 gave the title compound.

Yield: 90.0%. $^1$H-NMR(DMSO-d$_6$): δ 7.09(1H, d, J=9.0 Hz), 7.53(1H, dd, J=8.7, 3.0 Hz), 7.82(1H, dd, J=8.7, 2.4 Hz), 7.95(1H, d, J=3.0Hz), 8.07(1H, d, J=2.4 Hz), 8.36(1H, d, J=9.0 Hz), 11.11(1H, s), 12.36(1H, s).

Example 366

Preparation of the Compound of Compound No. 366

Using 5-chlorosalicylic acid and 5-(N,N-diethylsulfamoyl)-2-methoxyaniline as the raw materials, the same operation as the Example 16 gave the title compound.

Yield: 44.8%. $^1$H-NMR(CDCl$_3$): δ 1.17(6H, t, J=7.3 Hz), 3.29(4H, q, J=7.3 Hz), 4.05(3H, s), 7.00(2H, dd, J=2.3, 8.9 Hz), 7.41(1H, dd, J=2.3, 8.9 Hz), 7.48(1H, d, J=2.6 Hz), 7.65(1H, dd, J=2.3, 8.6 Hz), 8.56(1H, br.s), 8.84(1H, d, J=2.3 Hz), 11.82(1H, s).

Example 367

Preparation of the Compound of Compound No. 367

Using 5-chlorosalicylic acid and 2-chloro-5-nitroaniline as the raw materials, the same operation as the Example 16 gave the title compound.

Yield: 73.3%. $^1$H-NMR(CD$_3$OD): δ 6.98(1H, d, J=8.6 Hz), 7.43(1H, dd, J=2.6, 8.6 Hz), 7.74(1H, d, J=8.9 Hz), 7.99(1H, dd, J=3.0, 8.9 Hz), 8.08(1H, d, J=2.6 Hz), 9.51(1H, d, J=2.6 Hz).

Example 368

Preparation of the Compound of Compound No. 368

Using 5-chlorosalicylic acid and 5-(N-phenylcarbamoyl)-2-methoxyaniline as the raw material, the same operation as the Example 16 gave the title compound.

Yield: 40.3%. $^1$H-NMR(DMSO-d$_6$): δ 3.99(3H, s), 7.09 (2H, dd, J=6.6, 6.9 Hz), 7.24(1H, d, J=8.6 Hz), 7.35(2H, dd, 6.9, 7.3 Hz), 7.49(1H, d, J=2.3, 8.9 Hz), 7.77(3H, d, J=8.6 Hz), 8.00(1H, s), 8.97(1H, s), 10.17(1H, s), 10.91(1H, s), 12.11(1H, s).

Example 369

Preparation of the Compound of Compound No. 369

Using 5-chlorosalicylic acid and 2,5-dimethoxyaniline as the raw materials, the same operation as the Example 16 gave the title compound.

Example 370

Preparation of the Compound of Compound No. 370

Using 5-chlorosalicylic acid and 5-acetylamino-2-methoxyaniline as the raw materials, the same operation as the Example 16 gave the title compound.

Yield: 16.9%. $^1$H-NMR(DMSO-d$_6$): δ 2.01(3H, s), 3.85 (3H, s), 7.03(2H, t, J=9.6 Hz), 7.49(2H, dd, J=8.9, 9.2 Hz), 7.96(1H, s), 8.51(1H, s), 9.87(1H, s), 10.82(1H, s), 12.03(1H, d, J=4.0 Hz).

Example 371

Preparation of the Compound of Compound No. 371

Using 5-chlorosalicylic acid and 5-methoxy-2-methylaniline as the raw materials, the same operation as the Example 16 gave the title compound.

Yield: 100%. $^1$H-NMR(CDCl$_3$): δ 2.29(3H, s), 3.82(3H, s), 6.75(1H, dd, J=2.6, 8.2 Hz), 7.00(1H, d, J=8.9 Hz), 7.16 (1H, d, J=8.6 Hz), 7.38(1H, d, 2.3 Hz), 7.41(1H, dd, J=2.3, 8.9 Hz), 7.48(1H, d, J=2.3 Hz), 7.70(1H, br.s), 11.92(1H, s).

Example 372

Preparation of the Compound of Compound No. 372

Using 5-chlorosalicylic acid and 2,5-dibutoxyaniline as the raw materials, the same operation as the Example 16 gave the title compound.

Yield: 73.9%. $^1$H-NMR(CDCl$_3$): δ 0.98(3H, t, J=7.2 Hz), 1.05(3H, t, J=7.2 Hz), 1.44-1.65(4H, m), 1.72-1.79(2H, m), 1.81-1.91(2H, m), 3.97(2H, t, J=6.3 Hz), 4.07(2H, t, J=6.3 Hz), 6.64(1H, dd, J=9.0, 3.0 Hz), 6.85(1H, d, J=9.3 Hz), 6.99(1H, d, J=9.0 Hz), 7.39(1H, dd, J=8.7, 2.4 Hz), 7.44(1H, d, J=2.7 Hz), 8.08(1H, d, J=3.0 Hz), 8.76(1H, s), 12.08(1H, s).

Example 373

Preparation of the Compound of Compound No. 373

Using 5-chlorosalicylic acid and 2,5-diisopentyloxyaniline as the raw materials, the same operation as the Example 16 gave the title compound.

Yield: 59.7%. $^1$H-NMR(CDCl$_3$): δ 0.97(6H, d, J=6.6 Hz), 1.03(6H, d, 6.6 Hz), 1.64-1.98(6H, m), 3.99(2H, t, J=6.6 Hz), 4.09(2H, t, J=6.3 Hz), 6.63(1H, dd, J=8.7, 3.0 Hz), 6.85(1H, d, J=8.7 Hz), 6.98(1H, d, J=8.7 Hz), 7.38(1H, dd, J=9.0, 2.4 Hz), 7.43(1H, d, J=2.7 Hz), 8.09(1H, d, J=3.0 Hz), 8.75(1H, s), 12.08(1H, s).

Example 374

Preparation of the Compound of Compound No. 374

Using 5-chlorosalicylic acid and 5-carbamoyl-2-methoxyaniline as the raw materials, the same operation as the Example 16 gave the title compound.

Yield: 73.9%. $^1$H-NMR(CDCl$_3$): δ 3.82(3H, s), 3.93(3H, s), 6.66(1H, dd, J=3.0, 8.9 Hz), 6.86(1H, d, J=8.9 Hz), 6.98 (1H, d, J=8.9 Hz), 7.39(1H, dd, J=2.6, 8.9 Hz), 7.47(1H, d, J=2.6 Hz), 8.08(1H, d, J=3.0 Hz), 8.60(1H, br.s), 12.03(1H, s).

Yield: 31.2%. $^1$H-NMR(CD$_3$OD): δ 4.86(3H, s), 6.93(1H, d, J=7.6 Hz), 7.18(1H, d, J=8.6 Hz), 7.35(1H, dd, J=3.0, 7.6 Hz), 7.47(1H, dd, J=2.0, 8.6 Hz), 8.00(1H, d, J=3.0 Hz), 8.80(1H, d, J=2.0 Hz).

Example 375

Preparation of the Compound of Compound No. 375

Using 5-chlorosalicylic acid and 5-[(1,1-dimethyl)propyl]-2-phenoxyaniline as the raw materials, the same operation as the Example 16 gave the title compound.

Yield: 65.2%. $^1$H-NMR(CDCl$_3$): δ 0.69(3H, t, J=7.6 Hz), 1.29(6H, s), 1.64(2H, q, J=7.6 Hz), 6.91(1H, dd, J=1.7, 7.6 Hz), 6.96(1H, d, J=8.9 Hz), 7.03(2H, d, J=8.9 Hz), 7.10(1H, dt, J=1.7, 7.6 Hz), 7.16(1H, dt, J=1.7, 7.6 Hz), 7.40-7.31(4H, m), 8.42(1H, dd, J=2.0, 7.9 Hz), 8.53(1H, br.s) 11.94(1H, s).

Example 376

Preparation of the Compound of Compound No. 376

Using 5-chlorosalicylic acid and 2-hexyloxy-5-(methylsulfonyl)aniline as the raw materials, the same operation as the Example 16 gave the title compound.

Yield: 33.0%. $^1$H-NMR(CDCl$_3$): δ 0.92(3H, t, J=6.9 Hz), 1.40-1.59(6H, m), 1.90-2.01(2H, m), 3.09(3H, s), 4.22(2H, t, J=6.3 Hz), 7.01(1H, d, J=8.9 Hz), 7.06(1H, d, J=8.6 Hz), 7.40-7.43(2H, m), 7.73(1H, dd, J=8.6, 2.3 Hz), 8.74(1H, brs), 8.99(1H, d, J=2.3 Hz), 11.76(1H, s).

Example 377

Preparation of the Compound of Compound No. 377

Using 5-chlorosalicylic acid and 3'-amino-2,2,4'-trimethylpropiophenone as the raw materials, the same operation as the Example 16 gave the title compound.

Yield: 44.8%. $^1$H-NMR(CDCl$_3$): δ 1.38(9H, s), 2.38(3H, s), 7.01(1H, d, J=8.9 Hz), 7.31(1H, d, J=7.9 Hz), 7.42(1H, dd, J=8.9, 2.6 Hz), 7.53(1H, d, J=2.6 Hz), 7.57(1H, dd, J=7.9, 2.0 Hz), 7.83(1H, brs), 8.11(1H, d, J=2.0 Hz), 11.82(1H, s).

Example 378

Preparation of the Compound of Compound No. 378

Using 5-chlorosalicylic acid and 5-methoxy-2-(1-pyrrolyl)aniline as the raw materials, the same operation as the Example 16 gave the title compound.

Yield: 53.4%. $^1$H-NMR(CDCl$_3$): δ 2.46(3H, s), 6.51-6.52 (2H, m), 6.82-6.85(3H, m), 6.93(1H, d, J=8.9 Hz), 7.06(1H, d, J=7.9 Hz), 7.30(1H, d, J=7.9 Hz), 7.32(1H, dd, J=2.3, 8.9 Hz), 7.61(1H, s), 8.29(1H, s), 11.86(1H, br.s).

Example 379

Preparation of the Compound of Compound No. 379

Using 5-chlorosalicylic acid and 5-chloro-2-tosylaniline as the raw materials, the same operation as the Example 16 gave the title compound.

Yield: 8.0%. $^1$H-NMR(CDCl$_3$): δ 2.38(3H, s), 7.02(1H, d, J=8.9 Hz), 7.25-7.31(3H, m), 7.46(1H, dd, J=2.6, 8.9 Hz), 7.68(2H, d, J=8.6 Hz), 7.74(1H, d, J=2.3 Hz), 7.96(1H, d, J=8.6 Hz), 8.56(1H, d, J=2.0 Hz), 10.75(1H, s), 11.70(1H, s).

Example 380

Preparation of the Compound of Compound No. 380

Using 5-chlorosalicylic acid and 2-chloro-5-tosylaniline as the raw materials, the same operation as the Example 16 gave the title compound.

Yield: 43.5%. $^{1}$H-NMR(CDCl$_{3}$): δ 2.38(3H, s), 7.02(1H, d, J=8.9 Hz), 7.27(1H, d, J=7.9 Hz), 7.29(1H, dd, J=2.0, 6.6 Hz), 7.46(1H, dd, J=2.3, 8.9 Hz), 7.68(2H, d, J=8.6 Hz), 7.73(2H, d, J=2.3 Hz), 7.97(1H, d, J=8.6 Hz), 8.56(1H, d, J=2.0 Hz), 10.73(1H, s), 11.71(1H, s).

Example 381

Preparation of the Compound of Compound No. 381

Using 5-chlorosalicylic acid and 2-fluoro-5-(methylsulfonyl)aniline as the raw materials, the same operation as the Example 16 gave the title compound.

Yield: 28.8%. $^{1}$H-NMR(CDCl$_{3}$): δ 3.12(3H, s), 7.03(1H, d, J=8.9 Hz), 7.38(1H, dd, J=8.6, 10.2 Hz), 7.45(1H, dd, J=2.3, 8.9 Hz), 7.53(1H, d, J=2.3 Hz), 7.80(1H, ddd, J=2.3, 4.6, 8.6 Hz), 8.25(1H, s), 8.98(1H, dd, J=2.3, 7.7 Hz), 11.33 (1H, br.s).

Example 382

Preparation of the Compound of Compound No. 382

Using 5-chlorosalicylic acid and 2-methoxy-5-phenoxyaniline as the raw materials, the same operation as the Example 16 gave the title compound.

Yield: 77.0%. $^{1}$H-NMR(CDCl$_{3}$): δ 3.98(3H, s), 6.80(1H, d, J=8.8 Hz), 6.90(1H, d, J=8.8 Hz), 6.95-7.00(3H, m), 7.04-7.09(1H, m), 7.29-7.35(2H, m), 7.38(1H, dd, J=8.8, 2.6 Hz), 7.47(1H, d, J=2.6 Hz), 8.19(1H, d, J=2.9 Hz), 8.61(1H, brs), 11.92(1H, s).

Example 383

Preparation of the Compound of Compound No. 383

Using 5-chlorosalicylic acid and 3-amino-4-methylbiphenyl as the raw materials, the same operation as the Example 16 gave the title compound.

Yield: 47.7%. $^{1}$H-NMR(DMSO-d$_{6}$): δ 2.33(3H, s), 7.06 (1H, d, J=8.7 Hz), 7.43-7.52(4H, m), 7.64-7.67(2H, m), 8.04 (1H, d, J=2.7 Hz), 8.19(1H, d, J=1.5 Hz), 10.40(1H, s), 12.22 (1H, s).

Example 384

Preparation of the Compound of Compound No. 384

Using 5-chlorosalicylic acid and 5-(α,α-dimethylbenzyl)-2-methoxyaniline as the raw materials, the same operation as the Example 16 gave the title compound.

Yield: 89.0%. $^{1}$H-NMR(CDCl$_{3}$): δ 1.72(6H, s), 3.93(3H, s), 6.83(1H, d, J=8.8 Hz), 6.93(1H, dd, J=2.6, 8.8 Hz), 6.96 (1H, d, J=9.2 Hz), 7.15-7.20(1H, m), 7.25-7.28(4H, m), 7.36 (1H, dd, J=2.6, 8.8 Hz), 7.46(1H, d, J=2.6 Hz), 8.35(1H, d, J=2.6 Hz), 8.51(1H, s), 12.04(1H, s).

Example 385

Preparation of the Compound of Compound No. 385

Using 5-chlorosalicylic acid and 5-morpholino-2-nitroaniline as the raw materials, the same operation as the Example 16 gave the title compound.

Yield: 4.1%. $^{1}$H-NMR(DMSO-d$_{6}$): δ 3.46-3.52(4H, m), 3.85-3.94(4H, m), 7.03(1H, d, J=8.8 Hz), 7.47(1H, dd, J=2.9, 8.8 Hz), 7.80(1H, dd, J=2.6, 8.8 Hz), 7.82(1H, d, J=2.6 Hz), 7.88(1H, d, J=8.8 Hz), 8.20(1H, d, J=2.2 Hz), 10.70(1H, s), 11.43(1H, s)

Example 386

Preparation of the Compound of Compound No. 386

Using 5-chlorosalicylic acid and 5-fluoro-2-(1-imidazolyl)aniline as the raw materials, the same operation as the Example 16 gave the title compound.

Yield: 33.8%. $^{1}$H-NMR(DMSO-d$_{6}$): δ 6.99(1H, d, J=8.8 Hz), 7.12-7.19(2H, m), 7.42-7.51(3H, m), 7.89(1H, d, J=2.8 Hz), 7.93(1H, d, J=1.1 Hz), 8.34(1H, dd, J=11.4, 2.8 Hz), 10.39(1H, s), 11.76(1H, brs).

Example 387

Preparation of the Compound of Compound No. 387

Using 5-chlorosalicylic acid and 2-butyl-5-nitroaniline as the raw materials, the same operation as the Example 16 gave the title compound.

Yield: 15.3%. $^{1}$H-NMR(CDCl$_{3}$): δ 0.99(3H, t, J=7.3 Hz), 1.39-1.51(2H, m), 1.59-1.73(2H, m), 2.71-2.79(2H, m), 7.03 (1H, d, J=8.9 Hz), 7.41-7.49(3H, m), 7.92(1H, s), 8.07(1H, dd, J=2.3, 8.4 Hz), 8.75(1H, d, J=2.4 Hz), 11.51(1H, s).

Example 388

Preparation of the Compound of Compound No. 388

Using 5-chlorosalicylic acid and 5-[(1,1-dimethyl)propyl]-2-hydroxyaniline as the raw materials, the same operation as the Example 16 gave the title compound.

Yield: 36.0%. $^{1}$H-NMR(CDCl$_{3}$): δ 0.70(3H, t, J=7.4 Hz), 1.28(6-H, s), 1.63(2H, q, J=7.4 Hz), 6.97(1H, d, J=6.3 Hz), 7.00(1H, d, J=6.6 Hz), 7.08(1H, s), 7.14(1H, dd, J=2.5, 8.6 Hz), 7.36(1H, d, J=2.2 Hz), 7.42(1H, dd, J=2.5, 8.8 Hz), 7.57(1H, d, J=2.5 Hz), 8.28(1H, s), 11.44(1H, s).

Example 389

Preparation of the Compound of Compound No. 389

Using 5-chlorosalicylic acid and 2-methoxy-5-methylaniline as the raw materials, the same operation as the Example 16 gave the title compound.

Yield: 74.2%. $^{1}$H-NMR(DMSO-d$_{6}$): δ 2.27(3H, s), 3.85 (3H, s), 6.90(1H, dd, J=9.0, 2.4 Hz), 6.98(1H, d, J=9.0 Hz), 7.05(1H, d, J=9.0 Hz), 7.47(1H, dd, J=9.0, 3.0 Hz), 7.97(1H, d, J=3.0 Hz), 8.24(1H, d, J=2.4 Hz), 10.79(1H, s), 12.03(1H, s).

Example 390

Preparation of the Compound of Compound No. 390

Using 5-chlorosalicylic acid and 2,5-difluoroaniline as the raw materials, the same operation as the Example 16 gave the title compound.

Yield: 81.5%. $^1$H-NMR(DMSO-d$_6$): δ 6.98-7.07(1H, m), 7.07(1H, d, J=9.0 Hz), 7.37-7.49(1H, m), 7.52(1H, dd, J=8.7, 3.0 Hz), 7.95(1H, d, J=2.7 Hz), 8.15-8.22(1H, m), 10.83(1H, s), 12.25(1H, s).

Example 391

Preparation of the Compound of Compound No. 391

Using 5-chlorosalicylic acid and 3,5-difluoroaniline as the raw materials, the same operation as the Example 16 gave the title compound.

Yield: 82.0%. $^1$H-NMR(DMSO-d$_6$): δ 7.00(1H, tt, J=9.3, 2.1), 7.03(1H, d, J=9.0 Hz), 7.47(1H, dd, J=7.5, 2.7 Hz), 7.49(1H, d, J=2.7 Hz), 7.51(1H, d, J=2.1 Hz), 7.82(1H, d, J=3.0 Hz), 10.63(1H, s), 11.43(1H, brs).

Example 392

Preparation of the Compound of Compound No. 392

Using 2-(5-bromo-2-hydroxybenzoyl)amino-4-[(1,1-dimethyl)ethyl]thiazole-5-carboxylic acid ethyl ester (Compound No. 197) as the raw material, the same operation as the Example 82 gave the title compound.

Yield: 85.5%. $^1$H-NMR(DMSO-d$_6$): δ 1.44(9H, s), 7.00 (1H, d, J=9.0 Hz), 7.62(1H, dd, J=9.0, 2.7 Hz), 8.02(1H, d, J=2.4 Hz), 11.83(1H, brs), 12.04(1H, brs), 12.98(1H, brs).

Example 393

Preparation of the Compound of Compound No. 393

Using 5-bromosalicylic acid and 2-amino-4-phenylthiazole-5-acetic acid methyl ester as the raw materials, the same operation as the Example 195(3) gave the title compound. (This compound is the compound of Example 203(1).)

Yield: 32.1%. mp 288.5-229.5° C. $^1$H-NMR(DMSO-d$_6$): δ 3.66(3H, s), 3.95(2H, s), 6.99(1H, d, J=8.0 Hz), 7.42(1H, d, J=6.0 Hz), 7.48(2H, brt, J=7.6 Hz), 7.56-7.61(3H, m), 8.07 (1H, d, J=2.4 Hz), 11.85(1H, brs), 11.98(1H, brs).

Example 394

Preparation of the Compound of Compound No. 394

Using 2-(5-bromo-2-hydroxybenzoyl)amino-4-phenylthiazole-5-carboxylic acid ethyl ester (Compound No. 209) as the raw material, the same operation as the Example 82 gave the title compound. (This compound is the compound of Example 212(1).)

Yield: 67.0%. $^1$H-NMR(DMSO-d$_6$): δ 7.00(1H, d, J=8.8 Hz), 7.42-7.44(3H, m), 7.62(1H, dd, J=8.8, 2.4 Hz), 7.70-7.72(2H, m), 8.04(1H, d, J=2.4 Hz), 12.31(1H, brs), 12.99 (1H, brs).

Example 395

Preparation of the Compound of Compound No. 395

(1)

2-Amino-4-[3,5-bis(trifluoromethyl)phenyl]thiazole

Phenyltrimethylammonium tribromide (753 mg, 2 mmol) was added to a solution of 3',5'-bis(trifluoromethyl)acetophenone (0.51 g, 2.0 mmol) in tetrahydrofuran (5 mL) and the mixture was stirred at room temperature for 5 hours. The reaction mixture was poured into water and extracted with ethyl acetate. After the ethyl acetate layer was washed with brine, dried over anhydrous sodium sulfate, ethanol (5 mL) and thiourea (152 mg, 2 mmol) were added to the residue obtained by evaporation of the solvent under reduced pressure, and the mixture was refluxed for 30 minutes. After the reaction mixture was cooled to room temperature, it was poured into saturated aqueous sodium hydrogen carbonate and extracted with ethyl acetate. After the ethyl acetate layer was washed with brine and dried over anhydrous sodium sulfate, the residue obtained by evaporation of the solvent under reduced pressure was purified by column chromatography on silica gel (n-hexane:ethyl acetate=2:1) and washed with n-hexane under suspension to give the title compound (520.1 mg, 83.3%) as a light yellow white crystal.

$^1$H-NMR(CDCl$_3$): δ 5.03(2H, s), 6.93(1H, s), 7.77(1H, s), 8.23(2H, s).

(2) 5-Chloro-2-hydroxy-N-{4-[3,5-bis(trifluoromethyl)phenyl]thiazol-2-yl}benzamide (Compound No. 395)

A mixture of 5-chlorosalicylic acid (172.6 mg, 1 mmol), 2-amino-4-[3,5-bis(trifluoromethyl)phenyl]thiazole (312.2 mg, 1 mmol), phosphorus trichloride (44 µL, 0.5 mmol) and monochlorobenzene (5 mL) was refluxed for 4 hours. After the reaction mixture was cooled to room temperature, it was poured into water and extracted with ethyl acetate. After the ethyl acetate layer was washed with brine, dried over anhydrous sodium sulfate, the residue obtained by evaporation of the solvent under reduced pressure was purified by column chromatography on silica gel (n-hexane:ethyl acetate=3: 1→2:1) to give the title compound (109.8 mg, 23.5%) as a pale yellow white powder.

$^1$H-NMR(DMSO-d$_6$): δ 7.08(1H, d, J=8.7 Hz), 7.53(1H, dd, J=9.0, 3.0 Hz), 7.94(1H, d, J=3.0 Hz), 8.07(1H, s), 8.29 (1H, s), 8.60(2H, s), 11.77(1H, s), 12.23(1H, s).

Example 396

Preparation of the Compound of Compound No. 396

Using 5-chlorosalicylic acid and 3-aminopyridine as the raw materials, the same operation as the Example 16 gave the title compound.

Yield: 23.2%. $^1$H-NMR(DMSO-d$_6$): δ 7.02(1H, d, J=9.3 Hz), 7.42(1H, ddd, J=9.0, 4.8, 0.6 Hz), 7.47(1H, dd, J=8.7, 5.7 Hz), 7.92(1H, d, J=2.7 Hz), 8.15(1H, ddd, J=8.4, 2.4, 1.5 Hz), 8.35(1H, dd, J=7.8, 1.5 Hz), 8.86(1H, d, J=2.4 Hz), 10.70(1H, s).

Example 397

Preparation of the Compound of Compound No. 397

Using 5-chlorosalicylic acid and 2-amino-6-bromopyridine as the raw materials, the same operation as the Example 16 gave the title compound.

Yield: 12.3%. $^1$H-NMR(DMSO-d$_6$): δ 7.07(1H, d, J=8.7 Hz), 7.42(1H, d, J=7.8 Hz), 7.51(1H, dd, J=8.7, 2.7 Hz), 7.82(1H, t, J=7.5 Hz), 7.94(1H, d, J=3.0 Hz), 8.24(1H, d, J=7.8 Hz), 10.95(1H, s), 11.97(1H, s).

Example 398

Preparation of the Compound of Compound No. 398

(1) 2-Acetoxy-5-chloro-N-(pyridazin-2-yl)benzamide

Using 2-acetoxy-5-chlorobenzoic acid and 2-aminopyridazine as the raw materials, the same operation as the Example 198(3) gave the title compound.

Yield: 19.7%. $^1$H-NMR(CDCl$_3$): δ 2.42(3H, s), 7.19(1H, d, J=8.7 Hz), 7.54(1H, dd, J=8.7, 2.7 Hz), 8.01(1H, d, J=2.4 Hz), 8.28(1H, dd, J=2.4, 1.8 Hz), 8.42(1H, d, J=2.4 Hz), 9.09(1H, s), 9.66(1H, d, J=1.8 Hz).

(2) 5-Chloro-2-hydroxy-N-(pyridazin-2-yl)benzamide (Compound No. 398)

Using 2-acetoxy-5-chloro-N-(pyridazin-2-yl)benzamide as the raw material, the same operation as the Example 2(2) gave the title compound.

Yield: 72.6%. $^1$H-NMR(DMSO-d$_6$): δ 7.09(1H, d, J=9.0 Hz), 7.52(1H, dd, J=8.7, 2.7 Hz), 7.96(1H, d, J=2.7 Hz), 8.44-8.47(2H, m), 9.49(1H, s), 10.99(1H, s), 12.04(1H, s).

Example 399

Preparation of the Compound of Compound No. 399

Using 5-bromosalicylic acid and 2-amino-5-bromopyrimidine as the raw materials, the same operation as the Example 16 gave the title compound.

Yield: 10.3%. $^1$H-NMR(DMSO-d$_6$): δ 6.98(1H, d, J=8.8 Hz), 7.59(1H, dd, J=8.8, 2.4 Hz), 8.00(1H, d, J=2.8 Hz), 8.86(2H, s), 11.09(1H, s), 11.79(1H, s).

Example 400

Preparation of the Compound of Compound No. 400

Using 2-(5-bromo-2-hydroxybenzoyl)amino-4-phenylthiazole-5-carboxylic acid (Compound No. 394) and propylamine as the raw materials, the same operation as the Example 212(2) gave the title compound.

Yield: 23.1%. $^1$H-NMR(DMSO-d$_6$): δ 0.82(3H, t, J=7.5 Hz), 1.39-1.51(2H, m), 3.13(2H, q, J=6.6 Hz), 7.02(1H, d, J=9.0 Hz), 7.40-7.48(3H, m), 7.63(1H, dd, J=8.7, 2.7 Hz), 7.68-7.72(2H, m), 8.06(1H, d, J=2.7 Hz), 8.18(1H, t, J=5.7 Hz), 11.87(1H, brs), 12.14(1H, brs).

Example 401

Preparation of the Compound of Compound No. 401

Using 5-chlorosalicylic acid and 2-methyl-3,5-bis(trifluoromethyl)aniline as the raw materials, the same operation as the Example 16 gave the title compound.

Yield: 15.0%. $^1$H-NMR(DMSO-d$_6$): δ 2.49(3H, s), 7.07(1H, d, J=8.7 Hz), 7.52(1H, dd, J=8.7, 2.8 Hz), 7.84(1H, s), 7.97(1H, d, J=2.8 Hz), 8.60(1H, s), 10.69(1H, brs), 12.07(1H, brs).

Example 402

Preparation of the Compound of Compound No. 402

Using 5-chlorosalicylic acid and 4-chloro-3-(trifluoromethyl)aniline as the raw materials, the same operation as the Example 16 gave the title compound.

Yield: 66.5%. $^1$H-NMR(DMSO-d$_6$): δ 7.03(1H, d, J=8.7 Hz), 7.48(1H, dd, J=8.7, 2.7 Hz), 7.73(1H, d, J=8.7 Hz), 7.86(1H, d, J=2.4 Hz), 8.00(1H, dd, J=8.7, 2.4 Hz), 8.32(1H, d, J=2.4 Hz), 10.69(1H, s), 11.49(1H, s).

Example 403

Preparation of the Compound of Compound No. 403

Using 5-chlorosalicylic acid and 4-isopropyl-2-(trifluoromethyl)aniline as the raw materials, the same operation as the Example 16 gave the title compound.

Yield: 33.4%. $^1$H-NMR(DMSO-d$_6$): δ 1.24(6H, d, J=6.6 Hz), 2.97-3.06(1H, m), 7.06(1H, d, J=8.7 Hz), 7.51(1H, dd, J=8.7, 2.7 Hz), 7.61(1H, s), 7.62(1H, d, J=7.5 Hz), 7.98(1H, d, J=2.7 Hz), 8.03(1H, d, J=8.1 Hz), 10.67(1H, s), 12.21(1H, s).

Example 404

Preparation of the Compound of Compound No. 404

Using 5-chlorosalicylic acid and 3-(trifluoromethyl)aniline as the raw materials, the same operation as the Example 16 gave the title compound.

Yield: 68.5%. $^1$H-NMR(DMSO-d$_6$): δ 7.03(1H, d, J=8.6 Hz), 7.46-7.51(2H, m), 7.62(1H, t, J=7.9 Hz), 7.90(1H, d, J=3.0 Hz), 7.94(1H, d, J=9.2 Hz), 8.21(1H, s), 10.64(1H, s), 11.58(1H, brs).

Example 405

Preparation of the Compound of Compound No. 405

Using 5-chlorosalicylic acid and 2-nitro-4-(trifluoromethyl)aniline as the raw materials the same operation as the Example 16 gave the title compound.

Yield: 18.7%. $^1$H-NMR(DMSO-d$_6$): δ 7.08(1H, d, J=9.0 Hz), 7.54(1H, dd, J=8.7, 2.7 Hz), 7.94(1H, d, J=2.7 Hz), 8.17(1H, dd, J=9.0, 2.4 Hz), 8.46(1H, d, J=1.8 Hz), 8.88(1H, d, J=9.0 Hz), 12.19(1H, s), 12.25(1H, s).

Example 406

Preparation of the Compound of Compound No. 406

Using 5-chlorosalicylic acid and 2,6-dichloro-4-(trifluoromethyl)aniline as the raw materials, the same operation as the Example 16 gave the title compound.

Yield: 22.1%. $^1$H-NMR(DMSO-d$_6$): δ 7.07(1H, d, J=8.7 Hz), 7.55(1H, dd, J=8.7, 2.7 Hz), 7.99(1H, d, J=2.4 Hz), 8.10(2H, s), 10.62(1H, s), 11.88(1H, s).

Example 407

Preparation of the Compound of Compound No. 407

Using 5-chlorosalicylic acid and 4-cyano-3-(trifluoromethyl)aniline as the raw materials, the same operation as the Example 16 gave the title compound.
Yield: 55.8%. $^1$H-NMR(DMSO-d$_6$): δ 7.04(1H, d, J=8.7 Hz), 7.49(1H, dd, J=8.7, 2.7 Hz), 7.80(1H, d, J=2.7 Hz), 8.17(2H, s), 8.43(1H, s), 10.94(1H, s), 11.34(1H, s).

Example 408

Preparation of the Compound of Compound No. 408

Using 5-chlorosalicylic acid and 4-bromo-3-(trifluoromethyl)aniline as the raw materials, the same operation as the Example 16 gave the title compound.
Yield: 81.2%. $^1$H-NMR(DMSO-d$_6$): δ 7.03(1H, d, J=8.7 Hz), 7.48(1H, dd, J=9.0, 2.7 Hz), 7.85-7.94(3H, m), 8.31(1H, d, J=1.8 Hz), 10.67(1H, s), 11.48(1H, s).

Example 409

Preparation of the Compound of Compound No. 409

Using 5-chlorosalicylic acid and 4-bromo-2-(trifluoromethyl)aniline as the raw materials, the same operation as the Example 16 gave the title compound.
Yield: 41.8%. $^1$H-NMR(DMSO-d$_6$): δ 7.07(1H, d, J=8.7 Hz), 7.52(1H, dd, J=9.0, 2.7 Hz), 7.93-7.97(3H, m), 8.21(1H, d, J=9.3 Hz), 10.81(1H, s), 12.28(1H, s).

Example 410

Preparation of the Compound of Compound No. 410

Using 5-chlorosalicylic acid and 2-bromo-4-(trifluoromethyl)aniline as the raw materials, the same operation as the Example 16 gave the title compound.
Yield: 17.6%. $^1$H-NMR(DMSO-d$_6$): δ 7.10(1H, d, J=9.0 Hz), 7.53(1H, dd, J=8.7, 3.0 Hz), 7.82(1H, dd, J=9.0, 1.8 Hz), 7.98(1H, d, J=3.0 Hz), 8.11(1H, d, J=1.5 Hz), 8.67(1H, d, J=8.7 Hz), 11.05(1H, s), 12.40(1H, s).

Example 411

Preparation of the Compound of Compound No. 411

Using 5-chlorosalicylic acid and 4-fluoro-2-(trifluoromethyl)aniline as the raw materials, the same operation as the Example 16 gave the title compound.
Yield: 36.0%. $^1$H-NMR(DMSO-d$_6$): δ 7.06(1H, d, J=9.0 Hz), 7.52(1H, dd, J=8.7, 2.7 Hz), 7.63(1H, td, J=8.7, 3.3 Hz), 7.71(1H, dd, J=8.7, 3.0 Hz), 7.97(1H, d, J=2.7 Hz), 8.11(1H, dd, J=8.7, 5.1 Hz), 10.67(1H, s), 12.20(1H, s).

Example 412

Preparation of the Compound of Compound No. 412

Using 5-chlorosalicylic acid and 4-isopropyloxy-2-(trifluoromethyl)aniline as the raw materials, the same operation as the Example 16 gave the title compound.
Yield: 39.2%. $^1$H-NMR(DMSO-d$_6$): δ 1.29(6H, d, J=5.7 Hz), 4.67-4.79(1H, m), 7.04(1H, d, J=9.0 Hz), 7.22(1H, d, J=2.7 Hz), 7.30(1H, dd, J=8.7, 2.7 Hz), 7.51(1H, dd, J=8.7, 2.4 Hz), 7.86(1H, d, J=9.0 Hz), 7.99(1H, d, J=3.0 Hz), 10.50 (1H, s), 12.18(1H, s).

Example 413

Preparation of the Compound of Compound No. 413

Using 5-chlorosalicylic acid and 2,4-dimethoxy-5-(trifluoromethyl)aniline as the raw materials, the same operation as the Example 16 gave the title compound.
Yield: 19.0%. $^1$H-NMR(CDCl$_3$): δ 3.93(3H, s), 4.03(3H, s), 6.70(1H, s), 6.98(1H, d, J=8.9 Hz), 7.39(1H, dd, J=8.9, 2.6 Hz), 7.45(1H, d, J=2.6 Hz), 8.29(1H, brs,), 8.54(1H, s), 11.92 (1H, s).

Example 414

Preparation of the Compound of Compound No. 414

Using 5-chlorosalicylic acid and 2,4-difluoro-5-(trifluoromethyl)aniline as the raw materials, the same operation as the Example 16 gave the title compound.
Yield: 66.0%. $^1$H-NMR(DMSO-d$_6$): δ 7.06(1H, d, J=8.8 Hz), 7.51(1H, dd, J=8.8, 2.8 Hz), 7.82(1H, t, J=10.7 Hz), 7.94(1H, d, J=2.8 Hz), 8.64(1H, d, J=8.0 Hz), 10.78(1H, s), 12.37(1H, brs).

Example 416

Preparation of the Compound of Compound No. 415

Using 5-chlorosalicylic acid and 4-cyano-2-(trifluoromethyl)aniline as the raw materials, the same operation as the Example 16 gave the title compound.
Yield: 24.8%. $^1$H-NMR(DMSO-d$_6$): δ 7.06(1H, d, J=8.8 Hz), 7.52(1H, dd, J=2.8, 8.8 Hz), 7.94(1H, d, J=2.8 Hz), 8.17(1H, dd, J=1.8, 8.9 Hz), 8.31(1H, d, J=2.1 Hz), 8.63(1H, d, J=8.9 Hz), 11.16(1H, s), 12.45(1H, br.s).

Example 416

Preparation of the Compound of Compound No. 416

Using 5-chlorosalicylic acid and 4-chloro-2-(4-chlorobenzenesulfonyl)-5-(trifluoromethyl)aniline as the raw materials, the same operation as the Example 16 gave the title compound.
Yield: 8.5%. $^1$H-NMR(CDCl$_3$): δ 6.98(1H, d, J=8.9 Hz), 7.13(1H, d, J=2.6 Hz), 7.22(2H, d, J=8.6 Hz), 7.34(2H, d, J=8.6 Hz), 7.40(1H, dd, J=2.3, 8.9 Hz), 7.66(1H, s), 8.71(1H, s), 8.80(1H, s), 11.42(1H, s).

Example 417

Preparation of the Compound of Compound No. 417

Using 5-chlorosalicylic acid and 5-chloro-2-nitro-4-(trifluoromethyl)aniline as the raw materials, the same operation as the Example 16 gave the title compound.
Yield: 22.8%. $^1$H-NMR(DMSO-d$_6$): δ 7.08(1H, d, J=8.8 Hz), 7.55(1H, dd, J=8.8, 2.8 Hz), 7.93(1H, d, J=2.8 Hz), 8.52(1H, s), 9.13(1H, s), 12.38(1H, brs), 12.45(1H, s).

Example 418

Preparation of the Compound of Compound No. 418

Using 5-chlorosalicylic acid and 2,3-difluoro-4-(trifluoromethyl)aniline as the raw materials, the same operation as the Example 16 gave the title compound.

Yield: 21.8%. $^1$H-NMR(DMSO-d$_6$): δ 7.07(1H, d, J=8.8 Hz), 7.53(1H, dd, J=2.9, 8.8 Hz), 7.66(1H, dt, J=1.8, 7.7 Hz), 7.93(1H, d, J=2.6 Hz), 8.35(1H, t, J=7.7 Hz), 11.02(1H, d, J=1.5 Hz), 12.32(1H, s).

Example 419

Preparation of the Compound of Compound No. 419

Using 5-chlorosalicylic acid and 4,4'-diamino-2,2'-bis(trifluoromethyl)biphenyl as the raw materials, the same operation as the Example 16 gave the title compound.

Yield: 35.9%. $^1$H-NMR(DMSO-d$_6$): δ 7.05(2H, d, J=8.8 Hz), 7.39(2H, d, J=8.5 Hz), 7.49-7.51(2H, m), 7.91(2H, d, J=2.5 Hz), 7.99(2H, dd, J=2.0, 8.5 Hz), 8.31(2H, d, J=1.9 Hz), 10.71(2H, s), 11.54(2H, s).

Example 420

Preparation of the Compound of Compound No. 420

Using 5-chlorosalicylic acid and 2,3,5,6-tetrafluoro-4-(trifluoromethyl)aniline as the raw materials, the same operation as the Example 16 gave the title compound.

Yield: 42.5%. $^1$H-NMR(DMSO-d$_6$): δ 7.08(1H, d, J=8.8 Hz), 7.53(1H, dd, J=2.9, 8.8 Hz), 7.89(1H, d, J=2.6 Hz), 10.65(1H, br.s), 11.76(1H, br.s).

Example 421

Preparation of the Compound of Compound No. 421

Using 5-chlorosalicylic acid and 3'-aminoacetanilide as the raw materials, the same operation as the Example 16 gave the title compound.

Yield: 22.4%. $^1$H-NMR(DMSO-d$_6$): δ 2.05(3H, s), 7.01 (1H, d, J=8.7 Hz), 7.24-7.39(3H, m), 7.47(1H, dd, J=9.0, 3.0 Hz), 7.97(1H, d, J=3.0 Hz), 8.03(1H, s), 10.01(1H, s), 10.41 (1H, s), 11.87(1H, s).

Example 422

Preparation of the Compound of Compound No. 422

(1)
2-Acetoxy-5-chloro-N-(3-carbamoylphenyl)benzamide

Using 2-acetoxy-5-chlorobenzoic acid and 3-aminobenzamide as the raw materials, the same operation as the Example 24 gave the title compound.

Yield: 15.8%. $^1$H-NMR(CDCl$_3$): δ 2.33(3H, s), 5.89(1H, brs), 6.31(1H, brs), 7.14(1H, d, J=9.0 Hz), 7.42-7.49(2H, m), 7.55-7.58(1H, m), 7.80(1H, d, J=2.7 Hz), 7.93(1H, d, J=8.1 Hz), 8.07(1H, s), 8.71(1H, s).

(2) 5-Chloro-2-hydroxy-N-(3-carbamoylphenyl)benzamide (Compound No. 422)

Using 2-acetoxy-5-chloro-N-(3-carbamoylphenyl)benzamide as the raw material, the same operation as the Example 2(2) gave the title compound.

Yield: 76.0%. $^1$H-NMR(DMSO-d$_6$): δ 7.03(1H, d, J=8.7 Hz), 7.40(1H, brs), 7.45(1H, t, J=7.5 Hz), 7.48(1H, dd, J=8.7, 2.4 Hz), 7.62-7.65(1H, m), 7.86-7.89(1H, m), 7.98-7.99(2H, m), 8.15(1H, t, J=1.8 Hz), 10.51(1H, s), 11.85(1H, s).

Example 423

Preparation of the Compound of Compound No. 423

Using 5-chlorosalicylic acid and 3-amino-N-methylbenzamide as the raw materials, the same operation as the Example 16 gave the title compound.

Yield: 19.3%. $^1$H-NMR(DMSO-d$_6$): δ 2.79(3H, d, J=4.5 Hz), 7.03(1H, d, J=9.0 Hz), 7.43-7.51(2H, m), 7.59(1H, dt, J=8.1, 1.5 Hz), 7.87(1H, ddd, J=8.1, 2.1, 0.9 Hz), 7.99(1H, d, J=2.4 Hz), 8.15(1H, t, J=1.8 Hz), 8.46(1H, d, J=4.2 Hz), 10.52(1H, s), 11.84(1H, s).

Example 424

Preparation of the Compound of Compound No. 424

Using 5-chlorosalicylic acid and 2,6-diisopropylaniline as the raw materials, the same operation as the Example 16 gave the title compound.

Yield: 52.5%. $^1$H-NMR(DMSO-d$_6$): δ 1.14(12H, s), 2.96-3.13(2H, m), 7.16(1H, d, J=8.7 Hz), 7.23(1H, d, J=7.5 Hz), 7.33(1H, dd, J=8.4, 6.6 Hz), 7.52(1H, dd, J=8.7, 2.4 Hz), 8.11(1H, d, J=2.4 Hz), 10.09(1H, s), 12.40(1H, s).

Example 425

Preparation of the Compound of Compound No. 425

Using 5-chlorosalicylic acid and 4-methylaniline as the raw materials, the same operation as the Example 16 gave the title compound.

Yield: 58.6%. $^1$H-NMR(DMSO-d$_6$): δ 2.29(3H, s), 7.01 (1H, d, J=8.7 Hz), 7.18(1H, d, J=8.1 Hz), 7.47(1H, dd, J=8.7, 2.7 Hz), 7.58(1H, d, J=8.4 Hz), 7.98(1H, d, J=2.7 Hz), 10.35 (1H, s), 11.94(1H, s).

Example 426

Preparation of the Compound of Compound No. 426

Using 5-chlorosalicylic acid and 2,6-dimethylaniline as the raw materials, the same operation as the Example 16 gave the title compound.

Yield: 59.6%. $^1$H-NMR(DMSO-d$_6$): δ 2.19(6H, s), 7.01 (1H, d, J=9.0 Hz), 7.15-7.16(2H, m), 7.50(1H, dd, J=9.0, 2.7 Hz), 8.07(1H, d, J=2.7 Hz), 10.03(1H, s), 10.10(1H, s), 12.29 (1H, s).

Example 427

Preparation of the Compound of Compound No. 427

Using 5-chlorosalicylic acid and 3,4-dimethylaniline as the raw materials, the same operation as the Example 16 gave the title compound.

Yield: 68.3%. $^1$H-NMR(DMSO-d$_6$): δ 2.20(3H, s), 2.23 (3H, s), 7.01(1H, d, J=9.0 Hz), 7.13(1H, d, J=8.4 Hz), 7.40-7.47(2H, m), 7.47(1H, dd, J=9.0, 2.7 Hz), 7.99(1H, d, J=2.7 Hz), 10.29(1H, s), 11.97(1H, brs).

Example 428

Preparation of the Compound of Compound No. 428

Using 5-chlorosalicylic acid and 2,4,6-trimethylaniline as the raw materials, the same operation as the Example 16 gave the title compound.
Yield: 61.0%. $^1$H-NMR(DMSO-d$_6$): δ 2.14(6H, s), 2.26 (3H, s), 6.95(2H, s), 7.00(1H, d, J=9.3 Hz), 7.48(1H, dd, J=8.7, 2.7 Hz), 8.09(1H, d, J=2.4 Hz), 10.03(1H, s), 12.37 (1H, s).

Example 429

Preparation of the Compound of Compound No. 429

Using 5-chlorosalicylic acid and 3-(trifluoromethoxy) aniline as the raw materials, the same operation as the Example 16 gave the title compound.
Yield: 41.4%. $^1$H-NMR(CDCl$_3$): δ 7.00(1H, d, J=9.0 Hz), 7.09(1H, d, J=7.5 Hz), 7.40-7.48(3H, m), 7.51(1H, d, J=2.4 Hz), 7.64(1H, s), 7.94(1H, s), 11.66(1H, s).

Example 430

Preparation of the Compound of Compound No. 430

Using 5-chlorosalicylic acid and 2-benzylaniline as the raw materials, the same operation as the Example 16 gave the title compound.
Yield: 93.3%. $^1$H-NMR(CDCl$_3$): δ 4.08(2H, s), 6.56(1H, d, J=2.5 Hz), 6.92(1H, d, J=8.8 Hz), 7.20-7.46(9H, m), 7.53 (1H, brs), 7.85(1H, d, J=8.0 Hz), 12.01(1H, brs).

Example 431

Preparation of the Compound of Compound No. 431

Using 5-chlorosalicylic acid and 4-(trifluoromethoxy) aniline as the raw materials, the same operation as the Example 16 gave the title compound.
Yield: 20.4%. $^1$H-NMR(DMSO-d$_6$): δ 7.03(1H, d, J=9.3 Hz), 7.39(2H, d, J=9.0 Hz), 7.48(1H, dd, J=9.0, 2.7 Hz), 7.83(2H, d, J=9.3 Hz), 7.92(1H, d, J=2.7 Hz), 10.54(1H, s), 11.78(1H, s).

Example 432

Preparation of the Compound of Compound No. 432

Using 5-chlorosalicylic acid and 2,4-dichloroaniline as the raw materials, the same operation as the Example 16 gave the title compound.
Yield: 60.0%. $^1$H-NMR(DMSO-d$_6$): δ 7.08(1H, d, J=8.7 Hz), 7.48-7.54(2H, m), 7.75(1H, d, J=2.1 Hz), 7.98(1H, d, J=2.7 Hz), 8.44(1H, d, J=8.7 Hz), 10.93(1H, s), 12.31(1H, s).

Example 433

Preparation of the Compound of Compound No. 433

Using 5-chlorosalicylic acid and 4-(tert-butyl)aniline as the raw materials, the same operation as the Example 16 gave the title compound.
Yield: 69.0%. $^1$H-NMR(DMSO-d$_6$): δ 1.29(9H, s), 7.01 (1H, d, J=8.7 Hz), 7.39(2H, d, J=8.4 Hz), 7.47(1H, dd, J=8.7, 2.7 Hz), 7.61(2H, d, J=8.4 Hz), 7.99(1H, d, J=2.4 Hz), 10.37 (1H, s), 11.96(1H, s).

Example 434

Preparation of the Compound of Compound No. 434

Using 5-chlorosalicylic acid and 2,3-dimethylaniline as the raw materials, the same operation as the Example 16 gave the title compound.
Yield: 79.5%. $^1$H-NMR(DMSO-d$_6$): δ 2.14(3H, s), 2.29 (3H, s), 7.03(1H, d, J=9.0 Hz), 7.06-7.15(2H, m), 7.46-7.51 (2H, m), 8.05(1H, d, J=3.0 Hz), 10.32(1H, s), 12.28(1H, s).

Example 435

Preparation of the Compound of Compound No. 435

Using 5-chlorosalicylic acid and 5-aminoindane as the raw materials, the same operation as the Example 16 gave the title compound.
Yield: 80.7%. $^1$H-NMR(DMSO-d$_6$): δ 1.98-2.08(2H, m), 2.81-2.89(4H, m), 7.01(1H, d, J=8.8 Hz), 7.21(1H, d, J=8.0, Hz), 7.42(1H, dd, J=8.0, 1.9 Hz), 7.48(1H, dd, J=8.8, 2.8 Hz), 7.60(1H, s), 7.99(1H d, J=2.8, Hz), 10.34(1H, s), 12.00(1H, brs).

Example 436

Preparation of the Compound of Compound No. 436

Using 5-chlorosalicylic acid and 2,4-dimethylaniline as the raw materials, the same operation as the Example 16 gave the title compound.
Yield: 37.1%. $^1$H-NMR(DMSO-d$_6$): δ 2.23(3H, s), 2.28 (3H, s), 7.03(2H, d, J=8.7 Hz), 7.10(1H, s), 7.49(1H, dd, J=9.0, 2.7 Hz), 7.63(1H, d, J=8.1 Hz), 8.03(1H, d, J=2.4 Hz), 10.24(1H, s), 12.25(1H, s).

Example 437

Preparation of the Compound of Compound No. 437

Using 5-chlorosalicylic acid and 3-isopropyloxyaniline as the raw materials, the same operation as the Example 16 gave the title compound.
Yield: 21.5%. $^1$H-NMR(CDCl$_3$): δ 1.36(6H, d, J=6.0 Hz), 4.52-4.64(1H, m), 6.75(1H, ddd, J=8.4, 2.4, 0.9 Hz), 6.99 (1H, d, J=8.7 Hz), 7.03(1H, ddd, J=8.1, 2.1, 0.9 Hz), 7.25-7.31(3H, m), 7.39(1H, dd, J=8.7, 2.4 Hz), 7.49(1H, d, J=2.4 Hz), 7.81(1H, s).

Example 438

Preparation of the Compound of Compound No. 438

Using 5-chlorosalicylic acid and 2,6-dichloroaniline as the raw materials, the same operation as the Example 16 gave the title compound.
Yield: 10.3%. $^1$H-NMR(DMSO-d$_6$): δ 7.05(1H, d, J=8.7 Hz), 7.43(1H, dd, J=8.7, 7.8 Hz), 7.54(1H, dd, J=9.0, 2.7 Hz), 7.62(1H, d, J=8.1 Hz), 8.05(1H, d, J=2.4 Hz), 10.52(1H, s), 12.01(1H, s).

Example 439

Preparation of the Compound of Compound No. 439

Using 5-chlorosalicylic acid and 4-isopropyloxyaniline as the raw materials, the same operation as the Example 16 gave the title compound.

Yield: 76.8%. $^1$H-NMR(DMSO-$d_6$): δ 1.26(6H, d, J=6.3 Hz), 4.52-4.64(1H, m), 6.93(2H, dt, J=9.0, 2.1 Hz), 7.46(1H, dd, J=9.0, 2.7 Hz), 7.58(2H, dt, J=9.0, 2.1 Hz), 7.99(1H, d, J=3.0 Hz), 10.36(1H, s), 11.83(1H, brs).

Example 440

Preparation of the Compound of Compound No. 440

Using 5-chlorosalicylic acid and 4-bromo-2-(trifluoromethoxy)aniline as the raw materials, the same operation as the Example 16 gave the title compound.

Yield: 59.2%. $^1$H-NMR(CDCl$_3$): δ 7.01(1H, d, J=9.3 Hz), 7.42-7.52(4H, m), 8.23(1H, s), 8.31(1H, d, J=9.3 Hz), 11.35 (1H, s).

Example 441

Preparation of the Compound of Compound No. 441

Using 5-chlorosalicylic acid and 4-butylaniline as the raw materials, the same operation as the Example 16 gave the title compound.

Yield: 77.6% $^1$H-NMR(CDCl$_3$): δ 0.89(3H, t, J=6.9 Hz), 1.27-1.36(6H, m), 1.56-1.64(2H, m), 2.61(2H, t, J=7.8 Hz), 6.99(1H, d, J=9.0 Hz), 7.21(2H, d, J=8.7 Hz), 7.39(1H, dd, J=9.0, 2.7 Hz), 7.44-7.49(3H, m), 7.80(1H, s), 11.96(1H, s).

Example 442

Preparation of the Compound of Compound No. 442

Using 5-chlorosalicylic acid and 3-methylaniline as the raw materials, the same operation as the Example 16 gave the title compound.

Yield: 88.3%. $^1$H-NMR(CDCl$_3$): δ 2.38(3H, s), 6.98(1H, d, J=8.8 Hz), 7.03(1H, d, J=7.4 Hz), 7.25-7.40(4H, m), 7.48 (1H, d, J=2.2 Hz), 7.83(1H, brs), 11.92(1H, brs).

Example 443

Preparation of the Compound of Compound No. 443

Using 5-chlorosalicylic acid and 4-cyclohexylaniline as the raw materials, the same operation as the Example 16 gave the title compound.

Yield: 90.6%. $^1$H-NMR(CDCl$_3$): δ 1.15-1.47(5H, m), 1.56-1.87(5H, m), 2.40-2.53(2H, m), 7.01(1H, d, J=8.8 Hz), 7.21(2H, d, J=8.5 Hz), 7.47(1H, dd, J=8.8, 2.7 Hz), 7.60(2H, d, J=8.5 H), 8.00(1H, d, J=2.7 Hz), 10.36(1H, s), 11.98(1H, brs).

Example 444

Preparation of the Compound of Compound No. 444

Using 5-chlorosalicylic acid and 4-benzylaniline as the raw materials, the same operation as the Example 16 gave the title compound.

Yield: 90.3%. $^1$H-NMR(DMSO-$d_6$): δ 3.93(2H, s), 7.01 (1H, d, J=9.0 Hz), 7.16-7.32(7H, m), 7.57(1H, dd, J=9.0, 2.7 Hz), 7.61(2H, d, J=8.4 Hz), 7.96(1H, d, J=2.4 Hz), 10.37(1H, s).

Example 445

Preparation of the Compound of Compound No. 445

Using 5-chlorosalicylic acid and 2-amino-4,5-dimethoxybenzonitrile as the raw materials, the same operation as the Example 16 gave the title compound.

Yield: 52.8%. $^1$H-NMR(DMSO-$d_6$): δ 3.81(3H, s), 3.86 (3H, s), 7.08(1H, d, J=8.7 Hz), 7.40(1H, s), 7.52(1H, dd, J=8.7, 2.7 Hz), 7.89(1H, s), 7.99(1H, d, J=3.0 Hz), 10.93(1H, s), 12.31(1H, s).

Example 446

Preparation of the Compound of Compound No. 446

Using 5-chlorosalicylic acid and 6-amino-1,4-benzodioxane as the raw materials, the same operation as the Example 16 gave the title compound.

Yield: 79.7%. $^1$H-NMR(DMSO-$d_6$): δ 4.25(4H, s), 6.86 (1H, d, J=8.8 Hz), 7.00(1H, d, J=8.8 Hz), 7.12(1H, dd, J=8.8, 2.5 Hz), 7.33(1H, d, J=2.5 Hz), 7.46(1H, dd, J=8.8, 2.5 Hz), 7.97(1H, d, J=2.5 Hz), 10.27(1H, s), 11.96(1H, s).

Example 447

Preparation of the Compound of Compound No. 447

Using 5-chlorosalicylic acid and 2,4-dichloro-5-(isopropyloxy)aniline as the raw materials, the same operation as the Example 16 gave the title compound.

Yield: 76.1%. $^1$H-NMR(DMSO-$d_6$): δ 1.35(6H, d, J=6.0 Hz), 4.58-4.66(1H, m), 7.07(1H, d, J=9.0 Hz), 7.51(1H, dd, J=8.7, 3.0 Hz), 7.68(1H, s), 7.98(1H, d, J=3.0 Hz), 8.35(1H, s), 10.94(1H, s), 12.34(1H, s).

Example 448

Preparation of the Compound of Compound No. 448

Using 5-chlorosalicylic acid and 4-amino-2-chlorobenzonitrile as the raw materials, the same operation as the Example 16 gave the title compound.

Yield: 57.9%. $^1$H-NMR(DMSO-$d_6$): δ 7.04(1H, d, J=9.0 Hz), 7.48(1H, dd, J=8.7, 2.7 Hz), 7.78(1H, d, J=2.7 Hz), 7.82(1H, dd, J=9.0, 2.1 Hz), 7.97(1H, d, J=8.7 Hz), 8.19(1H, d, J=2.1 Hz), 10.79(1H, s), 11.38(1H, s).

Example 449

Preparation of the Compound of Compound No. 449

Using 5-chlorosalicylic acid and 3-chloro-4-(trifluoromethoxy)aniline as the raw materials, the same operation as the Example 16 gave the title compound.

Yield: 50.6%. $^1$H-NMR(DMSO-$d_6$): δ 7.03(1H, d, J=8.7 Hz), 7.48(1H, dd, J=8.7, 2.7 Hz), 7.60(1H, dd, J=9.0, 1.5 Hz), 7.76(1H, dd, J=9.0, 2.4 Hz), 7.85(1H, d, J=3.0 Hz), 8.13(1H, d, J=2.4 Hz), 10.61(1H, s), 11.51(1H, s).

Example 450

Preparation of the Compound of Compound No. 450

Using 5-chlorosalicylic acid and 4-amino-3-methylbenzonitrile as the raw materials, the same operation as the Example 16 gave the title compound.

Yield: 80.6%. $^1$H-NMR(DMSO-d$_6$): δ 2.36(3H, s), 7.06 (1H, d, J=8.7 Hz), 7.49(1H, dd, J=8.7, 2.4 Hz), 7.71(1H, dd, J=8.4, 1.8 Hz), 7.77(1H, s), 7.95(1H, d, J=3.0 Hz), 8.40(1H, d, J=8.4 Hz), 10.76(1H, s), 12.31(1H, brs).

Example 451

Preparation of the Compound of Compound No. 451

Using 5-chlorosalicylic acid and 2,3-dichloroaniline as the raw materials, the same operation as the Example 16 gave the title compound.

Yield: 37.1%. $^1$H-NMR(DMSO-d$_6$): δ 7.08(1H, d, J=9.0 Hz), 7.40-7.48(2H, m), 7.52(1H, dd, J=9.0, 2.7 Hz), 7.98(1H, d, J=2.7 Hz), 8.40(1H, dd, J=7.2, 2.4 Hz), 11.00(1H, s), 12.32(1H, s).

Example 452

Preparation of the Compound of Compound No. 452

Using 5-chlorosalicylic acid and 2-chloroaniline as the raw materials, the same operation as the Example 16 gave the title compound.

Yield: 67.3%. $^1$H-NMR(DMSO-d$_6$): δ 7.08(1H, d, J=8.7 Hz), 7.20(1H, td, J=8.1, 1.8 Hz), 7.40(1H, td, J=8.4, 1.8 Hz), 7.52(1H, dd, J=8.7, 2.7 Hz), 7.57(1H, dd, J=8.4, 1.8 Hz), 8.00(1H, d, J=2.7 Hz), 8.40(1H, dd, J=8.4, 1.8 Hz), 10.89(1H, s), 12.27(1H, s).

Example 453

Preparation of the Compound of Compound No. 453

Using 5-chlorosalicylic acid and 4-isopropyl-3-methylaniline as the raw materials, the same operation as the Example 16 gave the title compound.

Yield: 21.6%. $^1$H-NMR(CDCl$_3$): δ 1.23(6H, d, J=6.9 Hz), 2.36(3H, s), 3.12(1H, m), 6.89(1H, d, J=9.0 Hz), 7.15-7.40 (5H, m), 7.48(1H, d, J=2.1 Hz), 7.83(1H, brs).

Example 454

Preparation of the Compound of Compound No. 454

Using 5-chlorosalicylic acid and 2-amino-5-[(1,1-dimethyl)propyl]phenol as the raw materials, the same operation as the Example 16 gave the title compound.

Yield: 24.9%. $^1$H-NMR(CDCl$_3$): δ 0.69(3H, t, J=7.5 Hz), 1.28(6H, s), 1.63(2H, q, J=7.5 Hz), 6.98(1H, d, J=8.7 Hz), 7.01(1H, d, J=9.0 Hz), 7.06(1H, s), 7.15(1H, dd, =8.4, 2.4 Hz), 7.35(1H, d, J=2.1 Hz), 7.42(1H, dd, J=8.7, 2.4 Hz), 7.56(1H, d, J=2.4 Hz), 8.26(1H, s), 11.44(1H, s).

Example 455

Preparation of the Compound of Compound No. 455

Using 5-chlorosalicylic acid and 2-methylaniline as the raw materials, the same operation as the Example 16 gave the title compound.

Yield: 64.7%. $^1$H-NMR(DMSO-d$_6$): δ 2.28(3H, s), 7.05 (1H, d, J=8.7 Hz), 7.13(1H, td, J=7.5, 1.5 Hz), 7.22-7.30(2H, m), 7.50(1H, dd, J=9.0, 2.7 Hz), 7.83(1H, d, J=7.8 Hz), 8.03 (1H, d, J=3.0 Hz), 10.32(1H, s), 12.22(1H, s).

Example 456

Preparation of the Compound of Compound No. 456

Using 5-chlorosalicylic acid and 4-butylaniline as the raw materials, the same operation as the Example 16 gave the title compound.

Yield: 82.1%. $^1$H-NMR(DMSO-d$_6$): δ 0.90(3H, t, J=7.2 Hz), 1.24-1.36(2H, m), 1.50-1.60(2H, m), 2.56(2H, t, J=7.2 Hz), 7.01(1H, d, J=8.7 Hz), 7.19(2H, d, J=8.7 Hz), 7.47(1H, dd, J=8.7, 2.4 Hz), 7.59(2H, d, J=8.4 Hz), 7.98(1H, d, J=2.7 Hz), 10.36(1H, s), 11.94(1H, s).

Example 457

Preparation of the Compound of Compound No. 457

Using 5-chlorosalicylic acid and 2-amino-6-chlorobenzonitrile as the raw materials, the same operation as the Example 16 gave the title compound.

Yield: 12.7%. $^1$H-NMR(DMSO-d$_6$): δ 7.09(1H, d, J=8.7 Hz), 7.52(1H, d, J=8.1 Hz), 7.53(1H, dd, J=9.0, 3.0 Hz), 7.76(1H, t, J=8.7 Hz), 7.95(1H, d, J=3.0 Hz), 8.34(1H, d, J=8.4 Hz), 11.17(1H, s), 12.39(1H, s).

Example 458

Preparation of the Compound of Compound No. 458

Using 5-chlorosalicylic acid and 2-amino-5-methylbenzonitrile as the raw materials, the same operation as the Example 16 gave the title compound.

Yield: 9.0%. $^1$H-NMR(CDCl$_3$): δ 2.48(3H, s), 7.01(1H, d, J=9.0 Hz), 7.10(1H, dd, J=8.0, 0.9 Hz), 7.44(1H, d, J=9.0, 2.4 Hz), 7.56(1H, d, J=8.1 Hz), 7.62(1H, d, J=2.4 Hz), 8.22(1H, s), 8.54(1H, brs), 11.25(1H, brs).

Example 459

Preparation of the Compound of Compound No. 459

Using 5-chlorosalicylic acid and 4-benzyloxyaniline as the raw materials, the same operation as the Example 16 gave the title compound.

Yield: 26.8%. $^1$H-NMR(DMSO-d$_6$): δ 5.11(2H, s), 6.99-7.05(3H, m), 7.33-7.49(6H, m), 7.60(2H, d, J=9.0 Hz), 7.99 (1H, d, J=2.7 Hz), 10.33(1H, s), 12.02(1H, s).

Example 460

Preparation of the Compound of Compound No. 460

Using 5-chlorosalicylic acid and 4-amino-2,2-difluorobenzo[1,3]dioxole as the raw materials, the same operation as the Example 16 gave the title compound.

Yield: 66.9%. ¹H-NMR(DMSO-d$_6$): δ 7.05(1H, d, J=8.8 Hz), 7.31-7.32(2H, m), 7.51(1H, dd, J=8.8, 2.8 Hz), 7.70(1H, dd, J=5.6, 3.8 Hz), 7.96(1H, d, J=2.8 Hz), 10.59(1H, s), 12.05(1H, brs).

Example 461

Preparation of the Compound of Compound No. 461

Using 5-chlorosalicylic acid and 5-amino-2,2,3,3-tetrafluoro-2,3-dihydrobenzo[1,4]dioxene as the raw materials, the same operation as the Example 16 gave the title compound.
Yield: 67.9%. ¹H-NMR(CDCl$_3$): δ 6.99-7.03(2H, m), 7.21-7.27(2H, m), 7.45(1H, dd, J=8.9, 2.5 Hz), 7.52(1H, d, J=2.5 Hz), 8.13(1H, s), 11.44(1H, s).

Example 462

Preparation of the Compound of Compound No. 462

Using 5-chlorosalicylic acid and 3-chloro-4-(trifluoromethyl)sulfanylaniline as the raw materials, the same operation as the Example 16 gave the title compound.
Yield: 52.3%. ¹H-NMR(DMSO-d$_6$): δ 7.03(1H, d, J=8.8 Hz), 7.47(1H, dd, J=2.9, 8.8 Hz), 7.80(1H, dd, J=2.6, 8.8 Hz), 7.82(1H, d, J=2.6 Hz), 7.88(1H, d, J=8.8 Hz), 8.20(1H, d, J=2.2 Hz), 10.70(1H, s), 11.43(1H, s).

Example 463

Preparation of the Compound of Compound No. 463

Using 5-chlorosalicylic acid and 2-nitro-4-(trifluoromethoxy)aniline as the raw materials, the same operation as the Example 16 gave the title compound.
Yield: 68.4%. ¹H-NMR(DMSO-d$_6$): δ 7.07(1H, d, J=8.8 Hz), 7.52(1H, dd, J=2.6, 8.8 Hz), 7.85-7.89(1H, m), 7.93(1H, d, J=2.6 Hz), 8.17(1H, d, J=2.9 Hz), 8.67(1H, d, J=9.5 Hz), 11.92(1H, s), 12.14(1H, s).

Example 464

Preparation of the Compound of Compound No. 464

Using 5-chlorosalicylic acid and 5-amino-2,2-difluorobenzo[1,3]dioxole as the raw materials, the same operation as the Example 16 gave the title compound.
Yield: 75.8%. ¹H-NMR(DMSO-d$_6$): δ 7.02(1H, d, J=8.8 Hz), 7.42-7.43(2H, m), 7.48(1H, dd, J=8.8, 2.5 Hz), 7.90(1H, d, J=2.5 Hz), 10.54(1H, s), 11.69(1H, s).

Example 465

Preparation of the Compound of Compound No. 465

Using 5-chlorosalicylic acid and 3-benzylaniline as the raw materials, the same operation as the Example 16 gave the title compound.

Yield: 66.4%. ¹H-NMR(CDCl$_3$): δ 3.99(2H, s), 6.97(1H, d, J=9.1 Hz), 7.06(1H, d, J=7.4 Hz), 7.18-7.48(8H, m), 7.37 (1H, dd, J=9.1, 2.5 Hz), 7.45(1H, d, J=2.5 Hz), 7.80(1H, brs), 11.88(1H, s).

Example 466

Preparation of the Compound of Compound No. 466

Using 5-chlorosalicylic acid and 2-nitro-4-(trifluoromethoxy)aniline as the raw materials, the same operation as the Example 16 gave the title compound.
Yield: 40.9%. ¹H-NMR(DMSO-d$_6$): δ 2.33(3H, s), 7.05 (1H, d, J=8.8 Hz), 7.25(1H, dd, J=1.8, 8.8 Hz), 7.33(1H, d, J=1.8 Hz), 7.49(1H, dd, J=2.9, 8.8 Hz), 7.97-8.00(2H, m), 10.37(1H, s), 12.15(1H, s).

Example 467

Preparation of the Compound of Compound No. 467

Using 5-chlorosalicylic acid and 2,3,5-trifluoroaniline as the raw materials, the same operation as the Example 16 gave the title compound.
Yield: 54.2%. ¹H-NMR(DMSO-d$_6$): δ 7.06(1H, d, J=8.8 Hz), 7.28-7.37(1H, m), 7.51(1H, dd, J=2.6, 8.8 Hz), 7.92(1H, d, J=2.6 Hz), 7.98-8.04(1H, m), 10.93(1H, s), 12.27(1H, br.s)

Example 468

Preparation of the Compound of Compound No. 468

Using 5-chlorosalicylic acid and 4'-aminobenzo-15-crown-5 as the raw materials, the same operation as the Example 16 gave the title compound.
Yield: 45.1%. ¹H-NMR(CDCl$_3$): δ 3.74-3.77(8H, m), 3.90-3.92(4H, m), 4.10-4.15(4H, m), 6.83(1H, d, J=8.5 Hz), 6.96-6.99(2H, m), 7.24(1H, d, J=2.5 Hz), 7.36(1H, dd, J=2.5, 8.8 Hz), 7.53(1H, s), 8.06(1H, br.s), 11.92(1H, s).

Example 469

Preparation of the Compound of Compound No. 469

Using 5-chlorosalicylic acid and 4-bromo-2-fluoroaniline as the raw materials, the same operation as the Example 16 gave the title compound.
Yield: 45.1%. ¹H-NMR(DMSO-d$_6$): δ 7.05(1H, d, J=8.8 Hz), 7.43-7.53(2H, m), 7.64-7.71(1H, m), 7.94(1H, d, J=1.5 Hz), 8.20(1H, dd, J=8.4, 8.8 Hz), 10.70(1H, s), 12.16(1H, s).

Example 470

Preparation of the Compound of Compound No. 470

Using 5-chlorosalicylic acid and 2,4-bis(methanesulfonyl) aniline as the raw materials, the same operation as the Example 16 gave the title compound.
Yield: 7.2%. ¹H-NMR(CDCl$_1$): δ 3.13(3H, s), 3.21(3H, s), 7.04(1H, d, J=8.9 Hz), 7.48(1H, dd, J=2.2, 8.9 Hz), 7.62(1H, d, J=2.2 Hz), 8.24(1H, dd, J=2.4, 9.0 Hz), 8.56(1H, d, J=2.4 Hz), 8.91(1H, d, J=8.9 Hz), 10.96(1H, s), 11.57(1H, s).

Example 471

Preparation of the Compound of Compound No. 471

A mixture of 5-chlorosalicylic acid (87 mg, 0.5 mmol), 2,2-bis(3-amino-4-methylphenyl)-1,1,1,3,3,3-hexafluoropropane (363 mg, 1 mmol), phosphorus trichloride (44 μL, 0.5 mmol) and toluene (4 mL) was refluxed for 4 hours. After the reaction mixture was cooled to, room temperature, it was purified by column chromatography on silica gel (n-hexane: ethyl acetate=5:1) to give the white title compound (16 mg, 4.9%). (The compound of Compound No. 529 described in the following Example 529 was obtained as a by-product.)

$^1$H-NMR(DMSO-d$_6$): δ 2.34(6H, s), 7.04(4H, d, J=8.8 Hz), 7.39(2H, d, J=8.4 Hz), 7.48(2H, dd, J=2.9, 8.8 Hz), 7.96(2H, d, J=2.9 Hz), 8.19(2H, s), 10.44(2H, s), 12.17(2H, s).

Example 472

Preparation of the Compound of Compound No. 472

Using 5-chlorosalicylic acid and 6-amino-2,2,3,3-tetrafluoro-2,3-dihydrobenzo-[1,4]dioxene as the raw materials, the same operation as the Example 16 gave the title compound.

Yield: 10.1%. $^1$H-NMR(DMSO-d$_6$): δ 7.03(1H, d, J=8.8 Hz), 7.48(1H, dd, J=9.0, 2.7 Hz), 7.50(1H, d, J=9.0 Hz), 7.59(1H, dd, J=8.8, 2.2 Hz), 7.86(1H, d, J=2.7 Hz), 7.92(1H, d, J=2.2 Hz), 10.59(1H, s), 11.55(1H, s).

Example 473

Preparation of the Compound of Compound No. 473

Using 5-chlorosalicylic acid and 2-amino-5-chlorobenzophenone as the raw materials, the same operation as the Example 16 gave the title compound.

Yield: 27.6%. $^1$H-NMR(DMSO-d$_6$): δ 6.96(1H, d, J=8.7 Hz), 7.43(1H, dd, J=8.7, 3.0 Hz), 7.49-7.56(3H, m), 7.64-7.75(5H, m), 8.21(1H, d, J=9.3 Hz), 11.21(1H, s), 11.83(1H, s).

Example 474

Preparation of the Compound of Compound No. 474

Using 5-chlorosalicylic acid and 2-bromo-4-fluoroaniline as the raw materials, the same operation as the Example 16 gave the title compound.

Yield: 77.1%. $^1$H-NMR(DMSO-d$_6$): δ 7.07(1H, d, J=9.0 Hz), 7.31-7.38(1H, m), 7.51(1H, dd, J=9.0, 3.0 Hz), 7.72(1H, d, J=8.1, 3.0 Hz), 8.00(1H, d, J=3.0 Hz), 8.23(1H, dd, J=9.3, 5.4 Hz), 10.70(1H, s), 12.24(1H, s).

Example 475

Preparation of the Compound of Compound No. 475

Using 5-chlorosalicylic acid and 4-hexyloxyaniline as the raw materials, the same operation as the Example 16 gave the title compound.

Yield: 74.8%. $^1$H-NMR(DMSO-d$_6$): δ 0.88(3H, t, J=6.6 Hz), 1.28-1.46(6H, m), 2.49-2.52(2H, m), 3.95(2H, t, J=6.6 Hz), 6.91-6.96(2H, m), 7.00(1H, d, J=8.8 Hz), 7.46(1H, dd, J=8.8, 2.9 Hz), 7.55-7.61(2H, m), 8.00(1H, d, J=2.9 Hz), 10.31(1H, s), 12.03(1H, s).

Example 476

Preparation of the Compound of Compound No. 476

Using 5-chlorosalicylic acid and 2,2-bis(3-aminophenyl)-1,1,1,3,3,3-hexafluoropropane as the raw materials, the same operation as the Example 16 gave the title compound.

Yield: 64.5%. $^1$H-NMR(DMSO-d$_6$): δ 6.99(2H, d, J=8.8 Hz), 7.11(2H, d, J=8.0 Hz), 7.45(2H, dd, J=8.8, 2.6 Hz), 7.50(2H, t, J=8.4 Hz), 7.86(2H, d, J=2, 6 Hz), 7.88-7.91(4H, m), 10.53(2H, s), 11.56(2H, s).

Example 477

Preparation of the Compound of Compound No. 477

Using 5-chlorosalicylic acid and 2,4,5-trichloroaniline as the raw materials, the same operation as the Example 16 gave the title compound.

Yield: 38.9%. $^1$H-NMR(CDCl$_3$): δ 7.02(1H, d, J=8.6 Hz), 7.46(1H, d, J=8.6 Hz), 7.49(1H, s), 7.57(1H, s), 8.41(1H, br.s), 8.63(1H, s), 11.42(1H, s).

Example 478

Preparation of the Compound of Compound No. 478

Using 5-chlorosalicylic acid and 3-isopropylaniline as the raw materials, the same operation as the Example 16 gave the title compound.

Yield: 55.3%. $^1$H-NMR(DMSO-d$_6$): δ 1.22(6H, d, 6.9 Hz), 2.76-2.94(1H, m), 7.01(1H, d, J=8.6 Hz), 7.04(1H, d, J=7.9 Hz), 7.29(1H, t, J=7.9 Hz), 7.47(1H, dd, J=8.6, 2.6 Hz), 7.54(1H, d, J=7.9 Hz), 7.57(1H, s), 7.98(1H, d, J=2.6 Hz), 10.37(1H, s), 11.90(1H, brs).

Example 479

Preparation of the Compound of Compound No. 479

Using 5-chlorosalicylic acid and 4-aminobenzonitrile as the raw materials, the same operation as the Example 16 gave the title compound.

Yield: 45.6%. $^1$H-NMR(DMSO-d$_6$): δ 7.03(1H, d, J=8.6 Hz), 7.47(1H, dd, J=8.6, 2.6 Hz), 7.83(1H, d, J=2.6 Hz), 7.84(2H, d, J=8.9 Hz), 7.92(2H, d, J=8.9 Hz), 10.71(1H, s), 11.59(1H, brs).

Example 480

Preparation of the Compound of Compound No. 480

Using 5-chlorosalicylic acid and 3-aminobenzonitrile as the raw materials, the same operation as the Example 16 gave the title compound.

Yield: 97.1%. $^1$H-NMR(DMSO-d$_6$): δ 7.03(1H, d, J=8.7 Hz), 7.48(1H, dd, J=9.0, 2.7 Hz), 7.56-7.63(2H, m), 7.88(1H, d, J=2.7 Hz), 7.95-8.02(1H, m), 8.20-8.21(1H, m), 10.62(1H, s), 11.57(1H, s).

Example 481

Preparation of the Compound of Compound No. 481

Using 5-chlorosalicylic acid and 3,4-dimethoxyaniline as the raw materials, the same operation as the Example 16 gave the title compound.

Yield: 73.3%. $^1$H-NMR(DMSO-d$_6$): δ 3.75(3H, s), 3.76 (3H, s), 6.95(1H, d, J=8.7 Hz), 7.01(1H, d, J=9.0 Hz), 7.24 (1H, dd, J=8.7, 2.7 Hz), 7.38(1H, d, J=2.1 Hz), 7.47(1H, dd, J=8.7, 2.7 Hz), 8.00(1H, d, J=2.4 Hz), 10.30(1H, s), 12.01 (1H, s).

Example 482

Preparation of the Compound of Compound No. 482

Using 5-chlorosalicylic acid and 4-aminophenylacetic acid ethyl ester as the raw materials, the same operation as the Example 16 gave the title compound.

Yield: 66.1%. $^1$H-NMR(DMSO-d$_6$): δ 1.19(3H, t, J=7.5 Hz), 3.64(2H, s), 4.08(2H, q, J=7.2 Hz), 7.01(1H, d, J=8.7 Hz), 7.26(2H, d, J=8.7 Hz), 7.47(1H, dd, J=8.7, 3.0 Hz), 7.64(1H, d, J=8.4 Hz), 7.96(1H, d, J=2.4 Hz), 10.40(1H, s), 11.87(1H, s).

Example 483

Preparation of the Compound of Compound No. 483

Using 5-chlorosalicylic acid and 3-[(trifluoromethyl)sulfanyl]aniline as the raw materials, the same operation as the Example 16 gave the title compound.

Yield: 67.1%. $^1$H-NMR(CDCl$_3$): δ 7.01(1H, d, J=8.9 Hz), 7.42(1H, dd, J=8.9, 2.3 Hz), 7.47-7.53(2H, m), 7.51(1H, d, J=2.3 Hz), 7.76(1H, dt, J=7.6 Hz, 2.0 Hz), 7.88(1H, brs), 7.92(1H, s), 11.64(1H, s).

Example 484

Preparation of the Compound of Compound No. 484

Using 5-chlorosalicylic acid and 4-[(trifluoromethyl)sulfanyl]aniline as the raw materials, the same operation as the Example 16 gave the title compound.

Yield: 63.2%. $^1$H-NMR(CDCl$_3$): δ 7.01(1H, d, J=8.9 Hz), 7.43(1H, dd, J=8.9, 2.3 Hz), 7.50(1H, d, J=2.3 Hz), 7.70(4H, s), 7.90(1H, brs), 11.60(1H, s).

Example 485

Preparation of the Compound of Compound No. 485

Using 5-chlorosalicylic acid and 4-(trifluoromethanesulfonyl)aniline as the raw materials, the same operation as the Example 16 gave the title compound.

Yield: 38.7%. $^1$H-NMR(DMSO-d$_6$): δ 7.04(1H, d, J=8.6 Hz), 7.49(1H, dd, J=8.6, 2.6 Hz), 7.80(1H, d, J=2.6 Hz), 8.12(2H, d, J=9.4 Hz), 8.17(2H, d, J=9.4 Hz), 8.16(1H, s), 10.95(1H, s), 11.37(1H, brs).

Example 486

Preparation of the Compound of Compound No. 486

Using 5-chlorosalicylic acid and 3,4-difluoroaniline as the raw materials, the same operation as the Example 16 gave the title compound.

Yield: 75.4%. $^1$H-NMR(DMSO-d$_6$): δ 7.02(1H, d, J=8.9 Hz), 7.39-7.51(3H, m), 7.85-7.93(2H, m), 10.51, (1H, s), 11.60(1H, s).

Example 487

Preparation of the Compound of Compound No. 487

Using 5-chlorosalicylic acid and 3-ethynylaniline as the raw materials, the same operation as the Example 16 gave the title compound.

Yield: 35.8%. $^1$H-NMR(DMSO-d$_6$): δ 4.22(1H, s), 7.02 (1H, d, J=8.6 Hz), 7.25(1H, d, J=7.6 Hz), 7.39(1H, t, J=7.6 Hz), 7.47(1H, dd, J=8.6, 2.6 Hz), 7.70(1H, d, J=7.6 Hz), 7.89(1H, s), 7.91(1H, d, J=2.6 Hz), 10.46(1H, s), 11.69(1H, brs).

Example 488

Preparation of the Compound of Compound No. 488

Using 5-chlorosalicylic acid and 4-(sec-butyl)aniline as the raw materials, the same operation as the Example 16 gave the title compound.

Yield: 40.1%. $^1$H-NMR(DMSO-d$_6$): δ 0.77(3H, t, 7.4 Hz), 1.19(3H, d, 6.9 Hz), 1.50-1.61(2H, m), 2.52-2.62(1H, m), 7.01(1H, d, J=8.9 Hz), 7.20(2H, d, J=8.6 Hz), 7.47(1H, dd, J=8.9, 2.6 Hz), 7.60(2H, d, J=8.6 Hz), 7.98(1H, d, J=2.6 Hz), 10.36(1H, s), 11.94(1H, brs).

Example 489

Preparation of the Compound of Compound No. 489

Using 5-chlorosalicylic acid and 3-chloro-4-methoxyaniline as the raw materials, the same operation as the Example 16 gave the title compound.

Yield: 75.7%. $^1$H-NMR(CDCl$_3$): δ 6.98(2H, t, J=9.2 Hz), 7.38-7.44(2H, m), 7.47(1H, d, J=2.6 Hz), 7.66(1H, d, J=2.6 Hz), 7.73(1H, br.s), 11.81(1H, s).

Example 490

Preparation of the Compound of Compound No. 490

Using 5-chlorosalicylic acid and 3-aminobenzophenone as the raw materials, the same operation as the Example 16 gave the title compound.

Yield: 34.3%. $^1$H-NMR(DMSO-d$_6$): δ 7.02(1H, d, J=8.6 Hz), 7.48(1H, dd, J=9.1, 2.6 Hz), 7.52-7.62(4H, m), 7.68-7.79(3H, m), 7.93(1H, d, J=2.6 Hz), 8.02(1H, d, J=7.9 Hz), 8.16(1H, s), 10.60(1H, s), 11.68(1H, brs).

Example 491

Preparation of the Compound of Compound No. 491

Using 5-chlorosalicylic acid and 3-methoxyaniline as the raw materials, the same operation as the Example 16 gave the title compound.

Yield: 23.5%. $^1$H-NMR(DMSO-d$_6$): δ 3.76(3H, s), 6.69-6.75(1H, m), 7.01(1H, d, J=8.6 Hz), 7.25-7.28(2H, m), 7.39 (1H, s), 7.47(1H, dd, J=8.6, 2.6 Hz), 7.94(1H, d, J=2.6 Hz), 10.39(1H, s), 11.81(1H, brs).

Example 492

Preparation of the Compound of Compound No. 492

Using 5-chlorosalicylic acid and 4'-aminoacetanilide as the raw materials, the same operation as the Example 16 gave the title compound.

Yield: 36.2%. $^1$H-NMR(DMSO-d$_6$): δ 2.50(3H, s), 7.01 (1H, d, J=8.6 Hz), 7.47(1H, dd, J=8.6, 2.6 Hz), 7.57(2H, d, J=9.1 Hz), 7.61(2H, d, J=9.1 Hz), 7.98(1H, d, J=2.6 Hz), 9.95(1H, s), 10.38(1H, s), 11.99(1H, brs).

Example 493

Preparation of the Compound of Compound No. 493

Using 5-chlorosalicylic acid and sulfanilamide as the raw materials, the same operation as the Example 16 gave the title compound.

Yield: 25.7%. $^1$H-NMR(DMSO-d$_6$): δ 7.03(1H, d, J=8.9 Hz), 7.31(2H, s), 7.47(1H, dd, J=8.9, 2.3 Hz), 7.81(2H, d, J=8.9 Hz), 7.89(2H, d, J=8.9 Hz), 7.89(1H, d, J=2.3 Hz), 10.70(1H, s), 11.55(1H, brs).

Example 494

Preparation of the Compound of Compound No. 494

Using 5-chlorosalicylic acid and 2-(4-aminophenyl)-1,1,1,3,3,3-hexafluoro-2-propanol as the raw materials, the same operation as the Example 16 gave the title compound. (The compound was obtained by separation from the mixture with the compound of Compound No. 498 described in the following Example 498.)

Yield: 11.7%. $^1$H-NMR(DMSO-d$_6$): δ 7.02(1H, d, J=8.6 Hz), 7.47(1H, dd, J=8.6, 2.6 Hz), 7.68(2H, d, J=8.7 Hz), 7.85(2H, d, J=8.7 Hz), 7.91(1H, d, J=2.6 Hz), 8.69(1H, s), 10.62(1H, s).

Example 495

Preparation of the Compound of Compound No. 495

Using 5-chlorosalicylic acid and 2-chloro-4-nitroaniline as the raw materials, the same operation as the Example 16 gave the title compound.

Yield: 39.6%. $^1$H-NMR(CDCl$_3$): δ 7.04(1H, d, J=8.9 Hz), 7.47(1H, dd, J=2.3, 8.9 Hz), 7.54(1H, d, J=2.3 Hz), 8.25(1H, dd, J=2.6, 8.9 Hz), 8.39(1H, d, J=2.3 Hz), 8.73(1H, d, J=9.2 Hz), 8.76(1H, br.s), 11.22(1H, s).

Example 496

Preparation of the Compound of Compound No. 496

Using 5-chlorosalicylic acid and 2,4-difluoroaniline as the raw materials, the same operation as the Example 16 gave the title compound.

Yield: 67.8%. $^1$H-NMR(DMSO-d$_6$): δ 7.05(1H, dd, J=1.7, 8.9 Hz), 7.15(1H, dt, J=1.7, 9.2 Hz), 7.41(1H, ddd, J=2.3, 8.9, 9.2 Hz), 7.51(1H, dt, J=2.3, 8.9 Hz), 7.98(1H, d, J=2.3 Hz), 8.11(1H, dd, J=8.9, 15.1 Hz), 10.59(1H, s), 12.13(1H, s).

Example 497

Preparation of the Compound of Compound No. 497

Using 5-chlorosalicylic acid and 4-(difluoromethoxy)aniline as the raw materials, the same operation as the Example 16 gave the title compound.

Yield: 85.9%. $^1$H-NMR(DMSO-d$_6$): δ 7.01(1H, d, J=8.6 Hz), 7.19(1H, t, J=74.2 Hz), 7.20(2H, d, J=8.6 Hz), 7.47(1H, dd, J=8.6, 2.6 Hz), 7.74(2H, d, J=8.9 Hz), 7.94(1H, d, J=2.6 Hz), 10.47(1H, s), 11.80(1H, brs).

Example 498

Preparation of the Compound of Compound No. 498

This compound was obtained by separation from the mixture with the compound of Compound No. 494 described in the aforementioned Example 494.

Yield: 11.6%. $^1$H-NMR(DMSO-d$_6$): δ 7.02(1H, d, J=8.6 Hz), 7.46(1H, dd, J=8.6, 2.3 Hz), 7.83(2H, d, J=8.1 Hz), 7.88(1H, d, J=2.3 Hz), 7.95(2H, d, J=8.1 Hz), 10.71(1H, s).

Example 499

Preparation of the Compound of Compound No. 499

Using 5-chlorosalicylic acid and 3-(methylsulfanyl)aniline as the raw materials, the same operation as the Example 16 gave the title compound.

Yield: 67.2%. $^1$-NMR(DMSO-d$_6$): δ 2.49(3H, s), 7.00-7.05(1H, m), 7.01(1H, d, J=8.9 Hz), 7.31(1H, t, J=7.9 Hz), 7.46(1H, dd, J=8.9, 2.6 Hz), 7.44-7.49(1H, m), 7.68(1H, d, J=1.7 Hz), 7.93(1H, d, J=2.6 Hz), 10.47(1H, s).

Example 500

Preparation of the Compound of Compound No. 500

Using 5-chlorosalicylic acid and 4-methanesulfonylaniline as the raw materials, the same operation as the Example 16 gave the title compound.

Yield: 28.6%. $^1$H-NMR(DMSO-d$_6$): δ 3.20(3H, s), 7.03 (1H, d, J=8.3 Hz), 7.48(1H, dd, J=8.3, 2.6 Hz), 7.87(1H, d, J=2.6 Hz), 7.92(2H, d, J=8.9 Hz), 7.98(2H, d, J=8.9 Hz), 10.75(1H, s), 11.45(1H, brs).

Example 501

Preparation of the Compound of Compound No. 501

Using 5-chlorosalicylic acid and 2-amino-4-methylbenzophenone as the raw materials, the same operation as the Example 16 gave the title compound.

Yield: 8.7%. $^1$H-NMR(CDCl$_3$): δ 2.50(3H, s), 6.98(1H, d, J=8.3 Hz), 6.99(1H, d, J=7.3 Hz), 7.39(1H, dd, J=2.0, 8.6 Hz), 7.48-7.64(4H, m), 7.72(2H, d, J=7.6 Hz), 7.83(1H, d, J=2.3 Hz), 8.57(1H, s), 12.18(1H, s), 12.34(1H, br.s).

Example 502

Preparation of the Compound of Compound No. 502

Using 5-chlorosalicylic acid and 3-amino-N-butylbenzenesulfonamide as the raw materials, the same operation as the Example 16 gave the title compound.

Yield: 46.7%. $^1$H-NMR(DMSO-d$_6$): δ 0.80(3H, t, J=7.3 Hz), 1.17-1.41(4H, m), 2.73-2.80(2H, m), 7.03(1H, d, J=8.9 Hz), 7.48(1H, dd, J=8.9, 2.0 Hz), 7.53-7.64(2H, m), 7.87-7.92(1H, m), 7.92(1H, d, J=2.0 Hz), 8.27(1H, s), 10.62(1H, s), 11.63(1H, s).

Example 503

Preparation of the Compound of Compound No. 503

Using 5-chlorosalicylic acid and 3-(benzyloxy)aniline as the raw materials, the same operation as the Example 16 gave the title compound.

Yield: 68.5%. $^1$H-NMR(DMSO-d$_6$): δ 5.11(2H, s), 6.79-6.83(1H, m), 7.01(1H, d, J=8.9 Hz), 7.27-7.49(9H, m), 7.93 (1H, d, J=3.0 Hz), 10.40(1H, s), 11.79(1H, brs).

Example 504

Preparation of the Compound of Compound No. 504

Using 5-chlorosalicylic acid and N-(4-aminophenyl)-4-methylbenzenesulfonamide as the raw materials, the same operation as the Example 16 gave the title compound.

Yield: 40.6%. $^1$H-NMR(DMSO-d$_6$): δ 2.33(3H, s), 6.99 (1H, d, J=8.6 Hz), 7.07(2H, d, J=8.6 Hz), 7.34(2H, d, J=8.3 Hz), 7.45(1H, dd, J=8.6, 2.1 Hz), 7.53(2H, d, J=8.6 Hz), 7.63(2H, d, J=8.3 Hz), 7.90(1H, d, J=2.1 Hz), 10.14(1H, s), 10.33(1H, s), 11.81(1H, brs).

Example 505

Preparation of the Compound of Compound No. 505

Using 5-chlorosalicylic acid and 4-(morpholino)aniline as the raw materials, the same operation as the Example 16 gave the title compound.

Yield: 29.8%. $^1$H-NMR(DMSO-d$_6$): δ 3.09(4H, t, J=4.6 Hz), 3.74(4H, t, J=4.6 Hz), 6.94-7.01(3H, m), 7.46(1H, dd, J=8.9, 2.6 Hz), 7.55(2H, d, J=8.9 Hz), 8.01(1H, d, J=2.6 Hz), 10.29(1H, s), 12.10(1H, brs).

Example 506

Preparation of the Compound of Compound No. 506

Using 5-chlorosalicylic acid and 3-(tert-butyl)aniline as the raw materials, the same operation as the Example 16 gave the title compound.

Yield: 76.1%. $^1$H-NMR(CDCl$_3$): δ 1.35(9H, s), 6.99(1H, d, J=8.9 Hz), 7.24-7.28(1H, m), 7.32-7.35(1H, m), 7.40(1H, dd, J=8.9, 2.3 Hz), 7.46-7.50(2H, m), 7.51(1H, d, J=2.3 Hz), 7.81(1H, brs), 11.94(1H, s).

Example 507

Preparation of the Compound of Compound No. 507

Using 5-chlorosalicylic acid and 3-(5-methylfuran-2-yl)aniline as the raw materials, the same operation as the Example 16 gave the title compound.

Yield: 61.1%. $^1$H-NMR(DMSO-d$_6$): δ 2.36(3H, s), 6.22-6.23(1H, m), 6.81(1H, d, J=3.0 Hz), 7.02(1H, d, J=8.9 Hz), 7.36-7.51(3H, m), 7.58-7.61(1H, m), 7.99-8.01(2H, m), 10.49(1H, s), 11.85(1H, brs).

Example 508

Preparation of the Compound of Compound No. 508

Using 5-chlorosalicylic acid and 3-(1-hydroxyethyl)aniline as the raw materials, the same operation as the Example 16 gave the title compound.

Yield: 37.6%. $^1$H-NMR(DMSO-d$_6$): δ 1.80(3H, d, J=6.6 Hz), 5.33(1H, q, J=6.6 Hz), 7.01(1H, d, J=8.9 Hz), 7.25(1H, d, J=7.9 Hz), 7.38(1H, t, J=7.9 Hz), 7.47(1H, dd, J=8.9, 2.3 Hz), 7.65(1H, d, J=7.9 Hz), 7.85(1H, s), 7.96(1H, d, J=2.3 Hz), 10.48(1H, s), 11.80(1H, brs).

Example 509

Preparation of the Compound of Compound No. 509

Using 5-chlorosalicylic acid and 3-aminobenzenesulfonamide as the raw materials, the same operation as the Example 16 gave the title compound.

Yield: 18.7%. $^1$H-NMR(DMSO-d$_6$): δ 7.03(1H, d, J=8.9 Hz), 7.41(2H; s), 7.48(1H, dd, J=8.9, 2.6 Hz), 7.54-7.62(2H, m), 7.84-7.88(1H, m), 7.93(1H, d, J=2.6 Hz), 8.30(1H, s), 10.64(1H, s), 11.68(1H, brs).

Example 510

Preparation of the Compound of Compound No. 510

Using 5-chlorosalicylic acid and 3-(trifluoromethanesulfonyl)aniline as the raw materials, the same operation as the Example 16 gave the title compound.

Yield: 62.6%. $^1$H-NMR(DMSO-d$_6$): δ 7.03(1H, d, J=8.6 Hz), 7.48(1H, dd, J=8.6, 2.6 Hz), 7.82-7.88(3H, m), 8.23-8.26(1H, m), 8.67(1H, s), 10.88(1H, s), 11.45(1H, brs).

Example 511

Preparation of the Compound of Compound No. 511

Using 5-chlorosalicylic acid and 2-bromo-4-(trifluoromethoxy)aniline as the raw materials, the same operation as the Example 16 gave the title compound.

Yield: 17.1%. $^1$H-NMR(CDCl$_3$): δ 7.02(1H, d, J=8.9 Hz), 7.26-7.31(1H, m), 7.44(1H, dd, J=8.9, 2.6 Hz), 7.53(2H, d, J=2.6 Hz), 8.41(1H, brs,), 8.42(1H, d, J=8.9 Hz), 11.57(1H, s).

Example 512

Preparation of the Compound of Compound No. 512

Using 5-chlorosalicylic acid and 3,4-(dihexyloxy)aniline as the raw materials, the same operation as the Example 16 gave the title compound.

Yield: 60.5%. $^1$H-NMR(CDCl$_3$): δ 0.91(6H, t, J=6.3 Hz), 1.34-1.61(12H, m), 1.76-1.89(4H, m), 3.97-4.04(4H, m), 6.88(1H, d, J=8.9 Hz), 6.97-7.00(2H, m), 7.22(1H, d, J=2.6 Hz), 7.38(1H, dd, J=8.9, 2.6 Hz), 7.47(1H, d, J=2.6 Hz), 7.73(1H, s), 11.97(1H, s).

Example 513

Preparation of the Compound of Compound No. 513

Using 5-chlorosalicylic acid and 3,4-dichloroaniline as the raw materials, the same operation as the Example 16 gave the title compound.

Yield: 16.4%. $^1$H-NMR(DMSO-d$_6$): δ 7.03(1H, d, J=8.7 Hz), 77.47(1H, dd, J=8.7, 2.7 Hz), 7.61-7.70(2H, m), 7.86 (1H, d, J=2.7 Hz), 8.11(1H, d, J=2.1 Hz), 10.56(1H, s), 11.53 (1H, s).

Example 514

Preparation of the Compound of Compound No. 514

Using 5-chlorosalicylic acid and 3-hexyloxyaniline as the raw materials, the same operation as the Example 16 gave the title compound.

Yield: 88.2%. $^1$H-NMR(DMSO-d$_6$): δ 0.89(3H, t, J=7.0 Hz), 1.28-1.47(6H, m), 1.67-1.76(2H, m), 3.95(2H, t, J=6.6 Hz), 6.69-6.73(1H, m), 7.01(1H, d, J=8.8 Hz), 7.21-7.28(2H, m), 7.39-7.40(1H, m), 7.67(1H, dd, J=8.8, 2.6 Hz), 7.94(1H, d, J=2.6 Hz), 10.34(1H, s), 11.80(1H, s).

Example 515

Preparation of the Compound of Compound No. 515

Using 5-chlorosalicylic acid and 5-ethoxy-4-fluoro-2-nitroaniline as the raw materials, the same operation as the Example 16 gave the title compound.

Yield: 20.2%. $^1$H-NMR(DMSO-d$_6$): δ 1.43(3H, t, J=7.0 Hz), 4.27(2H, q, J=7.0 Hz), 7.07(1H, d, J=8.8 Hz), 7.52(1H, dd, J=8.8, 2.9 Hz), 7.95(1H, d, J=2.9 Hz), 8.15(1H, d, J=11.4 Hz), 8.57(1H, d, J=8.4 Hz), 12.16(1H, s), 12.26(1H, s).

Example 516

Preparation of the Compound of Compound No. 516

Using 5-chlorosalicylic acid and 4-hydroxy-3-methyl-1-naphthylamine as the raw materials, the same operation as the Example 16 gave the title compound.

Yield: 5.9%. $^1$H-NMR(DMSO-d$_6$): δ 2.38(3H, s), 7.03 (1H, d, J=9.3 Hz), 7.43(2H, s), 7.46(1H, d, J=2.4 Hz), 7.50-7.54(2H, m), 7.67(1H, d, J=2.1 Hz), 7.78(1H, dd, J=6.0, 2.7 Hz), 8.03(1H, brs), 8.18(1H, dd, J=6.0, 3.6 Hz), 11.98(1H, brs).

Example 517

Preparation of the Compound of Compound No. 517

This compound is a known compound.

Reference which describes the preparation method: the pamphlet of International Publication WO99/65449.

Example 518

Preparation of the Compound of Compound No. 518

This compound is a known compound.

Reference which describes the preparation method: the pamphlet of International Publication WO99/65449.

Example 519

Preparation of the Compound of Compound No. 519

This compound is a known compound.

Reference which describes the preparation method: the pamphlet of International Publication WO99/65449.

Example 520

Preparation of the Compound of Compound No. 520

This compound is a known compound.

Reference which describes the preparation method: the pamphlet of International Publication WO99/65449.

Example 521

Preparation of the Compound of Compound No. 521

This compound is a known compound.

Reference which describes the preparation method: the pamphlet of International Publication WO99/65449.

Example 522

Preparation of the Compound of Compound No. 522

This compound is a known compound.

Reference which describes the preparation method: the pamphlet of International Publication WO99/65449.

Example 523

Preparation of the Compound of Compound No. 523

This compound is a known compound.

Reference which describes the preparation method: the pamphlet of International Publication WO99/65449.

Example 524

Preparation of the Compound of Compound No. 524

Using 5-chlorosalicylic acid and 4-aminobiphenyl as the raw materials, the same operation as the Example 16 gave the title compound.

Yield: 52.4%. $^1$H-NMR(DMSO-d$_6$): δ 7.03(1H, d, J=8.7 Hz), 7.33-7.38(1H, m), 7.44-7.51(3H, m), 7.67-7.72(4H, m), 7.82(2H, d, J=8.7 Hz), 7.98(1H, d, J=2.4 Hz), 10.49(1H, s), 11.84(1H, s).

Example 525

Preparation of the Compound of Compound No. 525

A mixture of 5-sulfosalicylic acid (218 mg, 1 mmol), 3,5-bis(trifluoromethyl)aniline (229 mg, 1 mmol), phosphorus trichloride (88 μL, 1 mmol) and o-xylene (5 mL) was refluxed for 3 hours. After the reaction mixture was cooled to room temperature, it was purified by column chromatography on silica gel (n-hexane:ethyl acetate=3:1) to give the title compound (29 mg, 9.2%) as a white solid.

$^1$H-NMR(DMSO-d$_6$): δ 7.15(1H, d, J=8.8 Hz), 7.65(2H, s), 7.73(1H, s), 7.81(1H, s), 7.82(1H, dd, J=8.7, 2.5 Hz), 8.23(1H, d, J=2.5 Hz), 8.38(2H, s), 10.87(1H, s), 11.15(1H, brs).

Example 526

Preparation of the Compound of Compound No. 526

Using 5-chlorosalicylic acid and 2,4-bis(trifluoromethyl) aniline as the raw materials, the same operation as the Example 16 gave the title compound.

Yield: 6.9%. ¹H-NMR(CDCl₃): δ 7.03(1H, dd, J=8.7, 0.6 Hz), 7.43-7.48(2H, m), 7.91(1H, d, J=9.0 Hz), 7.96(1H, s), 8.42(1H, s), 8.49(1H, d, J=8.7 Hz), 11.26(1H, s).

Example 527

Preparation of the Compound of Compound No. 527

Using 3-phenylsalicylic acid and 3,5-bis(trifluoromethyl) aniline as the raw materials, the same operation as the Example 16 gave the title compound.

Yield: 64.6%. ¹H-NMR(DMSO-d₆): δ 7.12(1H, t, J=8.1 Hz), 7.37(1H, tt, J=7.5, 1.5 Hz), 7.43-7.48(2H, m), 7.56-7.60 (3H, m), 7.91(1H, s), 8.07, (1H, dd, J=8.1, 1.5 Hz), 8.48(2H, s), 11.00(1H, s), 12.16(1H, s).

Example 528

Preparation of the Compound of Compound No. 528

Using 4-fluorosalicylic acid and 3,5-bis(trifluoromethyl) aniline as the raw materials, the same operation as the Example 16 gave the title compound.

Yield: 65.7%. ¹H-NMR(DMSO-d₆): δ 6.81-6.90(2H, m), 7.84(1H, s,), 7.93-7.98(1H, m,), 8.45(2H, s,), 10.78(1H, s), 11.81(1H, s,).

Example 529

Preparation of the Compound of Compound No. 529

This compound was obtained by separation from the mixture with the compound of Compound No. 471 described in the aforementioned Example 471.

Yield: 9.4%. ¹H-NMR(CD₃OD): δ 2.16(3H, s), 2.34(3H, s), 6.69(1H, d, J=8.2 Hz), 6.76(1H, brs) 6.95(1H, d, J=8.8 Hz), 7.02(1H, d, J=8.0 Hz), 7.15(1H, d, J=8.2 Hz), 7.29(1H, d, J=8.2 Hz), 7.37(1H, dd, J=8.8, 2.6 Hz), 7.97(1H, d, J=2.6 Hz), 7.98(1H, s).

Example 530

Preparation of the Compound of Compound No. 530

Using 5-chlorosalicylic acid and 4-amino-3-(trifluoromethoxy)benzonitrile as the raw materials, the same operation as the Example 16 gave the title compound.

Yield: 75.2%. ¹H-NMR(DMSO-d₆): δ 7.13(1H, d, J=8.8 Hz), 7.54(1H, dd, J=8.8, 2.6 Hz), 7.94(1H, dd, J=8.4, 1.6 Hz), 7.95(1H, d, J=2.6 Hz), 8.15(1H, t, J=1.5 Hz), 8.75(1H, d, J=8.8 Hz), 11.25(1H, s), 12.45(1H, s).

Example 531

Preparation of the Compound of Compound No. 531

Using 5-chlorosalicylic acid and 4-[2-amino-4-(trifluoromethyl)phenoxy]benzonitrile as the raw materials, the same operation as the Example 16 gave the title compound.

Yield: 11.6%. ¹H-NMR(CD₃OD): δ 6.88(1H, d, J=8.6 Hz), 7.19(2H, d, J=8.9 Hz), 7.24(1H, d, J=8.6 Hz), 7.33(1H, dd, J=8.8, 2.8 Hz), 7.46(1H, dd, J=8.9, 1.9 Hz), 7.76(2H, d, J=8.9 Hz), 7.98(1H, d, J=2.7 Hz), 8.96(1H, s).

Example 532

Preparation of the Compound of Compound No. 532

Using 5-chlorosalicylic acid and 3-amino-4-(4-methoxyphenoxy)-benzotrifluoride as the raw materials, the same operation as the Example 16 gave the title compound.

Yield: 88.1%. ¹H-NMR(CDCl₃): δ 3.85(3H, s) 6.81(1H, d, J=8.5 Hz), 6.97-7.02(3H, m), 7.08(2H, d, J=8.8 Hz), 7.30(1H, m), 7.40(1H, dd, J=8.8, 1.9 Hz), 7.45(1H, d, J=2.2 Hz), 8.70 (1H, s), 8.78(1H, d, J=1.6 Hz), 11.76(1H, s).

Example 533

Preparation of the Compound of Compound No. 533

Using salicylic acid and 2,5-bis(trifluoromethyl)aniline as the raw materials, the same operation as the Example 16 gave the title compound.

Yield: 47.8%. ¹H-NMR(CD₃OD): δ 7.00-7.06(2H, m), 7.48(1H, dt, J=1.5, 7.5 Hz), 7.74(1H, d, J=8.4 Hz), 8.01-8.08 (2H, m), 8.79(1H, s), 11.09(1H, s), 12.03(1H, s).

Example 534

Preparation of the Compound of Compound No. 534

(1) 2-Amino-4-(2,4-dichlorophenyl)thiazole

Using 2',4'-dichloroacetophenone and thiourea as the raw materials, the same operation as the Example 395(1) gave the title compound.

Yield: 97.1%. ¹H-NMR(CDCl₃): δ 5.01(2H, s), 7.09(1H, s), 7.28(1H, dd, J=8.4, 2.1 Hz), 7.45(1H, d, J=2.1 Hz), 7.82 (1H, d, J=8.4 Hz).

(2) 5-Chloro-2-hydroxy-N-[4-(2,4-dichlorophenyl) thiazol-2-yl]benzamide (Compound No. 534)

Using 5-chlorosalicylic acid and 2-amino-4-(2,4-dichlorophenyl)thiazole as the raw materials, the same operation as the Example 16 gave the title compound.

Yield: 8.0%. ¹H-NMR(DMSO-d₆): δ 7.08(1H, d, J=8.7 Hz), 7.50-7.55(2H, m), 7.72-7.76(2H, m), 7.91(1H, d, J=8.4 Hz), 7.95(1H, d, J=2.4 Hz), 11.87(1H, brs), 12.09(1H, brs).

Example 535

Preparation of the Compound of Compound No. 535

Using 3-isopropylsalicylic acid and 3,5-bis(trifluoromethyl)aniline as the raw materials, the same operation as the Example 16 gave the title compound.

Yield: 99.2%. ¹H-NMR(CDCl₃): δ 1.26(6H, d, J=6.9 Hz), 3.44(1H, Hept, J=6.9 Hz), 6.92(1H, t, J=7.8 Hz), 7.38(1H, dd, J=8.1, 1.2 Hz), 7.44(1H, d, J=7.5 Hz), 7.69(1H, s), 8.13(3H, s), 11.88(1H, s).

Example 536

Preparation of the Compound of Compound No. 536

Bromine (14.4 μL, 0.28 mmol) and iron powder (1.7 mg, 0.03 mmol) were added to a solution of N-[3,5-bis(trifluoromethyl)phenyl]-2-hydroxy-3-isopropylbenzamide (Compound No. 535; 100 mg, 0.26 mmol) in carbon tetrachloride (5 mL) under argon atmosphere, and the mixture was stirred at room temperature for 2 hours. The reaction mixture was diluted with ethyl acetate. The ethyl acetate layer was washed with water and brine, and dried over anhydrous magnesium sulfate. The residue obtained by evaporation of the solvent under reduced pressure was crystallized from n-hexane/ethyl acetate to give the title compound (110 mg, 91.5%) as a white solid.

$^1$H-NMR(CDCl$_3$): δ 1.25(6H, d, J=6.9 Hz), 3.39(1H, Hept, J=6.9 Hz), 7.49-7.51(2H, m), 7.71(1H, brs), 8.11-8.14(3H, m), 11.81(1H, brs).

Example 537

Preparation of the Compound of Compound No. 537

N-Bromosuccinimide (88.2 mg, 0.50 mmol) was added to a solution of N-[3,5-bis(trifluoromethyl)phenyl]-2-hydroxy-3-methylbenzamide (Compound No. 328; 150 mg, 0.41 mmol) in a mixed solvent of methanol/water (3:1; 5 mL), and the mixture was stirred at room temperature for 10 minutes. The reaction mixture was diluted with ethyl acetate. The ethyl acetate layer was washed with 10% aqueous sodium thiosulfate, water and brine, and dried over anhydrous magnesium sulfate. The residue obtained by evaporation under reduced pressure was purified by column chromatography on silica gel (n-hexane:ethyl acetate=5:1) to give the title compound (167 mg, 91.5%) as a white powder.

$^1$H-NMR(CDCl$_3$): δ 2.28(3H, s), 7.47(1H, s), 7.50(1H, d, J=2.4 Hz), 7.71(1H, s), 8.08(1H, brs), 8.13(2H, s), 11.71(1H, s).

Example 538

Preparation of the Compound of Compound No. 538

(1) 1-(3-Nitrophenyl)-5-phenyl-3-(trifluoromethyl)pyrazole

A mixture of 4,4,4-trifluoro-1-phenyl-1,3-butanedione (432.3 mg, 2 mmol), 3-nitrophenylhydrazine hydrochloride (379.2 mg, 2 mmol), concentrated hydrochloric acid (0.2 mL) and ethanol (8 mL) was refluxed for 2 hours. After the reaction mixture was cooled to room temperature, it was poured into water and extracted with ethyl acetate. The ethyl acetate layer was washed with water and brine, and dried over anhydrous sodium sulfate. The residue obtained by evaporation under reduced pressure was purified by column chromatography on silica gel (n-hexane:ethyl acetate=4:1→3:1) to give the title compound (631.5 mg, 94.7%) as a light yellowish white powder.

$^1$H-NMR(CDCl$_3$): δ 6.80(1H, s), 7.23-7.26(2H, m), 7.35-7.45(3H, m), 7.54(1H, t, J=8.4 Hz), 7.63(1H, ddd, J=8.1, 1.8, 1.2 Hz), 8.19-8.25(2H, m).

(2) 1-(3-Aminophenyl)-5-phenyl-3-(trifluoromethyl)pyrazole

Acetic acid (3 mL) and ethanol (2 mL) were added to 1-(3-nitrophenyl)-5-phenyl-3-(trifluoromethyl)pyrazole (0.59 g, 1.77 mmol) and 5% palladium on carbon (0.06 g), and the mixture was hydrogenated at room temperature for 2 hours under hydrogen atmosphere. After the insoluble matter was filtered off, the residue obtained by evaporation under reduced pressure was purified by column chromatography on silica gel (n-hexane:ethyl acetate=2:1) to give the title compound (491.1 mg, 91.4%) as a white solid.

$^1$H-NMR(CDCl$_3$): δ 3.78(2H, s), 6.54(1H, ddd, J=7.8, 1.8, 0.6 Hz), 6.65(1H, ddd, J=8.4, 2.4, 0.9 Hz), 6.73-6.75(2H, m), 7.07(1H, t, J=8.1 Hz), 7.24-7.36(5H, m).

(3) 5-Chloro-2-hydroxy-N-{3-[5-phenyl-3-(trifluoromethyl)pyrazol-1-yl]phenyl}-benzamide (Compound No. 538)

Using 5-chlorosalicylic acid and 1-(3-aminophenyl)-5-phenyl-3-(trifluoromethyl)pyrazole as the raw materials, the same operation as the Example 16 gave the title compound.

Yield: 74.4%. $^1$H-NMR(CDCl$_3$): δ 6.77(1H, s), 6.97-7.03(2H, m), 7.27-7.45(8H, m), 7.65(1H, ddd, J=8.4, 2.1, 0.9 Hz), 7.74(1H, t, J=2.1 Hz), 7.93(1H, s), 11.63(1H, s).

Example 539

Preparation of the Compound of Compound No. 539

(1) 5-(tert-Butyl)-1-(4-nitrophenyl)-3-(trifluoromethyl)pyrazole

Using 1,1,1-trifluoro-5,5-dimethyl-2,4-hexanedione and 4-nitrophenylhydrazine hydrochloride as the raw materials, the same operation as the Example 538(1) gave the title compound.

Yield: 94.7%. $^1$H-NMR(CDCl$_3$): δ 1.23(9H, s), 6.51(1H, s), 7.62(2H, d, J=9.0 Hz), 8.37(2H, d, J=9.0 Hz).

(2) 1-(4-Aminophenyl)-5-(tert-butyl)-3-(trifluoromethyl)pyrazole

Using 5-(tert-butyl)-1-(4-nitrophenyl)-3-(trifluoromethyl)pyrazole as the raw material, the same operation as the Example 538(2) gave the title compound.

Yield: 98.9%. $^1$H-NMR(CDCl$_3$): δ 1.20(9H, s), 4.00(2H, br), 6.40(1H, s), 6.69(2H, d, J=8.7 Hz), 7.14(2H, d, J=9.0 Hz).

(3) N-{4-[5-(tert-butyl)-3-(trifluoromethyl)pyrazol-1-yl]phenyl}-5-chloro-2-hydroxy-benzamide (Compound No. 539)

Using 5-chlorosalicylic acid and 1-(5-aminophenyl)-5-(tert-butyl)-3-(trifluoromethyl)pyrazole as the raw materials, the same operation as the Example 16 gave the title compound.

Yield: 57.6%. $^1$H-NMR(CDCl$_3$): δ 1.23(9H, s), 6.47(1H, s), 7.00(1H, d, J=9.0 Hz), 7.40-7.44(3H, m), 7.57(1H, d, J=2.4 Hz), 7.72(2H, d, J=8.7 Hz), 8.15(1H, s), 11.58(1H, s).

Example 540

Preparation of the Compound of Compound No. 540

Using N-[3,5-bis(trifluoromethyl)phenyl]-2-hydroxy-3-phenylbenzamide (Compound No. 527), the same operation as the Example 537 gave the title compound.

Yield: 67.5%. $^1$H-NMR(DMSO-d$_6$): δ 7.36-7.50(3H, m), 7.55-7.59(2H, m), 7.71(1H, d, J=2.1 Hz), 7.93(1H, brs), 8.28 (1H, d, J=2.1 Hz), 8.45(2H, s), 11.06(1H, brs), 12.16(1H, brs).

Example 541

Preparation of the Compound of Compound No. 541

(1) 2-Amino-4-(3,4-dichlorophenyl)thiazole

Using 3',4'-dichloroacetophenone and thiourea as the raw materials, the same operation as the Example 395(1) gave the title compound.
Yield: 77.8%. $^1$H-NMR(DMSO-d$_6$): δ 7.17(2H, s), 7.24 (1H, s), 7.62(1H, d, J=8.4 Hz), 7.78(1H, dd, J=8.7, 2.7 Hz), 8.22(1H, d, J=2.4 Hz).

(2) 5-Chloro-2-hydroxy-N-[4-(3,4-dichlorophenyl) thiazol-2-yl]benzamide (Compound No. 541)

Using 5-chlorosalicylic acid and 2-amino-4-(3,4-dichlorophenyl)thiazole as the raw materials, the same operation as the Example 16 gave the title compound.
Yield: 15.1%. $^1$H-NMR(DMSO-d$_6$): δ 7.08(1H, d, J=8.7 Hz), 7.52(1H, dd, J=8.7, 2.7 Hz), 7.71(1H, d, J=8.4 Hz), 7.91(1H, d, J=1.8 Hz), 7.94(1H, s), 8.18(1H, d, J=1.5 Hz), 12.09(2H, bs).

Example 542

Preparation of the Compound of Compound No. 542

(1) 2-Amino-4-[4-(trifluoromethyl)phenyl]thiazole

Using 4'-(trifluoromethyl)acetophenone and thiourea as the raw materials, the same operation as the Example 395(1) gave the title compound.
Yield: 77.5%. $^1$H-NMR(DMSO-d$_6$): δ 7.18(2H, s), 7.26 (1H, s), 7.72(2H, d, J=8.4 Hz), 8.00(2H, d, J=8.1 Hz).

(2) 5-Chloro-2-hydroxy-N-{4-[4-(trifluoromethyl) phenyl]thiazol-2-yl}benzamide (Compound No. 542)

Using 5-chlorosalicylic acid and 2-amino-4-[4-(trifluoromethyl)phenyl]thiazole as the raw materials, the same operation as the Example 16 gave the title compound.
Yield: 16.0%. $^1$H-NMR(DMSO-d$_6$): δ 7.09(1H, d, J=9.0 Hz), 7.53(1H, dd, J=8.7, 2.7 Hz), 7.81(2H, d, J=8.4 Hz), 7.96(1H, d, J=2.4 Hz), 7.98(1H, s), 8.16(2H, d, J=8.1 Hz), 11.91(1H, bs), 12.13(1H, bs).

Example 543

Preparation of the Compound of Compound No. 543

(1) 2-Acetoxy-N-{4-[3,5-bis(trifluoromethyl)pyrazol-1-yl]phenyl}-5-chlorobenzamide Using 2-acetoxy-5-chlorobenzoic acid and 1-(4-aminophenyl)-3,5-bis(trifluoromethyl)pyrazole as the raw materials, the same operation as the Example 24 gave the title compound.
Yield: 77.8%. $^1$H-NMR(CDCl$_3$): δ 2.36(3H, s), 7.78(1H, s), 7.14(1H, d, J=8.7 Hz), 7.48-7.51(3H, m), 7.77(2H, d, J=9.0 Hz), 7.83(1H, d, J=2.7 Hz), 8.25(1H, s).

[1-(4-Aminophenyl)-3,5-bis(trifluoromethyl)pyrazole: Refer to "Journal of Medicinal Chemistry", 2000, Vol. 43, No. 16, p. 2975-2981.]

(2) N-{4-[3,5-Bis(trifluoromethyl)pyrazol-1-yl]phenyl}-5-chloro-2-hydroxybenzamide (Compound No. 543)

Using 2-acetoxy-N-{4-[3,5-bis(trifluoromethyl)pyrazol-1-yl]phenyl}-5-chlorobenzamide as the raw material, the same operation as the Example 2(2) gave the title compound.
Yield: 73.1%. $^1$H-NMR(DMSO-d$_6$): δ 7.04(1H, d, J=8.7 Hz), 7.48(1H, dd, J=8.7, 2.7 Hz), 7.63(2H, d, J=8.7 Hz), 7.84(1H, s), 7.89(1H, d, J=3.0 Hz), 7.94(2H, d, J=9.0 Hz), 10.65(1H, s), 11.58(1H, s).

Example 544

Preparation of the Compound of Compound No. 544

(1) 3,5-Bis(trifluoromethyl)-1-(3-nitrophenyl)pyrazole

Using hexafluoroacetylacetone and 3-nitrophenylhydrazine hydrochloride as the raw materials, the same operation as the Example 538(1) gave the title compound.
Yield: 94.0%. $^1$H-NMR(CDCl$_3$): δ 7.16(1H, s), 7.77(1H, dd, J=8.7, 8.1 Hz), 7.88-7.91(1H, m), 8.42-8.45(2H, m).

(2) 1-(3-Aminophenyl)-3,5-bis(trifluoromethyl)pyrazole

Using 3,5-bis(trifluoromethyl)-1-(3-nitrophenyl)pyrazole as the raw material, the same operation as the Example 538(2) gave the title compound.
Yield: 73.1%. $^1$H-NMR(CDCl$_3$): δ 3.89(2H, s), 6.77-6.87 (3H, m), 7.04(1H, s), 7.26(1H, t, J=8.7 Hz).

(3) 2-Acetoxy-N-{3-[3,5-bis(trifluoromethyl)pyrazol-1-yl]phenyl}-5-chlorobenzamide Using 2-acetoxy-5-chlorobenzoic acid and 1-(3-aminophenyl)-3,5-bis(trifluoromethyl)pyrazole as the raw materials, the same operation as the Example 24 gave the title compound.
Yield: 84.4%. $^1$H-NMR(CDCl$_3$): δ 2.33(3H, s), 7.09(1H, s), 7.11(1H, d, J=9.0 Hz), 7.30(1H, d, J=7.8 Hz), 7.45-7.52 (2H, m), 7.67(1H, d, J=8.4 Hz), 7.78(1H, d, J=2.4 Hz), 7.95 (1H, s), 8.29(1H, s).

(4) N-{3-[3,5-Bis(trifluoromethyl)pyrazol-1-yl]phenyl}-5-chloro-2-hydroxybenzamide (Compound No. 544)

Using 2-acetoxy-N-(3-[3,5-bis(trifluoromethyl)pyrazol-1-yl]phenyl)-5-chlorobenzamide as the raw material, the same operation as the Example 2(2) gave the title compound.
Yield: 69.9%. $^1$H-NMR(CDCl$_3$): δ 7.01(1H, d, J=8.7 Hz), 7.10(1H, s), 7.34-7.37(1H, m), 7.42(1H, dd, J=8.7, 2.4 Hz), 7.50(1H, d, J=2.4 Hz), 7.56(1H, t, J=8.1 Hz), 7.69-7.73(1H, m), 7.95-7.98(2H, m), 11.57(1H, s).

Example 545

Preparation of the Compound of Compound No. 545

(1) Methyl 2-methoxy-4-phenylbenzoate

Dichlorobis(triphenylphosphine)palladium (29 mg, 0.04 mmol) was added to a solution of methyl 4-chloro-2-methoxybenzoate (904 mg, 4.5 mmol), phenylboronic acid (500 mg, 4.1 mmol) and cesium carbonate (2.7 g, 8.2 mmol) in N,N-dimethylformamide (15 mL) under argon atmosphere, and the mixture was stirred at 120° C. for 8 hours. After the reaction mixture was cooled to room temperature, it was diluted with ethyl acetate. The ethyl acetate layer was washed successively with water and brine, and dried over anhydrous sodium sulfate. The residue obtained by evaporation of the solvent under reduced pressure was purified by column chromatography on silica gel (n-hexane:ethyl acetate=10:1) to give the title compound (410 mg, 41.2%) as a colourless oil.
$^1$H-NMR(CDCl$_3$): δ 3.91(3H, s), 3.98(3H, s), 7.17(1H, d, J=1.5 Hz), 7.20(1H, dd, J=8.1, 1.5 Hz), 7.31-7.50(3H, m), 7.59-7.63(2H, m), 7.89(1H, d, J=8.1 Hz).

(2) 2-Methoxy-4-phenylbenzoic acid

2N Aqueous sodium hydroxide (5 mL) was added to a solution of methyl 2-methoxy-4-phenylbenzoate (410 mg, 1.69 mmol) in methanol (5 mL), and the mixture was refluxed for 1 hour. After the reaction mixture was cooled to room temperature, the solvent was evaporated under reduced pressure. 2N hydrochloric acid was added to the obtained residue and the separated crystal was filtered to give the title compound (371 mg, 96.0%) as a crude product.
$^1$H-NMR(DMSO-d$_6$): δ 3.93(3H, s), 7.29(1H, dd, J=8.1, 1.5 Hz), 7.34(1H, d, J=1.5 Hz), 7.40-7.53(3H, m), 7.73-7.77 (3H, m), 12.60(1H, s).

(3) N-[3,5-Bis(trifluoromethyl)phenyl]-2-methoxy-4-phenylbenzamide

Using 2-methoxy-4-phenylbenzoic acid and 3,5-bis(trifluoromethyl)aniline as the raw materials, the same operation as the Example 16 gave the title compound.
Yield: 97.5%. $^1$H-NMR(CDCl$_3$): δ 4.19(3H, s), 7.25(1H, m), 7.38-7.53(4H, m), 7.62-7.65(3H, m), 8.12(2H, s), 8.35 (1H, d, J=8.1 Hz), 10.15(1H, brs).

(4) N-[3,5-Bis(trifluoromethyl)phenyl]-2-hydroxy-4-phenylbenzamide (Compound No. 545)

1M Boron tribromide-dichloromethane solution (0.71 mL, 0.71 mmol) was added to a solution of N-[3,5-bis(trifluoromethyl)phenyl]-2-methoxy-4-phenylbenzamide (100 mg, 0.24 mmol) in dichloromethane (5 mL), and the mixture was stirred at room temperature for 1 hour. The reaction mixture was diluted with ethyl acetate, washed with water and brine, and dried over anhydrous magnesium sulfate. The residue obtained by evaporation of the solvent under reduced pressure was purified by column chromatography on silica gel (n-hexane:ethyl acetate=5:1) to give the title compound (69.3 mg, 71.6%) as a white powder.
$^1$H-NMR(DMSO-d$_6$): δ 7.20(1H, dd, J=8.4,1.8 Hz), 7.30 (1H, d, J=1.8 Hz), 7.39-7.51(3H, m), 7.60-7.64(3H, m), 7.70 (1H, brs), 8.15(2H, s), 8.19(1H, brs), 11.59(1H, s).

Example 546

Preparation of the Compound of Compound No. 546

(1) 2-Amino-4-(2,5-difluorophenyl)thiazole

Using 2',5'-difluoroacetophenone and thiourea as the raw materials, the same operation as the Example 395(1) gave the title compound.
Yield: 77.8%. $^1$H-NMR(DMSO-d$_6$): δ 7.45(1H, d, J=2.7 Hz), 7.11-7.17(1H, m), 7.19(2H, s), 7.28-7.36(1H, m), 7.65-7.71(1H, m).

(2) 5-Chloro-2-hydroxy-N-[4-(2,5-difluorophenyl)thiazol-2-yl]benzamide (Compound No. 546)

Using 5-chlorosalicylic acid and 2-amino-4-(2,5-difluorophenyl)thiazole as the raw materials, the same operation as the Example 16 gave the title compound.
Yield: 36.5%. $^1$H-NMR(DMSO-d$_6$): δ 7.09(1H, d, J=8.7 Hz), 7.22-7.30(1H, m), 7.37(1H, m), 7.53(1H, dd, J=8.7, 3.0 Hz), 7.72(1H, d, J=2.4 Hz), 7.77-7.84(1H, m), 7.94(1H, d, J=3.0 Hz), 11.89(1H, bs), 12.12(1H, bs).

Example 547

Preparation of the Compound of Compound No. 547

(1) 2-Acetoxy-4-chlorobenzoic acid

Using 4-chlorosalicylic acid, concentrated sulfuric acid and acetic anhydride as the raw materials, the same operation as the Example 34(1) gave the title compound.
Yield: 88.1%. $^1$H-NMR(DMSO-d$_6$): δ 2.25(3H, s), 7.42 (1H, d, J=1.8 Hz), 7.48(1H, dd, J=8.4, 2.4 Hz), 7.94(1H, d, J=8.1 Hz), 13.31(1H, s).

(2) 2-Acetoxy-N-{4-[3,5-bis(trifluoromethyl)pyrazol-1-yl]phenyl}-4-chlorobenzamide Using 2-acetoxy-4-chlorobenzoic acid and 1-(4-aminophenyl)-3,5-bis(trifluoromethyl)pyrazole as the raw materials, the same operation as the Example 24 gave the title compound.
Yield: 74.0%. $^1$H-NMR(CDCl$_3$): δ 2.37(3H, s), 7.08(1H, s), 7.23(1H, d, J=1.8 Hz), 7.37(1H, dd, J=8.1, 2.1 Hz), 7.50 (2H, d, J=8.7 Hz), 7.77(2H, d, J=8.7 Hz), 7.82(1H, d, J=8.1 Hz), 8.23(1H, s).

(3) N-{4-[3,5-Bis(trifluoromethyl)pyrazol-1-yl]phenyl}-4-chloro-2-hydroxybenzamide (Compound No. 547)

Using 2-acetoxy-N-{4-[3,5-bis(trifluoromethyl)pyrazol-1-yl]phenyl}-4-chlorobenzamide as the raw material, the same operation as the Example 2(2) gave the title compound.
Yield: 56.6%. $^1$H-NMR(DMSO-d$_6$): δ 7.03-7.06(2H, m), 7.61(2H, d, J=8.7 Hz), 7.81(1H, s), 7.89-7.95(3H, m), 10.62 (1H, s), 11.82(1H, s).

Example 548

Preparation of the Compound of Compound No. 548

(1) 1-(4-Nitrophenyl)-5-phenyl-3-(trifluoromethyl)pyrazole

Using 4,4,4-trifluoro-1-phenyl-1,3-butanedione and 4-nitrophenylhydrazine hydrochloride as the raw materials, the same operation as the Example 538(1) gave the title compound.

Yield: 95.2%. 1H-NMR(CDCl$_3$): δ 6.80(1H, s), 7.22-7.26 (2H, m), 7.37-7.45(3H, m), 7.51(2H, d, J=9.3 Hz), 8.22(2H, d, J=9.0 Hz).

(2) 1-(4-Aminophenyl)-5-phenyl-3-(trifluoromethyl)pyrazole

Using 1-(4-nitrophenyl)-5-phenyl-3-(trifluoromethyl)pyrazole as the raw material, the same operation as the Example 538(2) gave the title compound.

Yield: 73.0%. $^1$H-NMR(CDCl$_3$): δ 3.80(2H, s), 6.62(2H, d, J=8.7 Hz), 6.72(1H, s), 7.08(2H, d, J=8.7 Hz), 7.22-7.26 (2H, m), 7.30-7.33(3H, m).

(3) 5-Chloro-2-hydroxy-N-{4-[5-phenyl-3-(trifluoromethyl)pyrazol-1-yl]phenyl}-benzamide (Compound No. 548)

Using 5-chlorosalicylic acid and 1-(4-aminophenyl)-5-phenyl-3-(trifluoromethyl)pyrazole as the raw materials, the same operation as the Example 16 gave the title compound.

Yield: 73.2%. $^1$H-NMR(CDCl$_3$): δ 7.02(1H, d, J=8.7 Hz), 7.21(1H, s), 7.30-7.42(7H, m), 7.47(1H, dd, J=8.7, 2.7 Hz), 7.79(2H, d, J=8.7 Hz), 7.89(1H, d, J=2.7 Hz), 10.56(1H, s), 11.61(1H, s).

Example 549

Preparation of the Compound of Compound No. 549

(1) 2-Amino-4-(4-methoxyphenyl)thiazole

Using 4'-methoxyacetophenone and thiourea as the raw materials, the same operation as the Example 395(1) gave the title compound.

Yield: 85.2%. $^1$H-NMR(DMSO-d$_6$): δ 3.76(3H, s), 6.82 (1H, s), 6.92(2H, d, J=9.0 Hz), 7.01(2H, s), 7.72(2H, d, J=8.7 Hz).

(2) 5-Chloro-2-hydroxy-N-[4-(4-methoxyphenyl)thiazol-2-yl]benzamide (Compound No. 549)

Using 5-chlorosalicylic acid and 2-amino-4-(4-methoxyphenyl)thiazole as the raw materials, the same operation as the Example 16 gave the title compound.

Yield: 16.4%. $^1$H-NMR(DMSO-d$_6$): δ 3.80(3H, s), 7.01 (2H, d, J=9.0 Hz), 7.07(1H, d, J=8.7 Hz), 7.50-7.55(2H, m), 7.86(2H, d, J=9.0 Hz), 7.96(1H, d, J=2.7 Hz), 11.90(1H, bs), 12.04(1H, bs).

Example 550

Preparation of the Compound of Compound No. 550

(1) 2-Amino-4-[3-(trifluoromethyl)phenyl]thiazole

Using 3'-(trifluoromethyl)acetophenone and thiourea as the raw materials, the same operation as the Example 395(1) gave the title compound.

Yield: 94.1%. $^1$H-NMR(DMSO-d$_6$): δ 7.19(2H, s), 7.27 (1H, s), 7.61(2H, dd, J=3.9, 1.5 Hz), 8.07-8.13(2H, m).

(2) 5-Chloro-2-hydroxy-N-{4-[3-(trifluoromethyl)phenyl]thiazol-2-yl}benzamide (Compound No. 550)

Using 5-chlorosalicylic acid and 2-amino-4-[3-(trifluoromethyl)phenyl]thiazole as the raw materials, the same operation as the Example 16 gave the title compound.

Yield: 31.0%. $^1$H-NMR(DMSO-d$_6$): δ 7.13(1H, d, J=8.7 Hz), 7.53(1H, dd, J=9.0, 2.7 Hz), 7.70(1H, d, J=2.4 Hz), 7.71(1H, d, J=1.2 Hz), 7.95(1H, d, J=2.7 Hz), 8.00(1H, s), 8.24-8.27(2H, m), 12.16(2H, bs).

Example 551

Preparation of the Compound of Compound No. 551

(1) 2-Amino-4-(2,3,4,5,6-pentafluorophenyl)thiazole

Using 2',3',4',5',6'-pentafluoroacetophenone and thiourea as the raw materials, the same operation as the Example 395(1) gave the title compound.

Yield: 86.7%. $^1$H-NMR(CDCl$_3$): δ 5.19(2H, s), 6.83(1H, s).

(2) 5-Chloro-2-hydroxy-N-[4-(2,3,4,5,6-pentafluorophenyl)thiazol-2-yl]benzamide (Compound No. 551)

Using 5-chlorosalicylic acid and 2-amino-4-(2,3,4,5,6-pentafluorophenyl)-thiazole as the raw materials, the same operation as the Example 16 gave the title compound.

Yield: 23.8%. $^1$H-NMR(DMSO-d$_6$): δ 7.08(1H, d, J=8.7 Hz), 7.53(1H, dd, J=8.7, 2.7 Hz), 7.73(1H, s), 7.93(1H, d, J=2.7 Hz), 11.85(1H, bs), 12.15(1H, bs).

Example 552

Preparation of the Compound of Compound No. 552

Iron (3 mg, 0.05 mmol) and bromine (129 μl, 2.5 mmol) were added to a solution of 2-hydroxy-N-[2,5-bis(trifluoromethyl)phenyl]benzamide (Compound No. 533; 175 mg, 0.5 mmol) in carbon tetrachloride (5 mL), and the mixture was stirred at 50° C. for 12 hours. After the reaction mixture was cooled to room temperature, it was washed with saturated aqueous sodium hydrogen carbonate, water and brine, and dried over anhydrous magnesium sulfate. The residue obtained by evaporation of the solvent under reduced pressure was purified by column chromatography on silica gel (n-hexane:ethyl acetate=2:1) to give the title compound (184.2 mg, 72.7%) as a white crystal.

$^1$H-NMR(DMSO-d$_6$): δ 7.92-7.98(1H, m), 8.06(1H, d, J=2.1 Hz), 8.09(1H, d, J=8.4 Hz), 8.22(1H, d, J=2.1 Hz), 8.27-8.32(1H, m), 11.31(1H, s).

Example 553

Preparation of the Compound of Compound No. 553

Using 2,3-dihydroxybenzaldehyde and 3-[3,5-bis(trifluoromethyl)benzyl]-thiazolidine-2,4-dione (compound of Example 319(1)) as the raw materials, the same operation as the Example 319(2) gave the title compound.

Yield: 88.5%. $^1$H-NMR(DMSO-d$_6$): δ 5.02(2H, s), 6.88 (1H, d, J=7.8 Hz), 7.00-7.04(2H, m), 7.79(1H, s), 8.03(2H, s), 8.07(1H, s), 9.49(1H, s), 9.91(1H, s).

Example 554

Preparation of the Compound of Compound No. 554

A mixture of 5-chlorosalicylaldehyde (157 mg, 1 mmol), 2-amino-4-tert-amylphenyl phenyl ether (255 mg, 1 mmol) and ethanol (2 mL) was stirred at room temperature for 18 hours. The residue obtained by evaporation of the solvent under reduced pressure was purified by column chromatography on silica gel (n-hexane:ethyl acetate=100:1) to give the title compound (57 mg, 14.4%) as a white solid.

$^1$H-NMR(CDCl$_3$): δ 0.66(3H, t, J=7.5 Hz), 1.26(6H, s), 1.61(2H, q, J=7.5 Hz), 6.88-6.94(3H, m), 7.04(1H, dd, J=8.0, 1.6 Hz), 7.15-7.32(7H, m), 8.61(1H, s), 13.20(1H, s).

Example 555

Preparation of the Compound of Compound No. 555

A mixture of 4-chloro-2-({[2-phenoxy-5-(tert-amyl)phenyl]imino}-methyl)phenol (Compound No. 554; 13 mg, 0.03 mmol), sodium borohydride (1.2 mg, 0.03 mmol) and methanol (1 mL) was stirred at room temperature for 5 minutes. The residue obtained by evaporation of the solvent under reduced pressure was purified by thin layer chromatography on silica gel (n-hexane:ethyl acetate=5:1) to give the title compound (13 mg, 100%) as a colourless oil.

$^1$H-NMR(CDCl$_3$): δ 0.69(3H, t, J=7.6 Hz), 1.28(6H, s), 1.63(2H, q, J=7.6 Hz), 4.41(2H, s), 6.78(1H, m), 6.93-6.83 (5H, m), 7.03(1H, m), 7.15(2H, m), 7.28(3H, m).

Test Example 1

Proliferation Inhibitory Test of Mast Cell Under Stimulation by SCF and IL-3

Bone marrow-derived cultured mast cells ($10^5$ cells/ml) of NC/Nga mouse were cultured with rmIL-3 (100 U/ml) and SCF (100 ng/ml) in the presence or absence of a test drug in α-Modified Eagle's Medium containing 10% of bovine fetal serum without phenol red, and then stained with trypan blue, and the number of living cells was counted. The results are shown in the following table.

| Compound Number | Concentration (μM) | Culture Time Number of Cell (×$10^5$/ml) | | | |
|---|---|---|---|---|---|
| | | 0 hr | 24 hr | 48 hr | 72 hr |
| — | 0 | 1.0 | 1.3 | 1.7 | 2.6 |
| 50 | 1 | 1.0 | 0.86 | 0.84 | 1.16 |
| | 5 | 1.0 | 0.7 | 0.52 | 0.22 |

Test Example 2

Degranulation Inhibitory Test of Mast Cell

Anti DNP IgE was added to mouse bone marrow-derived cultured mast cells (BMCMC) which were treated beforehand with anti DNP IgE for 4 days for expression of IgE receptor. The cells were cultured for 3 days, and treated for 1 hour with or without the addition of a test substance. Then, the medium was changed to α-Modified Eagle's Medium containing 10% of bovine fetal serum without phenol red. After cultivation for 60 minutes with rmIL-3 (100 U/ml) and DNP-BSA (50 ng/ml) in the presence or absence of the test substance, the concentrations of β-hexosaminidase in the culture medium and in the cells were determined, and the progress of degranulation was measured from a ratio of the amounts. The inhibitory ratio of the degranulation by the drug was calculated when degranulation in the absence of the test substance was taken as 100%, and degranulation in the presence of anti DNP-IgE only and in the absence of the test substance was taken as 0%. The results are shown in the following table.

| Compound Number | Inhibitory Ration of Degranulation(%) at 10 μM Drug Concentration |
|---|---|
| 50 | >99 |
| 56 | 92 |
| 63 | 62 |
| 73 | 91 |
| 100 | 83 |
| 101 | 90 |
| 113 | 93 |
| 114 | 88 |
| 122 | 91 |
| 163 | 88 |
| 195 | 72 |

Test Example 3

IgE Production Inhibitory Test of Spleen B Cell

B cells isolated from mouse spleen were cultured with 200 U/ml of rmIL-4 and 100 ng/ml of soluble mCD40 ligand in the presence or absence of a test drug in PRMI 1640 medium containing 10% of bovine fetal serum for 9 days, and the amount of IgE in the culture medium was measured by ELISA method. The results are shown in the following table.

| Compound Number | Concentration(μM) Amount of IgE(ng/ml) | | |
|---|---|---|---|
| | 0 | 0.1 | 1.0 |
| — | 45.6 | — | — |
| 50 | — | 24 | ND |

ND = not detected

Test Example 4

Immediate Type Allergy Reaction Inhibitory Test (Ear Swelling Test)

To NC/Nga mouse sensitized by an intravenous administration of anti DNP-IgE, a diluent with a test compound for the drug administered group or that without a test drug for the control group was intraperitoneally administered. Two hours after the administration, picryl chloride dissolved in olive oil was applied to auricle to induce immediate allergy, and then swelling of the auricle was measured with passage of time for comparison of the drug administered group and the control group. The results of Compound 50 (dose: 15 mg/kg) are shown in FIG. 1.

Test Example 6

Dermatitis Inhibitory Test by Atopic Dermatitis Model Using NC/Nga Mouse

Figure 2:
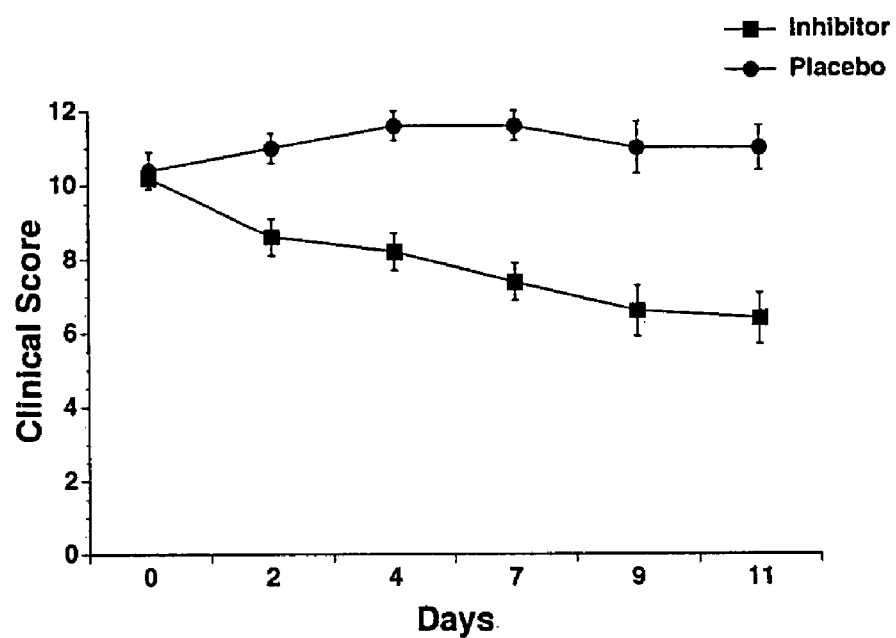
FIG. 2 shows inhibitory effect of the medicament of the present invention (compound No. 50) against dermatitis with an atopic dermatitis model.
Figure 2:
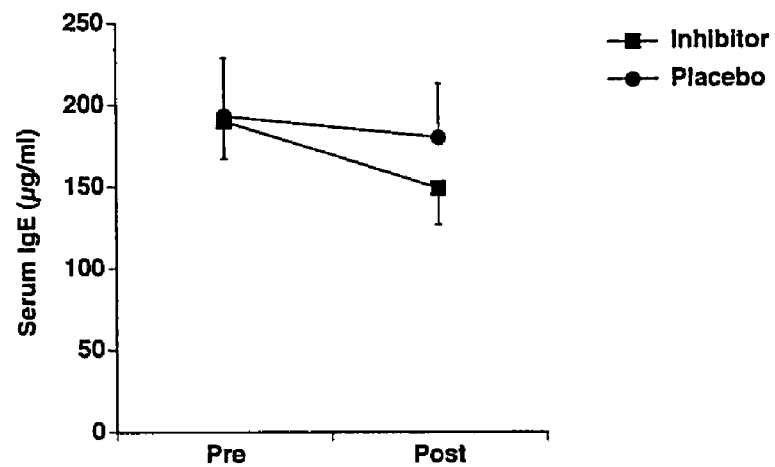

To the conventional NC/Nga mouse with the onset of severe dermatitis, an ointment containing 1% of a test substance for the drug treated group or a base material of the ointment for the control group was applied once a day, and clinical symptoms were recorded as scores with passage of day. Furthermore, the amounts of IgE in blood before and after the test were measured by ELISA. The results for Compound 50 are shown in FIG. 2.

Test Example 6

Proliferation Inhibitory Test of Fibrosarcoma (HT-1080) Under PDGF Stimulation

HT-1080 cells were cultured for 2 hours in EMEM medium containing 1% of FBS and NEAA in the presence or absence of a test substance. PDGF was added and the cells were cultured for 48 hours, and the proliferation of the cells was measured by MTT assay. The results are shown in the following table.

| Compound Number | Inhibitory Ratio of Proliferation(%) Drug Concentration | |
| --- | --- | --- |
|  | 500 nM | 250 nM |
| 50 | 96.6 | 65.4 |
| 51 | 97.6 | 62.4 |
| 67 | 70.9 | 38.5 |
| 73 | 84.9 | 52.0 |
| 63 | 77.9 | 48.3 |
| 114 | 95.7 | 48.8 |
| 163 | 80.8 | 16.9 |
| 71 | 83.1 | 57.9 |
| 56 | 96.9 | 37.5 |
| 98 | 59.4 | 26.4 |
| 196 | 80.2 | 47.3 |
| 122 | 51.1 | 32.9 |
| 195 | 81.7 | 44.7 |
| 199 | 24.2 | 26.2 |
| 201 | 76.2 | 60.3 |
| 532 | 91.8 | 42.2 |
| 552 | 19.4 | 24.0 |
| 101 | 80.0 | 53.2 |

INDUSTRIAL APPLICABILITY

The medicaments of the present invention are useful for the preventive and/or therapeutic treatment of allergic diseases and/or endometriosis and/or hysteromyoma.

What is claimed is:

1. A method for the therapeutic treatment of contact dermatitis, atopic dermatitis, or otitis media, or for the therapeutic treatment of an adhesion of a tissue in endometriosis in a mammal, which comprises administering to a mammal a therapeutically effective amount of a compound represented by the following general formula (I) or a pharmacologically acceptable salt thereof:

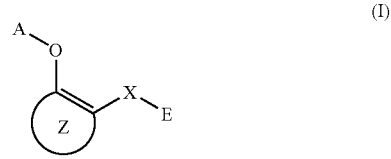

wherein X represents a group represented by the following formula:

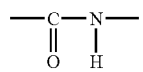

wherein the bond at the left end binds to ring Z and the bond at the right end binds to E, A represents a hydrogen atom or an acetyl group, E represents a di-substituted phenyl group wherein at least one of said substituents is a trifluoromethyl group, ring Z represents a benzene ring which may have one or more substituents in addition to the group represented by formula —O-A and the group represented by formula —X-E.

2. The method according to claim 1, wherein:

ring Z is a benzene ring which may have one substituent that locates on the position of $R^z$ when the following partial formula (Iz-1) in the general formula containing ring Z

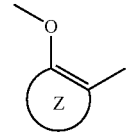

is represented by the following formula (Iz-2):

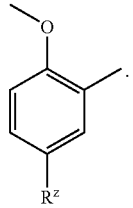

3. The method according to claim 2, wherein:

$R_Z$ is a hydrogen atom, a halogen atom, a nitro group, a cyano group, a methoxy group, a methyl group, an isopropyl group, a tert-butyl group, a 1,1,3,3-tetramethylbutyl group, a 2-phenylethen-1-yl group, a 2,2-dicyanoethen-1-yl group, a 2-cyano-2-(methoxycarbonyl) ethen-1-yl group, a 2-carboxy-2-cyanoethen-1-yl group, an ethynyl group, a phenylethynyl group, a (trimethylsilyl)ethynyl group, a trifluoromethyl group, a pentafluoroethyl group, a phenyl group, a 4-(trifluoromethyl)phenyl group, a 4-fluorophenyl group, a 2,4-difluorophenyl group, a 2-phenethyl group, a 1-hydroxyethyl group, a 1-(methoxyimino)ethyl group, a 1-[(benzyloxy)imino]ethyl group, a 2-thienyl group, a 3-thienyl group, a 1-pyrrolyl group, a 2-methylthiazol-4-yl group, an imidazo[1,2-a]pyridin-2-yl group, a 2-pyridyl group, an acetyl group, an isobutyryl group, a piperidinocarbonyl group, a 4-benzylpiperidinocarbonyl group, a (pyrrol-1-yl)sulfonyl group, a carboxy group, a methoxycarbonyl group, an N-[3,5-bis(trifluoromethyl)phenyl]carbamoyl group, an N,N-dimethylcarbamoyl group, a sulfamoyl group, an N-[3,5-bis(trifluoromethyl)phenyl]sulfamoyl group, an N,N-dimethylsulfamoyl group, an amino group, an N,N-dimethylamino group, an acetylamino group, a benzoylamino group, a methanesulfonylamino group, a benzenesulfonylamino group, a 3-phenylureido group, a (3-phenyl)thioureido group, a (4-nitrophenyl)diazenyl group, or a {[4-(pyridin-2-yl)sulfamoyl]phenyl}diazenyl group.

4. The method according to claim 1, wherein
E is a 2-chloro-5-(trifluoromethyl)phenyl group, a 2,5-bis(trifluoromethyl)phenyl group, a 2-fluoro-5-(trifluoromethyl)phenyl group, a 2-nitro-5-(trifluoromethyl)phenyl group, a 2-methyl-5-(trifluoromethyl)phenyl group, a 2-methoxy-5-(trifluoromethyl)phenyl group, a 2-methylsulfanyl-5-(trifluoromethyl)phenyl group, a 2-(1-pyrrolidinyl)-5-(trifluoromethyl)phenyl group, a 2-morpholino-5-(trifluoromethyl)phenyl group, a 2-bromo-5-(trifluoromethyl)phenyl group, a 2-(2-naphthyloxy)-5-(trifluoromethyl)phenyl group, a 2-(2,4-dichlorophenoxy)-5-(trifluoromethyl)phenyl group, a 2-[4(trifluoromethyl)piperidin-1-yl]-5-(trifluoromethyl)phenyl group, a 2-(2,2,2-trifluoroethoxy)-5-(trifluoromethyl)phenyl group, a 2-(2-methoxyphenoxy)-5-(trifluoromethyl)phenyl group, a 2-(4-chloro-3,5-dimethylphenoxy)-5-(trifluoromethyl)phenyl group, a 2-piperidino-5-(trifluoromethyl)phenyl group, a 2-(4-methylphenoxy)-5-(trifluoromethyl)phenyl group, a 2-(4-chlorophenoxy)-5-(trifluoromethyl)phenyl group, a 2-(4-cyanophenoxy)-5-(trifluoromethyl)phenyl group, a 2-(4-methoxyphenoxy)-5-(trifluoromethyl)phenyl group, a 3,5-bis(trifluoromethyl)phenyl group, a 3-fluoro-5-(trifluoromethyl)phenyl group, a 3-bromo-5-(trifluoromethyl)phenyl group, a 3-methoxy-5-(trifluoromethyl)phenyl group, a 3-methoxycarbonyl-5-(trifluoromethyl)phenyl group, or a 3-carboxy-5-(trifluoromethyl)phenyl group.

5. The method according to claim 1, wherein the mammal is a human.

6. The method according to claim 1, wherein:
ring Z is a benzene ring which may have one or more substituents selected from:
a halogen atom;
a nitro group;
a cyano group;
an alkoxy group;
an alkyl group which may be substituted with one or more substituents selected from:
   a hydroxy group,
   an alkoxy-imino group, and
   an aralkyl-oxy-imino group;
an alkenyl group which may be substituted with one or more substituents selected from:
   an aryl group,
   a cyano group,
   an alkyl-oxy-carbonyl group, and
   a carboxy group;
an alkynyl group which may be substituted with one or more substituents selected from:
   an aryl group, and
   a tri(alkyl)silyl group;
a halogenated alkyl group;
an aryl group which may be substituted with one or more substituents selected from:
   a halogen atom, and
   a halogenated alkyl group;
an aralkyl group;
a monocyclic or a fused polycyclic heteroaryl group which may be substituted with one or more alkyl groups;
an alkyl-carbonyl group;
a monocyclic nonaromatic heterocyclic-carbonyl group which may be substituted with one or more aralkyl groups;
a monocyclic heteroaryl-sulfonyl group;
a carboxy group;
an alkyl-oxy-carbonyl group;
a carbamoyl group which may be substituted with one or more substituents selected from:
   an aryl group which may be substituted with one or more halogenated alkyl
   groups, and
   an alkyl group;
a sulfamoyl group which may be substituted with one or more substituents selected from:
   an aryl group which may be substituted with one or more halogenated alkyl
   groups, and
   an alkyl group;
an amino group which may be substituted with one or more substituents selected from:
   an alkyl group,
   an alkyl-carbonyl group,
   an aryl-carbonyl group,
   an alkyl-sulfonyl group, and
   an aryl-sulfonyl group;
an ureido group which may be substituted with one or more aryl groups;
a thioureido group which may be substituted with one or more aryl groups;
a diazenyl group which may be substituted with one or more aryl groups wherein said aryl groups may be substituted with one or more substituents selected from:
   a nitro group, and
   a monocyclic heteroaryl-sulfamoyl group; and
a hydroxy group,
in addition to the group represented by formula —O-A and the group represented by formula —X-E.

7. The method according to claim 1, wherein:
ring Z is a benzene ring which may have one or more substituents selected from:
a halogen atom;
a nitro group;
a cyano group;
an alkoxy group;
an alkyl group which may be substituted with one or more substituents selected from:
   a hydroxy group,
   an alkoxy-imino group, and
   an aralkyl-oxy-imino group;
an alkenyl group which may be substituted with one or more substituents selected from:
   an aryl group,
   a cyano group, an alkyl-oxy-carbonyl group, and
a carboxy group;
an alkynyl group which may be substituted with one or more substituents selected from:
an aryl group, and
a tri(alkyl)silyl group;
a halogenated alkyl group;
an aryl group which may be substituted with one or more substituents selected from:
a halogen atom, and
a halogenated alkyl group;
an aralkyl group;
a 5 to 9-membered heteroaryl group which may be substituted with one or more alkyl groups;
an alkyl-carbonyl group;
a 6-membered nonaromatic heterocyclic-carbonyl group which may be substituted with one or more aralkyl groups;
a 5-membered heteroaryl-sulfonyl group;
a carboxy group;
an alkyl-oxy-carbonyl group;
a carbamoyl group which may be substituted with one or more substituents selected from:
an aryl group which may be substituted with one or more halogenated alkyl groups, and
an alkyl group;
a sulfamoyl group which may be substituted with one or more substituents selected from:
an aryl group which may be substituted with one or more halogenated alkyl groups, and
an alkyl group;
an amino group which may be substituted with one or more substituents selected from:
an alkyl group,
an alkyl-carbonyl group,
an aryl-carbonyl group,
an alkyl-sulfonyl group, and
an aryl-sulfonyl group;
an ureido group which may be substituted with one or more aryl groups;
a thioureido group which may be substituted with one or more aryl groups;
a diazenyl group which may be substituted with one or more aryl groups, wherein said aryl groups may be substituted with one or more substituents selected from:
a nitro group, and
a 6-membered heteroaryl-sulfamoyl group; and
a hydroxy group,
in addition to the group represented by formula —O-A and the group represented by formula —X-E.

8. The method according to claim 1, wherein:
ring Z is a benzene ring which may have one or more substituents selected from:
a halogen atom;
a nitro group;
a cyano group;
an alkoxy group;
an alkyl group which may be substituted with one or more substituents selected from:
a hydroxy group,
an alkoxy-imino group, and
a benzyl-oxy-imino group;
an alkenyl group which may be substituted with one or more substituents selected from:
a phenyl group,
a cyano group,
an alkoxy-carbonyl group, and
a carboxy group;
an alkynyl group which may be substituted with one or more substituents selected from:
a phenyl group, and
a tri(alkyl)silyl group;
a halogenated alkyl group;
a phenyl group which may be substituted with one or more substituents selected from:
a halogen atom, and
a halogenated alkyl group;
a phenyl-alkyl group;
a monocyclic or a fused polycyclic heteroaryl group wherein said monocyclic or a fused polycyclic heteroaryl group is a 1-pyrrolyl group, a 2-pyrrolyl group, a 3-pyrrolyl group, a 2-thienyl group, a 3-thienyl group, a 2-thiazolyl group, a 4-thiazolyl group, a 5-thiazolyl group, a 2-pyridyl group, a 3-pyridyl group, a 4-pyridyl group or an imidazo[1,2-a]pyridin-2-yl group, and said monocyclic or a fused polycyclic heteroaryl group may be substituted with one or more alkyl groups;
an alkyl-carbonyl group;
a monocyclic nonaromatic heterocyclic-carbonyl group wherein said monocyclic nonaromatic heterocyclic-carbonyl group is a piperidino-carbonyl group, and said monocyclic nonaromatic heterocyclic-carbonyl group may be substituted with one or more benzyl groups;
a monocyclic heteroaryl-sulfonyl group wherein said monocyclic heteroaryl-sulfonyl group is a 1-pyrrolyl-sulfonyl group, a 2-pyrrolyl-sulfonyl group or a 3-pyrrolyl-sulfonyl group;
a carboxy group;
an alkyl-oxy-carbonyl group;
a carbamoyl group which may be substituted with one or more substituents selected from:
a phenyl group which may be substituted with one or more halogenated alkyl groups, and
an alkyl group;
a sulfamoyl group which may be substituted with one or more substituents selected from:
a phenyl group which may be substituted with one or more halogenated alkyl groups, and
an alkyl group;
an amino group which may be substituted with one or more substituents selected from:
an alkyl group,
an alkyl-carbonyl group,
a phenyl-carbonyl group,
an alkyl-sulfonyl group, and
a phenyl-sulfonyl group;
an ureido group which may be substituted with one or more phenyl groups;
a thioureido group which may be substituted with one or more phenyl groups;
a diazenyl group which may be substituted with one or more phenyl groups wherein said phenyl groups may be substituted with one or more substituents selected from:
a nitro group, and
a monocyclic heteroaryl-sulfamoyl group wherein said monocyclic heteroaryl -sulfamoyl group is a 2-pyridyl-sulfamoyl group, a 3-pyridyl-sulfamoyl group or a 4-pyridyl-sulfamoyl group; and
a hydroxy group,
in addition to the group represented by formula —O-A and the group represented by formula —X-E.

9. The method according to claim 1, wherein:
ring Z is a benzene ring which may have one or more substituents selected from a halogen atom, a nitro group, a cyano group, a methoxy group, a methyl group, an isopropyl group, a tert-butyl group, a 1,1,3,3-tetramethylbutyl group, a 2-phenylethen-1-yl group, a 2,2-dicyanoethen-1-yl group, a 2-cyano-2-(methoxycarbonyl)ethen-1-yl group, a 2-carboxy-2-cyanoethen-1-yl group, an ethynyl group, a phenylethynyl group, a (trimethylsilyl)ethynyl group, a trifluoromethyl group, a pentafluoroethyl group, a phenyl group, a 4-(trifluoromethyl)phenyl group, a 4-fluorophenyl group, a 2,4-difluorophenyl group, a 2-phenethyl group, a 1-hydroxyethyl group, a 1-(methoxyimino)ethyl group, a 1-[(benzyloxy)imino]ethyl group, a 2-thienyl group, a 3-thienyl group, a 1-pyrrolyl group, a 2-methylthiazol-4-yl group, an imidazo[1,2-a]pyridin-2-yl group, a 2-pyridyl group, an acetyl group, an isobutyryl group, a piperidinocarbonyl group, a 4-benzylpiperidinocarbonyl group, a (pyrrol-1-yl)sulfonyl group, a carboxy group, a methoxycarbonyl group, an N-[3,5-bis(trifluoromethyl)phenyl]carbamoyl group, an N,N-dimethylcarbamoyl group, a sulfamoyl group, an N-[3,5-bis(trifluoromethyl)phenyl]sulfamoyl group, an N,N-dimethylsulfamoyl group, an amino group, an N,N-dimethylamino group, an acetylamino group, a benzoylamino group, a methanesulfonylamino group, a benzenesulfonylamino group, a 3-phenylureido group, a (3-phenyl)thioureido group, a (4-nitrophenyl)diazenyl group, and a {[4-(pyridin-2-yl)sulfamoyl]phenyl}diazenyl group.

10. The method according to claim 2, wherein:
$R^z$ is
a hydrogen atom;
a halogen atom;
a nitro group;
a cyano group;
an alkoxy group;
an alkyl group which may be substituted with one or more substituents selected from:
  a hydroxy group,
  an alkoxy-imino group, and
  an aralkyl-oxy-imino group;
an alkenyl group which may be substituted with one or more substituents selected from:
  an aryl group,
  a cyano group,
  an alkyl-oxy-carbonyl group, and
  a carboxy group;
an alkynyl group which may be substituted with one or more substituents selected from:
  an aryl group, and
  a tri(alkyl)silyl group;
a halogenated alkyl group;
an aryl group which may be substituted with one or more substituents selected from:
  a halogen atom, and
  a halogenated alkyl group;
an aralkyl group;
a monocyclic or a fused polycyclic heteroaryl group which may be substituted with one or more alkyl groups;
an alkyl-carbonyl group;
a monocyclic nonaromatic heterocyclic-carbonyl group which may be substituted with one or more aralkyl groups;
a monocyclic heteroaryl-sulfonyl group;
a carboxy group;
an alkyl-oxy-carbonyl group;
a carbamoyl group which may be substituted with one or more substituents selected from:
  an aryl group which may be substituted with one or more halogenated alkyl groups, and
  an alkyl group;
a sulfamoyl group which may be substituted with one or more substituents selected from:
  an aryl group which may be substituted with one or more halogenated alkyl groups, and
  an alkyl group;
an amino group which may be substituted with one or more substituents selected from:
  an alkyl group,
  an alkyl-carbonyl group,
  an aryl-carbonyl group,
  an alkyl-sulfonyl group, and
  an aryl-sulfonyl group;
an ureido group which may be substituted with one or more aryl groups;
a thioureido group which may be substituted with one or more aryl groups;
a diazenyl group which may be substituted with one or more aryl groups wherein said aryl groups may be substituted with one or more substituents selected from:
  a nitro group, and
  a monocyclic heteroaryl-sulfamoyl group; or
a hydroxy group.

11. The method according to claim 2, wherein:
$R^z$ is
a hydrogen atom;
a halogen atom;
a nitro group;
a cyano group;
an alkoxy group;
an alkyl group which may be substituted with one or more substituents selected from:
  a hydroxy group,
  an alkoxy-imino group, and
  an aralkyl-oxy-imino group;
an alkenyl group which may be substituted with one or more substituents selected from:
  an aryl group,
  a cyano group,
  an alkyl-oxy-carbonyl group, and
  a carboxy group;
an alkynyl group which may be substituted with one or more substituents selected from:
  an aryl group, and
  a tri(alkyl)silyl group;
a halogenated alkyl group;
an aryl group which may be substituted with one or more substituents selected from:
  a halogen atom, and
  a halogenated alkyl group;
an aralkyl group;
a 5 to 9-membered heteroaryl group which may be substituted with one or more alkyl groups;
an alkyl-carbonyl group;
a 6-membered nonaromatic heterocyclic-carbonyl group which may be substituted with one or more aralkyl groups;
a 5-membered heteroaryl-sulfonyl group;
a carboxy group;
an alkyl-oxy-carbonyl group;

a carbamoyl group which may be substituted with one or more substituents selected from:
   an aryl group which may be substituted with one or more halogenated alkyl groups, and
   an alkyl group;
a sulfamoyl group which may be substituted with one or more substituents selected from:
   an aryl group which may be substituted with one or more halogenated alkyl groups, and
   an alkyl group;
an amino group which may be substituted with one or more substituents selected from:
   an alkyl group,
   an alkyl-carbonyl group,
   an aryl-carbonyl group,
   an alkyl-sulfonyl group, and
   an aryl-sulfonyl group;
an ureido group which may be substituted with one or more aryl groups;
a thioureido group which may be substituted with one or more aryl groups;
a diazenyl group which may be substituted with one or more aryl groups wherein said aryl groups may be substituted with one or more substituents selected from:
   a nitro group, and
   a 6-membered heteroaryl-sulfamoyl group; and
a hydroxy group.

12. The method according to claim 2, wherein:
$R^z$ is
a hydrogen atom;
a halogen atom;
a nitro group;
a cyano group;
an alkoxy group;
an alkyl group which may be substituted with one or more substituents selected from:
   a hydroxy group,
   an alkoxy-imino group, and
   a benzyl-oxy-imino group;
an alkenyl group which may be substituted with one or more substituents selected from:
   a phenyl group,
   a cyano group,
   an alkoxy-carbonyl group, and
   a carboxy group;
an alkynyl group which may be substituted with one or more substituents selected from:
   a phenyl group, and
   a tri(alkyl)silyl group;
a halogenated alkyl group;
a phenyl group which may be substituted with one or more substituents selected from:
   a halogen atom, and
   a halogenated alkyl group;
a phenyl-alkyl group;
a monocyclic or a fused polycyclic heteroaryl group wherein said monocyclic or a fused polycyclic heteroaryl group is a 1-pyrrolyl group, a 2-pyrrolyl group, a 3-pyrrolyl group, a 2-thienyl group, a 3-thienyl group, a 2-thiazolyl group, a 4-thiazolyl group, a 5-thiazolyl group, a 2-pyridyl group, a 3-pyridyl group, a 4-pyridyl group or an imidazo[1,2-a]pyridin-2-yl group, and said monocyclic or a fused polycyclic heteroaryl group may be substituted with one or more alkyl groups;
an alkyl-carbonyl group;
a monocyclic non-aromatic heterocyclic-carbonyl group wherein said monocyclic non-aromatic heterocyclic-carbonyl group is a piperidino-carbonyl group, and said monocyclic non-aromatic heterocyclic-carbonyl group may be substituted with one or more benzyl groups;
a monocyclic heteroaryl-sulfonyl group wherein said monocyclic heteroaryl-sulfonyl group is a 1-pyrrolyl-sulfonyl group, a 2-pyrrolyl-sulfonyl group or a 3-pyrrolyl-sulfonyl group;
a carboxy group;
an alkoxy-carbonyl group;
a carbamoyl group which may be substituted with one or more substituents selected from:
   a phenyl group which may be substituted with one or more halogenated alkyl groups, and
   an alkyl group;
a sulfamoyl group which may be substituted with one or more substituents selected from:
   a phenyl group which may be substituted with one or more halogenated alkyl groups, and
   an alkyl group;
an amino group which may be substituted with one or more substituents selected from:
   an alkyl group,
   an alkyl-carbonyl group,
   a phenyl-carbonyl group,
   an alkyl-sulfonyl group, and
   a phenyl-sulfonyl group;
an ureido group which may be substituted with one or more phenyl groups;
a thioureido group which may be substituted with one or more phenyl groups;
a diazenyl group which may be substituted with one or more phenyl groups wherein said phenyl groups may be substituted with one or more substituents selected from:
   a nitro group, and
   a monocyclic heteroaryl-sulfamoyl group wherein said monocyclic heteroaryl -sulfamoyl group is a 2-pyridyl-sulfamoyl group, a 3-pyridyl-sulfamoyl group or a 4-pyridyl-sulfamoyl group; and
a hydroxy group.

13. The method according to claim 1, wherein:
E is a 2,5- or 3,5-di-substituted phenyl group wherein at least one of said substituents is a trifluoromethyl group, and the other substituent is selected from
a halogen atom;
a nitro group;
an alkyl group;
a halogenated alkyl group;
an alkoxy group;
a halogenated alkoxy group;
an aryl-oxy group which may be substituted with one or more substituents selected from
   a halogen atom,
   an alkoxy group,
   an alkyl group, and
   a cyano group;
an alkyl-sulfanyl group;
an alkoxy-carbonyl group;
a carboxy group; and
a monocyclic nonaromatic heterocyclic group which may be substituted with one or more halogenated alkyl group.

14. The method according to claim 13, wherein said monocyclic nonaromatic heterocyclic group is a 5 to 6-membered nonaromatic heterocyclic group.

15. The method according to claim 1, wherein:

E is a 2,5- or 3,5-di-substituted phenyl group wherein at least one of said substituents is a trifluoromethyl group, and the other substituent is selected from a halogen atom;
a nitro group;
an alkyl group;
a halogenated alkyl group;
an alkoxy group;
a halogenated alkoxy group;
an aryl-oxy group wherein said aryl-oxy group is a phenyl-oxy group, a 1-naphthyl-oxy group or a 2-naphthyl-oxy group, and said aryl-oxy group may be substituted with one or more substituents selected from:
   a halogen atom,
   an alkoxy group,
   an alkyl group, and
   a cyano group;
an alkyl-sulfanyl group;
an alkoxy-carbonyl group;
a carboxy group; and
a monocyclic nonaromatic heterocyclic group wherein said monocyclic nonaromatic heterocyclic group is a 1-pyrrolidinyl group, a piperidino group or a morpholino group, and said monocyclic nonaromatic heterocyclic group may be substituted with one or more halogenated alkyl group.

16. The method according to claim 1, wherein

E is a 2,5- or 3,5-di-substituted phenyl group wherein at least one of said substituents is a trifluoromethyl group.

* * * * *

UNITED STATES PATENT AND TRADEMARK OFFICE
CERTIFICATE OF CORRECTION

PATENT NO. : 7,700,655 B2
APPLICATION NO. : 11/783324
DATED : April 20, 2010
INVENTOR(S) : S. Muto et al.

It is certified that error appears in the above-identified patent and that said Letters Patent is hereby corrected as shown below:

On the Title Page, Item (56) under References Cited, FOREIGN PATENT DOCUMENTS, page 2, line 61, left column, "JP97/09315" should be --WO9709315--.

On the Title Page, Item (56) under References Cited, FOREIGN PATENT DOCUMENTS, page 2, line 30, right column, "WO1314712" should be --EP1314712--.

Signed and Sealed this

Thirtieth Day of November, 2010

David J. Kappos
*Director of the United States Patent and Trademark Office*